(12) United States Patent
Nam et al.

(10) Patent No.: US 11,945,822 B2
(45) Date of Patent: Apr. 2, 2024

(54) PYRAZOLO-TRIAZINE AND/OR PYRAZOLO-PXRIMIDINE DERIVATIVES AS SELECTIVE INHIBITOR OF CYCLIN DEPENDENT KINASE

(71) Applicants: QURIENT CO., LTD., Gyeonggi-Do (KR); LEAD DISCOVERY CENTER GMBH, Dortmund (DE)

(72) Inventors: Kiyean Nam, Gyeonggi-do (KR); Jaeseung Kim, Seoul (KR); Yeejin Jeon, Gyeonggi-do (KR); Donghoon Yu, Gyeonggi-do (KR); Mooyoung Seo, Gyeonggi-do (KR); Dongsik Park, Gyeonggi-do (KR); Jan Eickhoff, Herdecke (DE); Gunther Zischinsky, Dortmund (DE)

(73) Assignees: QURIENT CO., LTD., Gyeonggi-Do (KR); LEAD DISCOVERY CENTER GMBH, Dortmund (DE)

( * ) Notice: Subject to any disclaimer, the term of this patent is extended or adjusted under 35 U.S.C. 154(b) by 48 days.

(21) Appl. No.: 17/045,030

(22) PCT Filed: Apr. 11, 2019

(86) PCT No.: PCT/EP2019/059302
§ 371 (c)(1),
(2) Date: Oct. 2, 2020

(87) PCT Pub. No.: WO2019/197549
PCT Pub. Date: Oct. 17, 2019

(65) Prior Publication Data
US 2021/0147427 A1    May 20, 2021

Related U.S. Application Data

(60) Provisional application No. 62/656,070, filed on Apr. 11, 2018.

(51) Int. Cl.
| C07D 487/04 | (2006.01) |
| A61P 35/00 | (2006.01) |
| A61P 35/02 | (2006.01) |
| C07D 519/00 | (2006.01) |

(52) U.S. Cl.
CPC ............ *C07D 487/04* (2013.01); *A61P 35/00* (2018.01); *A61P 35/02* (2018.01); *C07D 519/00* (2013.01)

(58) Field of Classification Search
CPC ..... C07D 487/04; C07D 519/00; A61P 35/00; A61P 35/02; A61P 29/00; A61P 31/00; A61P 37/00; A61K 31/519; A61K 31/53
See application file for complete search history.

(56) References Cited

U.S. PATENT DOCUMENTS

| 7,119,200 B2 | 10/2006 | Guzi et al. |
| 9,096,608 B2 * | 8/2015 | Eickhoff ................. A61P 29/00 |
| 9,567,345 B2 * | 2/2017 | Eickhoff ................. A61P 33/00 |

FOREIGN PATENT DOCUMENTS

| JP | 2009007342 A * | 1/2009 | |
| RU | 2414472 C2 | 3/2011 | |
| WO | WO-2008130570 A1 * | 10/2008 | ............ A61K 31/33 |
| WO | 2013128028 A1 | 9/2013 | |
| WO | 2013128029 A1 | 9/2013 | |
| WO | WO-2013128028 A1 * | 9/2013 | ........... C07D 471/10 |
| WO | 2015/154022 A1 | 10/2015 | |
| WO | 2016/142855 A2 | 9/2016 | |
| WO | WO-2019144149 A2 * | 7/2019 | |

OTHER PUBLICATIONS

Kerns, E.,Drug-like Properties: Concepts, Structure Design and Methods: from ADME to Toxicity Optimization, (Elsevier, 2008) pp. 92-93.*
Goosen, C., Pharmaceutical Research vol. 19, No. 1, 13-19 (Jan. 2002).*
Fourie, L., International Journal of Pharmaceutics vol. 279, Issues 1-2, Jul. 26, 2004, pp. 59-66.*
Edwards, P. D., J. Med. Chem. 39 (1996), pp. 1112-1124.*
Rautio, J., Eur. J. Pharm. Sci. 11:157-163 (2000).*
Hazel, Pascale, "Inhibitor selectivity for cyclin-dependent kinase 7: a structural, thermodynamic, and modelling study." ChemMedChem 12.5 (2017): 372-380.*
McKim, A. S., "Dimethyl sulfoxide USP, PhEur in approved pharmaceutical products and medical devices." Pharmaceutical Technology 32.5 (2008): 1-6.*
Popowycz, F., "Synthesis and antiproliferative evaluation of pyrazolo [1, 5-a]-1, 3, 5-triazine myoseverin derivatives." Bioorganic & medicinal chemistry 17.9 (2009): 3471-3478.*
JP2009007342 A (2009) WIPO English machine translation; p. 1-43.*
Communication issued by the IPOS Intellectual Property Office of Singapore providing input and a screen shot regarding the D6 reference (Registry No. 2183667-57-2, Mar. 4, 2018; Registry No. 1211294-10-8, Mar. 18, 2010; and Registry No. 672321-00-5, Apr. 7, 2004 (The CAS Registry)) as listed in the Written Opinion issued by the IPOS in the related corresponding application 11202009724Y dated Mar. 21, 2022.

(Continued)

*Primary Examiner* — John M Mauro
(74) *Attorney, Agent, or Firm* — SALIWANCHIK, LLOYD & EISENSCHENK

(57) ABSTRACT

The present invention relates to pyrazolo[1,5-a][1,3,5]triazine and pyrazolo[1,5-a]pyrimidine derivatives and/or pharmaceutically acceptable salts thereof, the use of these derivatives as pharmaceutically active agents, especially for the prophylaxis and/or treatment of cell proliferative diseases, inflammatory diseases, immunological diseases, cardiovascular diseases and infectious diseases. Furthermore, the present invention is directed towards pharmaceutical compositions containing at least one of the pyrazolo[1,5-a] [1,3,5]triazine and pyrazolo[1,5-a]pyrimidine derivatives and/or pharmaceutically acceptable salts thereof.

20 Claims, 1 Drawing Sheet

(56) References Cited

OTHER PUBLICATIONS

Written Opinion issued by the IPOS Intellectual Property Office of Singapore in a related corresponding Application No. 11202009724Y dated Mar. 21, 2022.
Database Registry [Online], Chemical Abstracts Service, Columbus, Ohio, U.S., Database Accession No. 1378219-23-8 Abstract, Compounds with Registry No. 1378219-23-8, 1378096-86-6 and 1377884-89-3, Jun. 14, 2012.
Hutterer, Corina, et al., "A Novel CDK7 Inhibitor of the Pyrazolotriazine Class Exerts Broad-Spectrum Antiviral Activity at Nanomolar Concentrations", Antimicrobial Agent and Chemotherapy, vol. 59, No. 4, Apr. 1, 2015, pp. 2062-2071.
Also attached is an Office Action with an English Translation issued by the Russian Patent Office with respect to the European priority application No. PCT/EP2019/059302.
Office Action issued by the Japanese Patent Office dated Apr. 27, 2023 in parallel Japanese Patent Application No. 2020-555100.
Sava, Georgina P. et al. "CDK7 inhibitors as anticancer drugs." Cancer and Metastasis Reviews 39:805-823, May 8, 2020.

* cited by examiner

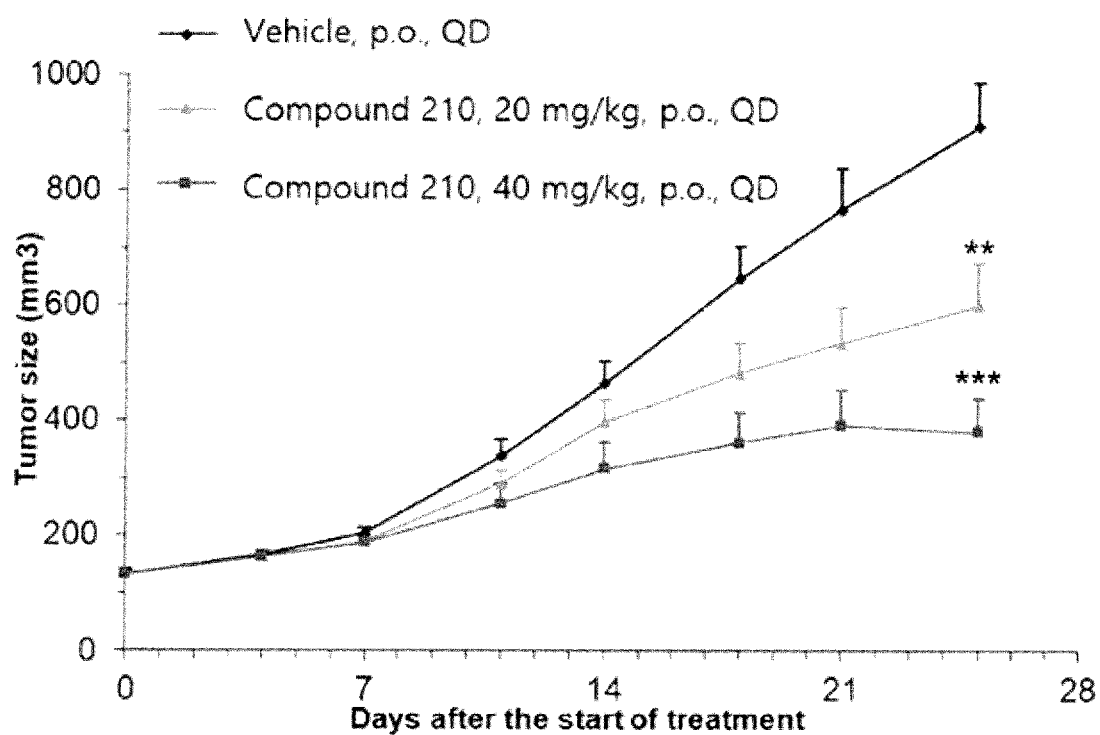
A one-way ANOVA was performed to compare tumor volume among vehicle group and treatment groups, * indicates $p<0.5$,  indicates $p<0.01$, * indicates $p<0.001$.

PYRAZOLO-TRIAZINE AND/OR PYRAZOLO-PXRIMIDINE DERIVATIVES AS SELECTIVE INHIBITOR OF CYCLIN DEPENDENT KINASE

CROSS REFERENCE TO RELATED APPLICATIONS

This application is a National Stage Application of International Application Number PCT/EP2019/059302, filed Apr. 11, 2019; which claims the benefit of U.S. Provisional Application Ser. No. 62/656,070, filed Apr. 11, 2018, in their entirety.

The present invention relates to pyrazolo[1,5-a][1,3,5] triazine and pyrazolo[1,5-a]pyrimidine derivatives and/or pharmaceutically acceptable salts thereof, the use of these derivatives as pharmaceutically active agents, especially for the prophylaxis and/or treatment of cell proliferative diseases, inflammatory diseases, immunological diseases, cardiovascular diseases and infectious diseases. Furthermore, the present invention is directed towards pharmaceutical compositions containing at least one of the pyrazolo[1,5-a][1,3,5]triazine and pyrazolo[1,5-a]pyrimidine derivatives and/or pharmaceutically acceptable salts thereof.

BACKGROUND OF THE INVENTION

Cyclin-dependent kinase (CDK) family members that trigger passage through the cell cycle are being considered as attractive therapeutic targets, especially for cancer. CDK family members that control other processes such as transcription and RNA processing have caught less attention so far, although experimental evidence for their involvement in different pathological processes is emerging. Together with cell cycle control, CDK/cyclin complexes also have been identified as conserved components of the RNA polymerase II (Pol II) transcriptional machinery (Bregman et al., 2000, *Front Biosci.* 5:244-257). There are currently 20 known mammalian CDKs. While CDK7-13 have been linked to transcription, only CDK 1, 2, 4, and 6 show demonstrable association with cell cycle. Unique among the mammalian CDKs, CDK7 has consolidated kinase activities, regulating both the cell cycle progression and transcription (Desai et al, 1995, Mol. Cell Biol. 15, 345-350).

The general transcription factor TFIIH purified from mammalian cells consists of ten subunits, seven of which (p62, p52, p44, p34, XPD, XPB, and TTDA) form the core complex. Three subunits (cyclin H, MAT1, and CDK7) from the CDK-activating kinase (CAK), which is linked to TFIIH's core via the XPD (ATP-dependent helicase) subunit of complex. During the process of transcription initiation, the helicase activity of TFIIH opens the core promoter DNA, while CDK7 phosphorylates the C-terminal domain (CTD) of Pol II at serine 5 and 7 (Akhtar et al., 2009, Mol. Cell 34, 387-393) as well as other transcription factors controlling the initiation-to-elongation transition (Larochelle et al., 2012, Nat. Strut. Mol. Biol. 19, 1108-1115 Therefore CDK7 is essential factor for transcription process, which suggests that CDK7 is a target for cancer therapy, especially transcription addicted cancer.

CDK7 has long been asserted as having an essential role in cellular metabolism and viability. Transcriptional CDK inhibitors down-regulate a large number of short-lived anti-apoptotic proteins, such as the anti-apoptotic proteins myeloid cell leukemia-1 (Mcl-1), B-cell lymphoma extra-long (Bcl-xL) and XIAP (X-linked IAP), D-cyclins, c-Myc, Mdm-2 (leading to p53 stabilization), p21$^{waf1}$ proteins whose transcription is mediated by nuclear factor-kappa B (NF-kB) and hypoxia-induced VEGF (Shapiro GI. 2006, *J Clin Oncol;* 24(11): 1770-83). The transcriptional non-selective cyclin-dependent kinase inhibitor flavopiridol induces apoptosis in multiple myeloma cells through transcriptional repression and down-regulation of Mcl-1. These findings supported previous postulates that CDK7 might be a valuable target for drugs directed toward the treatment of malignancies and cell cycle-associated diseases (Lolli G and Johnson L N. 2005. *Cell Cycle* 4:572-577).

The function of CDK7 as regulator of general transcription and CDK7 is a therapeutic target for treatment of many diseases and syndromes are associated with mutations in regulatory regions and in transcription factors, cofactors, chromatin regulators and noncoding RNAs. These mutations can contribute to cancer, autoimmunity, neurological disorders, developmental syndromes, diabetes, cardiovascular disease, and obesity, among others. Some transcription factors control RNA polymerase II pause release and elongation and, when their expression or function is altered, can produce aggressive tumor cells (c-Myc) or some forms of autoimmunity (AIRE) (Tong Ihn Lee and Richard A. Young, *Cell,* 2013, 152:1237-1251). Therefore, inhibition of human CDK7 kinase activity is likely to result in anti-proliferative activity through the function in cell cycle progression and transcriptional regulation by inhibition of some transcription factor related to oncogene through inhibition of general transcription process. More important thing is that CDK7 has been shown to regulate exponential expression of oncogenic transcription factors more dramatically than it does to other housekeeping genes in cancer cells. Thus Inhibition of CDK7 can differentially affect transcription of certain oncogenes and housekeeping gene, therefore therapeutic window can be secured. For this reason, transcriptional regulation and pharmacological inhibition through appropriate general transcription inhibition by CDK7 could be applied to treat proliferative disorder, including cancer. As a general regulator of transcription, CDK7 is a therapeutic target for treatment of disease like inflammation, virus replication such as HIV, EBV, cancer and cardiac hypertrophy.

HIV-1 gene expression is regulatory by a viral transactivator protein (Tat) which induces transcriptional elongation of HIV-1 long tandem repeat. This induction requires hyperphosphorylation of the C-terminal domain repeat of RNA polymerase II. To archives said hyperphosphorylation, Tat stimulates CTD kinases associated with general transcription factors of the promoter complex, specifically TFIIH-associated CDK7 (Nekhai et al.; Biochem J. (2002) 364, 649-657). The inventors of U.S. Pat. No. 615,968 also described that Tat binds to CDK7 and that this interaction increase the ability of CAK to phosphorylate CTD. The authors of U.S. Pat. No. 615,968 further disclose that the transcriptional activation by Tat is dependent upon the kinase activity of CDK7. Additionally, Young Kyeung Kim and colleagues conclude that the recruitment and activation of TFIIH represents a rate-limiting step for the emergence of HIV from latency (Young Kyeung Kim, EMBO (2006) 25, 3596-3604).

Levels of CDK7 and CDK9, as well as other components of the kinase complexes, MAT-1/cyclin H are upregulated during Human cytomegalovirus infection. In addition, there is an increase in the kinase activities of CDK7 and CDK9 (Tamrakar et al., Journal of Virology, 2005, 79; 15477-15493).

Many antiviral drugs target viral proteins. These have the disadvantage that viruses often develop resistance against these drugs. Antiviral drugs targeting cellular proteins essential for viral process, like CDK7, could bypass this disadvantage. These drugs may further be effective in treating several unrelated viruses and their effects should be additive to traditional antiviral agents. Inhibitors of CDK7, which has its dual function of CDK-activating kinase and transcription regulation is very effective in the treatment of several viruses.

It is an object of the present invention to provide compounds and/or pharmaceutically acceptable salts thereof which can be used as pharmaceutically active agents, especially for prophylaxis and/or treatment of cell proliferative diseases, inflammatory diseases, immunological diseases, cardiovascular diseases and infectious diseases, as well as compositions comprising at least one of those compounds and/or pharmaceutically acceptable salts thereof as pharmaceutically active ingredients.

In one aspect, the present invention relates to pyrazolo-triazine or pyrazolo-pyrimidine compounds which are defined by general formula I

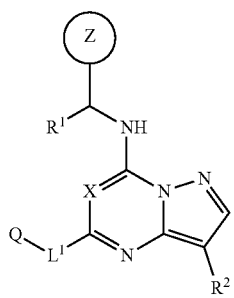

Formula I wherein
X is, independently at each occurrence, selected from CH and N;
$L^1$ is either absent or independently, at each occurrence, selected from the group consisting of —NH—, —NH(CH$_2$)—, —NH(C=O)—, —NHSO$_2$—, —O—, —O(CH$_2$)—, —(C=O)—, —(CO)NH— and —(CO)(CH$_2$)—;
Q is, independently at each occurrence, selected from the group consisting of C3-C8 cycloalkyl, aryl, heteroaryl, heterocyclyl, and C1-C6 alkyl, wherein C1-C6 alkyl is substituted with one or two of OR$^5$, —N(R$^5$)R$^5$, aryl, heteroaryl and heterocyclyl,
  C3-C8 cycloalkyl can be substituted with one or two of R$^3$ and R$^4$ and —(CO)R$^5$,
  heterocyclyl can be substituted with one or two of R$^3$ and R$^4$ and —(CO)R$^5$
  aryl or heteroaryl substituted with one or two of C1-C6 alkyl, —OR$^5$, —N(R$^5$)R$^5$, —(CO)R$^5$, halogen, heteroaryl and heterocyclyl;
$R^1$ is, at each occurrence, independently selected from the group consisting of hydrogen and methyl;
$R^2$ is, at each occurrence, independently selected from the group consisting of halogen, C1-C6 alkyl, C3-C10 cycloalkyl, —CN, —(C=O)CH$_3$, —NR$^9$R$^{12}$ and C1-C3 haloalkyl, any of which is optionally substituted;
$R^3$ is independently, at each occurrence, selected from the group consisting of hydrogen, —OR$^5$, halogen, —N(R$^5$)R$^5$, —NR$^9$R$^{12}$, —NH(C=O)R$^5$, —(C=O)NH$_2$, aryl, heteroaryl, heterocyclyl, C1-C6 alkyl and C1-C6 alkyl substituted with —OH or —NH$_2$;

$R^4$ is, independently, at each occurrence, selected from the group consisting of hydrogen, halogen, —OR$^5$, —N(R$^5$)R$^5$, (=O), aryl, heteroaryl, heterocyclyl, C1-C6 alkyl and C1-C6 alkyl substituted with —OH or —NH$_2$;
$R^5$ is, at each occurrence, independently selected from the group consisting of hydrogen, C1-C6 alkyl, C3-C8 cycloalkyl, C1-C3 haloalkyl, heteroaryl, heterocyclyl, heteroaryl substituted with one or two of halogen, —OR$^{11}$, —N(R$^{11}$)R$^{11}$, C1-C6 alkyl and C1-C6 alkyl substituted with —OH or —NH$_2$, heterocyclyl substituted with one or two of halogen, —OR$^{11}$, —N(R$^{11}$)R$^{11}$, C1-C6 alkyl and C1-C6 alkyl substituted with —OH or —NH$_2$;
Z is any structure of the following group A;

Group A

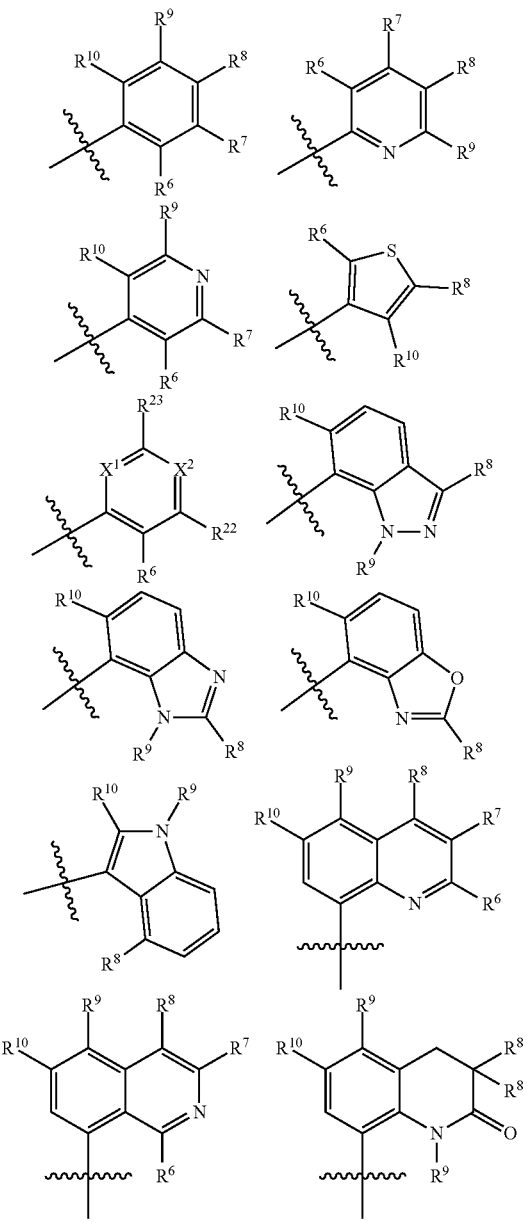

Wherein
- $X^1$ is, independently at each occurrence, selected from $CR^{24}$ and N;
- $X^2$ is, independently at each occurrence, selected from $CR^{25}$ and N;
- $R^6$ is, at each occurrence, independently selected from the group consisting of hydrogen, halogen, C1-C6 alkyl, C1-C6 alkyl substituted with —OH, C3-C10 cycloalkyl, C3-C10 heterocyclyl, —(C=O)NHR$^{11}$, —NHR$^9$, —NH(C=O)NHR$^{11}$, —N(CH$_3$)(C=O)CH$_3$, —NH(C=O)R$^{12}$, —NR$^9$R$^{12}$, —OR$^{12}$, and any structure of the following group B;

Group B

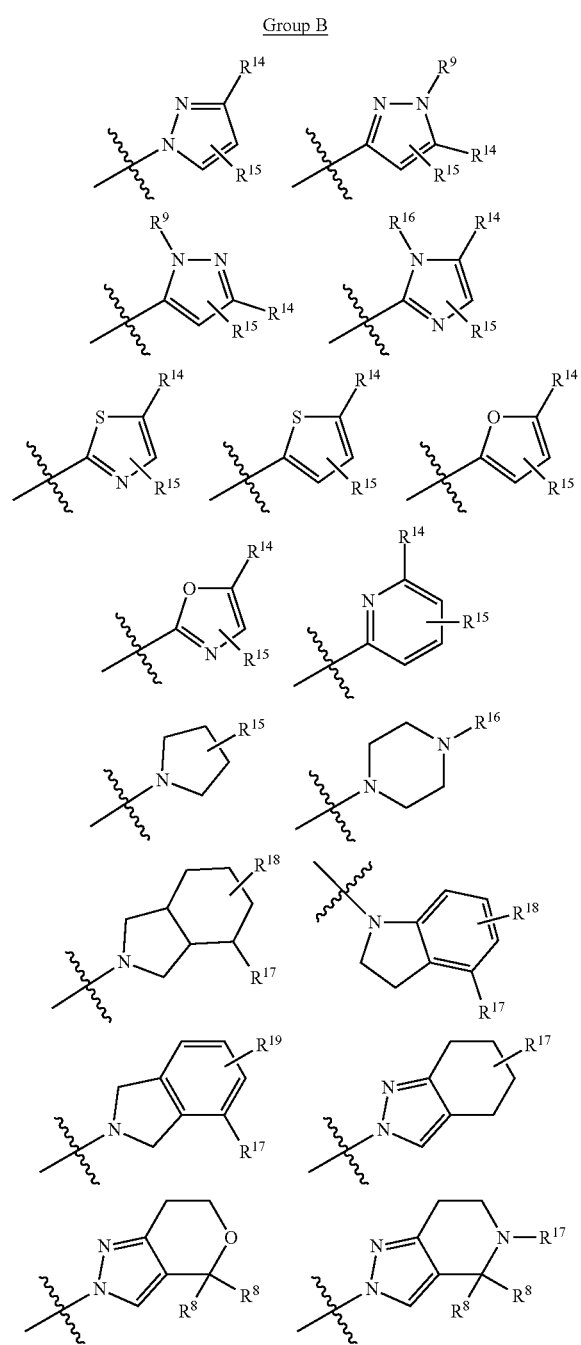
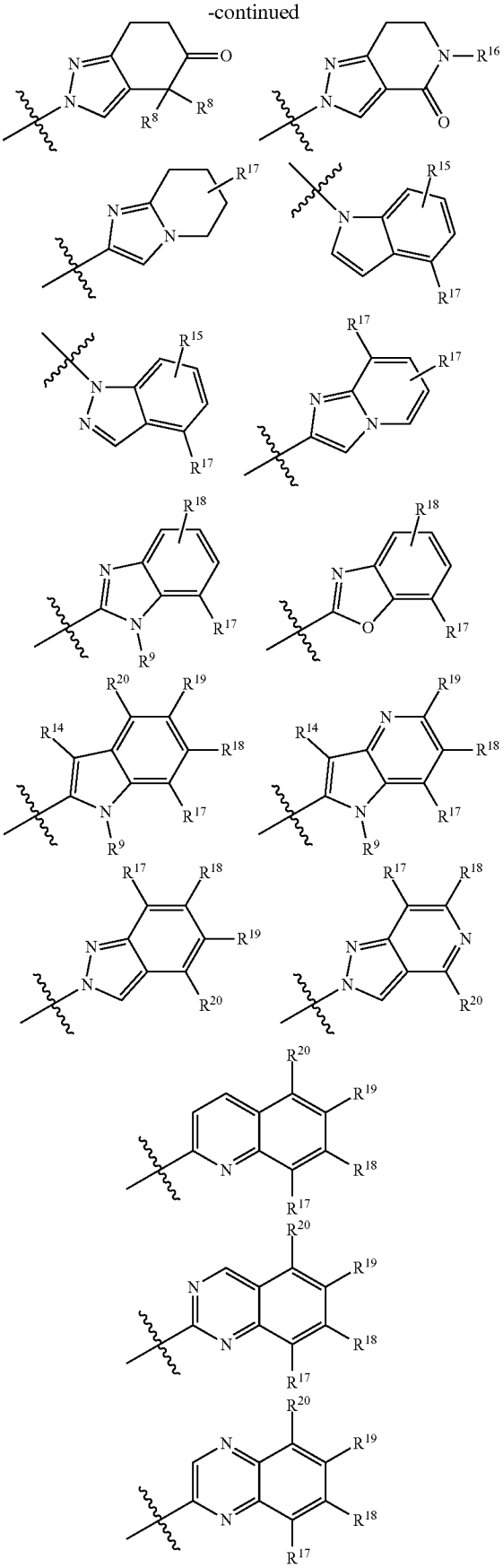

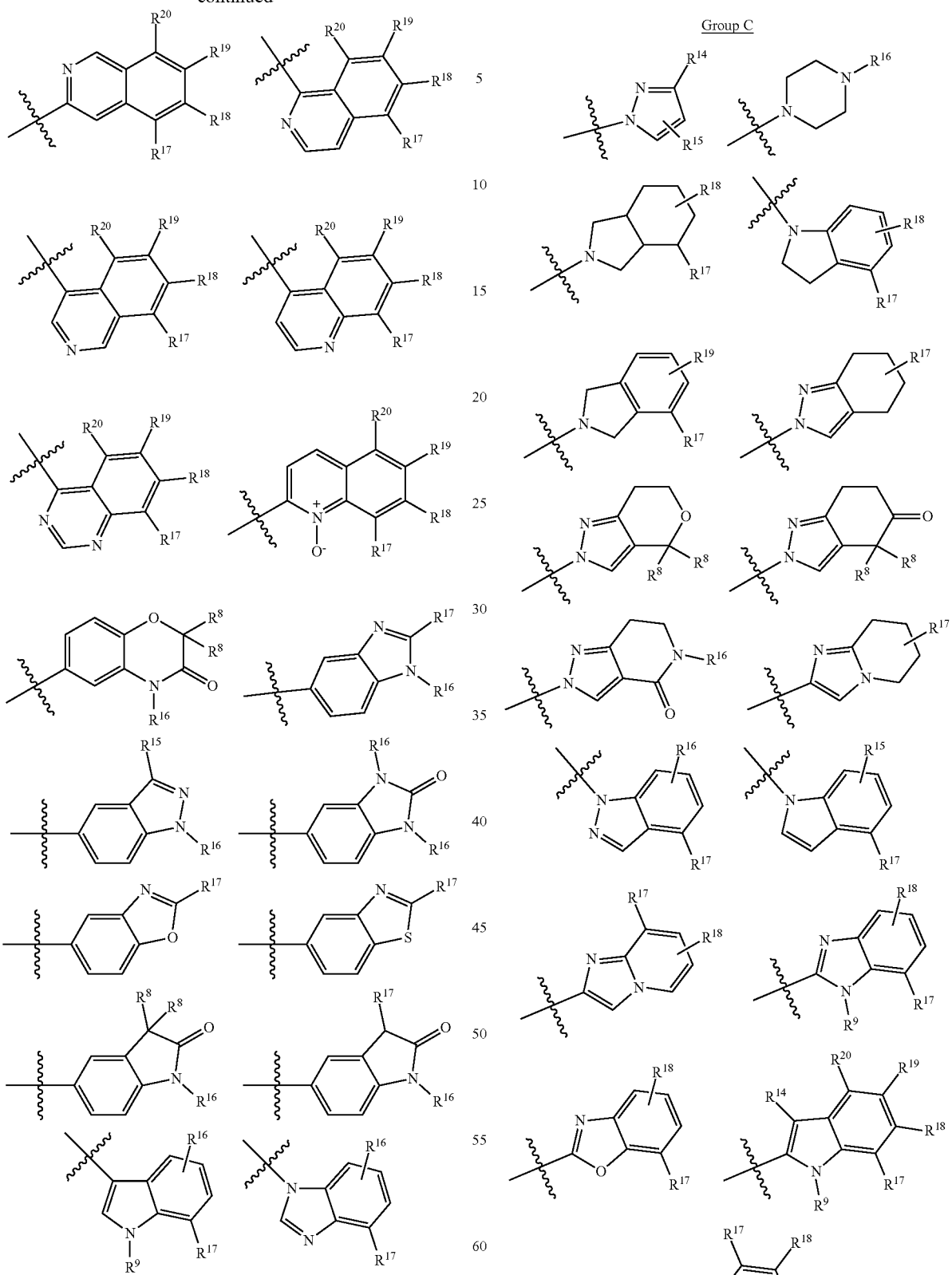
R⁷ is, at each occurrence, independently selected from the group consisting of hydrogen, halogen, C1-C6 alkyl, —NH(C=O)R¹², —NR⁹R¹², —OR¹² and any structure of the following group C;

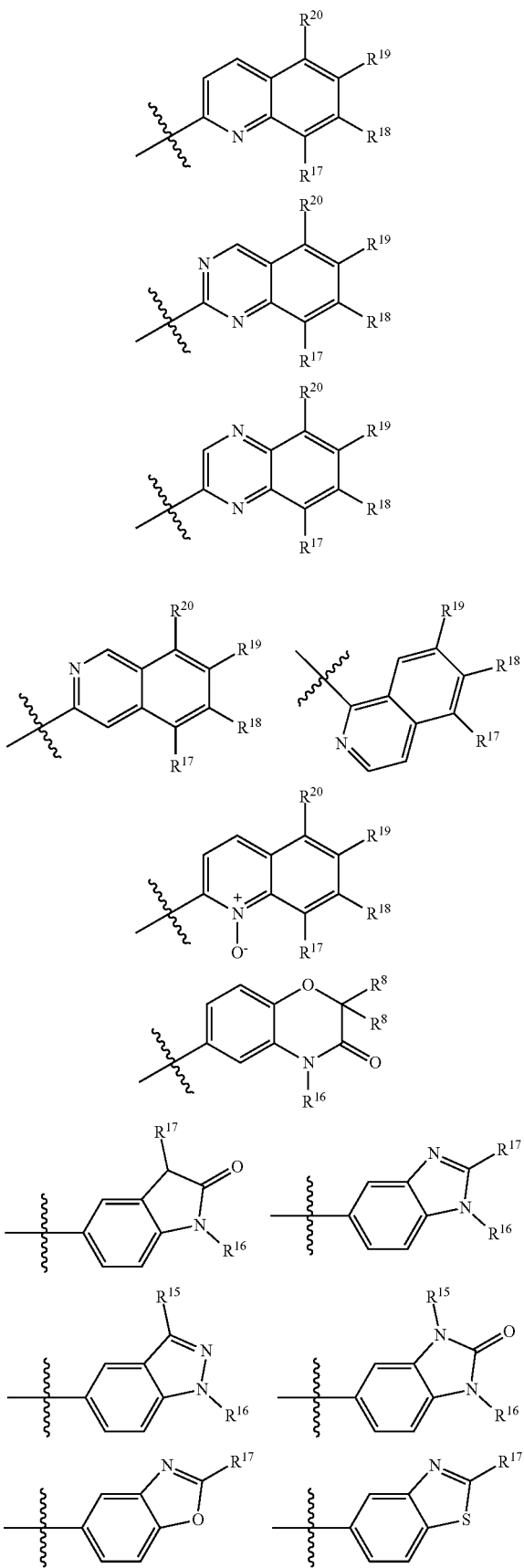

R[8] and R[10] are, at each occurrence, independently selected from the group consisting of hydrogen, halogen, C1-C6 alkyl, C1-C3 haloalkyl, —NH$_2$, —OH, —OR[5], —CN, —(C=O)R[5], —(C=O)OR[5], —(C=O)NH$_2$, —(C=O)NHR[21], —CH$_2$(C=O)NHR[21], —NH(C=O)R[13], —NHS(=O)$_2$R[5], —S(=O)$_2$NH$_2$, —S(=O)$_2$NHR[21], and C1-C6 alkyl substituted with —OH, —OR[5] or —NHR[9];

R[9] is, at each occurrence, independently selected from the group consisting of hydrogen, halogen, C1-C6 alkyl, C1-C3 haloalkyl, —OR[5], —CN, C3-C10 cycloalkyl, C3-C10 heterocyclyl and C1-C6 alkyl substituted with —OH or —OR[5];

R[11] is, at each occurrence, independently selected from the group consisting of hydrogen, C1-C6 alkyl and C3-C10 cycloalkyl;

R[12] is, at each occurrence, absent or independently selected from the group consisting of C1-C6 alkyl, C1-C6 alkyl substituted with —OR[5] or —N(R[5])R[5], C6-C10 aryl, phenyl, benzyl, C3-C9 heteroaryl, C3-C6 heterocyclyl, benzyl substituted with one to four halogens or C1-C3 alkyls, C3-C9 heteroaryl substituted with one to four halogens or C1-C3 alkyls, C3-C6 heterocyclyl substituted with C1-C3 alkyl, and C6-C10 aryl substituted with one to four halogens and/or one to four —NH(C=O)R[13];

R[13] is, at each occurrence, independently selected from the group consisting of hydrogen, C1-C6 alkyl, C1-C6 alkyl substituted with —CN, —OH, —OR[5], —NH$_2$, —NHR[5] or —N(R[5])R[5] and C3-C10 cycloalkyl;

R[14] and R[15] are, at each occurrence, independently selected from the group consisting of hydrogen, halogen, C1-C6 alkyl, C1-C6 alkyl substituted with —OH or —NH$_2$, C3-C10 cycloalkyl, —(C=O)R[5], —(C=O)NHR[21], —C(R[9])(R[11])OR[21], —NH(C=O)R[21], —NR[9]R[21], —OR[21], —OC(R[9])(R[11])(R[21]); C3-C10 heterocyclyl, C3-C10 heterocyclyl substituted with R[4], C3-C10 heterocyclyl substituted with one to four halogens or C1-C3 alkyl, C6-C10 aryl, e.g. phenyl and aryl substituted with —(C=O)R[5], —(C=O)OR[5], —(C=O)NH$_2$, —(C=O)NHR[21], —CH$_2$(C=O)NHR[21], —NH(C=O)R[13], —NHS(=O)$_2$R[5], —S(=O)$_2$NH$_2$ or —S(=O)$_2$NHR[21];

R[16] is, at each occurrence, independently selected from the group consisting of hydrogen, C1-C6 alkyl, —(C=O)R[13] and C1-C6 alkyl substituted with —OR[5];

R[17], R[18], R[19] and R[20] are, at each occurrence, independently selected from the group consisting of hydrogen, halogen, C1-C6 alkyl, C1-C3 haloalkyl, C6-C10 aryl, e.g. phenyl, —CN, —CHCF$_3$NR[9]R[11], —OH, —OR[21], —NO$_2$, —(C=O)R[5], —(C=O)OR[5], —(C=O)NH$_2$, —(C=O)NHR[21], —NH(C=O)R[13], —NHR[5], —NHS(=O)$_2$R[5], —S(=O)$_2$NH$_2$, —S(=O)$_2$NHR[21] and C1-C6 alkyl substituted with —CN, —OH, —OR[5], —(C=O)NHR[5], —NH$_2$, —NH(C=O)R[5], —NHR[5] or —N(R[5])R[5];

R[21] is, at each occurrence, independently selected from the group consisting of C1-C6 alkyl, C3-C10 cycloalkyl, C3-C10 heterocyclyl, C1-C3 haloalkyl, aryl, phenyl, benzyl, C1-C6 alkyl substituted with —CN, —OH, —OR$^5$, —NH$_2$, —NHR$^5$ or —N(R$^5$)R$^5$, aryl substituted with halogen or C1-C3 haloalkyl, C3-C10 heteroaryl substituted with one to four halogens or C1-C3 alkyl and C3-C10 heterocyclyl substituted with R$^4$;

R$^{22}$ and R$^{23}$ are, at each occurrence, independently selected from the group consisting of hydrogen, halogen, C1-C6 alkyl, C1-C3 haloalkyl, —OH, —OR$^5$, —CN and C1-C6 alkyl substituted with —OH, —OR$^5$ or —NHR$^9$;

R$^{24}$ and R$^{25}$ are, at each occurrence, independently selected from the group consisting of hydrogen, halogen, C1-C6 alkyl, C1-C3 haloalkyl, —NH$_2$, —OH, —OR$^5$, —CN, —(C=O)R$^5$, —(C=O)OR$^5$, —(C=O)NH$_2$, —(C=O)NHR$^{21}$, —CH$_2$(C=O)NHR$^{21}$, —NH(C=O)R$^{13}$, —NHS(=O)$_2$R$^5$, —S(=O)$_2$NH$_2$ or —S(=O)$_2$NHR$^{21}$ and C1-C6 alkyl substituted with —OH, —OR$^5$ or —NHR$^9$;

With the proviso that when Z is

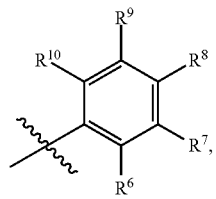

then one of R$^6$ and R$^7$ is not H;

Wherein, if R$^1$ is H, R$^2$ is CH(CH$_3$)$_2$, L$^1$ is absent, Q is heterocyclyl substituted with R$^3$ and R$^4$, R$^3$ is N(R$^5$)R$^5$, R$^4$ is H, R$^5$ is H, X is N, Z is phenyl, R$^7$ is H, R$^8$ is H, R$^9$ is H and R$^{10}$ is H, then R$^6$ is not 1H-pyrazole;

Wherein, if R$^1$ is H, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^7$ is H, R$^8$ is H, R$^9$ is H and R$^{10}$ is H, then R$^6$ is not CH$_3$, Cl or 1H-pyrazole;

Wherein, if R$^1$ is H, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^6$ is OR$^{12}$, R$^7$ is H, R$^8$ is H, R$^9$ is H and R$^{10}$ is H, then R$^{12}$ is not phenyl, CH(CH$_3$)$_2$, CH$_2$CH$_3$ or CH$_3$;

Wherein, if R$^1$ is H, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^6$ is Cl, R$^7$ is H, R$^8$ is H and R$^9$ is H, then R$^{10}$ is not Cl;

Wherein, if R$^1$ is H, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^7$ is H, R$^8$ is H, R$^9$ is H and R$^{10}$ is Cl, then R$^6$ is not Cl;

Wherein, if R$^1$ is H, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^6$ is Cl, R$^7$ is H, R$^8$ is H and R$^9$ is H, then R$^{10}$ is not CH$_3$;

Wherein, if R$^1$ is H, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^7$ is H, R$^8$ is H, R$^9$ is H and R$^{10}$ is Cl, then R$^6$ is not CH$_3$;

Wherein, if R$^1$ is H, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^6$ is F, R$^7$ is H, R$^8$ is H and R$^9$ is H, then R$^{10}$ is not F;

Wherein, if R$^1$ is H, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^7$ is H, R$^8$ is H, R$^9$ is H and R$^{10}$ is F, then R$^6$ is not F;

Wherein, if R$^1$ is CH$_3$, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^6$ is OR$^{12}$, R$^7$ is H, R$^8$ is H, R$^9$ is H and R$^{10}$ is H, then R$^{12}$ is not CH$_3$;

Wherein, if R$^1$ is H, R$^2$ is CH(CH$_3$)$_2$, L$^1$ is —(C=O)—, Q is heterocyclyl substituted with R$^3$ and R$^4$, R$^4$ is H, X is N, Z is phenyl, R$^6$ is 1H-pyrazole, R$^7$ is H, R$^8$ is H, R$^9$ is H and R$^{10}$ is H, then R$^3$ is not H;

Wherein, if R$^1$ is H, R$^2$ is CH(CH$_3$)$_2$, L$^1$ is —(C=O)—, Q is heterocyclyl substituted with R$^3$ and R$^4$, R$^3$ is N(R$^5$)R$^5$, R$^4$ is H, R$^5$ is H, X is N, Z is phenyl, R$^7$ is H, R$^8$ is H, R$^9$ is H and R$^{10}$ is H, then R$^6$ is not 1H-pyrazole, Wherein, if R$^1$ is H, R$^2$ is CH(CH$_3$)$_2$, L$^1$ is O, Q is heterocyclyl substituted with R$^3$ and R$^4$, R$^3$ is H, R$^4$ is H, X is N, Z is phenyl, R$^7$ is H, R$^8$ is H, R$^9$ is H and R$^{10}$ is H, then R$^6$ is not 1H-pyrazole;

Wherein, if R$^1$ is H, R$^2$ is CH(CH$_3$)$_2$, L$^1$ is O, Q is heterocyclyl substituted with R$^3$ and R$^4$, R$^3$ is H, R$^4$ is H, X is N, Z is phenyl, R$^6$ is OR$^{12}$, R$^7$ is H, R$^8$ is H, R$^9$ is H and R$^{10}$ is H, then R$^{12}$ is not CH(CH$_3$)$_2$;

Wherein, if R$^1$ is CH$_3$, R$^2$ is CH(CH$_3$)$_2$, L$^1$ is O, Q is heterocyclyl substituted with R$^3$ and R$^4$, R$^3$ is H, R$^4$ is H, X is N, Z is phenyl, R$^6$ is OR$^{12}$, R$^7$ is H, R$^8$ is H, R$^9$ is H and R$^{10}$ is H, then R$^{12}$ is not CH$_3$;

Wherein, if R$^1$ is H, R$^2$ is CH(CH$_3$)$_2$, L$^1$ is O, Q is C3-C8 cycloalkyl substituted with R$^3$ and R$^4$, R$^3$ is N(R$^5$)R$^5$, R$^4$ is H, R$^5$ is H, X is N, Z is phenyl, R$^7$ is H, R$^8$ is H, R$^9$ is H and R$^{10}$ is H, then R$^6$ is not 1H-pyrazole;

Wherein, if R$^1$ is H, R$^2$ is CH(CH$_3$)$_2$, L$^1$ is NH, Q is heterocyclyl substituted with R$^3$ and R$^4$, R$^3$ is H, R$^4$ is H, X is N, Z is phenyl, R$^7$ is H, R$^8$ is H, R$^9$ is H and R$^{10}$ is H, then R$^6$ is not 1H-pyrazole;

Wherein, if R$^1$ is H, R$^2$ is CH(CH$_3$)$_2$, L$^1$ is NH, Q is C3-C8 cycloalkyl substituted with R$^3$ and R$^4$, R$^3$ is N(R$^5$)R$^5$, R$^4$ is H, R$^5$ is H, X is N, Z is phenyl, R$^7$ is H, R$^8$ is H, R$^9$ is H and R$^{10}$ is H, then R$^6$ is not 1H-pyrazole;

Wherein, if R$^1$ is H, R$^2$ is CH(CH$_3$)$_2$, L$^1$ is O, Q is heterocyclyl substituted with R$^3$ and R$^4$, R$^3$ is H, R$^4$ is H, X is N, Z is phenyl, R$^7$ is H, R$^8$ is H, R$^9$ is H and R$^{10}$ is F, then R$^6$ is not 1H-pyrazole;

Wherein, if R$^1$ is CH$_3$, R$^2$ is CH(CH$_3$)$_2$, L$^1$ is O, Q is heterocyclyl substituted with R$^3$ and R$^4$, R$^3$ is H, R$^4$ is H, X is N, Z is phenyl, R$^7$ is H, R$^8$ is H, R$^9$ is H and R$^{10}$ is H, then R$^6$ is not 1H-pyrazole;

Wherein, if R$^1$ is CH$_3$, R$^2$ is CH(CH$_3$)$_2$, L$^1$ is O, Q is heterocyclyl substituted with R$^3$ and R$^4$, R$^3$ is H, R$^4$ is H, X is N, Z is phenyl, R$^7$ is H, R$^8$ is H, R$^9$ is H and R$^{10}$ is H, then R$^6$ is not 1H-pyrazole;

Wherein, if R$^1$ is CH$_3$, R$^2$ is CH(CH$_3$)$_2$, L$^1$ is O, Q is heterocyclyl substituted with R$^3$ and R$^4$, R$^3$ is H, R$^4$ is H, X is N, Z is phenyl, R$^6$ is H, R$^7$ is OR$^{12}$, R$^8$ is H, R$^9$ is H and R$^{10}$ is H, then R$^{12}$ is not CH$_3$;

Wherein, if R$^1$ is CH$_3$, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^6$ is H, R$^8$ is H, R$^9$ is H and R$^{10}$ is H, then R$^7$ is not Cl;

Wherein, if R$^1$ is CH$_3$, R$^2$ is CH(CH$_3$)$_2$, L$^1$ is O, Q is heterocyclyl substituted with R$^3$ and R$^4$, R$^3$ is CH$_3$, R$^4$ is H, X is N, Z is phenyl, R$^6$ is H, R$^7$ is OR$^{12}$, R$^8$ is H, R$^9$ is H and R$^{10}$ is H, then R$^{12}$ is not CH$_3$;

Wherein, if R$^1$ is CH$_3$, R$^2$ is CH(CH$_3$)$_2$, L$^1$ is O, Q is C3-C8 cycloalkyl substituted with R$^3$ and R$^4$, R$^3$ is N(R$^5$)R$^5$, R$^4$ is H, R$^5$ is H, X is N, Z is phenyl, R$^6$ is H, R$^7$ is OR$^{12}$, R$^8$ is H, R$^9$ is H and R$^{10}$ is H, then R$^{12}$ is not CH$_3$;

Wherein, if R$^1$ is CH$_3$, R$^2$ is CH(CH$_3$)$_2$, L$^1$ is NH, Q is heterocyclyl substituted with R$^3$ and R$^4$, R$^3$ is H, R$^4$ is H, X is N, Z is phenyl, R$^6$ is H, R$^7$ is OR$^{12}$, R$^8$ is H, R$^9$ is H and R$^{10}$ is H, then R$^{12}$ is not CH$_3$;

Wherein, if R$^1$ is CH$_3$, R$^2$ is CH(CH$_3$)$_2$, L$^1$ is absent, Q is heterocyclyl substituted with R$^3$ and R$^4$, R$^3$ is N(R$^5$)R$^5$, R$^4$ is H, R$^5$ is H, X is N, Z is phenyl, R$^6$ is H, R$^7$ is OR$^{12}$, R$^8$ is H, R$^9$ is H and R$^{10}$ is H, then R$^{12}$ is not CH$_3$;

Wherein, if R$^1$ is CH$_3$, R$^2$ is CH(CH$_3$)$_2$, L$^1$ is absent, Q is heterocyclyl substituted with R$^3$ and R$^4$, R$^3$ is N(R$^5$)R$^5$, R$^4$ is H, R$^5$ is H, X is N, Z is phenyl, R$^6$ is OR$^{12}$, R$^7$ is H, R$^8$ is H, R$^9$ is H and R$^{10}$ is H, then R$^{12}$ is not CH$_3$;

Wherein, if R$^1$ is CH$_3$, R$^2$ is CH(CH$_3$)$_2$, L$^1$ is NH, Q is C3-C8 cycloalkyl substituted with R$^3$ and R$^4$, R$^3$ is N(R$^5$)R$^5$, R$^4$ is H, R$^5$ is H, X is N, Z is phenyl, R$^6$ is H, R$^7$ is OR$^{12}$, R$^8$ is H, R$^9$ is H and R$^{10}$ is H, then R$^{12}$ is not CH$_3$;

Wherein, if R$^1$ is CH$_3$, R$^2$ is CH(CH$_3$)$_2$, L$^1$ is —(C=O)—, Q is heterocyclyl substituted with R$^3$ and R$^4$, R$^3$ is H, R$^4$ is H, X is N, Z is phenyl, R$^6$ is H, R$^7$ is OR$^{12}$, R$^8$ is H, R$^9$ is H and R$^{10}$ is H, then R$^{12}$ is not CH$_3$;

Wherein, if R$^1$ is CH$_3$, R$^2$ is CH(CH$_3$)$_2$, L$^1$ is —(C=O)—, Q is heterocyclyl substituted with R$^3$ and R$^4$, R$^3$ is N(R$^5$)R$^5$, R$^4$ is H, R$^5$ is H, X is N, Z is phenyl, R$^6$ is H, R$^7$ is OR$^{12}$, R$^8$ is H, R$^9$ is H and R$^{10}$ is H, then R$^{12}$ is not CH$_3$;

or an enantiomer, stereoisomeric form, mixture of enantiomers, diastereomer, mixture of diastereomers, racemate of the above mentioned compounds, or a pharmaceutically acceptable salt thereof.

In one embodiment, R$^1$ is hydrogen and the compound has the general formula II

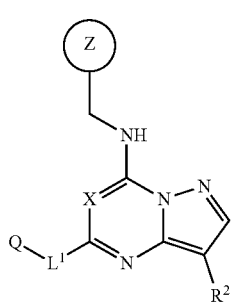

Formula II

Wherein X, Q, L$^1$, R$^2$ and Z are as defined above for general formula II.

In one embodiment, the present invention relates to compounds having the general formula III

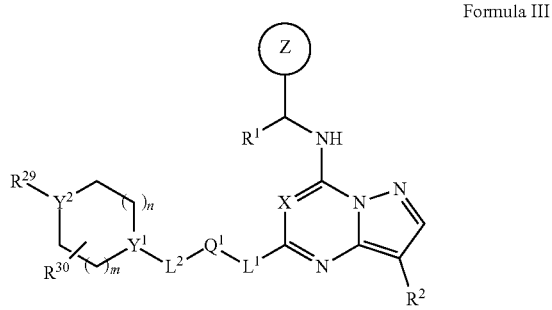

Formula III wherein X, L$^1$, R$^1$, R$^2$ and Z are as defined above for general formula I, and Q$^1$ is either absent or independently, at each occurrence, selected from the group consisting of aryl, heteroaryl, heterocyclyl, aryl substituted with one or two of C1-C6 alkyl, —OR$^5$, —N(R$^5$)R$^5$, and halogen; heteroaryl substituted with one or two of C1-C6 alkyl, —OR$^5$, —N(R$^5$)R$^5$ and halogen; and heterocyclyl substituted with one or two of R$^{29}$ and R$^{30}$;

R$^{29}$ is either absent or independently, at each occurrence, selected from the group consisting of hydrogen, —OR$^5$, halogen, —N(R$^5$)R$^5$, —NR$^9$R$^{12}$, —NH(C=O) R$^5$, —(C=O)NH$_2$, aryl, heteroaryl, heterocyclyl, C1-C6 alkyl and C1-C6 alkyl substituted with —OH or —NH$_2$;

R$^{30}$ is, independently, at each occurrence, selected from the group consisting of hydrogen, halogen, —OR$^5$, —N(R$^5$)R$^5$, (=O), aryl, heteroaryl, heterocyclyl, C1-C6 alkyl and C1-C6 alkyl substituted with —OH or —NH$_2$;

Wherein R$^5$, R$^9$ and R$^{12}$ are as defined in claim 1;

L$^2$ is either absent or independently, at each occurrence, selected from the group consisting of —O—, —NH—, —(C=O)— and —(C=O)NH—;

Y$^1$ is, independently at each occurrence, selected from CH, C(OH) and N;

Y$^2$ is, independently at each occurrence, selected from CH, CR$^{30}$, O and N;

m is, independently at each occurrence, selected from 0, 1 and 2;

n is, independently at each occurrence, selected from 0 and 1;

Wherein, if R$^1$ is H, R$^2$ is CH(CH$_3$)$_2$, L$^1$ is absent, Q$^1$ is absent, L$^2$ is absent, Y$^1$ is N, Y$^2$ is CH, m is 1, n is 1, R$^{29}$ is N(R$^5$)R$^5$, R$^{30}$ is H, R$^5$ is H, X is N, Z is phenyl, R$^7$ is H, R$^8$ is H, R$^9$ is H and R$^{10}$ is H, then R$^6$ is not 1H-pyrazole;

Wherein, if R$^1$ is H, R$^2$ is CH(CH$_3$)$_2$, L$^1$ is O, Q$^1$ is absent, L$^2$ is absent, Y$^1$ is CH, Y$^2$ is N, m is 1, n is 1, R$^{29}$ is CH$_3$, R$^{30}$ is H, X is N, Z is phenyl, R$^7$ is H, R$^8$ is H, R$^9$ is H and R$^{10}$ is H, then R$^6$ is not CH$_3$, Cl or 1H-pyrazole;

Wherein, if R$^1$ is H, R$^2$ is CH(CH$_3$)$_2$, L$^1$ is O, Q$^1$ is absent, L$^2$ is absent, Y$^1$ is CH, Y$^2$ is N, m is 1, n is 1, R$^{29}$ is CH$_3$, R$^{30}$ is H, X is N, Z is phenyl, R$^6$ is OR$^{12}$, R$^7$ is H, R$^8$ is H, R$^9$ is H and R$^{10}$ is H, then R$^{12}$ is not phenyl, CH(CH$_3$)$_2$, CH$_2$CH$_3$ or CH$_3$;

Wherein, if R$^1$ is H, R$^2$ is CH(CH$_3$)$_2$, L$^1$ is O, Q$^1$ is absent, L$^2$ is absent, Y$^1$ is CH, Y$^2$ is N, m is 1, n is 1, R$^{29}$ is CH$_3$, R$^{30}$ is H, X is N, Z is phenyl, R$^6$ is Cl, R$^7$ is H, R$^8$ is H and R$^9$ is H, then R$^{10}$ is not Cl;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^7$ is H, $R^8$ is H, $R^9$ is H and $R^{10}$ is Cl, then $R^6$ is not Cl;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^6$ is Cl, $R^7$ is H, $R^8$ is H and $R^9$ is H, then $R^{10}$ is not $CH_3$;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^7$ is H, $R^8$ is H, $R^9$ is H and $R^{10}$ is Cl, then $R^6$ is not $CH_3$;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^6$ is F, $R^7$ is H, $R^8$ is H and $R^9$ is H, then $R^{10}$ is not F;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^7$ is H, $R^8$ is H, $R^9$ is H and $R^{10}$ is F, then $R^6$ is not F;

Wherein, if $R^1$ is H, $R^2$ is $CH(CH_3)_2$, $L^1$ is —(C=O)—, $Q^1$ is absent, $L^2$ is absent, $Y^1$ is N, $Y^2$ is N, m is 1, n is 1, $R^{30}$ is H, X is N, Z is phenyl, $R^6$ is 1H-pyrazole, $R^7$ is H, $R^8$ is H, $R^9$ is H and $R^{10}$ is H, then $R^{29}$ is not H;

Wherein, if $R^1$ is H, $R^2$ is $CH(CH_3)_2$, $L^1$ is —(C=O)—, $Q^1$ is absent, $L^2$ is absent, $Y^1$ is N, $Y^2$ is CH, m is 1, n is 1, $R^{29}$ is $N(R^5)R^5$, $R^{30}$ is H, $R^5$ is H, $R^{30}$ is H, X is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is H, $R^{30}$ is H, X is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is H, $R^{30}$ is H, X is N, Z is phenyl, $R^6$ is $OR^{12}$, $R^7$ is H, $R^8$ is H, $R^9$ is H and $R^{10}$ is H, then $R^{12}$ is not $CH(CH_3)_2$;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 0, $R^{29}$ is H, $R^{30}$ is H, X is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 0, $R^{29}$ is H, $R^{30}$ is H, X is N, Z is phenyl, $R^6$ is $OR^{12}$, $R^7$ is H, $R^8$ is H, $R^9$ is H and $R^{10}$ is H, then $R^{12}$ is not $CH(CH_3)_2$;

Wherein, if $R^1$ is H, $R^2$ is $CH(CH_3)_2$, $L^1$ is O, $Q^1$ is absent, $L^2$ is absent, $Y^1$ is CH, $Y^2$ is CH, m is 1, n is 1, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $L^1$ is NH, $Q^1$ is absent, $L^2$ is absent, $Y^1$ is CH, $Y^2$ is N, m is 1, n is 0, $R^{29}$ is H, $R^{30}$ is H, X is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $L^1$ is absent, $Q^1$ is absent, $L^2$ is absent, $Y^1$ is N, $Y^2$ is CH, m is 1, n is 0, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $L^1$ is NH, $Q^1$ is absent, $L^2$ is absent, $Y^1$ is CH, $Y^2$ is CH, m is 1, n is 1, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $L^1$ is absent, $Q^1$ is absent, $L^2$ is absent, $Y^1$ is N, $Y^2$ is CH, m is 2, n is 0, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 2, n is 0, $R^{29}$ is H, $R^{30}$ is H, X is N, Z is phenyl, $R^7$ is H, $R^8$ is H, $R^9$ is H and $R^{10}$ is F, then $R^6$ is not 1H-pyrazole;

Wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^7$ is H, $R^8$ is H, $R^9$ is H and $R^{10}$ is H, then $R^6$ is not 1H-pyrazole;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^6$ is $OR^{12}$, $R^7$ is H, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 1, n is 0, $R^{29}$ is H, $R^{30}$ is H, X is N, Z is phenyl, $R^6$ is $OR^{12}$, $R^7$ is H, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is H, $R^{30}$ is H, X is N, Z is phenyl, $R^6$ is $OR^{12}$, $R^7$ is H, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 2, n is 0, $R^{29}$ is H, $R^{30}$ is H, X is N, Z is phenyl, $R^7$ is H, $R^8$ is H, $R^9$ is H and $R^{10}$ is H, then $R^6$ is not 1H-pyrazole;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is H, $R^{30}$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^6$ is H, $R^8$ is H, $R^9$ is H and $R^{10}$ is H, then $R^7$ is not Cl;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 1, n is 0, $R^{29}$ is H, $R^{30}$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is O, $Q^1$ is absent, $L^2$ is absent, $Y^1$ is CH, $Y^2$ is CH, m is 1, n is 1, $R^{29}$ is $N(R^5)R^5$, $R^{30}$ is H, $R^5$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is NH, $Q^1$ is absent, $L^2$ is absent, $Y^1$ is CH, $Y^2$ is N, m is 1, n is 0, $R^{29}$ is H, $R^{30}$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is absent, $Q^1$ is absent, $L^2$ is absent, $Y^1$ is N, $Y^2$ is CH, m is 1, n is 0, $R^{29}$ is $N(R^5)R^5$, $R^{30}$ is H, $R^5$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is absent, $Q^1$ is absent, $L^2$ is absent, $Y^1$ is N, $Y^2$ is CH, m is 1, n is 1, $R^{29}$ is $N(R^5)R^5$, $R^{30}$ is H, $R^5$ is H, X is N, Z is phenyl, $R^6$ is $OR^{12}$, $R^7$ is H, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is absent, $Q^1$ is absent, $L^2$ is absent, $Y^1$ is N, $Y^2$ is CH, m is 1, n is 1, $R^{29}$ is $N(R^5)R^5$, $R^{30}$ is H, $R^5$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is NH, $Q^1$ is absent, $L^2$ is absent, $Y^1$ is CH, $Y^2$ is CH, m is 1, n is 1, $R^{29}$ is $N(R^5)R^5$, $R^{30}$ is H, $R^5$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is —(C=O)—, $Q^1$ is absent, $L^2$ is absent, $Y^1$ is N, $Y^2$ is N, m is 1, n is 1, $R^{29}$ is H, $R^{30}$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is —(C=O)—, $Q^1$ is absent, $L^2$ is absent, $Y^1$ is N, $Y^2$ is CH, m is 1, n is 1, $R^{29}$ is $N(R^5)R^5$, $R^{30}$ is H, $R^5$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, $L^1$ is absent, $Q^1$ is absent, $L^2$ is absent, $Y^1$ is N, $Y^2$ is CH, m is 2, n is 0, $R^{29}$ is $N(R^5)R^5$, $R^{30}$ is H, $R^5$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

or an enantiomer, stereoisomeric form, mixture of enantiomers, diastereomer, mixture of diastereomers, racemate of the above mentioned compounds, or a pharmaceutically acceptable salt thereof.

In one embodiment, the present invention relates to compounds having the general formula Ia

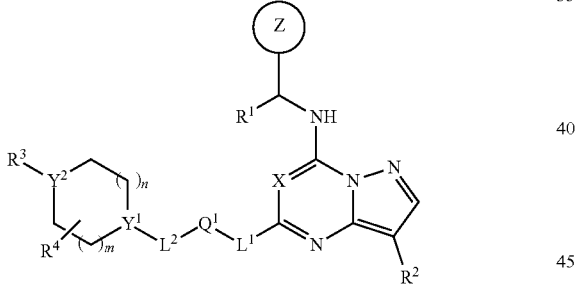

Formula Ia

Wherein

X is, independently at each occurrence, selected from CH and N;

$Y^1$ is, independently at each occurrence, selected from CH, C(OH) and N;

$Y^2$ is, independently at each occurrence, selected from CH, $CR^4$, O and N;

m is, independently at each occurrence, selected from 0, 1 and 2;

n is, independently at each occurrence, selected from 0 and 1;

$L^1$ is either absent or independently, at each occurrence, selected from the group consisting of —NH—, —NH($CH_2$)—, —NH(C=O)—, —$NHSO_2$—, —O—, —O($CH_2$)—, —(C=O)—, —(C=O)NH— and —(C=O)($CH_2$)—;

Q is either absent or independently, at each occurrence, selected from the group consisting of heterocyclyl, C3-C6 heteroaryl, aryl, e.g. phenyl, aryl substituted with halogen;

$L^2$ is either absent or independently, at each occurrence, selected from the group consisting of —O—, —NH—, —(C=O)— and —(C=O)NH—;

$R^1$ is, at each occurrence, independently selected from the group consisting of hydrogen and methyl;

$R^2$ is, at each occurrence, independently selected from the group consisting of halogen, C1-C6 alkyl, C3-C10 cycloalkyl, —CN, —(C=O)$CH_3$, —$NR^9R^{12}$ and C1-C3 haloalkyl, any of which is optionally substituted;

$R^3$ is, at each occurrence, absent or independently selected from the group consisting of hydrogen, —OH, halogen, —$NH_2$, —$NR^9R^{12}$, —NH(C=O)$R^5$, —(C=O)$NH_2$, heterocyclyl, C1-C6 alkyl and C1-C6 alkyl substituted with —OH or —$NH_2$;

$R^4$ is, at each occurrence, absent or independently selected from the group consisting of E hydrogen, halogen, —OH, —$OR^5$, —$NH_2$, (=O), C1-C6 alkyl and C1-C6 alkyl substituted with —OH or —$NH_2$;

$R^5$ is, at each occurrence, independently selected from the group consisting of C1-C6 alkyl, C3-C6 cycloalkyl, C3-C10 heterocyclyl, C1-C3 haloalkyl and C3-C10 heterocyclyl substituted with halogen, —OH, —$NH_2$, C1-C6 alkyl and C1-C6 alkyl substituted with —OH or —$NH_2$;

Z is any structure of the following group A;

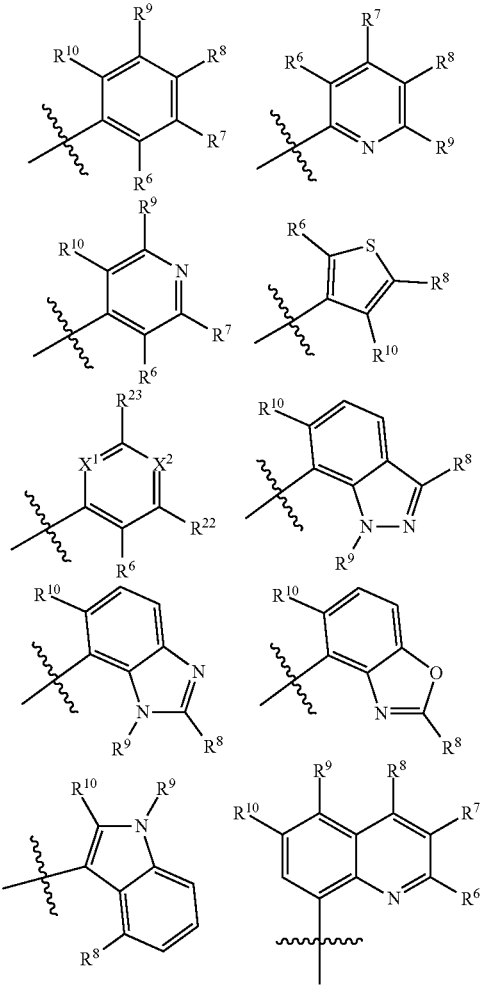

Group A

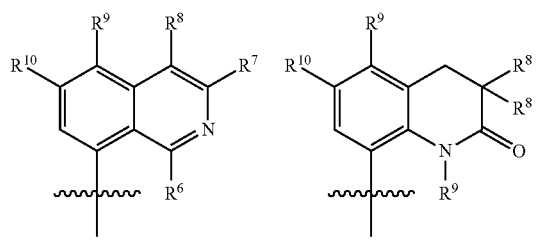

Wherein $X^1$ is, independently at each occurrence, selected from $CR^{24}$ and N;

$X^2$ is, independently at each occurrence, selected from $CR^{25}$ and N;

$R^6$ is, at each occurrence, independently selected from the group consisting of hydrogen, halogen, C1-C6 alkyl, C3-C10 cycloalkyl, C3-C10 heterocyclyl, —(C=O)NHR$^{11}$, —NHR$^9$, —NH(C=O)NHR$^{11}$, —N(CH$_3$)(C=O)CH$_3$, —NH(C=O)R$^{12}$, —NR$^9$R$^{12}$, —OR$^{12}$, and any structure of the following group B;

Group B

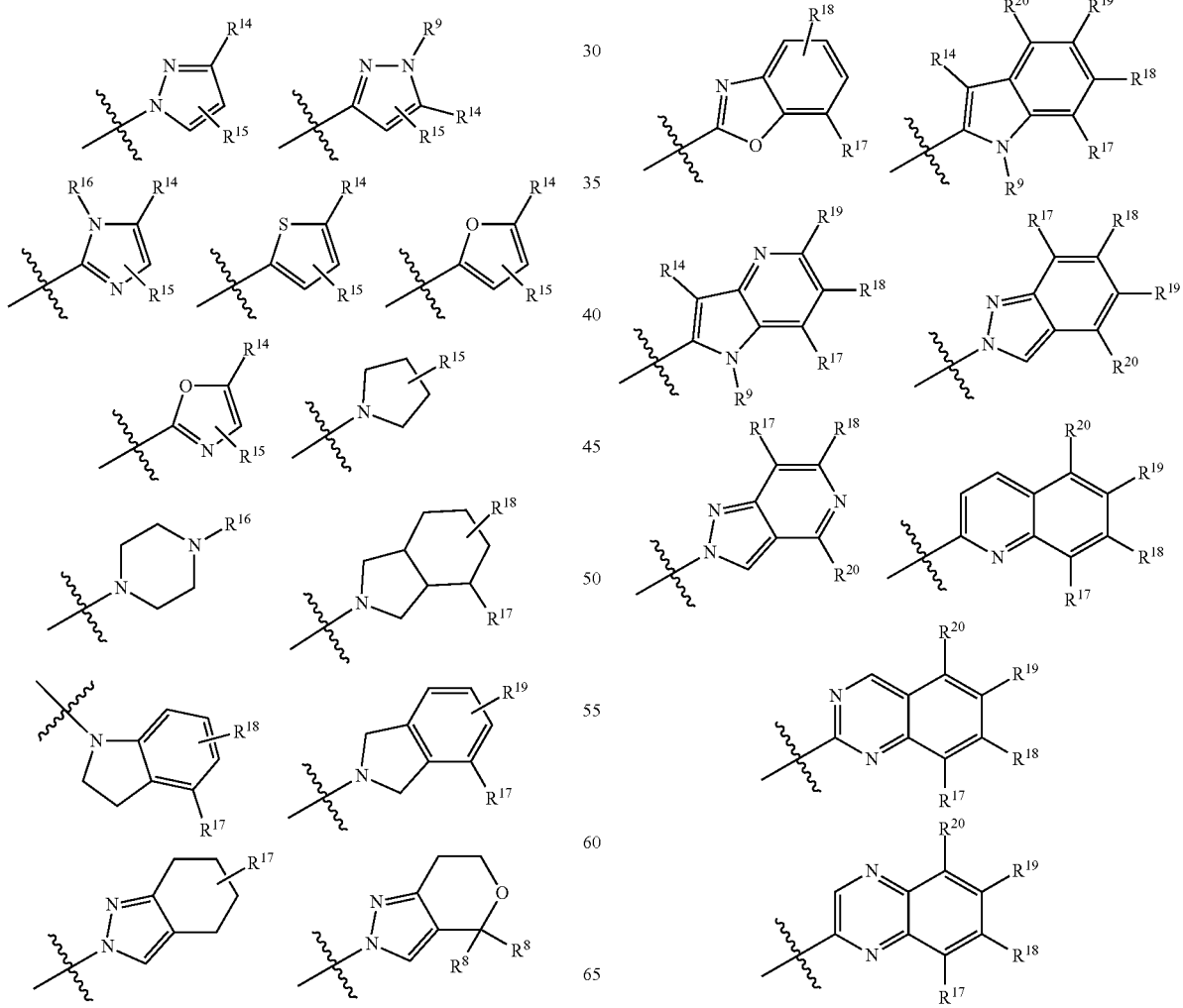
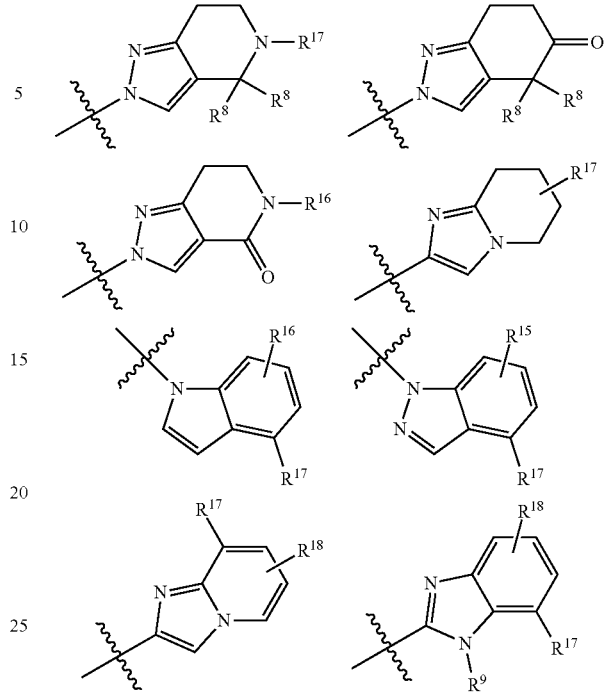

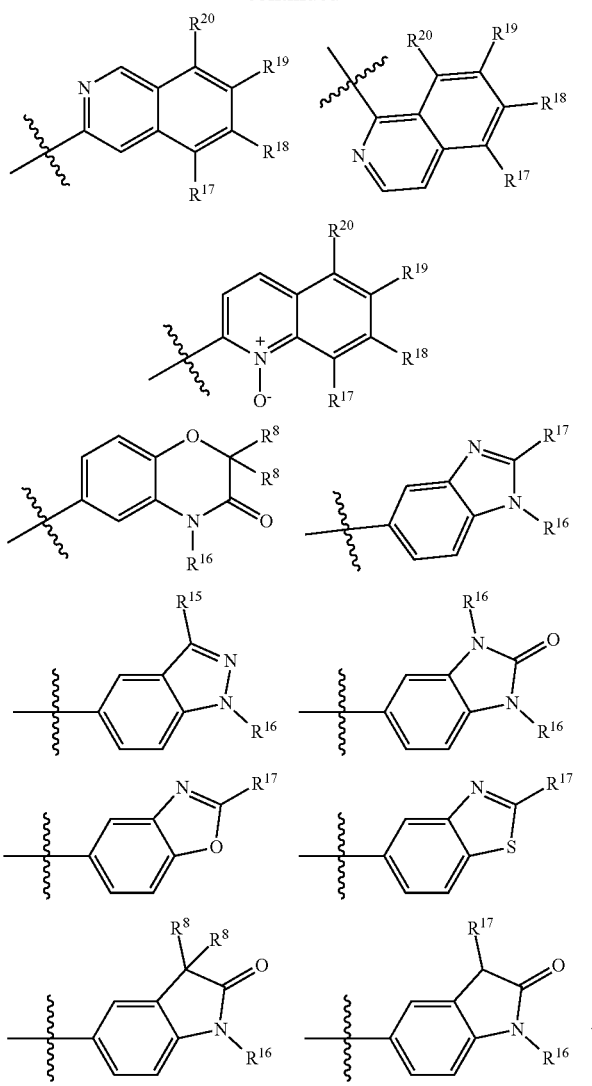
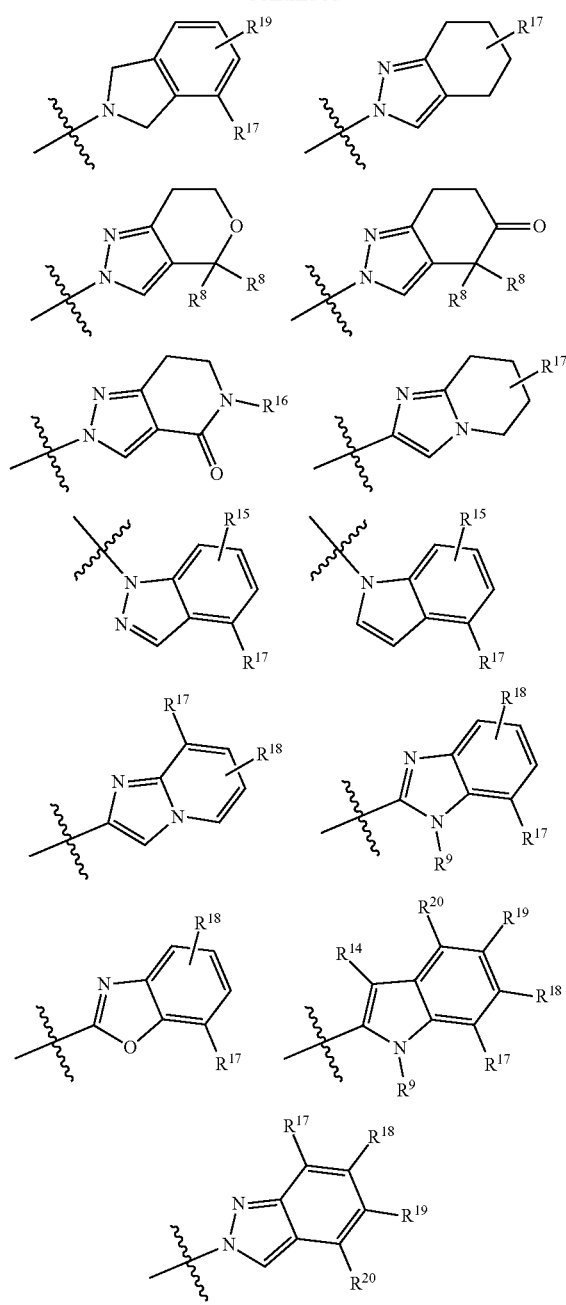
R[7] is, at each occurrence, independently selected from the group consisting of hydrogen, halogen, C1-C6 alkyl, —NH(C=O)R[12], —NR[9]R[12], —OR[12] and any structure of the following group C;
Group C
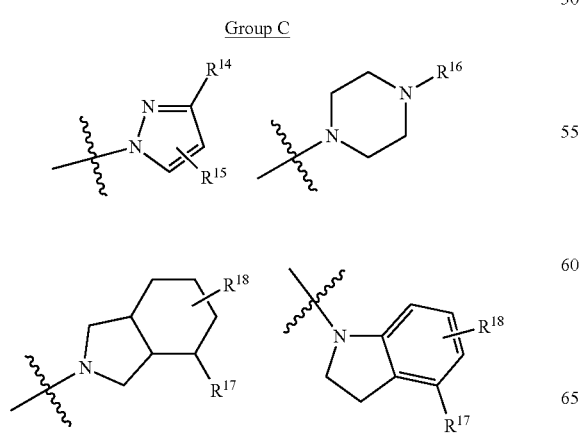

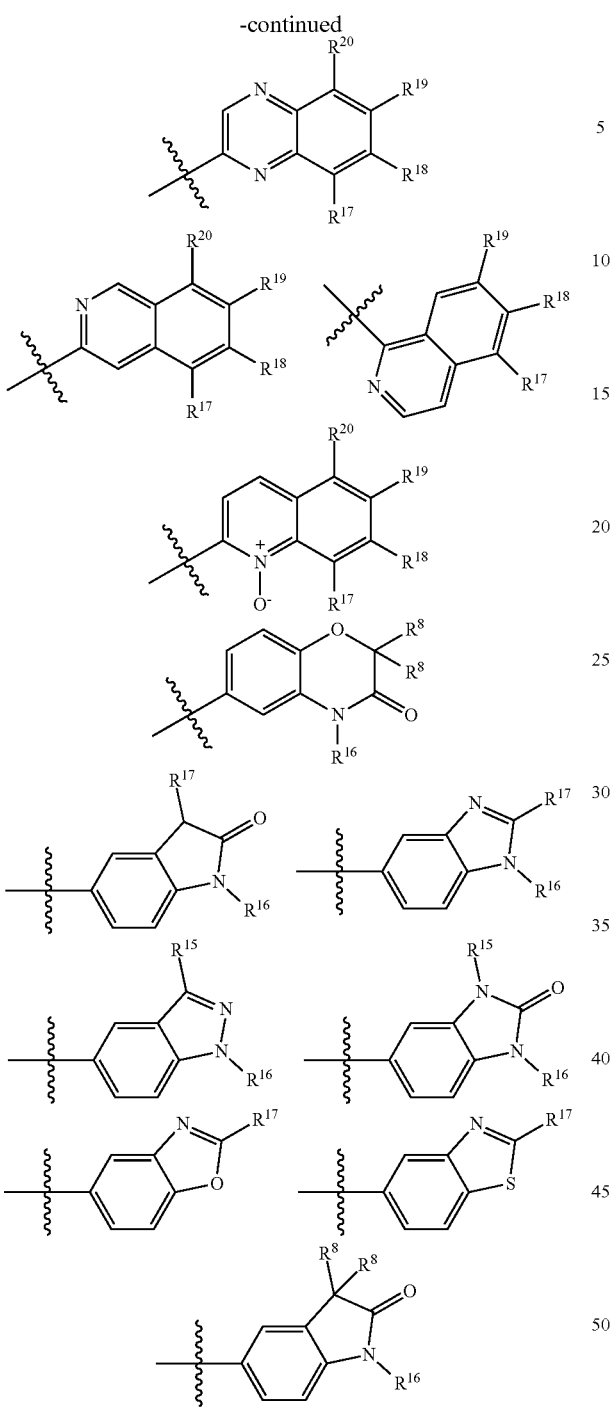

R⁸ and R¹⁰ are, at each occurrence, independently selected from the group consisting of hydrogen, halogen, C1-C6 alkyl, C1-C3 haloalkyl, —NH₂, —OH, —OR⁵, —CN, —(C═O)R⁵, —(C═O)OR⁵, —(C═O)NH₂, —(C═O)NHR²¹, —CH₂(C═O)NHR²¹, —NH(C═O)R¹³, —NHS(═O)₂R⁵, —S(═O)₂NH₂, —S(═O)₂NHR²¹, and C1-C6 alkyl substituted with OH, —OR⁵ or —NHR⁹;

R⁹ is, at each occurrence, independently selected from the group consisting of hydrogen, halogen, C1-C6 alkyl, C1-C3 haloalkyl, —OR⁵, —CN, C3-C10 cycloalkyl, C3-C10 heterocyclyl and C1-C6 alkyl substituted with —OH or —OR⁵;

R¹¹ is, at each occurrence, independently selected from the group consisting of hydrogen, C1-C6 alkyl and C3-C10 cycloalkyl;

R¹² is, at each occurrence, absent or independently selected from the group consisting of C1-C6 alkyl, C1-C6 alkyl substituted with —OR⁵ or —N(R⁵)R⁵, C6-C10 aryl, phenyl, benzyl, C3-C9 heteroaryl, C3-C6 heterocyclyl, benzyl substituted with one to four halogens or C1-C3 alkyls, C3-C9 heteroaryl substituted with one to four halogens or C1-C3 alkyls, C3-C6 heterocyclyl substituted with C1-C3 alkyl, and C6-C10 aryl substituted with one to four halogens and/or one to four —NH(C═O)R¹³;

R¹³ is, at each occurrence, independently selected from the group consisting of hydrogen, C1-C6 alkyl, C1-C6 alkyl substituted with —CN, —OH, —OR⁵, —NH₂, —NHR⁵ or —N(R⁵)R⁵ and C3-C10 cycloalkyl;

R¹⁴ and R¹⁵ are, at each occurrence, independently selected from the group consisting of hydrogen, halogen, C1-C6 alkyl, C1-C6 alkyl substituted with —OH or —NH₂, C3-C10 cycloalkyl, —(C═O)R⁵, —(C═O)NHR²¹, —C(R⁹)(R¹¹)OR²¹, —NH(C═O)R²¹, —NR⁹R²¹, —OR²¹, —OC(R⁹)(R¹¹)(R²¹), C3-C10 heterocyclyl, C3-C10 heterocyclyl substituted with R⁴, C3-C10 heteroaryl substituted with one to four halogens or C1-C3 alkyl, C6-C10 aryl, e.g. phenyl and aryl substituted with —(C═O)R⁵, —(C═O)OR⁵, —(C═O)NH₂, —(C═O)NHR²¹, —CH₂(C═O)NHR²¹, —NH(C═O)R¹³, —NHS(═O)₂R⁵, —S(═O)₂NH₂ or —S(═O)₂NHR²¹;

R¹⁶ is, at each occurrence, independently selected from the group consisting of hydrogen, C1-C6 alkyl, —(C═O)R¹³ and C1-C6 alkyl substituted with —OR⁵;

R¹⁷, R¹⁸, R¹⁹ and R²⁰ are, at each occurrence, independently selected from the group consisting of hydrogen, halogen, C1-C6 alkyl, C1-C3 haloalkyl, C6-C10 aryl, e.g. phenyl, —CN, —CHCF₃NR⁹R¹¹, —OH, —OR²¹, —NO₂, —(C═O)R⁵, —(C═O)OR⁵, —(C═O)NH₂, —(C═O)NHR²¹, —NH(C═O)R¹³, —NHR⁵, —NHS(═O)₂R⁵, —S(═O)₂NH₂, —S(═O)₂NHR²¹ and C1-C6 alkyl substituted with —CN, —OH, —OR⁵, —(C═O)NHR⁵, —NH₂, —NH(C═O)R⁵, —NHR⁵ or —N(R⁵)R⁵;

R²¹ is, at each occurrence, independently selected from the group consisting of C1-C6 alkyl, C3-C10 cycloalkyl, C3-C10 heterocyclyl, C1-C3 haloalkyl, aryl, phenyl, benzyl, C1-C6 alkyl substituted with —CN, —OH, —OR⁵, —NH₂, —NHR⁵ or —N(R⁵)R⁵, aryl substituted with halogen or C1-C3 haloalkyl, C3-C10 heteroaryl substituted with one to four halogens or C1-C3 alkyl and C3-C10 heterocyclyl substituted with R⁴;

R²² and R²³ are, at each occurrence, independently selected from the group consisting of hydrogen, halogen, C1-C6 alkyl, C1-C3 haloalkyl, —OH, —OR⁵, —CN and C1-C6 alkyl substituted with —OH, —OR⁵ or —NHR⁹;

R²⁴ and R²⁵ are, at each occurrence, independently selected from the group consisting of hydrogen, halogen, C1-C6 alkyl, C1-C3 haloalkyl, —NH₂, —OH, —OR⁵, —CN, —(C═O)R⁵, —(C═O)OR⁵, —(C═O)NH₂, —(C═O)NHR²¹, —CH₂(C═O)NHR²¹, —NH(C═O)R¹³, —NHS(═O)₂R⁵, —S(═O)₂NH₂ or —S(═O)₂NHR²¹ and C1-C6 alkyl substituted with —OH, —OR⁵ or —NHR⁹;

With the proviso that when Z is

[chemical structure showing a benzene ring with substituents R^8, R^9, R^10 on one side and R^6, R^7 on the other, with wavy line attachment point]

then one of $R^6$ and $R^7$ is not H.

Wherein, if $R^1$ is H, $R^2$ is $CH(CH_3)_2$, $R^3$ is $NH_2$, $R^4$ is H, $L^1$ is absent, Q is absent, $L^2$ is absent, X is N, n is 1, $Y^1$ is N, $Y^2$ is CH, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $R^3$ is $CH_3$, $R^4$ is H, $L^1$ is O, Q is absent, $L^2$ is absent, X is N, n is 1, $Y^1$ is CH, $Y^2$ is N, Z is phenyl, $R^7$ is H, $R^8$ is H, $R^9$ is H and $R^{10}$ is H, then $R^6$ is not $CH_3$, Cl or 1H-pyrazole;

Wherein, if $R^1$ is H, $R^2$ is $CH(CH_3)_2$, $R^3$ is $CH_3$, $R^4$ is H, $L^1$ is O, Q is absent, $L^2$ is absent, X is N, n is 1, $Y^1$ is CH, $Y^2$ is N, Z is phenyl, $R^6$ is $OR^{12}$, $R^7$ is H, $R^8$ is H, $R^9$ is H and $R^{10}$ is H, then $R^{12}$ is not phenyl, $CH(CH_3)_2$, $CH_2CH_3$ or $CH_3$;

Wherein, if $R^1$ is H, $R^2$ is $CH(CH_3)_2$, $R^3$ is $CH_3$, $R^4$ is H, $L^1$ is O, Q is absent, $L^2$ is absent, X is N, n is 1, $Y^1$ is CH, $Y^2$ is N, Z is phenyl, $R^6$ is Cl, $R^7$ is H, $R^8$ is H and $R^9$ is H, then $R^{10}$ is not Cl;

Wherein, if $R^1$ is H, $R^2$ is $CH(CH_3)_2$, $R^3$ is $CH_3$, $R^4$ is H, $L^1$ is O, Q is absent, $L^2$ is absent, X is N, n is 1, $Y^1$ is CH, $Y^2$ is N, Z is phenyl, $R^7$ is H, $R^8$ is H, $R^9$ is H and $R^{10}$ is Cl, then $R^6$ is not Cl;

Wherein, if $R^1$ is H, $R^2$ is $CH(CH_3)_2$, $R^3$ is $CH_3$, $R^4$ is H, $L^1$ is O, Q is absent, $L^2$ is absent, X is N, n is 1, $Y^1$ is CH, $Y^2$ is N, Z is phenyl, $R^6$ is Cl, $R^7$ is H, $R^8$ is H and $R^9$ is H, then $R^{10}$ is not $CH_3$;

Wherein, if $R^1$ is H, $R^2$ is $CH(CH_3)_2$, $R^3$ is $CH_3$, $R^4$ is H, $L^1$ is O, Q is absent, $L^2$ is absent, X is N, n is 1, $Y^1$ is CH, $Y^2$ is N, Z is phenyl, $R^7$ is H, $R^8$ is H, $R^9$ is H and $R^{10}$ is Cl, then $R^6$ is not $CH_3$;

Wherein, if $R^1$ is H, $R^2$ is $CH(CH_3)_2$, $R^3$ is $CH_3$, $R^4$ is H, $L^1$ is O, Q is absent, $L^2$ is absent, X is N, n is 1, $Y^1$ is CH, $Y^2$ is N, Z is phenyl, $R^6$ is F, $R^7$ is H, $R^8$ is H and $R^9$ is H, then $R^{10}$ is not F;

Wherein, if $R^1$ is H, $R^2$ is $CH(CH_3)_2$, $R^3$ is $CH_3$, $R^4$ is H, $L^1$ is O, Q is absent, $L^2$ is absent, X is N, n is 1, $Y^1$ is CH, $Y^2$ is N, Z is phenyl, $R^7$ is H, $R^8$ is H, $R^9$ is H and $R^{10}$ is F, then $R^6$ is not F;

Wherein, if $R^1$ is $CH_3$, $R^2$ is $CH(CH_3)_2$, X is N, $L^1$ is O, Q is absent, $L^2$ is absent, $Y^1$ is CH, $Y^2$ is N, n is 1, $R^3$ is $CH_3$, $R^4$ is H, Z is phenyl, $R^6$ is $OR^{12}$, $R^7$ is H, $R^8$ is H, $R^9$ is H and $R^{10}$ is H, then $R^{12}$ is not $CH_3$;

Wherein, if $R^1$ is H, $R^2$ is $CH(CH_3)_2$, X is N, $L^1$ is —(C=O)—, Q is absent, $L^2$ is absent, $Y^1$ is N, $Y^2$ is N, n is 1, $R^3$ is H, $R^4$ is H, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, X is N, $L^1$ is —(C=O)—, Q is absent, $L^2$ is absent, $Y^1$ is N, $Y^2$ is CH, n is 1, $R^3$ is $NH_2$, $R^4$ is H, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, X is N, $L^1$ is O, Q is absent, $L^2$ is absent, $Y^1$ is CH, $Y^2$ is N, n is 1, $R^3$ is H, $R^4$ is H, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, X is N, $L^1$ is O, Q is absent, $L^2$ is absent, $Y^1$ is CH, $Y^2$ is N, n is 1, $R^3$ is H, $R^4$ is H, Z is phenyl, $R^6$ is $OR^{12}$, $R^7$ is H, $R^8$ is H, $R^9$ is H and $R^{10}$ is H, then $R^{12}$ is not $CH(CH_3)_2$;

Wherein, if $R^1$ is H, $R^2$ is $CH(CH_3)_2$, X is N, $L^1$ is O, Q is absent, $L^2$ is absent, $Y^1$ is CH, $Y^2$ is N, n is 0, $R^3$ is H, $R^4$ is H, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, X is N, $L^1$ is O, Q is absent, $L^2$ is absent, $Y^1$ is CH, $Y^2$ is N, n is 0, $R^3$ is H, $R^4$ is H, Z is phenyl, $R^6$ is $OR^{12}$, $R^7$ is H, $R^8$ is H, $R^9$ is H and $R^{10}$ is H, then $R^{12}$ is not $CH(CH_3)_2$;

Wherein, if $R^1$ is $CH_3$, $R^2$ is $CH(CH_3)_2$, X is N, $L^1$ is O, Q is absent, $L^2$ is absent, $Y^1$ is CH, $Y^2$ is N, n is 0, $R^3$ is H, $R^4$ is H, Z is phenyl, $R^6$ is $OR^{12}$, $R^7$ is H, $R^8$ is H, $R^9$ is H and $R^{10}$ is H, then $R^{12}$ is not $CH_3$;

Wherein, if $R^1$ is $CH_3$, $R^2$ is $CH(CH_3)_2$, X is N, $L^1$ is O, Q is absent, $L^2$ is absent, $Y^1$ is CH, $Y^2$ is N, n is 1, $R^3$ is H, $R^4$ is H, Z is phenyl, $R^6$ is $OR^{12}$, $R^7$ is H, $R^8$ is H, $R^9$ is H and $R^{10}$ is H, then $R^{12}$ is not $CH_3$;

Wherein, if $R^1$ is H, $R^2$ is $CH(CH_3)_2$, $R^3$ is $NH_2$, $R^4$ is H, $L^1$ is O, Q is absent, $L^2$ is absent, X is N, n is 1, $Y^1$ is CH, $Y^2$ is CH, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $R^3$ is H, $R^4$ is H, $L^1$ is NH, Q is absent, $L^2$ is absent, X is N, n is 0, $Y^1$ is CH, $Y^2$ is N, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $R^3$ is $NH_2$, $R^4$ is H, $L^1$ is absent, Q is absent, $L^2$ is absent, X is N, n is 0, $Y^1$ is N, $Y^2$ is CH, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $R^3$ is $NH_2$, $R^4$ is H, $L^1$ is NH, Q is absent, $L^2$ is absent, X is N, n is 1, $Y^1$ is CH, $Y^2$ is CH, Z is phenyl, $R^7$ is H, $R^8$ is H, $R^9$ is H and $R^{10}$ is H, then $R^6$ is not 1H-pyrazole;

Wherein, if $R^1$ is H, $R^2$ is $CH(CH_3)_2$, $R^3$ is H, $R^4$ is $NH_2$, $L^1$ is absent, Q is absent, $L^2$ is absent, X is N, n is 1, $Y^1$ is N, $Y^2$ is CH, Z is phenyl, $R^7$ is H, $R^8$ is H, $R^9$ is H and $R^{10}$ is H, then $R^6$ is not 1H-pyrazole;

Wherein, if $R^1$ is $CH_3$, $R^2$ is $CH(CH_3)_2$, X is N, $L^1$ is O, Q is absent, $L^2$ is absent, $Y^1$ is CH, $Y^2$ is N, n is 1, $R^3$ is H, $R^4$ is H, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, X is N, $L^1$ is O, Q is absent, $L^2$ is absent, $Y^1$ is CH, $Y^2$ is N, n is 1, $R^3$ is $CH_3$, $R^4$ is H, Z is phenyl, $R^6$ is H, $R^7$ is H, $R^8$ is H, $R^9$ is H and $R^{10}$ is H, then $R^7$ is not Cl;

Wherein, if $R^1$ is $CH_3$, $R^2$ is $CH(CH_3)_2$, X is N, $L^1$ is O, Q is absent, $L^2$ is absent, $Y^1$ is CH, $Y^2$ is N, n is 1, $R^3$ is H, $R^4$ is H, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, X is N, $L^1$ is O, Q is absent, $L^2$ is absent, $Y^1$ is CH, $Y^2$ is N, n is 1, $R^3$ is $NH_2$, $R^4$ is H, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, X is N, $L^1$ is O, Q is absent, $L^2$ is absent, $Y^1$ is CH, $Y^2$ is CH, n is 1, $R^3$ is $NH_2$, $R^4$ is H, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, X is N, $L^1$ is absent, Q is absent, $L^2$ is absent, $Y^1$ is N, $Y^2$ is CH, n is 1, $R^3$ is $NH_2$, $R^4$ is H, Z is phenyl, $R^6$ is H, $R^7$ is $OR^{12}$, $R^8$ is H, $R^9$ is H and $R^{10}$ is H, then $R^{12}$ is not $CH_3$;

Wherein, if $R^1$ is $CH_3$, $R^2$ is $CH(CH_3)_2$, X is N, $L^1$ is NH, Q is absent, $L^2$ is absent, $Y^1$ is CH, $Y^2$ is N, n is 0, $R^3$ is H, $R^4$ is H, Z is phenyl, $R^6$ is H, $R^7$ is $OR^{12}$, $R^8$ is H, $R^9$ is H and $R^{10}$ is H, then $R^{12}$ is not $CH_3$;

Wherein, if R¹ is CH₃, R² is CH(CH₃)₂, X is N, L¹ is absent, Q is absent, L² is absent, Y¹ is N, Y² is CH, n is 0, R³ is NH₂, R⁴ is H, Z is phenyl, R⁶ is H, R⁷ is OR¹², R⁸ is H, R⁹ is H and R¹⁰ is H, then R¹² is not CH₃;

Wherein, if R¹ is CH₃, R² is CH(CH₃)₂, X is N, L¹ is NH, Q is absent, L² is absent, Y¹ is CH, Y² is CH, n is 1, R³ is NH₂, R⁴ is H, Z is phenyl, R⁶ is H, R⁷ is OR¹², R⁸ is H, R⁹ is H and R¹⁰ is H, then R¹² is not CH₃;

Wherein, if R¹ is CH₃, R² is CH(CH₃)₂, X is N, L¹ is —(C=O)—, Q is absent, L² is absent, Y¹ is N, Y² is N, n is 1, R³ is H, R⁴ is H, Z is phenyl, R⁶ is H, R⁷ is OR¹², R⁸ is H, R⁹ is H and R¹⁰ is H, then R¹² is not CH₃;

Wherein, if R¹ is CH₃, R² is CH(CH₃)₂, X is N, L¹ is —(C=O)—, Q is absent, L² is absent, Y¹ is N, Y² is CH, n is 1, R³ is NH₂, R⁴ is H, Z is phenyl, R⁶ is H, R⁷ is OR¹², R⁸ is H, R⁹ is H and R¹⁰ is H, then R¹² is not CH₃;

Wherein, if R¹ is CH₃, R² is CH(CH₃)₂, X is N, L¹ is absent, Q is absent, L² is absent, Y¹ is N, Y² is CH, n is 1, R³ is NH, R⁴ is NH₂, Z is phenyl, R⁶ is H, R⁷ is OR¹², R⁸ is H, R⁹ is H and R¹⁰ is H, then R¹² is not CH₃;

Or an enantiomer, stereoisomeric form, mixture of enantiomers, diastereomer, mixture of diastereomers, racemate of the above mentioned compounds, or a pharmaceutically acceptable salt thereof.

In one embodiment, the present invention relates to compounds having the general formula IV

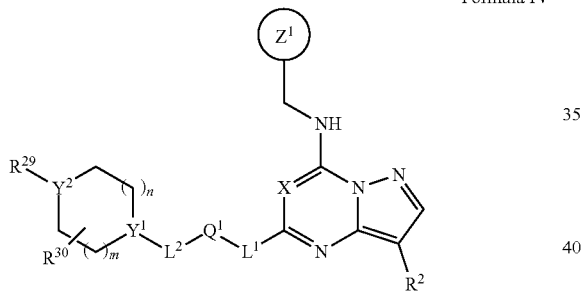

Formula IV wherein X, L¹ and R² are as defined above for general formula I;
wherein m, n, Y¹, Y², L², R²⁹, R³⁰ and Q are as defined above for general formula III;
wherein Z¹ is any structure of the following group D;

Group D

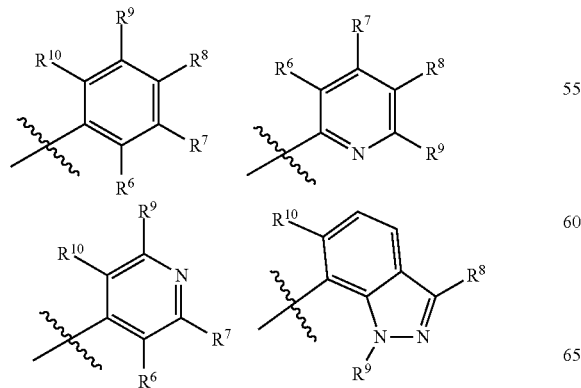

-continued

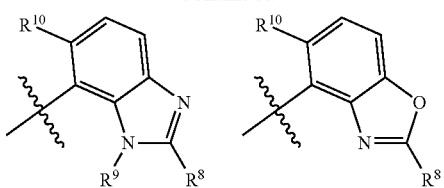

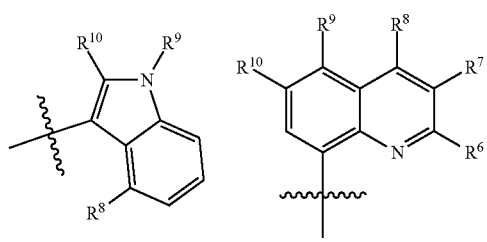

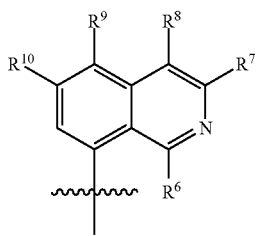

wherein R⁶, R⁷, R⁸, R⁹ and R¹⁰ are as defined above for general formula I.

In one embodiment, the present invention relates to compounds having the general formula V Formula V

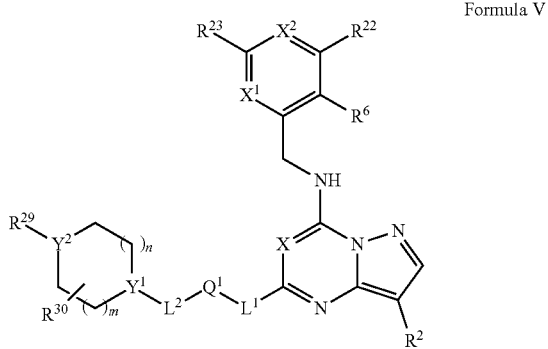

wherein X, X¹, X², L¹, R², R⁶, R²² and R²³ are as defined above for general formula I;
wherein m, n, Y¹, Y², L² R²⁹, R³⁰ and Q¹ are as defined above for general formula III.

In one embodiment, the present invention relates to compounds having the general formula VI

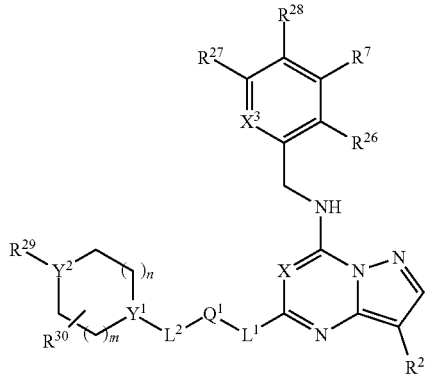

Formula VI wherein X, L¹ and R² are as defined above for general formula I;

wherein m, n, Y¹, Y², L², R²⁹, R³⁰ and Q are as defined above for general formula III;

X³ is, independently at each occurrence, selected from CR¹⁰ and N;

R²⁶, R²⁷ and R²⁸ are, at each occurrence, independently selected from the group consisting of hydrogen, halogen, C1-C6 alkyl, C1-C3 haloalkyl, —OR⁵, —CN and C1-C6 alkyl substituted with —OH, —OR⁵ or —NHR⁹;

R⁵, R⁹ and R¹⁰ are as defined above for general formula I;

R⁷ is any structure of the following group E;

Group E

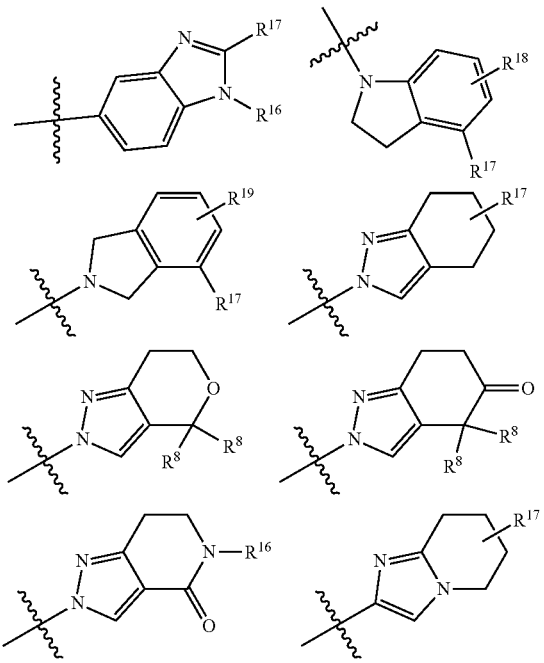

-continued

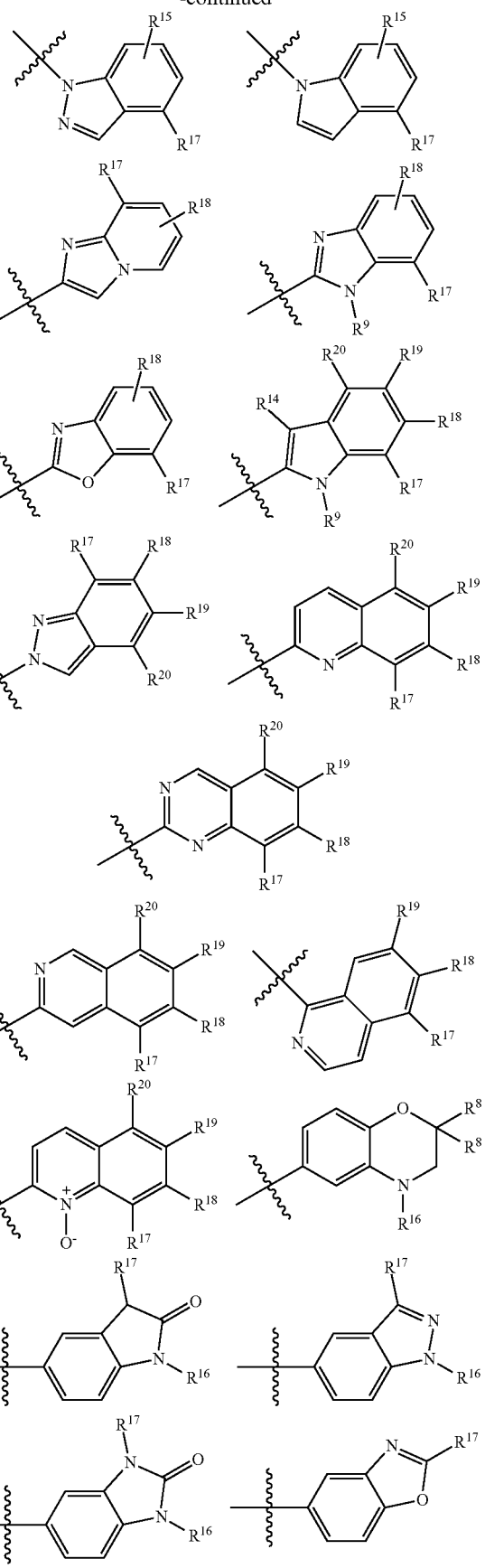

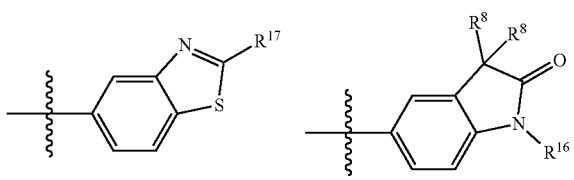

wherein $R^8$ and $R^{14}$-$R^{20}$ are as defined above for general formula I.

In one embodiment, the present invention relates to compounds having the general formula VII

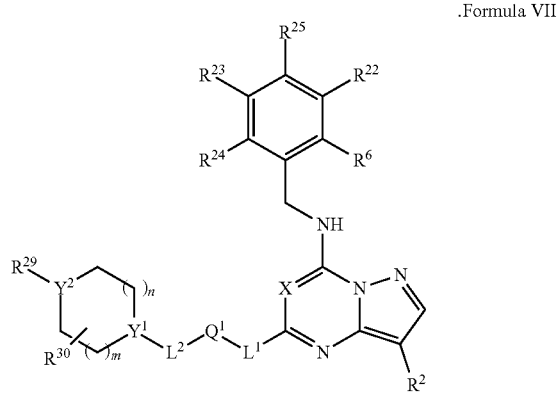

Formula VII wherein X, $L^1$, $R^2$, $R^6$, $R^{22}$, $R^{23}$, $R^{24}$ and $R^{25}$ are as defined above for general formula I;

m, n, $Y^1$, $Y^2$, $L^2$, $R^{29}$, $R^{30}$ and $Q^1$ are as defined above for general formula III.

In one embodiment, the present invention relates to compounds having the general formula VIII

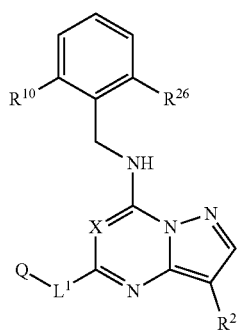

Formula VIII wherein X, $L^1$, $R^2$, $R^6$ and $R^{10}$ are as defined above for general formula I.

In one embodiment, the present invention relates to compounds having the general formula IX

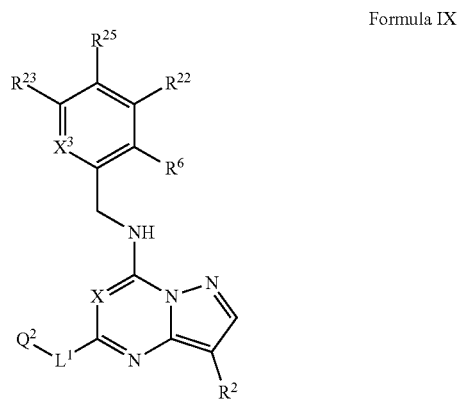

Formula IX wherein $L^1$, $R^2$, $R^6$, $R^{22}$, $R^{23}$, $R^{24}$ and $R^{25}$ are as defined above for general formula I, and $X^3$ is as defined above for general formula VI;

wherein $Q^2$ is any structure of the following group I;

Group F

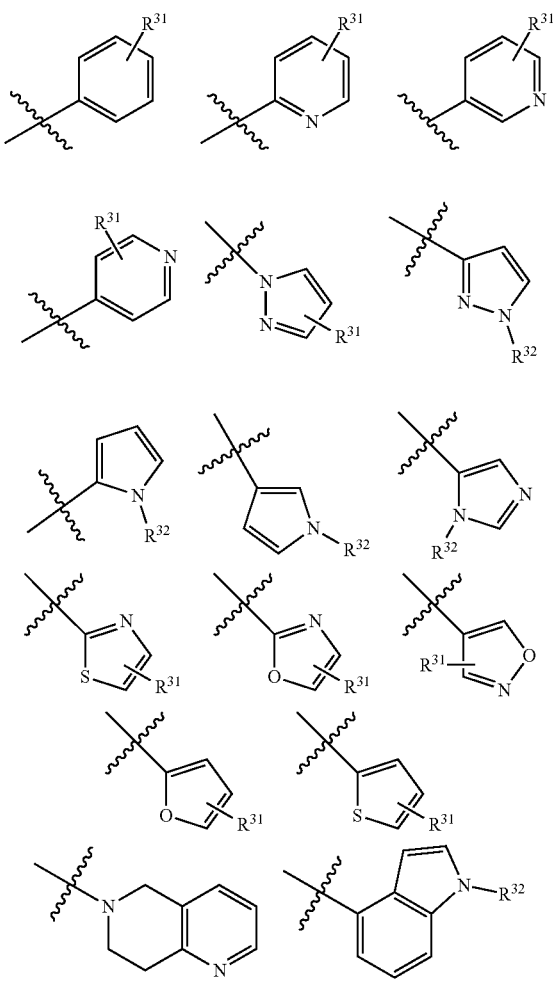

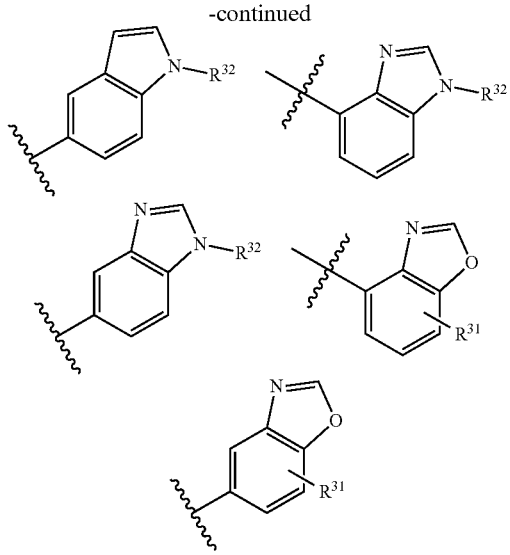

R³¹ and R³² are either absent or independently, at each occurrence, selected from the group consisting of hydrogen, —OR⁵, halogen, —N(R⁵)R⁵, —NR⁹R¹², —NH(C=O)R⁵, —(C=O)NH₂, aryl, heteroaryl, heterocyclyl, C1-C6 alkyl and C1-C6 alkyl substituted with —OH or —NH₂;

wherein R⁵, R⁹ and R¹² are as defined above for general formula I.

In one embodiment, the present invention also relates to pharmaceutically acceptable salts of the compounds according to the present invention, as defined herein.

In one embodiment, the compound according to the present invention is a compound selected from structures 1-279, as listed further below in table 11.

In a further aspect, the present invention relates to a pharmaceutical composition comprising a compound according to the present invention as defined herein, as an active ingredient, together with at least one pharmaceutically acceptable carrier, excipient and/or diluent.

In one aspect, the present invention also relates to a compound according to the present invention as defined herein, for use as a pharmaceutical or pharmaceutically active agent, wherein said pharmaceutical or pharmaceutically active agent preferably has an inhibitory activity on cyclin-dependent kinase 7 (CDK7).

In one aspect, the present invention also relates to a compound according to the present invention, as defined herein, for use in a method of prevention and/or treatment of a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases.

In one embodiment, the disease associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), is a disease associated with, accompanied by, caused by and/or induced by CDK7 dysfunction and/or hyperfunction. In one embodiment, the disease associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), is a proliferative disease. In one embodiment said proliferative disease is a cancer.

In one embodiment said cancer is selected from adenocarcinoma, choroidal melanoma, acute leukemia, acoustic neurinoma, ampullary carcinoma, anal carcinoma, astrocytoma, basal cell carcinoma, pancreatic cancer, Desmoid tumor, bladder cancer, bronchial carcinoma, estrogen dependent and independent breast cancer, Burkitt's lymphoma, corpus cancer, Carcinoma unknown primary tumor (CUP-syndrome), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic tumor, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymphomas, stomach cancer, malignant melanoma, malignant neoplasia, malignant tumors gastrointestinal tract, breast carcinoma, rectal cancer, medulloblastomas, melanoma, meningiomas, Hodgkin's/Non-Hodgkin's lymphoma, mycosis fungoides, nasal cancer, neurinoma, neuroblastoma, kidney cancer, renal cell carcinomas, oligodendroglioma, esophageal carcinoma, osteolytic carcinomas and osteoplastic carcinomas, osteosarcomas, ovarian carcinoma, pancreatic carcinoma, penile cancer, plasmacytoma, prostate cancer, pharyngeal cancer, rectal carcinoma, retinoblastoma, vaginal cancer, thyroid carcinoma, esophageal cancer, T-cell lymphoma, thymoma, tube carcinoma, eye tumors, urethral cancer, urologic tumors, urothelial carcinoma, vulva cancer, wart appearance, soft tissue tumors, soft tissue sarcoma, Nephroblastoma, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypothalamic glioma, cerebellar astrocytoma, cerebral astrocytoma, neuroectodermal tumor, pineal tumors, sarcoma of the uterus, salivary gland cancers, anal gland adenocarcinomas, mast cell tumors, pelvis tumor, ureter tumor, hereditary papillary renal cancers, sporadic papillary renal cancers, intraocular melanoma, hepatocellular carcinoma, cholangiocarcinoma, mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-cell lymphoma, lymphoma of the central nervous system, malignant fibrous histiocytoma, lymph sarcoma, rhabdomyosarcoma, malignant histiocytosis, fibroblastic sarcoma, hemangiosarcoma, hemangiopericytoma, leiomyosarcoma (LMS), canine mammary carcinoma, and feline mammary carcinoma.

In one embodiment, said infectious disease, including opportunistic diseases, is selected from AIDS, Adenovirus Infection, Alveolar Hydatid Disease (AHD), Amoebiasis, Angiostrongyliasis, Anisakiasis, Anthrax, Babesiosis, Balantidiasis, *Baylisascaris* Infection, *Bilharzia* (Schistosomiasis), *Blastocystis hominis* Infection, Lyme Borreliosis, Botulism, Brainerd Diarrhea, Brucellosis, Bovine Spongiform Encephalopathy (BSE), Candidiasis, Capillariasis, Chronic Fatigue Syndrome (CFS), Chagas Disease, Chickenpox, *Chlamydia pneumoniae* Infection, Cholera, Chronic Fatigue Syndrome, Creutzfeldt-Jakob Disease (CJD), Clonorchiasis, Cutaneous Larva migrans (CLM), Coccidioidomycosis, Conjunctivitis, Coxsackievirus A16 (Cox A16), Cryptococcal disease, Cryptosporidiosis, West Nile fever, Cyclosporiasis, Neurocysticercosis, Cytomegalovirus Infection, Dengue Fever, *Dipylidium caninum* Infection, Ebola Hemorrhagic Fever (EHF), Alveolar Echinococcosis (AE), Encephalitis, *Entamoeba coli* Infection, *Entamoeba dispar* Infection, *Entamoeba hartmanni* Infection, *Entamoeba polecki* Infection, Pinworm Infection, Enterovirus Infection (Polio/Non-Polio), Epstein Barr Virus Infection, *Escherichia coli* Infection, Foodborne Infection, Aphthae epizooticae, Fungal Dermatitis, Fungal Infections, Gastroenteritis, Group A streptococcal Disease, Group B streptococcal Disease, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis, Lassa Fever, Leishmaniasis, Visceral leishmaniasis (VL), Malaria, Marburg Hemorrhagic Fever, Measles, Meningitis, *Mycobacterium avium* Complex (MAC) Infection, *Naegleria* Infection, Nosocomial Infections, Nonpathogenic Intestinal Amebae Infection, Onchocerciasis, Opisthorchiasis, Papilloma virus Infection, Parvovirus Infection, Plague, *Pneumocystis* Pneumonia (PCP), Polyomavirus Infection, Q Fever, Rabies, Respiratory Syncytial Virus (RSV) Infection, Rheumatic Fever, Rift Valley Fever, Rotavirus Infection, Roundworms Infection, *Salmonellosis*, Scabies, Shigellosis, Shingles, Sleeping Sickness, Smallpox, Streptococcal Infection, Tapeworm Infection, Tetanus, Toxic Shock Syndrome, Tuberculosis, duodenum, *Vibrio parahaemolyticus* Infection, *Vibrio* septicemia, Viral Hemorrhagic Fever, Warts, Waterborne infectious Diseases, Varicella-Zoster Virus infection, Pertussis and Yellow Fever.

In one embodiment, the immunological disease and/or autoimmune disease is selected from asthma, diabetes, rheumatic diseases, rejection of transplanted organs and tissues, rhinitis, chronic obstructive pulmonary diseases, osteoporosis, ulcerative colitis, sinusitis, lupus erythematosus, recurrent infections, atopic dermatitis/eczema and occupational allergies, food allergies, drug allergies, severe anaphylactic reactions, anaphylaxis, manifestations of allergic diseases, primary immunodeficiencies, antibody deficiency states, cell mediated S immunodeficiencies, severe combined immunodeficiency, DiGeorge syndrome, Hyper IgE syndrome (HIES), Wiskott-Aldrich syndrome (WAS), ataxia-telangiectasia, immune mediated cancers, white cell defects, autoimmune diseases, systemic lupus erythematosus (SLE), rheumatoid arthritis (RA), multiple sclerosis (MS), immune-mediated or Type 1 Diabetes Mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, Hashimoto's disease, dermatomyositis, Goodpasture syndrome (GPS), myasthenia gravis (MG), Sympathetic ophthalmia, Phakogene Uveitis, chronical aggressive hepatitis, primary biliary cirrhosis, autoimmune hemolytic anemia, and Werlhof's disease.

In one embodiment, the inflammatory disease is caused, induced, initiated and/or enhanced by bacteria, viruses, prions, parasites, fungi, and/or caused by irritative, traumatic, metabolic, allergic, autoimmune, or idiopathic agents.

In one embodiment, the inflammatory disease is selected from the group comprising or consisting of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, and inflammatory diseases of the larynx.

In one embodiment, the inflammatory disease is selected from inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx, wherein preferably said inflammatory diseases are selected from the group comprising abscessation, *acanthamoeba* infection, acne vulgaris, actinomycosis, acute inflammatory dermatoses, acute laryngeal infections of adults, acute multifocal placoid pigment epitheliopathy, acute (thermal) injury, acute retinal necrosis, acute suppurative otitis media, algal disorders, allergic contact dermatitis, amyloidosis angioedema, ankylosing spondylitis, aspergillosis, atopic dermatitis, pseudorabies, autoantibodies in vasculitis, bacterial disorders, bacterial laryngitis, bacterial meningitis, Behçet's disease (BD), birdshot choroidopathy, Gilchrist's disease, Borna disease, brucellosis, bullous myringitis, bursitis, candidiasis, canine distemper encephalomyelitis, canine distemper encephalomyelitis in immature animals, canine hemorrhagic fever, canine herpes virus encephalomyelitis, cholesteatoma, chronic granulomatous diseases (CGD), chronic inflammatory dermatoses, chronic relapsing encephalomyelitis, chronic suppurative otitis media, Ocular Cicatricial pemphigoid (OCP), common upper respiratory infection, granuloma, Crohn's disease, cryptococcal disease, dermatomyositis, diphtheria, discoid lupus erythematosus (DLE), drug-induced vasculitis, drug or hypersensitivity reaction, encephalitozoonosis, eosinophilic meningoencephalitis, Erythema multiforme (EM), feline leukemia virus, feline immunodeficiency virus, feline infectious peritonitis, feline Polioencephalitis, feline spongiform encephalopathy, fibromyalgia, Fuchs Heterochromic Uveitis, gastroesophageal (laryngopharyngeal) reflux disease, giant cell arteritis, glanders, glaucomatocyclitic crisis, gonorrhea granular myringitis, Granulomatous meningoencephalitis (GME), herpes simplex, histoplasmosis, idiopathic diseases, idiopathic inflammatory disorders, immune and idiopathic disorders, infections of the immunocompromised host, infectious canine hepatitis, inhalation laryngitis, interstitial nephritis, irritant contact dermatitis, juvenile rheumatoid arthritis, Kawasaki's disease, La Crosse virus encephalitis, laryngeal abscess, laryngotracheobronchitis, leishmaniasis, lens-induced uveitis, leprosy, leptospirosis, leukemia, lichen planus, lupus, lymphoma, meningitis, meningoencephalitis in greyhounds, miscellaneous meningitis/meningoencephalitis, microscopic polyangiitis, multifocal choroiditis, multifocal distemper encephalomyelitis in mature animals, multiple sclerosis, Muscle Tension Dysphonia (MTD), mycotic (fungal) diseases, mycotic diseases of the CNS, necrotizing encephalitis, neosporosis, old dog encephalitis, onchocerciasis, parasitic encephalomyelitis, parasitic infections, Pars planitis, parvovirus encephalitis, pediatric laryngitis, pollution and inhalant allergy, polymyositis, post-vaccinal canine distemper encephalitis, prion protein induced diseases, protothecosis, protozoal encephalitis-encephalomyelitis, psoriasis, psoriatic arthritis, pug dog encephalitis, radiation injury, radiation laryngitis, radionecrosis, relapsing polychondritis, Reiter's syndrome, retinitis pigmentosa, retinoblastoma, rheumatoid arthritis, Rickettsial disorders, rocky mountain spotted fever, salmon poisoning disease (SPD), Sarcocystosis, sarcoidosis, schistosomiasis, scleroderma, Rhinoscleroma, serpiginous choroiditis, shaker dog disease, Sjogren's syndrome, spasmodic croup, spirochetal (syphilis) diseases, spongiotic dermatitis, sporotrichosis, steroid responsive meningitis-arteritis, Stevens-Johnson syndrome (SJS, EM major), epiglottitis, sympathetic ophthalmia, Syngamosis, syphilis, systemic vasculitis in sarcoidosis, Takayasu's arteritis, tendinitis (tendonitis), Thromboangiitis obliterans (Buerger Disease), tick-borne encephalitis in dogs, toxic epidermal necrolysis (TEN), toxocariasis, toxoplasmosis, trauma, traumatic laryngitis, trichinosis, trypanosomiasis, tuberculosis, tularemia, ulcerative colitis, urticaria (hives), vasculitis, vasculitis and malignancy, vasculitis and rheumatoid arthritis, vasculitis in the idiopathic inflammatory myopathies, vasculitis of the central nervous system, vasculitis secondary to bacterial, fungal, and parasitic infection, viral disorders, viral laryngitis, vitiligo, vocal abuse, vocal-cord hemorrhage, Vogt-Koyanagi-Harada syndrome (VKH), Wegener's granulomatosis, and Whipple's disease.

The present invention also relates to a method of treatment and/or prevention of a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases, wherein said method of treatment and/or prevention comprises administering a compound according to the present invention as defined herein, to a patient in need thereof.

In one embodiment, the patient in need thereof is a mammal. In one embodiment, the patient in need thereof is a human being. In another embodiment, the patient in need thereof is a non-human animal.

In one embodiment, the disease which is prevented or treated in said method is as defined herein.

The present invention also relates to the use of a compound according to the present invention as defined herein in the manufacture of a medicament for the prevention and/or treatment of a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases, as defined herein.

Further advantageous features, aspects and details of the invention are evident from the dependent claims, the description, the examples and the drawings.

The compounds of the present invention are highly efficient inhibitors of CDK7 threonine/serine kinase and/or its complex, CDK7/MAT1/CycH. The inventive compounds are suitable for the use as a pharmaceutically active agent. The inventive compounds are suitable for the treatment of disorders associated with, accompanied by, caused by and/or induced by CDK7 and its complex, in particular a hyperfunction or dysfunction thereof. The inventive compounds are thus suitable for the treatment of CDK7-associated diseases or disorders and CDK7 complex induced disorders.

The inventive compounds are also useful in the manufacture of a medicament or of a pharmaceutical composition for the treatment of disorders associated with, accompanied by, caused by and/or induced by CDK7 and its complex, in particular a hyperfunction or dysfunction thereof. The inventive compounds are further used in the manufacture of a medicament or of a pharmaceutical composition for the treatment and/or prevention of CDK7 and its complex induced disorders.

The term "optionally substituted" as used herein is meant to indicate that a hydrogen atom where present and attached to a member atom within a group, or several such hydrogen atoms, may be replaced by a suitable group, such as halogen including fluorine, $C_1$-$C_3$ alkyl, $C_1$-$C_3$ haloalkyl, methylhydroxyl, COOMe, C(O)H, COOH, OMe, or $OCF_3$;

The term "alkyl" refers to a monovalent straight, branched or cyclic chain, saturated aliphatic hydrocarbon radical having a number of carbon atoms in the specified range. Thus, for example, "$C_1$-$C_6$ alkyl" refers to any of the hexyl alkyl and pentyl alkyl isomers as well as n-, iso-, sec-, and t-butyl, n- and isopropyl, cyclic propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" refers to all of the hexenyl and pentenyl isomers as well as 1-butenyl, 2-butenyl, 3-butenyl, isobutenyl, 1-propenyl, 2-propenyl, and ethenyl (or vinyl).

The term "cycloalkyl", alone or in combination with any other term, refers to a group, such as optionally substituted or non-substituted cyclic hydrocarbon, having from, three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens. The term "haloalkyl" should be interpreted to include such substituents such as —$CHF_2$, —$CF_3$, —$CH_2$—$CH_2$—F, —$CH_2$—$CF_3$, and the like.

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or thioalkyl group (e.g., —$SCH_3$, etc.). If anon-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), alkyl amine (e.g., —$CH_2NHCH_3$, —$CH_2N(CH_3)_2$, etc.), or thioalkyl ether (e.g., —$CH_2$—S—$CH_3$).

The term "halogen" refers to fluorine, chlorine, bromine, or iodine.

The term "phenyl" as used herein is meant to indicate that optionally substituted or non-substituted phenyl group.

The term "benzyl" as used herein is meant to indicate that optionally substituted or non-substituted benzyl group.

The term "heteroaryl" refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl.

The term "heterocyclyl" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to S(O) or S(O)$_2$. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzenesulfonic acid, the benzoate derived from benzoic acid, the cinnamate derived from cinnamic acid, the citrate derived from citric acid, the embonate derived from embonic acid, the enanthate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Further aspects of the present invention are illustrated and exemplified by the following schemes, examples, tables and procedural descriptions which are given merely to illustrate, not to limit the present invention. The scope of protection for the present invention is merely limited by the appended claims.

TABLES AND FIGURE

Reference is now made to tables, wherein

Table 1 shows activity data in CDK1, CDK2, CDK5 and CDK7 enzymatic assay for selected compounds of the invention. Inhibition is indicated as IC$_{50}$ with the following key: A=IC$_{50}$ less than 100 nM; B=IC$_{50}$ greater than 100 nM, but less than 1,000 nM; C=IC$_{50}$ greater than 1,000 nM. Also table 1 shows selectivity data in CDK1/CDK7, CDK2/CDK7 and CDK5/CDK7 for selected compounds of the invention. Selectivity is indicated as CDK1/CDK7*, CDK2/CDK7 and CDK5/CDK7* with the following key: A=greater than 200 fold; B=less than 200 fold, but greater than 20 fold; C=less than 20 fold.

Table 2 shows activity data of cellular HCT116 viability assay for selected compounds of the invention. Inhibition is indicated as IC$_{50}$ with the following key: A=IC$_{50}$ less than 1 uM; B=IC$_{50}$ greater than 1 uM, but less than 10 uM; C=IC$_{50}$ greater than 10 uM.

Table 3 shows activity data cellular H460 viability assay for selected compounds of the invention. Inhibition is indicated as IC$_{50}$ with the following key: A=IC$_{50}$ less than 1 uM; B=IC$_{50}$ greater than 1 uM, but less than 10 uM; C=IC$_{50}$ greater than 10 uM.

Table 4 shows activity data of cellular MM.1S viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 5 shows activity data of cellular MV4-11 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 6 shows activity data of cellular MOLT-4 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 7 shows activity data of cellular RPMI-8226 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 8 shows activity data of cellular A2780 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 9 shows activity data of cellular OVCAR-3 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 10 shows comparative data of a panel assay showing the CDK7 selectivity profile in CDKs family for compound 210 of the invention.

Table 11 summarizes compounds 1-279 in terms of their structures and corresponding characteristics.

FIGURE shows in vivo antitumor activity of CDK7 inhibitor in OVCAR-3 xenograft model.

EXAMPLES

The invention is now further described by reference to the following examples which are intended to illustrate, not to limit the scope of the invention.

Example 1: Enzymatic Assay for CDK1, CDK2, CDK5 and CDK7

Enzymatic Binding Assay Protocol for CDK1, CDK2, CDK5 and CDK7

Inhibition activity of the respective compound on CDK kinase under Km value of ATP was tested in FRET based The LANCE® Ultra kinase assay (Perkin Elmer), which uses a ULight™-labeled peptide substrate and an appropriate Europium-labeled anti-phospho-antibody. Test compounds were made with DMSO solutions, and then 4-fold serial dilutions for 8 doses were prepared using automated liquid handler (POD810, LABCYTE) and 80 nL/well of diluted compound solutions were added into the 384-well plates (Greiner, Cat #784075). And then 68 nM of ULight-MBP peptide (Perkin Elmer, Cat #TRF0109-M) and 5 ul/well of ATP (Sigma, Cat #A7699) were added to the plate. After 1 min centrifugation at 1000 rpm, Purified CDKs/Cyclin complex were added following concentrations respectively. 24 uM for CDK1/Cyclin B (Invitrogen, Cat #PR4768C), 22 uM for CDK2/Cyclin A (Invitrogen, Cat #PV6290), 10 uM for CDK5/p25 (Invitrogen, Cat #PR8543B) and 400 uM for CDK7/Cyclin H/MNAT1 (Invitrogen, Cat #PR6749B) were added to the each corresponding plate for CDK1, CDK2, CDK5 and CDK7. Incubate at 23° C. for 60 min and then Eu-labeled anti-phospho-Myelin Basic Protein (PE, Cat #TRF0201-M) and EDTA (Invitrogen, Cat #15575038) mixture in Lance Detection Buffer (Perkin Elmer, Cat #CR97100) was added in each well. After additional incubation at 23° C. for 60 min, test articles were measured the fluorescence using Envision leader (Perkin Elmer, USA) [Laser as excitation light; APC 615 nm and Europium 665 as the first and the second emission filter]. Data was analyzed using XL Fit software.

Example 2: Cellular HCT116, H460, MV4-11, MM.1S, MOLT-4, RPMI-8226, A2780 and OVCAR-3 Viability Assay Cell Culture Human T-cell acute lymphoblastic leukemia cell line, MOLT-4 (ATCC, Cat #CRL-1582), Human multiple myeloma cell line, RPMI-8226 (Invitrogen, Cat #22400-089) and MM.1S (ATCC, Cat #CRL-2974), NSCLC (Non-small cell lung cancer) cell line H460 (ATCC, Cat #HTB-177), Human colon colorectal carcinoma cell line HCT116 (ATCC, Cat #CCL-247), Human acute monocytic leukemia cell line MV4-11 (ATCC, Cat #CRL-9591), OVCAR-3 (ATCC, Cat #HTB-161) and A2780 (ECACC, Cat #93112519) were obtained from ATCC. Cells were grown in RPMI-1640 media (Invitrogen, Cat #22400-089) supplemented with 10% FBS (Invitrogen, Cat #10099141) and 1% penicillin/streptomycin (Invitrogen, Cat #15070063) and cultured at 37° C., 5% $CO_2$ in a humidified chamber. All cell lines were routinely tested for *mycoplasma*.

Cell HCT116, H460, MV4-11, MM.1S, MOLT-4, RPMI-8226, A2780 and OVCAR-3 Viability Assay Protocol The effect of the CDK7 inhibitor to inhibit the growth of target cancer cells was evaluated through the 72 hours time period of viability assay. Briefly, the candidate cell line ware plated in 96 well plate at the following density of cells respectively. $1 \times 10^4$ cells/well for MOLT-4, RPMI-8226, MV4-11 and MM.1S, $5 \times 10^3$ for H460, HCT116 and OVCAR-3 and $1 \times 10^3$ for A2780. After 24 hours, the cells were treated with various concentrations of the compound (ranging from 0.0015 uM to 10 uM). DMSO solvent without compound served as a control and final DMSO concentration less than 0.1%. After 72 hours of incubation at 37° C., 5% $CO_2$ incubator, cells were analyzed for the viability using the CellTiter-Glo Luminescent Cell Viability Assay (Promega, Cat #G7570). All viability assays were performed in duplicate and Luminescence was read using an Envision (Perkin Elmer, USA). Data was analyzed using XLfit software.

Example 3: In Vitro $IC_{50}$ Profile for CDKs Family Kinase

In Vitro $IC_{50}$ Profile for CDK7 Inhibitor Among 28 CDKs Family Kinases.

The $IC_{50}$ profile of compounds were determined using 28 CDKs family protein kinases through ProQinase GmbH (Freiburg, Germany). All the protocol and materials had been provided by ProQinase GmbH. Briefly, in the process, 90 µl H$_2$O were added to each well of a compound dilution plate. To minimize potential precipitation, the H$_2$O was added to the plate only a few minutes before the transfer of the compound solutions into the assay plates. The plate was shaken thoroughly, resulting in a "compound dilution plate/10% DMSO". The compound dilution plate(s) were discarded at the end of the working day. For the assays (see below), 5 µl solution from each well of the compound dilution plate were transferred into the assay plates. The final volume of the assay was 50 µl. All compounds were tested at 10 final assay concentrations in the range from $1\times10^{-05}$ M to $3\times10^{-10}$ M. The final DMSO concentration in the reaction cocktails was 1% in all cases. All protein kinases provided by ProQinase were expressed in Sf9 insect cells or in E. coli as recombinant GST-fusion proteins or His-tagged proteins, either as full-length or enzymatically active fragments. All kinases were produced from human cDNAs and purified by either GSH affinity chromatography or immobilized metal affinity chromatography. The purity of the protein kinases was examined by SDS-PAGE/Coomassie staining, the identity was checked by mass spectroscopy. Kinases from external vendors, Carna Biosciences Inc.; Invitrogen Corp.; and Millipore Corp., were expressed, purified and quality-controlled by virtue of the vendors readings. A radiometric protein kinase assay ($^{33}$PanQinase® Activity Assay) was used for measuring the kinase activity of the 28 protein kinases. All kinase assays were performed in 96-well Flash-Plates™ from PerkinElmer (Boston, MA, USA) in a 50 µl reaction volume. The reaction cocktails were incubated at 30° C. for 60 minutes. The reaction was stopped with 50 µl of 2% (v/v) H$_3$PO$_4$, plates were aspirated and washed two times with 200 µl 0.9% (w/v) NaCl. Incorporation of $^{33}$Pi was determined with a microplate scintillation counter (Microbeta, Wallac). All assays were performed with a BeckmanCoulter/SAGIAN™ Core System. As part of the data evaluation the low control value from a particular plate was subtracted from the high control value as well as from all 80 "compound values" of the corresponding plate. The residual activity (in %) for each well of a particular plate was calculated by using the following formula: Res. Activity (%)=100×[(cpm of compound−low control)/(high control−low control)]. Results are represented in table (table 10).

Example 4: In Vivo Efficacy Study for OVCAR-3 Model

In Vivo Efficacy of CDK7 Inhibitor in the OVCAR-3 Human Epithelial Ovarian Cancer Xenograft Model.

To evaluate inhibitory activity to the growth of OVCAR-3 (ATCC, HTB-161) xenograft tumors, in vivo efficacy study was conducted. OVCAR-3 cells were grown in RPMI-1640 medium (Gibco, C2400500BT) supplemented with 20% fetal bovine serum (HyClone, SV30087.03), 0.01 mg/ml bovine insulin (Yuanyue, S12033) and 1% anti anti(Gibco, 15240-062) at 37° C. in an atmosphere of 5% CO$_2$ in air. To establish tumors, $10\times10^6$ OVCAR-3 cells were injected subcutaneously in 200 µl of PBS (Corning, 21-031-CVR) mixed with 50% of Matrigel (Corning, 354234) into the upper right flank of the female Balb/c nude mouse (Vital River Laboratory Animal Co., LTD., Beijing). Tumor volume was measured twice a week and body weight was monitored daily. Mice were measured for tumor size in two dimensions using a caliper, and the tumor volume (mm$^3$) was calculated using formula, "V=0.5 a×b$^2$" where a and b are the long and short diameters of the tumor in mm. respectively. The animals were randomized based on tumor volumes into three groups of eight animals each. To evaluate efficacy, compound-210 was administered orally using 70% PEG400 (Sigma-Aldrich, P3265) in distilled water as vehicle. Once the average tumor size had reached approximately 160 mm$^3$, the animals were treated with vehicle, 20 mg/kg or 40 mg/kg of compound-210 daily (q24 h/qd schedule) for 25 days post randomization. Statistical analysis of difference in tumor volume among the groups was conducted on the data obtained on PG-D25. All data was analyzed using Graphpad Prism (GraphPad, Prism 6.00). p<0.05 is considered to be statistically significant. Results are shown in graph (FIGURE).

Example 5: Derivatization of the Pyrazolo-Triazine and Pyrazolo-Pyrimidine General Scaffold Presented compounds underwent derivation according to the methods outlined below (Scheme 1-56). Resulting derivatives were examined for enzymatic binding cellular activity (HCT116, H460, MV4-11, MM.1S, MOLT-4, RPMI-8226, A2780 and OVCAR-3), CDK7 selectivity in CDKs family and in vivo efficacy study (OVCAR-3) using the assays described above (Example 1, 2, 3 and 4) and the results are summarized in Table 1-10 and FIGURE. The synthesized compounds 1-279 are shown in Table 11.

Scheme 1-a: General Synthetic route

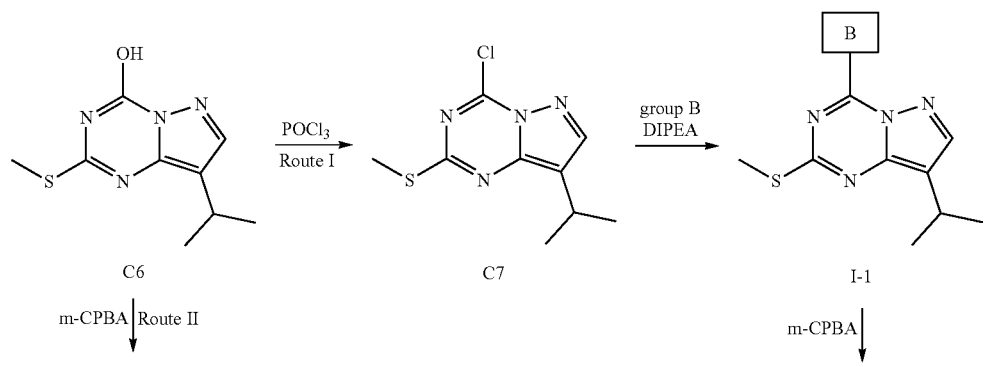

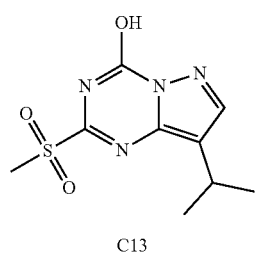

C13 group A ↓

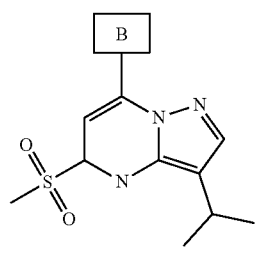

I-2 group A ↓

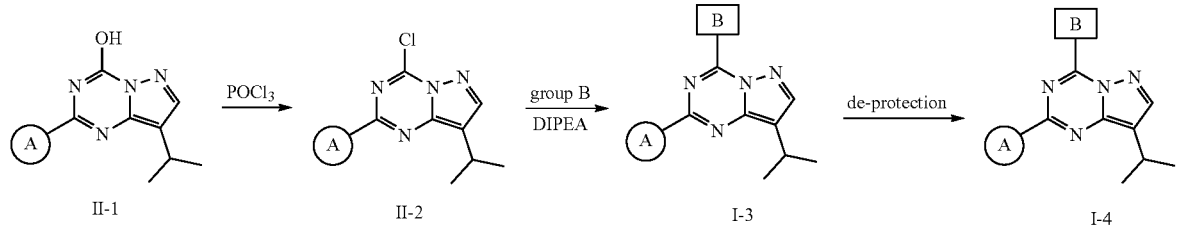

II-1      II-2      I-3      I-4

The method to prepare compounds of I-3 and I-4 is shown in Scheme 1-a.

Route I: Compound C7 can be synthesized by treating in presence of POCl$_3$. Compound C7 can be further treated with group B in presence of DIPEA to give compounds I-1. Compounds I-1 can be further treated with m-CPBA to provide the compounds of formula I-2. The compounds of formula I-3 can be synthesized by treating compounds I-2 with group A.

Route II: Route II having the similar reaction condition with Route I and different order.

Compound C$_{1-3}$ can be synthesized by treating in presence of m-CPBA. The compounds of formula II-1 can be synthesized by treating compounds C13 with appropriated group A. Compounds II-2 can be synthesized by treating in presence of POCl$_3$. The compounds of formula I-3 can be synthesized by treating compounds II-2 with DIPEA and group B.

De-protection step: The compounds of formula I-4 can be prepared by using compounds of formula I-3 in presence of acid such as TFA, HBr and AcOH, or base such as hydrazine.

Scheme 1-b: General Synthetic route

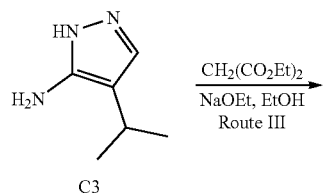

C3

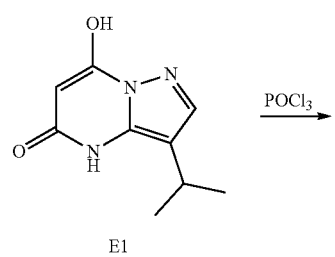

E1

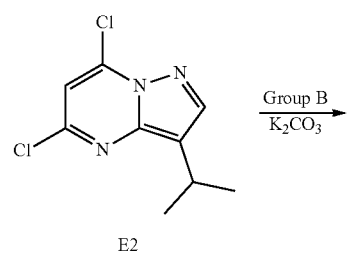

E2

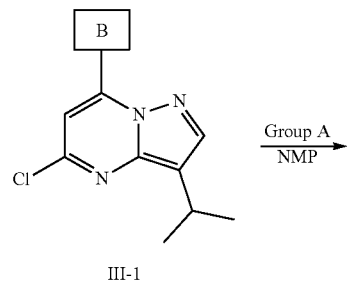

III-1

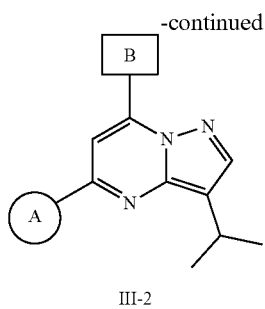

III-2

↓ de-protection

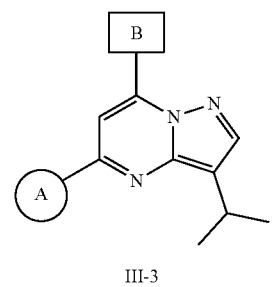

III-3

The method to prepare compounds of III-2 and III-3 is shown in Scheme 1-b.

Route III: Compound E1 can be synthesized by treating in presence of NaOEt. Compound E2 can be synthesized by treating in presence of POCl$_3$. Compound E2 can be further treated with group B in presence of K$_2$CO$_3$ to give compounds III-1. Compounds III-1 can be further treated with group A to provide the compounds of formula III-2. The compounds of formula III-3 can be prepared by using compounds of formula III-2 in presence of acid such as TFA, HBr and AcOH, or base such as hydrazine.

Procedure for Synthesis of E1

Na (859 mg, 37.4 mmol) was added into anhydrous EtOH (100 mL) at 10° C., the resulting mixture was stirred for 1 hour at 10° C. under N$_2$ atmosphere, then compound C3 (3.90 g, 31.1 mmol) and diethyl propanedioate (5.99 g, 37.4 mmol) was added to the mixture. The mixture was heated at 80° C. and stirred for another 15 hours under N$_2$ atmosphere to give yellow solution. TLC showed the reaction was completed. The reaction mixture was cooled to room temperature and concentrated to obtain residue. The residue was dissolved in water (60 mL) and acidified to pH=3 with 3M HCl, filtered to give compound E1 (3.60 g) as an off-white solid.

Procedure for Synthesis of E2

To a solution of compound E1 (3.60 g, 18.6 mmol) in POCl$_3$ (57.1 g, 373 mmol) was added N, N-diethylaniline (2.78 g, 18.6 mmol). The resulting mixture was heated at 100° C. and stirred for 2 hours under N$_2$ atmosphere to give red solution. TLC showed the reaction was completed, one major spot was formed. The reaction mixture was concentrated most of solvent and poured into H$_2$O (40 mL), extracted with DCM (50 mL×3). The organic layer was washed with brine (50 mL×2), dried over anhydrous Na$_2$SO$_4$, filtered and concentrated under reduced pressure to give crude product. The crude product was purified by silica column to obtain compound E2 (2.85 g) as yellowish solid.

General Schemes of Group A

Scheme 2: Synthetic route for A1

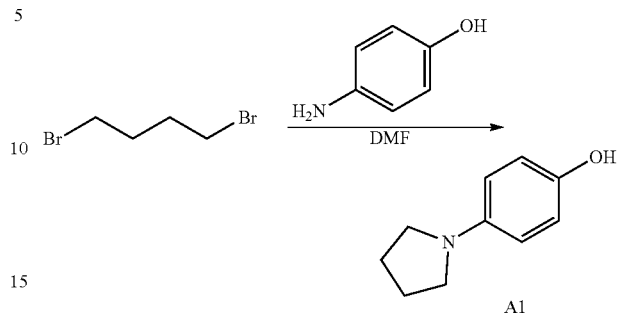

Procedure for Synthesis of A1

A mixture of 4-aminophenol (1.00 g, 9.16 mmol) and 1,4-dibromobutane (9.89 g, 45.8 mmol) in DMF (100 mL) was stirred at 65° C. for 18 hours. Saturated NaHCO$_3$ (150 mL) was added dropwise into the reaction mixture carefully to quench the reaction. The mixture was diluted with EtOAc (100 mL). The organic phase were separated and the aqueous phase was extracted with EtOAc (100 mL×2), the combined organic phase was washed with water (70 mL×4), brine (100 mL), dried over anhydrous Na$_2$SO$_4$, filtered and concentrated under reduced pressure to give crude product, The crude compound was purified by Combi-Flash to give compound A1 (110 mg) as a brown powder.

Scheme 3: Synthetic route for A5

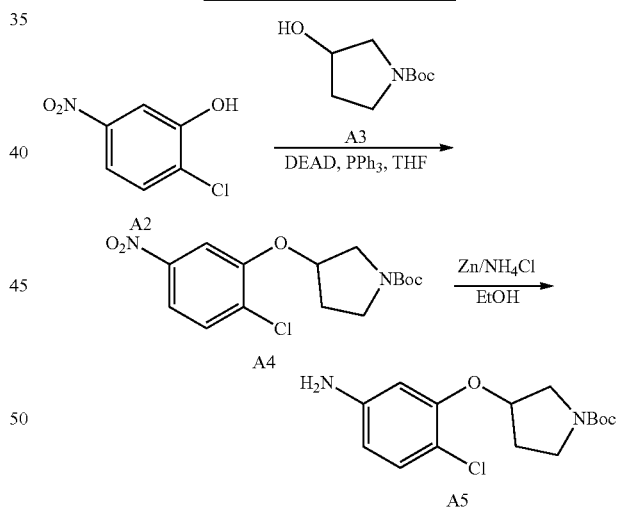

Procedure for Synthesis of A4

To a solution of compound A2 (1.00 g, 5.76 mmol), compound A3 (2.16 g, 11.5 mmol) and PPh$_3$ (3.02 g, 11.5 mmol) in anhydrous THF (15 mL) was added DEAD (2.01 g, 11.5 mmol), the mixture was stirred at 20° C. for 17 hours. TLC showed the reaction was completed. The reaction was quenched with water (50 mL), extracted with EtOAc (50 mL×3), the combined extracts was washed with brine (100 mL), dried over anhydrous Na$_2$SO$_4$, filtered, the filtrate was concentrated under reduced pressure to give a residue. The residue was purified by Combi flash to give 1.60 g of compound A4 as a white powder.

Procedure for Synthesis of A5

To a suspension of compound A4 (800 mg, 2.33 mmol) and NH$_4$Cl (1.25 g, 23.3 mmol) in EtOH (15 mL) was added Zn (1.53 g, 23.3 mmol), the mixture was stirred at 50° C. for 17 hours. TLC and LCMS showed the reaction was completed. The mixture was filtered, the filter cake was washed with DCM (50 mL×2), the combined organic phase was concentrated under reduced pressure to give a residue, the residue was dissolved in DCM (100 mL), washed with water (50 mL×3), dried over anhydrous Na$_2$SO$_4$, filtered, the filtrate was concentrated under reduced pressure to give 650 mg of compound A5 as a yellow gum.

Scheme 4: Synthetic route for A9

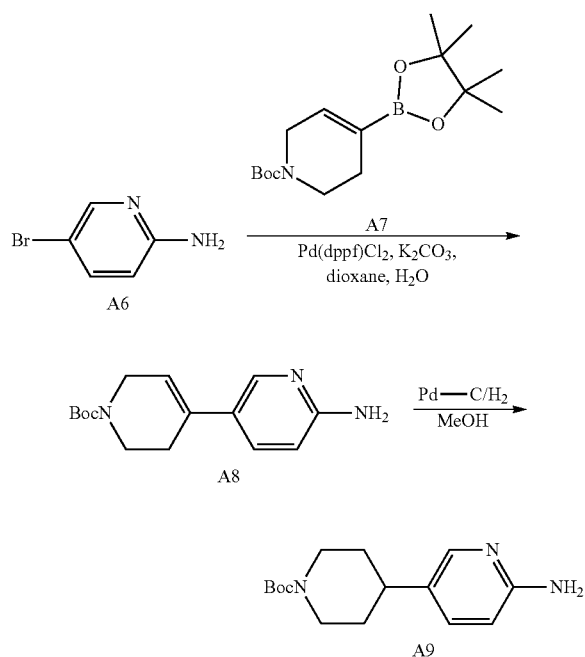

Procedure for Synthesis of A8

To a solution of compound A6 (1.00 g, 5.78 mmol) in H$_2$O (5 mL) and dioxane (10 mL) was added compound A7 (2.14 g, 6.94 mmol), K$_2$CO$_3$ (2.00 g, 14.5 mmol) and Pd(dppf)Cl$_2$ (422 mg, 0.578 mmol). The reaction mixture was stirred at 90° C. for 16 hour under N$_2$ atmosphere. LCMS showed 50.4% desired MS. The mixture was partitioned between DCM (50 mL) and H$_2$O (50 mL). The aqueous was extracted with DCM (50 mL). The combined organic extract was washed with water (50 mL×2), dried over anhydrous Na$_2$SO$_4$, filtered and concentrated under reduced pressure to give a residue. The residue was purified by Combi flash to give compound A8 (1.30 g) as a white powder.

Procedure for Synthesis of A9

To a suspension of compound A8 (1.30 g, 4.72 mmol) in MeOH (2 mL) was added Pd/C (0.13 g, 50% wet, 10% Pd), the mixture was stirred under H$_2$ balloon (15 psi) at 25° C. for 2 hours to give a black suspension. LCMS showed compound A8 was consumed, and desired MS was observed. The mixture was filtered and concentrated under reduced pressure to give compound A9 (1.20 g) as yellow powder Scheme 5: Synthetic route for A13

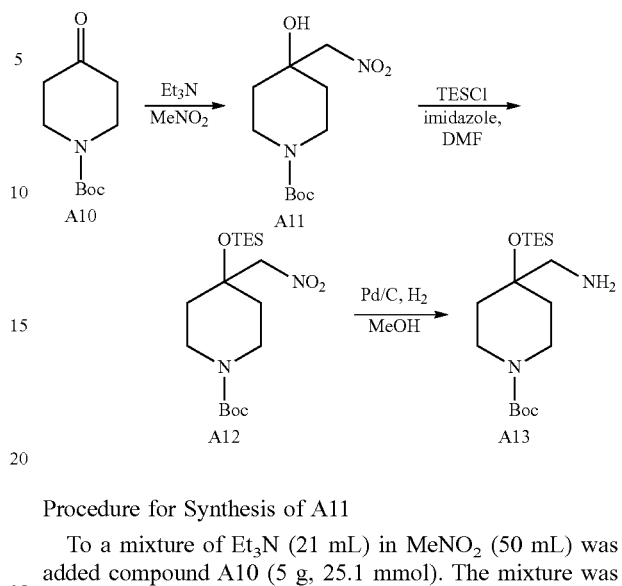

Procedure for Synthesis of A11

To a mixture of Et$_3$N (21 mL) in MeNO$_2$ (50 mL) was added compound A10 (5 g, 25.1 mmol). The mixture was stirred at 10-15° C. for 48 hours to give a yellow suspension. The suspension was diluted with EtOAc (100 mL) and washed with water (100 mL), saturated NH$_4$Cl (100 mL), brine (100 mL), dried over Na$_2$SO$_4$, filtered, concentrated under reduced pressure to give compound A11 (7.6 g) as a yellow solid.

Procedure for Synthesis of A12

To a mixture of compound A11 (2 g, 7.68 mmol), imidazole (2.62 g, 38.4 mmol) in DMF (5 mL) was added chloro(triethyl)silane (10 mL). The mixture was stirred at 70-80° C. for 12 hours to give a yellow mixture. The mixture was cooled to room temperature and diluted with water (50 mL). The aqueous phase was extracted with EtOAc (50 mL×3). The combined extracted phase was washed with brine (50 mL), dried over Na$_2$SO$_4$, filtered, concentrated under reduced pressure to give compound A12 (5 g) as yellow oil.

Procedure for Synthesis of A13

To a mixture of Pd/C (1 g, 10%) in MeOH (100 mL) was added compound A12 (4.9 g, 13.08 mmol). The suspension was degassed under vacuum and purged with H$_2$ several times. The mixture was stirred at 25° C. under H$_2$ (50 psi) for 30 hours to give a black mixture. Crude HNMR showed the reaction was completed. The mixture was filtered, the filtrate was concentrated under reduced pressure to give a yellow gum, which was purified by Combi flash to give compound A13 (2.3 g) as yellow oil.

Scheme 6: Synthetic route for A16

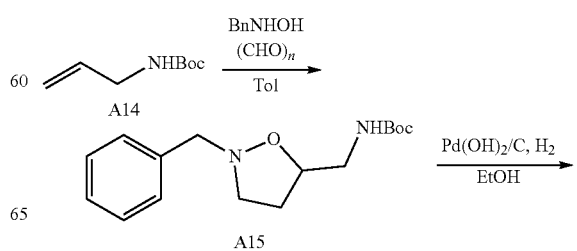

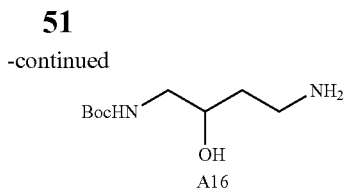

A16

Procedure for Synthesis of A15

The mixture of A14 (1.5 g, 9.54 mmol), N-benzylhydroxylamine (2.28 g, 14.3 mmol), (HCHO)n (2.15 g, 23.8 mmol) and TEA (1.45 g, 14.3 mmol, 2.0 mL) in toluene (100 mL) was refluxed for 20 hours. Much white solid was observed. LCMS showed the reaction was completed. Most of the solvent was removed under reduced pressure. The residue was partitioned between EtOAc (50 mL) and H$_2$O (50 mL). The aqueous phase was extracted with EtOAc (50 mL×2). The organic extract was washed with brine (100 mL×3), dried over anhydrous Na$_2$SO$_4$, filtered and concentrated under reduced pressure to give the crude product, which was purified by combi flash to give compound A15 (2.05 g) as a pale-yellow solid.

Procedure for Synthesis of A16;

To a solution of A15 (1.5 g, 5.13 mmol) in EtOH (10 mL) was added Pd(OH)$_2$/C (0.5 g, 20% purity). The reaction suspension was purged with H$_2$ (balloon, 15 psi) for several times and stirred at 15° C. for 16 hours to give a black mixture. TLC (PE/EA=1/1) showed new spot. The reaction was diluted with MeOH (200 mL) and filtered over celite pad. The filtrate was concentrated under reduced pressure to give A16 (1.15 g, crude) as white solid.

Scheme 7: Synthetic route for A18

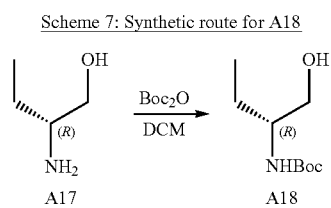

Procedure for Synthesis of A18

To a mixture of A17 (500 mg, 5.61 mmol) in DCM (10 mL) was added Boc$_2$O (1.35 g, 6.17 mmol), the mixture was stirred at 25° C. for 16 hours to give a colorless oil. TLC showed the reaction was completed. The mixture was concentrated under reduced pressure to give compound A18 (1.2 g, crude) as a colorless oil.

Scheme 8: Synthetic route for A21

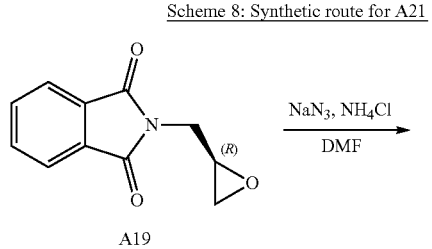

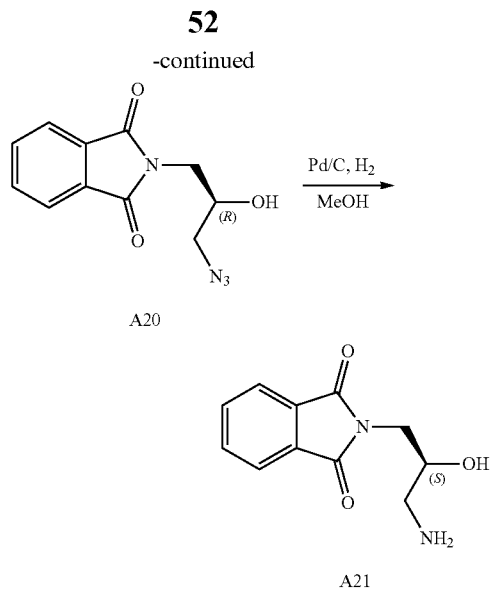

Procedure for Synthesis of A20

To the solution of compound A19 (500 mg, 2.46 mmol) in DMF (5 mL) was added NaN$_3$ (319 mg, 4.92 mmol) and NH$_4$Cl (158 mg, 2.95 mmol). The mixture was stirred at 80° C. for 3 hours to give a yellow mixture. LCMS showed the reaction was completed. The mixture was partitioned between EtOAc (30 mL) and H$_2$O (20 mL). The aqueous phase was extracted with EtOAc (30 mL×2). The combined organic extract was dried over anhydrous Na$_2$SO$_4$, filtered and concentrated under reduced pressure to give compound A20 (820 mg, crude) as a yellow oil.

Procedure for Synthesis of A21

To a mixture of compound A20 (820 mg, 3.33 mmol) in MeOH (10 mL) was added Pd/C (100 mg). The mixture was stirred at 25° C. for 16 hours to give a black mixture. TLC and LCMS showed the reaction was completed. The mixture was filtered. The filtrate was concentrated under reduced pressure to afford compound A21 (680 mg, crude) as a yellow oil.

Scheme 9: Synthetic route for A26

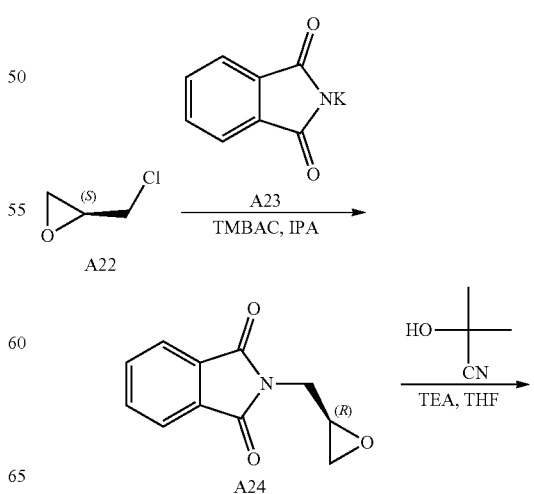

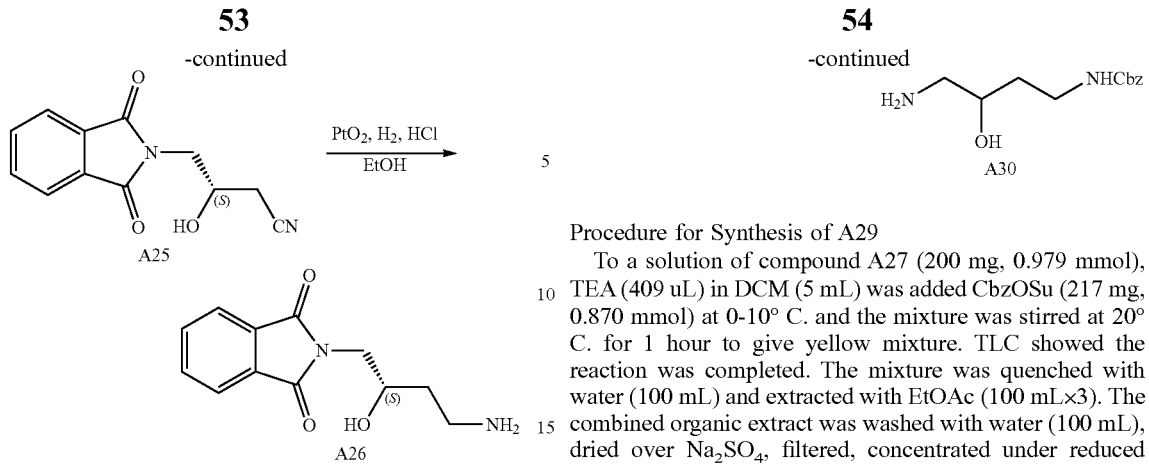

Procedure for Synthesis of A24

To a mixture of A23 (3.34 g, 18.0 mmol) and TMBAC (335 mg, 1.80 mmol) in IPA (50 mL) was added A22 (5.00 g, 54.1 mmol), the mixture was stirred at 20° C. for 72 hours to form a white mixture. TLC (eluent: PE/EtOAc=2/1) showed new spots. The mixture was partitioned between EtOAc (80 mL) and H₂O (80 mL). The aqueous phase was extracted with EtOAc (80 mL×2). The combined organic extract was washed with brine (80 mL×3), dried over anhydrous Na₂SO₄, filtered and concentrated under reduced pressure to give a residue, which was purified by combi flash to give A24 (1.1 g) as a white solid.

Procedure for Synthesis of A25

To a mixture of compound A24 (1 g, 4.92 mmol) in THF (10 mL) was added TEA (597 mg, 5.91 mmol, 822 uL) and 2-hydroxy-2-methyl-propanenitrile (502 mg, 5.91 mmol), the mixture was stirred at 75° C. for 12 hours to give a yellow mixture. LCMS showed the reactant was remained. The mixture was stirred for another 16 hours to give a brown mixture. TLC showed the reaction was completed. The mixture was partitioned between EtOAc (30 mL) and H₂O (20 mL). The aqueous phase was extracted with EtOAc (30 mL×2). The combined organic extract was dried over anhydrous Na₂SO₄, filtered and concentrated under reduced pressure to give a crude product. The crude product was purified by combi flash to afford compound A25 (450 mg) as an off-white solid.

Procedure for Synthesis of A26

To a mixture of A25 (40 mg, 0.17 mmol) in EtOH (10 mL) was added PtO₂ (4.0 mg, 0.017 mmol, 0.1 eq) and HCl (0.05 mL), the mixture was stirred at 25° C. for 1 hour to give a black mixture. TLC showed the reaction was completed. The mixture was filtered and concentrated under pressure to give compound A26 (40 mg, crude) as an off-white gum.

Procedure for Synthesis of A29

To a solution of compound A27 (200 mg, 0.979 mmol), TEA (409 uL) in DCM (5 mL) was added CbzOSu (217 mg, 0.870 mmol) at 0-10° C. and the mixture was stirred at 20° C. for 1 hour to give yellow mixture. TLC showed the reaction was completed. The mixture was quenched with water (100 mL) and extracted with EtOAc (100 mL×3). The combined organic extract was washed with water (100 mL), dried over Na₂SO₄, filtered, concentrated under reduced pressure to give a yellow oil, which was washed with PE (10 mL) to give compound A29 (310 mg) as yellow oil.

Procedure for Synthesis of A30

The compound A29 (290 mg) was followed the same procedure of B14 to obtain 270 mg of compound A30 as a yellow gum.

Commercial available reagent were used for group A such as tert-butyl piperidin-3-ylcarbamate, tert-butyl 4-aminopiperidine-1-carboxylate, piperidine-4-carboxamide, tert-butyl (4-methylpiperidin-4-yl)carbamate, tert-butyl piperidin-4-ylcarbamate, benzyl piperidin-4-ylcarbamate, piperidin-4-ol, piperazine, piperazin-2-one, tetrahydro-2H-pyran-4-amine, tert-butyl 3-methylpiperazine-1-carboxylate, N-(piperidin-4-yl)acetamide, 1-methylpiperidin-4-ol, tert-butyl ((4-hydroxypiperidin-4-yl)methyl)carbamate, tert-butyl (morpholin-2-ylmethyl)carbamate, tert-butyl 4-(aminomethyl)piperidine-1-carboxylate, tert-butyl (R)-3-hydroxypiperidine-1-carboxylate, tert-butyl 4-(piperidin-4-yl)piperazine-1-carboxylate, tert-butyl (piperidin-4-ylmethyl)carbamate, 1,2,3,4-tetrahydro-2,6-naphthyridine, tert-butyl (4-methylpiperidin-4-yl)carbamate, tert-butyl ((4-fluoropiperidin-4-yl)methyl)carbamate, (S)-2-(piperidin-2-yl)ethan-1-ol, (S)-piperidin-2-ylmethanol, (1s,4s)-4-aminocyclohexan-1-ol, (1r,4r)-4-aminocyclohexan-1-ol, 4-methoxycyclohexan-1-amine, (tetrahydro-2H-pyran-4-yl)methanamine, morpholine, cyclohexane-1,4-diol, tert-butyl (S)-3-(hydroxymethyl)piperazine-1-carboxylate, tert-butyl 2-(aminomethyl)morpholine-4-carboxylate, 1H-indol-4-amine, 4-(trifluoromethoxy)piperidine, 4-ethoxypiperidine, 4-isopropoxypiperidine, 4-methoxycyclohexan-1-amine, 4-isopropoxycyclohexan-1-amine, 1H-pyrrol-3-amine and tert-butyl 4-(hydroxymethyl)piperidine-1-carboxylate.

General Schemes of Group B

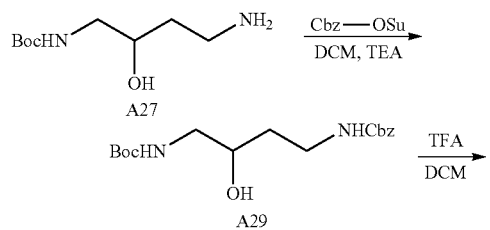

Scheme 10: Synthetic route for A29

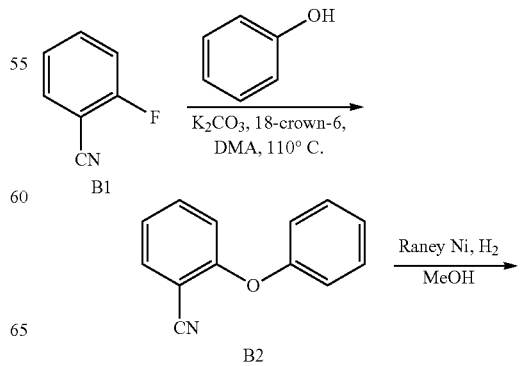

Scheme 11: Synthetic route for B3

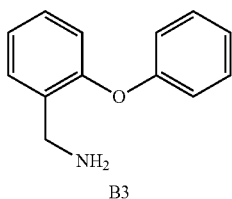

B3

Procedure for Synthesis of B2

To a solution of compound B1 (5.00 g, 41.3 mmol) and phenol (5.80 g, 61.9 mmol) in DMA (50 mL) was added 18-crown-6 (1.10 g, 4.13 mmol) and K$_2$CO$_3$ (11.4 g, 82.6 mmol), the reaction mixture was stirred at 110° C. for 16 hours to give a brown mixture. LCMS showed the reaction was complete. 1b the reaction mixture was added H$_2$O (50 mL), the reaction mixture was extracted with EtOAc (50 mL×3), the combined organic phase was washed with H$_2$O (40 mL×2) and brine (100 mL), dried over anhydrous Na$_2$SO$_4$, filtered and concentrated under reduced pressure to give a brown oil, which was purified by Combi Flash to give compound B2 (9.80 g) as a yellow oil.

Procedure for Synthesis of B3

To a solution of compound B2 (1.00 g, 5.12 mmol) in MeOH (30 mL) was added Raney-Ni (43.9 mg, 0.512 mmol) and NH$_3$·H$_2$O (3 mL), the reaction mixture was stirred under H$_2$ balloon (15 psi) at 15° C. for 16 hours to give a black suspension. TLC showed the reaction was complete. The reaction mixture was filtered, the filtrate was concentrated under reduced pressure to remove MeOH. The residue was diluted with DCM (20 mL), dried over anhydrous Na$_2$SO$_4$, filtered and concentrated under reduce pressure to give compound B3 (820 mg) as a yellow oil.

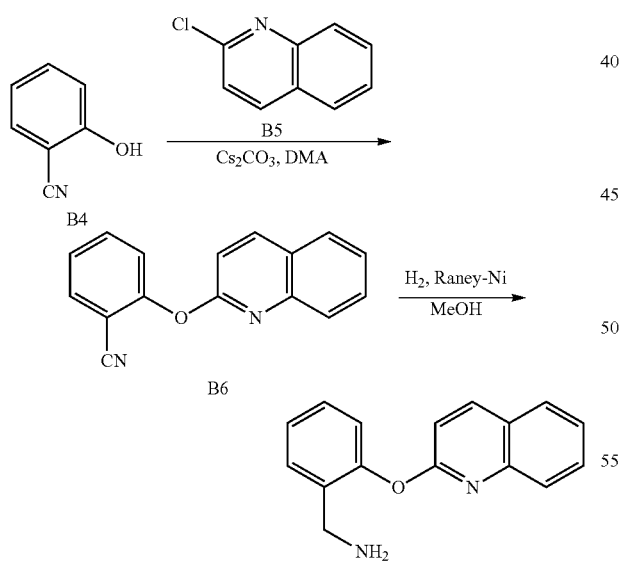

Procedure for Synthesis of B6

To a solution of 2-hydroxybenzonitrile B4 (200 mg, 1.68 mmol) and 2-chloroquinoline B5 (261 mg, 1.60 mmol) in DMA (3.0 mL) was added Cs$_2$CO$_3$ (1.04 g, 3.20 mmol). The reaction mixture was stirred at 100° C. for 5 hours. TLC showed the reaction was completed. The residue was partitioned between water (20 mL) and EtOAc (20 mL). The organic layer was washed with water (10 mL×2), brine (10 mL), dried over anhydrous Na2SO4, and concentrated under reduced pressure to give a residue. The residue was purified by Combi flash to give compound B6 (80 mg) as a yellow powder.

Procedure for Synthesis of B7

The compound B6 (80 mg) was followed the same procedure of B3 to obtain 64 mg of compound B7 as a yellow powder.

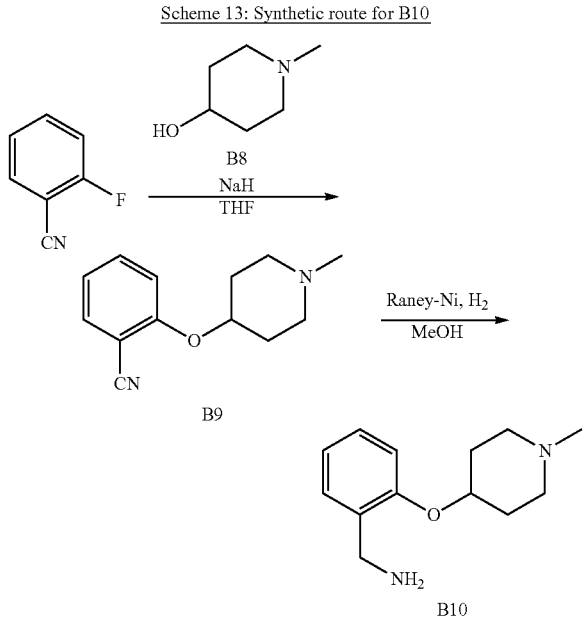

Procedure for Synthesis of B9

To a mixture of NaH (198 mg, 4.96 mmol, 60% in mineral oil) in THF (3 mL) was added a solution of compound B8 (571 mg, 4.96 mmol) in THF (3 mL) dropwise. After the reaction mixture was stirred for 5 minutes, to the mixture was added 2-fluorobenzonitrile (500 mg, 4.13 mmol). The reaction mixture was stirred at 40° C. for 2 hours. LCMS showed the reaction was completed. The reaction mixture was quenched by water (10 mL), extracted with DCM (10 mL×2). The organic layer was washed with water (10 mL), dried over anhydrous Na2SO4, filtered, concentrated under reduced pressure. The residue was purified by Combi flash to give compound B9 (432 mg) as a light brown oil.

Procedure for Synthesis of B10

The compound B9 (430 mg) was followed the same procedure of B102 to obtain 410 mg of compound B10 as a white powder.

Scheme 14: Synthetic route for B14

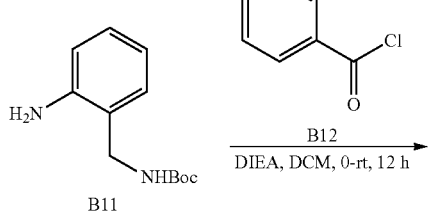

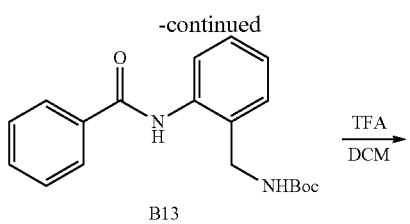

B13

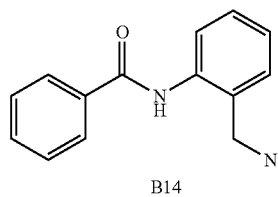

B14

Procedure for Synthesis of B13

To a solution of compound B11 (150 mg, 0.675 mmol) and compound B12 (114 mg, 0.81 mmol) in DCM (10 mL) was added DIPEA (174 mg, 1.35 mmol). The resulting mixture was stirred at 20° C. for 12 hours to give yellowish solution. TLC showed the reaction was completed, one major spot was formed. The reaction mixture was quenched by addition $H_2O$ (30 mL) and extracted with DCM (30 mL×2). The combined organic layers were washed with brine (10 mL), dried over $Na_2SO_4$, filtered and concentrated under reduced pressure to give a residue. The residue was purified by Combi flash to obtain compound B13 (200 mg) as a white solid.

Procedure for Synthesis of B14

To a solution of compound B13 (200 mg, 0.613 mmol) in DCM (7 mL) was added TFA (3 mL). The resulting mixture was stirred at 20° C. for 1 hour to give yellow solution. TLC showed the reaction was completed. The reaction mixture was concentrated under reduced pressure to give compound B14 (130 mg) as a yellow oil.

Scheme 15: Synthetic route for B18

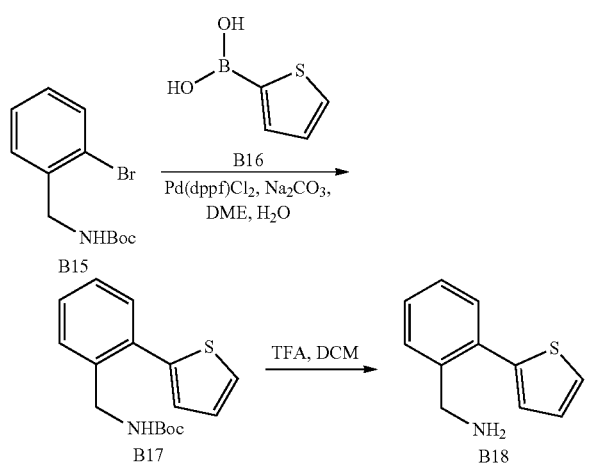

Procedure for Synthesis of B17

To a solution of compound B15 (1.00 g, 3.49 mmol) and compound B16 (536 mg, 4.19 mmol) in DME (10 mL) was added Pd(dppf)Cl$_2$ (128 mg, 0.174 mmol) and Na$_2$CO$_3$ (370 mg, 3.49 mmol) in H$_2$O (2.5 mL), the reaction mixture was stirred at 90° C. for 3 hours to give a black suspension. TLC showed the reaction was complete. To the reaction solution was added H$_2$O (10 ml), extracted with EtOAc (10 mL×2), the organic layer was washed with brine (10 mL), dried over anhydrous Na$_2$SO$_4$, filtered, concentrated under reduced pressure to give a brown oil, which was purified by Combi Flash to give compound B17 (705 mg) as a yellow oil.

Procedure for Synthesis of B18

The compound B17 (350 mg) was followed the same procedure of B14 to obtain 220 mg of compound B18 as a yellow powder.

Scheme 16: Synthetic route for B21

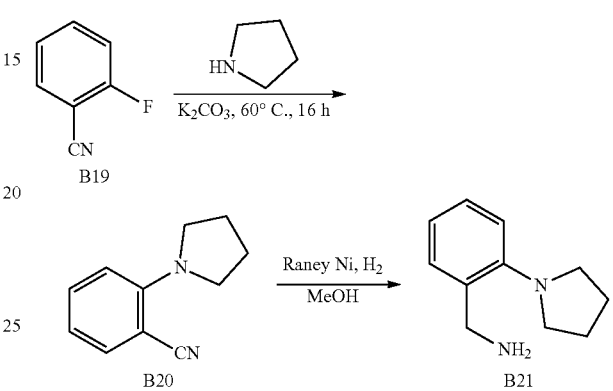

Procedure for Synthesis of B20

A mixture of compound B19 (2.00 g, 16.5 mmol), pyrrolidine (1.29 g, 18.1 mmol), K$_2$CO$_3$ (4.56 g, 33.0 mmol) in DMF (10 mL) was stirred at 60° C. for 16 hours. TLC showed that the reaction was completed. The mixture was poured into water (100 mL). The mixture was extracted with EtOAc (30 mL×3), the combined mixture were washed with water (50 mL×2), brine (50 mL×2), dried over anhydrous Na$_2$SO$_4$, filtered and concentrated under reduced pressure to give compound B20 (2.78 g) as a colorless oil.

Procedure for Synthesis of B21

The compound B20 (1.5 g) was followed the same procedure of B3 to obtain 1.5 g of compound B21 as a colorless oil.

Scheme 17: Synthethic route for B24

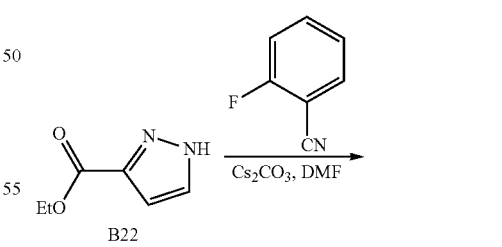

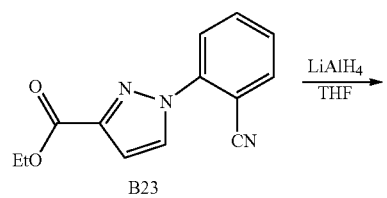

-continued

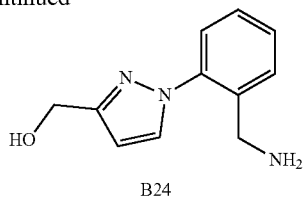

B24

Procedure for Synthesis of B23

To a solution of compound B22 (5 g, 35.7 mmol) and Cs$_2$CO$_3$ (29.1 g, 89.2 mmol) in DMF (50 mL) was added 2-fluorobenzonitrile (6.48 g, 53.5 mmol, 5.69 mL). The reaction mixture was stirred at 25° C. for 16 hours to give yellow mixture. TLC showed the reaction was completed. The reaction mixture was quenched by addition H$_2$O (200 mL) and extracted with EtOAc (150 mL×2). The combined organic layers was dried over Na$_2$SO$_4$, filtered and concentrated under reduced pressure to give crude product. The crude product was purified by silica gel column to give compound B23 (5 g) as a white powder.

Procedure for Synthesis of B24

To a solution of compound B23 (200 mg, 0.829 mmol) in THF (2 mL) was added LiAlH$_4$ (126 mg, 3.32 mmol) at 0° C. under N$_2$ atmosphere. The reaction mixture was stirred at 25° C. for 2 hours to give yellow solution. LCMS showed the reaction mixture was completed. The reaction was quenched by water (1 mL) and NaOH aqueous (1 mL, 2.0 M) slowly at 5° C. The mixture was stirred at 5° C. for 10 minutes. The mixture was filtered, the filtrate was extracted with EtOAc (5 mL×2). The combined organic phase was washed with brine (5 mL), dried over anhydrous Na$_2$SO$_4$, filtered and concentrated to give crude compound B24 (180 mg) as a light yellow gum Procedure for Synthesis of B26

To a solution of compound B25 (5 g, 35.7 mmol) in THF (50 mL) was added MeMgBr (3 M, 47.6 mL) dropwise at 0-5° C. under N$_2$ atmosphere. The resulting mixture was stirred at 10° C. for 15 hours to form a white suspension. TLC showed the reaction was completed. The mixture was poured into saturated aqueous NF$_4$Cl (50 mL). The mixture was extracted with EtOAc (50 mL×3). The combined organic extract was washed with brine (80 mL×2), dried over anhydrous Na$_2$SO$_4$, filtered and concentrated under reduced pressure to give compound B26 (2.6 g) as a white solid.

Procedure for Synthesis of B27

To a mixture of compound B26 (2.6 g, 20.6 mmol) and 2-fluorobenzonitrile (3.00 g, 24.7 mmol) in DMF (50 mL) was added Cs$_2$CO$_3$ (13.4 g, 41.2 mmol). The mixture was stirred at 15° C. for 15 hour's to form a white suspension. TLC showed the reaction was completed. The mixture was partitioned between EtOAc (150 mL) and H$_2$O (150 mL). The aqueous phase was extracted with EtOAc (150 mL×2). The combined organic extracts were washed with brine (100 mL×3), dried over anhydrous Na$_2$SO$_4$, filtered and concentrated under reduced pressure to give the crude product, which was purified by combi flash to give compound B27 (3.6 g) as a white solid.

Procedure for Synthesis of B28

To a solution of compound B27 (3.6 g, 15.84 mmol) in MeOH (100 mL) was added Raney-Ni (1 g, in water) under N$_2$ atmosphere. The suspension was degassed under vacuum and purged with H$_2$ several times. The mixture was stirred under H$_2$ (15 psi) at 20° C. for 15 hours to form a black suspension. TLC showed the reaction was completed. The reaction mixture was filtered over a pad of celite. The filter cake was washed with MeOH (80 mL). The filtrate was concentrated under reduced pressure to give compound B28 (3.5 g) as a colorless gum.

Scheme 18: Synthetic route for B28

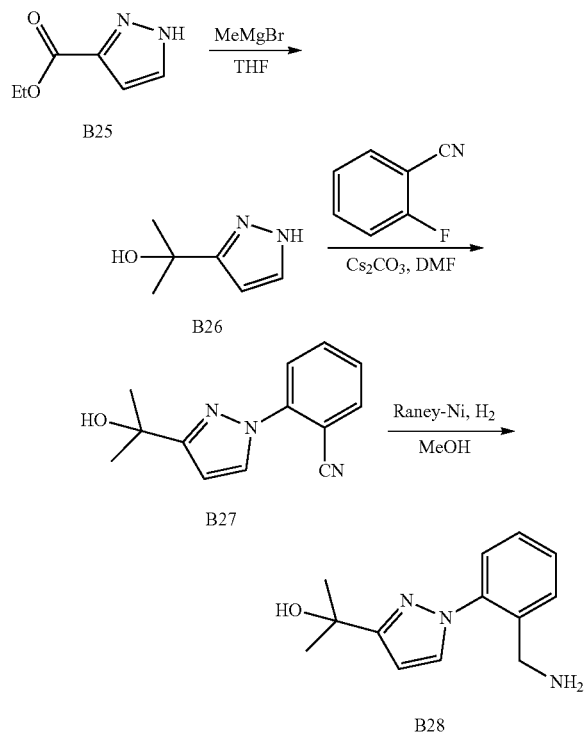

Scheme 19: Synthetic route for B31

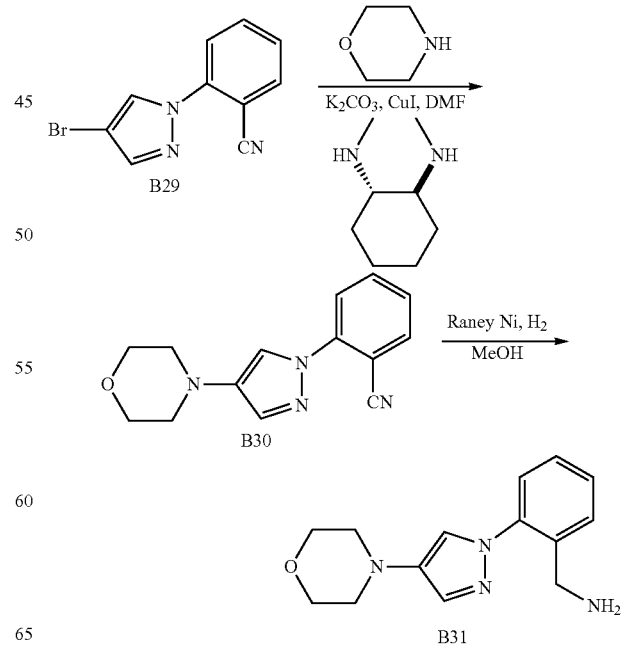

Procedure for Synthesis of B30

To a mixture of morpholine (2.63 g, 30.2 mmol) and compound B29 (500 mg, 2.02 mmol) in toluene (5 mL) was added XPhos (192 mg, 0.403 mmol), Cs$_2$CO$_3$ (1.64 g, 5.04 mmol) and Pd$_2$(dba)$_3$ (185 mg, 0.202 mmol), the reaction mixture was stirred at 110° C. for 16 hours under N$_2$ atmosphere to give a black suspension. LCMS (Rt=0.908 min) shows the reaction was completed. The reaction mixture was partitioned between EtOAc (80 mL) and water (80 mL). The aqueous phase was extracted with EtOAc (70 mL×2). The combined organic layer was washed with water (100 mL×2), brine (100 mL×2) and dried over anhydrous Na$_2$SO$_4$, filtered and concentrated under reduced pressure to give residue. The reaction mixture was purified by Combi flash to give compound B30 (190 mg) as brown gum.

Procedure for Synthesis of B31

The compound B30 (190 mg) was followed the same procedure of B3 to obtain 170 mg of compound B31 as a colorless gum.

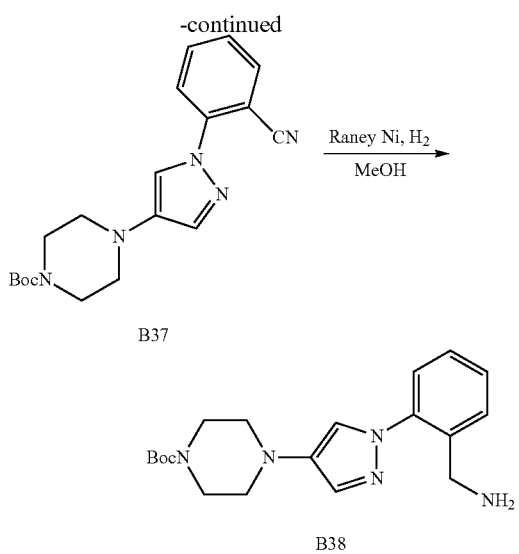

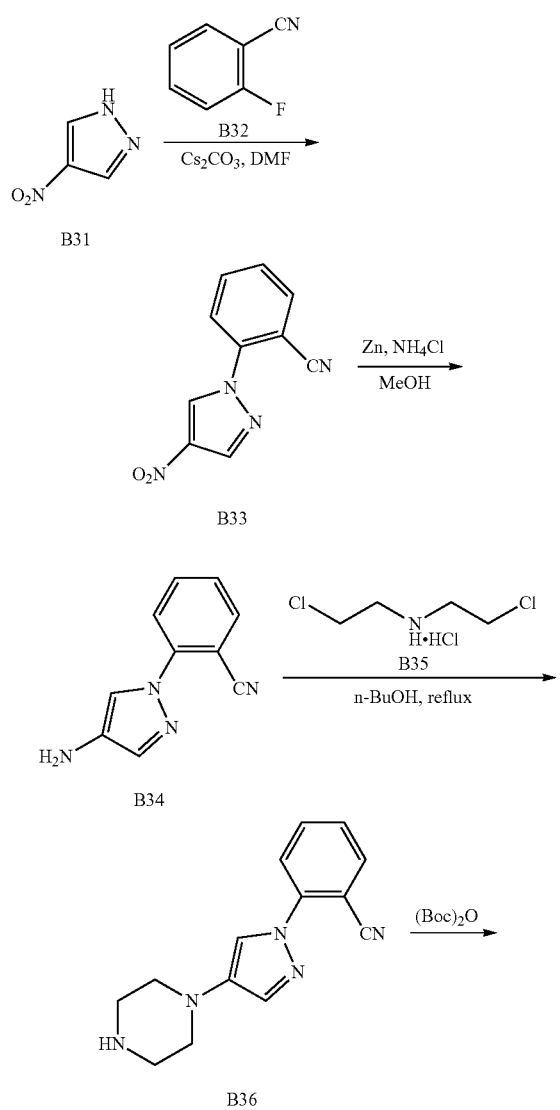

Procedure for Synthesis of B33

To a mixture of compound B31 (10 g, 37.7 mmol) in DMF (5 mL) was added compound B32 (9.13 g, 75.3 mmol). The mixture was stirred at 50° C. for 12 hours to give a yellow suspension. LCMS showed the reaction was completed. The mixture was added with water (30 mL×2), which was filtered and concentrated under reduced pressure to give a yellow powder, which was washed with PE (50 mL) to give compound B32 (7 g) as a brown powder.

Procedure for Synthesis of B34

To a mixture of compound B33 (4 g, 18.7 mmol) in MeOH (30 mL) was added NH$_4$Cl (9.99 g, 186 mmol) and Zn (12.2 g, 186 mmol). The mixture was stirred at 25° C. for 15 hours to give an off-white suspension. LCMS showed the reaction was completed. After filtration, the filter cake was washed with MeOH (50 mL), the filtrate was partitioned between DCM (50 mL) and water (50 mL). The aqueous phase was extracted with DCM (50 mL×2), the combined extracted phase was washed with water (50 mL×2), dried over anhydrous Na$_2$SO$_4$, concentrated under reduced pressure to give compound B34 (2 g) as a yellow powder.

Procedure for Synthesis of B36

To a mixture of compound B34 (2 g, 10.8 mmol) in n-BuOH (20 mL) was added compound B35 (1.94 g, 10.8 mmol). The reaction was refluxed at 117° C. for 48 hours to give a yellow suspension. LCMS showed the reaction was completed. The mixture was added with NaOH (868 mg, 21.7 mmol) and H$_2$O (10 mL), dioxane (10 mL), tert-butoxycarbonyl tert-butyl carbonate (3.56 g, 16.2 mmol). The mixture was stirred at 25° C. for 2 hours to give a yellow suspension. LCMS (Rt=1.268 min) showed the reaction was completed. The mixture was partitioned between DCM (50 mL) and water (50 mL). The aqueous phase was extracted with DCM (50 mL×2), the combined extracted phase was washed with water (50 mL×2), dried over anhydrous Na$_2$SO$_4$ concentrated under reduced pressure to give a yellow gum, which was purified by Combi flash to give compound B36 (400 mg) as a yellow oil.

Procedure for Synthesis of B37

The compound B36 (1.0 g) was followed the same procedure of B72 to obtain 400 mg of compound B37 as a yellow solid.

Procedure for Synthesis of B38

The compound B37 (200 mg) was followed the same procedure of B3 to obtain 200 mg of compound B38 as a yellow powder.

Scheme 21: Synthetic route for B42

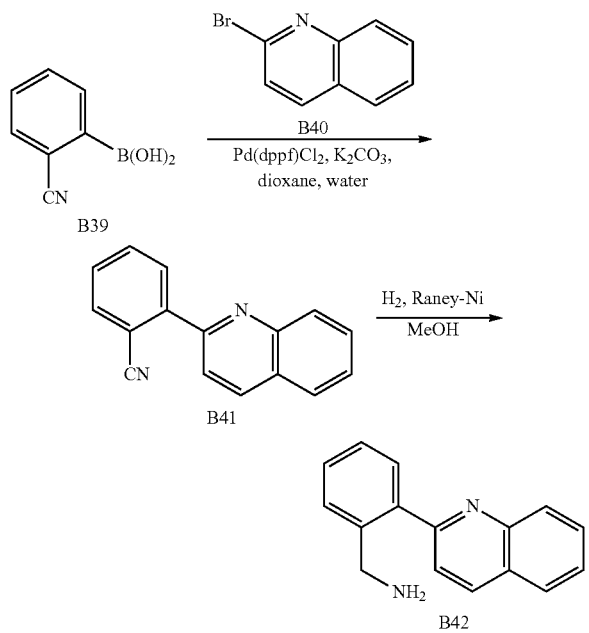

Procedure for Synthesis of B41

To a mixture of compound B39 (423 mg, 2.88 mmol), compound B40 (500 mg, 2.40 mmol), K$_2$CO$_3$ (663 mg, 4.80 mmol) in dioxane (5 mL)/H$_2$O (1 mL) was added Pd(dppf)Cl$_2$ (175 mg, 0.24 mmol). The mixture was stirred at 110° C. for 16 hours. TLC showed a new spot. The mixture was poured into water (20 mL). The mixture was extracted with DCM (30 mL×3). The combined mixture was washed with water (50 mL×2), dried over anhydrous Na$_2$SO$_4$, then filtered and concentrated under reduced pressure to give a residue (brown gum). The residue was purified by Combi Flash to give compound B41 (200 mg) as a red powder.

Procedure for Synthesis of B42

The compound B41 (200 mg) was followed the same procedure of B3 to obtain 200 mg of compound B42 as a brown oil.

Scheme 22: Synthetic route for B46

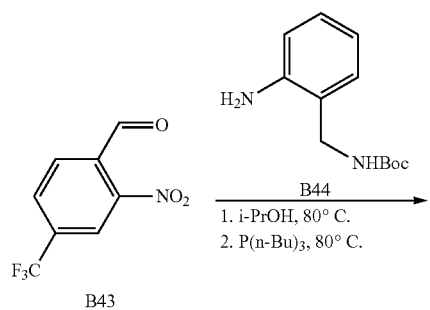

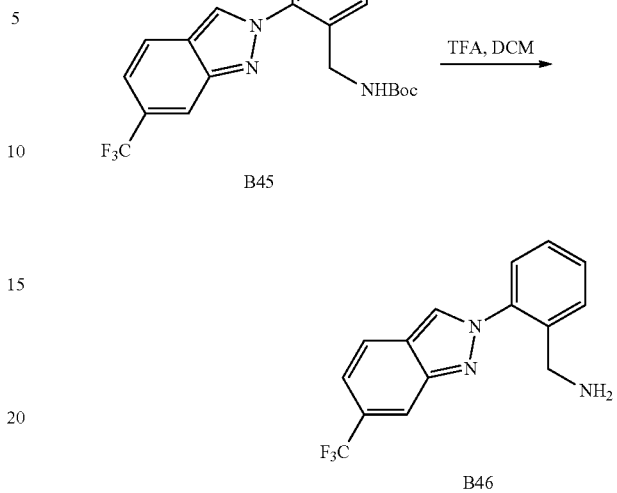

Procedure for Synthesis of B45

To a solution of compound B43 (300 mg, 1.37 mmol) and compound B44 (335 mg, 1.51 mmol) in i-PrOH (10 mL) was heated at 80° C. and stirred for 4 hours, then tributylphosphane (1.39 g, 6.85 mmol) was added to the mixture and stirred for another 12 hours to give yellow solution. LCMS and TLC showed the reaction was completed. The reaction mixture was quenched by addition H$_2$O (50 mL) and extracted with EtOAc (50 mL×2). The combined organic layers were washed with brine (20 mL×2), dried over Na$_2$SO$_4$, filtered and concentrated under reduced pressure to give a residue. The residue was purified by Combi flash to obtain compound B45 (524 mg) as a yellow solid.

Procedure for Synthesis of B46

The compound B45 (524 mg) was followed the same procedure of B14 to obtain 430 mg of compound B46 as a yellow solid.

Scheme 23: Synthetic route for B50

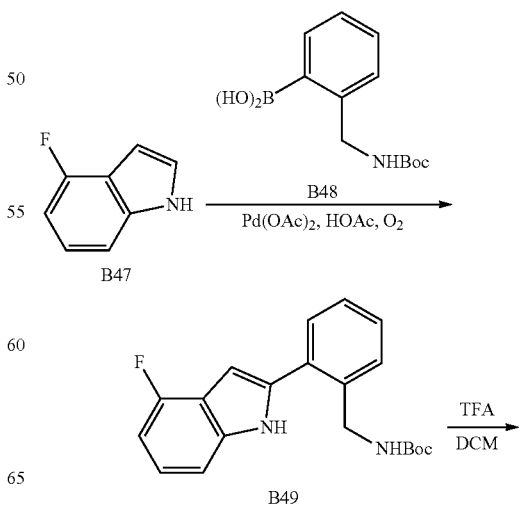

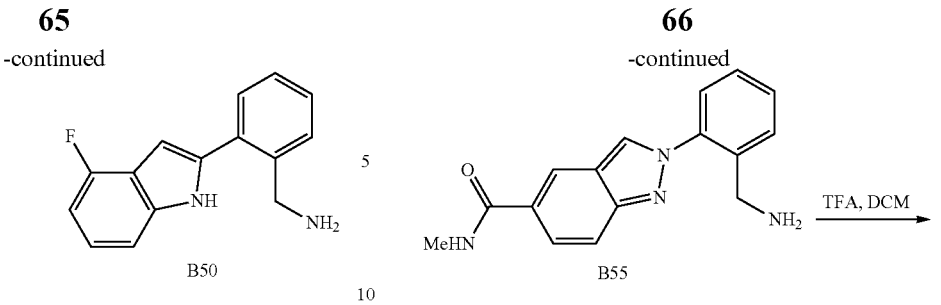

Procedure for Synthesis of B49

To a solution of compound B47 (500 mg, 3.70 mmol) in AcOH (10 mL) was added compound B48 (1.11 g, 4.44 mmol), Pd(OAc)$_2$ (415 mg, 1.85 mmol), then the reaction mixture was stirred at 25° C. under O$_2$ (15 psi) for 16 hours to give a black suspension. LCMS and TLC showed the reaction was completed. The reaction was poured into water (50 mL) and partitioned between EtOAc (100 mL) and water (100 mL). The aqueous phase were extracted with EtOAc (100 mL×2), The combined organic layers were washed with water (100 mL×2), brine (100 mL), dried over anhydrous Na$_2$SO$_4$, filtered and concentrated under reduced pressure to give a residue. The residue was purified by Combi flash to give compound B49 (240 mg, 0.705 mmol) as a yellow gum.

Procedure for Synthesis of B50

The compound B49 (240 mg) was followed the same procedure of B14 to obtain 170 mg of compound B50 as a yellow gum.

Scheme 24: Synthetic route for B56

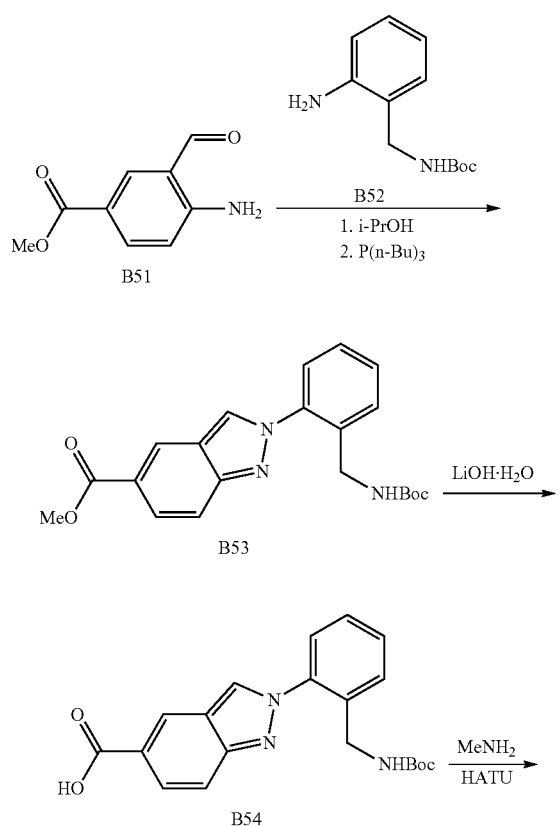

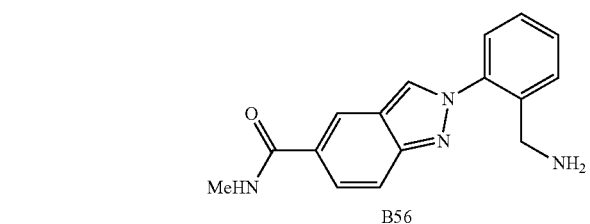

Procedure for Synthesis of B53

To a solution of compound B51 (600 mg, 3.35 mmol) in i-PrOH (10 mL) was added compound B52 (744 mg, 3.35 mmol). The reaction solution was heated to 80° C. and stirred for 3 hours to give a yellow solution. The reaction was cooled to 30-40° C. and tributylphosphane (2.03 g, 2.48 mL) was added and stirred for another 16 hours at 80° C. to give a black solution. TLC showed the reaction was completed. The reaction mixture was quenched by addition H$_2$O (100 mL) and extracted with EtOAc (100 mL×2). The combined organic layers were washed with saturated NH$_4$Cl (50 mL) and brine (10 mL×2), dried over Na$_2$SO$_4$, filtered and concentrated under reduced pressure to give a residue. The residue was purified by Combi flash to give compound B53 (784 mg) as a yellow solid.

Procedure for Synthesis of B54

To a solution of compound B53 (784 mg, 2.06 mmol) in MeOH (5 mL) and H$_2$O (1 mL) was added LiOH·H$_2$O (431 mg, 10.3 mmol). The resulting mixture was stirred at 20° C. for 12 hrs to give yellow suspension. TLC showed the reaction was completed. The reaction mixture was concentrated most of MeOH under reduced pressure, then acidified with 1M HCl to pH ~4 and lots of white solid was precipitated, the mixture was filter under reduced pressure to give filter cake compound B54 (724 mg) as a white solid.

Procedure for Synthesis of B55

To a solution of compound B54 (625 mg, 1.70 mmol) and methanamine (230 mg, 3.40 mmol) in DMF (10 mL) was added Et$_3$N (516 mg, 5.10 mmol) and HATU (647 mg, 1.70 mmol, 1 eq). The resulting mixture was stirred at 20° C. for 2 hr to give yellow solution. TLC showed the reaction was completed, one main new spot was formed. The reaction mixture was quenched with H$_2$O (20 mL) and lots of white solid was precipitated, then filtered under reduced pressure to give filter cake compound B55 (693 mg) as a white solid.

Procedure for Synthesis of B56

The compound B55 (200 mg) was followed the same procedure of B14 to obtain 130 mg of compound B56 as a yellow oil.

Scheme 25: Synthetic route for 61

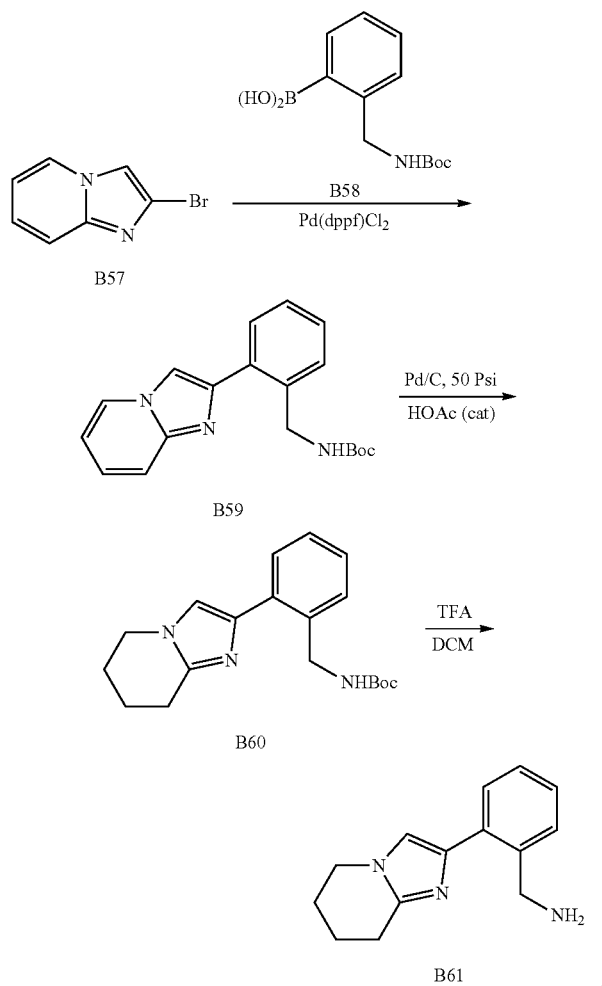

Scheme 26: Synthetic route for B66

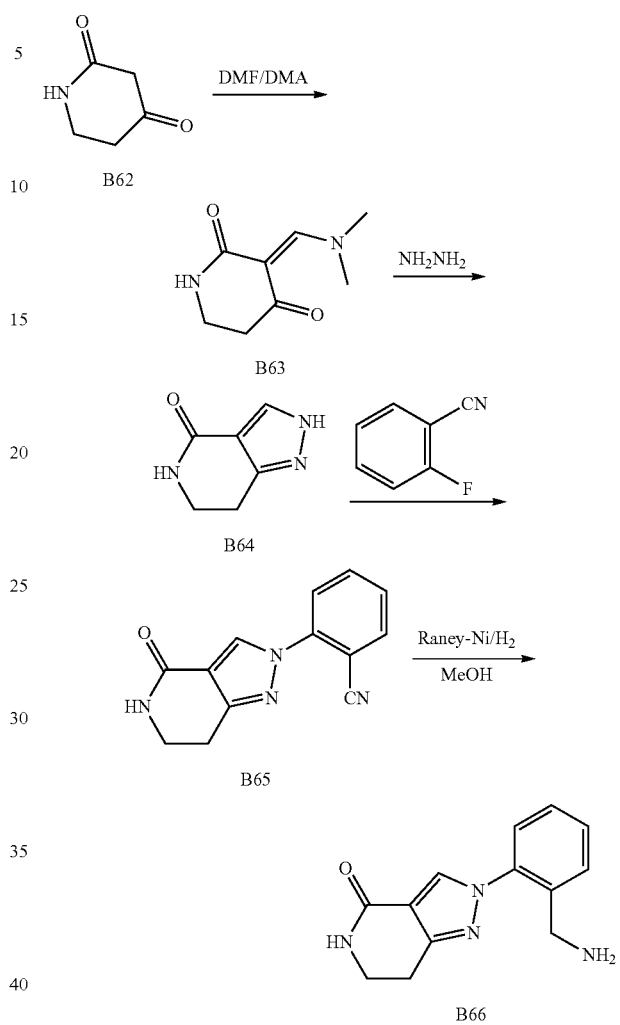

Procedure for Synthesis of B59

The compound B57 (500 mg) was followed the same procedure of B41 to obtain 840 mg of compound B59 as a yellow solid.

Procedure for Synthesis of B60

To a solution of compound B59 (350 mg, 1.08 mmol) in MeOH (10 mL) was added Pd/C (20 mg, 10% purity, wet) under $N_2$ atmosphere. The suspension was degassed under vacuum and purged with $H_2$ several times. The mixture was stirred under $H_2$ (50 psi) at 20° C. for 12 hours to give black suspension, LCMS showed the reaction didn't work, the reaction was added acetic acid (0.1 mL), The suspension was degassed under vacuum and purged with $H_2$ several times. The mixture was stirred under $H_2$ (50 psi) at 20° C. for 12 hours to give black suspension. LCMS showed the reaction was completed. The reaction mixture was filtered by pad celite and concentrated under reduced pressure to give compound B60 (450 mg, crude) as yellowish oil, the crude product was used in the next step without purification.

Procedure for Synthesis of B61

The compound B60 (450 mg) was followed the same procedure of B14 to obtain 330 mg of compound B61 as a yellow oil.

Procedure for Synthesis of B63

A solution of compound B62 (1.00 g, 8.84 mmol) in DMF/DMA (20 mL) was heated at 110° C. and stirred for 2 hours to give red solution. The reaction mixture was concentrated under reduced pressure to give crude product compound B63 (1.20 g) as a red solid.

Procedure for Synthesis of B64

To a solution of compound B63 (700 mg, 4.16 mmol) in EtOH (10 mL) was added $NH_2NH_2 \cdot H_2O$ (208 mg, 4.16 mmol). The resulting mixture was heated at 100° C. and stirred for 16 hrs to give yellow solution. The reaction mixture was concentrated under reduced pressure to give compound B64 (550 mg) as a yellow solid.

Procedure for Synthesis of B65

The compound B64 (400 mg) was followed the same procedure of B33 to obtain 445 mg of compound B65 as a yellow solid.

Procedure for Synthesis of B66

The compound B65 (100 mg) was followed the same procedure of B3 to obtain 91 mg of compound B66 as a white powder.

69

Scheme 27: Synthetic route for B70

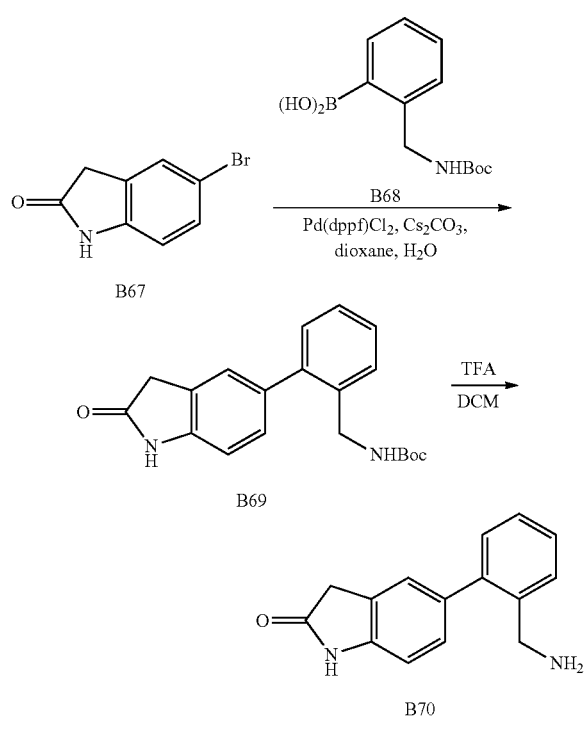

Procedure for Synthesis of B69

To a mixture of compound B67 (300 mg, 1.41 mmol), compound B68 (710 mg, 2.83 mmol), Cs$_2$CO$_3$ (1.15 g, 3.54 mmol) in dioxane (3 mL), H$_2$O (0.9 mL) was added Pd(dppf)Cl$_2$ (104 mg, 0.141 mmol). The mixture was stirred at 100° C. under N2 atmosphere for 12 hours to give a brown suspension. LCMS showed the reaction was completed. The mixture was cooled to room temperature, partitioned between DCM (50 mL) and water (50 mL). The aqueous phase was extracted with DCM (30 mL×2). The combined extracted phase was washed with water (30 mL×2), dried over anhydrous Na$_2$SO$_4$, filtered and concentrated under reduced pressure to crude product as red oil, which was purified by Combi flash to give compound B69 (108 mg) as brown oil.

Procedure for Synthesis of B70

To a mixture of compound B69 (100 mg, 0.296 mmol) in DCM (4 mL) was added TFA (1 mL). The mixture was stirred at 15° C. for 20 minutes to give a yellow mixture. LCMS showed the reaction was completed. The mixture was concentrated under reduced pressure to give compound B70 (90 mg) as yellow oil.

Scheme 28: Synthetic route for B75

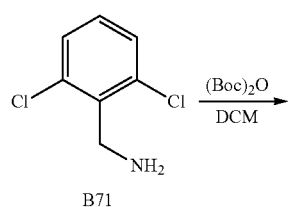

70

-continued

Procedure for Synthesis of B72

To a mixture of compound B71 (1 g, 5.68 mmol) in DCM (5 mL) was added Boc$_2$O (1.49 g, 6.82 mmol). The mixture was stirred at 25° C. for 2 hours to give a yellow mixture. LCMS showed the reaction was completed. The mixture was partitioned between DCM (50 mL) and water (50 mL). The aqueous phase was extracted with DCM (30 mL×2), the combined extracts was washed with water (50 mL×2), dried over anhydrous Na$_2$SO$_4$, filtered and concentrated under reduced pressure to give compound B72 (950 mg) as a white powder.

Procedure for Synthesis of B74

To a mixture of compound B72 (850 mg, 3.08 mmol), compound B73 (804 mg, 3.08 mmol) and Cs$_2$CO$_3$ (2.51 g, 7.69 mmol) in dioxane (5 mL) and H$_2$O (1.5 mL) was added Pd(dppf)Cl$_2$ (225 mg, 0.308 mmol), the mixture was stirred at 100° C. under N$_2$ atmosphere for 12 hours to give a red mixture. LCMS showed the reaction was completed. The mixture was cooled to room temperature and partitioned between DCM (50 mL) and water (50 mL). The aqueous phase was extracted with DCM (50 mL×2). The combined extracted phase was washed with water (50 mL×2), dried over anhydrous Na$_2$SO$_4$, filtered and concentrated under reduced pressure to give crude product, which was purified by Combi flash to give compound B74 (420 mg) as a white powder.

Procedure for Synthesis of B75

The compound B74 (230 mg) was followed the same procedure of B14 to obtain 170 mg of compound B75 as a yellow oil.

Scheme 29: Synthetic route for B81

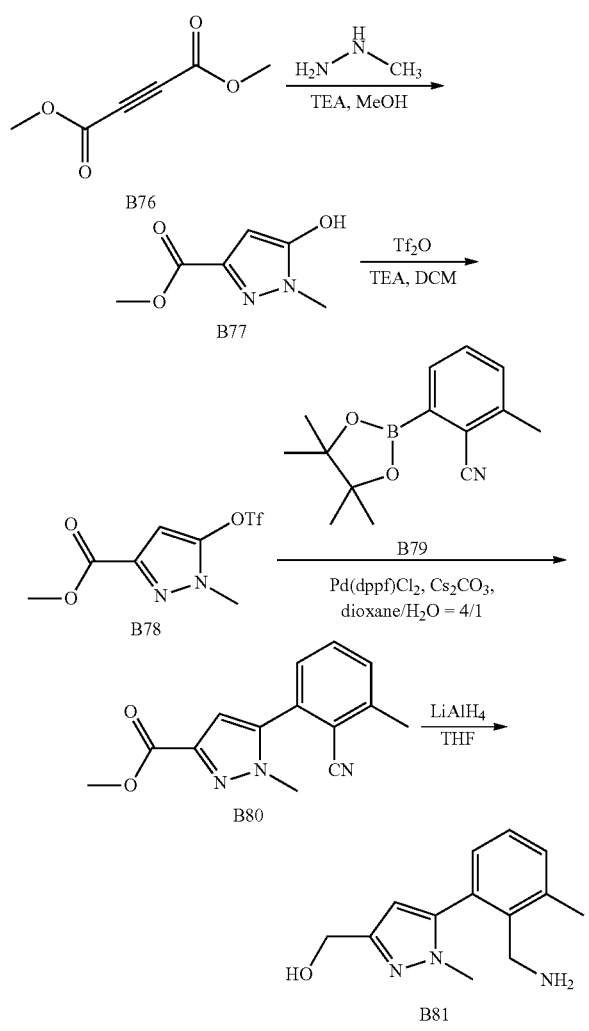

Procedure for Synthesis of B77

To a mixture of compound B76 (8.00 g, 56.3 mmol) in MeOH (60 mL) was added TEA (11.4 g, 113 mmol) and methylhydrazine (8.11 g, 56.3 mmol). The mixture was stirred at 60° C. for 15 hours to form a brown mixture. Desired MS value was detected by LC-MS. The mixture was cooled to 5° C., allowed to stand for 2 hours, until the white crystals precipitated, filtered, washed with ethanol, and dried to obtain compound B77 (3.5 g) as a white solid.

Procedure for Synthesis of B78

A mixture of compound B77 (750 mg, 4.80 mmol) and TEA (1.34 mL) in DCM (5 mL) was cooled to 0° C. in a salt water/ice bath. Then Tf$_2$O (2.71 g, 9.61 mmol) was added dropwise keeping the temperature at 0° C. After the addition was complete, the reaction mixture was warmed to 20° C. and stirred for 1 hour to form a colorless mixture. LCMS showed the starting material was consumed completely. The reaction mixture was quenched with water (30 mL) and the layers were separated. The aqueous phase was extracted with DCM (50 mL×2). The combined organic extract was washed with brine (80 mL×3), dried over anhydrous Na$_2$SO$_4$, filtered and concentrated under reduced pressure to give a residue, which was purified by Combi flash to give compound B78 (530 mg) as a yellow oil.

Procedure for Synthesis of B80

To a mixture of compound B78 (430 mg, 1.49 mmol) and compound B79 (544 mg, 2.24 mmol) in dioxane (4 mL) and H$_2$O (1 mL) was added Cs$_2$CO$_3$ (1.22 g, 3.73 mmol) and Pd(dppf)Cl$_2$ (109 mg, 0.15 mmol), the mixture was stirred at 80° C. for 12 hours under N$_2$ atmosphere to form a brown mixture. LCMS showed the reaction was completed. The mixture was filtered over a pad of celite. The filtrate was partitioned between EtOAc (30 mL) and H$_2$O (30 mL). The aqueous phase was extracted with EtOAc (30 mL×2). The combined organic extract was washed with brine (80 mL×3), dried over anhydrous Na$_2$SO$_4$, filtered and concentrated under reduced pressure to give a residue, which was purified by Combi flash to give compound B80 (200 mg) as a white solid.

Procedure for Synthesis of B81

To a mixture of methyl compound B80 (150 mg, 0.58 mmol) in THF (4 mL) was added LiAlH$_4$ (111 mg, 2.94 mmol) at 0° C., the mixture was stirred at 10° C. for 12 hours to form a white mixture. LCMS showed the reaction was completed. The mixture was quenched with saturated NH$_4$Cl (10 mL). The mixture was filtered over a pad of celite and washed with EtOAc (10 mL), The filtrate was partitioned between EtOAc (30 mL) and H$_2$O (30 mL). The aqueous phase was extracted with EtOAc (30 mL×2). The combined organic extract was washed with brine (50 mL×3), dried over anhydrous Na$_2$SO$_4$, filtered and concentrated under reduced pressure to give compound B81 (100 mg) as a white solid, which was used for next step without further purification.

Scheme 30: Synthetic route for B88

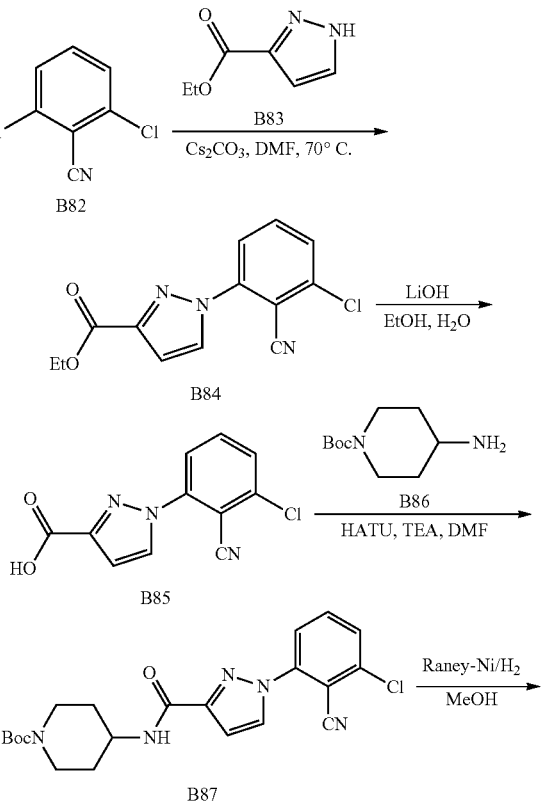

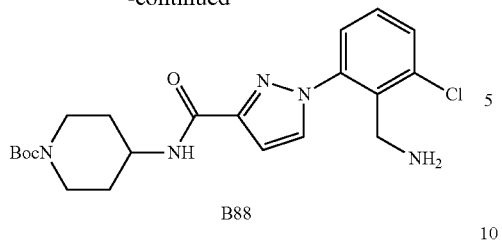

B88

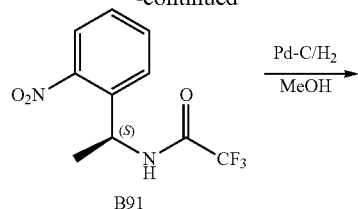

B91

Procedure for Synthesis of B84

To a mixture of compound B82 (1 g, 7.14 mmol), Cs$_2$CO$_3$ (5.81 g, 17.8 mmol) in DMF (15 mL) was added compound B83 (6.14 g, 35.68 mmol). The mixture was stirred at 20° C. for 12 hours to give a yellow suspension. TLC showed the reaction was completed. The mixture was partitioned between EtOAc (100 mL) and water (100 mL), the aqueous phase was extracted with EtOAc (80 mL×2), the combined extracted phase was washed with water (80 mL), dried over Na$_2$SO$_4$, filtered, concentrated under reduced pressure to give a yellow oil, which was purified by Combi flash to give compound B84 (1.9 g) as a white solid.

Procedure for Synthesis of B85

To a mixture of compound B84 (300 mg, 1.09 mmol) in THF (2 mL), MeOH (2 mL), H$_2$O (1 mL) was added LiOH (130 mg, 5.44 mmol). The mixture was stirred at 15° C. for 12 hours to give a yellow mixture. LCMS showed the reaction was completed. The mixture was concentrated under reduced pressure to remove MeOH. The aqueous phase was diluted with water (30 mL), acidized with HCl (3 M) to pH=4-5 and lyophilized to give compound B85 (201 mg) as a white solid Procedure for Synthesis of B87

To a mixture of compound B85 (200 mg, 0.808 mmol), HOBt (131 mg, 0.969 mmol), EDCI (186 mg, 0.969 mmol) in DMF (3 mL) was added DIEA (313 mg, 2.42 mmol), compound B86 (324 mg, 1.62 mmol). The mixture was stirred at 20° C. for 12 hours to give a yellow mixture. LCMS showed the reaction was completed. The reaction mixture was quenched with H$_2$O (20 mL) and lots of white solid was precipitated, then filtered under reduced pressure to give compound B87 (205 mg) as a white powder.

Procedure for Synthesis of B88

The compound B87 (200 mg) was followed the same procedure of B3 to obtain 254 mg of compound B88 as a yellow solid.

Scheme 31: Synthetic route for B95

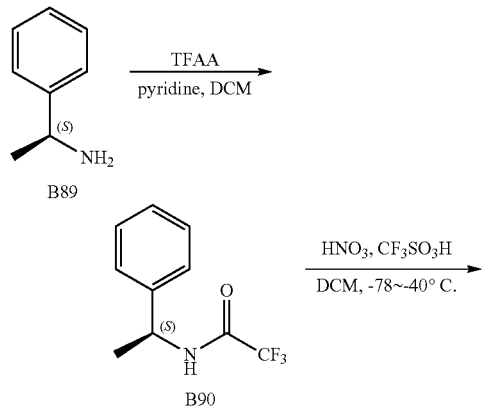

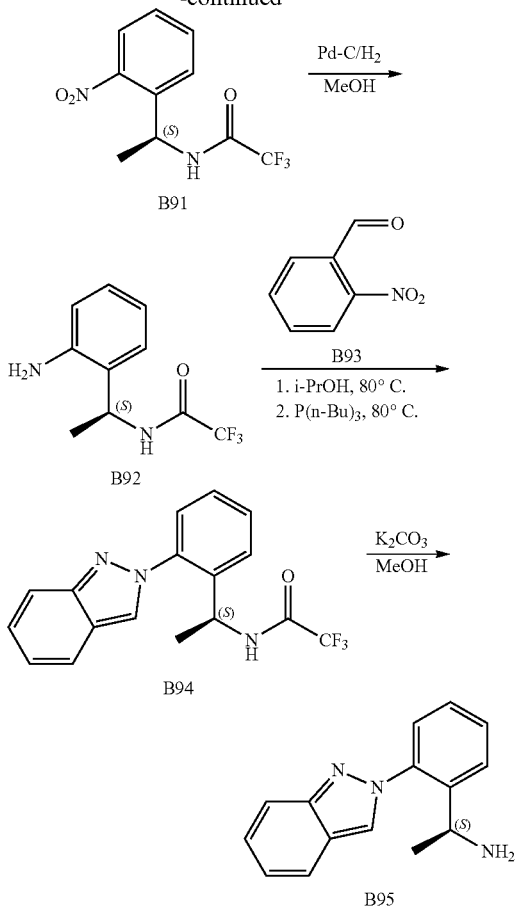

Procedure for Synthesis of B90

To a solution of compound B89 (5 g, 41.3 mmol), Pyridine (8.33 mL) in DCM (50 mL) was added TFAA (7.17 mL) at 0° C. The mixture was stirred at 20° C. for 12 hours to give yellow mixture. LCMS showed the reaction was completed. The reaction mixture was poured into 0.5 N HCl (30 mL) and vigorously stirred for 5 min. The layers were separated, and the aqueous layer was extracted with CH$_2$Cl$_2$ (3×10 mL). The combined organic layers were washed with 0.5 N HCl (20 mL), H2O (2×20 mL), and saturated NaHCO$_3$ (20 mL) and dried over anhydrous Na$_2$SO$_4$, filtered and concentrated under reduced pressure to give compound B90 (9.3 g, crude) as a yellow gum.

Procedure for Synthesis of B91

To a solution of CF$_3$SO$_3$H (2.44 mL) in DCM (50 mL) was added HNO$_3$ (622 uL) at 0° C. and stirred at 0° C. for 30 mins. The mixture was cooled to −70° C. and added the solution of compound B90 (3.00 g, 13.8 mmol) in DCM (20 mL) for 1 hour. The mixture was stirred at −70° C. for 30 minutes then. The mixture was stirred at −40° C. for 12 hour to give a yellow mixture. LCMS showed the reaction was completed. The yellow-orange reaction mixture was poured into ice (50 g) and stirred vigorously for 10 minutes. The layers were separated, and the aqueous layer was extracted with CH$_2$Cl$_2$ (3×25 mL). The organic layers were combined, washed with H$_2$O (3×50 mL), saturated NaHCO$_3$ (50 mL), and H$_2$O (50 mL), and dried over anhydrous Na$_2$SO$_4$, filtered and concentrated under reduced pressure to give Compound B91 (3.12 g) as a yellow solid.

Procedure for Synthesis of B92

To a mixture of compound B91 (500 mg, 1.91 mmol) in EtOH (10 mL) was added Pd/C (0.1 g, 10% purity, 50% water). The suspension was degassed under vacuum and purged with $H_2$ atmosphere several times. The mixture was stirred at 15° C. under $H_2$ atmosphere (15 psi) for 12 hours to give a black suspension. LCMS showed the reaction was completed. The combined batches mixture was filtrated, the filtrate was concentrated under reduced pressure to give compound B92 (480 mg) as yellow oil.

Procedure for Synthesis of B94

To a solution of compound B92 (390 mg, 2.58 mmol) in i-PrOH (15 mL) was added compound B93 (600 mg, 2.58 mmol). The reaction solution was heated to 80° C. and stirred for 3 hours to give a yellow solution. The reaction was cooled to 30-40° C., P(n-Bu)$_3$ (1.57 g, 7.74 mmol) was added and stirred for another 12 hours at 80° C. to give a black brown solution. LCMS showed the reaction was completed. The reaction mixture was quenched by addition $H_2O$ (100 mL) and extracted with EtOAc (100 mL×2). The combined organic layers were washed with saturated $NH_4Cl$ (50 mL) and brine (10 mL×2), dried over $Na_2SO_4$, filtered and concentrated under reduced pressure to give a residue, which was purified by Combi flash to give compound B94 (200 mg) as yellow gum.

Procedure for Synthesis of B95

To a solution of compound B94 (200 mg, 0.600 mmol) in MeOH (8 mL) was added $K_2CO_3$ (415 mg, 3.00 mmol). The resulting mixture was stirred at 60-70° C. for 2 hours to give yellow solution. TLC showed the starting material was consumed. The reaction mixture was concentrated under reduced pressure to give compound B95 (141 mg) as yellow gum.

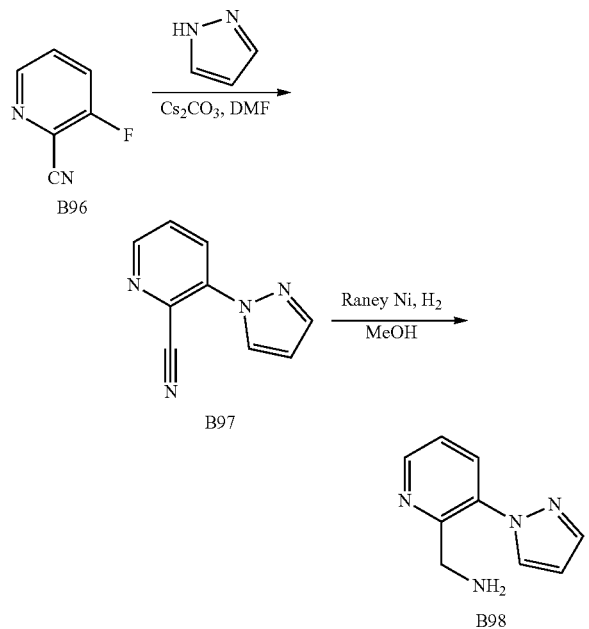

water (250 mL) and EtOAc (250 mL). The organic layer was washed with water (100 mL×2), brine (10 mL), dried over anhydrous $Na_2SO_4$, and concentrated under reduced pressure to give a residue. The residue was purified by Combi Flash to give compound B97 (4.76 g) as a white powder.

Procedure for Synthesis of B98

To a solution of compound B97 (1.3 g, 7.64 mmol) in MeOH (30 mL) was added Raney-Ni (497 mg, 5.81 mmol). The reaction mixture was stirred at 20° C. for 3 hours under $H_2$ atmosphere (15 psi). TLC showed the reaction was complete. The reaction mixture was filtered through a pad of Celite. The filtrate was concentrated under reduced pressure to give 560 mg of dark brown gum as the crude product. The crude product was purified by Combi Flash to give compound B98 (350 mg) as a light purple oil.

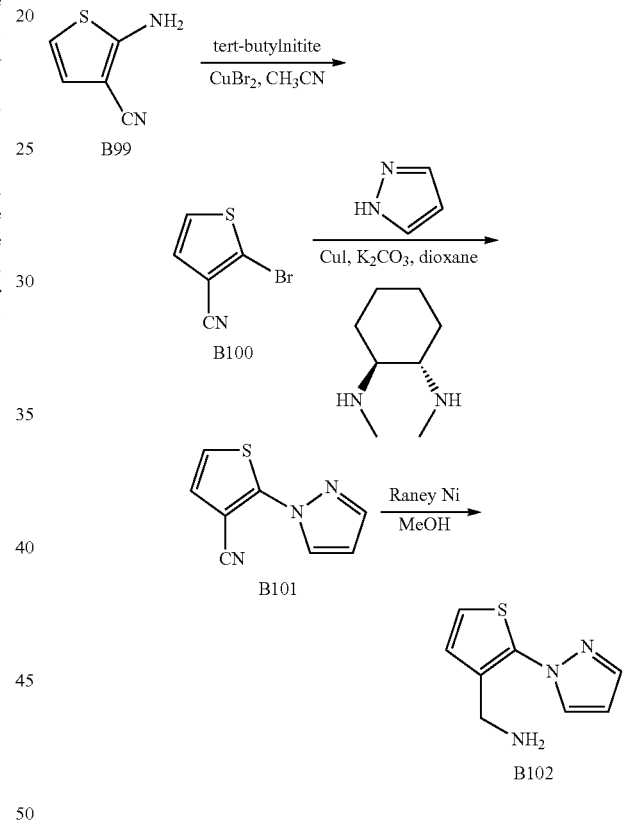

Procedure for Synthesis of B100

To a solution of compound B99 (1.00 g, 8.05 mmol) and $CuBr_2$ (2.16 g, 9.66 mmol) in $CH_3CN$ (10 mL) was added tert-butylnitrile (1.25 g, 12.1 mmol) at 0° C., the reaction mixture was stirred at 15° C. for 3 hours to give a brown solution. TLC showed the reaction was complete. To the reaction mixture was added 2M HCl (50 mL), extracted with EtOAc (30 mL×3), the organic phase was washed with brine (50 mL), dried over anhydrous $Na_2SO_4$, filtered and concentrated under reduce pressure to give a brown oil. The product was purified by Combi Flash to give compound B100 (380 mg) as a yellow oil.

Procedure for Synthesis of B101

To a solution of compound B100 (380 mg, 2.02 mmol) in dioxane (6 mL) was added CuI (115 mg, 0.606 mmol) and $K_2CO_3$ (559 mg, 4.04 mmol) and trans-$N_1,N_2$-dimethylcyclohexane-1,2-diamine (86.2 mg, 0.606 mmol) and 1H pyrazole (165 mg, 2.42 mmol), the reaction was stirred at 80° C. for 16 hours to give a brown suspension. TLC showed a new spot. To the reaction solution was added 1H pyrazole (500 mg), the solution was stirred at 110° C. for 8 hours. TLC showed the reaction wasn't complete. The mixture was filtered. The filtrate was partitioned between EtOAc (20 mL) and water (20 mL). The organic layer was washed with 28% $NH_3 \cdot H_2O$ (30 mL×2), brine (20 mL×2), dried over anhydrous $Na_2SO_4$, then filtered and concentrated under reduced pressure to give a yellow oil. The product was purified by Combi Flash to give compound B101 (180 mg) as a white solid.

Procedure for Synthesis of B102

The compound B102 (180 mg) was followed the same procedure of B3 to obtain 143 mg of compound B101 as a yellow oil.

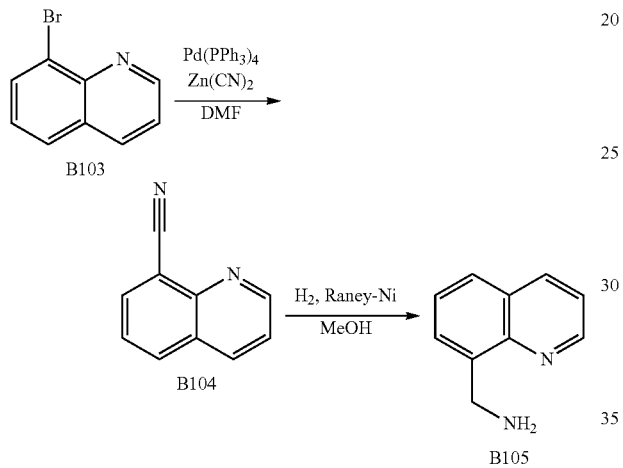

Procedure for Synthesis of B104

To a mixture of compound B103 (1.00 g, 4.81 mmol) and Pd(PPh₃)₄ (556 mg, 0.481 mmol) in anhydrous DMF (10 mL) was added Zn(CN)₂ (678 mg, 5.77 mmol). The reaction mixture was heated at 80° C. under N₂ atmosphere for 16 hours. LCMS showed the reaction was complete. The reaction mixture was cooled to room temperature, then the mixture was poured into water (50 mL) and the crude product was extracted with EtOAc (100 mL), the organic layer was washed with water (50 mL×2), brine (50 mL), dried over anhydrous Na₂SO₄, filtered, concentrated under reduced pressure to provide the crude product as an brown oil. The crude product was purified by Combi Flash to give compound B104 (700 mg) as a white powder.

Procedure for Synthesis of B105

The compound B104 (700 mg) was followed the same procedure of B102 to obtain 660 mg of compound B105 as a brown oil.

Scheme 35: Synthetic route for B111

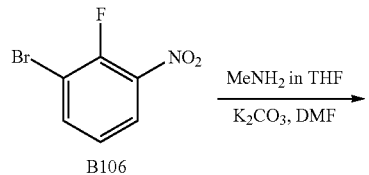

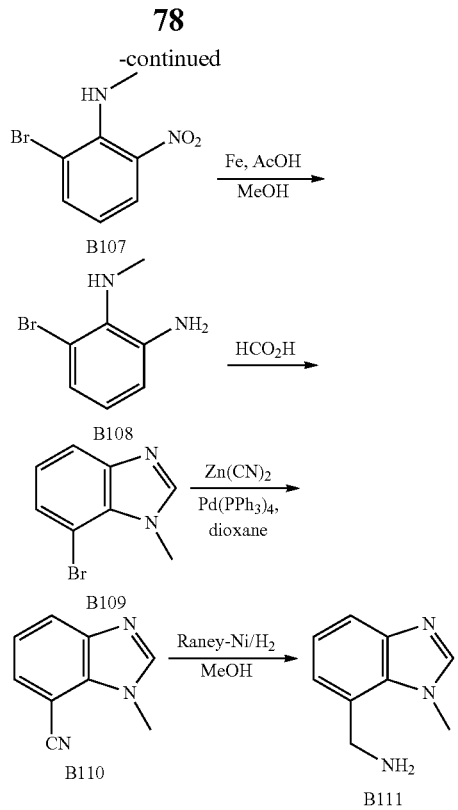

Procedure for Synthesis of B107

To a mixture of compound B106 (10.0 g, 45.4 mmol) in DMF (5 mL) was added MeNH₂ (2M in THF, 68.2 mL), then K₂CO₃ (9.42 g, 68.2 mmol) was added, the resulting mixture was stirred at 25° C. for 12 hours to give a yellow suspension. TLC showed the reaction was completed. The mixture was diluted with EtOAc (300 mL), washed with water (200 mL×3) and brine (200 mL), dried with anhydrous Na₂SO₄, filtered and concentrated under reduced pressure to give compound B107 (13.0 g) as a yellow oil, which was used directly for next step without further purification.

Procedure for Synthesis of B108

To a mixture of compound B107 (6.00 g) in MeOH (60 mL) was added AcOH (15.6 g, 259 mmol), then Fe powder (7.25 g, 129.9 mmol) was added, the resulting mixture was stirred at 25° C. for 12 hours. Crude LCMS showed the reaction worked well. The suspension was filtered and washed with MeOH (80 mL). The filtrate was concentrated under reduced pressure. The residue was basified by saturated NaHCO₃ to pH=9-10, extracted with EtOAc (200 mL×2), the combined organic phase was dried over anhydrous Na₂SO₄, filtered and concentrated under reduced pressure to give compound B108 (4.60 g) as a brown oil. The crude product was directly used for next step.

Procedure for Synthesis of B109

To compound B108 (4.60 g, crude) was added HCOOH (20 mL), the resulting mixture was stirred at 90° C. for 12 hours. LCMS showed the reaction worked well. 50 mL water was added to quench the reaction, neutralized with saturated NaHCO₃ to adjusted to pH=8-9, the resulting mixture was extracted with EtOAc (200 mL×3), the combined organic phase was washed with brine (150 mL), dried over anhydrous Na₂SO₄, filtered and concentrated under reduced pressure to give compound B109 (3.70 g, 3-step yield: 83.6%) as a brown solid.

Procedure for Synthesis of B110

The compound B109 (2.0 g) was followed the same procedure of B104 to obtain 900 mg of compound B110 as a purple powder.

Procedure for Synthesis of B111

The compound B110 (1.2 g) was followed the same procedure of B3 to obtain 1.0 g of compound B111 as a white powder.

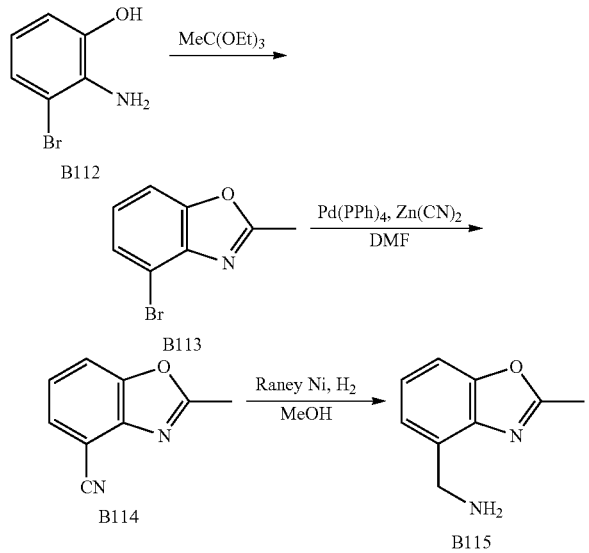

Scheme 36: Synthetic route for B115

Procedure for Synthesis of B113

A mixture of compound B112 (1.00 g, 5.32 mmol) in 1,1,1-triethoxyethane (4.40 g, 27.1 mmol) was stirred at 120° C. under $N_2$ for 2 hours to form a black red solution. LCMS showed 91.7% of desired MS. Most of MeC(OEt)$_3$ was removed under reduced pressure to give compound B113 (950 mg) as a red powder.

Procedure for Synthesis of B114

The compound B113 (950 mg) was followed the same procedure of B104 to obtain 230 mg of compound B114 as a pink powder.

Procedure for Synthesis of B115

The compound B114 (257 mg) was followed the same procedure of B3 to obtain 250 mg of compound B115 as a yellow gum.

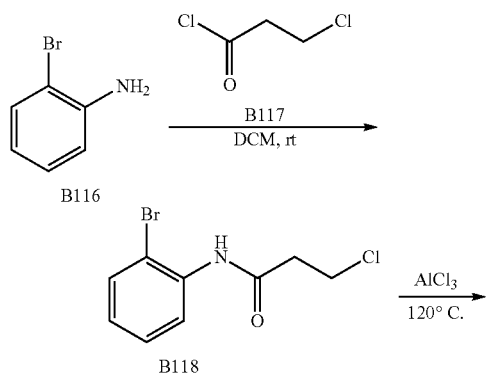

Scheme 37: Synthetic route for B122

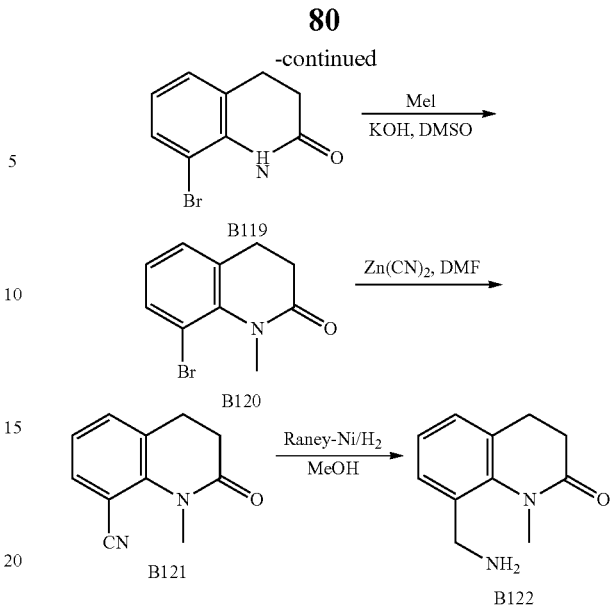

Procedure for Synthesis of B118

To a stirred solution of compound B116 (6.80 g, 53.5 mmol) in DCM (50 mL) was added dropwise compound B117 (8.38 g, 48.6 mmol) dissolved in DCM (50 mL) at −5-0° C. Then the mixture was stirred at 1-11° C. for 64 hours. TLC showed compound B116 was completely consumed. The mixture was washed with water (100 mL) and brine (100 mL), dried over anhydrous sodium sulfate and concentrated to afford compound B118 (10.0 g) as a brown solid.

Procedure for Synthesis of B119

Compound B118 (10.0 g, 38.0 mmol) and AlCl$_3$ (12.7 g, 95.2 mmol) was stirred at 120° C. for 4 hours under $N_2$ atmosphere. TLC showed compound B90 was completely consumed. The mixture was dissolved in DCM (30 mL), poured into ice water (50 mL) and separated. The organic layer was dried over anhydrous sodium sulfate and concentrated under reduced pressure to afford the crude product as a brown oil. The crude product was purified by Combi flash to afford compound B119 (1.10 g) as yellow solid.

Procedure for Synthesis of B120

To a stirred solution of compound B119 (1.10 g, 4.87 mmol) in DMSO (30 mL) was added KOH (1.09 g, 19.4 mmol) and MeI (2.07 g, 14.5 mmol). Then the mixture was stirred at 10° C. for 64 hours. LCMS showed compound B119 was completely consumed. The mixture was poured into water (100 mL), extracted with EtOAc (50 mL×3). The combined organic layers were washed with brine (50 mL×2), dried over anhydrous sodium sulfate and concentrated to afford the crude product as a brown oil. The crude product was purified by Combi flash to afford compound B120 (840 mg) as a yellow oil.

Procedure for Synthesis of B121

The compound B120 (600 mg) was followed the same procedure of B104 to obtain 450 mg of compound B121 as a yellow solid.

Procedure for Synthesis of B122

The compound B121 (400 mg) was followed the same procedure of B3 to obtain 180 mg of compound B122 as a red oil.

81

Scheme 38: Synthetic route for B125

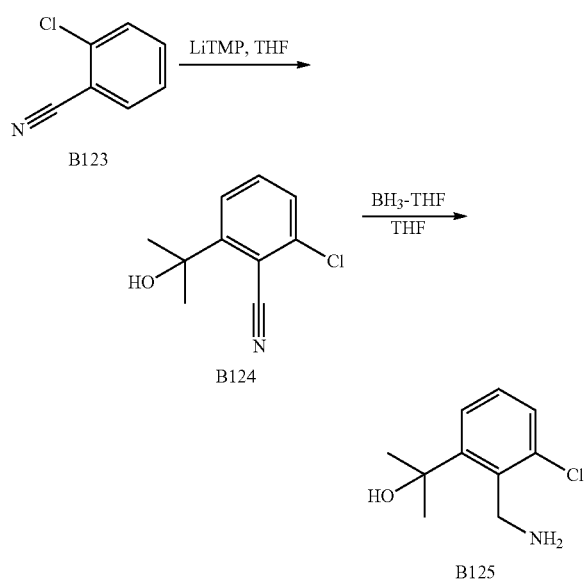

Procedure for Synthesis of B124

To a solution of 2,2,6,6-tetramethylpiperidine (1.23 g, 8.72 mmol) in THF (18 mL) was added n-BuLi (2.5 M, 2.91 mL) at −10° C. under $N_2$ atmosphere for 10 min. Then a solution of B123 (1 g, 7.27 mmol) in THF (10 mL) was added to the mixture and the reaction mixture was stirred at −78° C. for 10 min. Then acetone (844 mg, 14.5 mmol, 1.07 mL) was added to the reaction mixture. The reaction mixture was stirred at 15° C. for 16 hr to give a brown mixture. TLC showed new spot. The reaction mixture was quenched with $NH_4Cl$ (200 mL) and extracted with EA (150 mL×2). The organic layer was dried over anhydrous $Na_2SO_4$, filtered and concentrated under reduced pressure to give crude product. The residue was purified by column chromatography to give compound B124 (1.3 g) as light yellow oil.

Procedure for Synthesis of B125

To a solution of B124 (1.3 g, 6.64 mmol) in THF (15 mL) was added $BH_3·THF$ (1 M, 33.2 mL) at 0° C. under $N_2$ atmosphere and stirred for 30 min. Then the reaction mixture was stirred at 60° C. for 16 hours to give colorless mixture. LCMS showed the desired MS and the R1 was consumed up. The reaction mixture was quenched with MeOH (20 mL) and adjust pH=2 by 0.5M HCl aq. Then the mixture was extracted with DCM (100 mL*2). The water phase was basified to pH=8 with 2M NaOH and extracted with DCM (100 mL*2). The organic layer was dried over anhydrous $Na_2SO_4$, filtered and concentrated under reduced pressure to B125 (800 mg, crude) as white solid.

Scheme 39: Synthetic route for B129

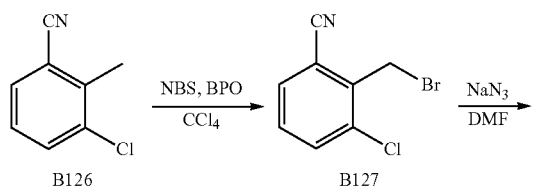

82

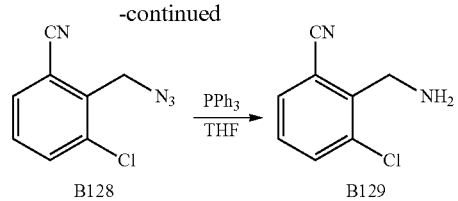

Procedure for Synthesis of B127

To a solution of B126 (1 g, 6.60 mmol) in $CCl_4$ (10 mL) was added NBS (1.29 g, 7.25 mmol) and BPO (16 mg, 66 umol). The reaction mixture was stirred at 85° C. for 16 hr to give a light yellow mixture. TLC showed new spot. The reaction mixture was filtered and the filter cake was washed with $CCl_4$ (100 mL). The filtrate was concentrated to give a residue. The residue was purified by column chromatography to give B127 (1.5 g) as a light yellow solid.

Procedure for Synthesis of B128

To a solution of B127 (1.5 g, 6.51 mmol) in DMF (15 mL) was added $NaN_3$ (570 mg, 8.77 mmol). Then the reaction mixture was stirred at 60° C. under $N_2$ atmosphere for 16 hours to give light yellow mixture. TLC showed new spot. The reaction mixture was quenched with brine (150 mL) and extracted with MTBE (150 mL). The organic layer was washed with brine (100 mL), dried over anhydrous $Na_2SO_4$, filtered and concentrated under reduced pressure to give B128 (1.1 g, crude) as a light yellow oil.

Procedure for Synthesis of B129

To a solution of B128 (1.1 g, 5.71 mmol) in THF (9 mL)/$H_2O$ (1 mL) was added $PPh_3$ (2.25 g, 8.57 mmol). The reaction mixture was stirred at 80° C. for 16 hr to give a brown mixture. LCMS showed the desired MS value. The reaction mixture was diluted with water (100 mL) and adjusted to pH=3 with HCl (0.5 M), then extracted with EtOAc (100 mL×2). The water phase was adjusted to pH=8 with aqueous $NaHCO_3$ and extracted with EtOAc (100 mL). No product was observed by TLC in organic extract. The water phase was concentrated to give B129 (2.3 g, crude) as a brown solid Scheme 40: Synthetic route for B136

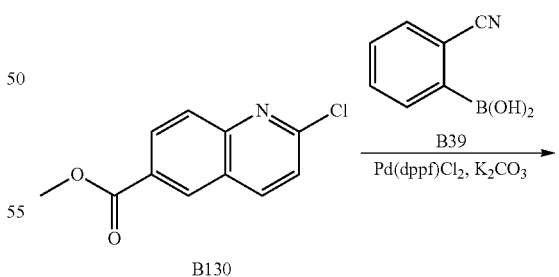

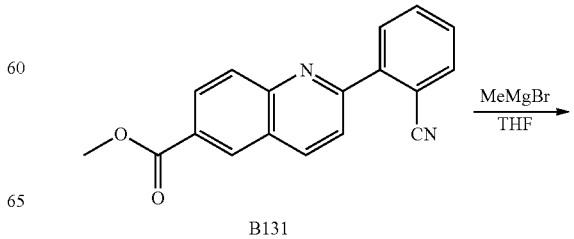

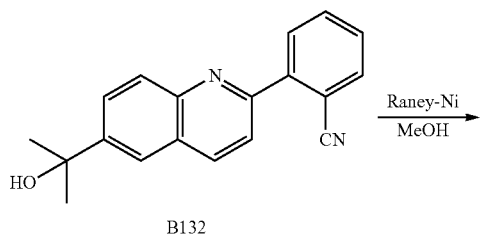
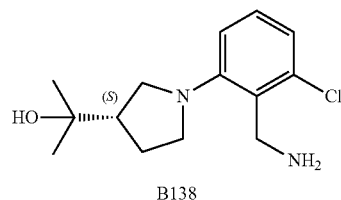

Procedure for Synthesis of B131

The compound B130 (100 mg) was followed the same procedure of B41 to obtain 87 mg of compound B131 as a brown solid.

Procedure for Synthesis of B132

The compound B131 (87 mg) was followed the same procedure of B26 to obtain 90 mg of compound B132 as a brown gum.

Procedure for Synthesis of B133

The compound B132 (90 mg) was followed the same procedure of B28 to obtain 80 mg of compound B133 as a brown solid.

Procedure for Synthesis of B135

To a solution of SOCl$_2$ (2.07 g, 17.4 mmol, 1.26 mL) in MeOH (20 mL) at 0° C. was added B134 (1 g, 8.69 mmol). The reaction mixture was stirred at 20° C. for 3 hours to give colorless mixture. TLC showed new spot. The reaction mixture was concentrated under reduced pressure to give B135 (1.3 g) as colorless oil.

Procedure for Synthesis of B136

The compound B135 (1.3 g) was followed the same procedure of B21 to obtain 1.8 g of compound B136 as a white solid.

Procedure for Synthesis of B137

The compound B136 (1.8 g) was followed the same procedure of B26 to obtain 1.81 g of compound B137 as a yellow gum.

Procedure for Synthesis of B138

The compound B137 (1 g) was followed the same procedure of B125 to obtain 600 mg of compound B138 as a yellow gum.

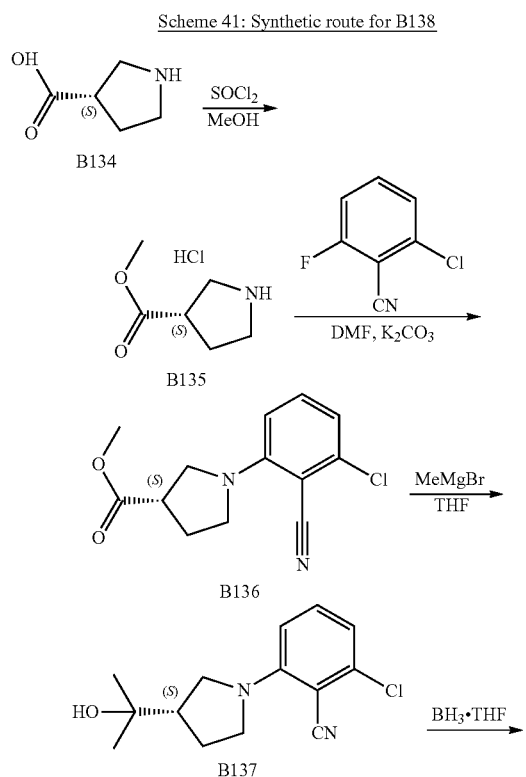
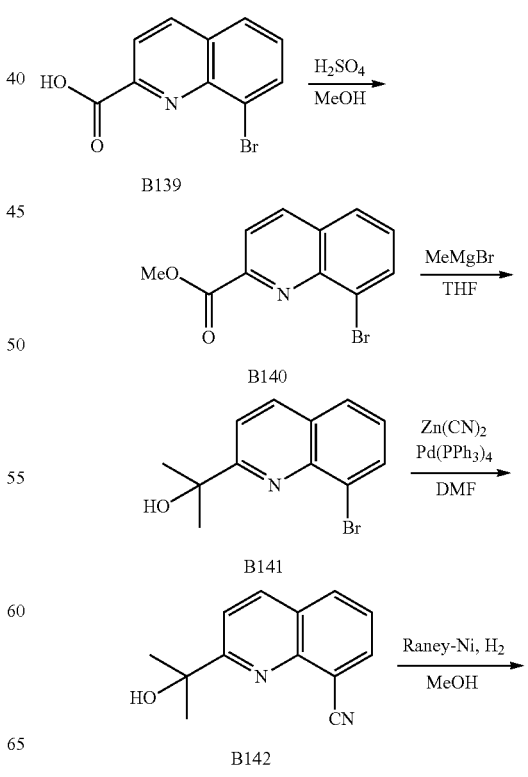

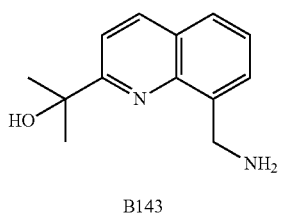

B143

Procedure for Synthesis of B140

To a solution of compound B139 (3 g, 11.9 mmol) in MeOH (20 mL) was added $H_2SO_4$ (2.38 g, 23.8 mmol, 1.29 mL). The mixture was refluxed for 17 hours to form a brown solution. TLC showed the reaction was completed. The mixture was partitioned between EtOAc (30 mL) and $H_2O$ (30 mL). The aqueous phase was extracted with EtOAc (30 mL×2). The combined organic extracts were washed with brine (50 mL×3), dried over anhydrous $Na_2SO_4$, filtered and concentrated under reduced pressure to give compound B140 (2.8 g) as a yellow solid.

Procedure for Synthesis of B141

The compound B140 (500 mg) was followed the same procedure of B26 to obtain 910 mg of compound B141 as a yellow powder.

Procedure for Synthesis of B142

The compound B141 (910 mg) was followed the same procedure of B104 to obtain 560 mg of compound B142 as a pale-yellow powder.

Procedure for Synthesis of B143

The compound B142 (100 mg) was followed the same procedure of B28 to obtain 100 mg of compound B143 as a pale-yellow powder.

Scheme 43: Synthetic route for B147

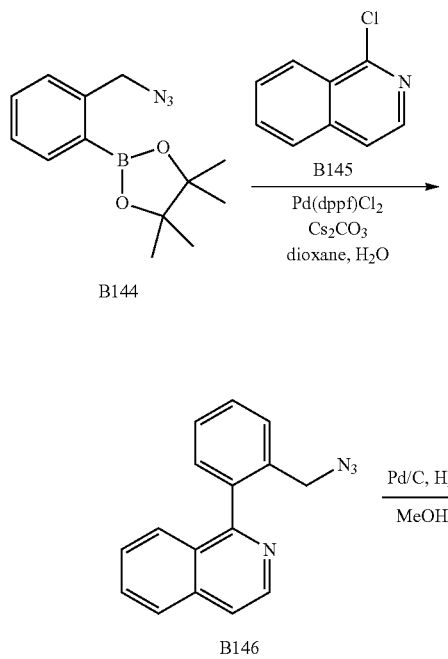

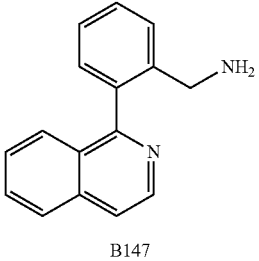

B147

Procedure for Synthesis of B146

To a solution of compound B144 (792.88 mg, 3.06 mmol) and compound B145 (500 mg, 3.06 mmol) in dioxane (10 mL) and $H_2O$ (2 mL) were added $Pd(dppf)Cl_2$ (111.95 mg, 153.00 umol) and $Cs_2CO_3$ (1.99 g, 6.12 mmol) under $N_2$. The resulting mixture was heated at 100° C. and stirred for 3 hours to give gray suspension. LCMS showed the reaction was not completed. Then the reaction mixture was stirred at 100° C. for 18 hours, and LCMS showed the reaction have 32% of desired product and 36% of material. The mixture was partitioned between EtOAc (50 mL) and water (30 mL). The aqueous layer was extracted with EtOAc (30 mL*3). The combined organic layer was washed with saturated brine (30 mL), dried over anhydrous $Na_2SO_4$, filtered, and concentrated under reduced pressure to give the crude product as a yellow oil. It was purified by column chromatography to obtain compound B146 (236 mg) as yellow oil.

Procedure for Synthesis of B147

The compound B146 (236 mg) was followed the same procedure of A30 to obtain 200 mg of compound B147 as yellow oil Scheme 44: Synthetic route for compound 209 through Route I

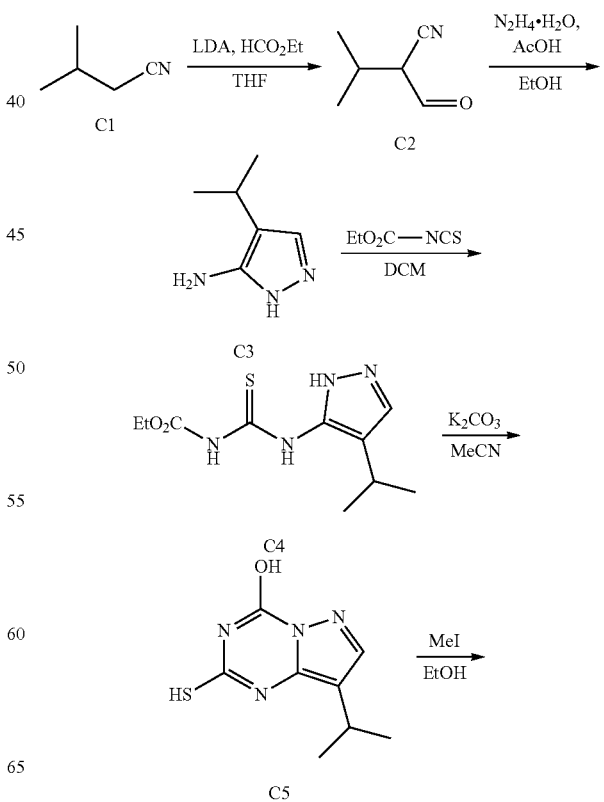

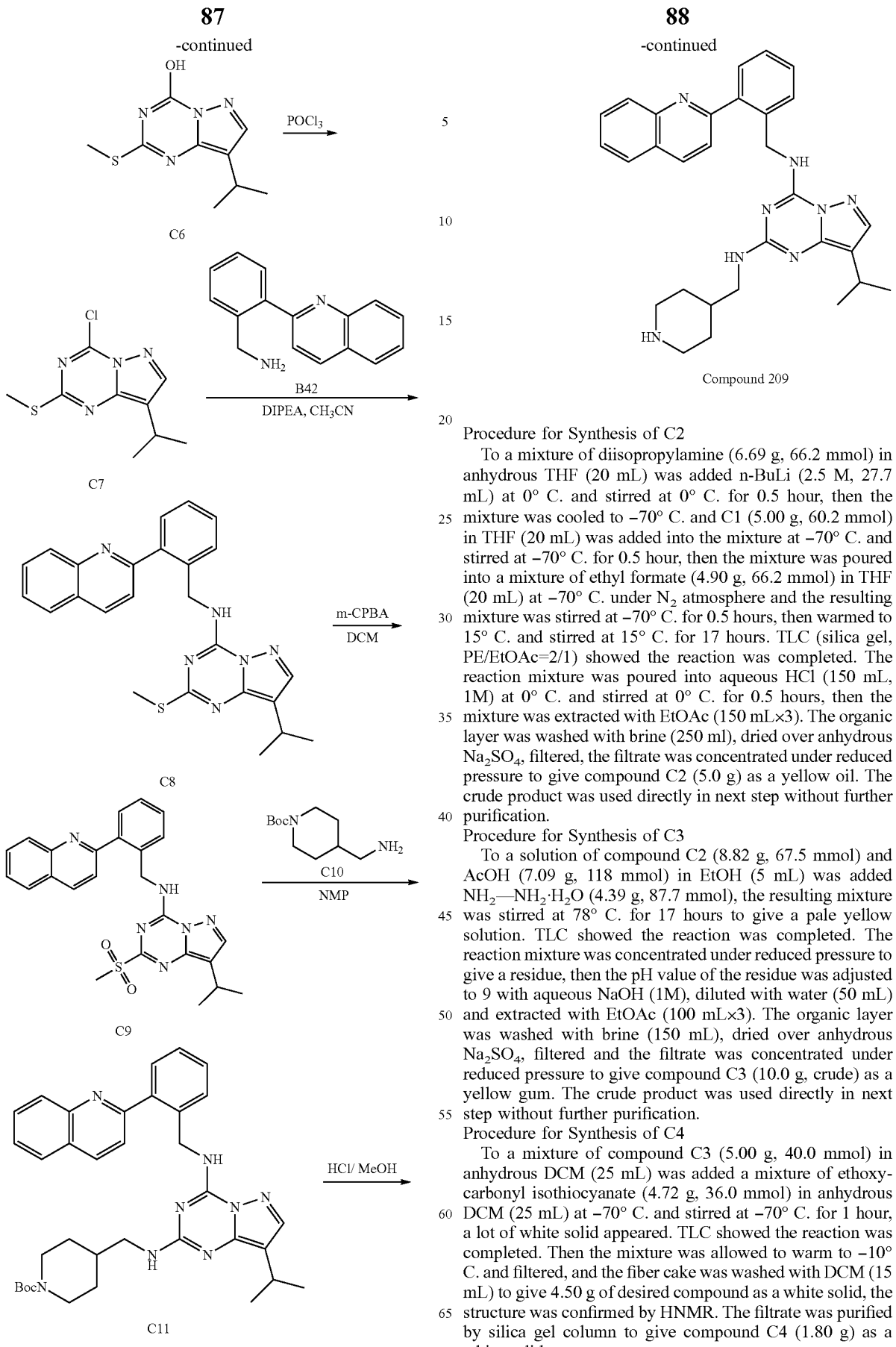

Procedure for Synthesis of C2

To a mixture of diisopropylamine (6.69 g, 66.2 mmol) in anhydrous THF (20 mL) was added n-BuLi (2.5 M, 27.7 mL) at 0° C. and stirred at 0° C. for 0.5 hour, then the mixture was cooled to −70° C. and C1 (5.00 g, 60.2 mmol) in THF (20 mL) was added into the mixture at −70° C. and stirred at −70° C. for 0.5 hour, then the mixture was poured into a mixture of ethyl formate (4.90 g, 66.2 mmol) in THF (20 mL) at −70° C. under $N_2$ atmosphere and the resulting mixture was stirred at −70° C. for 0.5 hours, then warmed to 15° C. and stirred at 15° C. for 17 hours. TLC (silica gel, PE/EtOAc=2/1) showed the reaction was completed. The reaction mixture was poured into aqueous HCl (150 mL, 1M) at 0° C. and stirred at 0° C. for 0.5 hours, then the mixture was extracted with EtOAc (150 mL×3). The organic layer was washed with brine (250 ml), dried over anhydrous $Na_2SO_4$, filtered, the filtrate was concentrated under reduced pressure to give compound C2 (5.0 g) as a yellow oil. The crude product was used directly in next step without further purification.

Procedure for Synthesis of C3

To a solution of compound C2 (8.82 g, 67.5 mmol) and AcOH (7.09 g, 118 mmol) in EtOH (5 mL) was added $NH_2$—$NH_2 \cdot H_2O$ (4.39 g, 87.7 mmol), the resulting mixture was stirred at 78° C. for 17 hours to give a pale yellow solution. TLC showed the reaction was completed. The reaction mixture was concentrated under reduced pressure to give a residue, then the pH value of the residue was adjusted to 9 with aqueous NaOH (1M), diluted with water (50 mL) and extracted with EtOAc (100 mL×3). The organic layer was washed with brine (150 mL), dried over anhydrous $Na_2SO_4$, filtered and the filtrate was concentrated under reduced pressure to give compound C3 (10.0 g, crude) as a yellow gum. The crude product was used directly in next step without further purification.

Procedure for Synthesis of C4

To a mixture of compound C3 (5.00 g, 40.0 mmol) in anhydrous DCM (25 mL) was added a mixture of ethoxycarbonyl isothiocyanate (4.72 g, 36.0 mmol) in anhydrous DCM (25 mL) at −70° C. and stirred at −70° C. for 1 hour, a lot of white solid appeared. TLC showed the reaction was completed. Then the mixture was allowed to warm to −10° C. and filtered, and the fiber cake was washed with DCM (15 mL) to give 4.50 g of desired compound as a white solid, the structure was confirmed by HNMR. The filtrate was purified by silica gel column to give compound C4 (1.80 g) as a white solid.

Procedure for Synthesis of C5

To a mixture of compound C4 (6.30 g, 24.6 mmol) in MeCN (50 mL) was added K₂CO₃ (6.79 g, 49.2 mmol), the mixture was stirred at 80° C. for 8 hours. Crude LCMS showed the reaction was completed. The mixture was cooled to room temperature, then AcOH (15 mL) was added into the mixture and stirred at 15° C. for 20 minutes, then the resulting mixture was concentrated under reduced pressure to give a residue, which was washed with water (50 mL×3) to give compound C5 (4.20 g) as a white solid.

Procedure for Synthesis of C6

To a mixture of compound C5 (4.20 g, 20.0 mmol) in EtOH (40 mL) was added NaOH (2.00 g, 50.0 mmol) in H₂O (20 mL) at 15° C., then MeI (2.84 g, 20.0 mmol) was added into above mixture and the resulting mixture was stirred at 15° C. for 2 hours. Crude LCMS showed the reaction was completed. The mixture was concentrated under reduced to give a residue, which was treated with ice cold water (50 mL) and aqueous HCl (20 mL, 6M) for 30 minutes, a lot of white solid appeared, filtered to give the crude product. The crude product was poured into MeCN (50 mL) to give a suspension, then the suspension was concentrated under reduced pressure to give compound C6 (3.60 g) as a white solid.

Procedure for Synthesis of C7

To a solution of Compound C6 (500 mg, 2.23 mmol) in POCl₃ (5 mL) was added N,N-diethylaniline (998 mg, 6.69 mmol) dropwise. The reaction mixture was stirred at 90° C. for 2 hours. The reaction solution was concentrated under reduced pressure to give crude compound C7 (710 mg) as a dark oil, which was used directly in the next step without further purification.

Procedure for Synthesis of C8

To a mixture of compound B42 (700 mg, 2.99 mmol) in CH₃CN (20 mL) was added DIEA (772 mg, 5.98 mmol) and compound C7 (652 mg, 2.69 mmol), the mixture was stirred at 15° C. for 2 hours to give a yellow mixture. LCMS showed the reaction was completed. The reaction was concentrated under reduced pressure to give crude product. The crude product was purified by Combi flash to give compound C8 (650 mg) as yellow gum.

Procedure for Synthesis of C9

To a mixture of compound C8 (650 mg, 1.48 mmol) in DCM (10 mL) was added m-CPBA (659 mg, 3.25 mmol) in portions at 15° C. The reaction mixture was stirred at 15° C. for 2 hours under N₂ atmosphere to give yellow mixture. LCMS showed the reaction was completed. The reaction mixture was filtered, combined filtrate and concentrated under reduced pressure to give crude product. The crude product was purified by Combi flash to give compound C9 (350 mg) as yellow gum.

Procedure for Synthesis of C11

A mixture of compound C9 (350 mg, 0.740 mmol) and compound C10 (317 mg, 1.48 mmol) in NMP (10 mL) was stirred at 140° C. for 16 hours to give brown mixture. LCMS showed the reaction was completed. The reaction was quenched by water (50 mL), and extracted by EtOAc (100 mL×2). The combined organic phase was washed with brine (100 mL×2), dried over anhydrous Na₂SO₄, filtered and concentrated under reduced pressure to give crude product, which was purified by Combi flash to afford compound C11 (220 mg) as yellow gum.

Procedure for Synthesis of Compound 209

A solution of compound C11 (220 mg, 0.362 mmol) in HCl/MeOH (3 mL, 4M) was stirred at 15° C. for 16 hours to give yellow solution. LCMS showed the reaction was completed. The solution was concentrated under reduced pressure to give crude product. The crude product was purified by prep-HPLC (0.1% TFA), the fraction was basified to pH=8 with saturated NaHCO₃, extracted with DCM (20 mL×2), the separated organic layer was washed with brine (20 mL×2), dried over anhydrous Na₂SO₄, filtered and lyophilized to afford compound 209 (62 mg) as a white powder.

Scheme 45: Synthetic route for compound 245 through Route I

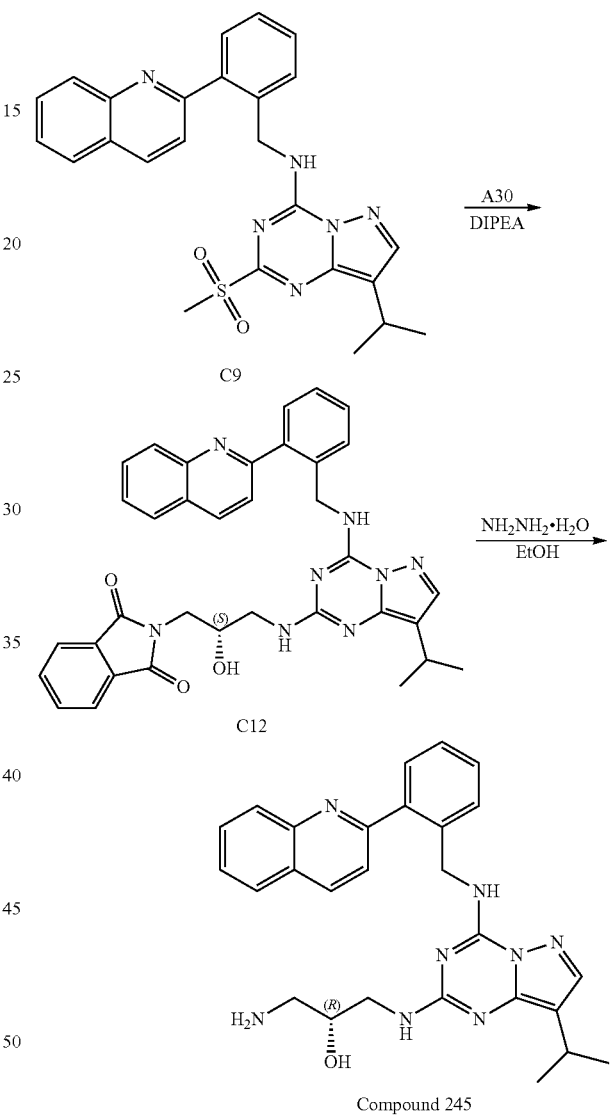

Compound 245

Procedure for Synthesis of C12

The compound C9 (1.46 g) and compound A30 (680 mg) were followed the same procedure of C11 to obtain 110 mg of compound C12 as a yellow solid.

Procedure for Synthesis of Compound 245

To a mixture of compound C12 (110 mg, 0.179 mmol) in EtOH (5 mL) was added N₂H₄·H₂O (12.7 mg, 12.3 uL, 85% purity). The mixture was stirred at 25° C. for 2 hours to give a colorless mixture. LCMS showed the reaction was completed. The reaction mixture was concentrated under reduced pressure to remove EtOH, residue was diluted with H₂O extracted with EtOAc (10 mL×3). The combined organic layers were washed with brine (20 mL), dried over Na₂SO₄, filtered and concentrated under reduced pressure to give the crude product, which was purified by prep-TLC to afford compound 245 (17.6 mg) as a white powder.

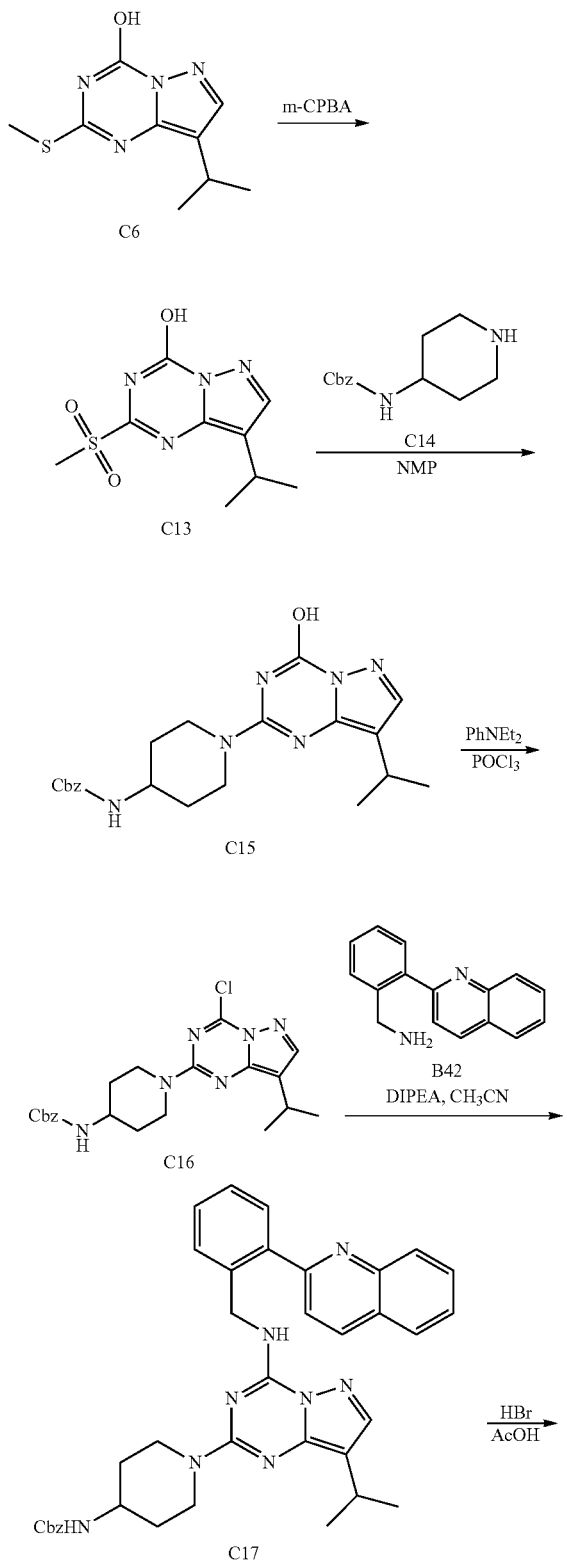

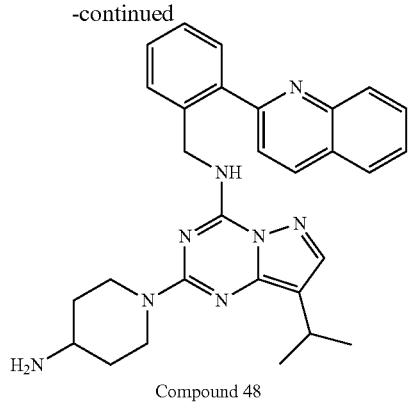

Compound 48

Procedure for Synthesis of C13

To a mixture of compound C6 (5.00 g, 22.3 mmol) in DCM (100 mL) was added m-CPBA (10.1 g, 46.8 mmol) in portions at 25° C. The mixture was stirred at 25° C. for 2 hours under N₂ atmosphere. Much white solid appeared. TLC showed the reaction was completed. The reaction mixture was filtered. Most of DCM was moved under reduce pressure, then the mixture was filtered. The filter cake was washed with cold DCM (15 mL×2). This process was repeated twice. The filtrate was dried over anhydrous Na₂SO₄, then filtered and concentrated under reduce pressure to give compound C13 (5.7 g) as a white powder. The crude product was used for next step directly without further purification.

Procedure for Synthesis of C15

To a solution of compound C13 (6.62 g, 25.83 mmol) in NMP (100 mL) was added compound C14 (18.15 g, 77.5 mmol). The reaction mixture was stirred at 140° C. for 16 hours. TLC showed the reaction was complete. The reaction mixture was partitioned between brine (500 mL) and EtOAc (400 mL). The organic layer was washed with water (100 mL×2), brine (100 mL), dried over anhydrous Na₂SO₄, and concentrated under reduced pressure to give a residue. The residue was purified by Combi Flash to give a brown gum, which was triturated with CH₃CN (50 mL) to give compound C15 (2.06 g) as an off-white powder.

Procedure for Synthesis of C16

To a mixture of compound C15 (89 mg, 0.22 mmol) in POCl₃ (4.41 g, 28.7 mmol) was added N,N-diethylaniline (97 mg, 0.65 mmol) at 20° C. The reaction mixture was stirred at 80° C. for 2 hours. The reaction mixture was concentrated under reduced pressure to give compound C16 (93 mg) as an brown gum as the crude product. The crude product was used directly in next step without further purification.

Procedure for Synthesis of C17

To a mixture of compound C16 (100 mg, 0.233 mmol), DIPEA (60.3 mg, 0.466 mmol) in MeCN (3 mL) was added compound B42 (109 mg, 0.466 mmol). The mixture was stirred at 15° C. for 2 hours. TLC showed that the reaction was completed. The mixture was filtered. The filter cake was washed with MeCN (1 mL×2), PE (1 mL×2) to give compound C17 (100 mg) as a yellow powder.

Procedure for Synthesis of Compound 48

A mixture of compound C17 (90 mg, 0.143 mmol) in HBr/HOAc (2.5 mL, 35% purity) was stirred at 15° C. for 20 minutes. TLC showed a new spot. The mixture was concentrated under reduced pressure to give a residue. The residue was added sat. NaHCO₃ solution to pH=8. The mixture was extracted with DCM (30 mL×2). The combined extracts were washed with water (40 mL×2), dried over anhydrous Na$_2$SO$_4$, then filtered and concentrated under reduced pressure to give a residue (as a yellow gum). The residue was purified by prep-HPLC and remaining solvent was removed by lyophilization to afford compound 48 (24.3 mg) as a white powder.

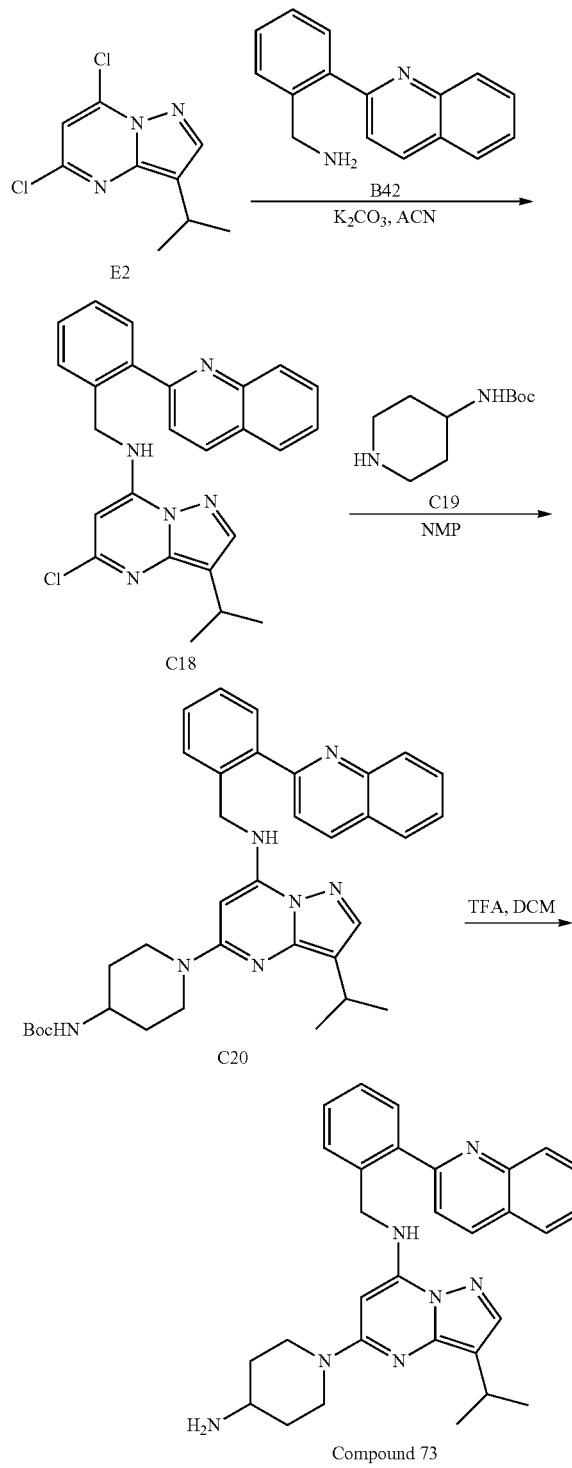

Procedure for Synthesis of C18

To a solution of compound E2 (300 mg, 1.30 mmol) in CH$_3$CN (20 mL) was added compound B42 (305 mg, 1.30 mmol) and K$_2$CO$_3$ (180 mg, 1.30 mmol). The resulting mixture was heated at 80° C. and stirred for 3 hours to give yellow suspension. TLC showed the reaction was completed. The reaction mixture was quenched by addition H$_2$O (50 mL) and extracted with EtOAc (50 mL×2). The combined organic layers were washed with brine (20 mL), dried over Na$_2$SO$_4$, filtered and concentrated under reduced pressure to give a residue. The crude product was purified by silica column, the fraction was concentrated to obtain compound C18 (420 mg) as a yellow solid.

Procedure for Synthesis of C20

To a solution of compound C18 (200 mg, 0.467 mmol) in NMP (20 mL) was added compound C19 (468 mg, 2.34 mmol). The resulting mixture was heated at 140° C. and stirred for 12 hrs to give yellow solution. TLC showed most of compound 5 was consumed, one major spot was formed. The reaction mixture was quenched by addition H$_2$O (100 mL) and extracted with EtOAc (50 mL×2). The combined organic layers were washed with brine (10 mL), dried over Na$_2$SO$_4$, filtered and concentrated under reduced pressure to give a residue. The residue was purified by silica column to obtain compound C20 (168 mg) as an off-white solid.

Procedure for Synthesis of Compound 73

To a solution of compound C20 (168 mg, 0.284 mmolq) in DCM (14 mL) was added TFA (6 mL). The resulting mixture was stirred for 1.5 hours at 20° C. to give yellow solution. LCMS and HPLC showed the reaction was completed. The reaction mixture was concentrated to remove most of TFA, then basified with saturated aqueous NaHCO$_3$ to pH~9 and extracted with EtOAc (50 mL×5). The combined organic layers were washed with brine (5 mL×5), dried over anhydrous Na$_2$SO$_4$, filtered and concentrated under reduced pressure to give a residue. The residue was purified by triturated with MTBE (20 mL), filtered under reduced pressure to obtain compound 73 (122.3 mg) as an off-white solid.

Exceptional Synthetic Route

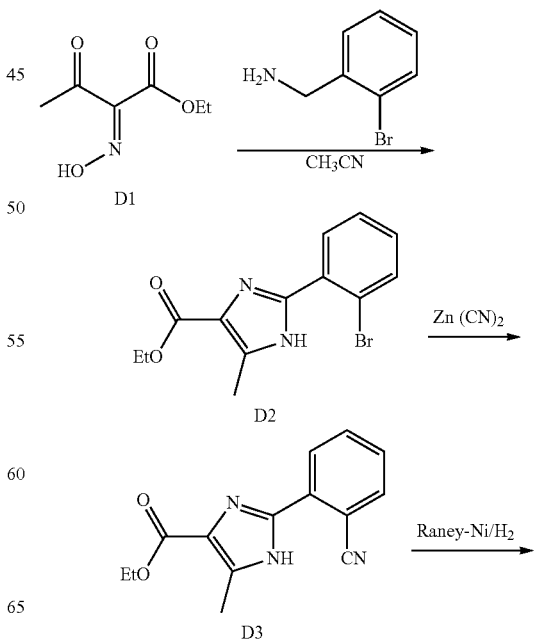

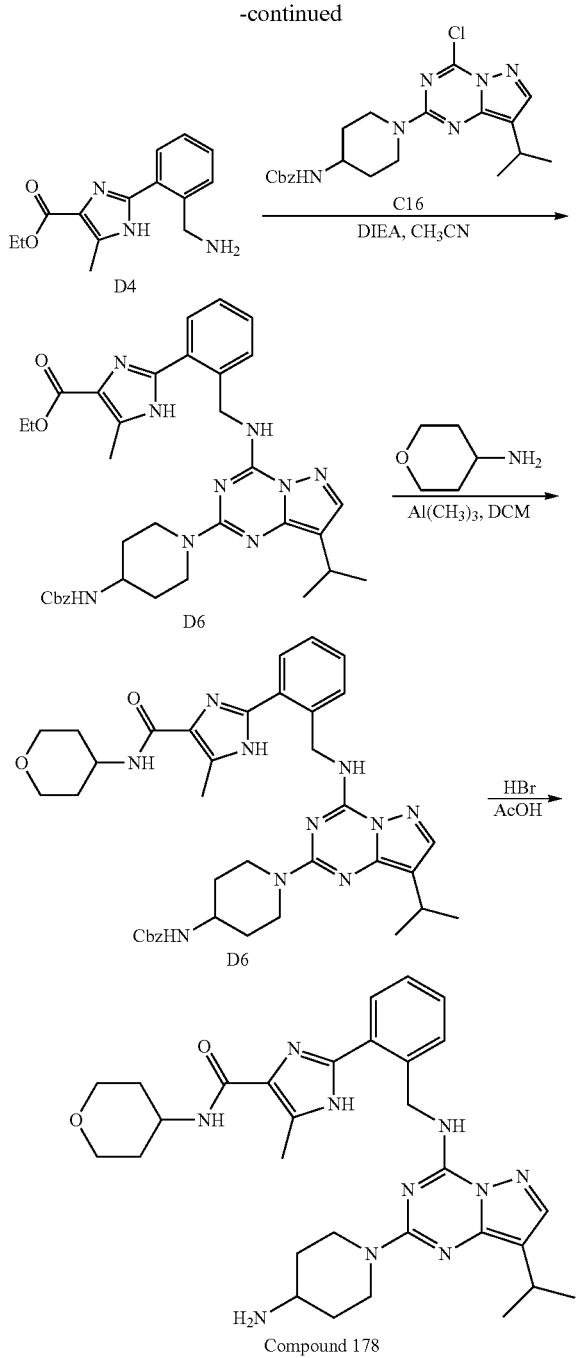

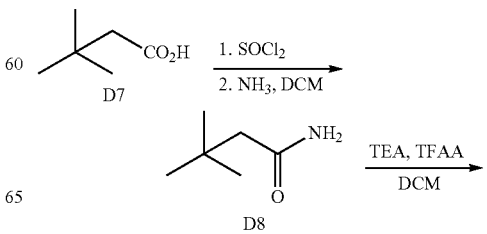

Scheme 49: Synthetic route for compound 24

Procedure for Synthesis of D2

To a mixture of (2-bromophenyl)methanamine (5.14 g, 27.7 mmol) in CH$_3$CN (50 mL) was added compound D1 (4.00 g, 25.1 mmol). The mixture was stirred at 85° C. for 12 hours to give a yellow mixture. LCMS showed the reaction was completed. The mixture was concentrated under reduced pressure to give a yellow residue, which was purified by Combi flash to give compound D2 (3.2 g) as a yellow powder.

Procedure for Synthesis of D3

To a solution of compound D2 (1 g, 3.23 mmol) in DMA (8 mL) was added Pd$_2$(dba)$_3$ (296 mg, 0.323 mmol), DPPF (359 mg, 0.647 mmol), Zn(CN)$_2$ (228 mg, 1.94 mmol), Zn (21.2 mg, 0.323 mmol). The reaction was stirred at 150° C. under microwave condition for 0.5 hour under N$_2$ atmosphere to give a red brown suspension. TLC showed the reaction was completed. The mixture was partitioned between with water (50 mL) and EtOAc (50 mL). The aqueous phase was extracted with EtOAc (50 mL). The combined extracts were washed with brine (30 mL×3), dried over anhydrous Na$_2$SO$_4$, filtered and concentrated under reduced pressure to give crude product as a brown oil, which was purified by Combi flash to give compound D3 (530 mg) as a yellow gum.

Procedure for Synthesis of D4

To a mixture of Raney-Ni (100 mg in water) in MeOH (30 mL) was added compound D3 (500 mg, 1.96 mmol), NH$_3$·H$_2$O (2 mL). The suspension was degassed under vacuum and purged with H$_2$ several times. The mixture was stirred at 15° C. under H$_2$ (15 psi) for 2 hours to give a black suspension. TLC showed the reaction was completed. The mixture was filtered, the filtrate was concentrated under reduced pressure to give compound D4 (500 mg) as a yellow powder.

Procedure for Synthesis of D5

To a mixture of compound D4 (500 mg, 1.93 mmol) in MeCN (5 mL) was added DIEA (1 mL) compound C16 (827 mg, 1.93 mmol). The mixture was stirred at 15° C. for 12 hours to give a yellow mixture. TLC showed the reaction was completed. The mixture was partitioned between EtOAc (50 mL) and water (50 mL). The aqueous was extracted with EtOAc (50 mL×2). The combined extracted was washed with brine (50 mL), dried over Na$_2$SO$_4$, filtered, concentrated under reduced pressure to give a yellow oil, which was purified by Combi flash to give compound D5 (830 mg) as yellow powder.

Procedure for Synthesis of D6

To a mixture of tetrahydro-2H-pyran-4-amine (111 mg, 1.10 mmol) in DCM (2 mL) was added Al(CH$_3$)$_3$ (2 M, 405 uL) at −60° C. under N$_2$ atmosphere. The mixture was stirred at 20° C. for 1 hour. Then a solution of compound D5 (100 mg, 0.162 mmol) in dry DCM (1 mL) was added dropwise. The mixture was stirred at 20° C. for 12 hours to give a yellow suspension. LCMS showed the reaction was completed. The reaction mixture was filtered through Celite, and concentrated under reduced pressure to give a yellow residue, which was purified by prep-TLC to give compound D6 (53 mg) as a yellow gum.

Procedure for Synthesis of Compound 178

To a mixture of compound D6 (53.0 mg, 0.0750 mmol) in HBr/HOAc (1 mL, 35% HBr in HO Ac) was stirred at 0-10° C. for 0.5 hour to give a yellow mixture. TLC (PE/EA=1/1) showed the reaction was completed. To the reaction mixture was added MTBE (10 mL) to precipitate red powder. The red was collected by filtration and washed with MTBE (5 mL×2). The red solid was purified by cation exchange resin eluting with 5% NH$_3$·H$_2$O, then lyophilized to give a white powder, which was purified by prep-TLC and lyophilized to give compound 178 (20.5 mg) as a white powder.

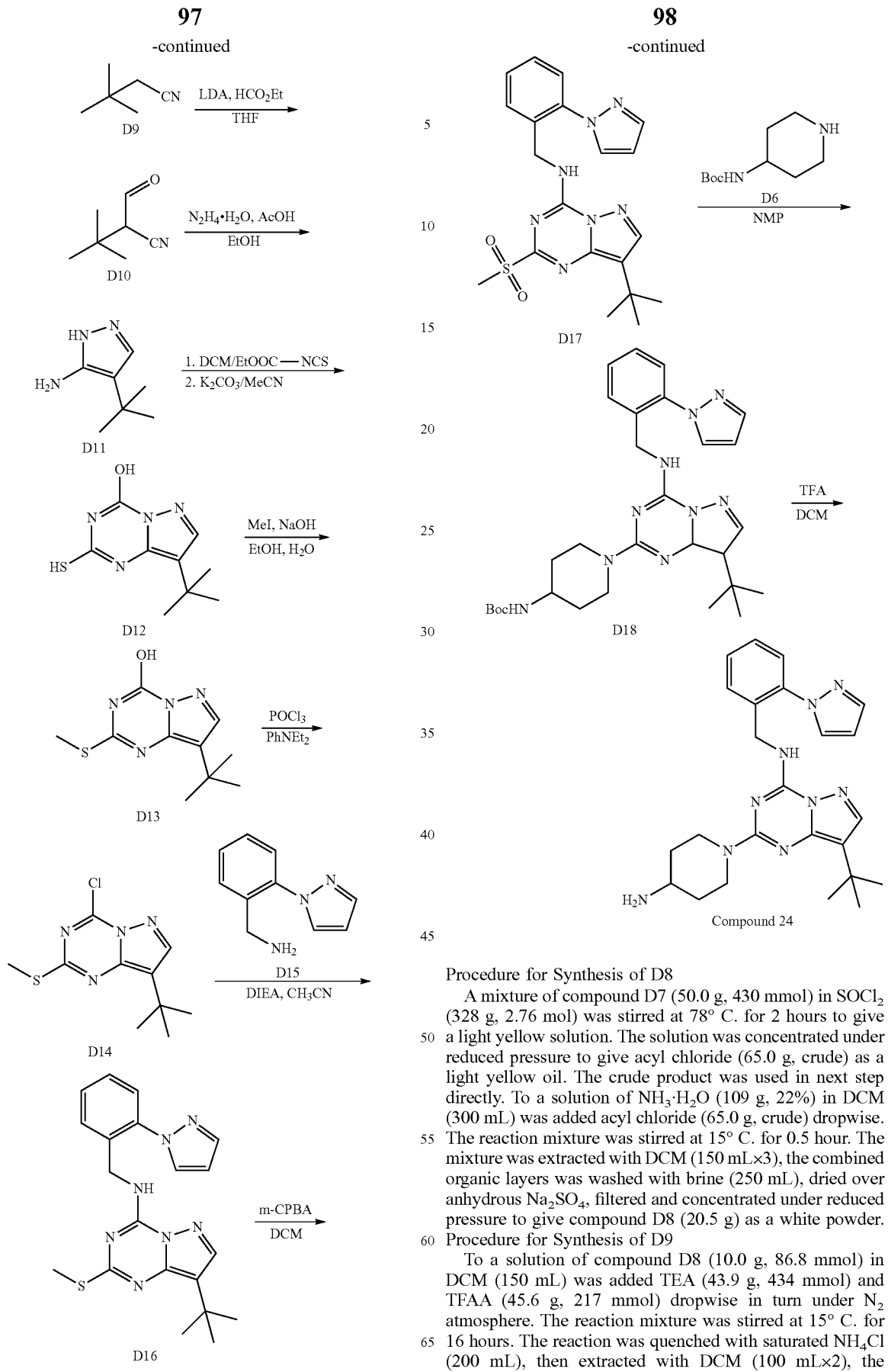

Procedure for Synthesis of D8

A mixture of compound D7 (50.0 g, 430 mmol) in $SOCl_2$ (328 g, 2.76 mol) was stirred at 78° C. for 2 hours to give a light yellow solution. The solution was concentrated under reduced pressure to give acyl chloride (65.0 g, crude) as a light yellow oil. The crude product was used in next step directly. To a solution of $NH_3·H_2O$ (109 g, 22%) in DCM (300 mL) was added acyl chloride (65.0 g, crude) dropwise. The reaction mixture was stirred at 15° C. for 0.5 hour. The mixture was extracted with DCM (150 mL×3), the combined organic layers was washed with brine (250 mL), dried over anhydrous $Na_2SO_4$, filtered and concentrated under reduced pressure to give compound D8 (20.5 g) as a white powder.

Procedure for Synthesis of D9

To a solution of compound D8 (10.0 g, 86.8 mmol) in DCM (150 mL) was added TEA (43.9 g, 434 mmol) and TFAA (45.6 g, 217 mmol) dropwise in turn under $N_2$ atmosphere. The reaction mixture was stirred at 15° C. for 16 hours. The reaction was quenched with saturated $NH_4Cl$ (200 mL), then extracted with DCM (100 mL×2), the combined organic layers was washed with brine (150 mL), dried over anhydrous Na$_2$SO$_4$, filtered, concentrated under vacuum to give compound D9 (16.2 g, crude) as a yellow oil.

Procedure for Synthesis of D1P

To a solution of n-BuLi (2.5 M, 56.8 mL) in anhydrous THF (200 mL) was added N-isopropylpropan-2-amine (13.7 g, 135 mmol) dropwise at −70° C. under N$_2$ atmosphere. The mixture was stirred at 15° C. for 1 hour under N$_2$ atmosphere. Then compound D9 (12.0 g, 123 mmol) in anhydrous THF (20 mL) was added into the mixture at −70° C. under N$_2$ atmosphere and the resulting mixture was stirred at −70° C. under N$_2$ atmosphere for 2 hours. HCO$_2$Et (12.8 g, 173 mmol) in anhydrous THF (20 mL) was added dropwise at −70° C. under N$_2$ atmosphere, the reaction mixture was stirred at 15° C. for 16 hours. TLC showed a new spot. The reaction was quenched with aqueous HCl (10%), adjusted pH=3~4, extracted with EtOAc (120 mL×2), the combined organic layers was washed with brine (150 mL), dried over anhydrous Na$_2$SO$_4$, filtered and concentrated under vacuum to give compound D10 (13.0 g, crude) as a brown oil. The crude product was used in next step without any purification.

Procedure for Synthesis of D11

To a solution of compound D10 (900 mg, 7.19 mmol) in EtOH (15 mL) was added NH$_2$NH$_2$·H$_2$O (478 mg, 9.35 mmol) and AcOH (734 mg, 12.2 mmol) dropwise in turn. The solution was stirred at 78° C. for 16 hours. TLC showed a new spot. The solution was concentrated under reduced pressure to give yellow oil. EtOAc (20 mL) and H$_2$O (50 mL) was added to the residue, the aqueous phase was neutralized by 1M NaOH and adjusted pH to 9, extracted by EtOAc (20 mL×2). The combined organic layers and washed with brine (30 mL), dried over anhydrous Na$_2$SO$_4$, filtered and concentrated under reduced pressure to give compound D11 (550 mg, crude) as a yellow oil, which was used in next step without any purification.

Procedure for Synthesis of D12

To a solution of compound D11 (550 mg, 3.95 mmol) in DCM (10 mL) at −78° C. was added EtO$_2$C—NCS (518 mg, 3.95 mmol) dropwise under N$_2$ atmosphere. The reaction solution was stirred at −78° C. for 10 minutes. TLC showed the starting material was consumed and some new spots were formed. The reaction solution was concentrated under reduced pressure to give a yellow crude oil, which was purified by Combi Flash to give an intermediate (230 mg) as a yellow solid. To a solution of an intermediate (230 mg, 0.850 mmol) in MeCN (4 mL) was added K$_2$CO$_3$ (235 mg, 1.70 mmol) in one portion. The suspension was stirred at 80° C. for 1 hour. LCMS showed the reaction was completed. This suspension was neutralized by AcOH and adjusted pH to 4, concentrated under reduced pressure to give a yellow oil. DCM (20 mL) was added to dissolve the product, washed with H$_2$O (2×20 mL) and brine (20 mL). The organic layers was dried over anhydrous Na$_2$SO$_4$, filtered and concentrated under reduced pressure to give compound D12 (300 mg) as a yellow solid.

Procedure for Synthesis of D13

To a solution of compound D12 (300 mg, 1.34 mmol) in EtOH (7 mL) and NaOH (2 M, 1.34 mL) was added MeI (190 mg, 1.34 mmol) dropwise. The mixture was stirred at 15° C. for 0.5 hour. LCMS showed the reaction was completed. The mixture was concentrated under vacuum to give the residue, DCM (15 mL) was added, 6M HCl (2 mL) was added and the resulting mixture was stirred for 10 minutes. The mixture was extracted with DCM (20 mL×2), the combined organic layers were washed by water (20 mL×2) and brine (30 mL), dried over anhydrous Na$_2$SO$_4$, filtered and concentrated under vacuum to give compound D13 (160 mg) as a yellow solid, which was used in next step without any purification.

Procedure for Synthesis of D14

To a solution of compound D13 (500 mg, 2.10 mmol) in N,N-diethylaniline (1.57 g, 10.5 mmol was added POCl$_3$ (16.5 g, 107 mmol), the reaction mixture was stirred at 90° C. for 2 hours to give a brown solution. The mixture was concentrated under reduced pressure to remove POCl$_3$. The product was used for next without further purification.

Procedure for Synthesis of D16

To a solution of compound D14 (500 mg, 1.95 mmol) in MeCN (2.00 mL) was added DIEA (1.26 g, 9.75 mmol), then compound D15 (675 mg, 3.90 mmol) was added into above mixture, the resulting mixture was stirred at 20° C. for 2 hours. LCMS show desired MS value. The mixture was poured into water (50 mL), extracted with EtOAc (50 mL×3), the combined extracts was washed with brine (100 mL), dried over anhydrous Na$_2$SO$_4$, filtered, the filtrate was concentrated under reduced pressure to give a residue. The residue was purified by Combi flash to give compound D16 (524 mg) as a white powder.

Procedure for Synthesis of D17

To a solution of compound D16 (524 mg, 1.33 mmol) in CH$_2$Cl$_2$ (5.00 mL) was added m-CPBA (573 mg, 2.66 mmol) the mixture was stirred at 20° C. for 1 hour. LCMS showed compound D16 was consumed, and desired MS has been got. The reaction was quenched with saturated aqueous Na$_2$S$_2$O$_3$ (20 mL), the mixture was extracted with DCM (30 mL×3), the combined extracts was washed with saturated aqueous NaHCO$_3$ (30 mL) and water (30 mL×2), the organic phase was dried over anhydrous Na$_2$SO$_4$, filtered, the filtrate was concentrated under reduced pressure to give compound D17 (450 mg) as yellow oil.

Procedure for Synthesis of D18

To a mixture of compound D17 (450 mg, 1.06 mmol) in NMP (5.00 mL) was added compound D5 (423 mg, 2.12 mmol) in one portion at 120° C. under N$_2$. The mixture was stirred at 120° C. for 3 hours to give a yellow solution. TLC showed compound D17 was consumed, and an new spot was formed. The mixture was poured into water (10 mL), a lot of white solid appeared, the mixture was filtered, the filter cake was washed with water (10 mL) and dried over high vacuum to give compound D18 (390 mg) as white powder.

Procedure for Synthesis of Compound 24

To a mixture of compound D18 (390 mg, 0.714 mmol) in CH$_2$Cl$_2$ (10.0 mL) was added TFA (4.84 g, 42.4 mmol) in one portion. The mixture was stirred at 25° C. for 2 hours to give a yellow solution. LCMS showed the reaction was complete. To the reaction solution was added aqueous saturated NaHCO$_3$ solution to give pH=7-8, extracted with DCM (10 mL×2), the combined organic phase was concentrated under reduced pressure to give brown oil. The crude product was purified by prep-HPLC (0.01% TFA). Most of MeCN was removed under reduced pressure. The remaining solvent was removed by lyophilization to give compound 24 (161.1 mg) as a white powder.

Scheme 50: Synthetic route for compound 18

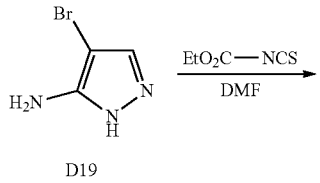

D19

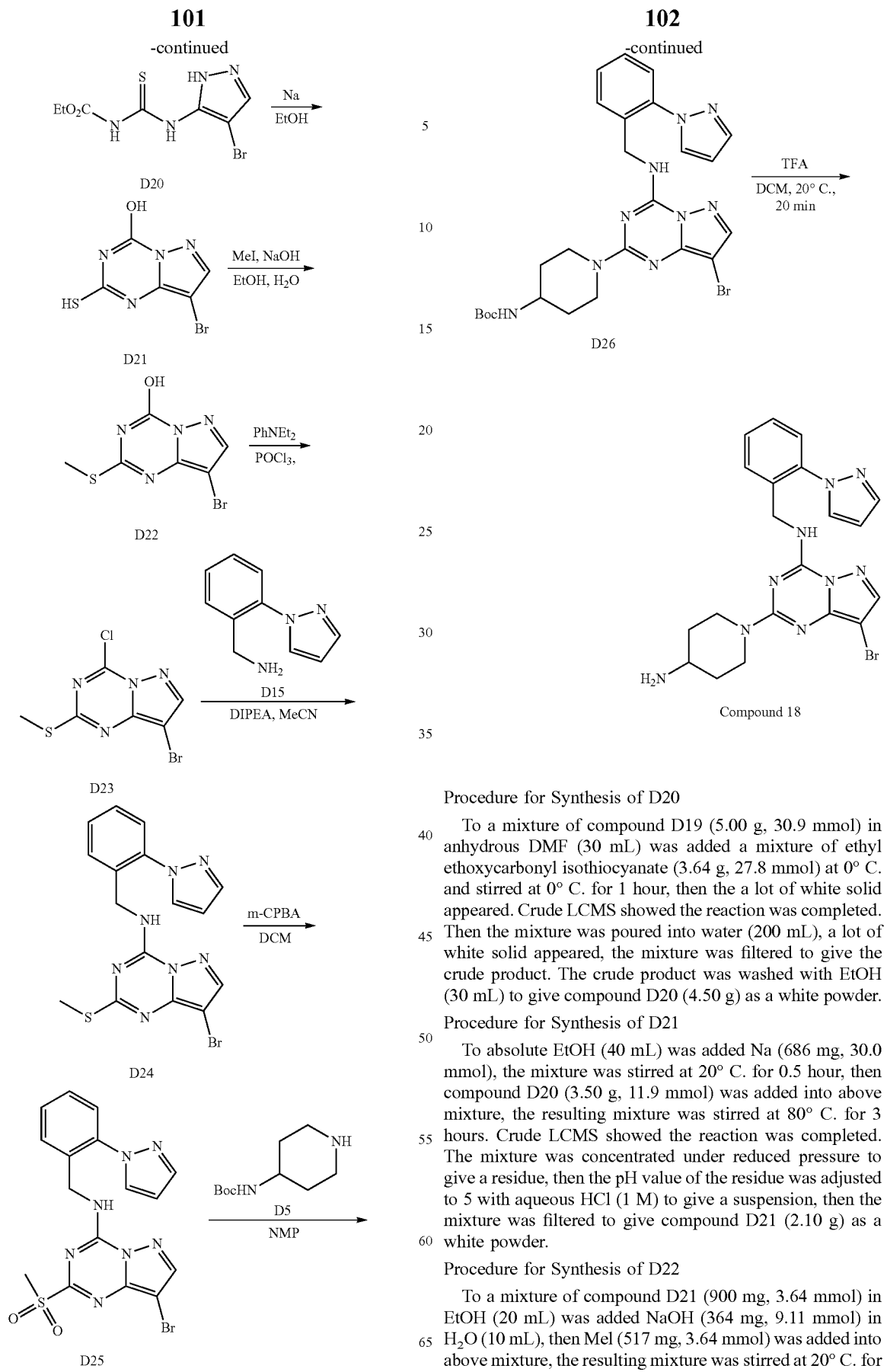

Procedure for Synthesis of D20

To a mixture of compound D19 (5.00 g, 30.9 mmol) in anhydrous DMF (30 mL) was added a mixture of ethyl ethoxycarbonyl isothiocyanate (3.64 g, 27.8 mmol) at 0° C. and stirred at 0° C. for 1 hour, then the a lot of white solid appeared. Crude LCMS showed the reaction was completed. Then the mixture was poured into water (200 mL), a lot of white solid appeared, the mixture was filtered to give the crude product. The crude product was washed with EtOH (30 mL) to give compound D20 (4.50 g) as a white powder.

Procedure for Synthesis of D21

To absolute EtOH (40 mL) was added Na (686 mg, 30.0 mmol), the mixture was stirred at 20° C. for 0.5 hour, then compound D20 (3.50 g, 11.9 mmol) was added into above mixture, the resulting mixture was stirred at 80° C. for 3 hours. Crude LCMS showed the reaction was completed. The mixture was concentrated under reduced pressure to give a residue, then the pH value of the residue was adjusted to 5 with aqueous HCl (1 M) to give a suspension, then the mixture was filtered to give compound D21 (2.10 g) as a white powder.

Procedure for Synthesis of D22

To a mixture of compound D21 (900 mg, 3.64 mmol) in EtOH (20 mL) was added NaOH (364 mg, 9.11 mmol) in H$_2$O (10 mL), then MeI (517 mg, 3.64 mmol) was added into above mixture, the resulting mixture was stirred at 20° C. for 17 hours. Two batches reaction was combined and crude LCMS showed the reaction was completed. The mixture was concentrated under reduced pressure to give a residue. The pH value of the residue was adjusted to 5 with aqueous HCl (1M), a lot of white solid appeared, filtered to give compound D22 (1.80 g) as a white powder.

Procedure for Synthesis of D23

To a mixture of compound D22 (800 mg, 3.06 mmol) in POCl₃ (6 mL) was added N, N-diethylaniline (2.74 g, 18.4 mmol), the mixture was stirred at 90° C. for 2 horns. The mixture was concentrated under reduced pressure to give 4.20 g (crude) of compound D23 as a yellow gum.

Procedure for Synthesis of D24

To a solution of compound D23 (4.20 g, crude) and DIPEA (11.7 g, 90.1 mmol) in MeCN (10 mL) was added compound D15 (1.20 g, 6.91 mmol), the mixture was stirred at 20° C. for 17 hours. Crude LCMS showed the reaction worked not well, then DIPEA (11.7 g, 90.1 mmol) was added into above mixture, the mixture was stirred at 20° C. for 17 hours. Crude LCMS showed the reaction completed. The mixture was poured into water (50 mL), extracted with EtOAc (50 mL×3), the combined extracts was washed with brine (100 mL), dried over anhydrous Na₂SO₄, filtered, the filtrate was concentrated under reduced pressure to give a residue, which was purified by Combi flash to give 300 mg of compound D24 as a yellow gum.

Procedure for Synthesis of D25

To a solution of compound D24 (300 mg, 0.721 mmol) in DCM (10 mL) was added m-CPBA (326 mg, 1.51 mmol, 80% purity), the mixture was stirred at 20° C. for 1 hour. A lot of white solid appeared. Crude LCMS showed the reaction was completed. The reaction was quenched with saturated aqueous Na₂S₂O₃ (3 mL), then the mixture was poured into DCM (100 mL), washed with saturated aqueous NaHCO₃ (100 mL×3) and brine (100 mL×2), the organic phase was dried over anhydrous Na₂SO₄, filtered, the filtrate was concentrated under reduced pressure to give 250 mg of compound D25 as a white powder.

Procedure for Synthesis of D26

To a solution of compound D25 (250 mg, 0.558 mmol) in NMP (3 mL) was added compound D5 (223 mg, 1.12 mmol), the mixture was stirred at 120° C. under N₂ atmosphere for 1 hour. Crude LCMS showed the reaction was completed. After cooling to room temperature, the mixture was poured into water (30 mL), a lot of white solid appeared, the mixture was filtered, the filter cake was washed with water (50 mL) to give 153 mg of compound D26 as a yellow powder.

Procedure for Synthesis of Compound 18

To a solution of compound D26 (150 mg, 0.264 mmol) in DCM (3 mL) was added TFA (4.62 g, 40.5 mmol), the mixture was stirred at 20° C. for 20 minutes. Crude LCMS showed the reaction was completed. The mixture was concentrated under reduced pressure to give a residue, the pH value of the residue was adjusted to 8 with saturated aqueous NaHCO₃, diluted with water (20 mL), the mixture was extracted with DCM (30 mL×3), the combined extracts was washed with brine (50 mL), dried over anhydrous Na₂SO₄, filtered, the filtrate was concentrated under reduced pressure to give a residue, which was purified by prep-HPLC (0.05%, HCl salt). Most of CH₃CN was removed by evaporation under reduced pressure, and the remaining solvent was removed by lyophilization to give 78.6 mg of compound 18 as a white powder.

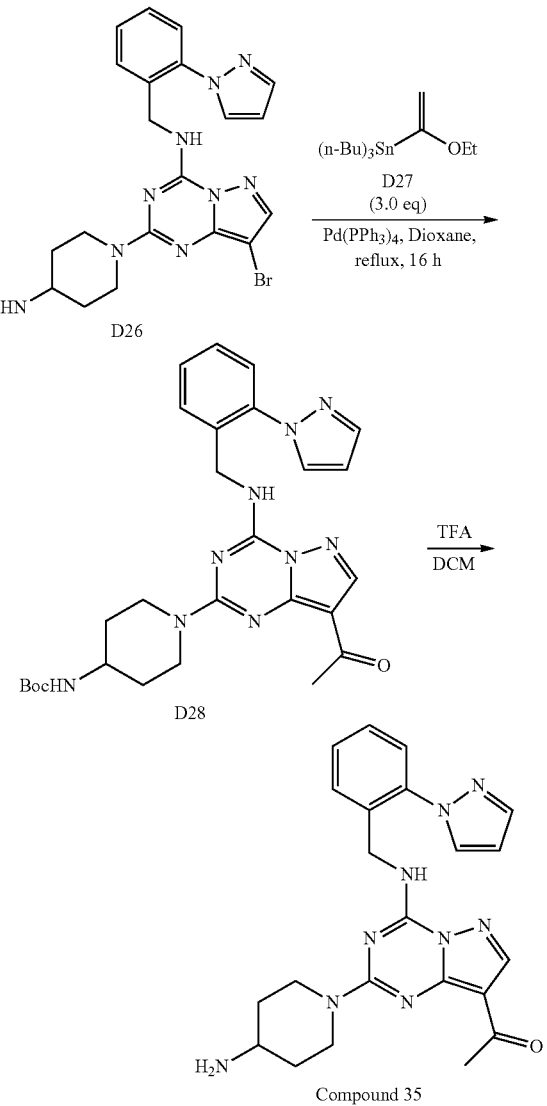

Scheme 51: Synthetic route for compound 35

Procedure for Synthesis of D28

To a mixture of compound D26 (500 mg, 0.879 mmol) in dioxane (5 mL) was added compound D27 (952 mg, 2.64 mmol) and Pd(PPh₃)₄ (101 mg, 0.0879 mmol) in one portion at 120° C. under N₂ atmosphere. The mixture was stirred at 120° C. for 16 h to give a yellow solution. LCMS showed 10.4% of desired MS. The mixture was poured into NH₄Cl aqueous (50 mL) and stirred for 10 minutes. The mixture was partitioned between EtOAc (50 mL) and water (50 mL). The aqueous was extracted with EtOAc (50 mL). The combined organic extract was washed with water (50 mL×2), dried over anhydrous Na₂SO₄, filtered and concentrated under reduced pressure to give a residue. The crude product was purified by Combi Flash to give compound D28 (91.6 mg) as a white powder.

Procedure for Synthesis of Compound 35

To a mixture of compound D28 (110 mg, 0.206 mmol) in CH₂Cl₂ (2 mL) was added TFA (1.40 g, 12.3 mmol) in one portion. The mixture was stirred at 25° C. for 1 hour to give a yellow solution. LCMS showed the reaction was complete and 52.8% desired MS was showed. To the reaction solution was added aqueous saturated NaHCO₃ solution to adjust pH=7~8, extracted with DCM (10 mL×2), the combined organic phase was concentrated under reduced pressure to give brown oil, which was purified by prep-HPLC (0.01% TFA). Most of MeCN was removed under reduced pressure. The remaining solvent was removed by lyophilization to give compound 35 (10.40 mg) as a white powder.

Scheme 52: Synthetic route for compound 30

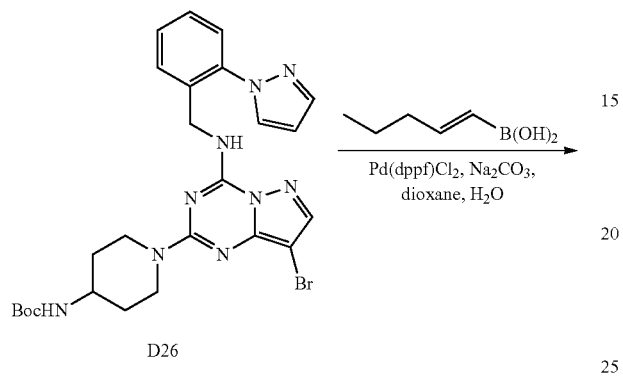

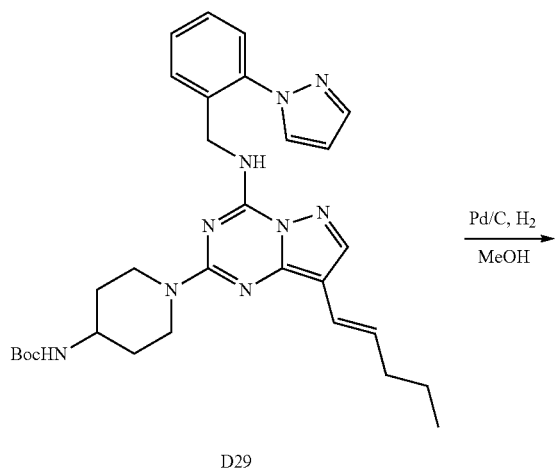

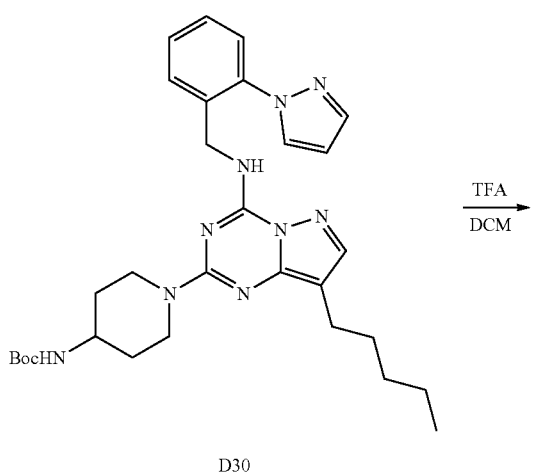

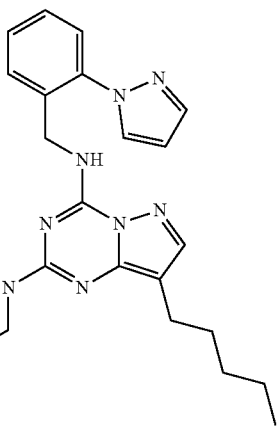

Compound 30

Procedure for Synthesis of D29

To a mixture of Compound D26 (50 mg, 0.088 mmol), 1-pentenylboronic acid (50 mg, 0.44 mmol), Na₂CO₃ (19 mg, 0.18 mmol) in H₂O (0.5 mL) and dioxane (2 mL) was added Pd(dppf)Cl₂ (13 mg, 0.018 mmol), the mixture was purged with N₂ for one time, then the mixture was stirred at 110° C. under microwave for 1 hour under N₂ atmosphere. Crude LCMS showed desired MS value. The mixture was poured into water (30 mL), extracted with DCM (30 mL×3), the combined extracts was washed with brine (50 mL), dried over anhydrous Na₂SO₄, filtered, the filtrate was concentrated under reduced pressure to give a residue. The residue was purified by Combi flash to give 150 mg of compound D29 as a yellow gum.

Procedure for Synthesis of D30

To a solution of compound D29 (120 mg, 0.215 mmol) in MeOH (10 mL) was added Pd/C (20 mg), the mixture was purged with H₂ for three times and stirred at 20° C. under H₂ balloon (15 psi) for 3 hours. Crude LCMS showed the reaction was completed. The mixture was filtered, the filtrate was concentrated under reduced pressure to give 100 mg of compound D30 as a yellow gum.

Procedure for Synthesis of Compound 30

To a solution of compound D30 (100 mg, 0.179 mmol) in DCM (3 mL) was added TFA (2 mL), the mixture was stirred at 20° C. for 1 hour. Crude LCMS showed the reaction was completed. The mixture was concentrated under reduced pressure to give a residue, the pH value of the residue was adjusted to 8 with saturated aqueous NaHCO₃, extracted with DCM (30 mL×3), dried over anhydrous Na₂SO₄, filtered, the filtrate was concentrated under reduced pressure to give a residue. The residue was purified by prep-HPLC (0.05% HCl). Most of CH₃CN was removed by evaporation under reduced pressure, and the remaining solvent was removed by lyophilization to give 10.5 mg of compound 30 as a white powder.

Scheme 53: General Synthetic route for compound 163

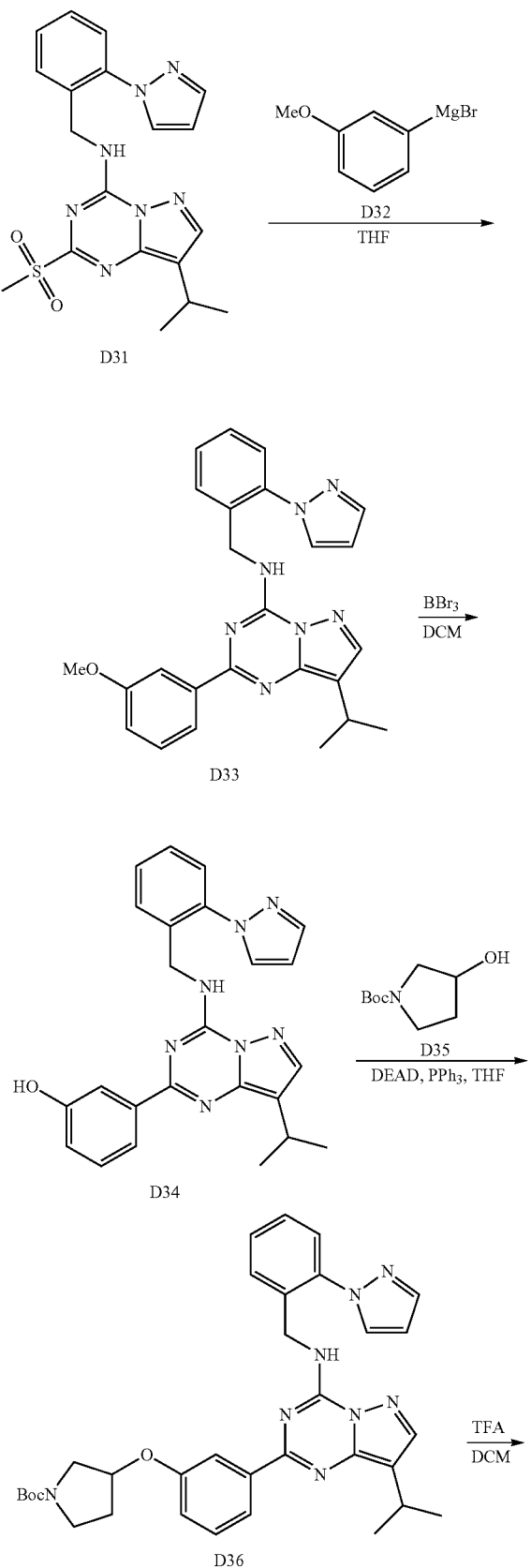

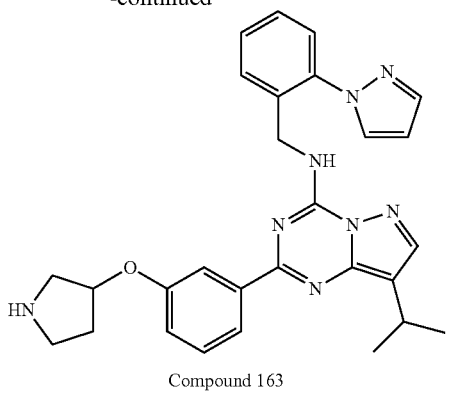

Compound 163

Procedure for Synthesis of D33

To a solution of compound D31 (1.00 g, 2.43 mmol) in anhydrous THF (10 mL) was added compound D32 (1.28 g, 6.08 mmol) at 0° C., the mixture was stirred at 0° C. for 2 hours. Crude LCMS showed the reaction was completed. The reaction was quenched with brine (100 mL), the mixture was extracted with EtOAc (100 mL×2), the combined extracts was washed with brine (100 mL), dried over anhydrous $Na_2SO_4$, filtered, the filtrate was concentrated under reduced pressure to give a residue. The residue was purified by combi flash to give 600 mg of compound D33 as a yellow gum.

Procedure for Synthesis of D34

To a solution of compound D33 (550 mg, 1.25 mmol) in DCM (3 mL) was added $BBr_3$ (627 mg, 2.50 mmol) at 0° C., then the mixture was allowed to warm to 20° C. and stirred at 20° C. for 3 hours. Crude LCMS showed the reaction worked well, the reaction was quenched with saturated aqueous $NH_4Cl$ (30 mL), the pH value of the mixture was adjusted to 8 with saturated aqueous $NaHCO_3$, extracted with EtOAc (50 mL×3), the combined extracts was washed with brine (100 mL), dried over anhydrous $Na_2SO_4$, filtered, the filtrate was concentrated under reduced pressure to give 600 mg of the crude product, confirmed by HNMR. 100 mg was used to next step, but no reaction. Then the crude product was purified by Combi flash to give 360 mg of compound D34 as a yellow gum.

Procedure for Synthesis of D36

To a mixture of compound D34 (310 mg, 0.729 mmol), compound D35 (409 mg, 2.19 mmol) and $PPh_3$ (382 mg, 1.46 mmol) in anhydrous THF (2 mL) was added DEAD (254 mg, 1.46 mmol) at 0° C., then the mixture was allowed to warm to 20° C. and stirred at 20° C. for 17 hours. Crude LCMS showed the reaction worked well. The reaction was quenched with water (30 mL), extracted with EtOAc (30 mL×3), the combined extracts was washed with brine (50 mL), dried over anhydrous $Na_2SO_4$, filtered, the filtrate was concentrated under reduced pressure to give a residue. The residue was purified by Combi flash to give 150 mg of compound D36 as a yellow gum.

Procedure for Synthesis of Compound 163

To a solution of compound D36 (150 mg, 0.252 mmol) in DCM (3 mL) was added TFA (3 mL), the mixture was stirred at 20° C. for 0.5 hour. Crude LCMS showed the reaction was completed. The mixture was concentrated under reduced pressure to give a residue, then the pH value of the mixture was adjusted to pH=8 with saturated aqueous $NaHCO_3$, then diluted with water (15 mL), extracted with DCM (30 mL×3), the combined extracts was washed with brine (50 mL), dried over anhydrous $Na_2SO_4$, filtered, the filtrate was concentrated under reduced pressure to give a residue. The residue was purified by prep-HPLC (0.05% HCl). Most of CH$_3$CN was removed by evaporation under reduced pressure, and the remaining solvent was removed by lyophilization to give 27.8 mg of compound 163 as a yellow gum.

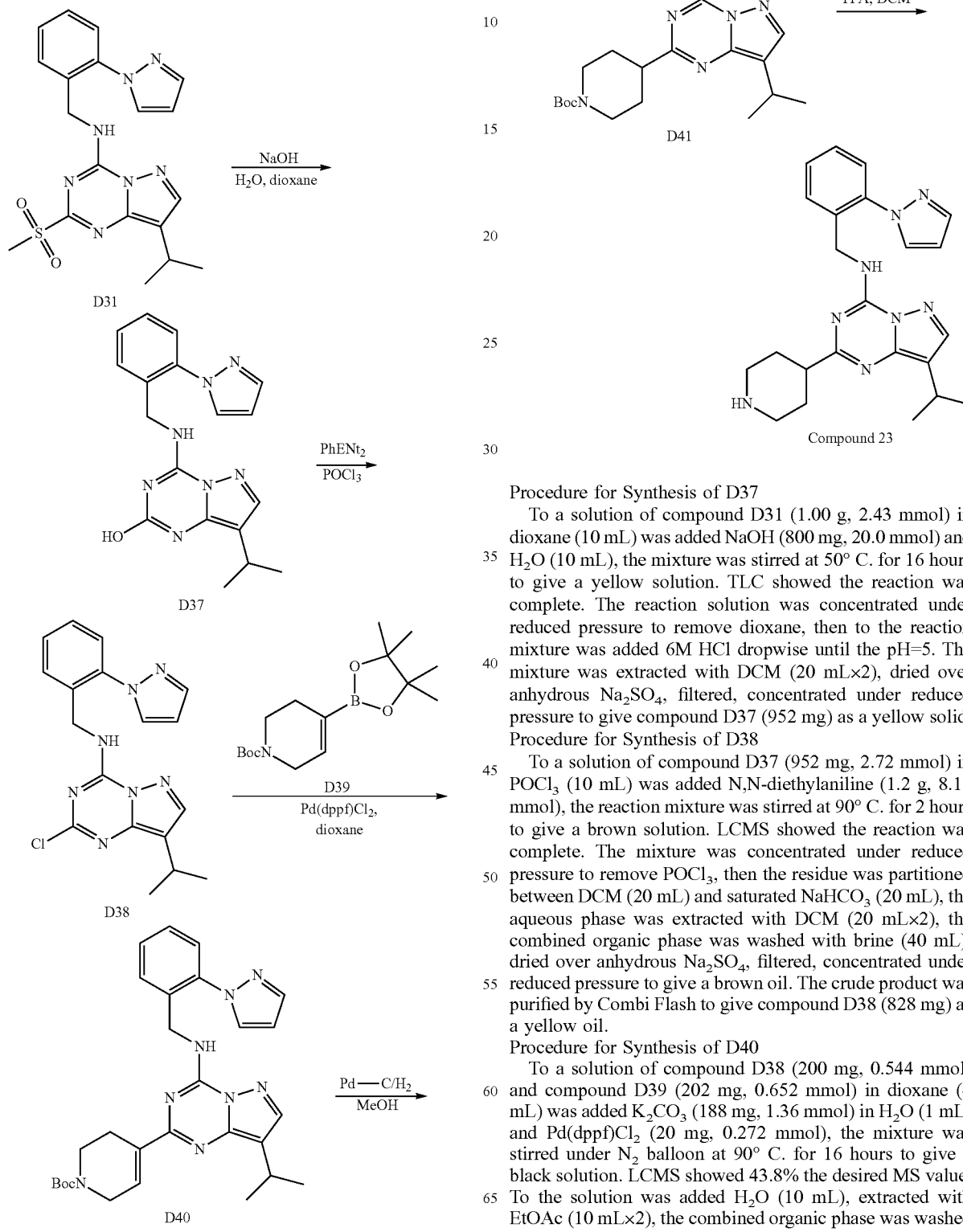

Procedure for Synthesis of D37

To a solution of compound D31 (1.00 g, 2.43 mmol) in dioxane (10 mL) was added NaOH (800 mg, 20.0 mmol) and H$_2$O (10 mL), the mixture was stirred at 50° C. for 16 hours to give a yellow solution. TLC showed the reaction was complete. The reaction solution was concentrated under reduced pressure to remove dioxane, then to the reaction mixture was added 6M HCl dropwise until the pH=5. The mixture was extracted with DCM (20 mL×2), dried over anhydrous Na$_2$SO$_4$, filtered, concentrated under reduced pressure to give compound D37 (952 mg) as a yellow solid.

Procedure for Synthesis of D38

To a solution of compound D37 (952 mg, 2.72 mmol) in POCl$_3$ (10 mL) was added N,N-diethylaniline (1.2 g, 8.16 mmol), the reaction mixture was stirred at 90° C. for 2 hours to give a brown solution. LCMS showed the reaction was complete. The mixture was concentrated under reduced pressure to remove POCl$_3$, then the residue was partitioned between DCM (20 mL) and saturated NaHCO$_3$ (20 mL), the aqueous phase was extracted with DCM (20 mL×2), the combined organic phase was washed with brine (40 mL), dried over anhydrous Na$_2$SO$_4$, filtered, concentrated under reduced pressure to give a brown oil. The crude product was purified by Combi Flash to give compound D38 (828 mg) as a yellow oil.

Procedure for Synthesis of D40

To a solution of compound D38 (200 mg, 0.544 mmol) and compound D39 (202 mg, 0.652 mmol) in dioxane (4 mL) was added K$_2$CO$_3$ (188 mg, 1.36 mmol) in H$_2$O (1 mL) and Pd(dppf)Cl$_2$ (20 mg, 0.272 mmol), the mixture was stirred under N$_2$ balloon at 90° C. for 16 hours to give a black solution. LCMS showed 43.8% the desired MS value. To the solution was added H$_2$O (10 mL), extracted with EtOAc (10 mL×2), the combined organic phase was washed with brine (10 mL), dried over anhydrous Na$_2$SO$_4$, filtered, concentrated under reduced pressure to give a brown oil, which was purified by Combi Flash to give compound D40 (119 mg) as a yellow oil.

Procedure for Synthesis of D41

To a suspension of compound D40 (181 mg, 0.352 mmol) in MeOH (5 mL) was added Pd/C (50% wet, 10% Pd), the mixture was stirred under H₂ balloon (15 psi) at 25° C. for 16 hours to give a black suspension. LCMS showed the reaction was complete. The suspension was filtered through a pad of Celite, the combined filtrates were concentrated under reduced pressure to give compound D41 (121 mg) as a yellow oil.

Procedure for Synthesis of Compound 23

To the solution of compound D41 (121 mg, 0.234 mmol) in DCM (4 mL) was added TFA (1 mL), the reaction solution was stirred at 25° C. for 2 hours to give a yellow solution. LCMS f showed the reaction was complete. To the reaction solution was added aqueous saturated NaHCO₃ solution (10 mL), extracted with DCM (10 mL×2), the combined organic phase was concentrated under reduced pressure to give an brown oil. The crude product was purified by prep-HPLC (0.05% HCl). To the eluent containing the desired product was added saturated NaHCO₃ until the pH=7, extracted with DCM (20 mL×3), the combined organic phase was concentrated under reduced pressure. The residual aqueous solution was lyophilized to give compound 23 (3.9 mg) as a white powder.

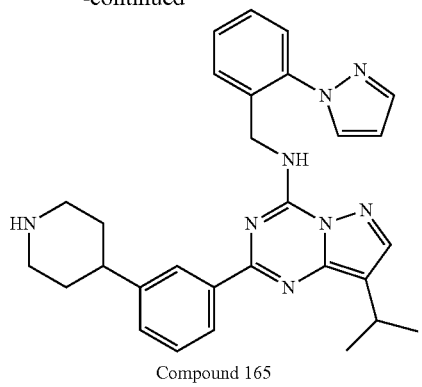

Compound 165

Procedure for Synthesis of D43

To a solution of compound D38 (120 mg, 0.326 mmol), compound D42 (235 mg, crude, about 0.489 mmol), Pd(PPh₃)₄ (65 mg, 0.056 mmol) in dioxane (3 mL) and H₂O (750 uL) was added Na₂CO₃ (86 mg, 0.82 mmol). The reaction mixture was stirred at 110° C. for 1 hour under N₂ under microwave condition. TLC (PE/EtOAc=5/1, SiO₂) showed the reaction was completed. The reaction mixture was diluted with DCM (10 mL) and water (10 mL), and then filtered. The filtrate was separated. The organic layer was dried over anhydrous Na₂SO₄, filtered, concentrated under reduced pressure to give the crude product as a brown gum, which was purified by Combi flash to give compound D43 (126 mg) as a colorless oil. The impure product was used directly in the next step without further purification.

Procedure for Synthesis of Compound 165

To a solution of compound D43 (133 mg, crude) in DCM (1.6 mL) was added TFA (400 uL). The reaction solution was stirred at 25° C. for 1 hour. LCMS showed the reaction was completed. The reaction solution was diluted with DCM (10 mL) and water (5 mL). To the mixture was added ammonia water (0.5 mL, 28%) until aqueous layer pH>7. The organic layer was separated and washed with water (10 mL), then concentrated under reduced pressure to give the crude product as a brown oil, which was purified by prep-HPLC (0.05% HCl as additive). Most of MeCN was removed under reduced pressure; the remaining solvent was removed by lyophilization to give compound 165 (35.9 mg) as an off-white powder.

Scheme 55: Synthetic route for compound 165

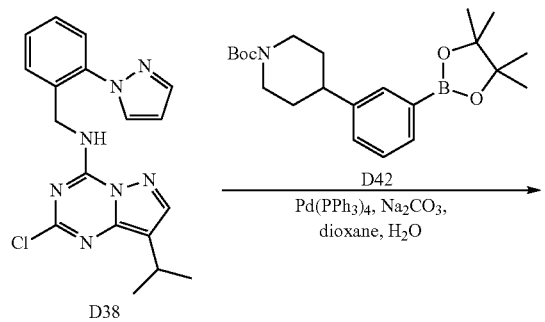

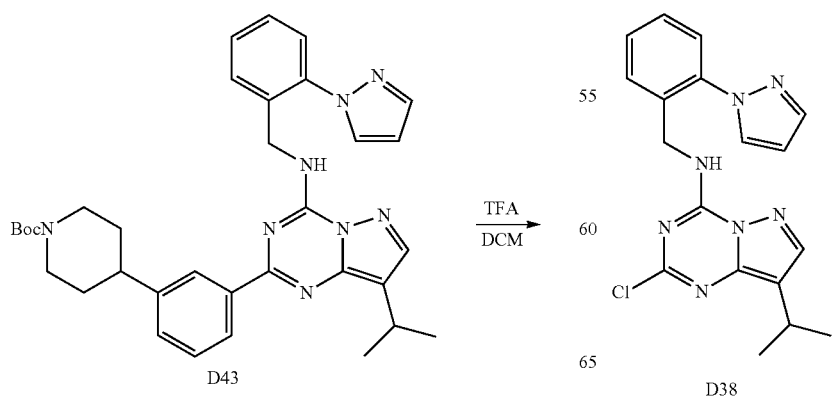

Scheme 56: Synthetic route for compound 171

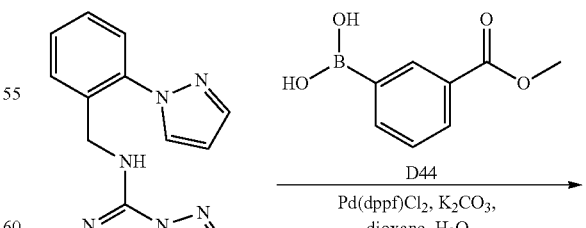

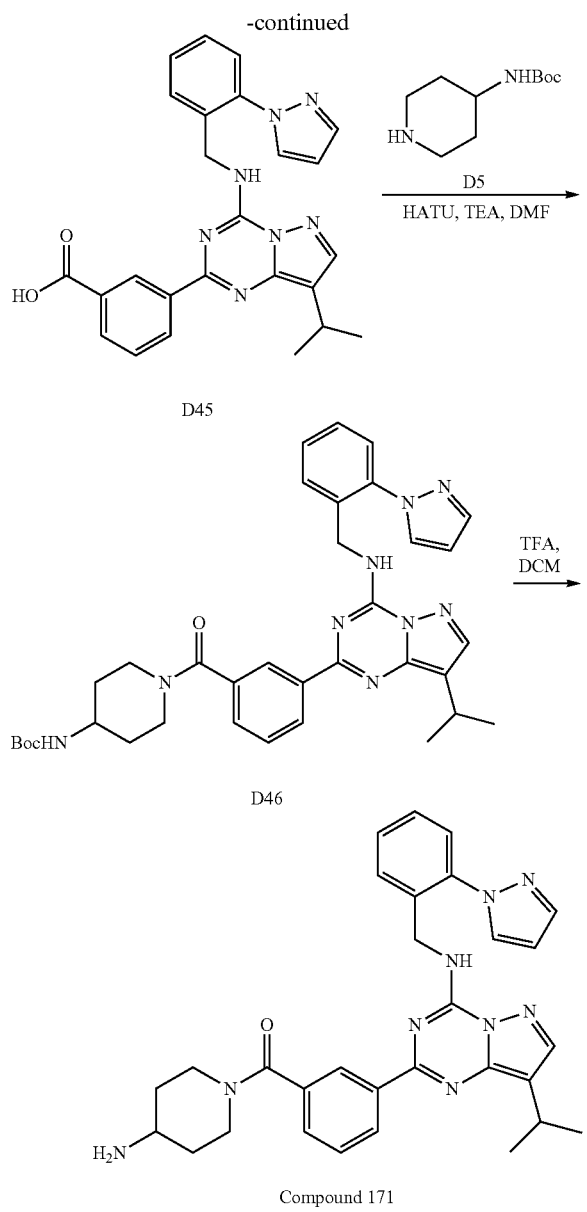

D45

D46

Compound 171

Procedure for Synthesis of D45

To compound D38 (200 mg, 0.54 mmol) and K₂CO₃ (187 mg, 1.36 mmol) in dioxane (1 mL) and H₂O (0.5 mL) was added compound D44 (176 mg, 0.979 mmol) and Pd(dppf)Cl₂ (39.7 mg, 0.54 mmol). The reaction mixture was stirred at 110° C. for 16 hours under N₂ atmosphere. LCMS showed 82.4% of desired MS value. The mixture was partitioned between EtOAc (100 mL) and H₂O (100 mL). The aqueous was extracted with EtOAc (100 mL). The combined organic extract was washed with water (50 mL×2), dried over anhydrous Na₂SO₄, filtered and concentrated under reduced pressure to give compound D45 as a red powder.

Procedure for Synthesis of D46

To a solution of compound D45 (100 mg, 0.221 mmol) and compound D5 (53 mg, 0.26 mmol) in anhydrous DMF (1 mL) was added HATU (104 mg, 0.276 mmol) and TEA (37 mg, 0.36 mmol) under N₂ atmosphere. The mixture was stirred at 25° C. under N₂ atmosphere for 16 hours. LCMS showed 74.3% desired MS value. The mixture was partitioned between EtOAc (50 mL) and H₂O (50 mL). The aqueous was extracted with EtOAc (50 mL). The combined organic extract was washed with water (50 mL×2), dried over anhydrous Na₂SO₄, filtered and concentrated under reduced pressure to give a residue. The residue was purified by Combi flash to give compound D46 (95.0 mg) as a yellow oil.

Procedure for Synthesis of Compound 171

To a mixture of compound D46 (95 mg, 0.15 mmol) in CH₂Cl₂ (4 mL) was added TEA (1 mL) in one portion. The mixture was stirred at 25° C. for 1 hour to give a yellow solution. LCMS showed the reaction was complete and 98.7% desired MS value. To the reaction solution was added aqueous saturated NaHCO₃ solution to adjust pH=7~8, extracted with DCM (10 mL x 2), the combined organic phase was concentrated under reduced pressure to give a yellow oil, which was purified by prep-HPLC (0.05% HCl). Most of MeCN was removed under reduced pressure. The remaining solvent was removed by lyophilization to compound 171 (41.8 mg) as a yellow powder.

REFERENCES

D. B. Bregman, R. G. Pestell and V. J. Kidd. Cell cycle regulation and RNA polymerase II. *Front Biosci.* 2000 February; 1 (5): D244-57.

D. Desai, H. C. Wessling, R. R Fisher, and D. O. Morgan. Effects of phosphorylation by CAK on cyclin binding by CDCl₂ and CDK2. *Mol. Cell Biol.* 1995 January; 15(1): 345-350.

S. Akhtar, M. Heidemann, J. R. Tietjen, D. W. Zhang, R. D. Chapman, D. Eick, and A. Z. Ansari. TFIIH Kinase Places Bivalent Marks on the Carboxy-Terminal Domain of RNA Polymerase II. *Mol. Cell.* 2009 May; 15; 34(3):387-93.

S. Larochelle, R. Amat, K. G. Cutter, M. Sansó, C. Zhang, J. J. Allen, K. M. Shokat, D. L. Bentley and R. P. Fisher. Cyclin-dependent kinase control of the initiation-to-elongation switch of RNA polymerase II. *Nat. Struct. Mol. Biol.* 2012 November; 19(11):1108-15.

G. I. Shapiro. Cyclin-Dependent Kinase Pathways as Targets for Cancer Treatment. *J. Clin. Oncol.* 2006 April; 10; 24(11):1770-83.

G. Lolli and L. N. Johnson. CAK-Cyclin-dependent Activating Kinase: a key kinase in cell cycle control and a target for drugs? *Cell Cycle.* 2005 April; 4(4):572-7. T. I. Lee and R. A. Young. Transcriptional Regulation and its misregulation in Disease. Cell. 2013 March; 14; 152(6): 1237-51.

S. Nekhai, M. Zhou, A. Fernandez, W. S. Lane, Ned J. C. Lamb, J. Brady, A. Kumar. *Biochem. J.* 2002 June; 15; 364(Pt 3):649-57.

Y. K. Kim, C. F. Bourgeois, R. Pearson, M. Tyagi, M. J. West, J. Wong, S. Y. Wu, C. M. Chiang, and J. Kam. Recruitment of TFIIH to the HIV LTR is a rate-limiting step in the emergence of HIV from latency. *EMBO. J.* 2006 August; 9; 25(15): 3596-3604.

A. J. Kapasi and D. H. Spector. Inhibition of the Cyclin-Dependent Kinases at the Beginning of Human Cytomegalovirus Infection Specifically Alters the Levels and Localization of the RNA Polymerase II Carboxyl-Terminal Domain Kinases cdk9 and cdk7 at the Viral Transcriptosome. *J. Virol.* 2008 January; 82(1): 394-407.

Eickhoff et al, Pyrazolo-triazine derivatives as selective cyclin-dependent kinase inhibitors. PCT WO2013/128028A1.

TABLE 1

Enzymatic activity of CDKs (1, 2, 5 and 7) and selectivity of CDK7

| #cpds | CDK1 | CDK2 | CDK5 | CDK7 | CDK1/CDK7* | CDK2/CDK7** | CDK5/CDK7*** |
|---|---|---|---|---|---|---|---|
| 1 | C | C | B | A | B | B | C |
| 2 | C | B | B | B | A | B | B |
| 3 | C | C | B | A | A | B | B |
| 4 | C | B | B | A | B | B | B |
| 8 | C | C | C | B | B | B | C |
| 9 | B | B | A | A | B | B | C |
| 10 | B | B | A | A | B | B | C |
| 11 | C | B | B | A | A | B | B |
| 12 | B | B | A | A | B | B | C |
| 13 | C | C | B | A | A | B | B |
| 14 | B | B | B | A | A | B | B |
| 15 | C | C | C | A | A | A | B |
| 16 | B | B | A | A | B | B | C |
| 17 | C | B | B | A | B | B | C |
| 18 | B | B | A | A | B | B | C |
| 19 | C | B | B | A | A | B | B |
| 20 | C | C | C | A | A | A | A |
| 21 | C | C | C | A | A | A | A |
| 24 | B | B | A | A | B | B | B |
| 25 | B | A | A | A | B | C | C |
| 27 | B | B | A | A | A | B | B |
| 28 | C | B | B | A | B | B | C |
| 31 | B | A | A | A | B | B | C |
| 33 | B | B | A | A | B | B | C |
| 34 | C | B | B | A | B | C | C |
| 36 | B | B | A | A | B | C | C |
| 38 | C | C | B | A | A | A | B |
| 39 | C | C | C | A | A | A | A |
| 40 | C | B | B | A | A | B | C |
| 42 | C | B | B | A | A | A | B |
| 43 | C | C | C | A | A | A | A |
| 44 | B | B | A | A | B | B | B |
| 46 | C | C | C | A | A | A | A |
| 47 | B | B | A | A | B | B | C |
| 48 | C | C | B | A | A | A | B |
| 51 | C | C | C | A | B | B | B |
| 52 | C | B | B | A | C | C | C |
| 54 | C | B | B | A | B | B | C |
| 55 | B | B | B | A | B | B | C |
| 56 | C | C | B | A | B | B | C |
| 57 | C | C | B | A | A | A | B |
| 61 | C | B | B | A | B | B | C |
| 62 | B | B | A | A | B | B | C |
| 63 | B | B | B | A | B | B | B |
| 64 | C | C | B | A | A | A | B |
| 65 | C | C | B | A | B | B | C |
| 66 | C | C | B | A | A | A | A |
| 67 | C | B | B | A | B | C | C |
| 69 | B | A | A | A | B | B | C |
| 70 | C | B | B | A | A | B | B |
| 71 | C | C | B | A | B | B | B |
| 72 | B | B | B | A | A | B | B |
| 73 | C | C | B | A | A | A | B |
| 74 | C | C | B | A | B | B | B |
| 75 | C | C | B | A | A | B | B |
| 76 | C | C | B | A | A | B | B |
| 77 | B | B | B | A | A | B | B |
| 78 | B | B | A | A | A | B | B |
| 79 | C | C | C | A | A | A | A |
| 80 | B | B | A | A | A | B | B |
| 81 | C | C | C | A | A | A | A |
| 83 | C | B | B | A | A | A | B |
| 86 | B | B | A | A | B | B | C |
| 87 | C | C | B | A | A | A | B |
| 88 | C | C | B | A | A | B | B |
| 89 | C | C | B | A | A | A | B |
| 90 | C | C | C | A | A | A | A |
| 91 | B | B | B | A | A | B | B |
| 92 | C | C | C | A | A | A | A |
| 93 | C | B | B | A | A | B | B |
| 94 | B | B | B | A | A | B | B |
| 95 | C | B | B | A | A | A | B |
| 96 | C | C | B | A | A | A | B |
| 97 | B | B | B | A | B | B | B |
| 98 | B | B | A | A | A | B | B |

TABLE 1-continued

Enzymatic activity of CDKs (1, 2, 5 and 7) and selectivity of CDK7

| #cpds | CDK1 | CDK2 | CDK5 | CDK7 | CDK1/CDK7* | CDK2/CDK7** | CDK5/CDK7*** |
|---|---|---|---|---|---|---|---|
| 99  | C | C | B | A | A | A | B |
| 102 | B | B | A | A | B | B | C |
| 103 | C | B | B | A | A | B | B |
| 104 | C | C | B | A | A | A | B |
| 105 | C | C | C | A | A | B | B |
| 106 | C | B | B | A | A | B | B |
| 107 | C | B | B | A | A | A | B |
| 108 | B | B | B | A | B | B | B |
| 109 | C | B | B | A | A | A | B |
| 110 | B | A | A | A | B | B | C |
| 111 | C | C | C | A | B | B | C |
| 112 | B | B | A | A | B | B | C |
| 114 | C | C | C | B | A | B | B |
| 115 | C | B | B | A | A | B | B |
| 116 | B | A | A | A | B | B | C |
| 117 | C | C | C | B | A | A | B |
| 118 | C | B | B | A | B | B | B |
| 119 | C | B | B | A | A | B | B |
| 120 | C | B | B | A | A | A | B |
| 121 | C | B | B | A | A | B | B |
| 122 | C | B | B | A | A | B | B |
| 123 | B | B | A | A | B | B | C |
| 124 | B | B | A | A | B | B | C |
| 125 | C | C | C | A | A | B | B |
| 126 | C | B | B | A | A | B | B |
| 127 | C | B | B | A | A | B | B |
| 128 | B | B | A | A | B | B | C |
| 129 | C | B | B | A | A | A | B |
| 130 | C | B | B | A | A | B | B |
| 131 | C | C | C | A | B | B | B |
| 132 | C | C | B | A | A | B | B |
| 133 | C | B | B | A | A | B | B |
| 134 | C | B | B | A | A | B | B |
| 135 | C | C | C | A | A | B | B |
| 136 | C | C | B | A | A | A | B |
| 137 | B | A | A | A | C | C | C |
| 138 | B | B | A | A | A | B | C |
| 139 | C | B | B | A | A | B | B |
| 140 | B | B | A | A | B | B | C |
| 141 | B | B | A | A | B | B | C |
| 142 | C | B | B | A | A | B | B |
| 143 | B | B | A | A | B | B | C |
| 144 | B | B | A | A | B | B | C |
| 145 | B | B | A | A | B | B | C |
| 146 | B | B | B | A | A | A | B |
| 147 | C | C | B | A | A | B | B |
| 148 | C | B | A | A | A | A | B |
| 149 | B | A | A | A | B | B | C |
| 150 | C | C | B | A | A | A | B |
| 151 | B | B | B | A | A | B | B |
| 152 | C | B | A | A | A | B | B |
| 153 | C | C | B | A | A | A | B |
| 154 | C | B | A | A | A | A | B |
| 155 | B | B | A | A | A | B | B |
| 156 | C | B | B | A | A | B | B |
| 157 | C | B | B | A | A | A | B |
| 158 | B | B | A | A | B | B | B |
| 159 | C | B | B | A | A | B | B |
| 160 | C | B | B | A | A | B | B |
| 161 | B | B | B | A | A | B | B |
| 163 | C | B | B | A | A | B | B |
| 164 | C | C | C | A | B | B | B |
| 165 | C | C | B | A | A | B | B |
| 167 | C | C | B | A | A | B | B |
| 168 | C | B | B | A | A | B | B |
| 169 | C | C | C | A | A | B | B |
| 170 | C | C | B | A | A | B | B |
| 171 | C | C | C | A | A | A | A |
| 172 | C | B | B | A | A | B | B |
| 173 | C | C | B | A | A | B | B |
| 174 | C | C | B | A | A | A | B |
| 175 | C | C | C | A | A | B | B |
| 176 | B | B | B | A | B | B | B |
| 177 | B | B | A | A | A | B | C |
| 178 | C | B | A | A | A | B | C |

TABLE 1-continued

Enzymatic activity of CDKs (1, 2, 5 and 7) and selectivity of CDK7

| #cpds | CDK1 | CDK2 | CDK5 | CDK7 | CDK1/CDK7* | CDK2/CDK7** | CDK5/CDK7*** |
|---|---|---|---|---|---|---|---|
| 179 | B | B | B | A | B | B | B |
| 180 | B | B | A | A | B | B | C |
| 181 | B | B | B | A | B | B | B |
| 182 | C | C | C | A | A | A | A |
| 183 | C | C | C | A | A | A | A |
| 184 | C | C | B | A | A | A | B |
| 185 | C | C | C | A | A | A | B |
| 186 | C | C | C | A | A | A | B |
| 187 | C | C | C | A | A | A | A |
| 188 | C | C | C | B | B | C | C |
| 189 | C | C | B | A | A | A | B |
| 190 | C | C | C | A | A | A | B |
| 191 | B | B | B | A | B | B | B |
| 192 | C | C | C | A | A | A | A |
| 193 | C | C | B | A | A | A | B |
| 194 | C | C | C | A | A | A | A |
| 195 | C | C | B | A | A | A | A |
| 196 | C | C | B | A | A | A | A |
| 197 | C | C | B | A | A | A | B |
| 198 | C | C | B | A | A | A | A |
| 199 | C | C | C | A | A | A | A |
| 200 | C | C | C | A | A | A | A |
| 201 | C | C | B | A | A | A | B |
| 202 | C | C | C | A | A | A | A |
| 203 | C | C | C | A | A | A | A |
| 204 | C | C | C | A | A | A | A |
| 205 | C | C | B | A | A | A | B |
| 206 | C | C | B | A | A | A | B |
| 207 | C | C | B | A | A | A | B |
| 208 | B | A | B | A | B | C | B |
| 209 | C | C | C | A | A | A | A |
| 210 | C | C | B | A | A | A | A |
| 211 | C | C | C | A | A | A | A |
| 212 | C | C | C | A | A | B | B |
| 213 | C | C | C | A | A | A | A |
| 214 | C | C | C | A | A | A | A |
| 215 | C | C | C | A | A | A | A |
| 216 | C | C | C | A | A | A | A |
| 217 | C | C | C | A | A | A | A |
| 218 | C | C | C | A | A | A | A |
| 219 | C | C | C | A | A | A | A |
| 220 | C | C | C | A | A | A | A |
| 221 | C | C | C | A | A | A | A |
| 222 | C | B | B | A | A | A | A |
| 223 | C | C | C | A | A | B | B |
| 224 | C | C | C | A | A | A | A |
| 225 | C | B | B | A | A | A | A |
| 226 | C | C | C | A | A | A | A |
| 227 | C | C | C | A | A | A | A |
| 228 | C | C | B | A | A | A | A |
| 229 | C | B | B | A | B | C | C |
| 230 | C | C | C | A | A | A | A |
| 231 | C | C | C | A | A | A | A |
| 232 | C | C | C | A | A | A | A |
| 233 | C | B | C | A | A | B | A |
| 234 | C | C | C | A | A | A | A |
| 235 | C | C | B | A | A | B | B |
| 236 | B | B | B | A | A | B | B |
| 237 | C | C | C | A | A | A | A |
| 238 | C | C | C | A | A | A | A |
| 239 | C | C | C | A | A | A | A |
| 240 | C | C | C | A | A | A | A |
| 241 | C | C | C | A | A | A | B |
| 242 | C | B | B | A | A | B | B |
| 243 | C | C | C | A | A | A | A |
| 244 | C | C | C | A | A | A | A |
| 245 | C | C | C | A | A | A | A |
| 246 | C | C | C | A | A | A | A |
| 247 | C | C | C | A | A | A | A |
| 248 | C | C | C | A | A | A | A |
| 249 | C | C | C | A | A | A | A |
| 250 | C | C | C | A | A | A | B |
| 251 | C | C | C | A | A | A | A |
| 252 | C | C | C | A | A | A | A |
| 253 | C | C | C | B | B | B | B |

TABLE 1-continued

Enzymatic activity of CDKs (1, 2, 5 and 7) and selectivity of CDK7

| #cpds | CDK1 | CDK2 | CDK5 | CDK7 | CDK1/CDK7* | CDK2/CDK7** | CDK5/CDK7*** |
|---|---|---|---|---|---|---|---|
| 254 | C | C | B | A | A | B | B |
| 255 | C | C | B | A | A | A | B |
| 256 | C | C | C | A | A | A | A |
| 257 | C | B | B | A | A | B | B |
| 258 | C | C | C | A | A | A | A |
| 259 | C | C | C | A | A | A | A |
| 260 | C | C | C | B | B | B | B |
| 261 | C | C | C | A | A | A | A |
| 262 | C | C | C | B | B | B | B |
| 263 | C | C | C | B | B | B | B |
| 264 | C | C | C | B | B | B | B |
| 265 | C | C | C | A | A | A | A |
| 266 | C | C | C | A | A | A | A |
| 267 | C | C | C | B | B | B | B |
| 268 | C | C | C | A | A | A | A |
| 269 | C | C | C | A | A | A | A |
| 270 | C | C | C | A | A | A | A |
| 271 | C | C | C | A | A | A | A |
| 272 | C | C | C | A | A | A | A |
| 273 | C | C | C | A | A | A | A |
| 274 | C | C | B | A | A | B | B |
| 275 | C | C | C | A | A | B | B |
| 276 | C | C | C | C | B | B | B |
| 277 | C | C | C | C | C | C | C |
| 278 | C | C | C | A | A | A | A |
| 279 | C | C | C | B | B | B | B |

Activity range: A indicates $IC_{50} \leq 100$ nM,
B indicates $100 < IC_{50} \leq 1{,}000$ nM,
C indicates $IC_{50} > 1{,}000$ nM
*CDK1/CDK7: Selectivity of CDK7 inhibition over CDK1 inhibition [fold]
**CDK2/CDK7: Selectivity of CDK7 inhibition over CDK2 inhibition [fold]
***CDK5/CDK7: Selectivity of CDK7 inhibition over CDK5 inhibition [fold]
Selectivity range: A indicates [fold] > 200,
B indicates $20 < $ [fold] $\leq 200$,
C indicates [fold] $\leq 20$

TABLE 2

| HCT116 viability assay | |
|---|---|
| #cpds | IC50 |
| 1 | B |
| 14 | A |
| 18 | A |
| 21 | A |
| 24 | A |
| 27 | A |
| 31 | A |
| 43 | A |
| 47 | A |
| 48 | A |
| 49 | B |
| 50 | B |
| 51 | B |
| 52 | C |
| 53 | B |
| 66 | A |
| 72 | A |
| 73 | A |
| 80 | A |
| 89 | B |
| 90 | B |
| 97 | A |
| 98 | A |
| 99 | A |
| 102 | A |
| 104 | A |
| 108 | A |
| 109 | A |
| 112 | A |
| 116 | A |
| 122 | A |
| 124 | A |
| 133 | A |
| 134 | A |
| 136 | A |
| 139 | A |
| 144 | A |
| 145 | A |
| 146 | A |
| 147 | A |
| 148 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 171 | A |
| 172 | B |
| 175 | B |
| 177 | A |
| 179 | A |
| 180 | A |
| 181 | A |

TABLE 2-continued

| HCT116 viability assay | |
|---|---|
| #cpds | IC50 |
| 182 | A |
| 183 | A |
| 184 | A |
| 189 | A |
| 192 | A |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | B |
| 212 | B |
| 213 | B |
| 214 | A |
| 215 | B |
| 216 | A |
| 217 | A |
| 218 | A |
| 219 | A |
| 220 | A |
| 221 | A |
| 222 | A |
| 223 | A |
| 224 | A |
| 225 | A |
| 226 | A |
| 227 | A |
| 228 | A |
| 229 | B |
| 230 | A |
| 231 | A |
| 232 | B |
| 233 | A |
| 234 | A |
| 235 | B |
| 236 | A |
| 237 | B |
| 238 | A |
| 239 | B |
| 240 | A |
| 241 | A |
| 257 | A |

Activity range: A indicates $IC_{50} \leq 1$ uM,
B indicates $1 < IC_{50} \leq 10$ uM,
C indicates $IC_{50} > 10$ uM

TABLE 3

| H460 viability assay | |
|---|---|
| #cpds | IC50 |
| 1 | A |
| 2 | A |
| 3 | B |
| 4 | B |
| 5 | B |
| 6 | A |
| 7 | C |
| 8 | C |

TABLE 3-continued

| H460 viability assay | |
|---|---|
| #cpds | IC50 |
| 9 | A |
| 10 | A |
| 11 | A |
| 12 | A |
| 13 | A |
| 14 | A |
| 16 | A |
| 17 | B |
| 18 | A |
| 20 | A |
| 21 | A |
| 22 | A |
| 23 | A |
| 24 | A |
| 25 | A |
| 27 | A |
| 29 | B |
| 31 | A |
| 33 | A |
| 34 | B |
| 38 | A |
| 39 | B |
| 40 | A |
| 41 | A |
| 42 | A |
| 43 | A |
| 44 | A |
| 45 | A |
| 46 | B |
| 47 | A |
| 48 | A |
| 49 | B |
| 50 | A |
| 51 | B |
| 52 | B |
| 53 | A |
| 54 | A |
| 55 | B |
| 56 | A |
| 57 | B |
| 59 | B |
| 60 | A |
| 61 | A |
| 62 | A |
| 63 | A |
| 64 | A |
| 65 | B |
| 66 | A |
| 67 | B |
| 68 | A |
| 69 | A |
| 70 | B |
| 71 | B |
| 72 | A |
| 73 | A |
| 74 | B |
| 75 | B |
| 76 | A |
| 77 | A |
| 78 | A |
| 79 | B |
| 80 | A |
| 90 | B |
| 96 | A |
| 97 | A |
| 98 | A |
| 99 | A |
| 100 | A |
| 101 | B |
| 102 | A |
| 103 | A |
| 104 | A |
| 105 | B |
| 106 | A |

TABLE 3-continued

H460 viability assay

| #cpds | IC50 |
|---|---|
| 107 | A |
| 108 | A |
| 109 | A |
| 110 | A |
| 112 | A |
| 113 | A |
| 116 | A |
| 118 | A |
| 119 | A |
| 120 | A |
| 121 | A |
| 122 | A |
| 123 | A |
| 124 | A |
| 126 | A |
| 127 | A |
| 128 | A |
| 129 | A |
| 130 | A |
| 132 | B |
| 133 | A |
| 134 | B |
| 135 | B |
| 136 | B |
| 137 | A |
| 138 | A |
| 139 | A |
| 140 | B |
| 141 | B |
| 142 | B |
| 143 | B |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | A |
| 157 | A |
| 160 | A |
| 161 | A |
| 163 | A |
| 165 | A |
| 167 | A |
| 170 | A |
| 171 | A |
| 172 | B |
| 173 | B |
| 174 | A |
| 175 | B |
| 176 | A |
| 177 | A |
| 178 | A |
| 179 | A |
| 180 | A |
| 181 | A |
| 182 | A |
| 183 | A |
| 184 | A |
| 185 | B |
| 186 | B |
| 187 | B |
| 188 | B |
| 189 | A |
| 190 | B |
| 191 | A |
| 192 | B |
| 193 | A |
| 194 | A |
| 195 | A |

TABLE 3-continued

H460 viability assay

| #cpds | IC50 |
|---|---|
| 196 | B |
| 197 | A |
| 198 | B |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | B |
| 212 | B |
| 213 | B |
| 214 | A |
| 215 | A |
| 216 | A |
| 217 | A |
| 218 | A |
| 219 | A |
| 220 | A |
| 221 | A |
| 222 | A |
| 223 | A |
| 224 | A |
| 225 | A |
| 226 | A |
| 227 | A |
| 228 | A |
| 229 | B |
| 230 | A |
| 231 | A |
| 232 | B |
| 233 | A |
| 234 | A |
| 235 | B |
| 236 | A |
| 237 | B |
| 238 | A |
| 239 | B |
| 240 | A |
| 241 | A |
| 242 | A |
| 243 | A |
| 244 | A |
| 245 | A |
| 246 | A |
| 247 | B |
| 248 | A |
| 249 | A |
| 250 | B |
| 251 | A |
| 252 | A |
| 253 | B |
| 254 | A |
| 255 | A |
| 256 | A |
| 257 | A |
| 258 | A |
| 260 | B |
| 261 | A |
| 262 | C |
| 263 | C |
| 264 | C |
| 265 | A |
| 266 | A |
| 267 | B |
| 268 | A |
| 269 | A |
| 270 | B |
| 271 | A |
| 272 | B |

TABLE 3-continued

H460 viability assay

| #cpds | IC50 |
|---|---|
| 273 | B |
| 274 | A |
| 275 | B |

Activity range: A indicates $IC_{50} \leq 1$ uM,
B indicates $1 < IC_{50} \leq 10$ uM,
C indicates $IC_{50} > 10$ uM

TABLE 4

MM.1S viability assay

| #cpds | IC50 |
|---|---|
| 13 | A |
| 14 | A |
| 20 | B |
| 21 | A |
| 38 | A |
| 39 | B |
| 42 | A |
| 43 | B |
| 46 | B |
| 48 | A |
| 66 | A |
| 72 | A |
| 73 | A |
| 79 | B |
| 90 | C |
| 102 | A |
| 104 | A |
| 105 | A |
| 108 | A |
| 134 | B |
| 143 | A |
| 150 | A |
| 153 | A |
| 154 | A |
| 160 | A |
| 163 | A |
| 171 | A |
| 174 | A |
| 175 | B |
| 176 | A |
| 177 | A |
| 178 | A |
| 180 | A |
| 181 | A |
| 182 | A |
| 183 | A |
| 184 | A |
| 185 | B |
| 186 | B |
| 187 | B |
| 188 | B |
| 189 | A |
| 192 | B |
| 193 | A |
| 194 | A |
| 195 | A |
| 196 | B |
| 197 | A |
| 198 | A |

Activity range: A indicates $IC_{50} \leq 1$ uM,
B indicates $1 < IC_{50} \leq 10$ uM,
C indicates $IC_{50} > 10$ uM

TABLE 5

MV4-11 viability assay

| #cpds | IC50 |
|---|---|
| 2 | A |
| 14 | A |
| 18 | A |
| 20 | A |
| 21 | A |
| 27 | A |
| 38 | A |
| 39 | B |
| 40 | A |
| 42 | A |
| 43 | A |
| 46 | B |
| 48 | A |
| 64 | A |
| 66 | A |
| 71 | B |
| 72 | A |
| 73 | A |
| 77 | A |
| 78 | A |
| 79 | B |
| 80 | A |
| 89 | A |
| 90 | A |
| 92 | A |
| 97 | A |
| 98 | A |
| 99 | A |
| 102 | A |
| 103 | A |
| 104 | A |
| 106 | A |
| 107 | A |
| 108 | A |
| 109 | A |
| 110 | A |
| 112 | A |
| 113 | A |
| 115 | A |
| 116 | A |
| 119 | B |
| 120 | A |
| 122 | A |
| 123 | A |
| 124 | A |
| 128 | A |
| 129 | A |
| 130 | A |
| 133 | A |
| 134 | A |
| 136 | A |
| 139 | A |
| 140 | A |
| 143 | A |
| 144 | A |
| 145 | A |
| 146 | A |
| 147 | A |
| 148 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 163 | A |
| 164 | B |
| 165 | A |
| 167 | A |
| 170 | A |

TABLE 5-continued

MV4-11 viability assay

| #cpds | IC50 |
|---|---|
| 171 | A |
| 174 | A |
| 175 | B |
| 176 | A |
| 177 | A |
| 178 | A |
| 179 | A |
| 180 | A |
| 181 | A |
| 182 | A |
| 183 | A |
| 184 | A |
| 185 | B |
| 186 | B |
| 187 | B |
| 188 | B |
| 189 | A |
| 190 | B |
| 191 | A |
| 192 | A |
| 193 | A |
| 194 | A |
| 195 | A |
| 196 | A |
| 197 | A |
| 198 | A |
| 199 | B |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | B |
| 212 | B |
| 213 | B |
| 214 | A |
| 215 | B |
| 216 | A |
| 217 | A |
| 218 | A |
| 219 | A |
| 220 | A |
| 221 | A |
| 222 | A |
| 223 | A |
| 224 | A |
| 225 | A |
| 226 | B |
| 227 | B |
| 228 | A |
| 229 | B |
| 230 | A |
| 231 | A |
| 232 | B |
| 233 | A |
| 234 | A |
| 235 | B |
| 236 | A |
| 237 | B |
| 238 | A |
| 239 | B |
| 240 | A |
| 241 | A |
| 242 | A |
| 243 | A |
| 244 | A |
| 245 | B |
| 246 | A |
| 247 | B |
| 248 | B |

TABLE 5-continued

MV4-11 viability assay

| #cpds | IC50 |
|---|---|
| 249 | A |
| 250 | B |
| 251 | A |
| 252 | A |
| 253 | B |
| 254 | A |
| 255 | A |
| 256 | A |
| 257 | A |
| 258 | A |
| 260 | B |
| 261 | B |
| 262 | C |
| 263 | C |
| 264 | C |
| 265 | B |
| 266 | B |
| 267 | C |
| 268 | C |
| 269 | B |
| 270 | B |
| 271 | A |
| 272 | B |
| 273 | B |
| 274 | A |
| 275 | B |
| 276 | A |

Activity range: A indicates $IC_{50} \leq 1$ uM,
B indicates $1 < IC_{50} \leq 10$ uM,
C indicates $IC_{50} > 10$ uM

TABLE 6

MOLT4 viability assay

| #cpds | IC50 |
|---|---|
| 1 | B |
| 2 | B |
| 3 | C |
| 4 | C |
| 5 | C |
| 6 | C |
| 9 | B |
| 18 | B |
| 24 | B |
| 27 | B |
| 36 | B |
| 37 | C |
| 38 | B |
| 39 | C |
| 40 | C |
| 41 | C |
| 42 | B |
| 43 | B |
| 44 | B |
| 45 | B |
| 46 | B |
| 47 | B |
| 48 | B |
| 49 | B |
| 50 | B |
| 51 | B |
| 52 | B |
| 53 | B |
| 54 | B |
| 55 | B |
| 56 | B |
| 57 | B |
| 58 | B |
| 59 | B |
| 60 | C |
| 61 | B |

TABLE 6-continued

MOLT4 viability assay

| #cpds | IC50 |
|---|---|
| 62 | B |
| 63 | C |
| 64 | C |
| 66 | B |
| 68 | B |
| 69 | B |
| 70 | C |
| 71 | B |
| 72 | A |
| 73 | B |
| 74 | C |
| 75 | B |
| 76 | B |
| 77 | B |
| 78 | B |
| 79 | C |
| 80 | B |
| 81 | C |
| 82 | B |
| 83 | B |
| 84 | B |
| 85 | C |
| 86 | B |
| 87 | B |
| 88 | B |
| 89 | B |
| 90 | C |
| 91 | B |
| 92 | C |
| 93 | B |
| 94 | B |
| 95 | B |
| 96 | B |
| 97 | B |
| 98 | A |
| 99 | B |
| 100 | B |
| 101 | B |
| 103 | B |
| 104 | B |
| 105 | B |
| 106 | B |
| 107 | B |
| 108 | B |
| 109 | A |
| 110 | A |
| 111 | B |
| 112 | A |
| 113 | A |
| 114 | B |
| 115 | B |
| 116 | A |
| 117 | B |
| 162 | C |
| 169 | B |
| 170 | B |
| 171 | B |
| 172 | B |
| 173 | B |
| 174 | C |

Activity range: A indicates IC$_{50}$ ≤ 1 uM,
B indicates 1 < IC$_{50}$ ≤ 10 uM,
C indicates IC$_{50}$ > 10 uM

TABLE 7

RPMI-8226 viability assay

| #cpds | IC50 |
|---|---|
| 17 | B |
| 14 | A |
| 18 | A |
| 19 | A |
| 21 | B |
| 27 | A |
| 38 | A |
| 39 | B |
| 42 | A |
| 43 | B |
| 44 | A |
| 46 | B |
| 48 | A |
| 54 | B |
| 56 | B |
| 58 | B |
| 59 | B |
| 61 | B |
| 63 | B |
| 66 | B |
| 69 | A |
| 71 | B |
| 72 | A |
| 73 | B |
| 76 | A |
| 77 | A |
| 78 | A |
| 79 | B |
| 80 | A |
| 87 | A |
| 90 | B |
| 92 | B |
| 95 | A |
| 96 | A |
| 97 | A |
| 98 | A |
| 99 | B |
| 100 | B |
| 101 | B |
| 102 | A |
| 103 | A |
| 104 | A |
| 105 | B |
| 106 | A |
| 107 | A |
| 108 | A |
| 109 | A |
| 110 | A |
| 111 | B |
| 112 | A |
| 113 | A |
| 114 | B |
| 115 | B |
| 116 | A |
| 117 | B |
| 118 | A |
| 119 | B |
| 120 | A |
| 121 | A |
| 122 | A |
| 123 | A |
| 124 | A |
| 125 | B |
| 126 | A |
| 127 | A |
| 128 | A |
| 129 | A |
| 130 | A |
| 131 | B |
| 132 | B |
| 133 | A |
| 134 | A |
| 135 | B |
| 136 | B |
| 137 | A |
| 138 | A |
| 139 | A |
| 140 | B |
| 141 | A |

TABLE 7-continued

RPMI-8226 viability assay

| #cpds | IC50 |
|---|---|
| 142 | B |
| 143 | B |
| 144 | A |
| 145 | A |
| 146 | A |
| 147 | B |
| 170 | B |
| 171 | B |
| 175 | B |
| 182 | A |
| 274 | B |

Activity range: A indicates $IC_{50} \leq 1$ uM,
B indicates $1 < IC_{50} \leq 10$ uM,
C indicates $IC_{50} > 10$ uM

TABLE 8

A2780 viability assay

| #cpds | IC50 |
|---|---|
| 2 | A |
| 4 | B |
| 48 | A |
| 102 | A |
| 129 | A |
| 130 | A |
| 144 | A |
| 163 | A |
| 182 | A |
| 183 | A |
| 194 | A |
| 210 | A |
| 219 | A |
| 225 | A |
| 230 | A |
| 231 | A |
| 233 | A |
| 234 | A |
| 238 | A |
| 241 | A |
| 242 | A |
| 243 | A |
| 244 | A |
| 244 | A |
| 245 | A |
| 246 | A |
| 247 | B |
| 248 | A |
| 249 | A |
| 250 | B |
| 251 | A |
| 252 | A |
| 253 | B |
| 254 | A |
| 255 | A |
| 256 | A |
| 258 | A |
| 260 | B |
| 261 | A |
| 262 | C |
| 263 | C |
| 264 | C |
| 265 | A |
| 266 | A |
| 267 | B |
| 268 | B |
| 269 | A |
| 270 | B |
| 271 | A |
| 272 | B |
| 273 | B |
| 274 | A |

TABLE 8-continued

A2780 viability assay

| #cpds | IC50 |
|---|---|
| 275 | B |
| 276 | B |
| 277 | C |
| 278 | B |
| 279 | A |

Activity range: A indicates $IC_{50} \leq 1$ uM,
B indicates $1 < IC_{50} \leq 10$ uM,
C indicates $IC_{50} > 10$ uM

TABLE 9

OVCAR-3 viability assay

| #cpds | IC50 |
|---|---|
| 48 | B |
| 144 | B |
| 163 | B |
| 182 | B |
| 183 | B |
| 194 | B |
| 210 | A |
| 219 | B |
| 225 | A |
| 251 | B |
| 265 | B |
| 266 | A |
| 271 | A |
| 277 | C |
| 278 | C |
| 279 | B |

Activity range: A indicates $IC_{50} \leq 1$ uM,
B indicates $1 < IC_{50} \leq 10$ uM,
C indicates $IC_{50} > 10$ uM

TABLE 10

Comparative data of CDK7 selectivity profile in CDKs family

| CDKs family | WO2013128028 VIII-59 (uM) | compound 210 (uM) |
|---|---|---|
| CDK1/CycA2 | 1.276 | >10 |
| CDK1/CycB1 | 2.131 | >10 |
| CDK1/CycE1 | 1.124 | >10 |
| CDK2/CycA2 | 0.407 | 3.606 |
| CDK2/CycD1 | 1.7 | >10 |
| CDK2/CycE1 | 0.172 | 3.481 |
| CDK3/CycC | 3.976 | >10 |
| CDK3/CycE1 | 0.592 | >10 |
| CDK4/CycD1 | 7.746 | >10 |
| CDK4/CycD2 | 5.434 | >10 |
| CDK4/CycD3 | >10 | >10 |
| CDK5/p25NCK | 0.317 | >10 |
| CDK5/p35NCK | 0.217 | 4.789 |
| CDK6/CycD1 | 7.498 | >10 |
| CDK6/CycD2 | >10 | >10 |
| CDK6/CycD3 | >10 | >10 |
| CDK7/CycH/MAT1 | 0.003 | 0.015 |
| CDK8/CycC | >10 | >10 |
| CDK9/CycK | 2.573 | >10 |
| CDK9/CycT1 | 2.006 | >10 |
| CDK12 wt/CycK | 2.812 | >10 |
| CDK12 R722C/CycK | N/A | >10 |
| CDK13/CycK | 7.415 | >10 |
| CDK16/CycY | 0.054 | 3.96 |
| CDK17/p35NCK | 1.729 | >10 |
| CDK19/CycC | >10 | >10 |
| CDK20/CycH | 8.786 | >10 |
| CDK20/CycT1 | 9.698 | >10 |

TABLE 11

Summarized compounds 1-279 in terms of their structures and corresponding characteristics.

| # cpds | Structure | Characterization Data |
|---|---|---|
| 1 | 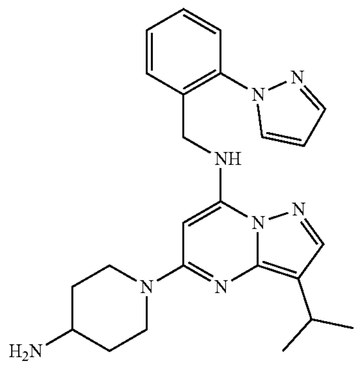 | white powder; ¹H-NMR (CDCl₃, 400 MHz): δ 7.79 (1H, s), 7.68 (1H, d, J = 2.0 Hz), 7.64 (1H, s), 7.51-7.58 (1H, m), 7.32-7.43 (3H, m), 6.44-6.57 (2H, m), 5.38 (1H, s), 4.52 (2H, d, J = 6.0 Hz), 4.25-4.35 (2H, m), 3.03-3.14 (1H, m), 2.85-2.96 (3H, m), 1.85-1.95 (2H, m), 1.10-1.40 (8H, m); LCMS: 100%, MS (ESI): m/z 431.0 [M + H]⁺ |
| 2 | 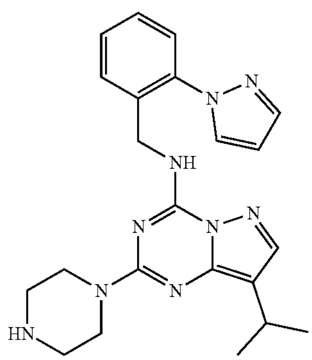 | white powder; ¹H-NMR (CDCl₃, 400 MHz): δ 7.86 (1H, s), 7.73 (1H, d, J = 2.0 Hz), 7.55-7.65 (3H, m), 7.31-7.36 (3H, m), 6.50 (1H, s), 4.69 (2H, d, J = 6.0 Hz), 3.80-3.90 (4H, m), 2.94-3.05 (5H, m), 1.27 (6H, d, J = 6.8 Hz); LCMS: 98.0%, MS (ESI): m/z = 418.0 [M + H]+ |
| 3 | 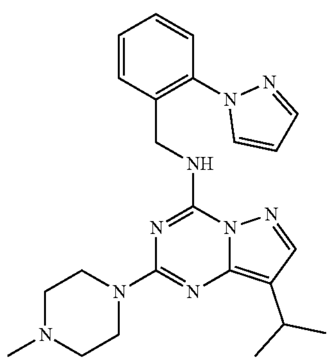 [SMILES: CC(C)c1cnn2c(NCc3ccccc3-n3cccn3)nc(N3CCN(C)CC3)nc12] | white powder; ¹H-NMR (CDCl₃, 400 MHz): δ 7.86 (1H, s), 7.73 (1H, d, J = 2.0 Hz), 7.60-7.65 (3H, m), 7.31-7.40 (3H, m), 6.50 (1H, s), 4.69 (2H, d, J = 6.0 Hz), 3.80-4.00 (4H, m), 2.97-3.04 (1H, m), 2.45-2.55 (4H, m), 2.38 (3H, s), 1.26 (6H, d, J = 6.8 Hz); LCMS: 100%, MS (ESI): m/z = 432.1 [M + H]+ |
| 4 | 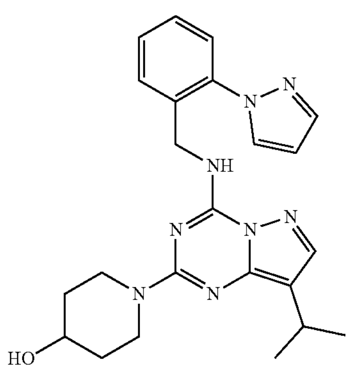 [SMILES: CC(C)c1cnn2c(NCc3ccccc3-n3cccn3)nc(N3CCC(O)CC3)nc12] | white powder; ¹H-NMR (CDCl₃, 400 MHz): δ 7.86 (1H, s), 7.73 (1H, d, J = 2.4 Hz), 7.61-7.68 (3H, m), 7.31-7.40 (3H, m), 6.50 (1H, s), 4.69 (2H, d, J = 6.4 Hz), 4.45-4.55 (2H, m), 3.92-4.00 (1H, m), 3.25-3.35 (2H, m), 2.99-3.05 (1H, m), 1.95-2.00 (2H, m), 1.50-1.55 (2H, m), 1.27 (6H, d, J = 7.2 Hz); LCMS: 100%, MS (ESI): m/z = 433.0 [M + H]+ |

TABLE 11-continued

Summarized compounds 1-279 in terms of their structures and corresponding characteristics.

| # cpds | Structure | Characterization Data |
|---|---|---|
| 5 | 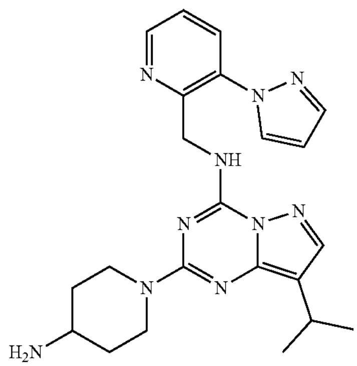 | white powder; $^1$H-NMR (CDCl$_3$, 400 MHz): δ 8.65 (1H, d, J =3.6 Hz), 7.83 (1H, s), 7.68-7.75 (2H, m), 7.50-7.67 (2H, m), 7.30-7.42 (1H, m), 6.53 (1H, s), 4.89 (2H, s), 4.60-4.70 (2H, m), 2.95-3.09 (1H, m), 2.76-2.94 (3H, m), 1.80-1.87 (2H, m), 1.27 (8H, d, J = 6.8 Hz); LCMS: 97.8%, MS (ESI): m/z 433.1 [M + H]+ |
| 6 | 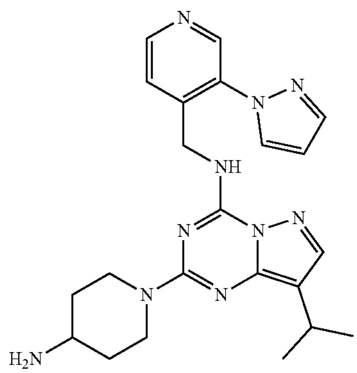 [SMILES: CC(C)c1cnn2c(NCc3ccncc3-n3cccn3)nc(N3CCC(N)CC3)nc12] | white powder; $^1$H-NMR (CDCl$_3$, 400 MHz): δ 8.62 (1H, s), 8.55 (1H, d, J = 4.4 Hz), 7.92 (1H, s), 7.80 (1H, d, J = 2.0 Hz), 7.62 (1H, s), 7.56 (1H, d, J = 4.8 Hz), 7.42 (1H, brs), 6.56 (1H, s), 4.78 (2H, d, J = 6.0 Hz), 4.65-4.75 (2H, m), 2.89-3.05 (4H, m), 1.85-1.95 (2H, m), 1.20-1.30 (8H, m); LCMS: 99.0%, MS (ESI): m/z 433.1 [M + H]+ |
| 7 | 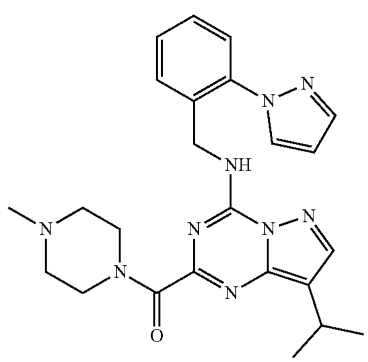 [SMILES: CC(C)c1cnn2c(NCc3ccccc3-n3cccn3)nc(C(=O)N3CCN(C)CC3)nc12] | yellow powder; $^1$H-NMR (CDCl$_3$, 400 MHz): δ 8.53 (1H, brs), 7.85-7.90 (2H, m), 7.74 (1H, s), 7.73 (1H, d, J = 7.2 Hz), 7.25-7.45 (3H, m), 6.53 (1H, s), 4.77 (2H, d, J = 6.8 Hz), 3.80-3.85 (2H, m), 3.45-3.55 (2H, m), 3.10-3.26 (1H, m), 2.55-2.60 (2H, m), 2.40-2.48 (2H, m), 2.36 (3H, s), 1.30 (6H, d, J = 6.8 Hz); LCMS: 94.7%, MS (ESI): m/z = 460.1 [M + H]+ |
| 8 | 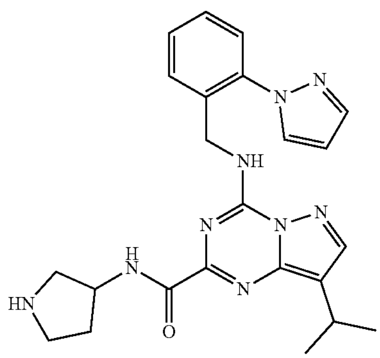 [SMILES: CC(C)c1cnn2c(NCc3ccccc3-n3cccn3)nc(C(=O)NC3CCNC3)nc12] | Racemic mixture; white powder; $^1$H-NMR (CDCl$_3$, 400 MHz): δ 8.07 (1H, brs), 7.92 (1H, s), 7.89 (1H, s), 7.75-7.80 (2H, m), 7.20-7.40 (3H, m), 6.53 (1H, s), 4.85 (2H, s), 4.50-4.60 (1H, m), 3.25-3.35 (2H, m), 3.15-3.20 (1H, s), 2.90-3.05 (2H, m), 2.25-2.30 (1H, m), 1.71-1.85 (1H, m), 1.32 (6H, d, J = 6.4 Hz); LCMS: 99.4%, MS (ESI): m/z 446.1 [M + H]+ |

TABLE 11-continued

Summarized compounds 1-279 in terms of their structures and corresponding characteristics.

| # cpds | Structure | Characterization Data |
|---|---|---|
| 9 | 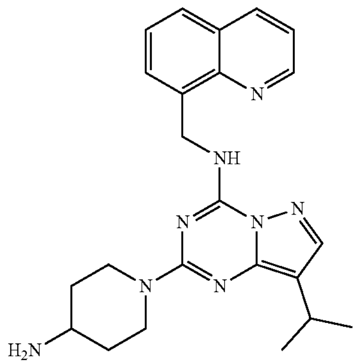 [SMILES: CC(C)c1cnn2c(NCc3cccc4cccnc34)nc(N3CCC(N)CC3)nc12] | off-white solid; $^1$H-NMR (CDCl$_3$, 400 MHz): δ 8.99 (1H, d, J = 2.4 Hz), 8.17 (1H, d, J = 8.4 Hz), 7.77 (2H, d, J = 7.6 Hz), 7.58 (1H, s), 7.37-7.51 (3H, m), 5.33 (2H, d, J = 6.0 Hz), 4.70-4.80 (2H, m), 2.88-3.05 (4H, m), 1.85-1.95 (2H, m), 1.21-1.38 (8H, m); LCMS: 100%, MS (ESI): m/z 417.5 [M + H]+ |
| 10 | 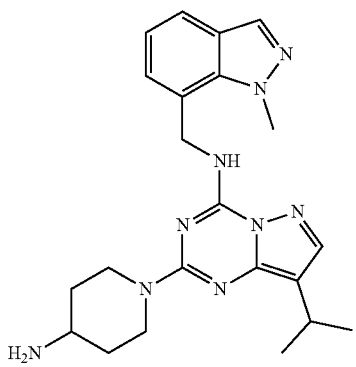 [SMILES: CC(C)c1cnn2c(NCc3cccc4cnn(C)c34)nc(N3CCC(N)CC3)nc12] | white powder; $^1$H-NMR (CDCl$_3$, 400 MHz); δ 7.98 (1H, s), 7.71 (1H, d, J = 8.0 Hz), 7.58 (1H, s), 7.34 (1H, d, J = 6.8 Hz), 7.10 (1H, t, J = 7.6 Hz), 6.43 (1H, brs), 5.13 (2H, d, J = 5.2 Hz), 4.70-4.80 (2H, m), 4.28 (3H, s), 2.91-3.08 (4H, m), 1.85-1.95 (2H, m), 1.26-1.40 (8H, m); LCMS: 100%, MS (ESI): m/z 420.1 [M + H]+ |
| 11 | 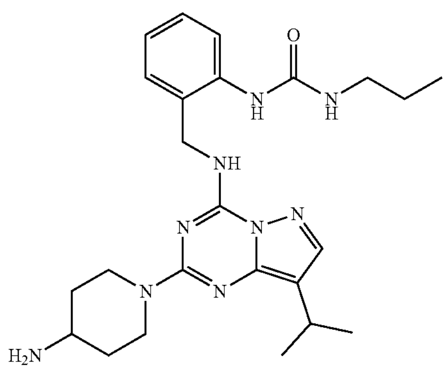 [SMILES: CCCNC(=O)Nc1ccccc1CNc1nc(N2CCC(N)CC2)nc2c(C(C)C)cnn12] | white powder; $^1$H-NMR (CDCl$_3$, 400 MHz): δ 7.97 (1H, d, J = 8.0 Hz), 7.62 (1H, s), 7.25-7.37 (2H, m), 7.04 (1H, t, J = 7.6 Hz), 6.69 (1H, brs), 4.75 (2H, d, J = 6.4 Hz), 4.60-4.72 (3H, m), 3.09-3.19 (2H, m), 2.91-3.09 (4H, m), 1.90-1.95 (2H, m), 1.41-1.45 (2H, m), 1.31-1.35 (2H, m), 1.29 (6H, d, J = 6.4 Hz), 0.83 (3H, t, J = 7.6 Hz); LCMS: 95.6%, MS (ESI): m/z 488.1 [M + Na]+ |
| 12 | 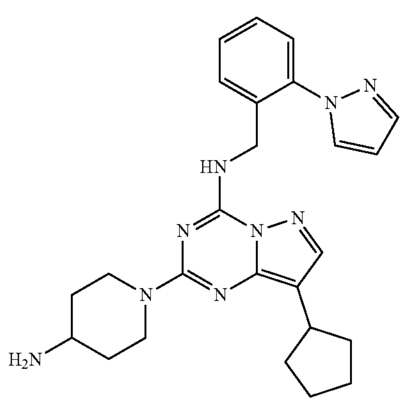 [SMILES: NC1CCN(c2nc(NCc3ccccc3-n3cccn3)n3ncc(C4CCCC4)c3n2)CC1] | white powder; $^1$H-NMR (CDCl$_3$, 400 MHz): δ 7.85 (1H, s), 7.73 (1H, d, J = 2.0 Hz), 7.63-7.65 (1H, m), 7.61 (1H, s), 7.56 (1H, brs), 7.29-7.40 (3H, m), 6.50 (1H, s), 4.76-4.80 (2H, m), 4.68 (2H, d, J = 6.4 Hz), 2.91-3.09 (4H, m), 2.00-2.10 (2H, m), 1.90-1.95 (2H, m), 1.70-1.75 (2H, m), 1.60-1.70 (4H, m), 1.30-1.44 (2H, m); LCMS: 100%, MS (ESI): m/z 458.1 [M + H]+ |

TABLE 11-continued

Summarized compounds 1-279 in terms of their structures and corresponding characteristics.

| # cpds | Structure | Characterization Data |
|---|---|---|
| 13 | 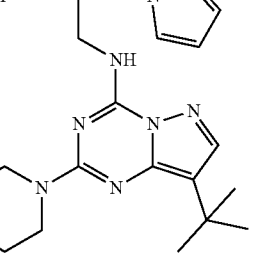 | white powder; $^1$H-NMR (DMSO-d6, 400 MHz); δ 8.24 (1H, d, J = 2.0 Hz), 8.10-8.23 (4H, m), 7.87 (1H, s), 7.68 (1H, s), 7.45-7.55 (1H, m), 7.35-7.40 (1H, m), 7.25-7.35 (1H, m), 6.55-6.65 (1H, m), 4.75 (2H, d, J = 5.6 Hz), 4.55-4.65 (2H, m), 3.20-3.35 (1H, m), 2.85-3.00 (2H, m), 1.90-2.05 (2H, m), 1.35-1.50 (2H, m), 1.31 (9H, s); LCMS: 100%, MS (ESI): m/z 464.1 [M + H]+ |
| 14 | 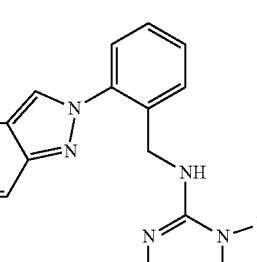 | White powder; $^1$H-NMR (CDCl$_3$, 400 MHz): δ 8.26 (1H, s), 8.17 (1H, s), 7.84 (1H, d, J = 9.2 Hz), 7.67-7.01 (2H, m), 7.63 (1H, s), 7.48-7.50 (3H, m), 7.39 (1H, t, J = 6.0 Hz), 6.43-6.44 (1H, m), 4.66-4.69 (4H, m), 3.06 (3H, d, J = 4.8 Hz), 2.86-3.04 (4H, m), 1.87-1.90 (2H, m), 1.25-1.34 (8H, m); LCMS: 100%, MS (ESI): m/z 539.1 [M + H]$^+$ |
| 15 | 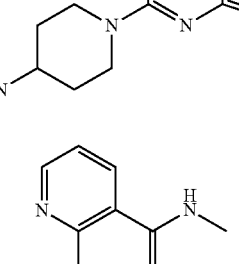 | white powder; $^1$H-NMR (CDCl$_3$, 400 MHz): δ 8.66 (1H, d, J = 4.0 Hz), 7.72 (1H, d, J = 6.8 Hz), 7.65 (1H, brs), 7.63 (1H, s), 7.24-7.28 (1H, m.), 6.07 (1H, brs), 5.01 (2H, d, J = 4.0 Hz), 4.68-4.70 (2H, m), 3.00 (3H, d, J = 4.8 Hz), 2.85-2.95 (3H, m), 1.84-1.88 (2H, m), 1.37 (9H, s), 1.21-1.32 (2H, m); LCMS: 96.2%, MS (ESI): m/z 438.1 [M + H]+ |
| 16 | 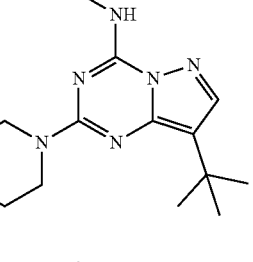 | white powder; $^1$H-NMR (DMSO-d6), 400 MHz): δ 7.70-7.75 (2H, m), 7.52 (1H, s), 7.14-7.20 (2H, m), 6.37 (1H, brs), 5.02 (2H, d, J = 5.2 Hz), 4.65-4.75 (2H, m), 3.95 (3H, s), 2.83-3.02 (4H, m), 1.80-1.85 (2H, m), 1.20-1.31 (8H, m); LCMS: 100%, MS (ESI): m/z 420.1 [M + H]+ |

TABLE 11-continued

Summarized compounds 1-279 in terms of their structures and corresponding characteristics.

| # cpds | Structure | Characterization Data |
|---|---|---|
| 17 | 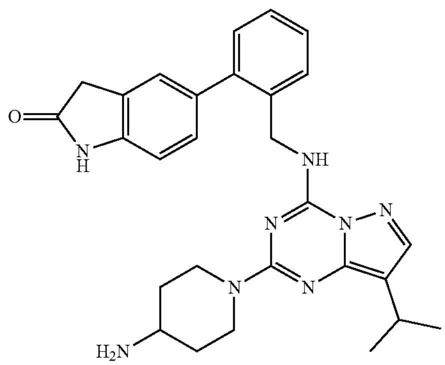 | White powder; $^1$H-NMR (CDCl$_3$, 400 MHz): δ 7.59 (1H, s), 7.32-7.46 (3H, m), 7.20-7.26 (1H, m), 6.84-7.09 (3H, m), 6.30 (1H, brs), 4.45-4.75 (4H, m), 3.37-3.49 (1H, m), 3.25-3.35 (2H, m), 2.96-3.07 (1H, m), 2.80-2.90 (2H, m), 2.15-2.25 (2H, m), 1.20-1.35 (8H, m); LCMS: 100%, MS (ESI): m/z 519.2 [M + Na]$^+$ |
| 18 | 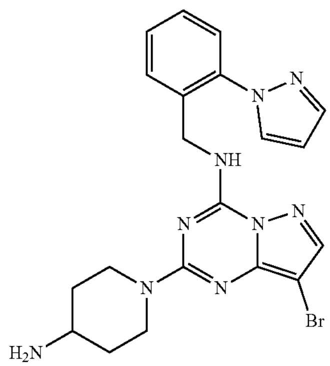 | white powder; $^1$H-NMR (DMSO-d6), 400 MHz): δ 8.00 (1H, s), 7.88 (1H, s), 7.74 (1H, s), 7.45-7.50 (1H, m), 7.30-7.45 (3H, m), 6.51 (1H, s), 4.55 (2H, s), 4.35-4.50 (2H, m), 3.15-3.30 (1H, m), 2.70-2.85 (2H, m), 1.80-1.95 (2H, m), 1.15-1.35 (2H, m); LCMS: 100%, MS (ESI): m/z 469.9 [M + H]+ |
| 19 | 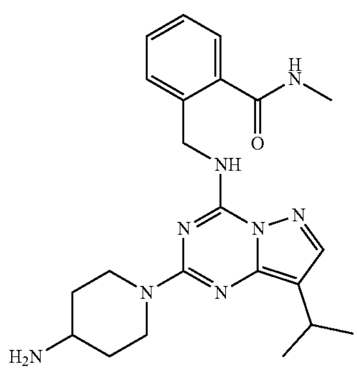 [SMILES: CNC(=O)c1ccccc1CNc1nc(N2CCC(N)CC2)nc2c(C(C)C)cnn12] | white powder; $^1$H-NMR (CDCl$_3$, 400 MHz): δ 7.54-7.65 (2H, m), 7.51 (1H, d, J = 7.6 Hz), 7.33-7.42 (2H, m), 7.24-7.26 (1H, m), 6.05 (1H, brs), 4.81 (2H, d, J = 5.2 Hz), 4.70-4.80 (2H, m), 3.01 (3H, d, J = 4.8 Hz), 2.84-3.00 (4H, m), 1.85-1.92 (2H, m), 1.25-1.39 (2H, m), 1.25 (6H, d, J = 6.8 Hz); LCMS: 100%, MS (ESI): m/z 445.1 [M + Na]+ |
| 20 | 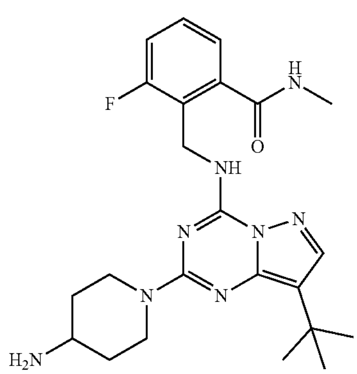 [SMILES: CNC(=O)c1cccc(F)c1CNc1nc(N2CCC(N)CC2)nc2c(C(C)(C)C)cnn12] | white powder; $^1$H-NMR (DMSO-d6, 400 MHz): δ 8.64 (1H, d, J = 4.4 Hz), 8.10-8.35 (4H, m), 7.67 (1H, s), 7.40-7.50 (1H, m), 7.25-7.40 (2H, m), 4.80 (2H, d, J = 5.2 Hz), 4.55-4.75 (2H, m), 3.20-3.40 (1H, m), 2.85-3.05 (2H, m), 2.78 (3H, d, J = 4.4 Hz), 1.90-2.05 (2H, m), 1.40-1.55 (2H, m), 1.31 (6H, s); LCMS: 100%, MS (ESI): m/z 477.1 [M + Na]+ |

TABLE 11-continued

Summarized compounds 1-279 in terms of their structures and corresponding characteristics.

| # cpds | Structure | Characterization Data |
|---|---|---|
| 21 | 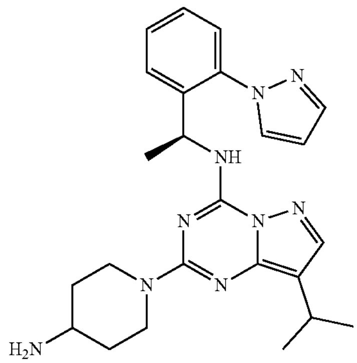 [SMILES: CC(C)c1cnn2c(N[C@@H](C)c3ccccc3-n3cccn3)nc(N3CCC(N)CC3)nc12] | (S)-methyl; off-white powder; ¹H-NMR (CDCl$_3$, 400 MHz): δ 7.79 (1H, s), 7.66 (1H, d, J = 2.0 Hz), 7.62 (1H, s), 7.56 (1H, d, J = 7.2 Hz), 7.27-7.42 (3H, m), 7.11 (1H, d, J = 7.6 Hz), 6.46 (1H, s), 5.37-5.50 (1H, m), 4.46-4.63 (2H, m), 2.95-3.05 (1H, m), 2.86-2.95 (1H, m), 2.74-2.86 (2H, m), 1.82-1.86 (2H, m), 1.50 (3H, d, J = 6.8 Hz), 1.13-1.35 (8H, m); LCMS: 100%, MS (ESI): m/z 446.1 [M + H]+ |
| 22 | 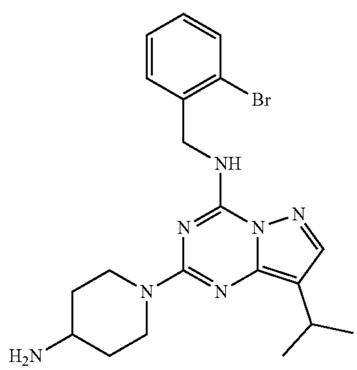 [SMILES: CC(C)c1cnn2c(NCc3ccccc3Br)nc(N3CCC(N)CC3)nc12] | white powder; ¹H-NMR (DMSO-d6, 400 MHz): δ 9.12 (1H, brs), 8.00-8.20 (3H, m), 7.83 (1H, s), 7.62 (1H, d, J = 8.0 Hz), 7.29-7.42 (2H, m), 7.21 (1H, t, J = 6.8 Hz), 4.70 (2H, d, J = 6.0 Hz), 4.50-4.60 (2H, m), 3.17-3.27 (1H, m), 2.95-3.05 (1H, m), 2.80-2.90 (2H, m), 1.85-1.95 (2H, m), 1.28-1.43 (2H, m), 1.23 (6H, d, J = 6.8 Hz); LCMS: 99.0%, MS (ESI): m/z 444.0 [M + H]+ |
| 23 | 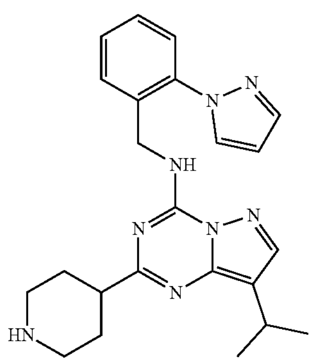 [SMILES: CC(C)c1cnn2c(NCc3ccccc3-n3cccn3)nc(C3CCNCC3)nc12] | white powder; ¹H-NMR (CDCl$_3$, 400 MHz): δ 7.93-8.25 (1H, m), 7.88 (1H, s), 7.67-7.84 (3H, m), 7.28-7.42 (3H, m), 6.51 (1H, s), 4.76 (2H, s), 3.25-3.30 (2H, m), 3.12-3.23 (1H, m), 2.80-3.00 (4H, m), 1.89-2.15 (4H, m), 1.29 (6H, d, J = 6.8 Hz); LCMS: 99.1%, MS (ESI): m/z 417.1 [M + H]+ |
| 24 | 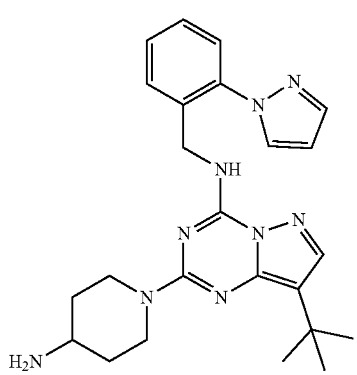 [SMILES: CC(C)(C)c1cnn2c(NCc3ccccc3-n3cccn3)nc(N3CCC(N)CC3)nc12] | white powder; ¹H-NMR (CDCl$_3$, 400 MHz): δ 8.79 (1H, t, J = 5.6 Hz), 8.16 (1H, d, J = 2.0 Hz), 7.95 (3H, brs), 7.81 (1H, s), 7.72 (1H, s), 7.51-7.58 (1H, m), 7.35-7.48 (3H, m), 6.56 (1H, s), 4.62 (2H, d, J = 5.6 Hz), 4.45-4.50 (2H, m), 3.20-3.30 (1H, m), 2.84 (2H, t, J = 12.4 Hz), 1.85-1.95 (2H, m), 1.20-1.40 (11H, m); LCMS: 100%, MS (ESI): m/z 445.2 [M + H]+ |

TABLE 11-continued

Summarized compounds 1-279 in terms of their structures and corresponding characteristics.

| # cpds | Structure | Characterization Data |
|---|---|---|
| 25 | 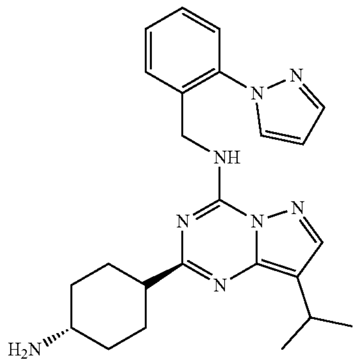 | (1R, 4R); white powder; $^1$H-NMR (CDCl$_3$, 400 MHz): δ 7.98 (1H, brs), 7.88 (1H, s), 7.79 (1H, s), 7.77 (1H, d, J = 2.0 Hz), 7.73 (1H, d, J = 6.4 Hz), 7.29-7.45 (3H, m), 6.52 (1H, s), 4.76 (2H, d, J = 6.0 Hz), 3.14-3.26 (1H, m), 2.76-2.86 (1H, m), 2.60-2.72 (1H, m), 1.95-2.16 (4H, m), 1.73-1.86 (2H, m), 1.12-1.43 (8H, m); LCMS: 98.1%, MS (ESI): m/z 431.1 [M + H]+ |
| 26 | 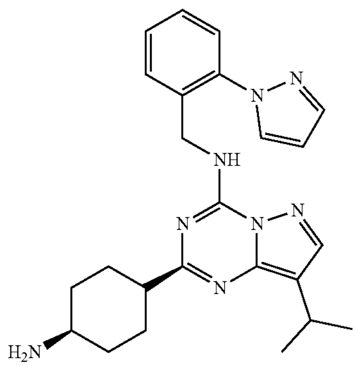 | (1S, 4S); white powder; $^1$H-NMR (CDCl$_3$, 400 MHz): δ 7.98 (1H, brs), 7.88 (1H, s), 7.79 (1H, s), 7.77 (1H, d, J = 2.0 Hz), 7.73 (1H, d, J = 6.8 Hz), 7.28-7.41 (3H, m), 6.51 (1H, s.), 4.76 (2H, s), 3.12-3.16 (1H, m), 3.03-3.13 (1H, s), 2.75-2.89 (1H, m), 2.18-2.34 (2H, m), 1.73-1.85 (4H, m), 1.56-1.68 (2H, m), 1.30 (6H, d, J = 7.2 Hz); LCMS: 100%, MS (ESI): m/z 431.1 [M + H]+ |
| 27 | 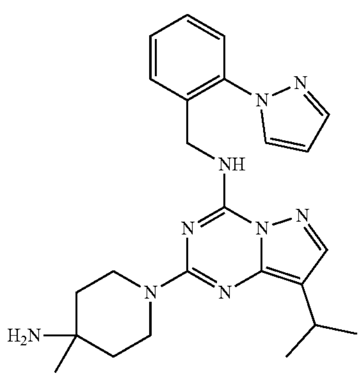 [SMILES: CC(C)c1cnn2c(NCc3ccccc3-n3cccn3)nc(N3CCC(C)(N)CC3)nc12] | white powder; $^1$H-NMR (CDCl$_3$, 400 MHz): δ 8.67 (1H, brs), 8.14 (1H, d, J = 2.0 Hz), 7.81 (1H, s), 7.71 (1H, s), 7.51-7.58 (1H, m), 7.36-7.46 (3H, m), 6.56 (1H, s), 4.59 (2H, s), 3.70-3.80 (2H, m), 3.40-3.50 (2H, m), 2.85-2.95 (1H, m), 1.25-1.30 (4H, m), 1.21 (6H, d, J = 7.2 Hz), 1.03 (3H, s); LCMS: 100%, MS (ESI): m/z 446.1 [M + H]+ |
| 28 | 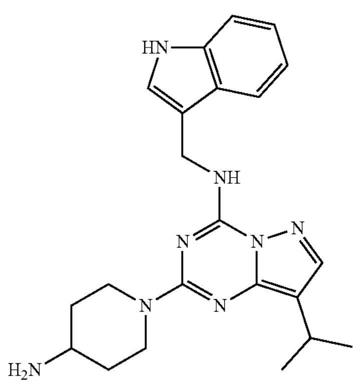 [SMILES: CC(C)c1cnn2c(NCc3c[nH]c4ccccc34)nc(N3CCC(N)CC3)nc12] | white powder; $^1$H-NMR (CDCl$_3$, 400 MHz): δ 8.12 (1H, s), 7.68 (1H, d, J = 7.6 Hz), 7.56 (1H, s), 7.39 (1H, d, J = 8.4 Hz), 7.18-7.25 (2H, m), 7.10-7.20 (1H, m), 6.41 (1H, s), 4.93 (2H, d, J = 5.2 Hz), 4.80-4.85 (2H, m), 2.88-3.08 (4H, m), 1.90-1.95 (2H, m), 1.33-1.42 (2H, m), 1.29 (6H, d, J = 6.8 Hz); LCMS: 96.9%, MS (ESI): m/z 405.1 [M + H]+ |

TABLE 11-continued

Summarized compounds 1-279 in terms of their structures and corresponding characteristics.

| # cpds | Structure | Characterization Data |
|---|---|---|
| 29 | 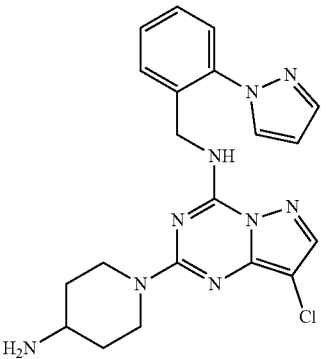 [SMILES: NC1CCN(c2nc(NCc3ccccc3-n3cccn3)n3ncc(Cl)c3n2)CC1] | yellow gum; $^1$H-NMR (DMSO-d6, 400 MHz): δ 9.05 (1H, brs), 8.17 (1H, s), 7.95-8.15 (4H, m), 7.80 (1H, s), 7.50-7.60 (1H, m), 7.35-7.50 (4H, m), 6.56 (1H, s), 4.63 (2H, d, J = 5.6 Hz), 4.35-4.60 (2H, m), 3.10-3.35 (1H, m), 2.80-2.95 (2H, m), 1.85-2.00 (2H, m), 1.25-1.45 (2H, m); LCMS: 99.2%, MS (ESI): m/z 424.0 [M + H]+ |
| 30 | 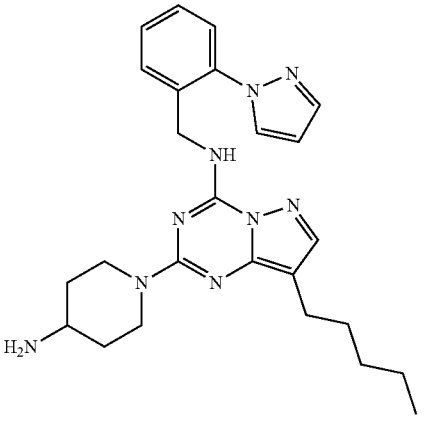 [SMILES: CCCCCc1cnn2c(NCc3ccccc3-n3cccn3)nc(N3CCC(N)CC3)nc12] | white powder; $^1$H-NMR (DMSO-d6, 400 MHz): δ 8.81 (1H, brs), 8.17 (1H, d, J = 2.4 Hz), 7.70-8.00 (5H, m), 7.50-7.60 (1H, m), 7.35-7.50 (3H, m), 6.57 (1H, s), 4.61 (2H, d, J = 5.6 Hz), 4.40-4.55 (2H, m), 3.20-3.30 (1H, m), 2.75-2.90 (2H, m), 2.40-2.50 (2H, m), 1.80-1.95 (2H, m), 1.50-1.60 (2H, m), 1.20-1.45 (6H, m), 0.80-0.90 (3H, m); LCMS: 100%, MS (ESI): m/z 460.1 [M + H]+ |
| 31 | 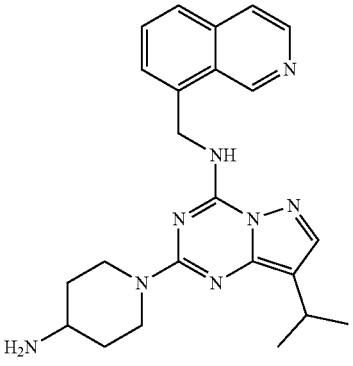 [SMILES: CC(C)c1cnn2c(NCc3cccc4ccncc34)nc(N3CCC(N)CC3)nc12] | white powder; $^1$H-NMR (CDCl$_3$, 400 MHz): δ 9.60 (1H, s), 8.59 (1H, d, J = 6.0 Hz), 7.80 (1H, d, J = 7.6 Hz), 7.60-7.73 (3H, m), 7.58 (1H, s), 6.60 (1H, s), 5.31 (2H, d, J = 6.0 Hz), 4.70-4.80 (2H, m), 2.88-3.07 (4H, m), 1.84-1.95 (2H, m), 1.23-1.39 (8H, m); LCMS: 95.0%, MS (ESI): m/z 417.2 [M + H]+ |
| 32 | 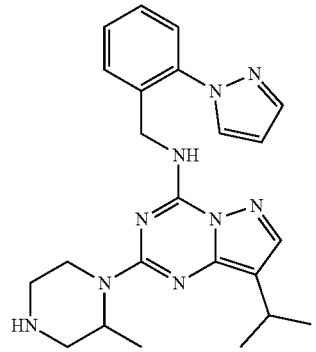 [SMILES: CC(C)c1cnn2c(NCc3ccccc3-n3cccn3)nc(N3CCNCC3C)nc12] | Racemic mixture; white powder; $^1$H-NMR (CDCl$_3$, 400 MHz): δ 7.86 (1H, s), 7.73 (1H, d, J = 1.6 Hz), 7.54-7.69 (3H, m), 7.28-7.42 (3H, m), 6.50 (1H, s), 4.95-5.05 (1H, m), 4.64-4.78 (2H, m), 4.54-4.62 (1H, m), 3.09-3.20 (2H, m), 2.94-3.09 (3H, m), 2.78-2.88 (1H, m), 1.32 (3H, d, J = 6.8 Hz), 1.27 (6H, d, J = 6.4 Hz); LCMS: 100%, MS (ESI): m/z 432.1 [M + H]+ |

TABLE 11-continued

Summarized compounds 1-279 in terms of their structures and corresponding characteristics.

| # cpds | Structure | Characterization Data |
|---|---|---|
| 33 | 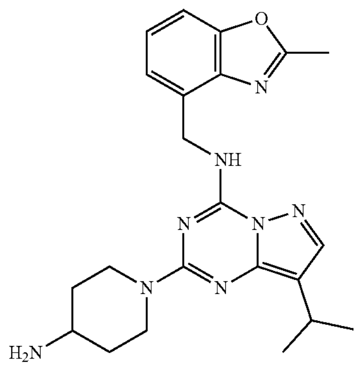 [SMILES: Cc1nc2c(CNc3nc(N4CCC(N)CC4)nc4c(C(C)C)cnn34)cccc2o1] | white powder; $^1$H-NMR (CDCl$_3$, 400 MHz): δ 7.61 (1H, s), 7.29-7.43 (2H, m), 7.20-7.25 (1H, m), 6.96 (1H, brs), 5.08 (2H, d, J = 6.0 Hz), 4.73-4.78 (2H, m), 2.85-3.09 (4H, m), 2.67 (3H, s), 1.84-1.89 (2H, m), 1.26-1.29 (8H, m); LCMS: 98.8%, MS (ESI): m/z 421.0 [M + H]+ |
| 34 | 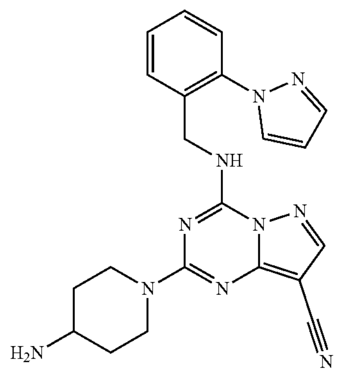 [SMILES: N#Cc1cnn2c(NCc3ccccc3-n3cccn3)nc(N3CCC(N)CC3)nc12] | white powder; $^1$H-NMR (CDCl$_3$, 400 MHz): δ 8.23 (1H, brs), 7.83-7.92 (2H, m), 7.78 (1H, s), 7.60 (1H, d, J = 6.8 Hz), 7.30-7.46 (3H, m), 6.52 (1H, s), 4.85-4.95 (2H, m), 4.67 (2H, s), 3.04-3.23 (3H, m), 2.01-2.15 (2H, m), 1.43-1.60 (2H, m); LCMS: 100%, MS (ESI): m/z 415.2 [M + H]+ |
| 35 | 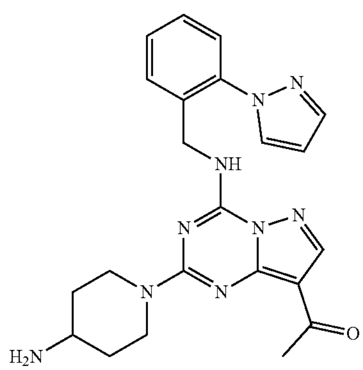 [SMILES: CC(=O)c1cnn2c(NCc3ccccc3-n3cccn3)nc(N3CCC(N)CC3)nc12] | white powder; $^1$H-NMR (CDCl$_3$, 400 MHz): δ 9.15 (1H, t, J = 5.6 Hz), 8.22 (1H, s), 8.18 (1H, d, J = 1.6 Hz), 7.80-7.90 (3H, m), 7.80 (1H, s), 7.51-7.59 (1H, m), 7.37-7.49 (3H, m), 6.56 (1H, s), 4.63-4.65 (3H, m), 4.40-4.55 (1H, m), 3.25-3.35 (1H, m), 2.85-3.05 (2H, m), 2.47 (3H, s), 1.90-2.00 (2H, m), 1.25-1.50 (2H, m); LCMS: 100%, MS (ESI): m/z 432.1 [M + H]+ |
| 36 | 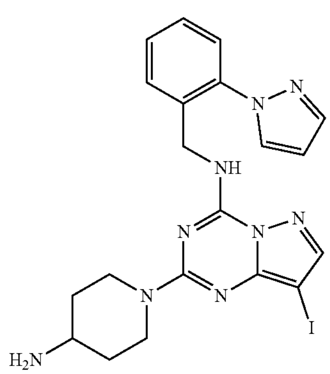 [SMILES: NC1CCN(c2nc(NCc3ccccc3-n3cccn3)n3ncc(I)c3n2)CC1] | white powder; $^1$H-NMR (DMSO-d6, 400 MHz): δ 9.01 (1H, brs), 8.17 (1H, d, J = 2.0 Hz), 7.94 (1H, s), 7.70-7.90 (4H, m), 7.53 (1H, d, J = 8.0 Hz), 7.35-7.50 (2H, m), 6.56 (1H, s), 4.62 (2H, d, J = 6.0 Hz), 4.40-4.60 (2H, m), 3.60-3.70 (1H, m), 2.80-2.90 (2H, m), 1.80-1.95 (2H, m), 1.40-1.55 (2H, m); LCMS: 89%, MS (ESI): m/z 516.1 [M + H]+ |

TABLE 11-continued

Summarized compounds 1-279 in terms of their structures and corresponding characteristics.

| # cpds | Structure | Characterization Data |
|---|---|---|
| 37 | 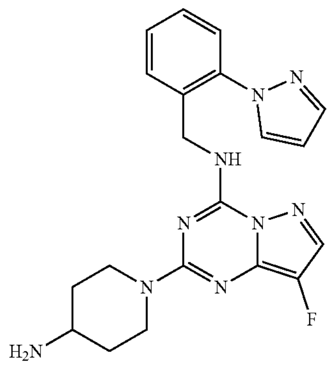 | white powder; $^1$H-NMR (DMSO-d6, 400 MHz): δ 9.02 (1H, t, J = 6.0 Hz), 8.17 (1H, d, J = 2.0 Hz), 7.90-8.10 (4H, m), 7.80 (1H, s), 7.50-7.60 (1H, m), 7.30-7.50 (3H, m), 6.56 (1H, s), 4.62 (2H, d, J = 6.0 Hz), 4.35-4.50 (2H, m), 3.15-3.35 (1H, m), 2.80-2.95 (2H, m), 1.80-1.95 (2H, m), 1.25-1.45 (2H, m); LCMS: 100%, MS (ESI): m/z 408.0 [M + H]+ |
| 38 | 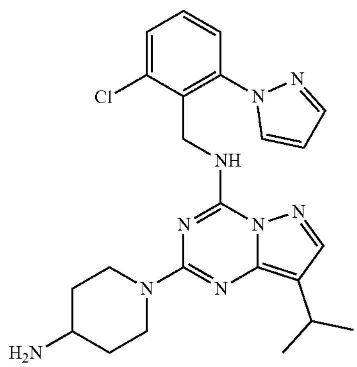 [SMILES: CC(C)c1cnn2c(NCc3c(Cl)cccc3-n3cccn3)nc(N3CCC(N)CC3)nc12] | white powder; $^1$H-NMR (DMSO-d6, 400 MHz): δ 8.21 (1H, d, J = 2.4 Hz), 8.10 (1H, brs), 7.75-7.85 (4H, m), 7.73 (1H, s), 7.62-7.64 (1H, m), 7.46-7.56 (2H, m), 6.57 (1H, s), 4.68-4.78 (2H, m), 4.60-4.70 (2H, m), 3.29-3.33 (1H, m), 2.88-2.97 (3H, m), 1.86-1.99 (2H, m), 1.32-1.47 (2H, m), 1.23 (6H, d, J = 6.8 Hz); LCMS: 100%, MS (ESI): m/z 466.0 [M + H]+ |
| 39 | 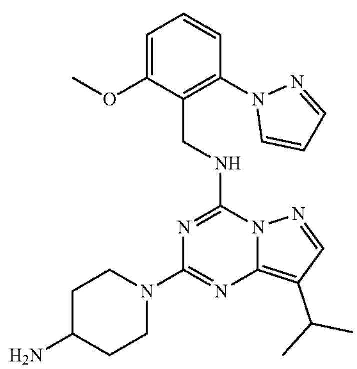 [SMILES: COc1cccc(-n2cccn2)c1CNc1nc(N2CCC(N)CC2)nc2c(C(C)C)cnn12] | white powder; $^1$H-NMR (CDCl$_3$, 400 MHz): δ 7.78 (1H, s), 7.68 (1H, s), 7.59 (1H, s), 7.30-7.39 (1H, m), 7.12-7.19 (1H, m), 6.93-7.01 (2H, m), 6.44 (1H, s), 4.77 (2H, d, J = 6.0 Hz), 4.63-4.69 (2H, m), 3.93 (3H, s), 2.96-3.06 (1H, m), 2.82-2.94 (3H, m), 1.82-1.93 (2H, m), 1.20-1.38 (8H, m); LCMS: 98.7%, MS (ESI): m/z 462.1 [M + H]+ |
| 40 | 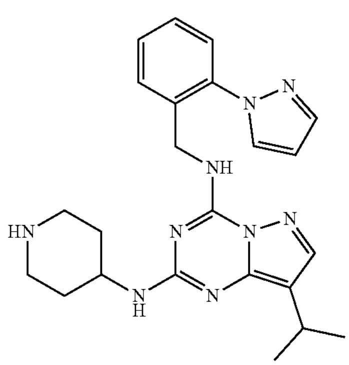 [SMILES: CC(C)c1cnn2c(NCc3ccccc3-n3cccn3)nc(NC3CCNCC3)nc12] | white powder; $^1$H-NMR (400 MHz, DMSO-d6): δ 10.17 (1H, brs), 9.21 (1H, brs), 8.85-9.00 (2H, m), 8.22 (1H, s), 8.05 (1H, s), 7.83 (1H, s), 7.53-7.55 (1 H, m), 7.37-7.48 (3H, m), 6.59 (1H, s), 4.70 (2H, d, J = 6.0 Hz), 3.90-4.00 (1H, m), 3.10-3.25 (2H, m), 2.87-3.05 (3H, m), 1.75-1.90 (2H, m), 1.60-1.75 (2 H, m), 1.23 (6 H, d, J = 6.4 Hz); LCMS: 100%, MS (ESI): m/z 432.1 [M + H]+ |

TABLE 11-continued

Summarized compounds 1-279 in terms of their structures and corresponding characteristics.

| # cpds | Structure | Characterization Data |
|---|---|---|
| 41 | 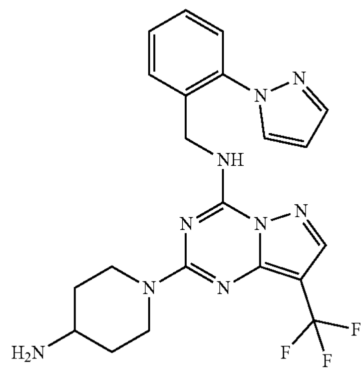 [SMILES: NC1CCN(c2nc(NCc3ccccc3-n3cccn3)n3ncc(C(F)(F)F)c3n2)CC1] | white powder; $^1$H-NMR (DMSO-d6, 400 MHz): δ 9.17 (1H, t, J = 6.0 Hz), 8.21 (1H, s), 8.17 (1H, d, J = 2.0 Hz), 7.95-8.15 (3H, m), 7.80 (1H, s), 7.53-7.60 (1H, m), 7.35-7.50 (3H, m), 6.56 (1H, s), 4.35-4.70 (4H, m), 3.20-3.45 (1H, m), 2.80-2.95 (2H, m), 1.80-2.00 (2H, m), 1.25-1.50 (2H, m); LCMS: 95.9%, MS (ESI): m/z 458.1 [M + H]+ |
| 42 | 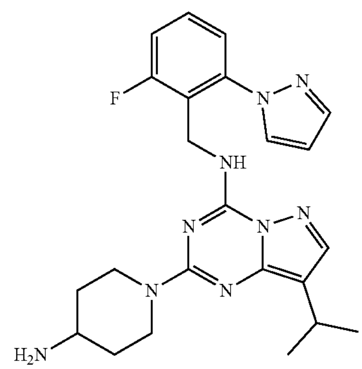 | white powder; $^1$H-NMR (CDCl$_3$, 400 MHz): δ 7.87 (1H, s), 7.73 (1H, s), 7.59 (1H, s), 7.44 (1H, s), 7.30-7.39 (1H, m), 7.07-7.18 (2H, m), 6.51 (1H, s), 4.71-4.88 (4H, m), 2.86-3.05 (4H, m), 1.84-1.93 (2H, m), 1.23-1.37 (8H, m); LCMS: 98.9%, MS (ESI): m/z 450.1 [M + H]+ |
| 43 | 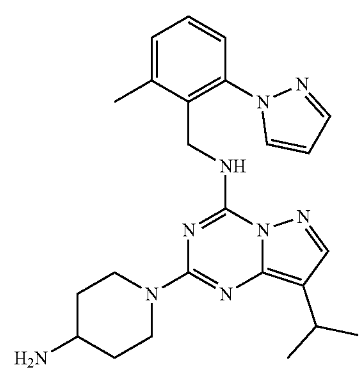 [SMILES: Cc1cccc(-n2cccn2)c1CNc1nc(N2CCC(N)CC2)nc2c(C(C)C)cnn12] | white powder; $^1$H-NMR (CDCl$_3$, 400 MHz): δ 7.81 (1H, s), 7.55-7.74 (3H, m), 7.27-7.37 (1H, m), 7.21-7.25 (1H, m), 7.12-7.19 (1H, m), 6.47 (1H, s), 4.71-4.84 (2H, m), 4.60 (2H, d, J = 5.6 Hz), 2.89-3.11 (4H, m), 2.55 (3H, s), 1.88-1.96 (2H, m), 1.20-1.44 (8H, m); LCMS: 91.7%, MS (ESI): m/z 446.1 [M + H]+ |
| 44 | 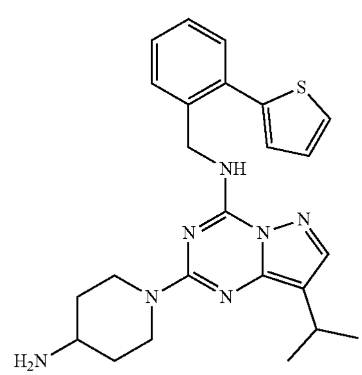 [SMILES: CC(C)c1cnn2c(NCc3ccccc3-c3cccs3)nc(N3CCC(N)CC3)nc12] | white powder; $^1$H-NMR (CDCl$_3$, 400 MHz): δ 7.59 (1H, s), 7.48-7.55 (1H, m), 7.40-7.46 (1H, m), 7.29-7.39 (3H, m), 7.03-7.13 (2H, m), 6.45 (1H, s), 4.80 (2H, d, J = 6.0 Hz), 4.64-4.75 (2H, m), 2.98-3.07 (1H, m), 2.85-2.97 (3H, m), 1.81-1.92 (2H, m), 1.21-1.39 (8H, m); LCMS: 100%, MS (ESI): m/z 448.0 [M + H]+ |

TABLE 11-continued

Summarized compounds 1-279 in terms of their structures and corresponding characteristics.

| # cpds | Structure | Characterization Data |
|---|---|---|
| 45 | 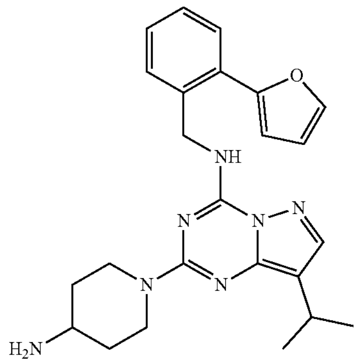 [SMILES: CC(C)c1cnn2c(NCc3ccccc3-c3ccco3)nc(N3CCC(N)CC3)nc12] | white powder; ¹H-NMR (DMSO-d6, 400 MHz): δ 8.96 (1H, brs), 7.84 (1H, s), 7.68-7.80 (3H, m), 7.62 (1H, d, J = 7.2 Hz), 7.40-7.46 (1H, m), 7.25-7.36 (2H, m), 6.81 (1H, d, J = 3.2 Hz), 6.67 (1H, s), 4.83 (2H, d, J = 5.6 Hz), 4.28-4.48 (2 1.70-1.88 (2H, m), 1.23 (6H, d, J = 6.8 Hz); LCMS: 100%, MS (ESI): m/z 432.1 [M + H]+ |
| 46 | 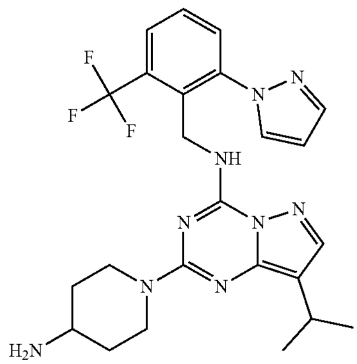 [SMILES: CC(C)c1cnn2c(NCc3c(-n4cccn4)cccc3C(F)(F)F)nc(N3CCC(N)CC3)nc12] | white powder; ¹H-NMR (DMSO-d6, 400 MHz): δ 8.23-8.30 (1H, m), 8.20 (1H, d, J = 2.0 Hz), 7.93 (1H, d, J = 7.6 Hz), 7.63-7.90 (7H, m), 6.57 (1H, s), 4.53-4.79 (4H, m), 3.27-3.35 (1H, m), 2.86-2.99 (3H, m), 1.87-1.99 (2H, m), 1.34-1.47 (2H, m), 1.23 (6H, d, J = 7.2 Hz); LCMS: 100%, MS (ESI): m/z 500.0 [M + H]+ |
| 47 | 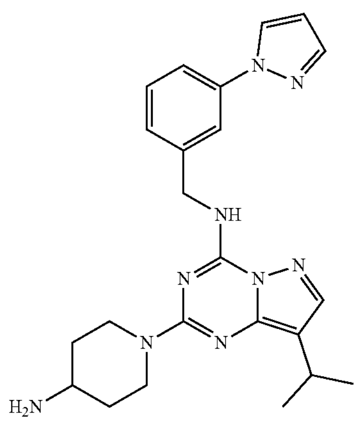 [SMILES: CC(C)c1cnn2c(NCc3cccc(-n4cccn4)c3)nc(N3CCC(N)CC3)nc12] | white powder; ¹H-NMR (DMSO-d6, 400 MHz): δ 9.07 (1H, t, J = 6.0 Hz), 8.46 (1H, d, J = 2.4 Hz), 7.96 (1H, s), 7.60-7.87 (6H, m), 7.39-7.46 (1H, m), 7.32 (1H, d, J = 7.2 Hz), 6.54 (1H, s), 4.60-4.69 (4H, m), 3.20-3.31 (1H, m), 2.83-2.97 (3H, m), 1.80-1.93 (2H, m), 1.18-1.41 (8H, m); LCMS: 98.8%, MS (ESI): m/z 432.0 [M + H]+ |
| 48 | 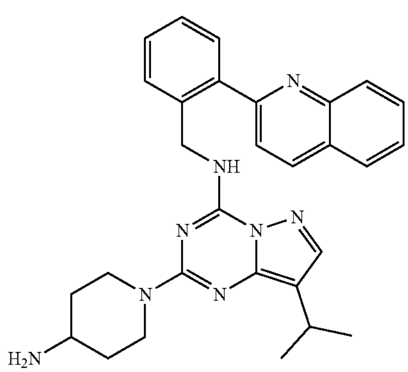 | white powder; ¹H-NMR (DMSO-d6, 400 MHz): δ 9.32 (1H, t, J = 6.0 Hz), 8.56 (1H, d, J = 8.4 Hz), 8.35 (1H, d, J = 8.4 Hz), 8.09 (1H, d, J = 8.4 Hz), 7.77-7.95 (6H, m), 7.67-7.75 (2H, m), 7.63 (1H, d, J = 6.4 Hz), 7.43-7.54 (2H, m), 4.76 (2H, d, J = 6.4 Hz), 4.55-4.67 (2H, m), 3.28 (1H, s), 2.83-2.98 (3H, m), 1.85-1.98 (2H, m), 1.30-1.45 (2H, m), 1.23 (6H, d, J = 6.8 Hz); LCMS: 99%, MS (ESI): m/z 493.1 [M + H]+ |

TABLE 11-continued

Summarized compounds 1-279 in terms of their structures and corresponding characteristics.

| # cpds | Structure | Characterization Data |
|---|---|---|
| 49 | 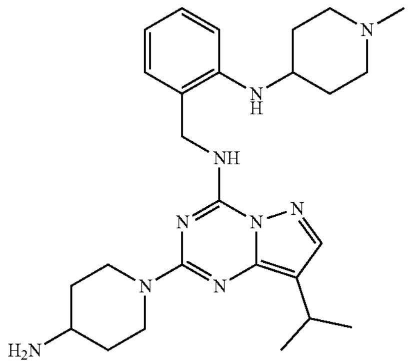 | white powder; ¹H-NMR (DMSO-d6, 400 MHz): δ 9.46-9.72 (2H, m), 8.64-8.85 (2H, m), 7.88 (3H, brs), 7.78 (1H, s), 7.25 (1H, d, J = 6.8 Hz), 7.05-7.14 (1H, m), 6.63-6.71 (1H, m), 6.54 (1H, t, J = 7.2 Hz), 4.65-4.75 (2H, m), 4.48 (2H, d, J = 5.6 Hz), 3.45-3.55 (2H, m), 3.24-3.38 (2H, m), 3.02-3.13 (2H, m), 2.87-2.99 (3H, m), 2.79 (3H, d, J = 4.0 Hz), 2.05-2.15 (2H, m), 1.90-1.97 (2H, m), 1.57-1.71 (2H, m), 1.31-1.43 (2H, m), 1.22 (6H, d, J = 6.8 Hz); LCMS: 100%, MS (ESI): m/z 478.1 [M + H]+ |
| 50 | 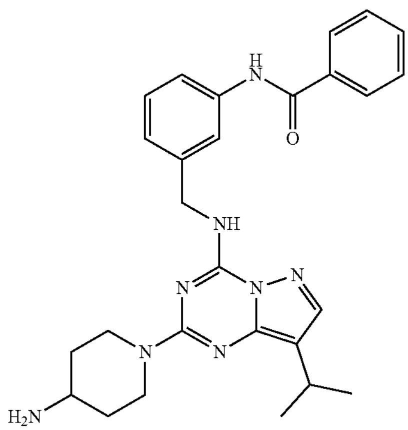 [SMILES: CC(C)c1cnn2c(NCc3cccc(NC(=O)c4ccccc4)c3)nc(N3CCC(N)CC3)nc12] | white powder; ¹H-NMR (CD₃OD, 400 MHz): δ 7.91 (2H, d, J = 7.2 Hz), 7.87 (1H, s), 7.80 (1H, s), 7.48-7.60 (4H, m), 7.35 (1H, t, J = 8.0 Hz), 7.21 (1H, d, J = 7.6 Hz), 4.71-4.81 (4H, m), 3.36-3.42 (1H, m), 3.04-3.10 (3H, m), 2.00-2.11 (2H, m), 1.50-1.59 (2H, m), 1.28 (6H, d, J = 7.2 Hz); LCMS: 100%, MS (ESI): m/z 485.1 [M + H]+ |
| 51 | 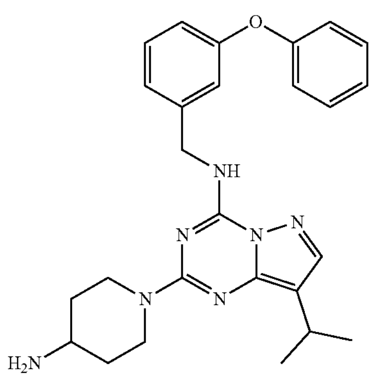 [SMILES: CC(C)c1cnn2c(NCc3cccc(Oc4ccccc4)c3)nc(N3CCC(N)CC3)nc12] | white powder; ¹H-NMR (CDCl₃, 400 MHz): δ 7.62 (1H, s), 7.27-7.37 (3H, m), 7.05-7.14 (2H, m), 6.95-7.03 (3H, m), 6.88-6.94 (1H, m), 6.60 (1H, t, J = 5.6 Hz), 4.77-4.91 (2H, m), 4.67 (2H, d, J = 5.6 Hz), 3.20-3.32 (1H, m), 2.98-3.09 (1H, m), 2.81-2.97 (2H, m), 1.97-2.12 (2H, m), 1.52-1.63 (2H, m), 1.28 (6H, d, J = 6.8 Hz); LCMS: 98.3%, MS (ESI): m/z 458.0 [M + H]+ |
| 52 | 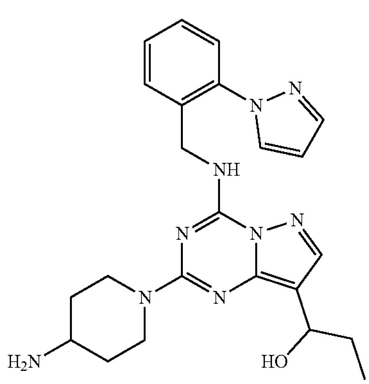 [SMILES: CCC(O)c1cnn2c(NCc3ccccc3-n3cccn3)nc(N3CCC(N)CC3)nc12] | Racemic mixture; white powder; ¹H-NMR (CDCl₃, 400 MHz): δ 7.86 (1H, s), 7.70-7.80 (2H, m), 7.57-7.67 (2H, m), 7.30-7.43 (3H, m), 6.51 (1H, s), 4.71-4.83 (3H, m), 4.69 (2H, d, J = 6.0 Hz), 2.91-3.07 (3H, m), 1.85-1.94 (4H, m), 1.28-1.40 (2H, m), 0.96 (3H, t, J = 7.4 Hz); LCMS: 94.1%, MS (ESI): m/z 470.0 [M + Na]+ |

TABLE 11-continued

Summarized compounds 1-279 in terms of their structures and corresponding characteristics.

| # cpds | Structure | Characterization Data |
| --- | --- | --- |
| 53 | 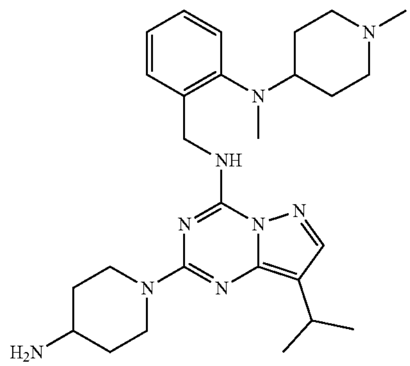 [SMILES: CC(C)c1cnn2c(NCc3ccccc3N(C)C3CCN(C)CC3)nc(N3CCC(N)CC3)nc12] | off-white powder; ¹H-NMR (DMSO-d6, 400 MHz): δ 10.64 (1H, brs), 9.23 (1H, brs), 8.22 (3H, brs), 7.85 (1H, s), 7.17-7.41 (3H, m), 7.01-7.12 (1H, m), 4.65-4.89 (2H, m), 4.49-4.63 (2H, m), 3.37-3.47 (2H, m), 3.20-3.29 (1H, m), 3.01-3.18 (3H, m), 2.86-3.00 (3H, m), 2.58-2.78 (6H, m), 1.77-2.19 (6H, m), 1.34-1.50 (2H, m), 1.22 (6H, d, J = 6.8 Hz); LCMS: 100%, MS (ESI): m/z 492.1 [M + H]+ |
| 54 | 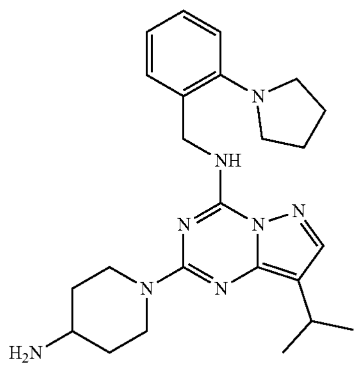 [SMILES: CC(C)c1cnn2c(NCc3ccccc3N3CCCC3)nc(N3CCC(N)CC3)nc12] | yellow powder; ¹H-NMR (CDCl₃, 400 MHz): δ 7.58 (1H, s), 7.28-7.32 (1H, m), 7.19-7.24 (1H, m), 7.08-7.15 (1H, m), 7.04 (1H, d, J = 8.0 Hz), 6.92 (1H, t, J = 7.2 Hz), 4.70-4.85 (4H, m), 3.15-3.25 (4H, m), 2.86-3.07 (4H, m), 1.84-2.02 (6H, m), 1.26-1.36 (8H, m); LCMS: 100%, MS (ESI): m/z 435.1 [M + H]+ |
| 55 | 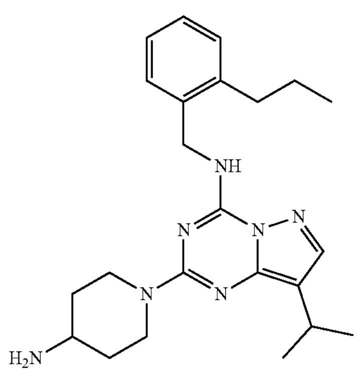 [SMILES: CCCc1ccccc1CNc1nc(N2CCC(N)CC2)nc2c(C(C)C)cnn12] | white powder; ¹H-NMR (DMSO-d6, 400 MHz): δ 9.17 (1H, brs), 8.15-8.25 (3H, m), 7.85 (1H, s), 7.32 (1H, d, J = 7.2 Hz), 7.09-7.21 (3H, m), 4.68 (2H, d, J = 6.0 Hz), 4.55-4.65 (2H, m), 3.22-3.32 (1H, m), 3.02-3.12 (1H, m), 2.93-3.03 (2H, m), 2.65-2.73 (2H, m), 1.89-1.99 (2H, m), 1.52-1.62 (2H, m), 1.38-1.48 (2H, m), 1.23 (6H, d, J = 6.8 Hz), 0.93 (3 H, t, J = 6.8 Hz); LCMS: 100%, MS (ESI): m/z 408.1 [M + H]+ |
| 56 | 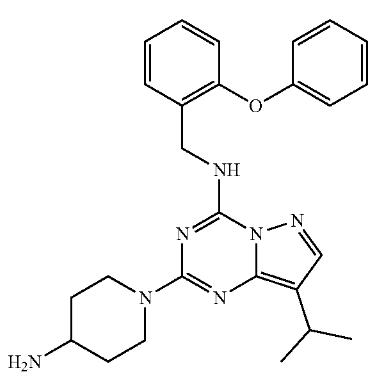 [SMILES: CC(C)c1cnn2c(NCc3ccccc3Oc3ccccc3)nc(N3CCC(N)CC3)nc12] | white powder; ¹H-NMR (CDCl₃, 400 MHz): δ 7.59 (1H, s), 7.46 (1H, d, J = 7.2 Hz), 7.26-7.32 (2H, m), 7.20-7.24 (1H, m), 7.04-7.13 (2H, m), 6.90-7.00 (2H, m), 6.87 (1H, d, J = 8.4 Hz), 6.63-6.71 (1H, m), 4.79 (2H, d, J = 6.4 Hz), 4.70-4.78 (2H, m), 2.86-3.07 (4H, m), 1.85-1.90 (2H, m), 1.21-1.38 (8H, m); LCMS: 98.8%, MS (ESI): m/z 458.1 [M + H]+ |

| # cpds | Structure | Characterization Data |
| --- | --- | --- |
| 57 | 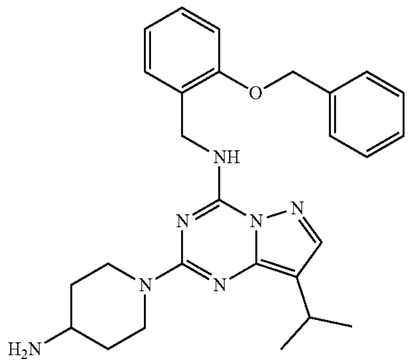 [SMILES: CC(C)c1cnn2c(NCc3ccccc3OCc3ccccc3)nc(N3CCC(N)CC3)nc12] | white powder; ¹H-NMR (CDCl₃, 400 MHz); δ 7.60 (1H, s), 7.41-7.48 (2H, m), 7.29-7.40 (4H, m), 7.21-7.25 (1H, m), 6.87-6.97 (2H, m), 6.67-6.76 (1H, m), 5.13 (2H, s), 4.68-4.82 (4H, m), 2.85-3.08 (4H, m), 1.82-1.92 (2H, m), 1.23-1.35 (8H, m); LCMS: 100%, MS (ESI): m/z 472.1 [M + H]+ |
| 58 | 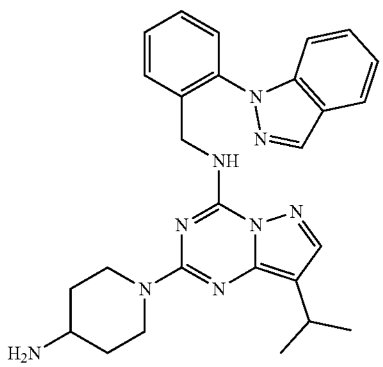 [SMILES: CC(C)c1cnn2c(NCc3ccccc3-n3ncc4ccccc43)nc(N3CCC(N)CC3)nc12] | white powder; ¹H-NMR (CDCl₃, 400 MHz): δ 8.30 (1H, s), 7.83 (1H, d, J = 7.6 Hz), 7.71 (1H, d, J = 6.4 Hz), 7.60 (1H, s), 7.34-(7.53 (5H, m), 7.28-7.32 (1H, m), 7.20-7.24 (1H, m), 4.70-4.75 (2H, m), 4.60 (2H, d, J = 6.0 Hz), 2.87-3.06 (4H, m), 1.83-1.92 (2H, m), 1.25-1.35 (8H, m); LCMS: 93.0%, MS (ESI): m/z 482.0 [M + H]+ |
| 59 | 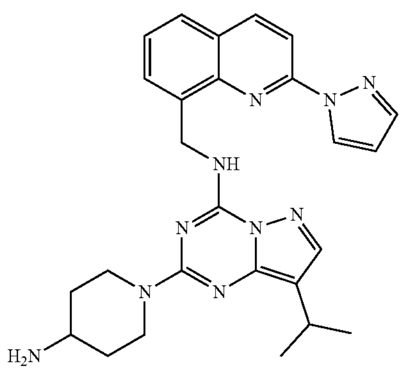 [SMILES: CC(C)c1cnn2c(NCc3cccc4ccc(-n5cccn5)nc34)nc(N3CCC(N)CC3)nc12] | white powder; ¹H-NMR (DMSO-d6, 400 MHz); δ 9.06 (1H, d, J = 2.4 Hz), 8.86 (1H, brs), 8.57 (1H, d, J = 8.8 Hz), 8.20 (1H, d, J = 8.8 Hz), 7.90-7.95 (2H, m), 7.80 (1H, d, J = 7.2 Hz), 7.71 (1H, s), 7.53 (1H, t, J = 7.6 Hz), 6.68 (1H, s), 5.28 (2H, brs), 4.31-4.44 (2H, m), 2.84-2.93 (1H, m), 2.71-2.83 (2H, m), 2.59-2.68 (1H, m), 1.40-1.60 (2H, m), 1.21 (6H, d, J = 6.8 Hz), 0.80-1.00 (2H, m); LCMS: 100%, MS (ESI): m/z 483.0 [M + H]+ |
| 60 | 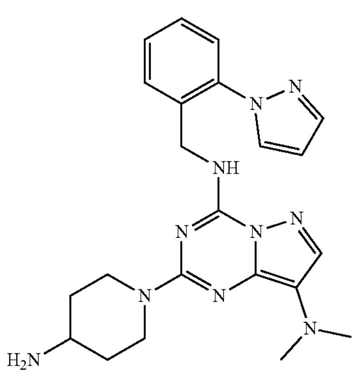 [SMILES: CN(C)c1cnn2c(NCc3ccccc3-n3cccn3)nc(N3CCC(N)CC3)nc12] | light pink powder; ¹H-NMR (DMSO-d6 + D2O, 400 MHz): δ 8.15 (1H, d, J = 1.6 Hz), 8.03 (1H, s), 7.79 (1H, d, J = 1.6 Hz), 7.51-7.58 (1H, m), 7.38-7.47 (3H, m), 6.54-6.59 (1H, m), 4.59-4.72 (2H, m), 4.36-4.58 (2H, m), 3.20-3.34 (1H, m), 3.10 (6H, s), 2.78-2.91 (2H, m), 1.80-1.97 (2H, m), 1.20-1.39 (2H, m); LCMS: 92.0%, MS (ESI-HRMS): m/z 433.2577 [M + H]+ |

TABLE 11-continued

Summarized compounds 1-279 in terms of their structures and corresponding characteristics.

| # cpds | Structure | Characterization Data |
|---|---|---|
| 61 | 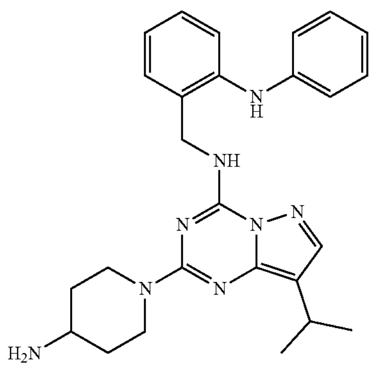 [SMILES: CC(C)c1cnn2c(NCc3ccccc3Nc3ccccc3)nc(N3CCC(N)CC3)nc12] | white powder; $^1$H-NMR (DMSO-d6, 400 MHz): δ 9.26 (1H, brs), 8.14-8.34 (3H, m), 7.87 (1H, s), 7.35 (1H, d, J = 7.6 Hz), 7.13-7.24 (4H, m), 6.85-6.98 (3H, m), 6.78 (1H, t, J = 7.2 Hz), 4.52-4.71 (4H, m), 3.21-3.35 (1H, m), 3.06-3.16 (1H, m), 2.91-3.04 (2H, m), 1.89-2.01 (2H, m), 1.37-1.52 (2H, m), 1.22 (6H, d, J = 6.4 Hz); LCMS: 100%, MS (ESI): m/z 457.1 [M + H]+ |
| 62 | 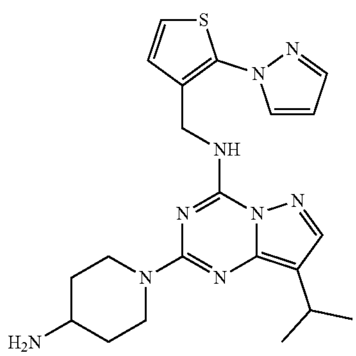 [SMILES: CC(C)c1cnn2c(NCc3ccsc3-n3cccn3)nc(N3CCC(N)CC3)nc12] | white powder; $^1$H-NMR (DMSO-d6, 400 MHz): δ 8.97 (1H, t, J = 6.0 Hz), 8.25 (1H, d, J = 1.6 Hz), 7.73-7.84 (4H, m), 7.36 (1H, d, J = 5.2 Hz), 7.08 (1H, d, J = 5.6 Hz), 6.57 (1H, s), 4.64 (2H, d, J = 6.0 Hz), 4.36-4.45 (2H, m), 3.20-3.25 (1H, m), 2.87-2.94 (1H, m), 2.77 (2H, t, J = 12.4 Hz), 1.79-1.92 (2H, m), 1.14-1.42 (8H, m); LCMS: 100%, MS (ESI): m/z 438.0 [M + H]+ |
| 63 | 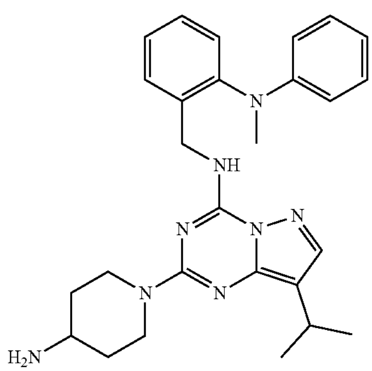 [SMILES: CC(C)c1cnn2c(NCc3ccccc3N(C)c3ccccc3)nc(N3CCC(N)CC3)nc12] | white powder; $^1$H-NMR (DMSO-d6, 400 MHz): δ 8.96 (1H, brs), 7.99-8.21 (3H, m), 7.81 (1H, s), 7.33-7.40 (2H, m), 7.23-7.30 (1H, m), 7.19 (1H, d, J = 8.0 Hz), 7.12 (2H, t, J = 7.2 Hz), 6.67 (1H, t, J = 7.6 Hz), 6.52 (2H, d, J = 8.0 Hz), 4.43-4.56 (4H, m), 3.18-3.29 (4H, m), 2.95-3.08 (1H, m), 2.80-2.93 (2H, m), 1.83-1.95 (2H, m), 1.30-1.44 (2H, m), 1.23 (6H, d, J = 6.8 Hz); LCMS: 100%, MS (ESI): m/z 471.0 [M + H]+ |
| 64 | 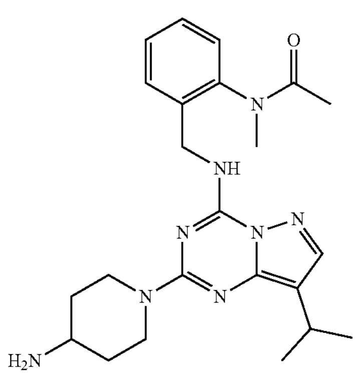 [SMILES: CC(=O)N(C)c1ccccc1CNc1nc(N2CCC(N)CC2)nc2c(C(C)C)cnn12] | yellow powder; $^1$H-NMR (DMSO-d6, 400 MHz): δ 8.89 (1H, brs), 7.75-7.85 (4H, m), 7.24-7.36 (4H, m), 4.50-4.61 (4H, m), 3.07 (3H, s), 2.79-2.94 (4H, m), 1.81-1.88 (2H, m), 1.63 (3H, s), 1.29-1.38 (2H, m), 1.21 (6H, d, J = 6.8 Hz); LCMS: 100%, MS (ESI): m/z 437.1 [M + H]+ |

TABLE 11-continued

Summarized compounds 1-279 in terms of their structures and corresponding characteristics.

| # cpds | Structure | Characterization Data |
|---|---|---|
| 65 | 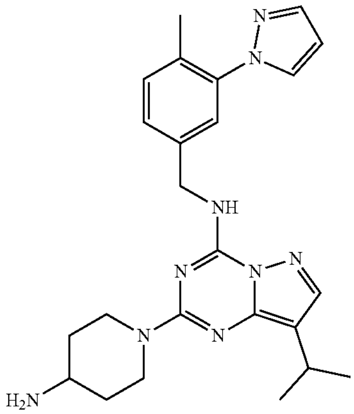 [SMILES: Cc1ccc(CNc2nc(N3CCC(N)CC3)nc3c(C(C)C)cnn23)cc1-n1cccn1] | white powder; $^1$H-NMR (DMSO-d6, 400 MHz): δ 9.02 (1H, brs), 7.99 (1H, d, J = 2.0 Hz), 7.72-7.90 (4H, m), 7.70 (1H, s), 7.42 (1H, s), 7.37 (1H, d, J = 8.0 Hz), 7.31 (1H, d, J = 8.0 Hz), 6.49 (1H, s), 4.55-4.67 (4H, m), 3.23-3.30 (1H, m), 2.85-2.94 (3H, m), 2.16 (3H, s), 1.82-1.93 (2H, m), 1.19-1.39 (8H, m); LCMS: 100%, MS (ESI): m/z 446.1 [M + H]+ |
| 66 | 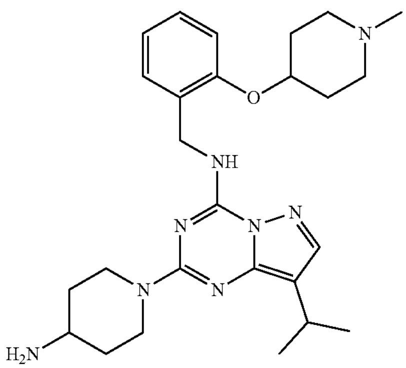 [SMILES: CC(C)c1cnn2c(NCc3ccccc3OC3CCN(C)CC3)nc(N3CCC(N)CC3)nc12] | white powder; $^1$H-NMR (CDCl$_3$, 400 MHz): δ 7.56 (1H, s), 7.34 (1H, d, J = 6.8 Hz), 7.33 (1H, d, J = 6.8 Hz), 7.20-7.30 (1H, m), 6.92 (1H, t, J = 7.2 Hz), 6.85 (1H, d, J = 7.2 Hz), 6.57-6.65 (1H, m), 4.68-4.87 (4H, m), 4.52-4.57 (1H, m), 2.95-3.09 (4H, m), 2.69-2.83 (4H, m), 2.40 (3H, s), 2.18-2.30 (2H, m), 1.95-2.09 (4H, m), 1.38-1.50 (2H, m), 1.26 (6H, d, J = 6.8 Hz); LCMS: 100%, MS (ESI): m/z 479.1 [M + H]+ |
| 67 | 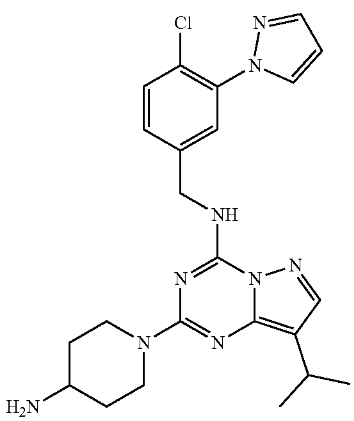 [SMILES: CC(C)c1cnn2c(NCc3ccc(Cl)c(-n4cccn4)c3)nc(N3CCC(N)CC3)nc12] | white powder; $^1$H-NMR (CD$_3$OD, 400 MHz): δ 9.09 (1H, t, J = 6.0 Hz), 8.12 (1H, d, J = 2.4 Hz), 7.74-7.84 (4H, m), 7.66 (1H, s), 7.61 (1H, d, J = 8.4 Hz), 7.49 (1H, d, J = 8.4 Hz), 6.53 (1H, s), 4.55-4.66 (4H, m), 3.24-3.28 (1H, m), 2.85-2.94 (3H, m), 1.82-1.92 (2H, m), 1.18-1.42 (8H, m); LCMS: 97.6%, MS (ESI): m/z 466.1 [M + H]+ |
| 68 | 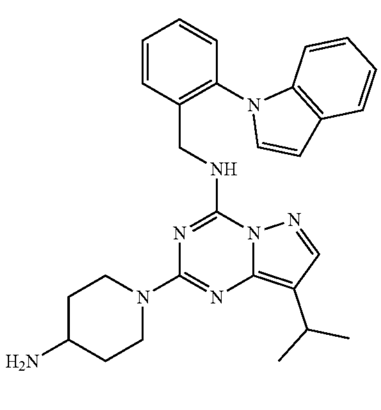 | white powder; $^1$H-NMR (DMSO-d6, 400 MHz): δ 8.95 (1H, t, J = 6.0 Hz), 7.70-7.80 (3H, m), 7.65-7.75 (1H, m), 7.41-7.62 (5H, m), 7.10-7.20 (1H, m), 7.01-7.05 (1H, m), 7.12 (1H, d, J = 3.2 Hz), 4.25-4.50 (4H, m), 3.10-3.25 (1H, m), 2.87-2.95 (1H, m), 2.55-2.65 (2H, m), 1.65-1.85 (4H, m), 1.24 (6H, d, J = 6.8 Hz); LCMS: 100%, MS (ESI): m/z 481.0 [M + H]+ |

TABLE 11-continued

Summarized compounds 1-279 in terms of their structures and corresponding characteristics.

| # cpds | Structure | Characterization Data |
|---|---|---|
| 69 | 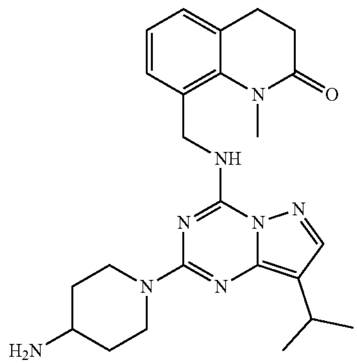 [SMILES: CC(C)c1cnn2c(NCc3cccc4c3N(C)C(=O)CC4)nc(N3CCC(N)CC3)nc12] | light blue solid; ¹H-NMR (CDCl₃, 400 MHz): δ 7.61 (1H, s), 7.30 (1H, d, J = 7.6 Hz), 7.13 (1H, d, J = 6.8 Hz), 7.05 (1H, t, J = 7.6 Hz), 6.50 (1H, t, J = 5.6 Hz), 4.78 (2H, d, J = 6.8 Hz), 4.65-4.73 (2H, m), 3.43 (3H, s), 3.00-3.10 (1H, m), 2.82-2.97 (5H, m), 2.57-2.63 (2H, m), 1.83-1.96 (2H, m), 1.22-1.36 (8H, m); LCMS: 100%, MS (ESI): m/z 449.1 [M + H]+ |
| 70 | 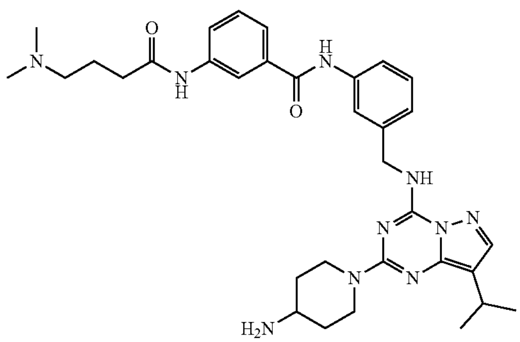 [SMILES: CC(C)c1cnn2c(NCc3cccc(NC(=O)c4cccc(NC(=O)CCCN(C)C)c4)c3)nc(N3CCC(N)CC3)nc12] | white powder; ¹H-NMR (DMSO-d6, 400 MHz): δ 10.24 (1H, brs), 10.14 (1H, brs), 8.87 (1H, brs), 8.06 (1H, s), 7.77-7.84 (2H, m), 7.72 (1H, s), 7.65 (1H, d, J = 8.4 Hz), 7.56 (1H, d, J = 7.6 Hz), 7.41 (1H, t, J = 7.6 Hz), 7.28 (1H, t, J = 8.0 Hz), 7.12 (1H, d, J = 7.6 Hz), 4.59 (2H, s), 4.44-4.55 (2H, m), 2.83-2.97 (3H, m), 2.70-2.78 (1H, m), 2.34 (2H, t, J = 7.2 Hz), 2.22 (2H, t, J = 7.2 Hz), 2.12 (6H, s), 1.65-1.76 (4H, m), 1.22 (6H, d, J = 6.8 Hz), 1.03-1.15 (2H, m); LCMS: 100%, MS (ESI): m/z 613.2 [M + H]+ |
| 71 | 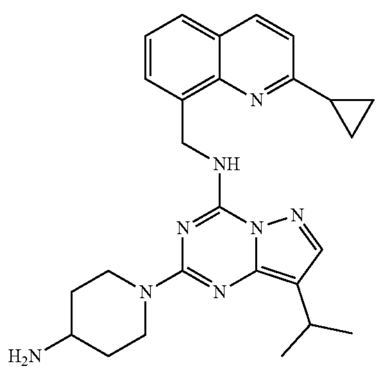 [SMILES: CC(C)c1cnn2c(NCc3cccc4ccc(C5CC5)nc34)nc(N3CCC(N)CC3)nc12] | off-white powder; ¹H-NMR (DMSO-d6, 400 MHz): δ 8.53 (1H, brs), 8.22 (1H, d, J = 8.4 Hz), 7.79 (1H, d, J = 8.4 Hz), 7.71 (1H, s), 7.62 (1H, d, J = 6.8 Hz), 7.51 (1H, d, J = 8.8 Hz), 7.41 (1H, t, J = 8.0 Hz), 5.19 (2H, s), 4.34-4.44 (2H, m), 2.86-2.94 (1H, m), 2.75-2.85 (2H, m), 2.64-2.74 (1H, m), 2.27-2.36 (1H, m), 1.54-1.66 (2H, m), 1.17-1.23 (8H, m), 1.06-1.15 (2H, m), 0.95-1.06 (2H, m); LCMS: 100%, MS (ESI): m/z 457.1 [M + H]+ |
| 72 | 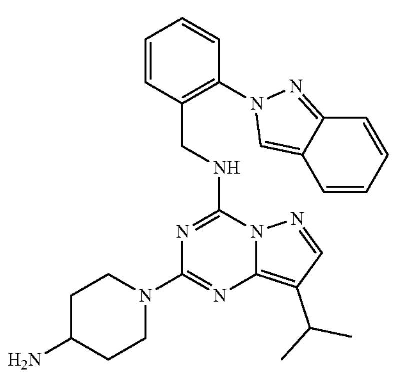 [SMILES: CC(C)c1cnn2c(NCc3ccccc3-n3cc4ccccc4n3)nc(N3CCC(N)CC3)nc12] | white powder; ¹H-NMR (CDCl₃, 400 MHz): δ 8.21 (1H, s), 7.87 (1H, d, J = 7.6 Hz), 7.67-7.75 (2H, m), 7.60-7.67 (2H, m), 7.41-7.49 (3H, m), 7.34-7.40 (1H, m), 7.11-7.21 (1H, m), 4.63-4.79 (4H, m), 2.87-3.06 (4H, m), 1.88 (2H, d, J = 10.0 Hz), 1.26-1.35 (8H, m), LCMS: 100%, MS (ESI): m/z 482.1 [M + H]+ |

TABLE 11-continued

Summarized compounds 1-279 in terms of their structures and corresponding characteristics.

| # cpds | Structure | Characterization Data |
|---|---|---|
| 73 | 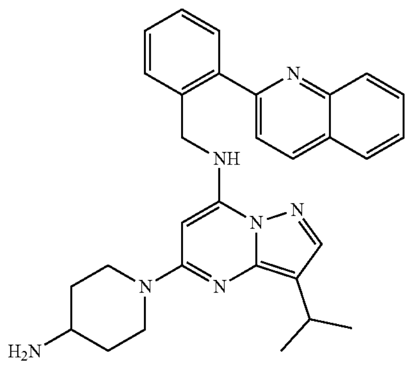 [SMILES: CC(C)c1cnn2c(NCc3ccccc3-c3ccc4ccccc4n3)cc(N3CCC(N)CC3)nc12] | off-white solid; $^1$H-NMR (DMSO-d6, 400 MHz): δ 8.55-8.59 (2H, m), 8.39 (1H, d, J = 8.8 Hz), 7.88 (1H, d, J = 8.4 Hz), 7.80-7.85 (2H, m), 7.69-7.75 (4H, m), 7.51-7.56 (2H, m), 7.45-7.50 (2H, m), 5.87 (1H, s), 4.64 (2H, d, J = 6.4 Hz), 4.38-4.13 (2H, m), 3.26-3.28 (1H, m), 2.86-2.99 (3H, m), 1.86-1.89 (2H, m), 1.39-1.42 (2H, m), 1.25 (6H, d, J = 6.8 Hz); LCMS: 100.0%, MS (ESI): m/z 492.1 [M + H]+ |
| 74 | 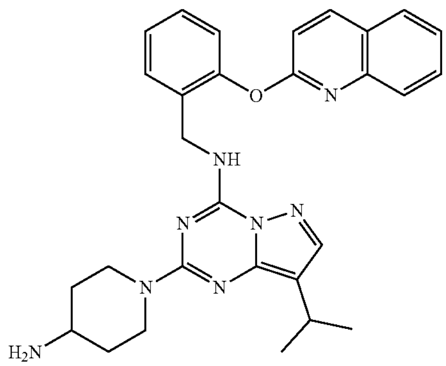 [SMILES: CC(C)c1cnn2c(NCc3ccccc3Oc3ccc4ccccc4n3)nc(N3CCC(N)CC3)nc12] | light brown powder; $^1$H-NMR (DMSO-d6, 400 Hz): δ 8.36 (1H, d, J = 8.8 Hz), 7.90 (1H, d, J = 8.0 Hz), 7.56-7.63 (2H, m), 7.51-7.56 (1H, m), 7.38-7.47 (2H, m), 7.29-7.38 (1H, m), 7.15-7.25 (3H, m), 4.54 (2H, s), 4.24-4.40 (2H, m), 2.80-2.89 (1H, m), 2.70-2.80 (2H, m), 2.61-2.70 (1H, m), 1.48-1.66 (2H, m), 1.18 (6H, d, J = 7.2 Hz), 0.90-1.04 (2H, m); LCMS: 99.2%, MS (ESI): m/z 531.1 [M + Na]+ |
| 75 | 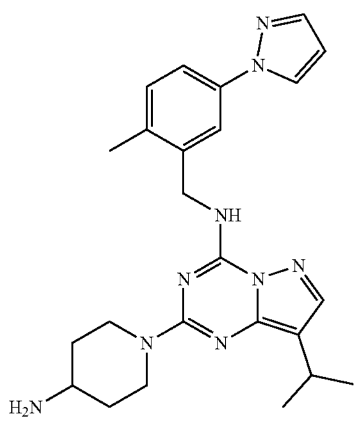 [SMILES: Cc1ccc(-n2cccn2)cc1CNc1nc(N2CCC(N)CC2)nc2c(C(C)C)cnn12] | white powder; $^1$H-NMR (DMSO-d6, 400 MHz): δ 8.83 (1H, brs), 8.37 (1H, d, J = 2.4 Hz), 7.87 (1H, s), 7.73 (1H, s), 7.67 (1H, s), 7.58 (1H, dd, J = 8.0, 2.0 Hz), 7.27 (1H, d, J = 8.0 Hz), 6.49 (1H, d, J = 1.6 Hz), 4.65 (2H, s), 4.43-4.46 (2H, m), 2.85-2.95 (3H, m), 2.74-2.76 (1H, m), 2.39 (3H, s), 1.63-1.66 (2H, m), 1.23 (6H, d, J = 6.8 Hz), 1.05-1.07 (2H, m); LCMS: 99.5%, MS (ESI): m/z 446.1 [M + H]+ |
| 76 | 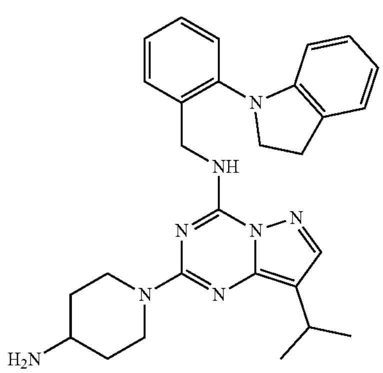 [SMILES: CC(C)c1cnn2c(NCc3ccccc3N3CCc4ccccc43)nc(N3CCC(N)CC3)nc12] | white powder; $^1$H-NMR (DMSO-d6, 400 MHz): δ 7.73 (1H, s), 7.39 (1H, d, J = 7.6 Hz), 7.28-7.35 (2H, m), 7.18-7.24 (1H, m), 7.17 (1H, d, J = 7.6 Hz), 6.94 (1H, t, J = 8.0 Hz), 6.67 (1H, t, J = 7.4 Hz), 6.09 (1H, d, J = 7.8 Hz), 4.64 (2H, s), 4.31-4.43 (2H, m), 3.79 (2H, t, J = 8.0 Hz), 3.11 (2H, t, J = 8.0 Hz), 2.87-2.95 (1H, m), 2.79-2.87 (2H, m), 2.67-2.76 (1H, m), 1.56-1.69 (2H, m), 1.23 (6H, d, J = 7.2 Hz), 0.94-1.11 (2H, m); LCMS: 97.8%, MS (ESI): m/z 483.0 [M + H]+ |

TABLE 11-continued

Summarized compounds 1-279 in terms of their structures and corresponding characteristics.

| # cpds | Structure | Characterization Data |
| --- | --- | --- |
| 77 | 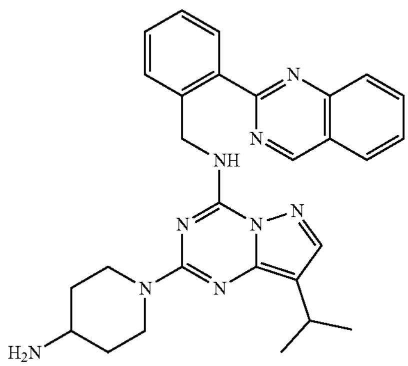 | white powder; ¹H-NMR (DMSO-d6, 400 MHz): δ 9.59 (1H, s), 8.84 (1H, t, J = 6.4 Hz), 8.38 (1H, d, J = 8.8 Hz), 8.19-8.29 (1H, m), 7.94-8.06 (2H, m), 7.65-7.76 (2H, m), 7.64 (1H, s), 7.40-7.52 (2H, m), 4.92 (2H, d, J = 6.4 Hz), 4.81-4.91 (2H, m), 2.92-3.08 (4H, m), 1.86-2.04 (2H, m), 1.34-1.46 (2H, m), 1.28 (6H, d, J = 6.8 Hz); LCMS: 100%, MS (ESI): m/z 494.0 [M + H]+ |
| 78 | 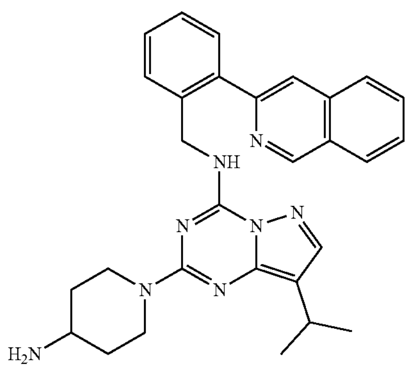 [SMILES: CC(C)c1cnn2c(NCc3ccccc3-c3cc4ccccc4cn3)nc(N3CCC(N)CC3)nc12] | white power; ¹H-NMR (CDCl₃, 400 MHz): δ 9.47 (1H, s), 8.26-8.28 (1H, m), 8.05 (2H, d, J = 8.4 Hz), 7.87-7.90 (2H, m), 7.73-7.75 (1H, m), 7.58-7.66 (4H, m), 7.39-7.41 (2H, m), 4.75-4.82 (4H, m), 2.93-3.05 (4H, m), 1.85-1.92 (2H, m), 1.28-1.38 (8H, m); LCMS: 99.4%, MS (ESI): m/z 493.1 [M + H]+ |
| 79 | 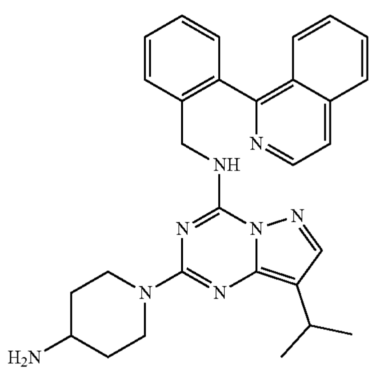 [SMILES: CC(C)c1cnn2c(NCc3ccccc3-c3nccc4ccccc34)nc(N3CCC(N)CC3)nc12] | white power; ¹H-NMR (CDCl₃, 400 MHz): δ 8.64 (1H, d, J = 5.6 Hz), 7.84 (1H, d, J = 8.0 Hz), 7.73 (1H, d, J = 8.4 Hz), 7.62-7.66 (3H, m), 7.54 (1H, s), 7.40-7.49 (4H, m), 7.15 (1H, m), 4.84-4.91 (1H, m), 4.63-4.66 (2H, m), 4.22-4.27 (1H, m), 2.96-3.03 (1H, m), 2.83-2.92 (3H, m), 2.78-2.92 (3H, m), 1.84-1.87 (2H, m), 1.26-1.28 (8H, m); LCMS: 100.0%, MS (ESI): m/z 493.1 [M + H]+ |
| 80 | 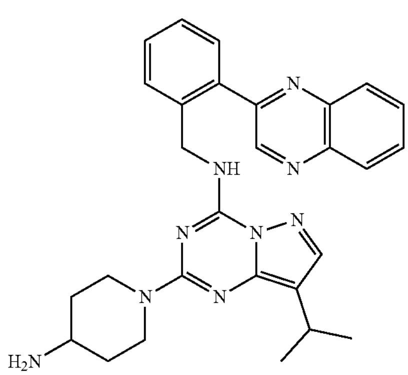 [SMILES: CC(C)c1cnn2c(NCc3ccccc3-c3cnc4ccccc4n3)nc(N3CCC(N)CC3)nc12] | yellow power; ¹H-NMR (CDCl₃, 400 MHz): δ 9.19 (1H, brs), 8.63 (1H, t, J = 6.6 Hz), 8.52 (1H, d, J = 8.0 Hz), 8.19 (1H, d, J = 8.0 Hz), 7.82-7.89 (2H, m), 7.69-7.75 (3H, m), 7.47-7.53 (2H, m), 4.78-4.86 (4H, m), 2.92-3.09 (4H, m), 1.92-1.97 (2H, m), 1.27-1.42 (8H, m); LCMS: 100.0%, MS (ESI): m/z 494.1 [M + H]+ |

TABLE 11-continued

Summarized compounds 1-279 in terms of their structures and corresponding characteristics.

| # cpds | Structure | Characterization Data |
| --- | --- | --- |
| 81 | 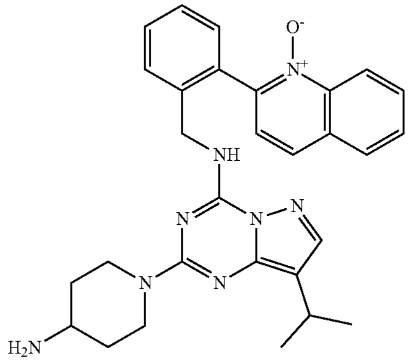 [SMILES: CC(C)c1cnn2c(NCc3ccccc3-c3ccc4ccccc4[n+]3[O-])nc(N3CCC(N)CC3)nc12] | white powder; $^1$H-NMR (CDCl$_3$, 400 MHz): δ 8.83 (1H, d, J = 8.0 Hz), 7.75-7.87 (2H, m), 7.58-7.68 (3H, m), 7.55 (1H, s), 7.39-7.52 (2H, m), 7.20-7.35 (2H, m), 7.04-7.14 (1H, m), 4.87-4.95 (1H, m), 4.50-4.62 (2H, m), 4.38-4.45 (1H, m), 2.93-3.02 (1H, m), 2.87 (1H, s), 2.68-2.80 (2H, m), 1.18-1.29 (8H, m); LCMS: 100%, MS (ESI): m/z 509.0 [M + H]+ |
| 82 | 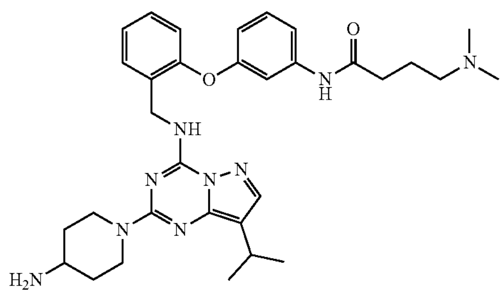 [SMILES: CC(C)c1cnn2c(NCc3ccccc3Oc3cccc(NC(=O)CCCN(C)C)c3)nc(N3CCC(N)CC3)nc12] | white powder; $^1$H-NMR (CDCl$_3$, 400 MHz): δ 10.14 (1H, brs), 7.57 (1H, s), 7.46 (1H, dd, J = 7.6, 1.6 Hz), 7.17-7.31 (3H, m), 7.13 (1H, brs), 7.05-7.11 (1H, m), 6.93 (1H, d, J = 7.6 Hz), 6.60-6.71 (2H, m), 4.77 (2H, d, J = 6.0 Hz), 4.69-4.76 (2H, m), 2.97-3.05 (1H, m), 2.86-2.97 (3H, m), 2.45-2.51 (2H, m), 2.42 (2H, t, J = 6.0 Hz), 2.24 (6H, s), 1.79-1.90 (4H, m), 1.22-1.35 (8H, m); LCMS: 100%, MS (ESI): m/z 608.3 [M + Na]+ |
| 83 | 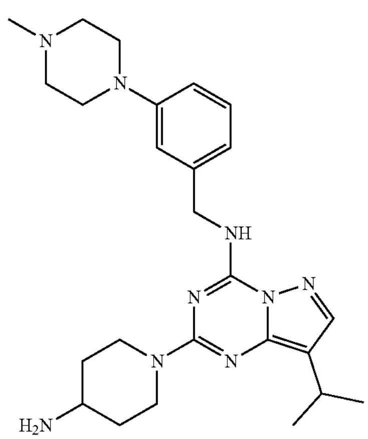 [SMILES: CC(C)c1cnn2c(NCc3cccc(N4CCN(C)CC4)c3)nc(N3CCC(N)CC3)nc12] | off-white power; $^1$H-NMR (CDCl$_3$, 400 MHz): δ 7.61 (1H, s), 7.23 (1H, t, J = 7.8 Hz), 6.94 (1H, s), 6.85-6.87 (2H, m), 6.55 (1H, t, J = 5.6 Hz), 4.74-4.78 (2H, m), 4.68 (2H, d, J = 5.6 Hz), 3.21 (4H, t, J = 5.0 Hz), 2.92-3.07 (4H, m), 2.57 (4H, t, J = 5.0 Hz), 3.35 (3H, s), 1.87-1.89 (2H, m), 1.26-1.35 (8H, m); LCMS: 97.4%, MS (ESI): m/z 464.1 [M + H]+ |
| 84 | 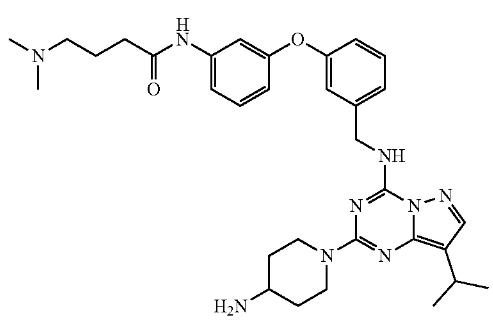 [SMILES: CC(C)c1cnn2c(NCc3cccc(Oc4cccc(NC(=O)CCCN(C)C)c4)c3)nc(N3CCC(N)CC3)nc12] | off-white powder; $^1$H-NMR (DMSO-d6, 400 MHz); δ 9.97 (1H, brs), 8.85 (1H, brs), 7.70 (1H, s), 7.28-7.39 (3H, m), 7.21-7.28 (1H, m), 7.17 (1H, d, J = 7.6 Hz), 7.07 (1H, s), 6.88 (1H, dd, J = 8.0, 2.0 Hz), 6.63 (1H, dd, J = 8.0, 2.0 Hz), 4.54 (2H, s), 4.39-4.60 (2H, m), 2.81-2.95 (3H, m), 2.69-2.79 (1H, m), 2.28 (2H, t, J = 7.4 Hz), 2.19 (2H, t, J = 7.0 Hz), 2.09 (6H, s), 1.60-1.72 (4H, m), 1.22 (6H, d, J = 6.8 Hz), 0.95-1.14 (2H, m); LCMS: 98.5%, MS (ESI): m/z 608.3 [M + Na]+ |

TABLE 11-continued

Summarized compounds 1-279 in terms of their structures and corresponding characteristics.

| # cpds | Structure | Characterization Data |
|---|---|---|
| 85 | 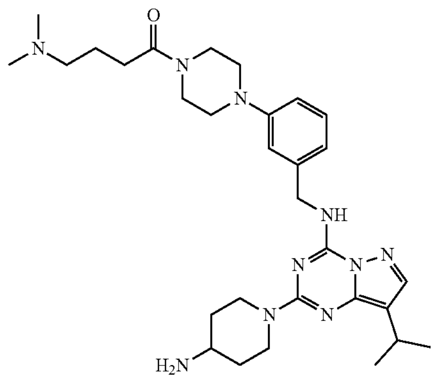 [SMILES: CC(C)c1cnn2c(NCc3cccc(N4CCN(C(=O)CCCN(C)C)CC4)c3)nc(N3CCC(N)CC3)nc12] | yellow solid; ¹H-NMR (CDCl₃, 400 MHz); δ 7.61 (1H, s), 7.23-7.25 (1H, m), 6.84-6.96 (3H, m), 6.56-6.59 (1H, m), 4.75-4.79 (2H, m), 4.68-4.70 (2H, m), 3.77 (2H, t, J = 7.8 Hz), 3.64 (2H, t, J = 7.2 Hz), 3.02-3.05 (1H, m), 2.92-2.99 (3H, m), 2.48-2.58 (4H, m), 2.40 (6H, s), 1.89-1.97 (4H, m), 1.26-1.37 (8H, m); LCMS: 96.6%, MS (ESI): m/z 563.3 [M + H]+ |
| 86 | 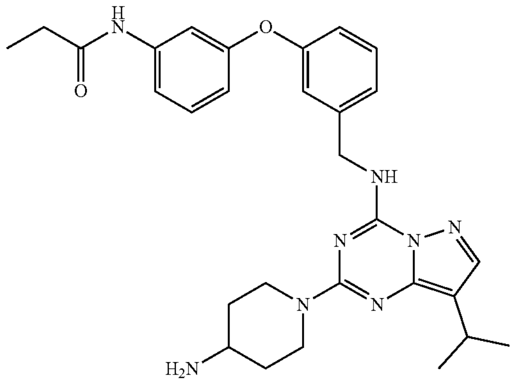 [SMILES: CCC(=O)Nc1cccc(Oc2cccc(CNc3nc(N4CCC(N)CC4)nc4c(C(C)C)cnn34)c2)c1] | white powder; ¹H-NMR (DMSO-d6, 400 MHz): δ 9.91 (1H, brs), 8.84 (1H, brs), 7.70 (1H, s), 7.29-7.38 (3H, m), 7.22-7.29 (1H, m), 7.14-7.20 (1H, m), 7.07 (1H, s), 6.85-6.92 (1H, m), 6.61-6.66 (1H, m), 4.54 (2H, s), 4.38-4.49 (2H, m), 2.81-2.94 (3H, m), 2.66-2.79 (1H, m), 2.27 (2H, q, J = 7.6 Hz), 1.59-1.73 (2H, m), 1.22 (6H, d, J = 6.8 Hz), 0.99-1.10 (5H, m); LCMS: 100%, MS (ESI): m/z 529.3 [M + H]+ |
| 87 | 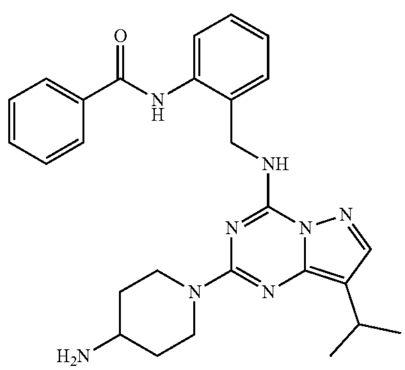 [SMILES: CC(C)c1cnn2c(NCc3ccccc3NC(=O)c3ccccc3)nc(N3CCC(N)CC3)nc12] | white solid; ¹H-NMR (CDCl₃, 400 MHz): δ 8.24 (1H, s), 7.93 (1H, d, J = 8.4 Hz), 7.62-7.65 (3H, m), 7.49-7.53 (1H, m), 7.34-7.41 (4H, m), 7.18-7.22 (1H, m), 7.68 (1H, t, J = 4.4 Hz), 4.82 (2H, d, J = 5.2 Hz), 4.53-4.57 (2H, m), 3.01-3.08 (1H, m), 2.89-2.95 (1H, m), 2.58-2.66 (2H, m), 1.82-1.95 (2H, m), 1.21-1.35 (8H, m); LCMS: 100.0%, MS (ESI): m/z 485.2 [M + H]+ |
| 88 | 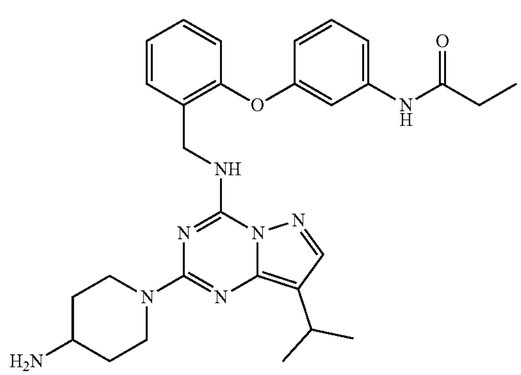 | off-white power; ¹H-NMR (CDCl₃, 400 MHz): δ 7.58 (1H, s), 7.48 (1H, dd, J = 7.6, 1.2 Hz), 7.29-7.32 (1H, m), 7.10-7.32 (3H, m), 7.02-7.25 (2H, m), 6.95 (1H, d, J = 8.0 Hz), 6.52-6.79 (2H, m), 4.61-4.92 (4H, m), 2.82-3.12 (4H, m), 2.37 (2H, q, J = 7.6 Hz), 1.81-1.95 (2H, m), 1.27-1.46 (8H, m), 1.13 (3H, t, J = 7.6 Hz); LCMS: 97%, MS (ESI): m/z 584.4 [M + H]+ |

TABLE 11-continued

Summarized compounds 1-279 in terms of their structures and corresponding characteristics.

| # cpds | Structure | Characterization Data |
|---|---|---|
| 89 | 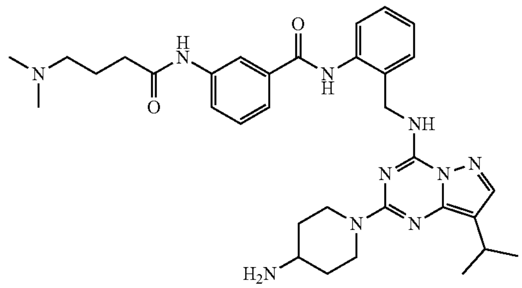 [SMILES: CC(C)c1cnn2c(NCc3ccccc3NC(=O)c3cccc(NC(=O)CCCN(C)C)c3)nc(N3CCC(N)CC3)nc12] | white powder; ¹H-NMR (CDCl₃, 400 MHz): δ 10.13 (1H, brs), 8.49 (1H, s), 8.20 (1H, d, J = 7.6 Hz), 7.76 (1H, d, J = 7.6 Hz), 7.70 (1H, s), 7.57 (1H, s), 7.31-7.39 (3H, m), 7.22-7.30 (2H, m), 7.13-7.16 (1H, m), 6.81-6.84 (1H, m), 4.75 (2H, s), 4.48-4.51 (2H, m), 2.95-3.02 (1H, m), 2.71-2.77 (1H, m), 2.59-2.66 (2H, m), 2.39-2.48 (4H, m), 2.26 (6H, s), 1.82-1.85 (4H, m), 1.69-1.73 (2H, m), 1.25 (6H, d, J = 6.4 Hz), 1.03-1.22 (2H, m); LCMS: 96.5%, MS (ESI): m/z 613.3 [M + H]+ |
| 90 | 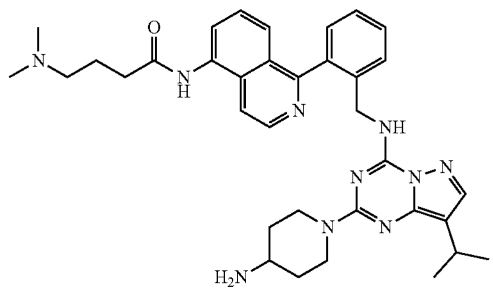 [SMILES: CC(C)c1cnn2c(NCc3ccccc3-c3nccc4c(NC(=O)CCCN(C)C)cccc34)nc(N3CCC(N)CC3)nc12] | white solid; ¹H-NMR (CDCl₃, 400 MHz): δ 10.03 (1H, brs), 8.55 (1H, d, J = 4.0 Hz), 8.09 (1H, d, J = 4.4 Hz), 7.71 (1H, d, J = 4.0 Hz), 7.57-7.59 (1H, m), 7.35-7.53 (7H, m), 6.98 (1H, brs), 4.77-4.79 (1H, m), 4.56-4.58 (2H, m), 4.24-4.27 (1H, m), 2.84-3.05 (4H, m), 2.66-2.67 (2H, m), 2.52-2.54 (2H, m), 2.32 (6H, s), 1.99-2.01 (2H, m), 1.80-1.83 (2H, m), 1.27-1.28 (8H, m); LCMS: 100%, MS (ESI): m/z 621.4 [M + H]+ |
| 91 | 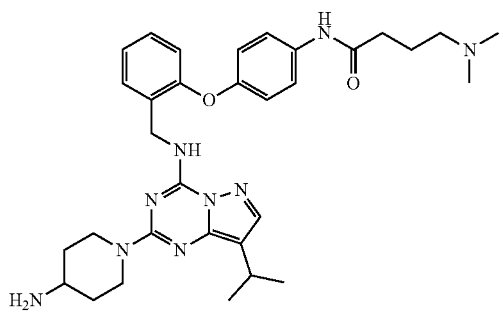 [SMILES: CC(C)c1cnn2c(NCc3ccccc3Oc3ccc(NC(=O)CCCN(C)C)cc3)nc(N3CCC(N)CC3)nc12] | white powder; ¹H-NMR (CDCl₃, 400 MHz): δ 9.86 (1H, brs), 7.59 (1H, s), 7.43-7.50 (3H, m), 7.21-7.23 (1H, m), 7.02-7.07 (1H, m), 6.93 (2H, d, J = 8.4 Hz), 6.80-6.83 (2H, m), 4.73-4.81 (4H, m), 2.90-3.04 (4H, m), 2.43-2.51 (4H, m), 2.31 (6H, s), 1.75-1.90 (4H, m), 1.27-1.29 (8H, m); LCMS: 100%, MS (ESI): m/z 586.4 [M + H]+ |
| 92 | 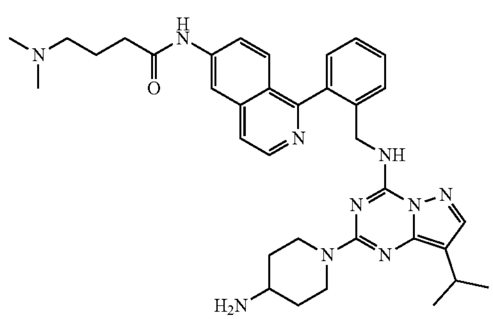 [SMILES: CC(C)c1cnn2c(NCc3ccccc3-c3nccc4cc(NC(=O)CCCN(C)C)ccc34)nc(N3CCC(N)CC3)nc12] | white powder ¹H-NMR (DMSO-d6, 400 MHz): δ 10.41 (1H, brs), 8.44-8.50 (2H, m), 7.73 (1H, d, J = 5.6 Hz), 7.66 (1H, s), 7.44-7.56 (4H, m), 7.42 (1H, t, J = 6.8 Hz), 7.32 (1H, d, J = 6.8 Hz), 4.22-4.44 (4H, m), 2.67-2.91 (4H, m), 2.42 (2H, t, J = 7.2 Hz), 2.25 (2H, t, J = 7.2 Hz), 2.13 (6H, s), 1.63-1.78 (4H, m), 1.20 (6H, d, J = 7.2 Hz), 1.04-1.07 (2H, m); LCMS: 100%, MS (ESI): m/z 621.4 [M + H]+ |
| 93 | 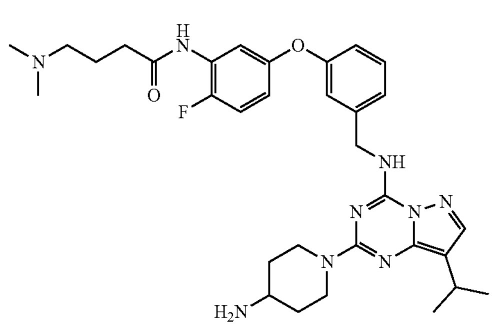 [SMILES: CC(C)c1cnn2c(NCc3cccc(Oc4ccc(F)c(NC(=O)CCCN(C)C)c4)c3)nc(N3CCC(N)CC3)nc12] | white powder; ¹H-NMR (DMSO-d6, 400 MHz): δ 9.89 (1H, brs), 7.68-7.71 (2H, m), 7.25-7.30 (1H, m), 7.22 (1H, dd, J = 10.8, 9.20 Hz), 7.15 (1H, d, J = 8.0 Hz), 7.05 (1H, s), 6.85 (1H, dd, J = 8.40, 2.0 Hz), 6.65-6.73 (1H, m), 4.49-4.54 (4H, m), 2.87-2.94 (4H, m), 2.38 (2H, t, J = 7.2 Hz), 2.18-2.22 (2H, t, J = 7.2 Hz), 2.10 (6H, s), 1.70-1.80 (2H, m), 1.64-1.68 (2H, m), 1.21-1.23 (8H, m); LCMS; 93.9%, MS (ESI): m/z 626.4 [M + Na]+ |

TABLE 11-continued

Summarized compounds 1-279 in terms of their structures and corresponding characteristics.

| # cpds | Structure | Characterization Data |
|---|---|---|
| 94 | 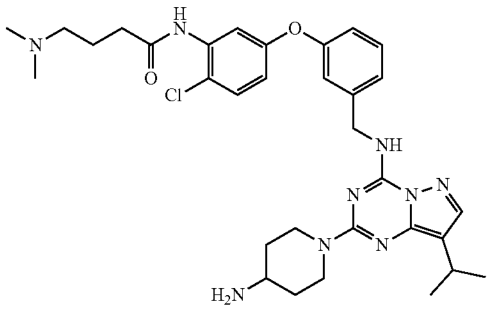 [SMILES: CC(C)c1cnn2c(NCc3cccc(Oc4ccc(Cl)c(NC(=O)CCCN(C)C)c4)c3)nc(N3CCC(N)CC3)nc12] | white powder; $^1$H-NMR (CDCl$_3$, 400 MHz): δ 8.59 (1H, brs), 8.11 (1H, s), 7.61 (1H, s), 7.29-7.30 (2H, m), 7.13 (1H, d, J = 7.6 Hz), 7.06 (1H, t, J = 3.6 Hz), 6.85-6.95 (1H, m), 6.64-6.67 (2H, m), 4.69-4.73 (4H, m), 2.94-3.03 (1H, m), 2.89-2.92 (3H, m), 2.50 (2H, t, J = 6.8 Hz), 2.41 (2H, t, J = 6.8 Hz), 2.27 (6H, s), 1.98-2.01 (2H, m), 1.86-1.91 (4H, m), 1.29-1.33 (8H, m); LCMS: 100.0%, MS (ESI): m/z 620.3 [M + H]+ |
| 95 | 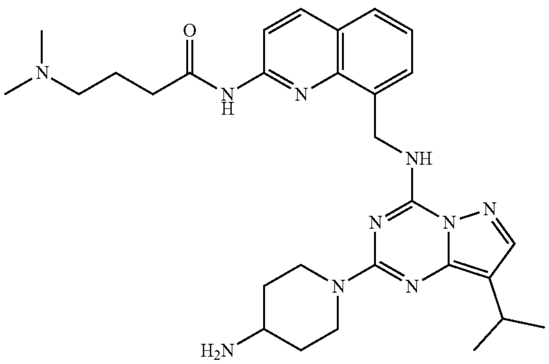 [SMILES: CC(C)c1cnn2c(NCc3cccc4ccc(NC(=O)CCCN(C)C)nc34)nc(N3CCC(N)CC3)nc12] | white powder; $^1$H-NMR (CDCl$_3$, 400 MHz): δ 10.62 (1H, brs), 8.46 (1H, d, J = 8.8 Hz), 8.14 (1H, d, J = 9.2 Hz), 7.63-7.74 (3H, m), 7.56 (1H, s), 7.35 (1H, t, J = 7.2 Hz), 5.17 (2H, d, J = 6.0 Hz), 4.75-85 (2H, m), 2.86-3.06 (4H, m), 2.62 (2H, t, J = 7.2 Hz), 2.49 (2H, t, J = 6.4 Hz), 2.35 (6H, s), 1.85-2.04 (4H, m), 1.24-1.32 (10H, m); LCMS: 93.5%, MS (ESI): m/z 567.4 [M + Na]+ |
| 96 | 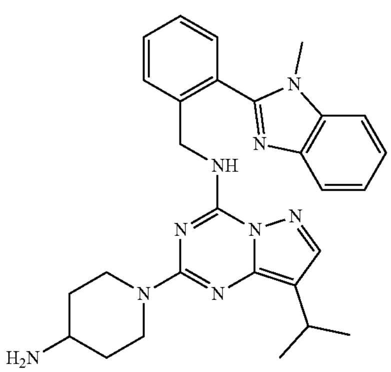 | white powder; $^1$H-NMR (CDCl$_3$, 400 MHz): δ 7.86-7.92 (2H, m), 7.68 (1H, d, J = 7.6 Hz), 7.62 (1H, s), 7.43-7.49 (3H, m), 7.33-7.41 (3H, m), 4.72-4.75 (4H, m), 3.71 (3H, s), 2.90-3.05 (4H, m), 1.87-1.91 (2H, m), 1.27-1.36 (8H, m).; LCMS: 97.4%, MS (ESI): m/z 496.3 [M + H]+ |
| 97 | 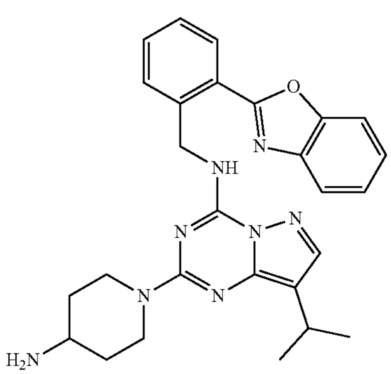 [SMILES: CC(C)c1cnn2c(NCc3ccccc3-c3nc4ccccc4o3)nc(N3CCC(N)CC3)nc12] | white powder; $^1$H-NMR (DMSO-d6, 400 MHz): δ 8.90 (1H, brs), 8.18 (1H, dd, J = 7.6, 1.2 Hz), 7.88-7.95 (1H, m), 7.82-7.88 (1H, m), 7.72 (1H, s), 7.78 (1H, d, J = 7.6 Hz), 7.55-7.62 (1H, m), 7.41-7.55 (3H, m), 5.21 (2H, s), 4.15-4.45 (2H, m), 2.85-3.00 (1H, m), 2.70-2.85 (2H, m), 2.60-2.70 (1H, m), 1.45-1.60 (2H, m), 1.21 (6H, d, J = 6.8 Hz), 0.85-1.00 (2H, m); LCMS: 97.4%, MS (ESI): m/z 483.3 [M + H]+ |

TABLE 11-continued

Summarized compounds 1-279 in terms of their structures and corresponding characteristics.

| # cpds | Structure | Characterization Data |
|---|---|---|
| 98 | 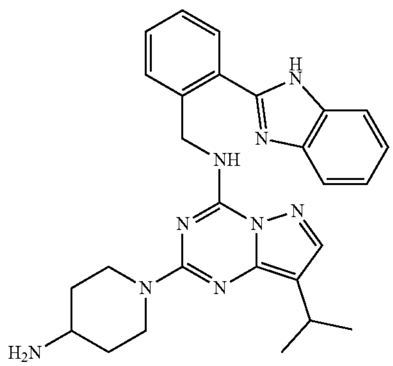 [SMILES: CC(C)c1cnn2c(NCc3ccccc3-c3nc4ccccc4[nH]3)nc(N3CCC(N)CC3)nc12] | white powder; $^1$H-NMR (CDCl$_3$, 400 MHz): δ 9.95 (1H, brs), 8.88 (1H, brs), 7.91 (1H, brs), 7.58-7.65 (3H, m), 7.36-7.39 (2H, m), 7.24-2.28 (2H, m), 4.95 (2H, d, J = 5.2 Hz), 4.82-4.85 (2H, m), 2.96-3.02 (4H, m), 1.91-1.94 (2H, m), 1.34-1.40 (2H, m), 1.24 (6H, d, J = 7.2 Hz); LCMS: 100.0%, MS (ESI): m/z 482.3 [M + H]+ |
| 99 | 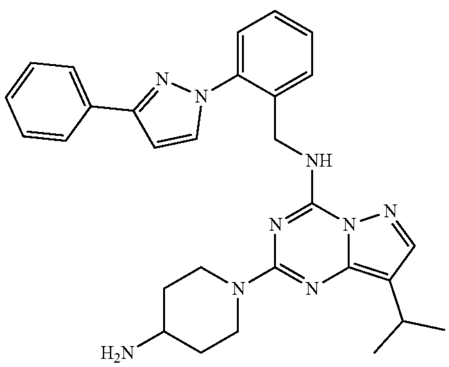 [SMILES: CC(C)c1cnn2c(NCc3ccccc3-n3ccc(-c4ccccc4)n3)nc(N3CCC(N)CC3)nc12] | white powder; $^1$H-NMR (DMSO-d6, 400 MHz): δ 8.24 (1H, d, J = 2.4 Hz), 8.00-8.05 (2H, m), 7.76 (1H, s), 7.51-7.52 (1H, m), 7.50-7.51 (1H, m), 7.44-7.48 (4H, m), 7.36-7.44 (1H, m), 7.08 (1H, d, J = 2.4 Hz), 4.70 (2H, s), 4.35-4.45 (2H, m), 2.84-2.92 (3H, m), 2.71-2.75 (1H, m), 1.66-1.69 (2H, m, 1.22 (6H, d, J = 7.2 Hz), 1.05-1.07 (2H, m); LCMS: 97.6%, MS (ESI): m/z 508.3 [M + H]+ |
| 100 | 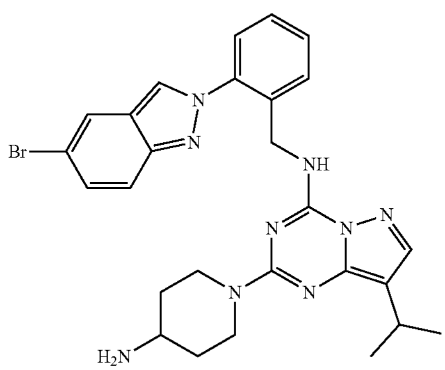 | white powder; $^1$H-NMR (DMSO-d6, 400 MHz): δ 8.73 (1H, s), 8.07 (1H, s), 7.70-7.71 (2H, m), 7.58-7.61 (2H, m), 7.44-7.52 (3H, m), 4.58 (2H, s), 4.24-4.57 (2H, m), 2.87-2.90 (1H, m), 2.70-2.80 (3H, m), 1.60-1.65 (2H, m), 1.21 (6H, d, J = 6.8 Hz), 0.97-1.02 (2H, m); LCMS: 100%, MS (ESI): m/z 560.1 [M + H]+ |
| 101 | 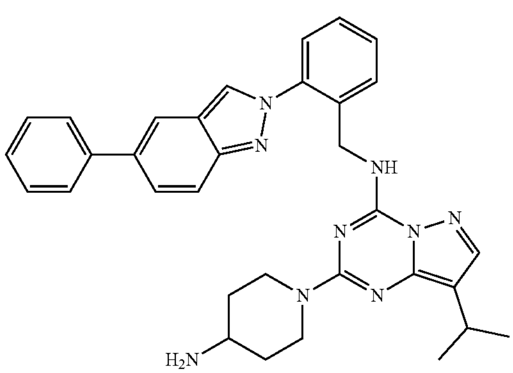 [SMILES: CC(C)c1cnn2c(NCc3ccccc3-n3cc4cc(-c5ccccc5)ccc4n3)nc(N3CCC(N)CC3)nc12] | white powder; $^1$H-NMR (CDCl$_3$, 400 MHz): δ 8.25 (1H, brs), 7.89-7.95 (2H, m), 7.64-7.68 (6H, m), 7.45-7.49 (5H, m), 7.34-7.44 (1H, m), 4.74-4.77 (2H, m), 4.69 (2H, d, J = 6.0 Hz), 2.91-3.03 (4H, m), 1.90-2.00 (2H, m), 1.39-1.41 (2H, m), 1.27 (6H, d, J = 6.8 Hz); LCMS: 95.1%, MS (ESI): m/z 580.3 [M + Na]+ |

TABLE 11-continued

Summarized compounds 1-279 in terms of their structures and corresponding characteristics.

| # cpds | Structure | Characterization Data |
|---|---|---|
| 102 | 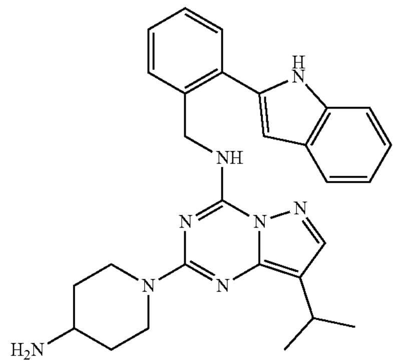 | white powder; ¹H-NMR (CDCl₃, 400 MHz): δ 8.56 (1H, brs), 7.65 (1H, d, J = 8.0 Hz), 7.60 (1H, s), 7.49-7.56 (2H, m), 7.33-7.42 (3H, m), 7.18-7.24 (1H, m), 7.11-7.17 (1H, m), 6.50-6.70 (2H, m), 4.86 (2H, d, J = 3.6 Hz), 4.55-4.69 (2H, m), 2.96-3.08 (1H, m), 2.79-2.92 (3H, m), 1.77-1.83 (2H, m), 1.19-1.31 (8H, m); LCMS: 100%, MS (ESI): m/z 481.3 [M + H]+ |
| 103 | 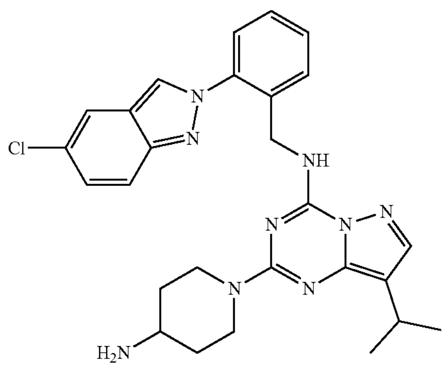 [SMILES: CC(C)c1cnn2c(NCc3ccccc3-n3cc4cc(Cl)ccc4n3)nc(N3CCC(N)CC3)nc12] | white powder; ¹H-NMR (CDCl₃, 400 MHz): δ 8.15 (1H, s), 7.80 (1H, d, J = 8.8 Hz), 7.70-7.75 (2H, m), 7.63 (1H, s), 7.49-7.51 (1H, m), 7.42-7.45 (3H, m), 7.27-7.32 (1H, m), 4.66-4.75 (4H, m); 2.92-3.04 (4H, m), 1.89-1.92 (2H, m), 1.28-1.34 (8H, m); LCMS: 100.0%, MS (ESI): m/z 516.2 [M + H]+ |
| 104 | 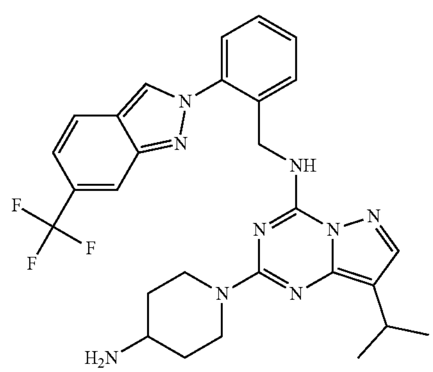 [SMILES: CC(C)c1cnn2c(NCc3ccccc3-n3cc4ccc(C(F)(F)F)cc4n3)nc(N3CCC(N)CC3)nc12] | white powder; ¹H-NMR (CDCl₃, 400 MHz): δ 8.29 (1H, s), 6.20 (1H, s), 7.85 (1H, d, J = 8.8 Hz), 7.72-7.73 (1H, m), 7.64 (1H, s), 7.42-7.51 (4H, m), 7.34 (1H, d, J = 8.8 Hz), 4.68-4.75 (4H, m), 2.91-3.06 (4H, m), 1.89-1.92 (2H, m), 1.28-1.38 (8H, m); LCMS: 100.0%, MS (ESI): m/z 550.3 [M + H]+ |
| 105 | 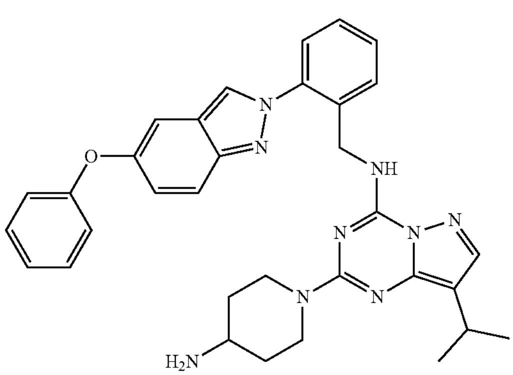 [SMILES: CC(C)c1cnn2c(NCc3ccccc3-n3cc4cc(Oc5ccccc5)ccc4n3)nc(N3CCC(N)CC3)nc12] | white powder; ¹H-NMR (CDCl₃, 400 MHz): δ 8.10 (1H, brs), 7.86 (1H, d, J = 10 Hz), 7.69-7.71 (1H, m), 7.62 (1H, s), 7.57 (1H, t, J = 6.60 Hz), 7.42-7.45 (3H, m), 7.30-7.35 (2H, m), 7.15-7.20 (2H, m), 7.06-7.15 (3H, m), 4.69-4.76 (4H, m), 2.91-3.05 (4H, m), 1.88-1.91 (2H, m), 1.32-1.35 (2H, m), 1.28 (6H, d, J = 6.4 Hz); LCMS: 100%, MS (ESI): m/z 574.3 [M + H]+ |

TABLE 11-continued

Summarized compounds 1-279 in terms of their structures and corresponding characteristics.

| # cpds | Structure | Characterization Data |
|---|---|---|
| 106 | 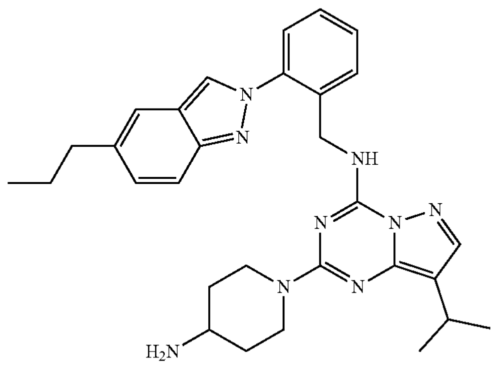 [SMILES: CCCc1ccc2nn(-c3ccccc3CNc3nc(N4CCC(N)CC4)nc4c(C(C)C)cnn34)cc2c1] | white powder; $^1$H-NMR (CDCl$_3$, 400 MHz): δ 8.12 (1H, s), 7.79 (1H, d, J = 8.8 Hz), 7.65-7.71 (2H, m), 7.64 (1H, s), 7.42-7.47 (4H, m), 7.23 (1H, d, J = 8.8 Hz), 4.74-4.77 (2H, m), 4.68 (2H, d, J = 6.4 Hz), 2.90-3.04 (4H, m), 2.70 (2H, t, J = 7.8 Hz), 1.89-1.91 (2H, m), 1.68-1.75 (2H, m), 1.33-1.37 (2H, m), 1.29 (6H, d, J = 6.4 Hz), 1.0 (3H, t, J = 7.4 Hz); LCMS: 100.0%, MS (ESI): m/z 524.3 [M + H]+ |
| 107 | 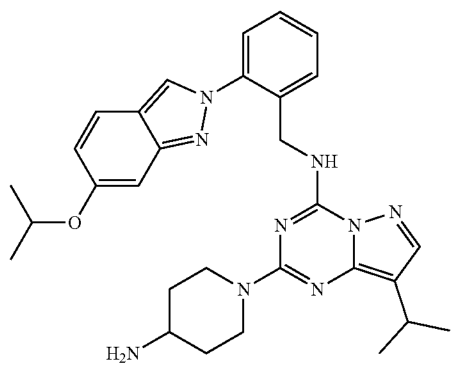 [SMILES: CC(C)Oc1ccc2cn(-c3ccccc3CNc3nc(N4CCC(N)CC4)nc4c(C(C)C)cnn34)nc2c1] | white powder; $^1$H-NMR (CDCl$_3$, 400 MHz): δ 7.87 (1H, s), 7.73 (1H, d, J = 8.8 Hz), 7.67 (1H, dd, J = 7.2, 2.0 Hz), 7.56 (1H, s), 7.45-7.56 (2H, m), 7.35 (1H, dd, J = 7.2, 2.0 Hz), 6.92 (1H, dd, J = 8.8, 2.4 Hz), 6.56 (1H, d, J = 2.0 Hz), 6.38 (1H, brs), 4.50-4.67 (4H, m), 4.41-4.45 (1H, m), 2.94-3.06 (1H, m), 2.80-2.92 (3H, m), 1.78-1.89 (2H, m), 1.20-1.31 (14H, m); LCMS: 100%, MS (ESI): m/z 540.3 [M + H]+ |
| 108 | 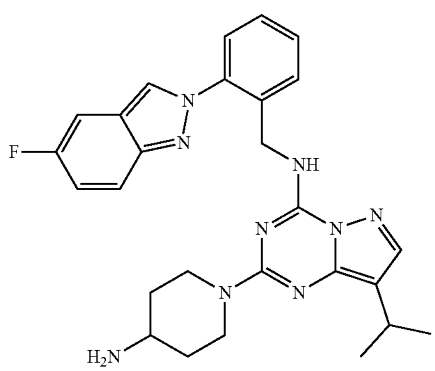 [SMILES: CC(C)c1cnn2c(NCc3ccccc3-n3cc4cc(F)ccc4n3)nc(N3CCC(N)CC3)nc12] | white powder; $^1$H-NMR (CDCl$_3$, 400 MHz): δ 8.16 (1H, s), 7.84 (1H, dd, J = 9.6, 4.8 Hz), 7.68-7.70 (1H, m), 7.62 (1H, brs), 7.54-7.57 (1H, m), 7.44-7.50 (3H, m), 7.27-7.30 (1H, m), 7.14-7.20 (1H, m), 4.66-4.77 (4H, m), 2.91-3.05 (4H, m), 1.86-1.99 (2H, m), 1.31-1.37 (2H, m), 1.28 (6H, d, J = 6.8 Hz); LCMS: 100%, MS (ESI): m/z 500.2 [M + H]+ |
| 109 | 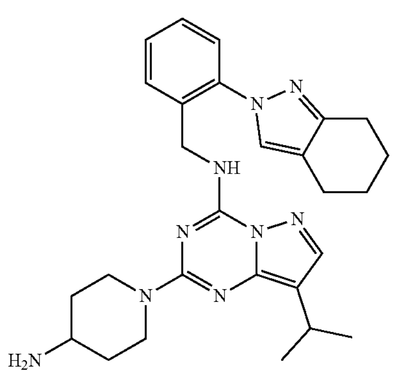 [SMILES: CC(C)c1cnn2c(NCc3ccccc3-n3cc4c(n3)CCCC4)nc(N3CCC(N)CC3)nc12] | white powder; $^1$H-NMR (CDCl$_3$, 400 MHz): δ 7.66 (1H, t, J = 6.2 Hz), 7.58-7.60 (2H, m), 7.39 (1H, s), 7.28-7.36 (3H, m), 4.78-4.81 (2H, m), 4.73 (2H, d, J = 6.4 Hz), 2.94-3.05 (4H, m), 2.82 (2H, t, J = 6.2 Hz), 2.61 (2H, t, J = 6.2 Hz), 1.85-1.95 (4H, m), 1.77-1.82 (2H, m), 1.31-1.41 (2H, m), 1.27 (6H, d, J = 6.8 Hz); LCMS: 100.0%, MS (ESI): m/z 486.4 [M + H]+ |

TABLE 11-continued

Summarized compounds 1-279 in terms of their structures and corresponding characteristics.

| # cpds | Structure | Characterization Data |
|---|---|---|
| 110 | 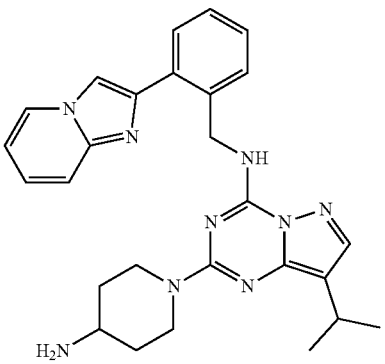 [SMILES: CC(C)c1cnn2c(NCc3ccccc3-c3cn4ccccc4n3)nc(N3CCC(N)CC3)nc12] | white powder; $^1$H-NMR (CDCl$_3$, 400 MHz): δ 8.92 (1H, t, J = 6.2 Hz), 8.16 (1H, d, J = 6.4 Hz), 7.76-7.79 (2H, m), 7.60-7.62 (3H, m), 7.31-7.33 (2H, m), 7.24-7.26 (1H, m), 6.82-6.87 (1H, m), 4.85-4.91 (4H, m), 2.98-3.08 (4H, m), 2.00-2.03 (2H, m), 1.47-1.52 (2H, m), 1.27 (6H, d, J = 6.8 Hz); LCMS: 100.0%, MS (ESI): m/z 482.3 [M + H]+ |
| 111 | 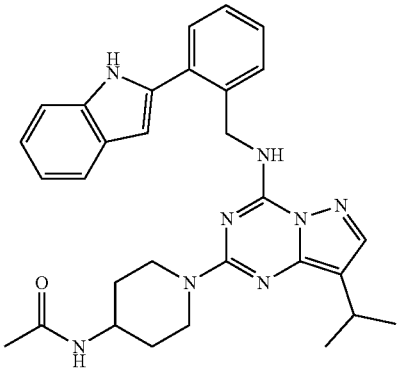 [SMILES: CC(=O)NC1CCN(c2nc(NCc3ccccc3-c3cc4ccccc4[nH]3)n3ncc(C(C)C)c3n2)CC1] | white powder; $^1$H-NMR (DMSO-d6, 400 MHz): δ 8.49 (1H, brs), 7.59-7.68 (2H, m), 7.48-7.57 (2H, m), 7.30-7.43 (3H, m), 7.11-7.24 (2H, m), 6.55-6.64 (2H, m), 5.26 (1H, d, J = 7.6 Hz), 4.85 (2H, d, J = 5.6 Hz), 4.50-4.60 (2H, m), 3.90-4.04 (1H, m), 2.86-3.08 (3H, m), 1.97 (3H, s), 1.88 (2H, d, J = 11.2 Hz), 1.20-1.31 (8H, d, J = 6.84 Hz); LCMS: 95.8%, MS (ESI): m/z 545.1 [M + Na]+ |
| 112 | 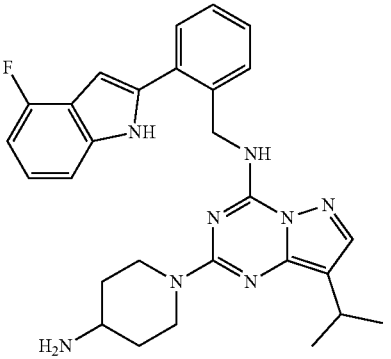 [SMILES: CC(C)c1cnn2c(NCc3ccccc3-c3cc4c(F)cccc4[nH]3)nc(N3CCC(N)CC3)nc12] | white powder; $^1$H-NMR (CDCl$_3$, 400 MHz); δ 8.71 (1H, brs), 7.60 (1H, s), 7.50-7.54 (2H, m), 7.37-7.39 (2H, m), 7.09-7.10 (2H, m), 6.78-6.83 (1H, m), 6.68 (1H, d, J = 2.0 Hz), 6.55-6.58 (1H, m), 4.86 (2H, d, J = 4.8 Hz), 4.55-4.62 (2H, m), 3.00-3.03 (1H, m), 2.82-2.88 (3H, m), 1.78-1.81 (2H, m), 1.22-1.30 (8H, m); LCMS: 100%, MS (ESI): m/z 499.4 [M + H]+ |
| 113 | 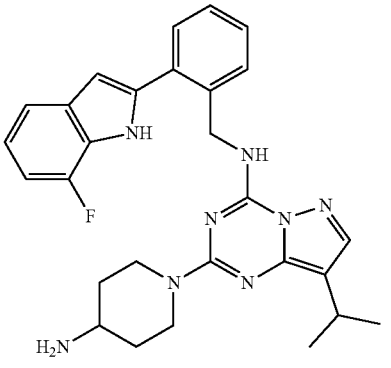 [SMILES: CC(C)c1cnn2c(NCc3ccccc3-c3cc4cccc(F)c4[nH]3)nc(N3CCC(N)CC3)nc12] | white powder; $^1$H-NMR (CDCl$_3$, 400 MHz): δ 8.92 (1H, brs), 7.58 (1H, s), 7.48-7.53 (2H, m), 7.35-7.38 (3H, m), 6.99-7.05 (1H, m), 6.87-6.92 (1H, m), 6.60-6.63 (2H, m), 4.83 (2H, d, J = 5.2 Hz), 4.60-4.65 (2H, m), 2.96-3.03 (2H, m), 2.81-2.87 (2H, m), 1.85-1.90 (2H, m), 1.33-1.41 (2H, m), 1.26 (6H, d, J = 6.8 Hz); LCMS: 97.0%, MS (ESI): m/z 499.2 [M + H]+ |

TABLE 11-continued

Summarized compounds 1-279 in terms of their structures and corresponding characteristics.

| # cpds | Structure | Characterization Data |
|---|---|---|
| 114 | 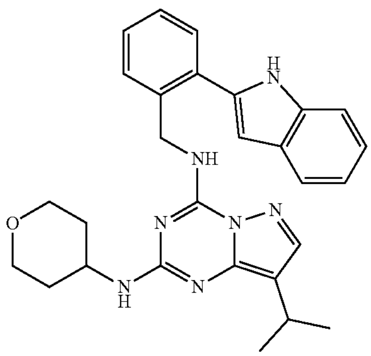 [SMILES: CC(C)c1cnn2c(NCc3ccccc3-c3cc4ccccc4[nH]3)nc(NC3CCOCC3)nc12] | white powder; ¹H-NMR (CDCl₃, 400 MHz): δ 7.66-7.69 (2H, m), 7.57-7.59 (1H, m), 7.52-7.54 (1H, m), 7.38-7.44 (3H, m), 7.24-7.25 (1H, m), 7.16-7.20 (1H, m), 6.89-6.91 (1H, m), 6.66 (1H, s), 4.85 (2H, d, J = 6.0 Hz), 4.76-4.81 (1H, m), 3.94-4.05 (3H, m), 3.44-3.51 (2H, m), 3.01-3.08 (1H, m), 2.00-2.06 (2H, m), 1.45-1.55 (2H, m), 1.30 (6H, d, J = 6.8 Hz); LCMS: 100.0%, MS (ESI): m/z 482.3 [M + H]+ |
| 115 | 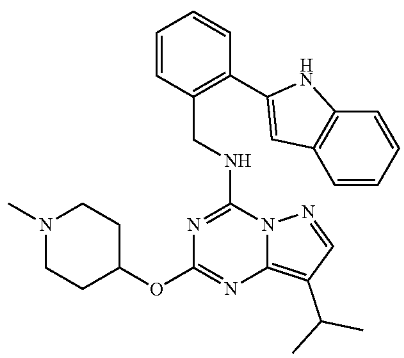 [SMILES: CC(C)c1cnn2c(NCc3ccccc3-c3cc4ccccc4[nH]3)nc(OC3CCN(C)CC3)nc12] | white powder; ¹H-NMR (DMSO-d6, 400 MHz): δ 11.53 (1H, brs), 7.76 (1H, s), 7.66 (1H, d, J = 8.0 Hz), 7.56-7.60 (2H, m), 7.48-7.51 (1H, m), 7.32-7.39 (2H, m), 7.30 (1H, t, J = 6.8 Hz), 7.21 (1H, t, J = 7.2 Hz), 7.13 (1H, t, J = 7.2 Hz), 6.59 (1H, d, J = 1.6 Hz), 5.08-5.12 (1H, m), 4.85 (2H, d, J = 6.8 Hz), 3.03-3.10 (1H, m), 2.76-2.80 (2H, m), 2.34-2.40 (2H, m), 2.33 (3H, s), 2.17-2.21 (2H, m), 1.96-2.03 (2H, m), 1.31 (6H, d, J = 6.8 Hz); LCMS: 100%, MS (ESI): m/z 518.3 [M + Na]+ |
| 116 | 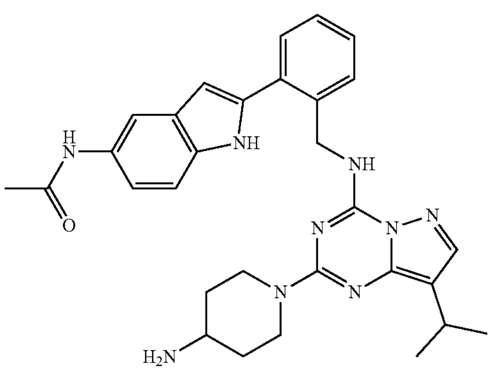 [SMILES: CC(=O)Nc1ccc2[nH]c(-c3ccccc3CNc3nc(N4CCC(N)CC4)nc4c(C(C)C)cnn34)cc2c1] | white powder; ¹H-NMR (DMSO-d6, 400 MHz): δ 8.48 (1H, brs), 7.78 (1H, s), 7.45-7.65 (3H, m), 7.33-7.43 (3H, m), 7.15-7.25 (2H, m), 6.45-6.60 (2H, m), 4.83 (2H, s), 4.55-4.65 (2H, m), 2.96-3.10 (1H, m), 2.75-2.90 (3H, m), 2.19 (3H, s), 1.70-1.85 (2H, m), 1.29 (6H, d, J = 6.8 Hz), 1.10-1.25 (2H, m); LCMS: 100%, MS (ESI): m/z 538.4 [M + H]+ |
| 117 | 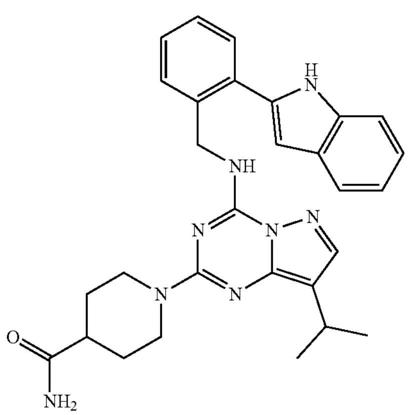 [SMILES: CC(C)c1cnn2c(NCc3ccccc3-c3cc4ccccc4[nH]3)nc(N3CCC(C(N)=O)CC3)nc12] | white powder; ¹H-NMR (CDCl₃, 400 MHz): δ 8.55 (1H, brs), 7.63 (1H, d, J = 9.6 Hz), 7.62 (1H, s), 7.52-7.54 (2H, m), 7.36-7.40 (3H, m), 7.22 (1H, t, J = 7.6 Hz), 7.15 (1H, t, J = 7.6 Hz), 6.63-6.65 (2H, m), 5.33-5.42 (2H, m), 4.88 (2H, d, J = 6.0 Hz), 4.70-4.74 (2H, m), 3.04-3.06 (1H, m), 2.80-2.87 (2H, m), 2.32-2.36 (1H, m), 1.83-1.86 (2H, m), 1.59-1.66 (2H, m), 1.27-1.31 (8H, m); LCMS: 100.0%, MS (ESI): m/z 531.3 [M + Na]+ |

TABLE 11-continued

Summarized compounds 1-279 in terms of their structures and corresponding characteristics.

| # cpds | Structure | Characterization Data |
|---|---|---|
| 118 | 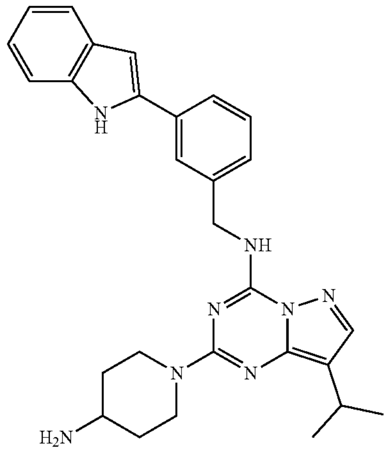 [SMILES: CC(C)c1cnn2c(NCc3cccc(-c4cc5ccccc5[nH]4)c3)nc(N3CCC(N)CC3)nc12] | white powder; ¹H-NMR (CDCl₃, 400 MHz): δ 8.52 (1H, brs), 7.59-7.66 (4H, m), 7.38-7.42 (2H, m), 7.29-7.31 (1H, m), 7.20 (1H, t, J = 7.8 Hz), 7.13 (1H, t, J = 7.4 Hz), 6.82 (1H, s), 6.75 (1H, t, J = 5.8 Hz), 4.73-4.79 (4H, m), 3.02-3.08 (1H, m), 2.87-2.98 (3H, m), 1.84-1.87 (2H, m), 1.23-1.32 (8H, m); LCMS: 99.3%, MS (ESI): m/z 481.3 [M + H]+ |
| 119 | 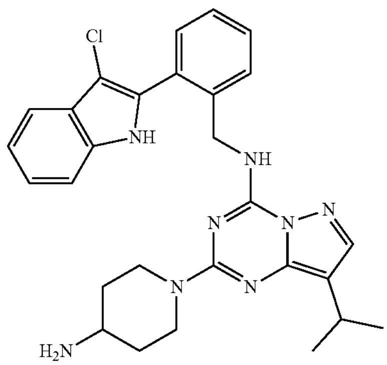 [SMILES: CC(C)c1cnn2c(NCc3ccccc3-c3[nH]c4ccccc4c3Cl)nc(N3CCC(N)CC3)nc12] | white powder; ¹H-NMR (CDCl₃, 400 MHz): δ 8.68 (1H, brs), 7.61-7.63 (1H, m), 7.55-7.57 (2H, m), 7.39-7.43 (3H, m), 7.21-7.26 (3H, m), 6.58 (1H, brs), 4.73 (2H, d, J = 4.8 Hz), 4.56-4.60 (2H, m), 2.97-3.00 (2H, m), 2.76-2.82 (2H, m), 1.84-1.86 (2H, m), 1.25-1.44 (8H, m): LCMS: 100%, MS (ESI): m/z 515.2 [M + H]+ |
| 120 | 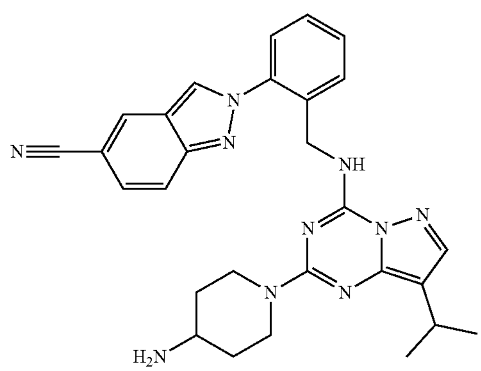 [SMILES: CC(C)c1cnn2c(NCc3ccccc3-n3cc4cc(C#N)ccc4n3)nc(N3CCC(N)CC3)nc12] | white powder; ¹H-NMR (CDCl₃, 400 MHz): δ 8.36 (1H, s), 8.21 (1H, s), 7.92 (1H, d, J = 8.8 Hz), 7.71-7.73 (1H, m), 7.62 (1H, s), 7.45-7.53 (4H, m), 7.30-7.40 (1H, m), 4.68-4.76 (4H, m), 2.91-3.04 (4H, m), 1.92-1.95 (2H, m), 1.35-1.39 (2H, m), 1.28 (6H, d, J = 6.8 Hz); LCMS: 95.5%, MS (ESI): m/z 507.2 [M + H]+ |
| 121 | 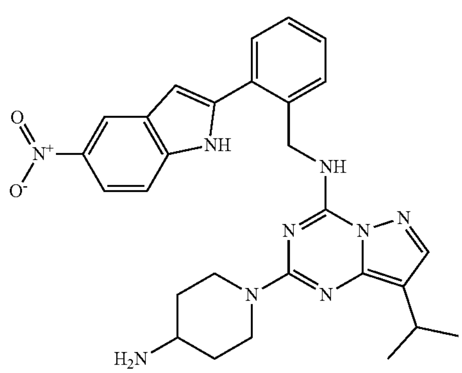 [SMILES: CC(C)c1cnn2c(NCc3ccccc3-c3cc4cc([N+](=O)[O-])ccc4[nH]3)nc(N3CCC(N)CC3)nc12] | white powder; ¹H-NMR (CDCl₃, 400 MHz): δ 9.19 (1H, brs), 8.58 (1H, d, J = 2.0 Hz), 8.10 (1H, dd, J = 8.8 Hz, 2.4 Hz), 7.60 (1H, s), 7.52-7.58 (2H, m), 7.43-7.46 (2H, m), 7.31 (1H, d, J = 8.8 Hz), 6.76 (1H, d, J = 0.8 Hz), 6.55 (1H, t, J = 5.2 Hz), 4.82 (2H, d, J = 5.2 Hz), 4.55-4.58 (2H, m), 2.98-3.03 (1H, m), 2.81-2.91 (3H, m), 1.78-1.82 (2H, m), 1.29 (6H, d, J = 6.8 Hz), 1.21-1.26 (2H, m); LCMS: 99.2%, MS (ESI): m/z 526.3 [M + H]+ |

TABLE 11-continued

Summarized compounds 1-279 in terms of their structures and corresponding characteristics.

| # cpds | Structure | Characterization Data |
|---|---|---|
| 122 | 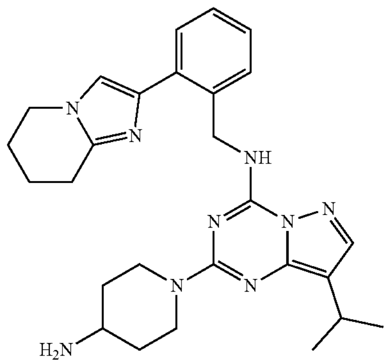 [SMILES: CC(C)c1cnn2c(NCc3ccccc3-c3cn4c(n3)CCCC4)nc(N3CCC(N)CC3)nc12] | white powder; $^1$H-NMR (CDCl$_3$, 400 MHz): δ 8.94 (1H, t, J = 6.0 Hz), 7.59 (1H, s), 7.51 (1H, d, J = 6.4 Hz), 7.46 (1H, d, J = 6.8 Hz), 7.18-7.25 (2H, m), 6.95 (1H, s), 4.82-4.87 (4H, m), 4.01 (2H, t, J = 5.6 Hz), 2.96-3.04 (6H, m), 1.94-2.04 (6H, m), 1.35-1.45 (2H, m), 1.26 (6H, d, J = 6.8 Hz); LCMS: 100%, MS (ESI): m/z 486.3 [M + H]+ |
| 123 | 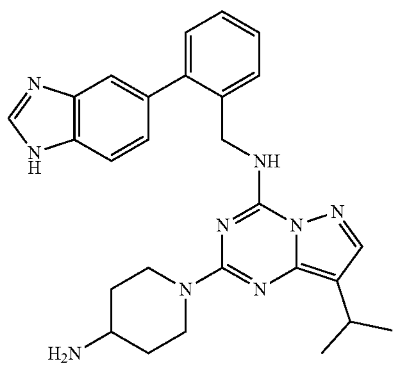 [SMILES: CC(C)c1cnn2c(NCc3ccccc3-c3ccc4[nH]cnc4c3)nc(N3CCC(N)CC3)nc12] | Pink powder; $^1$H-NMR (CDCl$_3$, 400 MHz): δ 8.15 (1H, s), 7.59 (1H, d, J = 8.0 Hz), 7.52-7.54 (2H, m), 7.47-7.48 (1H, m), 7.27-7.31 (3H, m), 7.10-7.20 (1H, m), 6.61 (1H, brs), 4.65-4.70 (2H, m), 4.56-4.59 (2H, m), 2.95-3.01 (2H, m), 2.75-2.81 (2H, m), 1.83-1.85 (2H, m), 1.20-1.32 (8H, m); LCMS: 97.6%, MS (ESI): m/z 482.2 [M + H]+ |
| 124 | 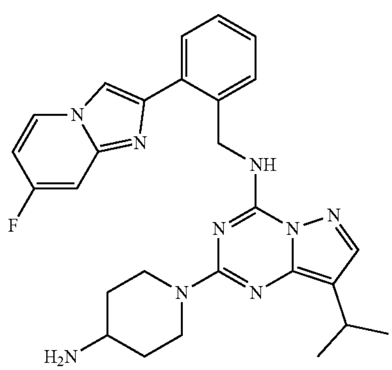 [SMILES: CC(C)c1cnn2c(NCc3ccccc3-c3cn4ccc(F)cc4n3)nc(N3CCC(N)CC3)nc12] | white powder; $^1$H-NMR (DMSO-d6, 400 MHz): δ 9.06 (1H, brs), 8.65-8.75 (1H, m), 8.33 (1H, s), 7.75 (1H, d, J = 8.0 Hz), 7.71 (1H, s), 7.46-7.52 (2H, m), 7.30-7.37 (2H, m), 7.06 (1H, td, J = 7.6, 2.8 Hz), 4.93 (2H, s), 4.42-4.45 (2H, m), 2.82-2.91 (4H, m), 1.69-1.72 (2H, m), 1.21 (6H, d, J = 6.8 Hz), 1.12-1.14 (2 H, m); LCMS: 98.6%, MS (ESI): m/z 522.2 [M + Na]+ |
| 125 | 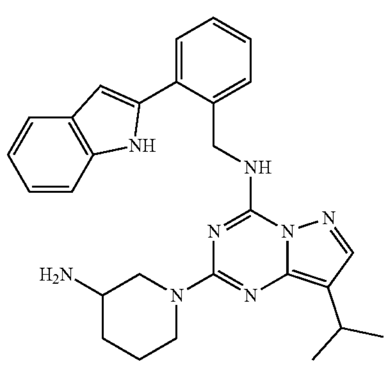 [SMILES: CC(C)c1cnn2c(NCc3ccccc3-c3cc4ccccc4[nH]3)nc(N3CCCC(N)C3)nc12] | Racemic mixture; white powder; $^1$H-NMR (DMSO-d6, 400 MHz): δ 8.91 (1 H, t, J = 5.6 Hz), 7.75 (1H, s), 7.58 (1H, d, J = 7.6 Hz), 7.52-7.56 (1H, m), 7.44-7.51 (2H, m), 7.30-7.37 (2H, m), 7.09-7.15 (1H, m), 7.00-7.05 (1H, m), 6.59 (1H, s), 4.78-4.89 (2H, m), 4.00-4.30 (2H, m), 3.35-3.45 (2H, m), 2.80-2.95 (1H, m), 2.30-2.35 (1H, m), 1.70-1.80 (1H, m), 1.40-1.50 (1H, m), 1.21 (6H, d, J = 7.2 Hz), 1.05-1.15 (2H, m); LCMS: 100%, MS (ESI): m/z = 481.2 [M + H]+ |

TABLE 11-continued

Summarized compounds 1-279 in terms of their structures and corresponding characteristics.

| # cpds | Structure | Characterization Data |
| --- | --- | --- |
| 126 | 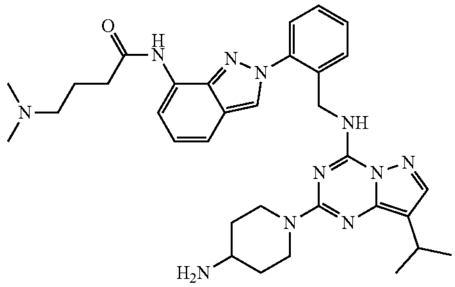 [SMILES: CC(C)c1cnn2c(NCc3ccccc3-n3cc4cccc(NC(=O)CCCN(C)C)c4n3)nc(N3CCC(N)CC3)nc12] | white powder; $^1$H-NMR (CDCl$_3$, 400 MHz): δ 8.84 (1H, brs), 8.66 (1H, t, J = 6.4 Hz), 8.37 (1H, d, J = 8.0 Hz), 8.25 (1H, s), 7.71-7.73 (1H, m), 7.67 (1H, s), 7.45-7.47 (4H, m), 7.19 (1H, t, J = 8.0 Hz), 7.82-7.86 (2H, m), 4.58 (2H, d, J = 6.4 Hz), 2.94-3.07 (4H, m), 2.69 (2H, t, J = 7.4 Hz), 2.34-2.37 (2H, m), 1.93-1.97 (4H, m), 1.35-1.41 (2H, m), 8.66 (6H, d, J = 7.2 Hz); LCMS: 100.0%, MS (ESI): m/z 610.4 [M + H]+ |
| 127 | 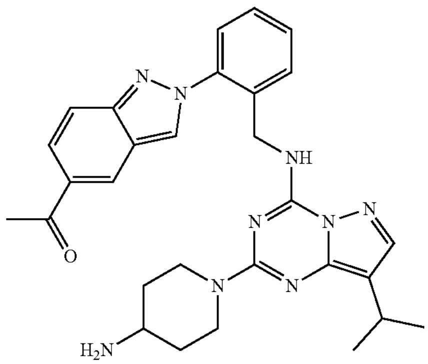 [SMILES: CC(=O)c1ccc2nn(-c3ccccc3CNc3nc(N4CCC(N)CC4)nc4c(C(C)C)cnn34)cc2c1] | white powder; $^1$H-NMR (CDCl$_3$, 400 MHz): δ 8.86 (1H, s), 8.38 (1H, s), 7.98-8.01 (1H, m), 7.88 (1H, d, J = 8.8 Hz), 7.72-7.74 (1H, m), 7.64 (1H, s), 7.44-7.48 (4H, m), 4.69-4.75 (4H, m), 2.89-3.06 (4H, m), 2.70 (3H, s), 1.85-1.91 (2H, m), 1.28-1.35 (8H, m); LCMS: 100%, MS (ESI): m/z 524.3 [M + H]+ |
| 128 | 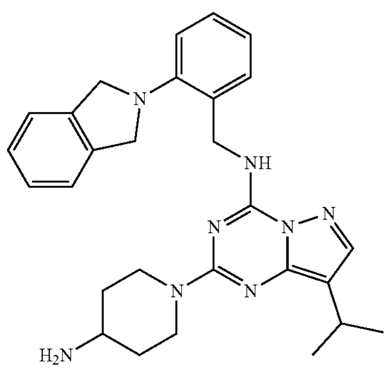 [SMILES: CC(C)c1cnn2c(NCc3ccccc3N3Cc4ccccc4C3)nc(N3CCC(N)CC3)nc12] | white powder; $^1$H-NMR (CDCl$_3$, 400 MHz): δ 7.57 (1H, s), 7.38 (2H, d, J = 7.6 Hz), 7.25-7.30 (5H, m), 7.21 (1H, d, J = 8.0 Hz), 7.01 (1H, t, J = 7.2 Hz), 6.75-6.82 (1H, m), 4.87 (2H, d, J = 5.2 Hz), 4.70-4.80 (1H, m), 4.62 (4H, s), 2.87-3.06 (4H, m), 1.85-1.94 (2H, m), 1.23-1.38 (8H, m); LCMS: 99.7%, MS (ESI): m/z = 483.3 [M + H]+ |
| 129 | 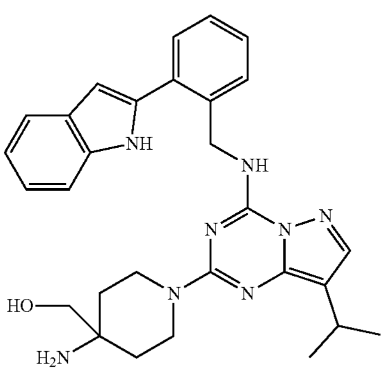 [SMILES: CC(C)c1cnn2c(NCc3ccccc3-c3cc4ccccc4[nH]3)nc(N3CCC(N)(CO)CC3)nc12] | white powder; $^1$H-NMR (CDCl$_3$, 400 MHz): δ 8.84 (1H, brs), 7.62-7.65 (2H, m), 7.51-7.53 (2H, m), 7.35-7.38 (3H, m), 7.21 (1H, t, J = 7.4 Hz), 7.14 (1H, t, J = 7.4 Hz), 6.61-6.64 (2H, m), 4.86 (2H, d, J = 6.4 Hz), 3.99-4.03 (2H, m), 3.49-3.54 (2H, m), 3.40 (2H, s), 2.99-3.05 (1H, m), 2.19-2.24 (2H, m), 1.43-1.45 (2H, m), 1.29 (6H, d, J = 6.8 Hz); LCMS: 98.3%, MS (ESI): m/z 511.2 [M + H]+ |

TABLE 11-continued

Summarized compounds 1-279 in terms of their structures and corresponding characteristics.

| # cpds | Structure | Characterization Data |
|---|---|---|
| 130 | 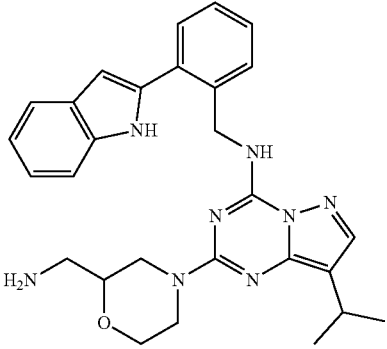 [SMILES: CC(C)c1cnn2c(NCc3ccccc3-c3cc4ccccc4[nH]3)nc(N3CCOC(CN)C3)nc12] | Racemic mixture; white powder; $^1$H-NMR (DMSO-d6, 400 MHz): δ 9.17 (1H, brs), 7.61-7.63 (2H, m), 7.49-7.52 (2H, m), 7.34-7.39 (3H, m), 7.20 (1H, t, J = 7.2 Hz), 7.12 (1H, t, J = 7.2 Hz), 6.69 (1H, brs), 6.56 (1H, s), 4.88 (2H, s), 4.33-4.36 (2H, m), 3.82-3.85 (2H, m), 3.05-3.50 (2H, m), 2.88-3.03 (1H, m), 2.80-2.84 (3H, m), 2.58-2.64 (1H, m), 1.27 (6H, d, J = 6.8 Hz); LCMS: 1005, MS (ESI): m/z 497.2 [M + H]+. |
| 131 | 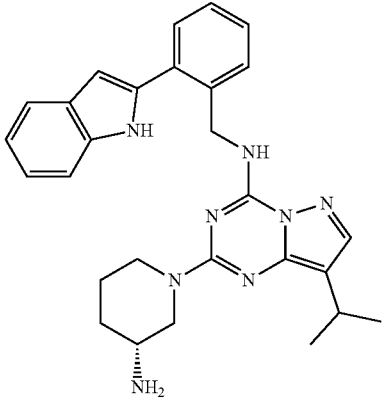 [SMILES: CC(C)c1cnn2c(NCc3ccccc3-c3cc4ccccc4[nH]3)nc(N3CCC[C@@H](N)C3)nc12] | (3R); white powder; $^1$H-NMR (CDCl$_3$, 400 MHz): δ 10.45 (1H, brs), 7.65 (1H, d, J = 7.2 Hz), 7.62 (1H, s), 7.46-7.53 (2H, m), 7.40 (1H, d, J = 7.6 Hz), 7.29-7.35 (2H, m), 7.20 (1H, t, J = 7.6 Hz), 7.12 (1H, t, J = 7.6 Hz), 6.89 (1H, brs), 6.53 (1H, s), 4.75-5.01 (2H, m), 4.20-4.35 (2H, m), 2.83-3.06 (2H, m), 2.45-2.65 (2H, m), 1.58-1.70 (2H, m), 1.24-1.29 (8H, m); LCMS: 100%, MS (ESI): m/z 481.3 [M + H]+ |
| 132 | 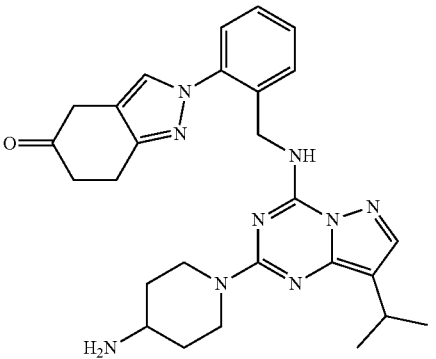 [SMILES: CC(C)c1cnn2c(NCc3ccccc3-n3cc4c(n3)CCC(=O)C4)nc(N3CCC(N)CC3)nc12] | White powder; $^1$H NMR (CDCl$_3$, 400 MHz): δ 7.54-7.59 (2H, m), 7.47-7.52 (2H, m), 7.32-7.38 (2H, m), 7.27-7.29 (1H, m), 4.80-4.84 (2H, m), 4.69-4.72 (2H, m), 3.50 (2H, s), 3.15-3.21 (3H, m), 2.93-3.02 (3H, m), 2.76 (2H, t, J = 7.0 Hz), 2.02-2.07 (2H, m), 1.24-1.28 (8H, m); LCMS: 100%, MS (ESI): m/z 500.2 [M + H]$^+$ |
| 133 | 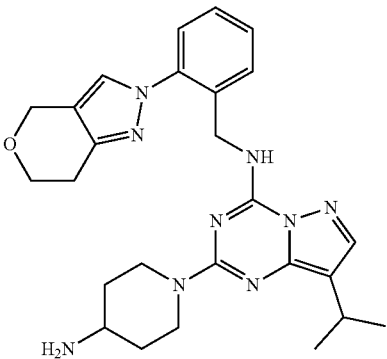 [SMILES: CC(C)c1cnn2c(NCc3ccccc3-n3cc4c(n3)CCOC4)nc(N3CCC(N)CC3)nc12] | White powder; $^1$H-NMR (CDCl$_3$, 400 MHz): δ 7.57-7.63 (2H, m), 7.51 (1H, t, J = 6.4 Hz), 7.40 (1H, s), 7.30-7.40 (2H, m), 7.27-7.30 (1H, m), 4.75-4.83 (4H, m), 4.71 (2H, d, J = 6.4 Hz), 4.02 (2H, t, J = 5.2 Hz), 2.92-3.06 (6H, m), 1.93-2.00 (2H, m), 1.31-1.44 (2 H, m), 1.27 (6H, d, J = 6.8 Hz); LCMS: 100%, MS (ESI): m/z 488.2 [M + H]$^+$ |

TABLE 11-continued

Summarized compounds 1-279 in terms of their structures and corresponding characteristics.

| # cpds | Structure | Characterization Data |
|---|---|---|
| 134 | 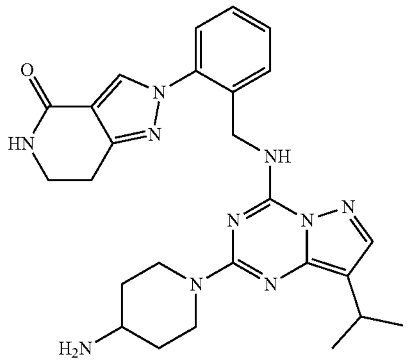 [SMILES: CC(C)c1cnn2c(NCc3ccccc3-n3cc4c(n3)CCNC4=O)nc(N3CCC(N)CC3)nc12] | White powder; ¹H-NMR (CDCl₃, 400 MHz): δ 8.15 (1H, s), 7.63-7.65 (1H, m), 7.61 (1H, s), 7.39-7.42 (3H, m), 7.31-7.34 (1H, m), 5.95-6.03 (1H, m), 4.68-4.82 (4H, m), 3.65 (2H, t, J = 7.8 Hz), 2.93-3.10 (6H, m), 1.93-1.99 (2H, m), 1.32-1.42 (2H, m), 1.27 (6H, d, J = 6.8 Hz); LCMS: 98.2%, MS (ESI): m/z 523.3 [M + Na]⁺ |
| 135 | 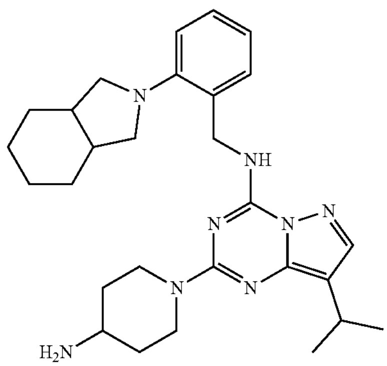 [SMILES: CC(C)c1cnn2c(NCc3ccccc3N3CC4CCCCC4C3)nc(N3CCC(N)CC3)nc12] | White powder; ¹H-NMR (CDCl₃, 400 MHz): δ 7.57 (1H, s), 7.23-7.28 (1H, m), 7.16-7.22 (1H, m), 6.93 (1H, d, J = 7.6 Hz), 6.75-6.84 (2H, m), 4.73-4.81 (4H, m), 3.28-3.36 (2H, m), 3.19-3.26 (2H, m), 2.86-3.08 (4H, m), 2.23-2.33 (2H, m), 1.84-1.94 (2H, m), 1.51-1.64 (4H, m), 1.39-1.46 (2H, m), 1.23-1.38 (10H, m); LCMS: 1005, MS (ESI): m/z = 489.3 [M + H]⁺ |
| 136 | 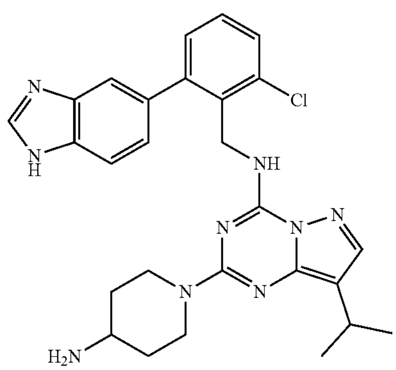 [SMILES: CC(C)c1cnn2c(NCc3c(Cl)cccc3-c3ccc4[nH]cnc4c3)nc(N3CCC(N)CC3)nc12] | White powder; ¹H-NMR (CDCl₃, 400 MHz): δ 8.10 (1H, s), 7.63 (1H, d, J = 8.0 Hz), 7.59 (1H, s), 7.51 (1H, s), 7.46 (1H, dd, J = 8.0, 1.2 Hz), 7.29-7.35 (1H, m), 7.27 (1H, d, J = 1.6 Hz), 7.15-7.20 (1H, m), 6.41-6.51 (1H, m), 4.81 (2H, d, J = 5.2 Hz), 4.38-4.42 (2H, m), 2.95-3.05 (1H, m), 2.80-2.90 (1H, m), 2.60-2.70 (2H, m), 1.68-1.75 (2H, m), 1.27 (6H, d, J = 7.2 Hz), 1.10-1.22 (2 H, m); LCMS: 100%, MS (ESI): m/z 516.2 [M + H]⁺ |
| 137 | 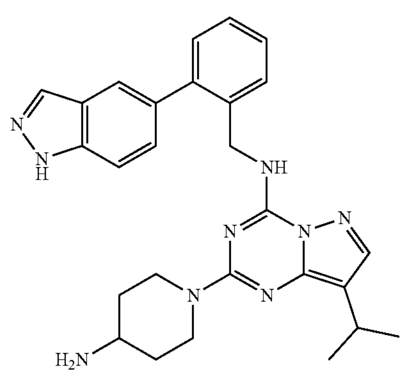 [SMILES: CC(C)c1cnn2c(NCc3ccccc3-c3ccc4[nH]ncc4c3)nc(N3CCC(N)CC3)nc12] | White powder; ¹H-NMR (CDCl₃, 400 MHz): δ 7.96 (1H, s), 7.59-7.61 (2H, m), 7.50-7.52 (1H, m), 7.46-7.48 (1H, m), 7.32-7.41 (3H, m), 7.28-7.30 (1H, m), 6.39 (1H, t, J = 5.6 Hz), 4.63 (2H, d, J = 5.2 Hz), 4.53-4.56 (2H, m), 2.98-3.05 (2H, m), 2.72-2.78 (2H, m), 1.82-1.84 (2H, m), 1.18-1.29 (8H, m); LCMS: 100%, MS (ESI): m/z 482.3 [M + H]⁺ |

TABLE 11-continued

Summarized compounds 1-279 in terms of their structures and corresponding characteristics.

| # cpds | Structure | Characterization Data |
| --- | --- | --- |
| 138 | 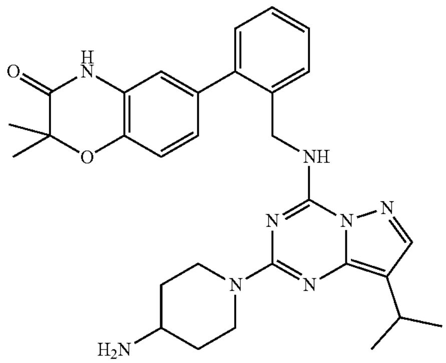 [SMILES: CC(C)c1cnn2c(NCc3ccccc3-c3ccc4c(c3)NC(=O)C(C)(C)O4)nc(N3CCC(N)CC3)nc12] | Yellow powder; $^1$H-NMR (CDCl$_3$, 400 MHz): δ 7.58 (1H, s), 7.48-7.51 (1H, m), 7.33-7.35 (2H, m), 7.24-7.26 (1H, m), 6.91-6.98 (2H, m), 6.70 (1H, s), 6.37 (1H, t, J = 5.2 Hz), 4.66-4.69 (4H, m), 2.88-3.03 (1H, m), 2.89-2.95 (3H, m), 1.85-1.89 (2H, m), 1.55 (6H, s), 1.24-1.34 (8H, m); LCMS: 100%, MS (ESI): m/z 541.3 [M + H]$^+$ |
| 139 | 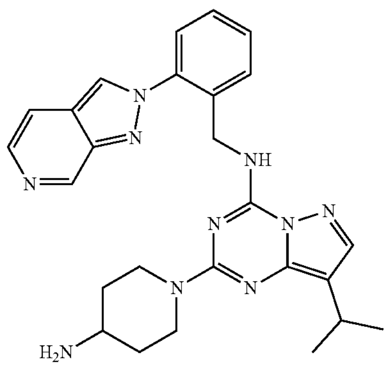 [SMILES: CC(C)c1cnn2c(NCc3ccccc3-n3cc4ccncc4n3)nc(N3CCC(N)CC3)nc12] | white powder; $^1$H-NMR (CDCl$_3$, 400 MHz): δ 9.43 (1H, s), 8.25-8.26 (2H, m), 7.73 (1H, d, J = 6.4 Hz), 7.63 (1H, s), 7.57-7.59 (1H, m), 7.48-7.53 (3H, m), 7.32 (1H, t, J = 6.2 Hz), 4.68-4.73 (4H, m), 2.0-3.04 (4H, m), 1.90-1.93 (2H, m), 1.28-1.37 (8H, m); LCMS: 97.6%, MS (ESI): m/z 483.1 [M + H]$^+$ |
| 140 | 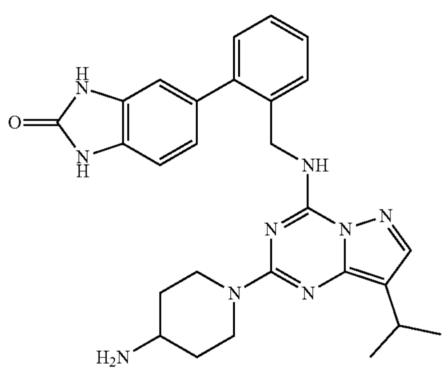 [SMILES: CC(C)c1cnn2c(NCc3ccccc3-c3ccc4[nH]c(=O)[nH]c4c3)nc(N3CCC(N)CC3)nc12] | white powder; $^1$H-NMR (DMSO-d6, 400 MHz): δ 8.81 (1H, brs), 7.72 (1H, s), 7.38-7.46 (1H, m), 7.25-7.32 (2H, m), 7.18-7.24 (1H, m), 6.96-7.01 (1H, m), 6.86-6.94 (2H, m), 4.59 (2H, s), 4.18-4.32 (2H, m), 2.84-2.96 (1H, m), 2.65-2.81 (3H, m), 1.60-1.72 (2H, m), 1.21 (6H, d, J = 7.2 Hz), 0.94-1.09 (2H, m); LCMS: 99.1%, MS (ESI): m/z 498.1 [M + H]$^+$ |
| 141 | 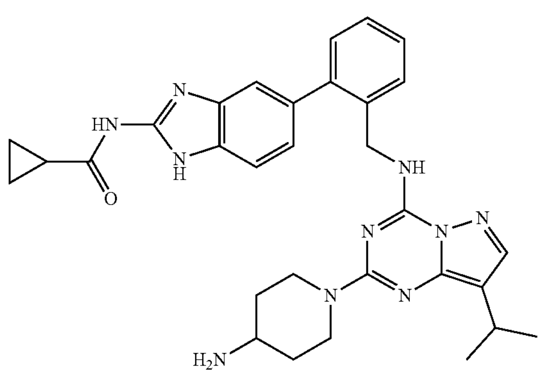 [SMILES: CC(C)c1cnn2c(NCc3ccccc3-c3ccc4[nH]c(NC(=O)C5CC5)nc4c3)nc(N3CCC(N)CC3)nc12] | white powder; $^1$H-NMR (DMSO-d6, 400 MHz): δ 8.79 (1H, brs), 7.71 (1H, brs), 7.37-7.51 (3H, m), 7.27-7.31 (3H, m), 7.08 (1H, d, J = 7.6 Hz), 4.61 (2H, s), 4.20-4.25 (2H, m), 2.82-2.95 (1H, m), 2.63-2.79 (3H, m), 1.97-2.10 (1H, m), 1.55-1.65 (2H, m), 1.21 (2H, d, J = 7.2 Hz), 0.86-1.15 (6H, m); LCMS: 100%, MS (ESI): m/z 565.2 [M + H]$^+$ |

TABLE 11-continued

Summarized compounds 1-279 in terms of their structures and corresponding characteristics.

| # cpds | Structure | Characterization Data |
|---|---|---|
| 142 | 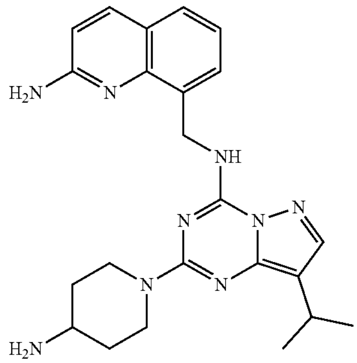 [SMILES: CC(C)c1cnn2c(NCc3cccc4ccc(N)nc34)nc(N3CCC(N)CC3)nc12] | white powder; $^1$H-NMR (CDCl$_3$, 400 MHz): δ 7.82-7.91 (2H, m), 7.51-7.61 (3H, m), 7.17 (1H, t, J = 7.6 Hz) 6.72 (1H, d, J = 8.4 Hz), 5.13 (2H, d, J = 6.0 Hz), 4.93 (2H, brs), 4.75-4.82 (2H, m), 2.86-3.06 (4H, m), 1.85-1.92 (2H, m), 1.29-1.38 (2H, m), 1.26 (6H, d, J = 6.8 Hz); LCMS: 100%, MS (ESI): m/z 432.2 [M + H]$^+$ |
| 143 | 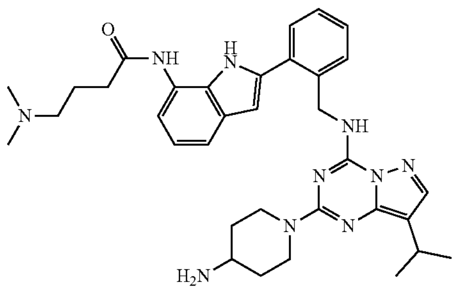 [SMILES: CC(C)c1cnn2c(NCc3ccccc3-c3cc4cccc(NC(=O)CCCN(C)C)c4[nH]3)nc(N3CCC(N)CC3)nc12] | white powder; $^1$H-NMR (DMSO-d6, 400 MHz): δ 11.10 (1H, brs), 9.62 (1H, brs), 8.91 (1H, brs), 7.71 (1H, s), 7.62 (1H, d, J = 7.6 Hz), 7.50-7.57 (2H, m), 7.31-7.42 (3H, m), 6.98 (1H, t, J = 8.0 Hz), 6.62 (1H, s), 4.85 (2H, s), 4.10-4.28 (2H, m), 2.85-2.91 (1H, m), 2.58-2.78 (3H, m), 2.43-2.47 (2H, m), 2.26 (2 H, t, J = 7.2 Hz), 2.12 (6H, s), 1.72-1.80 (2H, m), 1.42-1.52 (2H, m), 1.20 (6H, d, J = 7.2 Hz), 0.81-0.98 (2H, m); LCMS: 100%, MS (ESI): m/z 609.2 [M + H]$^+$ |
| 144 | 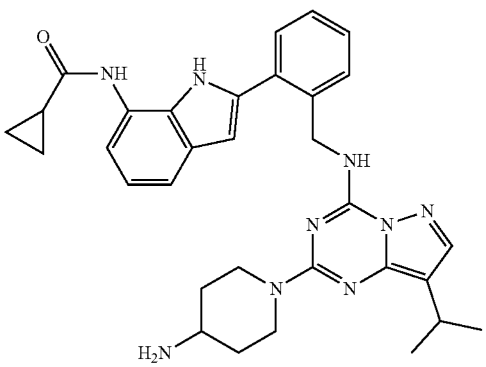 [SMILES: CC(C)c1cnn2c(NCc3ccccc3-c3cc4cccc(NC(=O)C5CC5)c4[nH]3)nc(N3CCC(N)CC3)nc12] | white powder; $^1$H-NMR (DMSO-d6, 400 MHz): δ 11.30 (1H, brs), 10.08 (1H, brs), 8.90 (1H, brs), 7.72 (1H, s), 7.65 (1H, d, J = 7.6 Hz), 7.49-7.61 (2 H, m), 7.30-7.42 (3 H, m), 6.98 (1 H, t, J = 8.0 Hz), 6.62 (1H, s), 4.88 (2H, s), 4.10-4.65 (2H, m), 2.85-2.96 (1H, m), 2.65-2.77 (3H, m), 1.91-2.01 (1H, m), 1.49-1.61 (2H, m), 1.21 (6H, d, J = 6.8 Hz), 0.91-1.01 (2H, m), 0.81-0.90 (4H, m); LCMS: 96.9%, MS (ESI): m/z 564.1 [M + H]$^+$ |
| 145 | 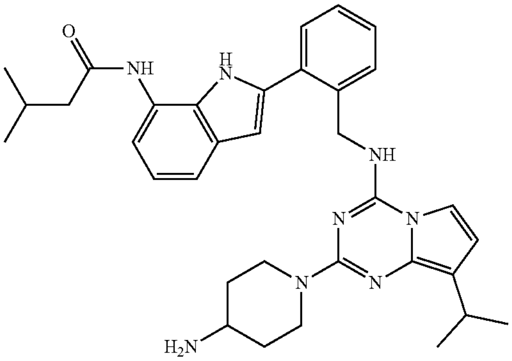 [SMILES: CC(C)CC(=O)Nc1cccc2cc(-c3ccccc3CNc3nc(N4CCC(N)CC4)nc4c(C(C)C)ccn34)[nH]c12] | white powder; $^1$H-NMR (DMSO-d6, 400 MHz): δ 11.17 (1H, brs), 9.68 (1H, s), 8.89 (1H, brs), 7.73 (1H, s), 7.67 (1H, d, J = 7.6 Hz), 7.49-7.60 (2H, m), 7.31-7.43 (3H, m), 6.99 (1H, t, J = 7.6 Hz), 6.62 (1H, s), 4.87 (2H, s), 4.10-4.30 (2H, m), 2.85-2.92 (1H, m), 2.64-2.81 (3H, m), 2.32 (2H, d, J = 7.2 Hz), 2.09-2.20 (1H, m), 1.50-1.62 (2H, m), 1.21 (6H, d, J = 7.2 Hz), 0.95-1.02 (8H, m); LCMS: 97.7%, MS (ESI): m/z 580.1 [M + H]$^+$ |

TABLE 11-continued

Summarized compounds 1-279 in terms of their structures and corresponding characteristics.

| # cpds | Structure | Characterization Data |
|---|---|---|
| 146 | 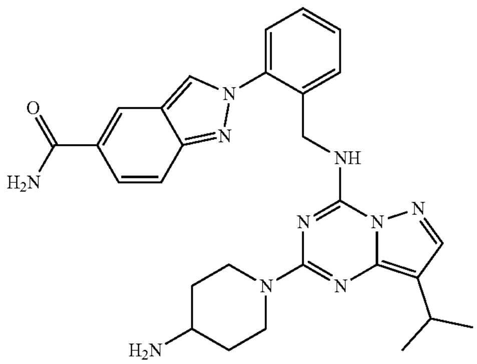 [SMILES: CC(C)c1cnn2c(NCc3ccccc3-n3cc4cc(C(N)=O)ccc4n3)nc(N3CCC(N)CC3)nc12] | white powder; ¹H-NMR (DMSO-d6, 400 MHz): δ 8.95 (1H, s); 8.45 (1H, s), 8.05 (1H, s), 7.81-7.88 (1H, m), 7.70-7.77 (2H, m), 7.58-7.66 (2H, m), 7.46-7.55 (2H, m), 7.35 (1H, s), 4.61 (2H, s), 4.18-4.39 (2H, m), 2.85-2.95 (1H, m), 2.70-2.82 (3H, m), 1.60-1.70 (2H, m), 1.21 (6H, d, J = 6.4 Hz), 0.93-1.10 (2H, m); LCMS: 98.7%, MS (ESI): m/z 525.1 [M + H]⁺ |
| 147 | 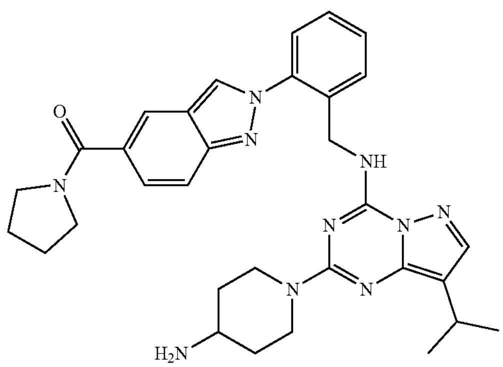 [SMILES: CC(C)c1cnn2c(NCc3ccccc3-n3cc4cc(C(=O)N5CCCC5)ccc4n3)nc(N3CCC(N)CC3)nc12] | white powder; ¹H-NMR (DMSO-d6, 400 MHz): δ 8.83 (1H, s), 8.03 (1H, s), 7.69-7.79 (2H, m), 7.59-7.67 (2H, m), 7.44-7.56 (3H, m), 4.61 (2H, s), 4.15-4.32 (2H, m), 3.45-3.57 (4H, m), 2.83-2.93 (1H, m), 2.66-2.79 (3H, m), 1.81-1.92 (4H, m), 1.55-1.66 (2H, m), 1.20 (6H, d, J = 6.8 Hz) 0.91-1.05 (2H, m); LCMS: 100%, MS (ESI): m/z 579.3 [M + H]⁺ |
| 148 | 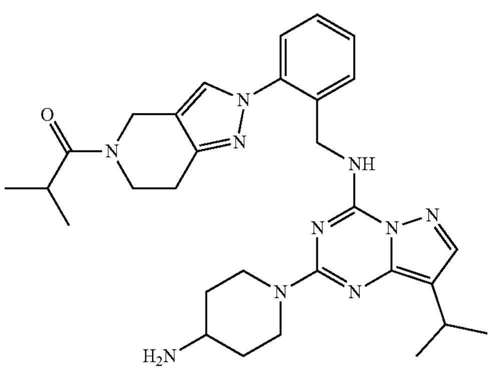 [SMILES: CC(C)C(=O)N1CCc2nn(-c3ccccc3CNc3nc(N4CCC(N)CC4)nc4c(C(C)C)cnn34)cc2C1] | white powder; ¹H-NMR (CDCl₃, 400 MHz): δ 7.56-7.65 (2H, m), 7.43-7.56 (2H, m), 7.26-7.39 (3H, m), 4.56-4.85 (6H, m), 3.82-3.95 (2H, m), 2.85-3.05 (6H, m), 1.85-1.95 (2H, m), 1.23-1.40 (8H, m), 1.13-1.23 (6H, m); LCMS: 100%, MS (ESI): m/z 579.2 [M + Na]⁺ |
| 149 | 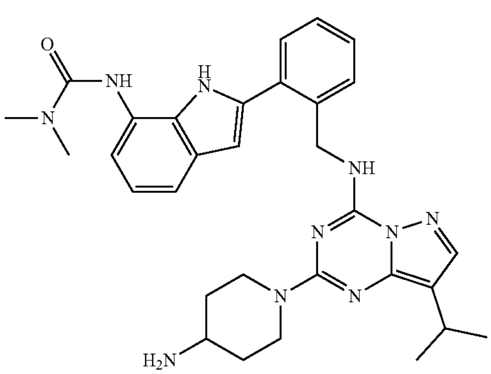 [SMILES: CC(C)c1cnn2c(NCc3ccccc3-c3cc4cccc(NC(=O)N(C)C)c4[nH]3)nc(N3CCC(N)CC3)nc12] | white powder; ¹H-NMR (CDCl₃, 400 MHz): δ 10.30 (1H, brs), 7.53-7.62 (3H, m), 7.42 (1H, d, J = 7.6 Hz), 7.31-7.40 (2H, m), 6.98-7.05 (1H, m), 6.69 (1H, d, J = 7.2 Hz), 6.65 (1 H, brs), 6.58-6.62 (2H, m), 4.89 (2H, d, J = 5.2 Hz), 4.62-4.70 (2H, m), 2.98-3.03 (1H, m), 3.02 (6H, s), 2.81-2.90 (3H, m), 1.75-1.82 (2H, m), 1.29 (8H, d, J = 6.8 Hz); LCMS: 97.1%, MS (ESI): m/z 567.3 [M + H]⁺ |

TABLE 11-continued

Summarized compounds 1-279 in terms of their structures and corresponding characteristics.

| # cpds | Structure | Characterization Data |
| --- | --- | --- |
| 150 | 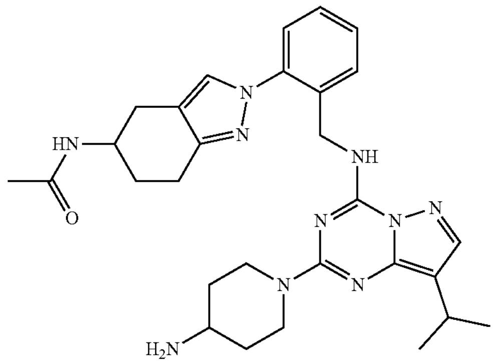 [SMILES: CC(=O)NC1CCc2nn(-c3ccccc3CNc3nc(N4CCC(N)CC4)nc4c(C(C)C)cnn34)cc2C1] | white powder; ¹H-NMR (DMSO-d6, 400 MHz): δ 8.71 (1H, brs), 7.97 (1H, d, J = 5.2 Hz), 7.79 (1H, s), 7.70 (1H, s), 7.44-7.51 (1H, m), 7.28-7.39 (4H, m), 4.56-4.68 (2H, m), 4.26-4.38 (2H, m), 3.88-4.00 (1H, m), 2.75-2.93 (5H, m), 2.68-2.75 (1H, m), 1.90-2.02 (2H, m), 1.84 (3H, s), 1.62-1.78 (4H, m), 1.17-1.24 (9H, m); LCMS: 100%, MS (ESI): m/z 565.2 [M + Na]⁺ |
| 151 | 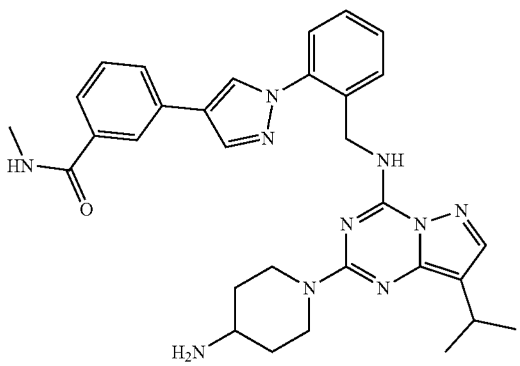 [SMILES: CNC(=O)c1cccc(-c2cnn(-c3ccccc3CNc3nc(N4CCC(N)CC4)nc4c(C(C)C)cnn34)c2)c1] | white powder; ¹H-NMR (CDCl₃, 400 MHz): δ 8.12 (1H, s), 7.99 (1H, s), 7.94 (1H, s), 7.57-7.68 (4H, m), 7.35-7.47 (5H, m), 6.40 (1H, brs), 4.68-4.82 (4H, m), 2.89-3.08 (7H, m), 1.88-1.93 (2H, m), 1.29-1.38 (2H, m), 1.26 (6H, d, J = 7.2 Hz); LCMS: 98.5%, MS (ESI): m/z 565.2 [M + H]⁺ |
| 152 | 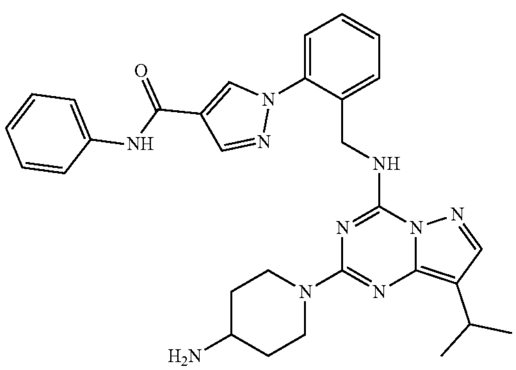 [SMILES: CC(C)c1cnn2c(NCc3ccccc3-n3cc(C(=O)Nc4ccccc4)cn3)nc(N3CCC(N)CC3)nc12] | white powder; ¹H-NMR (CDCl₃, 400 MHz): δ 8.22 (1H, s), 8.15 (1H, s), 7.75 (1H, s), 7.57-7.69 (4H, m), 7.30-7.44 (5H, m), 7.20-7.25 (1H, m), 7.12-7.19 (1H, m), 4.60-4.82 (4H, m), 2.85-3.06 (4H, m), 1.80-1.99 (2H, m), 1.20-1.40 (8H, m); LCMS: 99.5%, MS (ESI): m/z 551. [M + H]⁺ |
| 153 | 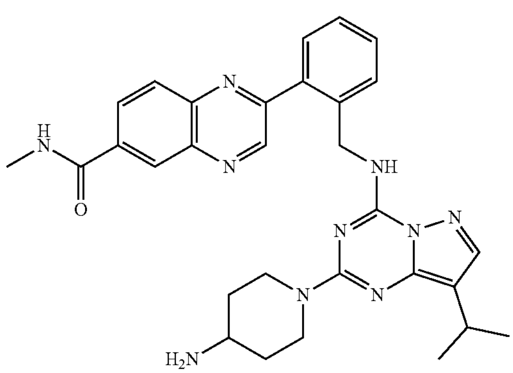 [SMILES: CNC(=O)c1ccc2nc(-c3ccccc3CNc3nc(N4CCC(N)CC4)nc4c(C(C)C)cnn34)cnc2c1] | white powder; ¹H-NMR (DMSO-d6, 400 MHz): δ 9.34 (1H, s), 8.88-8.92 (2H, m), 8.65 (1H, s), 8.31-8.37 (1H, m), 8.24-8.29 (1H, m), 7.82 (1H, d, J = 6.8 Hz), 7.66-7.75 (2H, m), 7.48-7.58 (2H, m), 4.84 (2H, s), 4.29-4.33 (2H, m), 2.73-2.93 (7H, m), 1.62-1.67 (2H, m), 1.21 (6H, d, J = 6.8 Hz), 0.98-1.11 (2H, m); LCMS: 100%, MS (ESI): m/z 551.3 [M + H]⁺ |

TABLE 11-continued

Summarized compounds 1-279 in terms of their structures and corresponding characteristics.

| # cpds | Structure | Characterization Data |
|---|---|---|
| 154 | 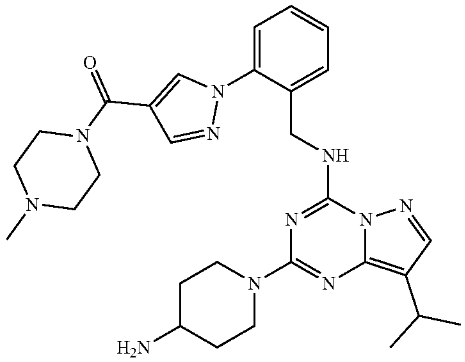 [SMILES: CC(C)c1cnn2c(NCc3ccccc3-n3cc(C(=O)N4CCN(C)CC4)cn3)nc(N3CCC(N)CC3)nc12] | white powder; ¹H-NMR (CDCl₃, 400 MHz): δ 8.04 (1H, s), 7.96 (1H, s), 7.63 (1H, t, J = 4.4 Hz), 7.59 (1H, s), 7.36-7.43 (3H, m), 7.29-7.35 (1H, m), 4.75-4.85 (2H, m), 4.69 (2H, d, J = 4.8 Hz), 3.70-3.80 (4H, m), 3.09-3.23 (1H, m), 2.95-3.01 (3H, m), 2.40-2.50 (4H, m), 2.33 (3H, s), 1.95-2.10 (2H, m), 1.40-1.55 (2H, m), 1.25 (6H, d, J = 6.8 Hz); LCMS: 98.8%, MS (ESI): m/z 558.4 [M + H]⁺ |
| 155 | 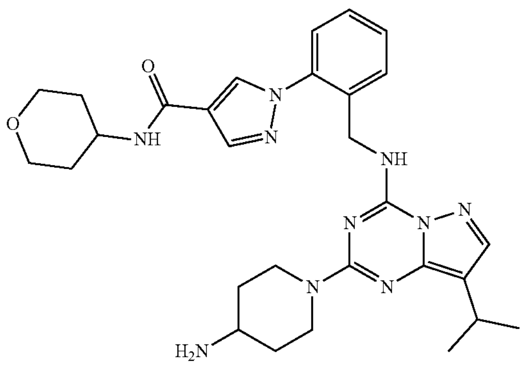 [SMILES: CC(C)c1cnn2c(NCc3ccccc3-n3cc(C(=O)NC4CCOCC4)cn3)nc(N3CCC(N)CC3)nc12] | white powder; ¹H-NMR (CDCl₃, 400 MHz): δ 8.17 (1H, s), 8.06 (1H, s), 7.64-7.69 (1H, m), 7.59 (1H, s), 7.37-7.41 (2H, m), 7.28-7.35 (2H, m), 5.76 (1H, d, J = 8.4 Hz), 4.72-4.82 (2H, m), 4.67 (2H, d, J = 6.8 Hz), 4.13-4.26 (1H, m), 3.98-4.05 (2H, m), 3.49-3.58 (2H, m), 2.93-3.05 (4H, m) 1.98-2.05 (2H, m), 1.87-1.94 (2H, m), 1.25-1.34 (10H, m); LCMS: 99.1%, MS (ESI): m/z 559.3 [M + H]⁺ |
| 156 | 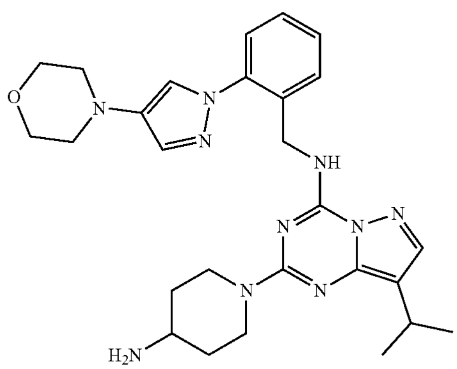 [SMILES: CC(C)c1cnn2c(NCc3ccccc3-n3cc(N4CCOCC4)cn3)nc(N3CCC(N)CC3)nc12] | white powder; ¹H-NMR (DMSO-d6, 400 MHz): δ 8.65 (1H, brs), 7.71-7.75 (2H, m), 7.64 (1H, s), 7.51 (1H, d, J = 7.2 Hz), 7.31-7.44 (3H, m), 4.65 (2H, s), 4.35-4.41 (2H, m), 3.69-3.76 (4H, m), 2.92-2.97 (4H, m), 2.76-2.90 (4H, m), 1.65-1.76 (2H, m), 1.19-1.25 (8H, m); LCMS: 100%, MS (ESI): m/z 517.3 [M + H]⁺ |
| 157 | 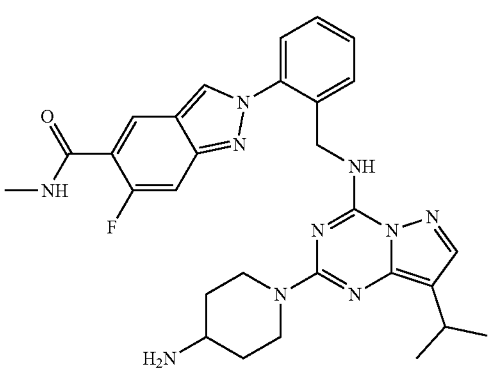 | white powder; ¹H-NMR (CDCl₃, 400 MHz): δ 8.55 (1H, d, J = 7.6 Hz), 8.33 (1H, s), 7.63 (1H, d, J = 7.6 Hz), 7.60 (1H, s), 7.44-7.51 (1H, m), 7.39-7.43 (2H, m), 7.34 (1H, d, J = 13.2 Hz), 7.26-7.30 (1H, m), 6.98 (1H, dd, J = 12.8, 4.8 Hz), 4.66-4.75 (2H, m), 4.63 (2H, d, J = 5.6 Hz), 3.21-3.43 (1H, m), 3.05 (3 H, d, J = 4.4 Hz), 2.86-2.99 (3H, m), 2.08-2.18 (2H, m), 1.48-1.63 (2H, m), 1.25 (6H, d, J = 7.2 Hz); LCMS: 96.8%, MS (ESI): m/z 557.3 [M + H]⁺ |

TABLE 11-continued

Summarized compounds 1-279 in terms of their structures and corresponding characteristics.

| # cpds | Structure | Characterization Data |
|---|---|---|
| 158 | 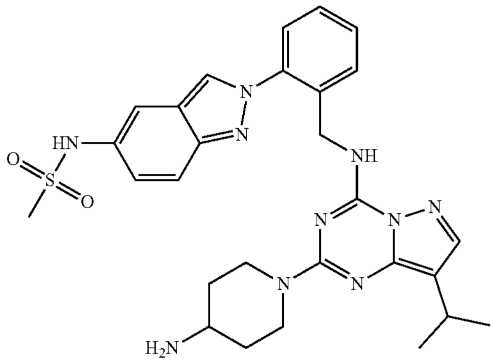 [SMILES: CC(C)c1cnn2c(NCc3ccccc3-n3cc4cc(NS(C)(=O)=O)ccc4n3)nc(N3CCC(N)CC3)nc12] | white powder; ¹H-NMR (CDCl₃, 400 MHz): δ 8.16 (1H, s), 7.82 (1H, d, J = 9.6 Hz), 7.65-7.72 (2H, m), 7.61 (1H, s), 7.39-7.49 (4H, m), 7.18 (1H, dd, J = 8.8, 2.0 Hz), 4.61-4.74 (4H, m), 3.03 (3H, s), 2.86-3.02 (4H, m), 1.82-1.89 (2H, m), 1.20-1.35 (8H, m); LCMS: 98.3%, MS (ESI): m/z 575.3 [M + H]⁺ |
| 159 | 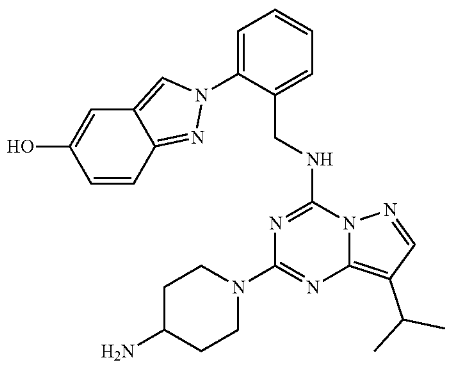 [SMILES: CC(C)c1cnn2c(NCc3ccccc3-n3cc4cc(O)ccc4n3)nc(N3CCC(N)CC3)nc12] | white powder; ¹H-NMR (DMSO-d6, 400 MHz): δ 8.90 (1H, brs), 8.44 (1H, s), 7.75 (1H, s), 7.52-7.61 (3H, m), 7.44-7.49 (2H, m), 6.93-7.00 (2H, m), 4.60 (2H, s), 4.35-4.41 (2H, m), 2.95-3.05 (1H, m), 2.85-2.95 (1H, m), 2.72-2.80 (2H, m), 1.74-1.83 (2H, m), 1.05-1.25 (8H, m); LCMS: 98.3%, MS (ESI): m/z 498.2 [M + H]⁺. |
| 160 | 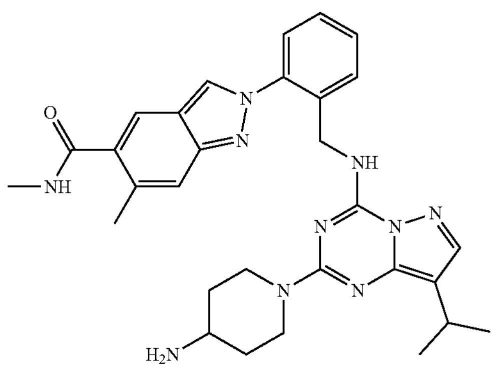 [SMILES: CNC(=O)c1cc2cn(-c3ccccc3CNc3nc(N4CCC(N)CC4)nc4c(C(C)C)cnn34)nc2cc1C] | white powder; ¹H-NMR (CDCl₃, 400 MHz): δ 7.99 (1H, s), 7.54-7.61 (2H, m), 7.49 (1H, s), 7.41-7.47 (2H, m), 7.34-7.40 (2H, m), 7.11 (1H, d, J = 5.2 Hz), 6.64 (1H, q, J = 4.4 Hz), 4.50-4.68 (4H, m) 3.10-3.21 (1H, m), 2.90-3.00 (3H, m), 2.92-2.96 (1H, m), 2.77-2.83 (2H, m), 2.47 (3H, s), 1.94-2.05 (2H, m), 1.31-1.45 (2H, m), 1.25 (6 H, d, J = 7.2 Hz); LCMS: 100%, MS (ESI): m/z 553.3 [M + H]⁺. |
| 161 | 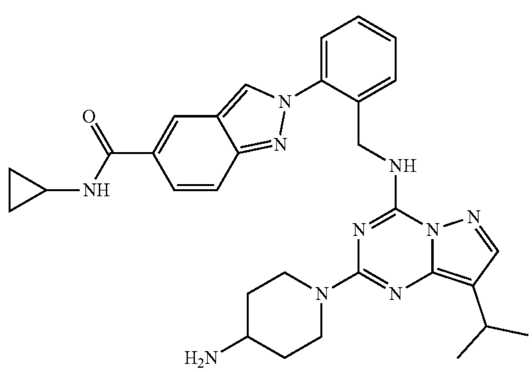 [SMILES: CC(C)c1cnn2c(NCc3ccccc3-n3cc4cc(C(=O)NC5CC5)ccc4n3)nc(N3CCC(N)CC3)nc12] | white powder; ¹H-NMR (CDCl₃, 400 MHz): δ 8.12 (1H, s), 7.99 (1H, s), 7.81 (1H, d, J = 9.2 Hz), 7.63-7.70 (3H, m), 7.45-7.55 (3H, m), 7.43-7.47 (1H, m), 6.52 (1H, brs), 4.63-4.90 (4H, m), 2.85-3.10 (5H, m), 1.90-1.94 (2H, m), 1.25-1.28 (2H, m), 1.27 (6H, d, J = 6.8 Hz), 0.85-1.90 (2H, m), 0.65-0.70 (2H, m); LCMS: 98.7%, MS (ESI): m/z 565.3 [M + H]⁺. |

TABLE 11-continued

Summarized compounds 1-279 in terms of their structures and corresponding characteristics.

| # cpds | Structure | Characterization Data |
|---|---|---|
| 162 | 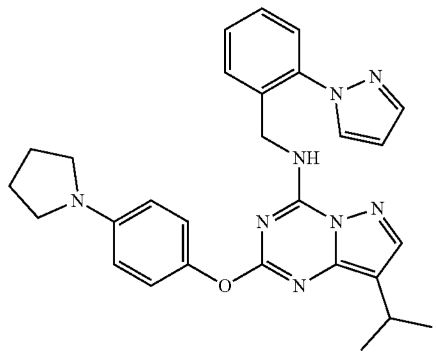 [SMILES: CC(C)c1cnn2c(NCc3ccccc3-n3cccn3)nc(Oc3ccc(N4CCCC4)cc3)nc12] | off-white powder; $^1$H-NMR (CDCl$_3$, 400 MHz): δ 8.20-8.30 (1H, m), 7.88 (1H, s), 7.70-7.76 (2H, m), 7.38 (1H, d, J = 8.0 Hz), 7.28 (1H, d, J = 6.0 Hz), 7.20-7.30 (2H, m), 7.14 (2H, d, J = 9.2 Hz), 6.61 (2H, d, J = 8.8 Hz), 6.5 (1H, s), 4.56 (2H, d, J = 6.4 Hz), 3.30-3.40 (4H, m), 3.05-3.15 (1H, m), 2.00-2.15 (4H, m), 1.24 (6H, d, J = 6.8 Hz); LCMS: 100%, MS (ESI): m/z 495.1 [M + H]+ |
| 163 | 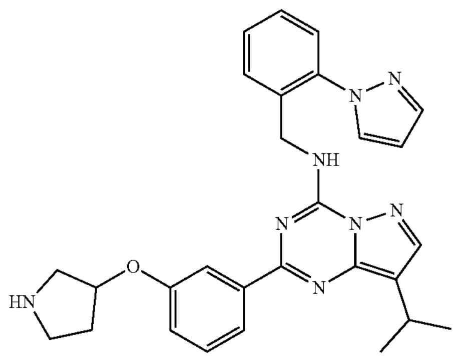 [SMILES: CC(C)c1cnn2c(NCc3ccccc3-n3cccn3)nc(-c3cccc(OC4CCNC4)c3)nc12] | Racemic mixture; yellow gum; $^1$H-NMR (DMSO-d6, 400 MHz): δ 9.59 (1H, brs), 9.38 (1H, brs), 9.22 (1H, t, J = 6.0 Hz), 8.24 (6H, d, J = 2.0 Hz), 8.10 (1H, s), 7.85-7.95 (2H, m), 7.80 (1H, m), 7.57 (2H, d, J = 2.4 Hz), 7.35-7.50 (4H, m), 7.05-7.20 (1H, m), 6.62 (1H, s), 5.21 (1H, m), 4.82 (2H, d, J = 5.6 Hz), 3.45-3.55 (1H, m), 3.25-3.45 (3H, m), 3.10-3.25 (1H, m), 2.15-2.30 (1H, m), 1.34 (6H, d, J = 6.8 Hz); LCMS: 100%, MS (ESI): m/z 495.2 [M + H]+. |
| 164 | 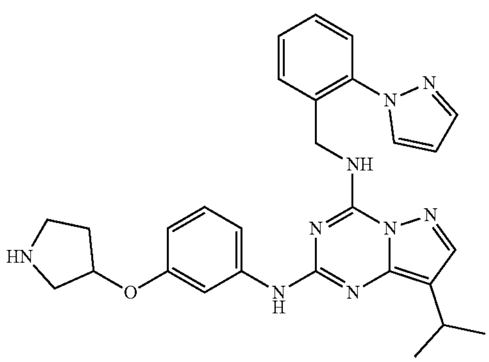 [SMILES: CC(C)c1cnn2c(NCc3ccccc3-n3cccn3)nc(Nc3cccc(OC4CCNC4)c3)nc12] | Racemic mixture; colorless gum; $^1$H-NMR (DMSO-d6, 400 MHz): δ 9.20-9.75 (3H, brs), 8.88 (1H, brs), 8.18 (1H, s), 7.89 (1H, s), 7.84 (1H, s), 7.30-7.60 (6H, m), 7.10-7.25 (1H, m), 6.50-6.70 (2H, m), 4.95-5.10 (1H, m), 4.73 (2H, d, J = 6.0 Hz), 3.40-3.55 (1H, m), 3.15-3.40 (3H, m), 2.95-3.10 (1H, m), 2.05-2.25 (2H, m), 1.30 (6H, d, J = 6.4 Hz); LCMS: 100%, MS (ESI): m/z 532.1 [M + Na]+ |
| 165 | 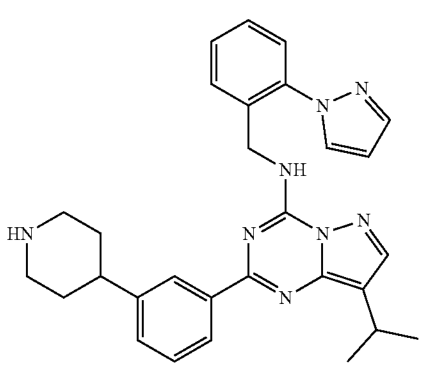 [SMILES: CC(C)c1cnn2c(NCc3ccccc3-n3cccn3)nc(-c3cccc(C4CCNCC4)c3)nc12] | off-white powder; $^1$H-NMR (DMSO-d6, 400 MHz): δ 9.13-9.25 (2H, m), 98.93-9.06 (1H, m), 8.25 (1H, d, J = 2.0 Hz), 8.14 (1H, s), 8.04-8.12 (2H, m), 7.87 (1H, s), 7.55-7.63 (1H, m), 7.43-7.51 (2H, m), 7.37-7.43 (2H, m), 7.35 (1H, d, J = 7.7 Hz), 6.61 (1H, s), 4.83 (2H, d, J = 6.0 Hz), 3.35-3.40 (2H, m), 3.15-3.20 (1H, m), 2.97-3.09 (2H, m), 2.89-2.97 (1H, m), 1.84-2.00 (4H, m), 1.34 (6H, d, J = 6.8 Hz); LCMS: 100%, MS (ESI): m/z 493.2 [M + H]+ |

TABLE 11-continued

Summarized compounds 1-279 in terms of their structures and corresponding characteristics.

| # cpds | Structure | Characterization Data |
|---|---|---|
| 166 | 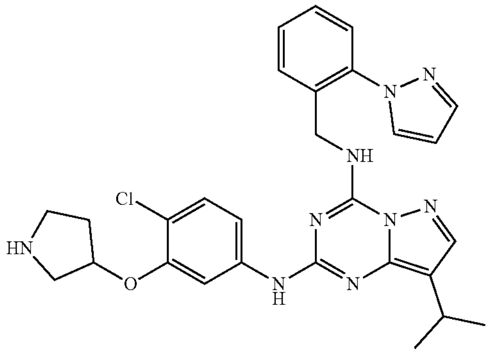 [SMILES: CC(C)c1cnn2c(NCc3ccccc3-n3cccn3)nc(Nc3ccc(Cl)c(OC4CCNC4)c3)nc12] | Racemic mixture; white powder; ¹H-NMR (DMSO-d6, 400 MHz): δ 9.45 (1H, brs), 8.84 (1H, brs), 8.19 (1H, s), 7.89 (1H, s), 7.75-7.84 (2H, m), 7.35-7.55 (6H, m), 7.29 (1H, d, J = 8.4 Hz), 6.59 (1H, s), 5.00-5.10 (1H, m), 4.73 (2H, d, J = 6.0 Hz), 3.20-3.40 (4H, m), 2.95-3.10 (1H, m), 2.100-2.25 (2H, m), 1.30 (6H, d, J = 6.8 Hz); LCMS: 100%, MS (ESI): m/z 544.1 [M + H]+ |
| 167 | 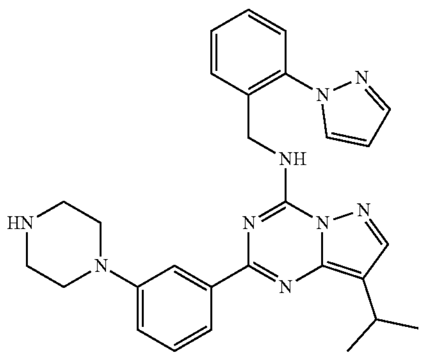 | white powder; ¹H-NMR (CDCl₃, 400 MHz): δ 8.17 (1H, s), 8.00-8.15 (2H, m), 7.90 (1H, s), 7.84 (1H, s), 7.80-7.82 (1H, m), 7.78 (1H, d, J = 1.6 Hz), 7.30-7.45 (4H, m), 7.07 (1H, d, J = 8.4 Hz), 6.53 (1H, s), 4.89 (2H, d, J = 6.4 Hz), 3.23-3.35 (5H, m), 3.10-3.15 (4H, m), 1.37 (6H, d, J = 6.8 Hz); LCMS: 100%, MS (ESI): m/z 494.1 [M + H]+ |
| 168 | 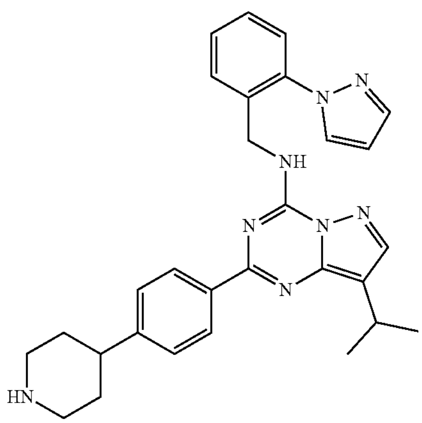 [SMILES: CC(C)c1cnn2c(NCc3ccccc3-n3cccn3)nc(-c3ccc(C4CCNCC4)cc3)nc12] | off-white powder; ¹H-NMR (DMSO-d6, 400 MHz): δ 9.21 (1H, t, J = 6.0 Hz), 8.55-8.65 (1H, m), 8.25-8.35 (1H, m), 8.26 (1H, d, J = 2.0 Hz), 8.21 (2H, d, J = 8.4 Hz), 8.08 (1H, s), 7.87 (1H, s), 7.55-7.60 (1H, m), 7.45-7.49 (1H, m), 7.38-7.43 (2H, m), 7.33 (2H, d, J = 8.4 Hz), 6.62 (1H, s), 4.83 (2H, d, J = 6.0 Hz), 3.14-3.18 (1H, m), 2.86-3.10 (4H, m), 1.95-2.00 (2H, m), 1.75-1.88 (2H, m), 1.34 (6H, d, J = 6.8 Hz); LCMS: 100%, MS (ESI): m/z 493.1 [M + H]+ |
| 169 | 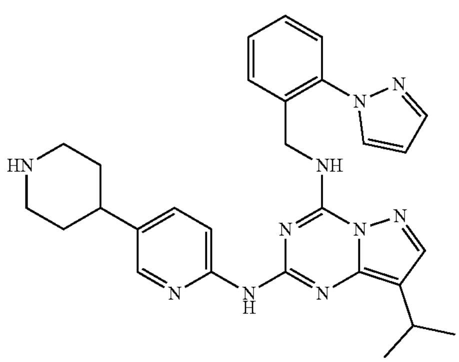 [SMILES: CC(C)c1cnn2c(NCc3ccccc3-n3cccn3)nc(Nc3ccc(C4CCNCC4)cn3)nc12] | white powder; ¹H-NMR (DMSO-d6, 400 MHz): δ 10.47 (1H, brs), 9.21-9.22 (1H, m), 8.71-8.72 (1H, m), 8.49-8.50 (1H, m), 8.27 (1H, s), 8.21 (1H, s), 8.02 (1H, s), 7.77-7.95 (3H, m), 7.50-7.56 (1H, m), 7.43-7.47 (3H, m), 6.60 (1H, s), 4.75 (2H, d, J = 4.8 Hz), 3.39-3.45 (2H, m), 3.14-3.18 (1H, m), 3.00-3.03 (2H, m), 2.90-2.92 (1H, m), 1.95-2.01 (2H, m), 1.72-1.85 (2H, m), 1.30 (6H, d, J = 6.8 Hz); LCMS: 100%, MS (ESI): m/z 531.1 [M + Na]+ |

TABLE 11-continued

Summarized compounds 1-279 in terms of their structures and corresponding characteristics.

| # cpds | Structure | Characterization Data |
|---|---|---|
| 170 | 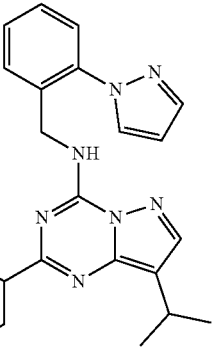 | white powder; $^1$H-NMR (CDCl$_3$, 400 MHz): δ 9.81 (1H, brs), 9.16 (1H, brs), 8.44 (1H, s), 8.30-8.40 (1H, m), 8.10-8.25 (1H, m), 7.83-7.91 (2H, m), 7.69-7.78 (2H, m), 7.51 (1H, d, J = 8.4 Hz), 7.30-7.42 (3H, m), 6.52 (1H, s), 4.88 (2H, d, J = 6.4 Hz), 3.55-3.65 (2H, m), 3.24-3.42 (2H, m) 3.10-3.20 (2H, m), 2.15-2.30 (4H, m), 1.36 (6H, d, J = 6.8 Hz); LCMS: 99.4%, MS (ESI): m/z 527.1 [M + H]+ |
| 171 | 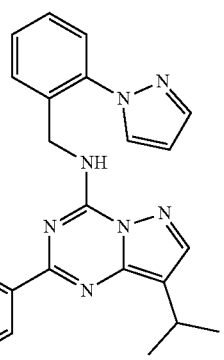 | yellow powder; $^1$H-NMR (DMSO-d6, 400 MHz): δ 9.30 (1H, t, J = 6.0 Hz), 8.25-8.45 (4H, m), 8.16-8.25 (2H, m), 8.11 (1H, s), 7.85 (1H, s), 7.51-7.63 (2H, m), 7.35-7.51 (4H, m), 6.60 (1H, s), 4.80 (2H, d, J = 6.0 Hz), 4.45-4.55 (1H, m), 3.55-3.65 (1H, m), 3.25-3.35 (1H, m), 3.15-3.25 (2H, m), 2.90-3.00 (1H, m), 2.00-2.10 (1H, m), 1.85-1.95 (1H, m), 1.45-1.63 (2 H, m), 1.34 (6H, d, J = 6.8 Hz); LCMS: 100%, MS (ESI): m/z 536.1 [M + H]+. |
| 172 | 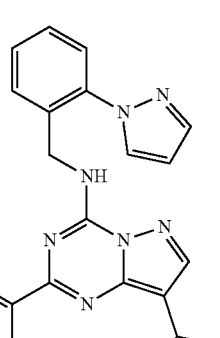 | yellow powder; $^1$H-NMR (DMSO-d6, 400 MHz): δ 9.31 (1H, t, J = 6.0 Hz), 8.24-8.35 (3H, m), 8.16-8.26 (2H, m), 8.11 (1H, s), 7.88 (1H, s), 7.68-7.66 (1H, m), 7.29-7.55 (5H, m), 6.63 (1H, s), 4.84 (2H, d, J = 6.0 Hz), 4.43-4.53 (1H, m), 3.58-3.68 (1H, m), 3.25-3.34 (1H, m), 3.08-3.23 (2H, m), 2.84-2.94 (1H, m), 1.85-2.05 (2H, m), 1.46-1.56 (2H, m), 1.35 (6H, d, J = 6.8 Hz); LCMS: 97.7%, MS (ESI): m/z 558.1 [M + Na]+ |
| 173 | 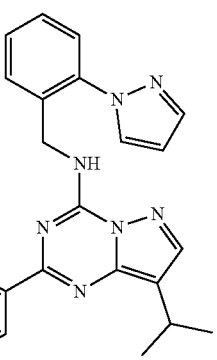 | white powder; $^1$H-NMR (CDCl$_3$, 400 MHz): δ 8.10-8.23 (3H, m), 7.89 (1H, d, J = 1.2 Hz), 7.86 (1H, s), 7.78 (1H, d, J = 1.6 Hz), 7.72 (1H, d, J = 7.6 Hz), 7.51 (1H, d, J = 7.6 Hz), 7.29-7.43 (3H, m), 6.53 (1H, s), 4.91-4.98 (1H, m), 4.83-4.91 (2H, m), 3.42-3.58 (2H, m), 3.20-3.35 (3H, m), 2.16-2.38 (4H, m), 1.37 (6H, d, J = 6.4 Hz); LCMS: 96.6%, MS (ESI): m/z 543.0 [M + H]+ |

TABLE 11-continued

Summarized compounds 1-279 in terms of their structures and corresponding characteristics.

| # cpds | Structure | Characterization Data |
|---|---|---|
| 174 | 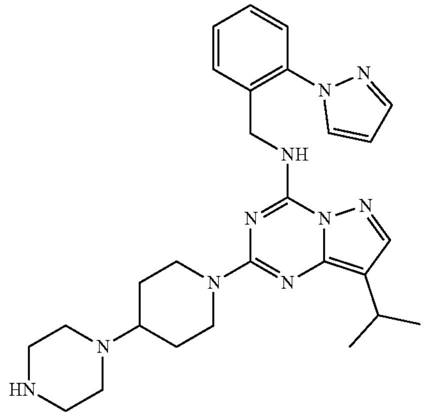 [SMILES: CC(C)c1cnn2c(NCc3ccccc3-n3cccn3)nc(N3CCC(N4CCNCC4)CC3)nc12] | white powder; $^1$H-NMR (DMSO-d6, 400 MHz): δ 12.09 (1H, brs), 9.93 (1H, brs), 9.66 (1H, brs), 9.09 (1H, brs), 8.18 (1H, d, J = 2.0 Hz), 7.83 (2H, s), 7.50-7.62 (1H, m), 7.35-7.48 (3H, m), 6.58 (1H, s), 4.63 (4H, d, J = 6.0 Hz), 3.59-3.75 (2H, m), 3.42-3.59 (5H, m), 3.26-3.42 (2H, m), 2.95-3.11 (1H, m), 2.71-2.90 (2H, m), 2.04-2.20 (2H, m), 1.44-1.66 (2H, m), 1.21 (6H, d, J = 7.2 Hz); LCMS: 100%, MS (ESI): m/z 501.1 [M + H]+ |
| 175 | 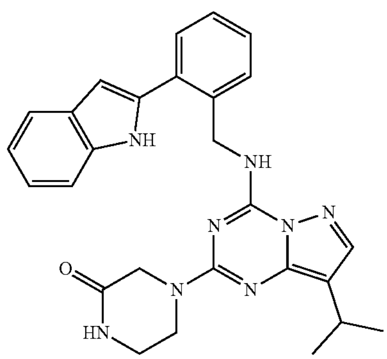 [SMILES: CC(C)c1cnn2c(NCc3ccccc3-c3cc4ccccc4[nH]3)nc(N3CCNC(=O)C3)nc12] | white powder; $^1$H-NMR (CDCl$_3$, 400 MHz): δ 9.30 (1H, brs), 7.64-7.66 (2H, m), 7.52-7.58 (2H, m), 7.43-7.47 (1H, m), 7.32-7.39 (2H, m), 7.19-7.26 (1H, m), 7.13-7.16 (1H, m), 6.82-6.86 (1H, m), 6.5 (1H, d, J = 4.8 Hz), 5.99 (1H, brs), 4.92 (2H, d, J = 6.0 Hz), 4.20 (2H, s), 3.86-3.91 (2H, m), 3.32-3.37 (2H, m), 2.97-3.04 (1H, m), 1.28 (6H, d, J = 7.2 Hz); LCMS: 100.0%, MS (ESI): m/z 481.3 [M + H]+ |
| 176 | 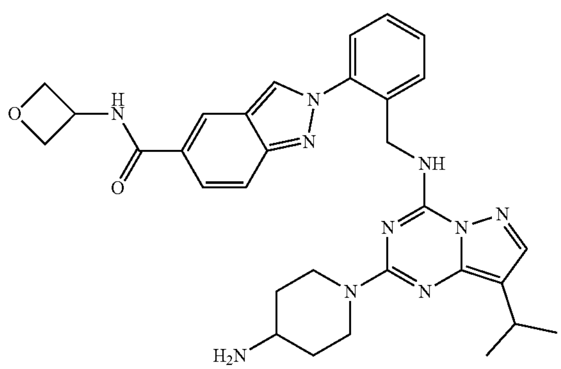 [SMILES: CC(C)c1cnn2c(NCc3ccccc3-n3cc4cc(C(=O)NC5COC5)ccc4n3)nc(N3CCC(N)CC3)nc12] | white powder; $^1$H-NMR (DMSO-d6, 400 MHz): δ 8.89 (1H, brs), 8.32 (1H, s), 7.85 (1H, d, J = 7.6 Hz), 7.70-7.75 (2H, m), 7.55-7.60 (2H, m), 7.45-7.51 (2H, m), 4.59 (2H, s), 4.43-4.49 (1H, m), 4.27-4.30 (4H, m), 3.60-3.63 (1H, m), 3.45-3.51 (1H, m), 2.82-2.91 (2H, m), 2.74-2.80 (2H, m), 1.60-1.68 (2H, m), 1.10-1.22 (8H, m); LCMS: 98.8%, MS (ESI): m/z 581.3 [M + H]+ |
| 177 | 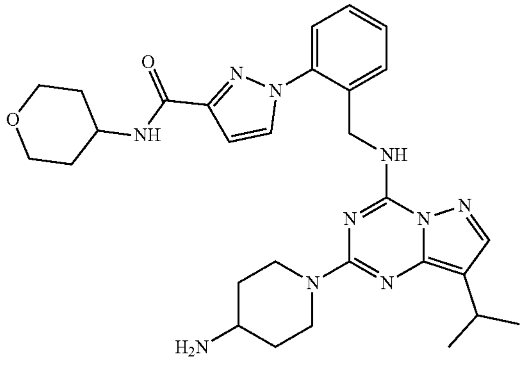 [SMILES: CC(C)c1cnn2c(NCc3ccccc3-n3ccc(C(=O)NC4CCOCC4)n3)nc(N3CCC(N)CC3)nc12] | white powder; $^1$H-NMR (CDCl$_3$, 400 MHz): δ 7.87 (1H, brs), 7.74 (1H, d, J = 2.4 Hz), 7.62-7.67 (2H, m), 7.38-7.46 (2H, m), 7.29-7.38 (2H, m), 7.09 (1H, d, J = 2.4 Hz), 4.75-4.85 (2H, m), 4.54 (2H, d, J = 6.0 Hz), 4.06-4.33 (3H m), 3.90-4.05 (2H, m), 3.42-3.57 (2H, m), 3.25-3.30 (1H, m), 2.91-3.10 (3H, m), 2.10-2.15 (2H, m), 1.80-1.15 (2H, m), 1.55-1.76 (4H, m), 1.27 (6H, d, J = 7.2 Hz); LCMS: 98.1%, MS (ESI): m/z = 581.3 [M + Na]+ |

TABLE 11-continued

Summarized compounds 1-279 in terms of their structures and corresponding characteristics.

| # cpds | Structure | Characterization Data |
|---|---|---|
| 178 | 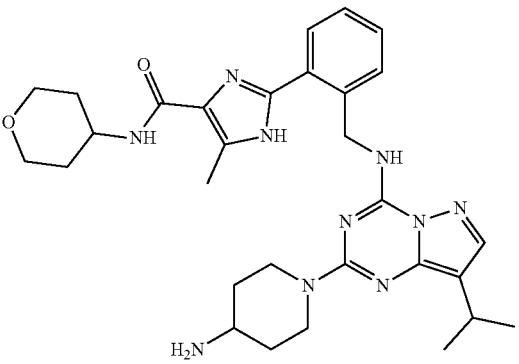 [SMILES: Cc1[nH]c(-c2ccccc2CNc2nc(N3CCC(N)CC3)nc3c(C(C)C)cnn23)nc1C(=O)NC1CCOCC1] | white powder; ¹H-NMR (DMSO-d6, 400 MHz): δ 13.00 (1H, brs), 9.76 (1H, t, J = 6.0 Hz), 7.72 (1H, s), 7.69 (1 H, d, J = 7.6 Hz), 7.60 (2H, d, J = 8.4 Hz), 7.42-7.47 (1H, m), 7.36-7.41 (1H, m), 4.64-4.82 (4H, m), 4.00-4.13 (1H, m), 3.81-3.93 (2H, m), 2.87-3.02 (3H, m), 2.56 (3H, s), 1.95-2.02 (2H, m), 1.75-1.82 (2H, m), 1.53-1.65 (2H, m), 1.37-1.48 (2H, m), 1.21 (6H, d, J = 6.8 Hz); LCMS: 100%, MS (ESI): m/z 573.3 [M + H]⁺ |
| 179 | 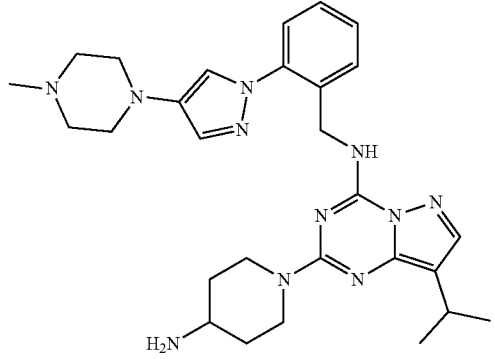 [SMILES: CC(C)c1cnn2c(NCc3ccccc3-n3cc(N4CCN(C)CC4)cn3)nc(N3CCC(N)CC3)nc12] | white powder; ¹H-NMR (DMSO-d6, 400 MHz): δ 8.71 (1H, brs), 7.74 (1H, s), 7.70 (1H, s), 7.61 (1H, s), 7.49-7.52 (1H, m), 7.31-7.48 (3H, m), 4.65 (2H, s), 4.45-4.51 (2H, m), 3.01-3.10 (1H, m), 2.60-2.90 (7H, m), 2.30-2.50 (4H, m), 2.22 (3H, s), 1.75-1.85 (2H, m), 1.10-1.30 (8H, m); LCMS: 98.3%, MS (ESI): m/z 530.3 [M + H]⁺ |
| 180 | 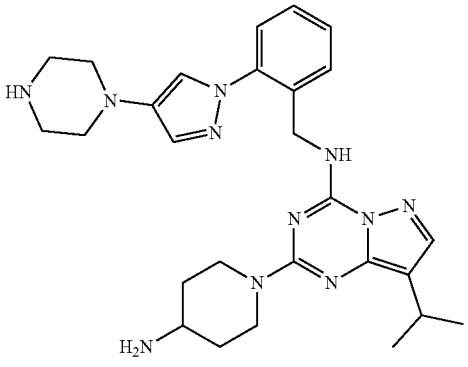 [SMILES: CC(C)c1cnn2c(NCc3ccccc3-n3cc(N4CCNCC4)cn3)nc(N3CCC(N)CC3)nc12] | white powder; ¹H-NMR (CD₃OD, 400 MHz): δ 7.67 (1H, s), 7.60-7.63 (3H, m), 7.40-7.42 (3H, m), 4.78-4.85 (2H, m), 4.71 (2H, s), 3.25-3.35 (1H, m), 3.05-3.20 (8H, m), 2.90-3.10 (3H, m), 1.95-2.05 (2H, m), 1.45-1.55 (2H, m), 1.27 (3H, d, J = 7.2 Hz); LCMS: 100%, MS (ESI): m/z 516.3 [M + H]⁺ |
| 181 | 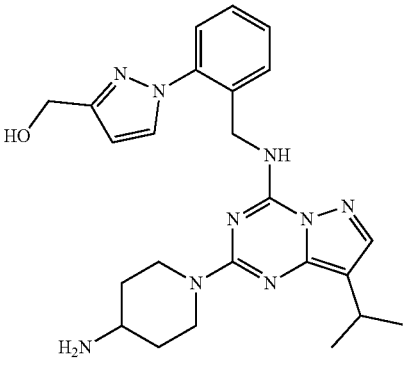 [SMILES: CC(C)c1cnn2c(NCc3ccccc3-n3ccc(CO)n3)nc(N3CCC(N)CC3)nc12] | white powder; ¹H-NMR (CDCl₃, 400 MHz): δ 8.68 (1H, brs), 7.64 (1H, d, J = 2.4 Hz), 7.50-7.59 (2H, m), 7.26-7.37 (2H, m), 7.21-7.25 (1H, m), 6.33 (1H, d, J = 2.4 Hz), 4.79 (2H, s), 4.70-4.80 (2H, m), 4.55 (2H, d, J = 6.0 Hz), 2.80-2.99 (4H, m), 1.81-1.85 (2H, m), 1.17-1.26 (8H, m); LCMS: 100%, MS (ESI): m/z 462.1 [M + H]⁺ |

TABLE 11-continued

Summarized compounds 1-279 in terms of their structures and corresponding characteristics.

| # cpds | Structure | Characterization Data |
|---|---|---|
| 182 | 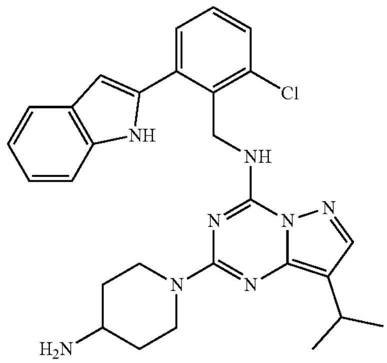 | white powder; $^1$H-NMR (CDCl$_3$, 400 MHz): δ 8.85 (1H, s), 7.60-7.66 (2H, m), 7.43-7.50 (2H, m), 7.30-7.35 (2H, m), 7.17-7.23 (1H, m), 7.10-7.16 (1H, m), 6.67 (1H, brs), 6.63 (1H, d, J = 1.2 Hz), 4.97 (2H, d, J = 5.2 Hz), 4.43-4.49 (2H, m), 2.97-3.08 (1H, m), 2.75-2.80 (1H, m), 2.72-2.75 (2H, m), 1.59-1.64 (2H, m), 1.28-1.30 (6H, m), 1.10-1.19 (2H, m); LCMS: 96.5%, MS (ESI): m/z 515.2 [M + H]$^+$ |
| 183 | 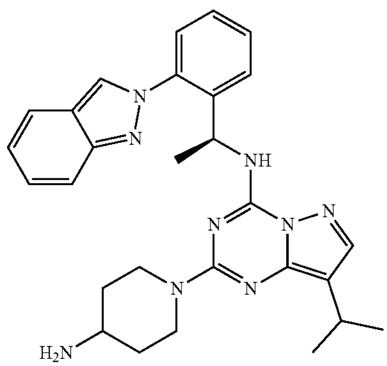 [SMILES: CC(C)c1cnn2c(N[C@@H](C)c3ccccc3-n3cc4ccccc4n3)nc(N3CCC(N)CC3)nc12] | (S)-methyl; white powder; $^1$H-NMR (CDCl$_3$, 400 MHz): δ 8.16 (1H, s), 7.82 (1H, dd, J = 8.8, 0.8 Hz), 7.70 (1H, d, J = 8.4 Hz), 7.60-7.65 (2H, m) 7.45-7.51 (1H, m), 7.39-7.43 (2H, m), 7.32-7.39 (1H, m), 7.10-7.18 (2H, m), 5.35-5.45 (1H, m), 4.36-4.54 (2H, m), 2.95-3.07 (1H, m), 2.66-2.88 (3H, m), 1.68-1.85 (2H, m), 1.50 (3H, d, J = 7.2 Hz), 1.27 (6H, d, J = 6.8 Hz), 1.05-1.22 (2H, m); LCMS: 100%, MS (ESI): m/z 496.2 [M + H]$^+$ |
| 184 | 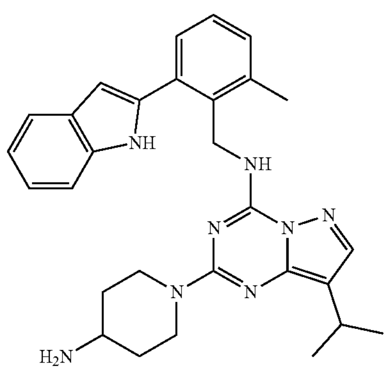 [SMILES: Cc1cccc(-c2cc3ccccc3[nH]2)c1CNc1nc(N2CCC(N)CC2)nc2c(C(C)C)cnn12] | white powder; $^1$H-NMR (DMSO-d6, 400 MHz): δ 11.37 (1H, brs), 7.70 (1H, s), 7.52 (1H, d, J = 7.6 Hz), 7.38 (1H, d, J = 8.4 Hz), 7.31-7.36 (2H, m), 7.26-7.28 (1H, m), 7.08 (1H, t, J = 7.2, 8.8 Hz), 7.00 (1H, t, J = 7.2 Hz), 6.52 (1H, s), 4.78 (2H, s), 4.39-4.42 (2H, m), 2.82-2.94 (3H, m), 2.67-2.77 (1H, m), 2.36 (3 H, s), 1.64-1.67 (2H, m), 1.21-1.23 (6H, d, J = 7.2 Hz), 1.01-1.11 (2H, m); LCMS: 98.1%, MS (ESI): m/z 495.3 [M + H]$^+$ |
| 185 | 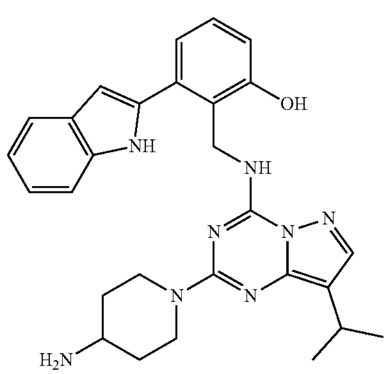 [SMILES: CC(C)c1cnn2c(NCc3c(O)cccc3-c3cc4ccccc4[nH]3)nc(N3CCC(N)CC3)nc12] | white powder; $^1$H-NMR (CD$_3$OD, 400 MHz) δ : 7.60 (1H, s), 7.56 (1H, d, J = 7.6 Hz), 7.39 (1H, d, J = 8.0 Hz), 7.23 (1H, t, J = 8.0 Hz), 7.13 (1H, t, J = 7.6 Hz), 7.01-7.07 (2H, m), 6.90 (1H, d, J = 8.0 Hz), 6.49 (1H, s), 5.07 (2H, s), 4.20-4.33 (2H, m), 2.90-3.03 (1H, m), 2.63-2.75 (1H, m), 2.41-2.55 (2H, m), 1.45-1.55 (2H, m), 1.24 (6H, d, J = 6.8 Hz), 0.95-1.10 (2H, m); LCMS: 100%, MS (ESI): m/z 497.3 [M + H]$^+$ |

TABLE 11-continued

Summarized compounds 1-279 in terms of their structures and corresponding characteristics.

| # cpds | Structure | Characterization Data |
|---|---|---|
| 186 | 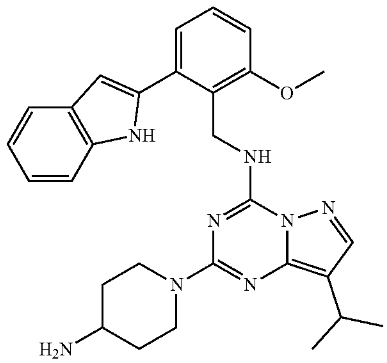 [SMILES: COc1cccc(-c2cc3ccccc3[nH]2)c1CNc1nc(N2CCC(N)CC2)nc2c(C(C)C)cnn12] | white powder; $^1$H-NMR (CDCl$_3$, 400 MHz): δ 8.67 (1H, s), 7.58-7.66 (2H, m), 7.31-7.39 (2H, m), 7.16-7.22 (1H, m), 7.09-7.15 (2H, m), 6.95 (1H, d, J = 7.6 Hz), 6.87 (1H, t, J = 6.0 Hz), 6.63 (1H, d, J = 1.2 Hz), 4.97 (2H, d, J = 5.6 Hz), 4.30-4.45 (2H, m), 3.96 (3H, s), 2.95-3.08 (1H, m), 2.71-2.82 (1H, m), 2.58-2.69 (2H, m), 1.53-1.63 (2H, m), 1.28 (6H, d, J = 6.8 Hz), 1.01-1.16 (2 H, m); LCMS: 100%, MS (ESI): m/z 511.3 [M + H]$^+$ |
| 187 | 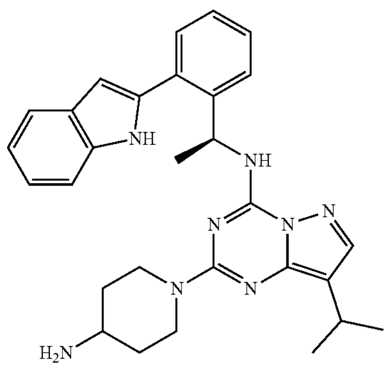 [SMILES: CC(C)c1cnn2c(N[C@@H](C)c3ccccc3-c3cc4ccccc4[nH]3)nc(N3CCC(N)CC3)nc12] | (S)-methyl; white powder; $^1$H-NMR (CDCl$_3$, 400 MHz): δ 8.85 (1H, brs), 7.60-7.67 (2H, m), 7.57 (1H, d, J = 7.6 Hz), 7.43-7.49 (1H, m), 7.29-7.40 (3H, m), 7.11-7.25 (2H, m), 6.58-6.65 (2H, m), 5.70-5.80 (1H, m), 4.24-4.29 (2H, m), 2.94-3.08 (1H, m), 2.75-2.85 (1H, m), 2.60-2.74 (2H, m), 1.53-1.67 (5H, m), 1.19-1.30 (8H, m); LCMS: 100%, MS (ESI): m/z 495.3 [M + H]$^+$ |
| 188 | 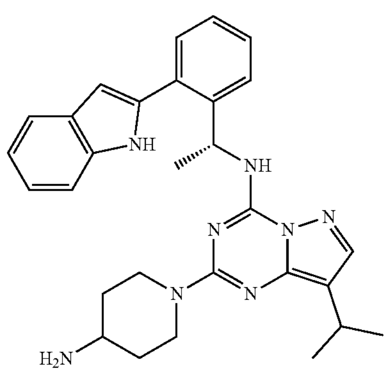 [SMILES: CC(C)c1cnn2c(N[C@H](C)c3ccccc3-c3cc4ccccc4[nH]3)nc(N3CCC(N)CC3)nc12] | (R)-methyl; white powder; $^1$H-NMR (CDCl$_3$, 400 MHz): δ 8.85 (1H, brs), 7.60-7.67 (2H, m), 7.57 (1H, d, J = 7.6 Hz), 7.43-7.49 (1H, m), 7.29-7.40 (3H, m), 7.11-7.25 (2H, m), 6.58-6.65 (2H, m), 5.70-5.80 (1H, m), 4.24-4.29 (2H, m), 2.94-3.08 (1H, m), 2.75-2.85 (1H, m), 2.60-2.74 (2H, m), 1.53-1.67 (5H, m), 1.19-1.30 (8H, m); LCMS: 100%, MS (ESI): m/z 495.3 [M + H]$^+$ |
| 189 | 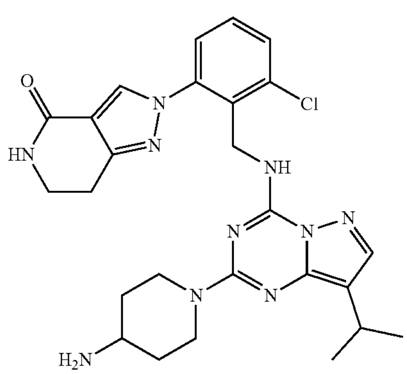 [SMILES: CC(C)c1cnn2c(NCc3c(Cl)cccc3-n3cc4c(n3)CCNC4=O)nc(N3CCC(N)CC3)nc12] | white powder; $^1$H-NMR (CDCl$_3$, 400 MHz): δ 8.04 (1H, s), 7.61 (1H, s), 7.50-7.55 (1H, m), 7.35-7.40 (1H, m), 6.87-6.96 (2H, m), 4.86 (2H, d, J = 5.6 Hz), 4.65-4.70 (2H, m), 3.55-3.59 (2H, m), 3.32-3.38 (2H, m), 2.96-3.04 (1H, m), 2.985-2.95 (2H, m), 2.81 (2H, t, J = 6.8 Hz), 2.10-2.20 (2H, m), 1.55-1.65 (2H, m), 1.26 (6H, d, J = 7.06 Hz); LCMS: 94.97%, MS (ESI): m/z 535.3 [M + H]$^+$ |

TABLE 11-continued

Summarized compounds 1-279 in terms of their structures and corresponding characteristics.

| # cpds | Structure | Characterization Data |
|---|---|---|
| 190 | 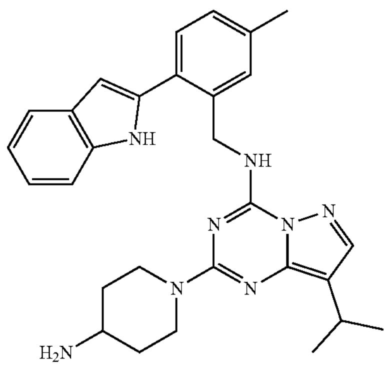 [SMILES: Cc1ccc(-c2cc3ccccc3[nH]2)c(CNc2nc(N3CCC(N)CC3)nc3c(C(C)C)cnn23)c1] | white powder; ¹H-NMR (CDCl₃, 400 MHz); δ 8.50 (1H, brs), 7.60-7.65 (2H, m), 7.41 (1H, d, J = 7.6 Hz), 7.32-7.37 (2H, m), 7.16-7.23 (2H, m), 7.09-7.16 (1H, m), 6.52-6.60 (2H, m), 4.82 (2H, d, J = 4.8 Hz), 4.58-4.68 (2H, m), 2.97-3.08 (1H, m), 2.8-2.93 (3H, m), 2.37 (3H, s), 1.77-1.87 (2H, m), 1.24-1.32 (8H, m); LCMS: 100%, MS (ESI): m/z 495.3 [M + H]⁺ |
| 191 | 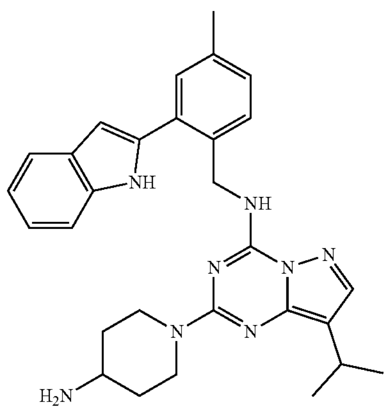 [SMILES: Cc1ccc(CNc2nc(N3CCC(N)CC3)nc3c(C(C)C)cnn23)c(-c2cc3ccccc3[nH]2)c1] | white powder; ¹H-NMR (CDCl₃, 400 MHz): δ 8.44 (1H, brs), 7.58-7.68 (2H, m), 7.42 (1H, d, J = 7.6 Hz) 7.31-7.38 (2H, m), 7.10-7.24 (3H, m), 6.60 (1H, d, J = 1.2 Hz), 6.45-6.54 (1H, m), 4.82 (2H, d, J = 5.6 Hz), 4.60-4.65 (2H, m), 2.97-3.08 (1H, m), 2.81-2.94 (3H, m), 2.39 (3H, s), 1.80-1.85 (2H, m), 1.23-1.33 (8H, m); LCMS: 100%, MS (ESI): m/z 495.3 [M + H]⁺ |
| 192 | 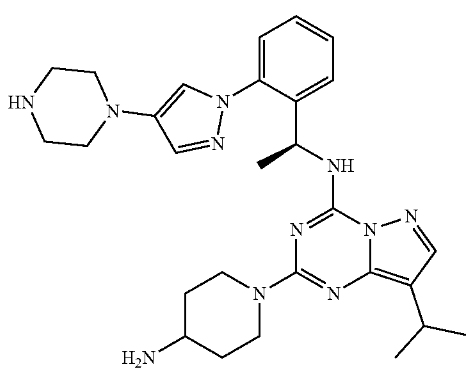 [SMILES: CC(C)c1cnn2c(N[C@@H](C)c3ccccc3-n3cc(N4CCNCC4)cn3)nc(N3CCC(N)CC3)nc12] | (S)-methyl; white powder; ¹H-NMR (CDCl₃, 400 MHz): δ 7.61 (1H, s), 7.50-7.56 (2H, m), 7.27-7.37 (3H, m), 7.12-7.20 (2H, m), 5.44-5.54 (1H, m), 4.52-4.64 (2H, m), 2.80-3.06 (12H, m), 1.80-1.90 (2H, m), 1.48 (3H, d, J = 7.2 Hz), 1.26-1.33 (8H, m); LCMS: 99.4%, MS (ESI): m/z 530.4 [M + H]⁺ |
| 193 | 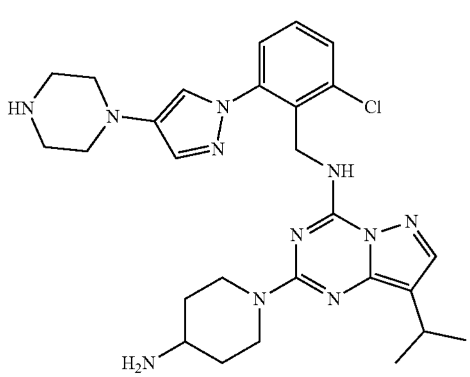 [SMILES: CC(C)c1cnn2c(NCc3c(Cl)cccc3-n3cc(N4CCNCC4)cn3)nc(N3CCC(N)CC3)nc12] | white powder; ¹H-NMR (CDCl₃, 400 MHz): δ 7.59 (1H, s), 7.56 (1H, s), 7.42 (1H, dd, J = 8.0, 1.2 Hz), 7.27-7.30 (1H, m), 7.20-7.26 (2H, m), 7.17 (1H, s), 4.87 (2H, d, J = 6.0 Hz), 4.72-4.77 (2H, m), 2.90-3.09 (12H, m), 1.85-1.88 (2H, m), 1.27 (8H, d, J = 7.2 Hz); LCMS: 100%, MS (ESI): m/z 550.3 [M + H]⁺ |

TABLE 11-continued

Summarized compounds 1-279 in terms of their structures and corresponding characteristics.

| # cpds | Structure | Characterization Data |
|---|---|---|
| 194 | 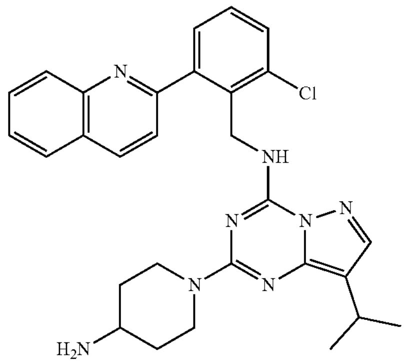 [SMILES: CC(C)c1cnn2c(NCc3c(Cl)cccc3-c3ccc4ccccc4n3)nc(N3CCC(N)CC3)nc12] | white powder; $^1$H-NMR (CDCl$_3$, 400 MHz): δ 8.71 (1H, t, J = 5.6 Hz), 8.55 (1H, d, J = 8.4 Hz), 8.28 (1H, d, J = 8.0 Hz), 7.87 (1H, d, J = 8.4 Hz), 7.76 (1H, t, J = 7.6 Hz), 7.71 (1H, s), 7.64 (1H, d, J = 8.4 Hz), 7.58 (1 H, d, J = 7.6 Hz), 7.44-7.54 (2H, m), 7.37 (1H, t, J = 7.2 Hz), 4.93 (2H, d, J = 6.0 Hz), 4.65-4.80 (2H, m), 3.00-3.13 (1H, m), 2.83-2.95 (3H, m), 1.83-1.89 (2H, m), 1.24-1.35 (8H, m); LCMS: 100%, MS (ESI): m/z 527.3 [M + H]$^+$ |
| 195 | 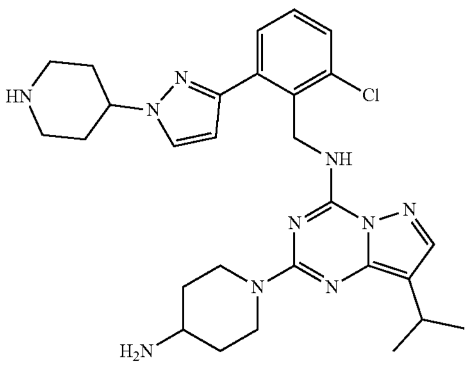 [SMILES: CC(C)c1cnn2c(NCc3c(Cl)cccc3-c3ccn(C4CCNCC4)n3)nc(N3CCC(N)CC3)nc12] | white powder; $^1$H-NMR (CDCl$_3$, 400 MHz): δ 8.14-8.20 (1H, m), 7.56 (1H, s) 7.50 (1H, d, J = 2.4 Hz) 7.45 (1H, dd, J = 7.6, 1.2 Hz), 7.39 (1H, dd, J = 8.0, 1.2 Hz), 7.27-7.30 (1H, m), 6.46 (1H, d, J = 2.4 Hz), 5.02 (2H, d, J = 6.0 Hz), 4.82-4.91 (2H, m), 4.25-4.37 (1H, m), 3.20-3.29 (2H, m), 2.89-3.05 (4H, m), 2.70-2.82 (2H, m), 2.16-2.24 (2H, m), 2.04-2.13 (2H, m), 1.91-1.96 (2H, m), 1.35-1.41 (2H, m), 1.28 (6H, d, J = 6.8 Hz); LCMS: 100%, MS (ESI): m/z 549.3 [M + H]$^+$ |
| 196 | 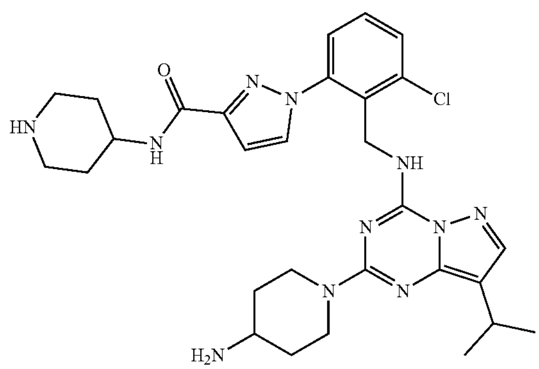 [SMILES: CC(C)c1cnn2c(NCc3c(Cl)cccc3-n3ccc(C(=O)NC4CCNCC4)n3)nc(N3CCC(N)CC3)nc12] | white powder; $^1$H-NMR (CDCl$_3$, 400 MHz): δ 7.71 (1H, d, J = 2.8 Hz), 7.68 (1H, s), 7.50-7.59 (2H, m), 7.39 (1H, t, J = 8.0 Hz), 7.29 (1H, dd, J = 8.0, 1.2 Hz), 7.15 (1H, d, J = 8.4 Hz), 7.07 (1H, d, J = 2.4 Hz), 4.70-4.85 (4H, m), 3.98-4.14 (1H, m), 2.89-3.13 (6H, m), 2.63-2.75 (2H, m), 1.83-1.94 (4H, m), 1.27-1.44 (10H, m); LCMS: 96.8%, MS (ESI): m/z 614.3 [M + Na]$^+$ |
| 197 | 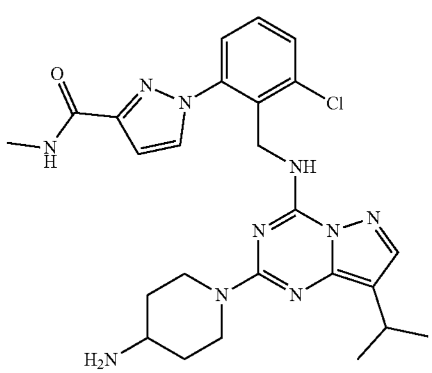 [SMILES: CNC(=O)c1ccn(-c2cccc(Cl)c2CNc2nc(N3CCC(N)CC3)nc3c(C(C)C)cnn23)n1] | white powder; $^1$H-NMR (CDCl$_3$, 400 MHz): δ 8.38 (1H, t, J = 6.0 Hz), 8.05 (1H, d, J = 4.4 Hz), 7.75 (1H, d, J = 2.0 Hz), 7.62 (1H, s), 7.54 (1 H, d, J = 8.0 Hz), 7.37 (1H, t, J = 8.0 Hz), 7.27 (1H, s), 7.10 (1H, d, J = 2.0 Hz), 4.70-4.91 (4H, m), 2.85-3.10 (7H, m), 1.89-1.95 (2H, m), 1.26-1.42 (8H, m); LCMS: 98.0%, MS (ESI): m/z 523.2 [M + H]$^+$ |

TABLE 11-continued

Summarized compounds 1-279 in terms of their structures and corresponding characteristics.

| # cpds | Structure | Characterization Data |
|---|---|---|
| 198 | 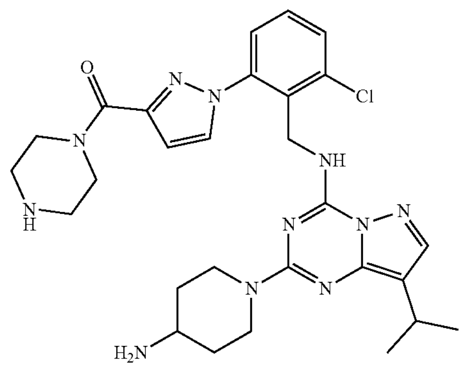 [SMILES: CC(C)c1cnn2c(NCc3c(Cl)cccc3-n3ccc(C(=O)N4CCNCC4)n3)nc(N3CCC(N)CC3)nc12] | white powder; ¹H-NMR (CDCl₃, 400 MHz): δ 7.69 (1H, d, J = 2.20 Hz), 7.58 (1H, s), 7.50-7.56 (1H, m), 7.39 (1H, t, J = 7.95 Hz), 7.29 (1H, d, J = 6.85 Hz), 6.93 (1H, d, J = 2.4 Hz), 6.81 (1H, t, J = 5.6 Hz), 4.76 (2H, d, J = 5.6 Hz), 4.70-4.75 (2H, m), 3.90-3.95 (2H, m), 3.70-3.75 (2H, m), 2.86-3.07 (6H, m), 2.72-2.75 (2H, m), 1.88-1.90 (2H, m), 1.28 (8H, d, J = 6.8 Hz); LCMS: 100%, MS (ESI): m/z 578.3 [M + H]⁺ |
| 199 | 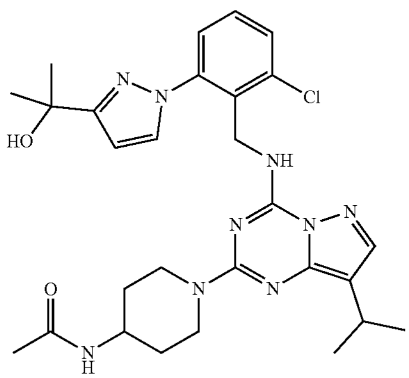 [SMILES: CC(=O)NC1CCN(c2nc(NCc3c(Cl)cccc3-n3ccc(C(C)(C)O)n3)n3ncc(C(C)C)c3n2)CC1] | white powder; ¹H-NMR (CDCl₃, 400 MHz): δ 8.93 (1H, t, J = 6.4 Hz), 7.62-7.71 (2H, m), 7.45-7.52 (1H, m) 7.32 (1H, t, J = 8.0 Hz), 7.20-7.25 (1H, m), 6.39 (1H, d, J = 2.0 Hz), 5.35 (1H, d, J = 8.4 Hz), 4.77-4.95 (4H, m), 3.97-4.16 (1H, m), 2.93-3.15 (3H, m), 1.93-2.04 (5H, m), 1.66 (6H, s), 1.31-1.44 (2H, m), 1.26 (6H, d, J = 7.2 Hz); LCMS: 100%, MS (ESI): m/z 566.2 [M + H]⁺ |
| 200 | 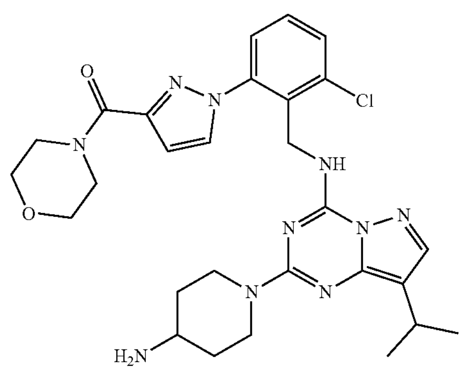 [SMILES: CC(C)c1cnn2c(NCc3c(Cl)cccc3-n3ccc(C(=O)N4CCOCC4)n3)nc(N3CCC(N)CC3)nc12] | white powder; ¹H-NMR (CDCl₃, 400 MHz): δ 7.70 (1H, s), 7.60 (1H, s), 7.55 (1H, d, J = 8.0 Hz), 7.40 (1H, t, J = 8.0 Hz), 7.25-7.29 (1H, m), 6.97 (1H, s), 6.79 (1H, brt, J = 5.2 Hz), 4.64-4.77 (4H, m), 3.95-4.05 (2H, m), 3.72-3.78 (4H, m), 3.50-3.75 (2H, m), 2.84-3.08 (4H, m), 1.93-2.05 (2H, m), 1.25-1.35 (8H, m); LCMS: 100%, MS (ESI): m/z 579.3 [M + H]⁺ |
| 201 | 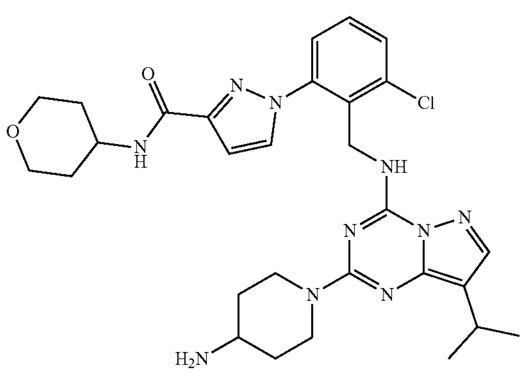 [SMILES: CC(C)c1cnn2c(NCc3c(Cl)cccc3-n3ccc(C(=O)NC4CCOCC4)n3)nc(N3CCC(N)CC3)nc12] | white powder; ¹H-NMR (CDCl₃, 400 MHz): δ 7.72 (1H, d, J = 2.45 Hz), 7.68 (1H, s), 7.51-7.61 (2H, m), 7.40 (1H, t, J = 8.07 Hz), 7.26-7.29 (1H, m), 7.18 (1H, d, J = 8.07 Hz), 7.09 (1H, d, J = 2.8 Hz), 4.69-4.83 (4H, m), 4.15-4.19 (1H, m), 3.92-3.97 (2H, m), 3.40-3.50 (2H, m), 2.88-3.08 (4H, m), 1.76-1.98 (4H, m), 1.49-1.57 (4H, m), 1.33-1.45 (2H, m), 1.27-1.31 (6H, d, J = 6.8 Hz); LCMS: 100%, MS (ESI): m/z 615.3 [M + Na]⁺ |

TABLE 11-continued

Summarized compounds 1-279 in terms of their structures and corresponding characteristics.

| # cpds | Structure | Characterization Data |
|---|---|---|
| 202 | 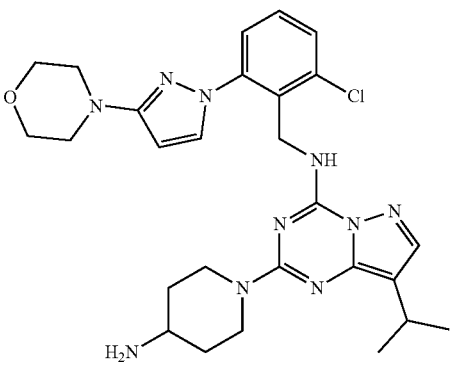 [SMILES: CC(C)c1cnn2c(NCc3c(Cl)cccc3-n3ccc(N4CCOCC4)n3)nc(N3CCC(N)CC3)nc12] | white powder; $^1$H-NMR (CDCl$_3$, 400 MHz): δ 7.79 (1H, t, J = 6.0 Hz), 7.55 (1H, d, J = 2.8 Hz), 7.51 (1H, s), 7.40 (1H, d, J = 8.0 Hz), 7.25-7.30 (1H, m), 7.17 (1H, d, J = 7.2 Hz), 5.93 (1H, d, J = 2.8 Hz), 4.89 (2H, d, J = 6.0 Hz), 4.75-4.85 (2H, m), 3.80 (4H, t, J = 4.8 Hz), 3.34 (4H, t, J = 4.8 Hz), 2.88-3.05 (4H, m), 1.85-1.95 (2H, m), 1.31-1.40 (2H, m), 1.28 (6H, d, J = 6.8 Hz); LCMS: 100%, MS (ESI): m/z 551.2 [M + H]$^+$ |
| 203 | 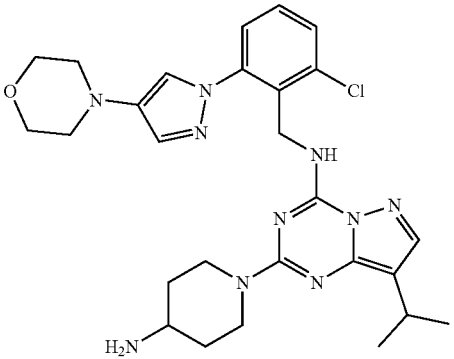 [SMILES: CC(C)c1cnn2c(NCc3c(Cl)cccc3-n3cc(N4CCOCC4)cn3)nc(N3CCC(N)CC3)nc12] | white powder; $^1$H-NMR (CDCl$_3$, 400 MHz): δ 7.59 (1H, s), 7.57 (1H, s), 7.43 (1H, d, J = 8.0 Hz), 7.30 (1H, t, J = 8.0 Hz), 7.22-7.25 (1H, m), 7.14-7.19 (2H, m), 4.88 (2H, d, J = 6.4 Hz), 4.71-4.83 (2H, m), 3.78-3.90 (4H, m), 2.84-3.08 (8H, m), 1.85-1.98 (2H, m), 1.31-1.41 (2H, m), 1.28 (6H, d, J = 6.8 Hz); LCMS: 100%, MS (ESI): m/z 551.2 [M + H]$^+$ |
| 204 | 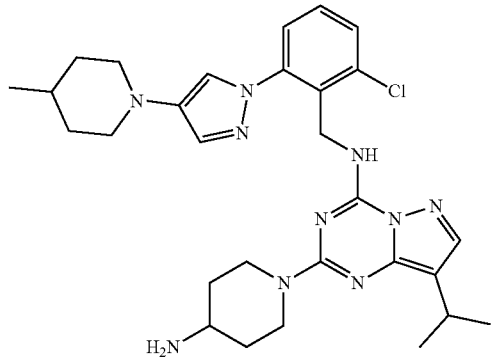 [SMILES: CC1CCN(c2cnn(-c3cccc(Cl)c3CNc3nc(N4CCC(N)CC4)nc4c(C(C)C)cnn34)c2)CC1] | white powder; $^1$H-NMR (CDCl$_3$, 400 MHz): δ 7.58 (1H, s), 7.56 (1H, s), 7.38-7.42 (1H, m), 7.28-7.32 (1H, m), 7.19-7.25 (2H, m), 7.14 (1H, s), 4.87 (2H, d, J = 6.0 Hz), 4.70-4.80 (2H, m), 3.28-3.35 (2H, m), 2.87-3.06 (4H, m), 2.49-2.59 (2H, m), 1.90-2.00 (2H, m), 1.68-1.72 (2H, m), 1.24-1.43 (11H, m), 0.98 (3H, d, J = 7.2 Hz); LCMS: 100%, MS (ESI): m/z 563.3 [M + H]$^+$ |
| 205 | 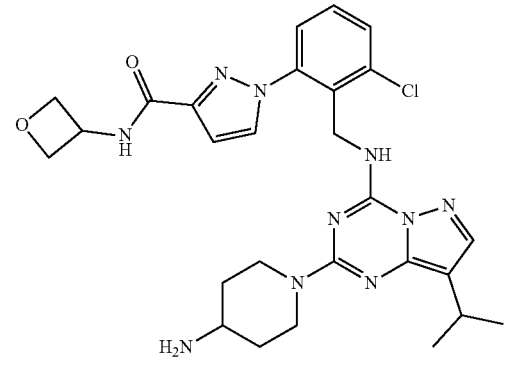 [SMILES: CC(C)c1cnn2c(NCc3c(Cl)cccc3-n3ccc(C(=O)NC4COC4)n3)nc(N3CCC(N)CC3)nc12] | white powder; $^1$H-NMR (CDCl$_3$, 400 MHz): δ 7.64 (1H, d, J = 2.4 Hz), 7.62 (1H, s), 7.56-7.62 (1H, m), 7.38-7.43 (1H, m), 7.34-7.37 (1H, m), 6.94 (1H, d, J = 2.4 Hz), 6.73-6.76 (1H, m), 4.77-4.94 (2H, m), 4.42-4.71 (4H, m), 4.33-4.39 (1H, m), 3.98 (1H, dd, J = 12.0, 3.6 Hz), 3.67 (1 H, dd, J = 12.0, 4.4 Hz), 2.83-3.09 (4H, m), 1.84-1.88 (2H, m), 1.27-1.33 (8 H, m); LCMS: 91.5%, MS (ESI): m/z 565.2 [M + H]$^+$ |

TABLE 11-continued

Summarized compounds 1-279 in terms of their structures and corresponding characteristics.

| # cpds | Structure | Characterization Data |
|---|---|---|
| 206 | 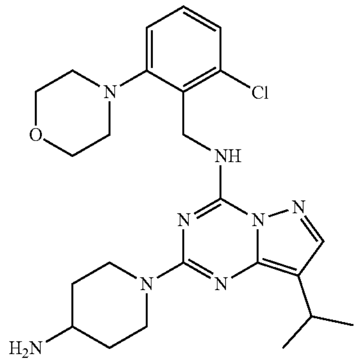 [SMILES: CC(C)c1cnn2c(NCc3c(Cl)cccc3N3CCOCC3)nc(N3CCC(N)CC3)nc12] | white powder; $^1$H-NMR (CDCl$_3$, 400 MHz): δ 7.58 (1H, s), 7.30 (1H, t, J = 5.2 Hz), 7.17-7.26 (2H, m), 7.10 (1H, d, J = 7.2 Hz), 5.01 (2H, d, J = 5.6 Hz), 4.76-4.91 (2H, m), 3.84-3.97 (4H, m), 2.89-3.07 (8H, m), 1.86-1.97 (2H, m), 1.25-1.40 (8H, m); LCMS: 100%, MS (ESI): m/z 485.2 [M + H]$^+$ |
| 207 | 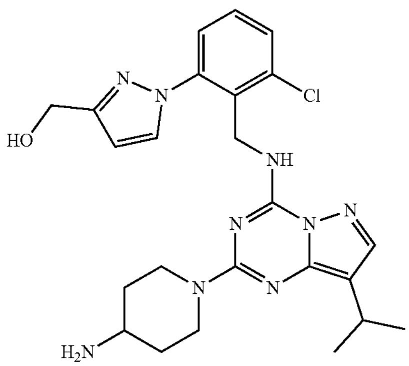 [SMILES: CC(C)c1cnn2c(NCc3c(Cl)cccc3-n3ccc(CO)n3)nc(N3CCC(N)CC3)nc12] | white powder; $^1$H-NMR (CDCl$_3$, 400 MHz): δ 8.47 (1H, brs), 7.62-7.65 (2H, m), 7.43-7.52 (1H, m), 7.29-7.33 (1H, m), 7.18-7.24 (1H, m), 6.41 (1H, s), 4.78-4.85 (6H, m), 3.20-3.30 (1H, m), 2.90-3.06 (3H, m), 2.00-2.05 (2H, m), 1.48-1.54 (2H, m), 1.19-1.34 (6H, m); LCMS: 97.4%, MS (ESI): m/z 518.1 [M + Na]$^+$ |
| 208 | 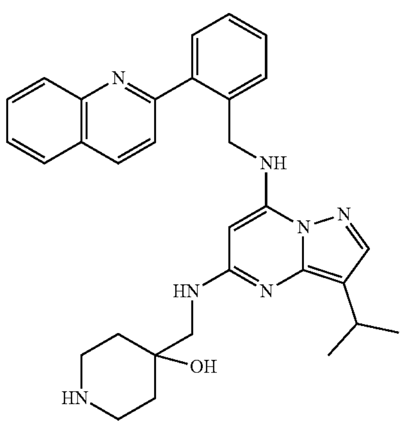 [SMILES: CC(C)c1cnn2c(NCc3ccccc3-c3ccc4ccccc4n3)cc(NCC3(O)CCNCC3)nc12] | white powder; $^1$H-NMR (CDCl$_3$, 400 MHz): δ 8.44 (1H, d, J = 8.8 Hz), 8.25 (1H, d, J = 8.0 Hz), 7.98 (1H, s), 7.85 (1H, d, J = 7.2 Hz), 7.76 (1H, t, J = 6.4 Hz), 7.35-7.70 (7H, m), 4.95-5.34 (2H, m), 4.44-4.64 (2H, m), 3.19-3.78 (6H, m), 2.95-3.13 (1H, m), 1.78-1.91 (4H, m), 1.24-1.29 (6H, m); LCMS: 97.1%, MS (ESI): m/z 522.3 [M + H]$^+$ |
| 209 | 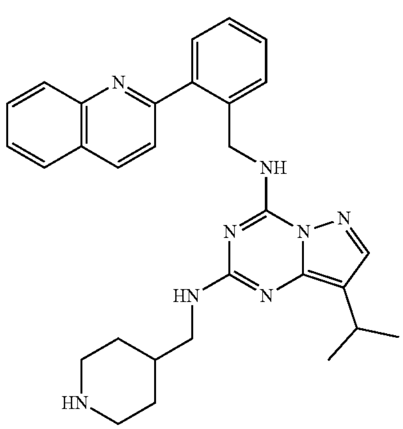 [SMILES: CC(C)c1cnn2c(NCc3ccccc3-c3ccc4ccccc4n3)nc(NCC3CCNCC3)nc12] | white powder; $^1$H-NMR (CDCl$_3$, 400 MHz): δ 9.26 (1H, brs), 8.62 (1H, d, J = 8.4 Hz), 8.30 (1H, d, J = 8.4 Hz), 7.88 (1H, d, J = 8.0 Hz), 7.80 (1H, t, J = 7.6 Hz), 7.68-7.75 (2H, m), 7.56-7.67 (3H, m), 7.40-7.45 (2H, m), 5.11 (1H, brs), 4.72 (2H, s), 3.40-3.45 (4H, m), 3.00-3.05 (1H, m), 2.85-2.90 (2H, m), 1.97-2.05 (3H, m), 1.53-1.69 (2H, m), 1.29 (6H, d, J = 6.8 Hz); LCMS: 100%, MS (ESI): m/z 507.3 [M + H]$^+$ |

TABLE 11-continued

Summarized compounds 1-279 in terms of their structures and corresponding characteristics.

| # cpds | Structure | Characterization Data |
|---|---|---|
| 210 | 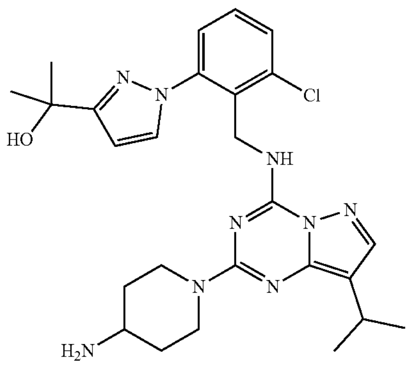 [SMILES: CC(C)c1cnn2c(NCc3c(Cl)cccc3-n3ccc(C(C)(C)O)n3)nc(N3CCC(N)CC3)nc12] | white powder; ¹H-NMR (CDCl₃, 400 MHz): δ 8.86 (1H, t, J = 6.0 Hz), 7.61-7.69 (2H, m), 7.48 (1H, d, J = 8.0 Hz), 7.32 (1H, t, J = 8.0 Hz), 7.22 (1H, d, J = 8.0 Hz), 6.39 (1H, d, J = 2.5 Hz), 4.73-4.95 (4H, m), 2.89-3.06 (4H, m), 1.85-1.95 (2H, m), 1.65 (6H, s), 1.29-1.38 (2H, m) 1.26 (6H, d, J = 7.0 Hz); LCMS: 94.9%, MS (ESI): m/z 524.1 [M + H]⁺ |
| 211 | 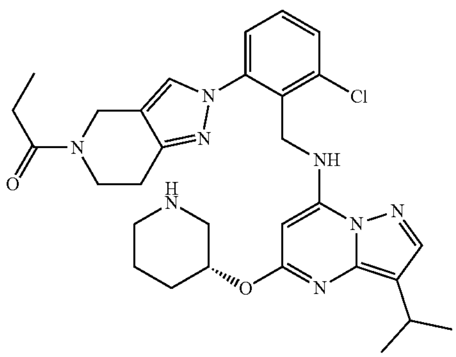 [SMILES: CCC(=O)N1CCc2nn(-c3cccc(Cl)c3CNc3cc(O[C@@H]4CCCNC4)nc4c(C(C)C)cnn34)cc2C1] | (3R); white powder; ¹H-NMR (CDCl₃, 400 MHz): δ 7.64-7.72 (1H, m), 7.47-7.52 (1H, m), 7.34-7.44 (2H, m), 7.27 (1H, d, J = 1.0 Hz), 6.78 (0.7H, t, J = 6.0 Hz) 6.56 (0.3H, t, J = 5.5 Hz), 5.28-5.39 (1H, m) 5.09-5.25 (1H, m), 4.46-4.79 (4H, m), 3.68-4.02 (2H, m), 3.20-3.27 (1H, m), 3.05-3.13 (1H, m), 2.78-3.02 (5H, m) 2.35-2.52 (2H, m), 2.01-2.10 (2H, m), 1.75-1.91 (1H, m) 1.53-1.66 (1H, m), 1.30 (6H, d, J = 6.5 Hz), 1.17-1.23 (3H, m); LCMS: 100%, MS (ESI): m/z 577.2 [M + H]⁺ |
| 212 | 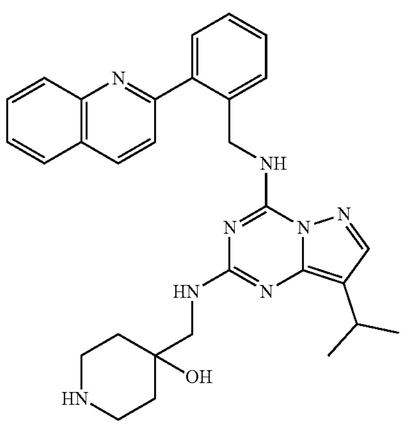 [SMILES: CC(C)c1cnn2c(NCc3ccccc3-c3ccc4ccccc4n3)nc(NCC3(O)CCNCC3)nc12] | white powder; ¹H-NMR (CDCl₃, 400 MHz): δ 9.28 (1H, brs), 8.56 (1H, d, J = 8.4 Hz), 8.25 (1H, d, J = 8.4 Hz), 7.82 (1H, d, J = 7.6 Hz), 7.63-7.77 (3H, m), 7.51-7.63 (3H, m), 7.38-7.42 (2H, m), 5.20 (1H, brs), 4.65 (2H, d, J = 5.6 Hz), 3.22-3.53 (6H, m), 2.88-3.01 (1H, m), 1.88-2.00 (4H, m), 1.21 (6H, d, J = 6.8 Hz); LCMS: 100%, MS (ESI): m/z 523.2 [M + H]⁺ |
| 213 | 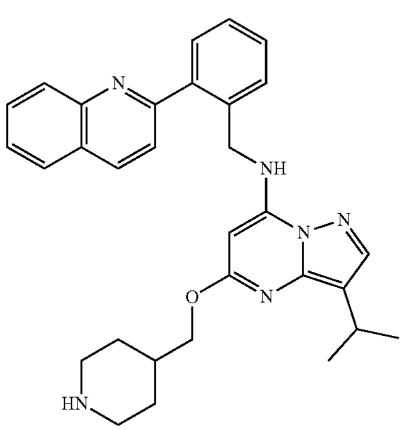 [SMILES: CC(C)c1cnn2c(NCc3ccccc3-c3ccc4ccccc4n3)cc(OCC3CCNCC3)nc12] | white powder; ¹H-NMR (CDCl₃, 400 MHz): δ 8.51 (1H, d, J = 8.5 Hz), 8.22-8.31 (2H, m), 7.87 (1H, d, J = 7.5 Hz), 7.73-7.81 (2H, m), 7.68 (1H, d, J = 9.0 Hz), 7.54-7.64 (3H, m), 7.38-7.49 (2H, m), 5.51 (1H, s), 4.56 (2H, d, J = 7.0 Hz), 4.25 (2H, d, J = 8.5 Hz), 3.34-3.43 (2H, m), 3.07-3.17 (1H, m), 2.76-2.88 (2H, m), 1.93-2.01 (3H, m), 1.55-1.70 (2H, m), 1.33 (7 H, d, J = 7.0 Hz); LCMS: 100%, MS (ESI): m/z 529.2 [M + Na]⁺ |

TABLE 11-continued

Summarized compounds 1-279 in terms of their structures and corresponding characteristics.

| # cpds | Structure | Characterization Data |
|---|---|---|
| 214 | 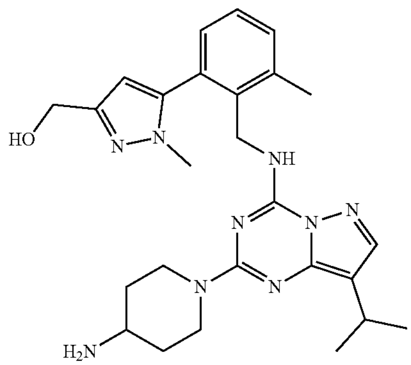 [SMILES: Cc1cccc(-c2cc(CO)nn2C)c1CNc1nc(N2CCC(N)CC2)nc2c(C(C)C)cnn12] | white powder; $^1$H-NMR (CDCl$_3$, 400 MHz): δ 7.56 (1H, s), 7.28-7.35 (2H, m), 7.08 (1H, dd, J = 6.4, 2.4 Hz), 6.07-6.14 (1H, m), 6.05 (1H, s), 4.65-4.75 (2H, m), 4.56-4.61 (4H, m), 3.58 (3H, s), 3.09-3.23 (1H, m), 2.84-3.06 (3H, m), 2.5 (3H, s), 1.96-2.04 (2H, m), 1.43-1.57 (2H, m), 1.27 (6H, d, J = 6.8 Hz); LCMS: 100%, MS (ESI): m/z 490.2 [M + H]$^+$ |
| 215 | 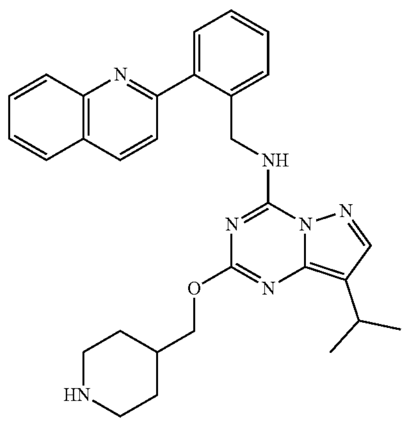 [SMILES: CC(C)c1cnn2c(NCc3ccccc3-c3ccc4ccccc4n3)nc(OCC3CCNCC3)nc12] | white powder; $^1$H-NMR (CDCl$_3$, 400 MHz): δ 9.78 (1H, brs), 8.66 (1H, d, J = 8.8 Hz), 8.32 (1H, d, J = 8.0 Hz), 7.89 (1H, d, J = 8.4 Hz), 7.85 (1H, s), 7.80 (1H, t, J = 7.6 Hz), 7.65-7.75 (2H, m), 7.57-7.67 (2H, m), 7.42-7.49 (2H, m), 4.78 (2H, d, J = 5.6 Hz), 4.31 (2H, d, J = 7.2 Hz), 3.35-3.40 (2H, m), 3.08-3.16 (1H, m), 2.80-2.90 (2H, m), 2.18-2.24 (1H, m), 2.10-2.20 (2H, m), 1.53-1.67 (2H, m), 1.32 (6H, d, J = 7.2 Hz); LCMS: 100%, MS (ESI): m/z 530.3 [M + H]$^+$ |
| 216 | 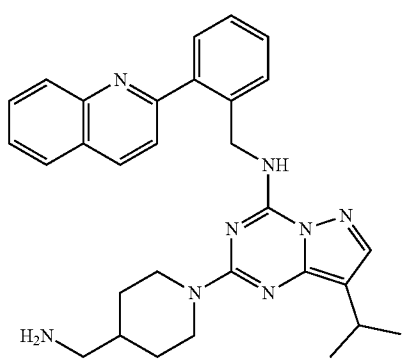 [SMILES: CC(C)c1cnn2c(NCc3ccccc3-c3ccc4ccccc4n3)nc(N3CCC(CN)CC3)nc12] | white powder; $^1$H-NMR (CDCl$_3$, 400 MHz): δ 9.08 (1H, brt, J = 6.4 Hz), 8.62 (1H, d, J = 8.8 Hz), 8.27 (1H, d, J = 8.8 Hz), 7.86 (1H, d, J = 8.4 Hz), 7.76-7.83 (1H, m), 7.67-7.73 (2H, m), 7.62-7.66 (1H, m), 7.55-7.61 (1H, m), 7.36-7.44 (2H, m), 4.90-5.02 (2H, m), 4.72 (2H, d, J = 6.4 Hz), 2.99-3.08 (1H, m), 2.85-2.96 (2H, m), 2.75 (2H, d, J = 6.8 Hz), 1.69-1.93 (3H, m), 1.23-1.30 (8H, m); LCMS: 100%, MS (ESI): m/z 507.2 [M + H]$^+$ |
| 217 | 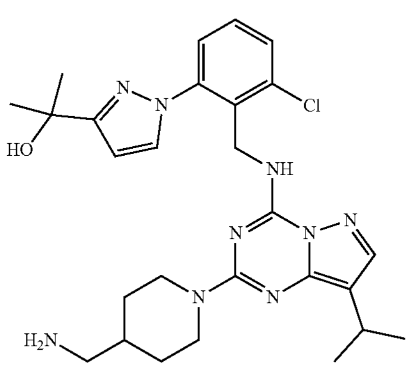 [SMILES: CC(C)c1cnn2c(NCc3c(Cl)cccc3-n3ccc(C(C)(C)O)n3)nc(N3CCC(CN)CC3)nc12] | white powder; $^1$H-NMR (CDCl$_3$, 400 MHz): δ 8.75-8.89 (1H, m), 7.57-7.68 (2H, m), 7.60-7.65 (1H, m), 7.26-7.33 (1H, m), 7.18-7.23 (1H, m), 6.38 (1H, d, J = 2.8 Hz), 4.88-5.01 (2H, m), 4.82 (2H, d, J = 6.0 Hz), 2.96-3.01 (1H, m), 2.82-2.92 (2H, m), 2.7 (2H, d, J = 6.4 Hz), 1.78-1.86 (2H, m), 1.60-1.77 (7H, m), 1.22-1.29 (8H, m); LCMS: 94.8%, MS (ESI): m/z 538.4 [M + H]$^+$ |

TABLE 11-continued

Summarized compounds 1-279 in terms of their structures and corresponding characteristics.

| # cpds | Structure | Characterization Data |
| --- | --- | --- |
| 218 | 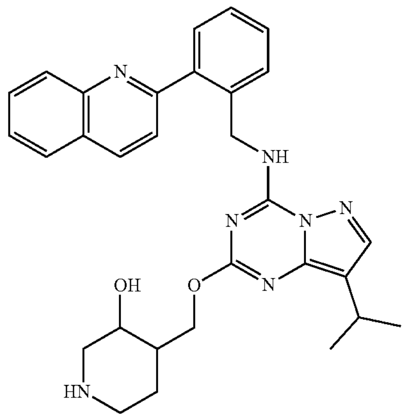 [SMILES: CC(C)c1cnn2c(NCc3ccccc3-c3ccc4ccccc4n3)nc(OCC3CCNCC3O)nc12] | Mixture of 2 trans-isomers; white powder; $^1$H-NMR (CD$_3$OD, 400 MHz): δ 9.03 (1H, d, J = 8.4 Hz), 8.29 (1H, d, J = 8.0 Hz), 8.21-8.26 (1H, m), 8.11-8.19 (2H, m), 7.93-8.02 (1H, m), 7.77-7.85 (2H, m), 7.61-7.77 (3H, m), 4.97-5.08 (2H, m), 4.56-4.63 (1H, m), 4.38-4.47 (1H, m), 3.75-3.86 (1H, m), 3.35-3.46 (2H, m), 2.93-3.05 (2H, m), 2.77-2.87 (1H, m), 1.95-2.16 (2H, m), 1.64-1.78 (1H, m), 1.27 (6 H, d, J = 6.8 Hz); LCMS: 100%, MS (ESI): m/z 546.2 [M + Na]$^+$ |
| 219 | 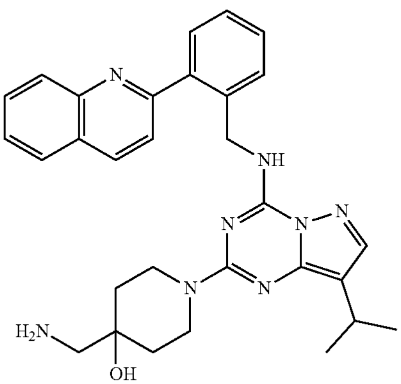 [SMILES: CC(C)c1cnn2c(NCc3ccccc3-c3ccc4ccccc4n3)nc(N3CCC(O)(CN)CC3)nc12] | white powder; $^1$H-NMR (CDCl$_3$, 400 MHz): δ 9.10 (1 H, brt, J = 6.0 Hz), 8.62 (1H, d, J = 8.4 Hz), 8.27 (1H, d, J = 8.8 Hz), 7.87 (1H, d, J = 8.4 Hz), 7.80 (1H, t, J = 8.0 Hz), 7.67-7.72 (2H, m), 7.62-7.66 (1H, m), 7.55-7.62 (2H, m), 7.35-7.44 (2H, m), 4.73 (2H, d, J = 6.4 Hz), 4.57-4.68 (2H, m), 3.37-3.51 (2H, m), 2.98-3.10 (1H, m), 2.78 (2H, s), 1.66-1.79 (2H, m), 1.52-1.65 (2H, m), 1.28 (6H, d, J = 7.2 Hz); LCMS: 100%, MS (ESI): m/z 523.1 [M + H]$^+$ |
| 220 | 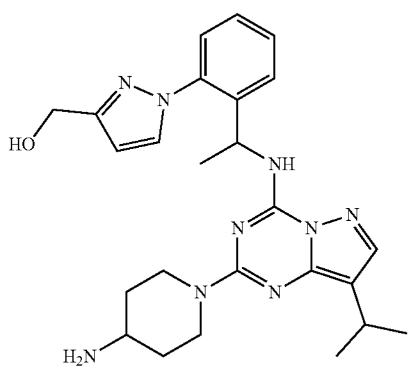 [SMILES: CC(C)c1cnn2c(NC(C)c3ccccc3-n3ccc(CO)n3)nc(N3CCC(N)CC3)nc12] | Racemic mixture; white powder; $^1$H-NMR (CDCl$_3$, 400 MHz): δ 9.16 (1H, d, J = 8.8 Hz), 7.60-7.70 (2H, m), 7.47-7.52 (2H, m), 7.32-7.42 (2H, m), 7.24-7.25 (2H, m), 6.33-6.41 (1H, m), 5.43-5.55 (1H, m), 4.86-4.93 (1H, m), 4.71-4.83 (3H, m), 2.86-2.98 (4H, m), 1.89-1.98 (2H, m), 1.23-1.26 (8H, m), 1.19 (3H, d, J = 7.09 Hz); LCMS: 100%, MS (ESI): m/z 476.2 [M + H]$^+$ |
| 221 | 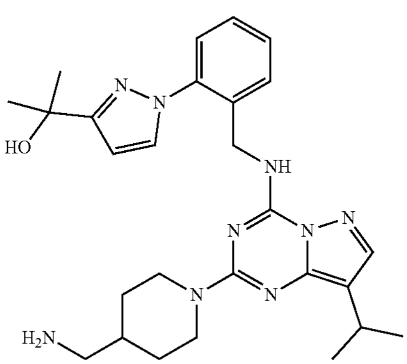 [SMILES: CC(C)c1cnn2c(NCc3ccccc3-n3ccc(C(C)(C)O)n3)nc(N3CCC(CN)CC3)nc12] | white powder; $^1$H-NMR (CDCl$_3$, 400 MHz): δ 8.95-9.10 (1H, m), 7.68 (1H, d, J = 2.4 Hz), 7.63 (1H, s), 7.56-7.61 (1H, m), 7.32-7.38 (2H, m), 7.26-7.31 (1H, m), 6.38 (1H, d, J = 2.8 Hz), 4.86-4.96 (2H, m), 4.57-4.64 (2H, m), 2.95-3.04 (1H, m), 2.83-2.93 (2H, m), 2.65 (2H, d, J = 6.4 Hz), 1.78-1.87 (2H, m), 1.57-1.70 (7H, m), 1.20-1.29 (8H, m); LCMS: 97.5%, MS (ESI): m/z 526.2 [M + Na]$^+$ |

TABLE 11-continued

Summarized compounds 1-279 in terms of their structures and corresponding characteristics.

| # cpds | Structure | Characterization Data |
|---|---|---|
| 222 | 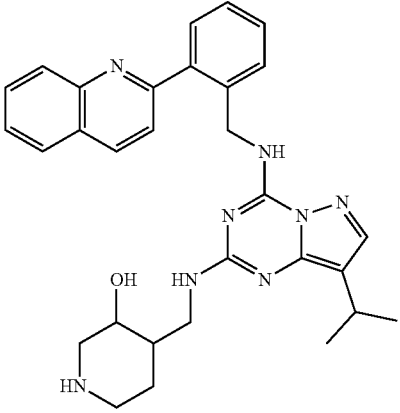 [SMILES: CC(C)c1cnn2c(NCc3ccccc3-c3ccc4ccccc4n3)nc(NCC3CCNCC3O)nc12] | Mixture of 2 trans-isomers; white powder; $^1$H-NMR (CDCl$_3$, 400 MHz): δ 9.04 (1H, d, J = 8.80 Hz), 8.29 (2H, t, J = 8.0 Hz), 8.09-8.22 (2 H, m), 7.94-8.04 (1H, m), 7.65-7.82 (5H, m), 5.07-5.15 (2H, m), 3.67-3.80 (2H, m), 3.54-3.61 (1H, m), 3.34-3.45 (2H, m), 2.86-3.00 (2H, m), 2.73-2.78 (1H, m), 2.03-2.08 (1H, m), 1.86-1.92 (1H, m), 1.51-1.67 (1H, m), 1.26 (6H, d, J = 7.2 Hz); LCMS: 99.6%, MS (ESI): m/z 523.2 [M + H]$^+$ |
| 223 | 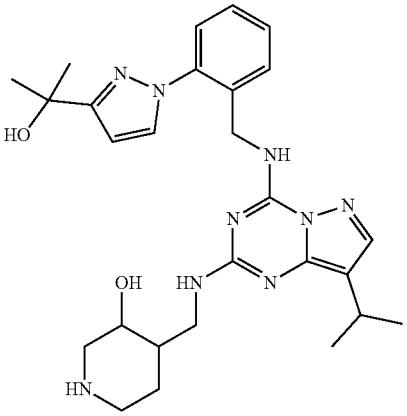 [SMILES: CC(C)c1cnn2c(NCc3ccccc3-n3ccc(C(C)(C)O)n3)nc(NCC3CCNCC3O)nc12] | Mixture of 2 trans-isomers; white powder; $^1$H-NMR (CDCl$_3$, 400 MHz): δ 9.25-9.38 (1H, m), 7.66-7.67 (2H, m), 7.58-7.59 (1H, d, J = 4.0 Hz), 7.35-7.37 (2H, m), 7.27-7.28 (1H, m), 6.36-6.40 (1H, m), 5.16-5.23 (1H, m), 4.52-3.63 (2H, m), 4.15-4.22 (1H, m), 3.50-3.55 (1H, m), 3.38-3.40 (2H, m), 3.29-3.32 (1H, m), 2.96-3.05 (1H, m), 2.73-2.77 (1H, m), 2.63-2.66 (1H, m), 1.67-1.75 (2H, m), 1.66-1.67 (6H, m), 1.20-1.24 (6H, d, J = 4.8 Hz); LCMS: 100%, MS (ESI): m/z 520.2 [M + H]$^+$ |
| 224 | 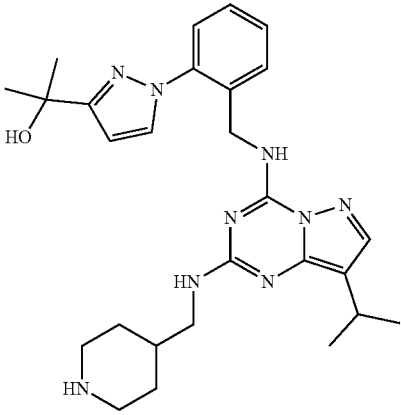 [SMILES: CC(C)c1cnn2c(NCc3ccccc3-n3ccc(C(C)(C)O)n3)nc(NCC3CCNCC3)nc12] | white powder; $^1$H NMR (500 MHz, CDCl$_3$): δ 9.07-9.18 (1H, m), 7.68 (1H, d, J = 2.0 Hz), 7.66 (1H, s), 7.54-7.61 (1H, m), 7.33-7.43 (2H, m), 7.28-7.32 (1H, m), 6.39 (1H, d, J = 2.5 Hz), 5.03 (1H, brs), 4.55-4.65 (2H, m), 3.36-3.43 (2H, m), 3.30-3.35 (2H, m), 2.95-3.02 (1H, m), 2.71-2.80 (1H, m), 1.83-1.95 (3H, m), 1.68 (6H, s), 1.43-1.56 (2H, m), 1.24 (6H, d, J = 7.0 Hz); LCMS: 100%, MS (ESI): m/z 504.2 [M + H]$^+$ |

TABLE 11-continued

Summarized compounds 1-279 in terms of their structures and corresponding characteristics.

| # cpds | Structure | Characterization Data |
|---|---|---|
| 225 | 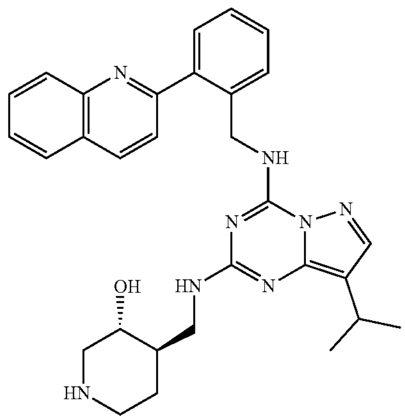 [SMILES: CC(C)c1cnn2c(NCc3ccccc3-c3ccc4ccccc4n3)nc(NC[C@H]3CCNC[C@@H]3O)nc12] | (3R, 4R); white powder; $^1$H-NMR (CD$_3$OD, 400 MHz): δ 8.30-8.39 (2H, m), 7.94 (1H, d, J = 8.0 Hz), 7.70-7.83 (2H, m), 7.58-7.69 (4H, m), 7.45-7.51 (2H, m), 4.55-4.75 (2H, m), 3.75-4.06 (1H, m), 3.35-3.40 (1H, m), 3.08-3.19 (2H, m), 2.90-3.06 (2H, m), 2.52-2.69 (1H, m), 2.38-2.50 (1H, m), 1.68-180 (1 H, m), 1.36-1.60 (2H, m), 1.20-1.31 (6H, m); LCMS: 100%, MS (ESI): m/z 522.3 [M + H]$^+$ |
| 226 | 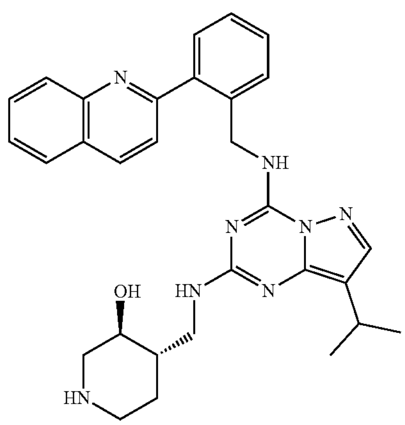 [SMILES: CC(C)c1cnn2c(NCc3ccccc3-c3ccc4ccccc4n3)nc(NC[C@@H]3CCNC[C@H]3O)nc12] | (3S, 4S); white powder; $^1$H-NMR (CD$_3$OD, 400 MHz): δ 8.30-8.39 (2H, m), 7.94 (1H, d, J = 8.0 Hz), 7.70-7.83 (2H, m), 7.58-7.69 (4H, m), 7.45-7.51 (2H, m), 4.55-4.75 (2H, m), 3.75-4.06 (1H, m), 3.35-3.40 (1H, m), 3.08-3.19 (2H, m), 2.90-3.06 (2H, m), 2.52-2.69 (1H, m), 2.38-2.50 (1H, m), 1.68-180 (1 H, m), 1.36-1.60 (2H, m), 1.20-1.31 (6H, m); LCMS: 100%, MS (ESI): m/z 522.3 [M + H]$^+$ |
| 227 | 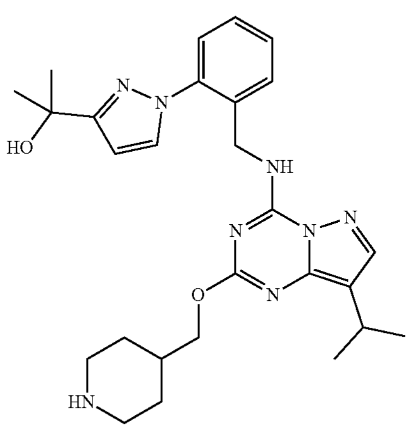 [SMILES: CC(C)c1cnn2c(NCc3ccccc3-n3ccc(C(C)(C)O)n3)nc(OCC3CCNCC3)nc12] | white powder; $^1$H NMR (500 MHz, CDCl$_3$): δ 9.55-9.71 (1H, m), 7.77 (1H, s), 7.70 (1H, d, J = 2.5 Hz), 7.67 (1H, dd, J = 7.5, 1.5 Hz), 7.34-7.43 (2H, m), 7.27-7.31 (1H, m), 6.39 (1H, d, J = 2.5 Hz), 4.63-4.72 (2H, m), 4.26 (2H, d, J = 7.0 Hz), 3.17-3.26 (2H, m), 3.00-3.12 (1H, m), 2.68-2.77 (2H, m), 2.04-2.13 (1H, m), 1.92-1.985 (2H, m), 1.68 (6H, s), 1.35-1048 (2H, m), 1.27 (6H, d, J = 6.5 Hz); LCMS: 100%, MS (ESI): m/z 527.2 [M + Na]$^+$ |

TABLE 11-continued

Summarized compounds 1-279 in terms of their structures and corresponding characteristics.

| # cpds | Structure | Characterization Data |
|---|---|---|
| 228 | 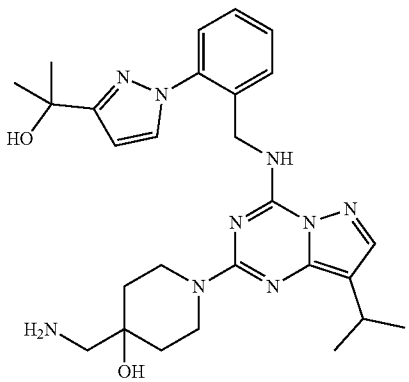 [SMILES: CC(C)c1cnn2c(NCc3ccccc3-n3ccc(C(C)(C)O)n3)nc(N3CCC(O)(CN)CC3)nc12] | white powder; $^1$H NMR (400 MHz, CDCl$_3$): δ 9.00-9.05 (1H, m), 7.68 (1H, d, J = 2.0 Hz), 7.63 (1H, s), 7.59 (1H, d, J = 7.2 Hz), 7.31-7.4 (2H, m), 7.27-7.3 (1H, m), 6.39 (1H, d, J = 2.4 Hz), 4.53-4.65 (4H, m), 3.35-3.49 (2H, m), 2.93-3.05 (1H, m), 2.65 (2H, s), 1.69 (6H, s), 1.6-1.65 (2H, m), 1.49-1.56 (2H, m), 1.25 (6H, d, J = 6.8 Hz); LCMS: 100%, MS (ESI): m/z 520.2 [M + H]$^+$ |
| 229 | 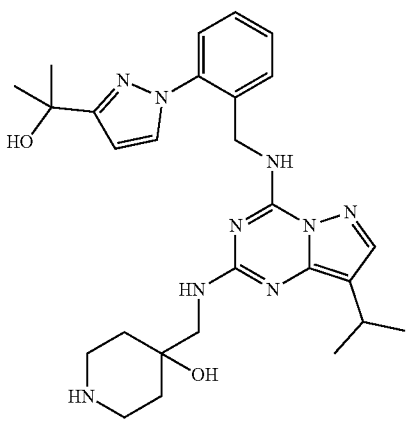 [SMILES: CC(C)c1cnn2c(NCc3ccccc3-n3ccc(C(C)(C)O)n3)nc(NCC3(O)CCNCC3)nc12] | white powder; $^1$H NMR (400 MHz, CDCl$_3$): δ 9.31-9.48 (1H, m), 7.65-7.75 (2H, m), 7.59-7.65 (1H, m), 7.33-7.43 (2H, m), 7.27-7.30 (1H, m), 6.39 (1H, s), 5.37-5.37 (1H, m), 4.60 (2H, s), 3.41-3.59 (2H, m), 3.10-3.22 (2H, m), 2.95-3.06 (3H, m), 1.6-1.81 (10H, m), 1.19-1.24 (6H, d, J = 7.2 Hz); LCMS: 100%, MS (ESI): m/z 520.2 [M + H]$^+$ |
| 230 | 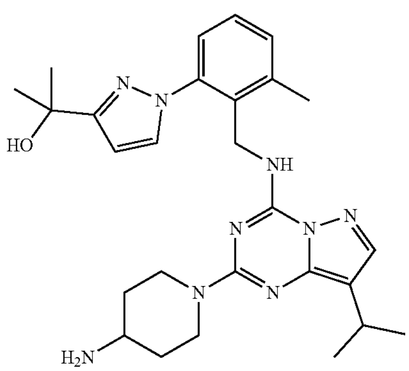 [SMILES: Cc1cccc(-n2ccc(C(C)(C)O)n2)c1CNc1nc(N2CCC(N)CC2)nc2c(C(C)C)cnn12] | white powder; $^1$H NMR (400 MHz, CDCl$_3$): δ 9.15-9.26 (1H, m), 7.64-7.69 (2H, m), 7.25-7.29 (2H, m), 7.10-7.17 (1H, m), 6.37 (1H, d, J = 2.8 Hz), 4.75-4.85 (2H, m), 4.60 (2H, d, J = 5.6 Hz), 2.89-3.06 (4H, m), 2.65 (3H, s), 1.86-1.94 (2H, m), 1.67 (6H, s), 1.30-1.40 (2H, m), 1.27 (6H, d, J = 6.8 Hz); LCMS: 100%, MS(ESI): m/z 504.3 [M + H]$^+$ |
| 231 | 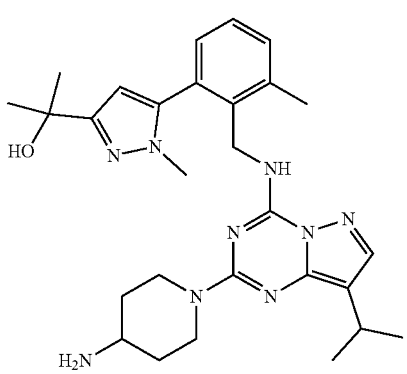 | White powder; $^1$H NMR (CDCl$_3$): δ 7.54-7.58 (1H, m), 7.28-7.33 (2H, m), 7.09-7.14 (1H, m), 6.03-6.11 (2H, m), 4.65-4.79 (2H, m), 4.48-4.63 (2H, m), 3.61 (3H, s), 2.86-3.07 (4H, m), 2.50 (3H, s), 1.89-1.98 (2H, m), 1.37-1.49 (8H, m), 1.26 (6H, d, J = 6.8 Hz); LCMS: 100%, MS (ESI): m/z 518.3 [M + H]$^+$ |

TABLE 11-continued

Summarized compounds 1-279 in terms of their structures and corresponding characteristics.

| # cpds | Structure | Characterization Data |
|---|---|---|
| 232 | 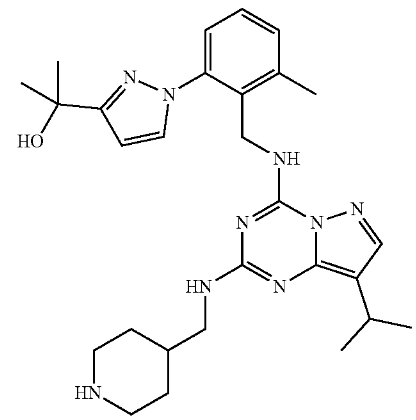 [SMILES: Cc1cccc(-n2ccc(C(C)(C)O)n2)c1CNc1nc(NCC2CCNCC2)nc2c(C(C)C)cnn12] | white powder; $^1$H NMR (400 MHz, CDCl$_3$): δ 9.15-9.35 (1H, m), 7.64-7.66 (2H, m), 7.23-7.30 (2H, m), 7.12-7.15 (1H, m), 6.36 (1H, d, J = 2.4 Hz), 4.98 (1H, brs), 4.58 (2H, d, J = 4.4 Hz), 3.36 (2H, t, J = 6.4 Hz), 3.12-3.13 (2H, m), 2.96-3.03 (1H, m), 2.56-2.64 (m, 5H), 1.77-1.80 (m, 3H), 1.66 (6H, s), 1.20-1.30 (8H, m); LCMS: 100%, MS (ESI): m/z 518.3 [M + H]$^+$ |
| 233 | 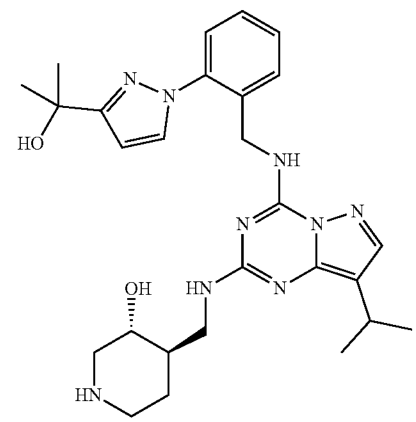 [SMILES: CC(C)c1cnn2c(NCc3ccccc3-n3ccc(C(C)(C)O)n3)nc(NC[C@H]3CCNC[C@@H]3O)nc12] | (3R, 4R); white powder; $^1$H NMR (400 MHz, CDCl$_3$): δ 9.20-9.33 (1H, m), 7.68 (1H, d, J = 2.4 Hz), 7.66 (1H, s), 7.58-7.63 (1H, m), 7.32-7.42 (2H, m) 7.28-7.32 (1H, m), 6.39 (1H, d, J = 2.4 Hz), 5.36 (1H, brs), 4.53-4.65 (2H, m), 4.16-4.32 (1H, m), 3.34-3.45 (1H, m), 3.23-3.28 (1H, m), 3.10-3.18 (1H, m), 2.92-3.07 (2H, m), 2.61-2.68 (1H, m), 2.53-2.58 (1H, m) 1.68 (6H, d, J = 2.4 Hz), 1.50-1.65 (3H, m), 1.20-1.27 (6H, m); LCMS: 100%, MS (ESI): m/z 520.3 [M + H]$^+$ |
| 234 | 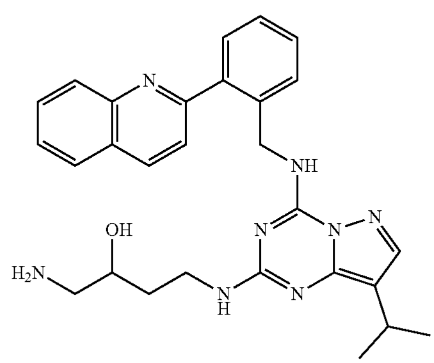 [SMILES: CC(C)c1cnn2c(NCc3ccccc3-c3ccc4ccccc4n3)nc(NCCC(O)CN)nc12] | Racemic mixture; white powder; $^1$H NMR (CDCl$_3$, 400 MHz): δ 9.20-9.31 (1H, m), 8.60 (1H, J = 8.4 Hz, d), 8.23 (1H, J = 8.4 Hz, d), 7.80 (1H, J = 8.0 Hz, d), 7.70-7.76 (1H, m), 7.62-7.68 (2H, m), 7.49-7.62 (3H, m), 7.32-7.41 (2H, m), 4.98-5.12 (1H, m), 4.55-4.74 (2H, m), 3.86-4.02 (1H, m), 3.45-3.60 (1H, m), 3.20-3.37 (1H, m), 2.91-3.08 (1H, m), 2.54-2.75 (2H, m), 1.40-1.65 (2H, m), 1.15-1.31 (6H, m); LCMS: 95.9%, MS (ESI): m/z 497.2 [M + H]$^+$ |
| 235 | 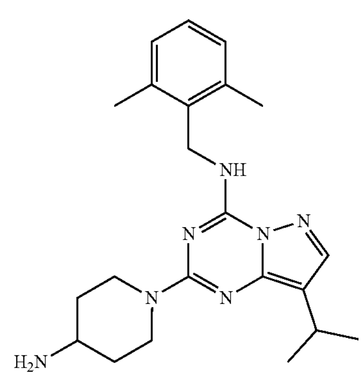 [SMILES: Cc1cccc(C)c1CNc1nc(N2CCC(N)CC2)nc2c(C(C)C)cnn12] | white solid; $^1$H NMR (CDCl$_3$, 400 MHz): δ 7.57 (1H, m), 7.12-7.16 (1H, m), 7.05-7.07 (2H, m), 6.04 (1H, t, J = 4 Hz), 4.79-4.83 (2H, m), 4.74-4.75 (2H, d, J = 5.2 Hz) 2.94-3.06 (4H, m), 2.41 (1H, s), 1.91-1.94 (2H, m), 1.34-1.41 (2H, m), 1.29-1.31 (6H, d, J = 6.8 Hz), LCMS: 100.0%, MS (ESI): m/z 394.2 [M + H]$^+$ |

TABLE 11-continued

Summarized compounds 1-279 in terms of their structures and corresponding characteristics.

| # cpds | Structure | Characterization Data |
|---|---|---|
| 236 | 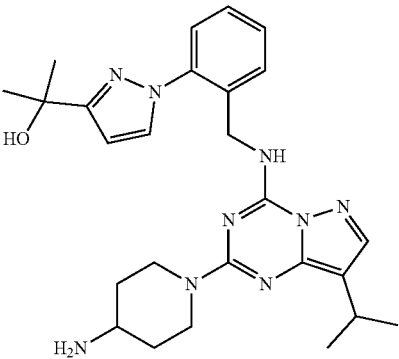 | white powder; $^1$H NMR (400 MHz, CDCl$_3$): δ 9.05 (1 H, t, J = 6.4 Hz), 7.68 (1H, d, J = 2.4 Hz), 7.64 (1H, s), 7.59 (1H, dd, J = 7.2 Hz, 1.6 Hz), 7.27-7.41 (3H, m), 6.39 (1H, d, J = 2.4 Hz), 4.77-4.87 (2H, m), 4.61 (2H, d, J = 6.4 Hz), 2.91-3.07 (4H, m), 1.90-1.98 (2H, m), 1.68 (6H, s), 1.31-1.44 (2H, m), 1.25 (6H, d, J = 6.8 Hz); LCMS: 100%, MS (ESI): m/z 590.3 [M + H]$^+$ |
| 237 | 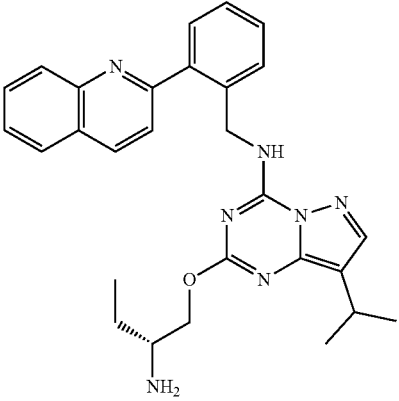 [SMILES: CC[C@@H](N)COc1nc(NCc2ccccc2-c2ccc3ccccc3n2)n2ncc(C(C)C)c2n1] | (3R); white powder; $^1$H-NMR (CDCl3, 400 MHz): δ 9.66-9.78 (1H, m), 8.59 (1H, d, J = 8.0 Hz), 8.24 (1H, d, J = 8.0 Hz), 7.70-7.85 (3H, m), 7.62-7.68 (2H, m), 7.50-7.59 (2H, m), 7.35-7.40 (2H, m), 4.71 (2H, d, J = 4.8 Hz), 4.40-4.50 (1H, m), 4.15-4.25 (1H, m), 3.15-3.26 (1H, m), 2.98-3.10 (1H, m), 1.45-1.68 (1H, m), 1.20-1.26 (6H, m), 1.00 (3H, t, J = 7.2 Hz); LCMS: 98.1%, MS (ESI): m/z 482.2 [M + H]$^+$ |
| 238 | 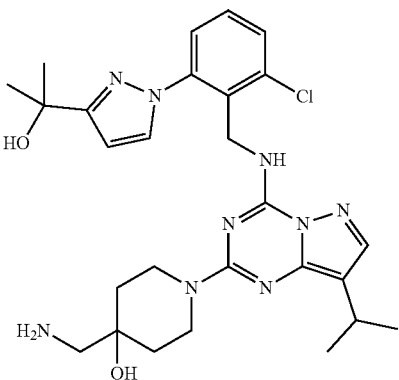 [SMILES: CC(C)c1cnn2c(NCc3c(Cl)cccc3-n3ccc(C(C)(C)O)n3)nc(N3CCC(O)(CN)CC3)nc12] | white powder; $^1$H NMR (400 MHz, CDCl$_3$): δ 8.81 (1H, t, J = 6.0 Hz), 7.57-7.71 (2H, m), 7.45 (1H, d, J = 8.0 Hz), 7.29 (1H, t, J = 8.0 Hz), 7.20 (1H, d, J = 7.6 Hz), 6.39 (1H, d, J = 2.0 Hz), 4.83 (2H, d, J = 6.0 Hz), 4.55-4.65 (2H, m), 3.34-3.46 (2H, m), 2.93-3.05 (1H, m), 2.67 (2H, s), 1.58-1.68 (8H, m), 1.45-1.55 (2H, m), 1.25 (6H, d, J = 7.2 Hz); LCMS: 100%, MS (ESI): m/z 554.2 [M + H]$^+$ |
| 239 | 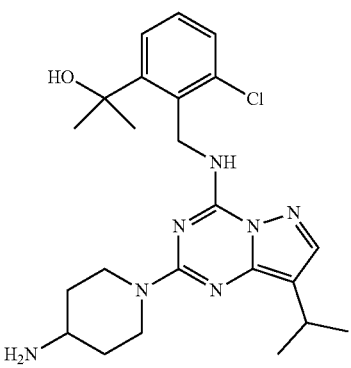 [SMILES: CC(C)c1cnn2c(NCc3c(Cl)cccc3C(C)(C)O)nc(N3CCC(N)CC3)nc12] | white powder; $^1$H NMR (400 MHz, CDCl$_3$): δ ppm 7.55 (1H, s), 7.34 (1H, d, J = 8.0 Hz), 7.28 (1H, d, J = 8.0, Hz), 7.19 (1H, t, J = 8.0 Hz), 6.79 (1H, t, J = 5.6 Hz), 5.27 (2H, d, J = 5.6 Hz), 4.71-4.85 (2H, m), 2.94-3.05 (4H, m), 1.91-1.93 (2H, m), 1.68 (6H, s), 1.31-1.44 (2H, m), 1.27 (6H, d, J = 6.8 Hz); LCMS: 100%, MS(ESI): m/z 458.2 [M + H]$^+$ |

TABLE 11-continued

Summarized compounds 1-279 in terms of their structures and corresponding characteristics.

| # cpds | Structure | Characterization Data |
|---|---|---|
| 240 | 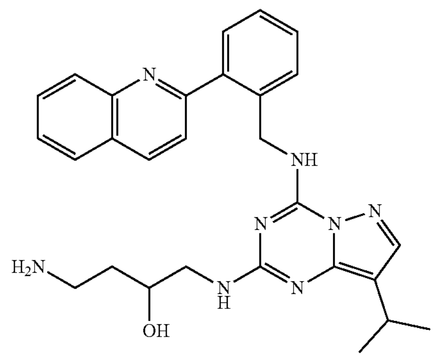 [SMILES: CC(C)c1cnn2c(NCc3ccccc3-c3ccc4ccccc4n3)nc(NCC(O)CCN)nc12] | Racemic mixture; white powder; $^1$H NMR (400 MHz, CDCl$_3$): δ 9.25-9.30 (1H, m), 8.61 (1 H, d, J = 8.4 Hz), 8.26 (1H, d, J = 8.4 Hz), 7.86 (1H, d, J = 8.4 Hz), 7.78 (1 H, t, J = 7.6 Hz), 7.53-7.73 (5H, m), 7.36-7.45 (2H, m), 5.44 (1H, brs), 4.68 (2H, s), 3.95-4.10 (1H, m), 3.54-3.65 (1H, m), 3.40-3.52 (1H, m), 3.08-3.24 (1H, m), 2.93-3.07 (3H, m), 1.65-1.81 (2H, m), 1.26 (6H, d, J = 6.8 Hz); LCMS: 100%, MS (ESI): m/z 497.2 [M + H]$^+$ |
| 241 | 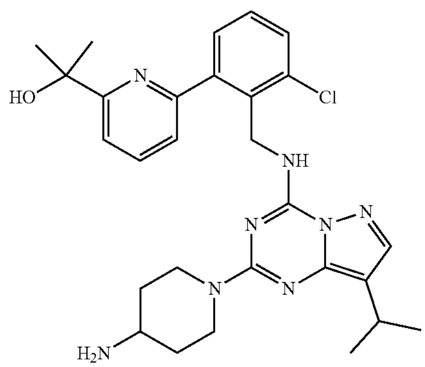 [SMILES: CC(C)c1cnn2c(NCc3c(Cl)cccc3-c3cccc(C(C)(C)O)n3)nc(N3CCC(N)CC3)nc12] | white powder; $^1$H-NMR (CDCl$_3$, 400 MHz): δ 8.32-8.40 (1H, m), 7.73 (1H, t, J = 8.0 Hz), 7.56 (1H, s), 7.39-7.43 (1H, m), 7.35-7.38 (1H, m), 7.27-7.31 (1H, m), 7.23-7.27 (1H, m), 4.82 (2H, d, J = 6.0 Hz), 4.7.-4.78 (2H, m), 2.80-2.99 (4H, m), 1.80-1.85 (2H, m), 1.59 (6 H, s), 1.18-1.23 (8H, m); LCMS: 100%, MS (ESI): m/z 535.2 [M + H]$^+$ |
| 242 | 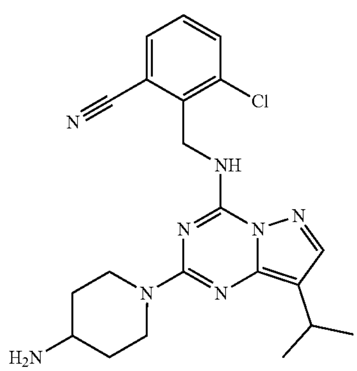 [SMILES: CC(C)c1cnn2c(NCc3c(Cl)cccc3C#N)nc(N3CCC(N)CC3)nc12] | white powder; $^1$H NMR (400 MHz, CDCl$_3$): δ 7.58-7.70 (3H, m), 7.37 (1H, t, J = 8.0 Hz), 6.85-6.94 (1H, m), 5.07 (2H, d, J = 6.0 Hz), 4.79-4.82 (2H, m), 2.89-3.05 (4H, m), 1.87-1.89 (2H, m), 1.25-1.33 (10H, m); LCMS: 95.5%, MS (ESI): m/z 425.1 [M + H]$^+$ |
| 243 | 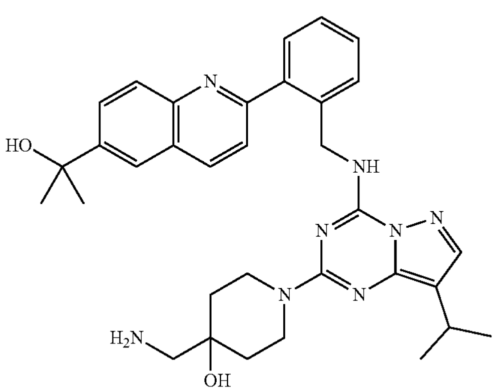 [SMILES: CC(C)c1cnn2c(NCc3ccccc3-c3ccc4cc(C(C)(C)O)ccc4n3)nc(N3CCC(O)(CN)CC3)nc12] | white powder; $^1$H NMR (400 MHz, CDCl$_3$): δ 8.86 (1H, t, J = 6.0 Hz), 8.55 (1H, d, J = 8.8 Hz), 8.26 (1H, d, J = 8.8 Hz), 7.98 (1H, d, J = 1.6 Hz), 7.91 (1H, dd, J = 8.8, 2.0 Hz), 7.66-7.69 (2H, m), 7.63-7.66 (1H, m), 7.58-7.62 (1H, m), 7.37-7.44 (2H, m), 4.74 (2H, d, J = 6.0 Hz), 4.53-4.56 (2H, m), 3.32-3.38 (2H, m), 3.0-3.07 (1H, m), 2.67 (2H, s), 1.71 (6H, s), 1.60-1.63 (3H, m), 1.50-1.52 (3H, m), 1.29 (6 H, d, J = 6.8 Hz); LCMS: 100%, MS (ESI): m/z 581.2 [M + H]$^+$ |

TABLE 11-continued

Summarized compounds 1-279 in terms of their structures and corresponding characteristics.

| # cpds | Structure | Characterization Data |
|---|---|---|
| 244 | 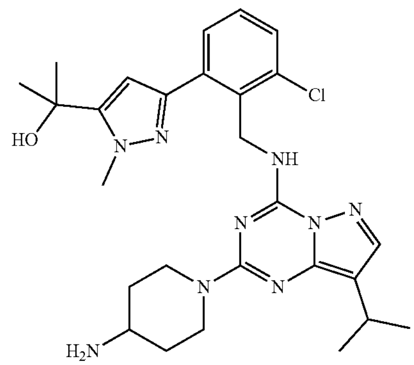 [SMILES: CC(C)c1cnn2c(NCc3c(Cl)cccc3-c3cc(C(C)(C)O)n(C)n3)nc(N3CCC(N)CC3)nc12] | white powder; $^1$H NMR (400 MHz, CDCl$_3$): δ 7.55-7.64 (2H, m), 7.31-7.40 (2H, m), 7.19-7.25 (1H, m), 6.14 (1H, s), 5.04 (2H, d, J = 6.4 Hz), 4.76-4.86 (2H, m), 4.12 (3H, s), 2.85-3.07 (4H, m), 1.83-1.95 (2H, m), 1.6 (6H, s), 1.30-1.40 (2H, m), 1.26 (6H, d, J = 7.2 Hz); LCMS: 98.0%, MS (ESI): m/z 538.2 [M + H]$^+$ |
| 245 | 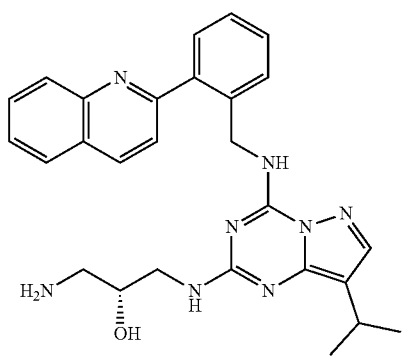 | (3R); white powder; $^1$H-NMR (CDCl$_3$, 400 MHz): δ 9.28-9.46 (1H, m), 8.65 (1H, d, J = 8.4 Hz), 8.33 (1H, d, J = 8.8 Hz), 7.91 (1H, d, J = 8.0 Hz), 7.83 (1H, t, J = 8.0 Hz), 7.72-7.78 (2H, m), 7.59-7.70 (3H, m), 7.42-7.52 (2H, m), 5.08-5.17 (1H, m), 4.74 (2H, d, J = 5.6 Hz), 3.75-3.86 (1H, m), 3.51-3.72 (2H, m), 3.03-3.14 (1H, m), 2.84 (2H, d, J = 5.6 Hz), 1.32 (6H, d, J = 6.8 Hz); LCMS: 100%, MS (ESI): m/z 497.3 [M + H]$^+$ |
| 246 | 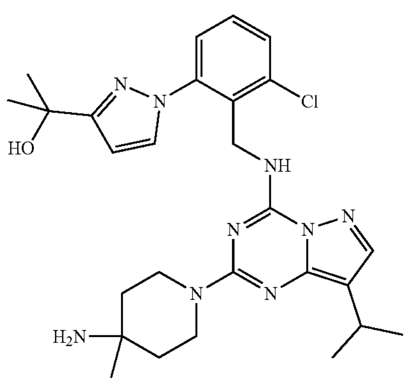 [SMILES: CC(C)c1cnn2c(NCc3c(Cl)cccc3-n3ccc(C(C)(C)O)n3)nc(N3CCC(C)(N)CC3)nc12] | white powder; $^1$H-NMR (CDCl$_3$, 400 MHz): δ 8.86 (1H, d, J = 6.4 Hz), 7.66-7.68 (2H, m), 7.48 (1H, d, J = 7.2 Hz), 7.32 (1H, t, J = 8.0 Hz), 7.23 (1H, d, J = 7.2 Hz), 6.41-6.42 (1H, d, J = 2.4 Hz), 4.85 (2H, d, J = 6.4 Hz), 3.98-4.00 (2H, m), 3.38-3.42 (1H, m), 2.97-3.06 (1H, m), 2.86 (1H, s), 2.37-2.42 (1H, m), 1.98-2.07 (2H, m), 1.68-1.76 (2H, m), 1.67 (6H, s), 1.36-1.39 (3H, s), 1.27 (6H, d, J = 6.8 Hz); LCMS: 97.0%, MS (ESI): m/z 538.2 [M + H]$^+$ |
| 247 | 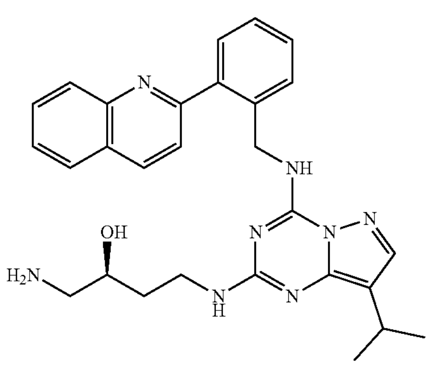 [SMILES: CC(C)c1cnn2c(NCc3ccccc3-c3ccc4ccccc4n3)nc(NCC[C@H](O)CN)nc12] | (4S); white powder; $^1$H-NMR (CDCl$_3$, 400 MHz): δ 9.32-9.55 (1H, m), 8.65 (1H, d, J = 8.8 Hz), 8.33 (1H, d, J = 8.8 Hz), 7.91 (1H, d, J = 8.0 Hz), 7.83 (1H, t, J = 8.0 Hz), 7.72-7.78 (2H, m), 7.59-7.70 (3H, m), 7.42-7.52 (2H, m), 5.11-5.20 (1H, m), 4.66-4.80 (2H, m), 3.97-4.11 (1H, m), 3.55-3.69 (1H, m), 3.28-3.42 (1H, m), 3.03-3.14 (1H, m), 2.65-2.80 (2H, m), 1.25-1.34 (8H, m); LCMS: 100%, MS (ESI): m/z 497.2 [M + H]$^+$ |

TABLE 11-continued

Summarized compounds 1-279 in terms of their structures and corresponding characteristics.

| # cpds | Structure | Characterization Data |
|---|---|---|
| 248 | 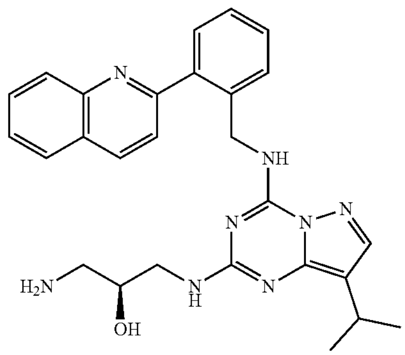 [SMILES: CC(C)c1cnn2c(NCc3ccccc3-c3ccc4ccccc4n3)nc(NC[C@@H](O)CN)nc12] | (3S); white powder; ¹H NMR (400 MHz, CDCl₃): δ 9.23-9.49 (1H, m), 8.52-8.61 (1H, m), 8.12-8.23 (1H, m), 7.69-7.84 (2H, m), 7.45-7.67 (5H, m), 7.28-7.4 (2H, m), 4.47-4.71 (2H, m), 4.12-4.33 (1H, m), 3.58-3.77 (2H, m), 3.09-3.30 (3H, m), 2.87-3.00 (2H, m), 1.19 (6H, d, J = 5.6 Hz); LCMS: 100%, MS (ESI): m/z 483.2 [M + H]⁺ |
| 249 | 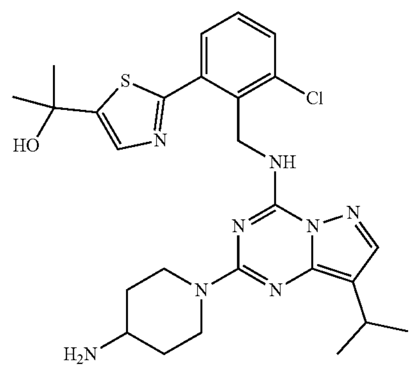 [SMILES: CC(C)c1cnn2c(NCc3c(Cl)cccc3-c3ncc(C(C)(C)O)s3)nc(N3CCC(N)CC3)nc12] | white powder; ¹H NMR (400 MHz, CDCl₃): δ 7.77-7.84 (2H, m), 7.58 (1H, s), 7.47-7.54 (2H, m), 7.30 (1H, d, J = 8.0 Hz), 5.12 (2H, d, J = 6.0 Hz), 4.75-4.86 (2H, m), 2.85-3.11 (4H, m), 1.84-1.92 (2H, m), 1.71 (6H, s), 1.29-1.34 (2H, m), 1.27 (6H, d, J = 6.8 Hz); LCMS: 100%, MS (ESI): m/z 541.2 [M + H]⁺ |
| 250 | 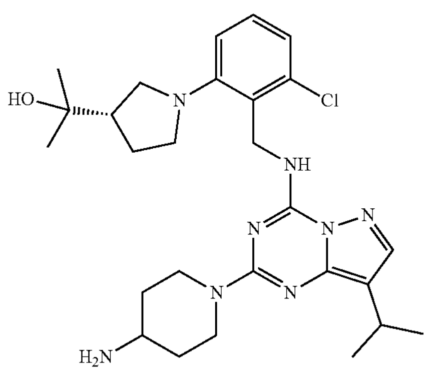 [SMILES: CC(C)c1cnn2c(NCc3c(Cl)cccc3N3CC[C@H](C(C)(C)O)C3)nc(N3CCC(N)CC3)nc12] | (3S); white powder; ¹H NMR (400 MHz, CDCl₃): δ ppm 7.81 (1H, brt, J = 5.6 Hz), 7.56 (1H, s), 7.11-7.17 (1H, m), 7.05-7.09 (1H, m), 7.02-7.05 (1H, m), 5.08-5.20 (1H, m), 4.81-4.90 (3H, m), 3.32-3.36 (1H, m), 3.20-3.26 (1H, m), 2.89-3.09 (6H, m), 2.30-2.38 (4H, m), 1.92-2.09 (4H, m), 1.36-1.48 (2H, m), 1.20-1.30 (12H, m); LCMS: 98%, MS (ESI): m/z 527.10 [M + H]⁺ |
| 251 | 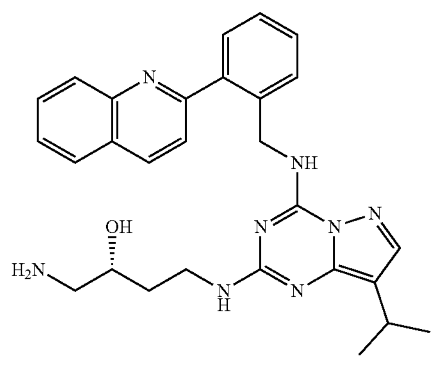 | (4R); white powder; ¹H NMR (400 MHz, CDCl₃): δ 9.19-9.47 (1H, m), 8.58-8.67 (1H, m), 8.25-8.33 (1H, m), 7.85-7.91 (1H, m), 7.76-7.84 (1H, m), 7.57-7.74 (5H, m), 7.39-7.46 (2H, m), 5.04-5.31 (1H, m), 4.64-4.76 (2H, m), 3.91-4.08 (1H, m), 3.55-3.76 (1H, m), 3.26-3.43 (1H, m), 2.93-3.15 (2H, m), 2.68-2.87 (1H, m), 1.47-1.74 (2H, m), 1.24-1.30 (6H, m); LCMS: 100%, MS (ESI): m/z 497.2 [M + H]⁺ |

TABLE 11-continued

Summarized compounds 1-279 in terms of their structures and corresponding characteristics.

| # cpds | Structure | Characterization Data |
|---|---|---|
| 252 | 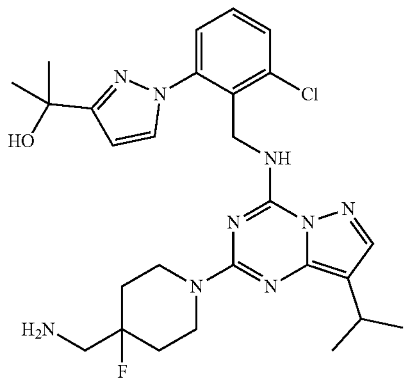 [SMILES: CC(C)c1cnn2c(NCc3c(Cl)cccc3-n3ccc(C(C)(C)O)n3)nc(N3CCC(F)(CN)CC3)nc12] | white powder; $^1$H-NMR (CDCl$_3$, 400 MHz): δ 8.81-8.87 (1H, m), 7.57-7.61 (2H, m), 7.42 (1H, d, J = 8.0 Hz), 7.26 (1H, d, J = 8.0 Hz), 7.13-7.18 (1H, m), 6.33 (1H, d, J = 2.4 Hz), 4.78 (2H, d, J = 6.0 Hz), 4.60-4.68 (2H, m), 3.19-3.28 (2H, m), 2.89-2.98 (1H, m), 2.74 (2H, d, J = 20.4 Hz), 1.82-1.91 (2H, m), 1.57-1.63 (6H, m), 1.19 (6H, d, J = 7.2 Hz); LCMS: 100%, MS (ESI): m/z 556.2 [M + H]$^+$ |
| 253 | 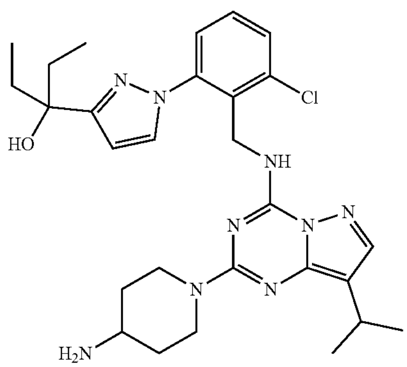 [SMILES: CCC(O)(CC)c1ccn(-c2cccc(Cl)c2CNc2nc(N3CCC(N)CC3)nc3c(C(C)C)cnn23)n1] | white powder; $^1$H-NMR (CDCl$_3$, 400 MHz): δ 9.16-9.62 (1H, m), 7.57-7.62 (1H, m), 7.48-7.54 (1H, m), 7.50 (1H, d, J = 8.0 Hz), 7.19-7.24 (1H, m), 7.07-7.13 (1H, m), 6.33-6.38 (1H, m), 6.22-6.28 (1H, m), 4.75-4.90 (4H, m), 2.76-3.01 (4H, m), 1.75-1.98 (6H, m), 1.15-1.26 (8H, m), 0.91-1.02 (3H, m), 0.69-0.77 (3H, m); LCMS: 100%, MS (ESI): m/z 552.2 [M + H]$^+$ |
| 254 | 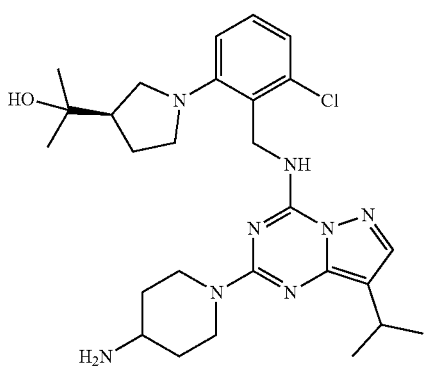 [SMILES: CC(C)c1cnn2c(NCc3c(Cl)cccc3N3CC[C@@H](C(C)(C)O)C3)nc(N3CCC(N)CC3)nc12] | (3R); white powder; 1H NMR (400 MHz, CDCl$_3$): δ ppm 7.85 (1H, brt, J = 5.2 Hz), 7.55 (1H, s), 7.12-7.16 (1H, m), 7.04-7.08 (2H, m), 5.15 (1H, dd, J = 14.8, 6.40 Hz), 4.83-4.89 (3H, m), 3.36 (1H, dd, J = 9.6, 4.8 Hz), 3.20-3.29 (1H, m), 3.05-3.09 (1H, m), 2.91-3.04 (5H, m), 2.36 (1H, m), 1.96-2.14 (3H, m), 1.91 (2H, m), 1.29-1.40 (2H, m), 1.16-25 (12H, m); LCMS: 96.5%, MS (ESI): m/z 527.2 [M + H]$^+$ |
| 255 | 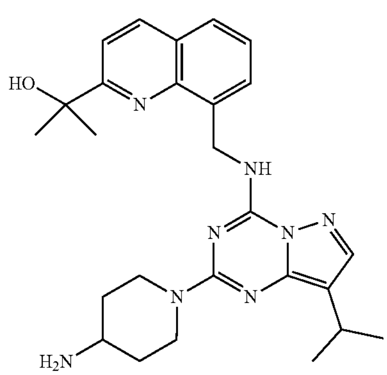 [SMILES: CC(C)c1cnn2c(NCc3cccc4ccc(C(C)(C)O)nc34)nc(N3CCC(N)CC3)nc12] | white powder; $^1$H NMR (400 MHz, CDCl$_3$): δ 8.21 (1H, d, J = 8.8 Hz), 7.89 (1H, t, J = 5.6 Hz), 7.77 (2H, t, J = 8.4 Hz), 7.59 (1 H, s), 7.56 (1H, d, J = 8.4 Hz), 7.49 (1H, t, J = 7.6 Hz), 5.38 (2H, d, J = 6.0 Hz), 4.72-4.82 (2H, m), 2.86-3.10 (4H, m), 1.84-1.92 (2H, m), 1.69 (6H, s), 1.30-1.37 (1H, m), 1.28 (6H, d, J = 6.8 Hz); LCMS: 100%, MS (ESI): m/z 475.2 [M + H]$^+$ |

TABLE 11-continued

Summarized compounds 1-279 in terms of their structures and corresponding characteristics.

| # cpds | Structure | Characterization Data |
|---|---|---|
| 256 | 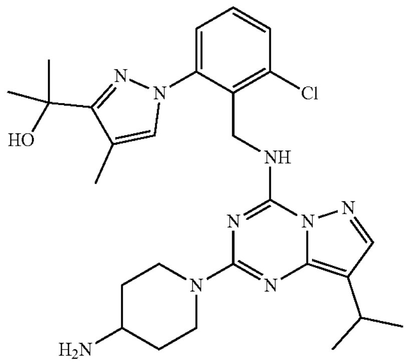 [SMILES: Cc1cn(-c2cccc(Cl)c2CNc2nc(N3CCC(N)CC3)nc3c(C(C)C)cnn23)nc1C(C)(C)O] | white powder; ¹H NMR (CDCl₃, 400 MHz); δ 8.31 (1H, t, J = 6.0 Hz), 7.56 (1H, s), 7.34-7.40 (2H, m), 7.23 (1H, t, J = 8.0 Hz), 7.12 (1H, d, J = 7.2 Hz), 4.81 (2H, d, J = 6.0 Hz), 4.70-4.78 (2H, m), 4.44 (1H, brs), 2.79-2.98 (4H, m), 2.15 (3H, s), 1.75-1.84 (2H, m), 1.58 (6H, s), 1.22-1.29 (2H, m), 1.19 (6H, d, J = 6.4 Hz); LCMS: 100%, MS (ESI): m/z 538.2 [M + H]⁺ |
| 257 | 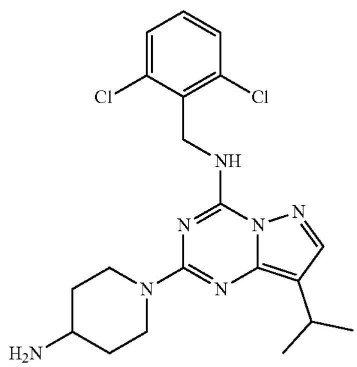 [SMILES: CC(C)c1cnn2c(NCc3c(Cl)cccc3Cl)nc(N3CCC(N)CC3)nc12] | yellow powder; ¹H NMR (CDCl₃, 400 MHz): δ 7.60 (1H, s), 7.33-7.35 (2H, m), 7.18-7.23 (1H, m), 6.59 (1H, t, J = 4.0 Hz), 5.08 (2H, d, J = 5.6 Hz), 4.82-4.85 (2H, m), 2.95-3.04 (4H, m), 1.89-1.92 (2H, m), 1.34-1.37 (2H, m), 1.28 (6H, d, J = 6.8 Hz); LCMS: 100.0%, MS (ESI): m/z 434.1 [M + H]⁺ |
| 258 | 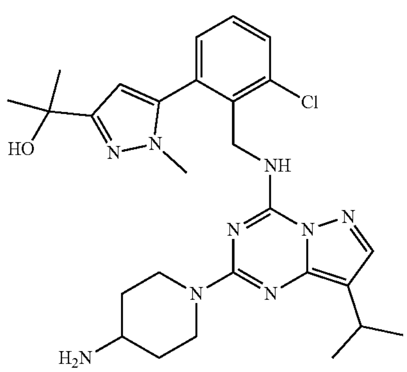 [SMILES: CC(C)c1cnn2c(NCc3c(Cl)cccc3-c3cc(C(C)(C)O)nn3C)nc(N3CCC(N)CC3)nc12] | white powder; ¹H-NMR (CDCl₃, 400 MHz): δ 7.51 (1H, s), 7.46 (1H, d, J = 6.8 Hz), 7.28 (1H, t, J = 7.6 Hz), 7.12 (1H, d, J = 6.4 Hz), 6.19-6.26 (1H, m), 6.04-6.08 (1H, m), 4.72 (2H, br s), 4.55-4.60 (2H, m), 3.52 (3H, s), 2.79-2.97 (4H, m), 1.71-1.99 (2H, m), 1.44 (6H, s), 1.24-1.27 (2H, m), 1.20 (6H, d, J = 6.8 Hz); LCMS: 100%, MS (ESI): m/z 538.3 [M + H]⁺ |
| 259 | 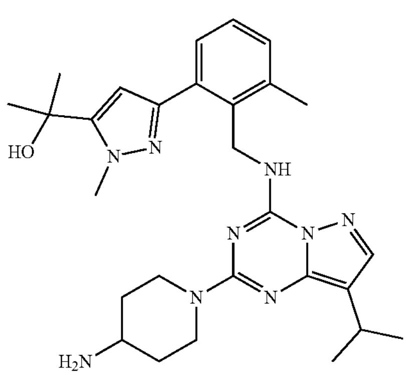 [SMILES: Cc1cccc(-c2cc(C(C)(C)O)n(C)n2)c1CNc1nc(N2CCC(N)CC2)nc2c(C(C)C)cnn12] | white powder; ¹H NMR (CDCl₃, 400 MHz): δ 8.16 (1H, d, J = 6.0 Hz), 7.59 (1H, s), 7.10-7.30 (3H, m), 6.20 (1H, s), 4.75-4.85 (4H, m), 4.15 (3H, s), 2.85-3.05 (4H, m), 2.60 (3H, s), 1.65-1.90 (2H, m), 1.64 (3H, s), 1.25-1.35 (2H, m), 1.26 (6H, d, J = 6.8 Hz); LCMS: 98.70%, MS (ESI): m/z 518.3 [M + H]⁺ |

TABLE 11-continued

Summarized compounds 1-279 in terms of their structures and corresponding characteristics.

| # cpds | Structure | Characterization Data |
|---|---|---|
| 260 | 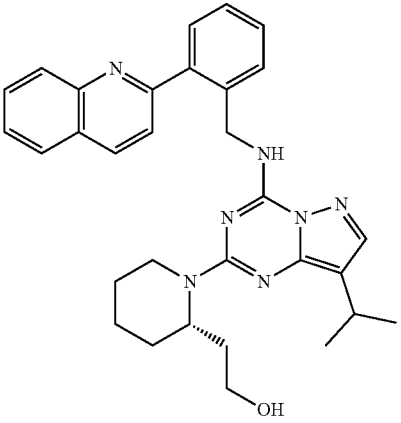 [SMILES: CC(C)c1cnn2c(NCc3ccccc3-c3ccc4ccccc4n3)nc(N3CCCC[C@H]3CCO)nc12] | (2S); white powder; $^1$H-NMR (CDCl$_3$, 400 MHz): δ 9.25 (1H, br s), 8.62 (1H, d, J = 8.0 Hz), 8.31 (1H, d, J = 8.8 Hz), 7.88 (1H, d, J = 8.4 Hz), 7.78-7.83 (1H, m), 7.70-7.75 (2H, m), 7.63-7.68 (2H, m), 7.58-7.62 (1H, m), 7.38-7.50 (2H, m), 4.93-5.14 (2H, m), 4.74 (2H, d, J = 6.4 Hz), 3.60-3.64 (1H, m), 3.33-3.44 (1H, m), 2.96-3.09 (1H, m), 2.84-2.90 (1H, m), 2.05-2.21 (1H, m), 1.61-1.89 (7H, m), 1.24-1.29 (6H, m); LCMS: 96.9%, MS (ESI): m/z 522.3 [M + H]$^+$ |
| 261 | 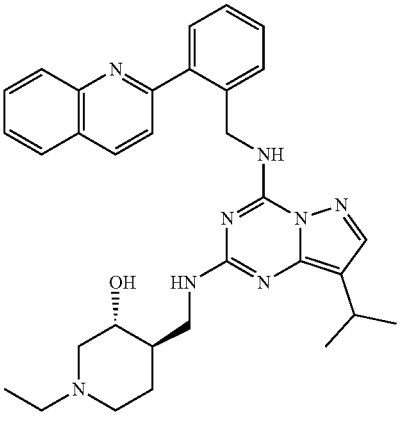 [SMILES: CCN1CC[C@H](CNc2nc(NCc3ccccc3-c3ccc4ccccc4n3)n3ncc(C(C)C)c3n2)[C@@H](O)C1] | (3R, 4R); white powder; $^1$H-NMR (CDCl$_3$, 400 MHz): δ 9.35-9.37 (1H, m), 8.63 (1H, d, J = 7.6 Hz), 8.31 (1H, d, J = 8.4 Hz), 7.88 (1H, d, J = 8.0 Hz), 7.76-7.85 (1H, m), 7.73-7.74 (1H, m), 7.57-7.69 (3H, m), 7.43-7.48 (2H, m), 5.16-5.18 (1H, m), 4.66-4.73 (2H, m), 4.24-4.27 (1H, m), 3.57-3.64 (2H, m), 3.24-3.27 (1H, m), 2.98-3.15 (3H, m), 2.55-2.61 (2H, m), 1.98-2.19 (2H, m), 1.48-1.51 (1H, m), 1.25-1.31 (6H, m), 1.15-1.18 (3H, m); LCMS: 98.9%, MS (ESI): m/z 551.2 [M + H]$^+$ |
| 262 | 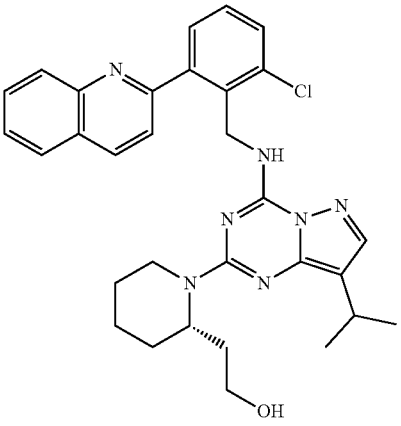 [SMILES: CC(C)c1cnn2c(NCc3c(Cl)cccc3-c3ccc4ccccc4n3)nc(N3CCCC[C@H]3CCO)nc12] | (2S); white powder; $^1$H-NMR (CDCl$_3$, 400 MHz): δ 8.91 (1H, br t, J = 6.0 Hz), 8.56 (1H, d, J = 8.4 Hz), 8.30 (1H, d, J = 8.4 Hz), 7.88 (1H, d, J = 8.0 Hz), 7.77 (1H, t, J = 7.2 Hz), 7.72 (1H, s), 7.66 (1H, d, J = 8.4 Hz), 7.57-7.62 (1H, m), 7.48-7.53 (2H, m), 7.39 (1H, t, J = 8.0 Hz), 5.64 (1H, br s), 4.81-5.09 (4H, m), 3.57-3.63 (1H, m), 3.32-3.38 (1H, m), 2.96-3.08 (1H, m), 2.68-2.76 (1H, m), 2.08-2.14 (1H, m), 1.74-1.85 (1H, m), 1.63-1.70 (4H, m), 1.40-1.52 (2H, m), 1.27-1.32 (6H, m); LCMS: 98.1%, MS (ESI): m/z 556.2 [M + H]$^+$ |

TABLE 11-continued

Summarized compounds 1-279 in terms of their structures and corresponding characteristics.

| # cpds | Structure | Characterization Data |
|---|---|---|
| 263 | 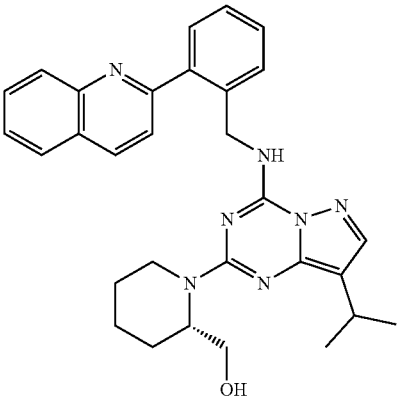 [SMILES: CC(C)c1cnn2c(NCc3ccccc3-c3ccc4ccccc4n3)nc(N3CCCC[C@H]3CO)nc12] | (2S); white powder; $^1$H-NMR (CDCl$_3$, 400 MHz): δ 9.11-9.23 (1H, m), 8.64 (1H, d, J = 8.0 Hz), 8.33 (1H, d, J = 8.4 Hz), 7.91 (1H, d, J = 8.0 Hz), 7.83 (1H, t, J = 7.6 Hz), 7.70-7.76 (2H, m), 7.60-7.69 (3H, m) 7.42-7.50 (2H, m), 4.97-5.05 (1H, m), 4.72-4.89 (3H, m), 4.47 (1H, brs), 3.98-4.13 (1H, m), 3.70-3.84 (1H, m), 3.15-3.25 (1H, m), 2.98-3.08 (1H, m), 1.63-1.84 (5H, m), 1.27-1.34 (6H, m); LCMS: 100%, MS (ESI): m/z 508.2 [M + H]$^+$ |
| 264 | 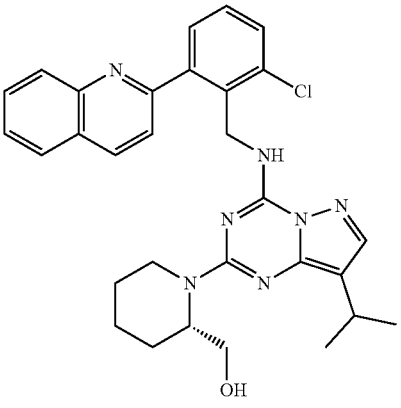 [SMILES: CC(C)c1cnn2c(NCc3c(Cl)cccc3-c3ccc4ccccc4n3)nc(N3CCCC[C@H]3CO)nc12] | (2S); white powder; $^1$H NMR (400 MHz, DMSO-d$_6$): δ 8.97-9.03 (1H, m), 8.59 (1H, d, J = 8.4 Hz), 8.45 (1H, d, J = 8.0 Hz), 8.09 (1H, d, J = 8.0 Hz), 7.90 (1H, d, J = 8.4 Hz), 7.80-7.87 (2H, m), 7.65-7.71 (3H, m), 7.53-7.59 (1H, m), 4.88-4.98 (2H, m), 4.74-4.84 (1H, m), 4.61-4.69 (2H, m), 3.65 (1H, m), 3.47 (1H, m), 2.94 (1 H, m), 2.79-2.89 (1H, m), 1.91 (1 H, m), 1.49-1.69 (3H, m), 1.21-1.29 (8H, m); LCMS: 100%, MS (ESI): m/z 542.2 [M + H]+ |
| 265 | 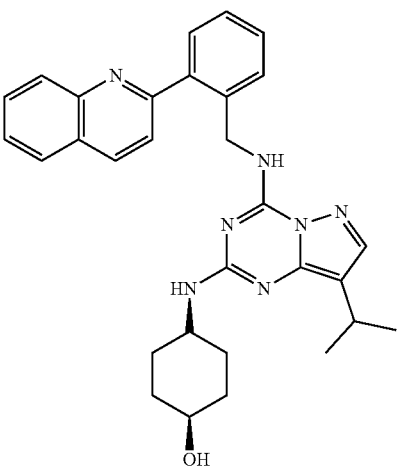 | (1S, 4S); white powder; $^1$H NMR (400 MHz, DMSO-d$_6$): δ ppm 8.86-9.27 (1H, m), 8.56 (1 H, d, J = 8.4 Hz), 8.35 (1H, d, J = 8.4 Hz), 8.08 (1H, d, J = 8.0 Hz), 7.81-7.93 (2H, m), 7.56-7.79 (4H, m), 7.46-7.53 (2H, m), 6.58-6.90 (1H, m), 4.75 (2H, d, J = 6.4 Hz), 4.33 (1H, brs), 3.66-3.74 (2H, m), 2.85-2.96 (1H, m), 1.32-1.81 (8H, m), 1.23 (6H, d, J = 5.6 Hz); LCMS: 100%, MS (ESI): m/z 508.2 [M + H]$^+$ |

TABLE 11-continued

Summarized compounds 1-279 in terms of their structures and corresponding characteristics.

| # cpds | Structure | Characterization Data |
|---|---|---|
| 266 | 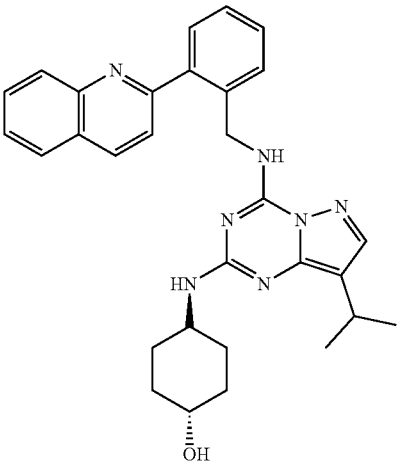 | (1R, 4R); white powder; $^1$H NMR (400 MHz, DMSO-d$_6$): δ ppm 8.87-9.28 (1H, m), 8.56 (1H, d, J = 8.4 Hz), 8.30-8.45 (1H, m), 8.08 (1H, d, J = 8.0 Hz), 7.82-7.95 (2H, m), 7.64-7.79 (3H, m), 7.56-7.62 (1H, m), 7.40-7.55 (2H, m), 6.58-6.95 (1H, m), 4.74 (2H, d, J = 6.4 Hz), 4.53 (1H, brs), 3.55-3.75 (1H, m), 3.35-3.41 (2H, m), 2.82-2.98 (1H, m), 1.73-2.02 (4H, m), 1.15-1.35 (10H, m); LCMS: 100%, MS (ESI): m/z 508.2 [M + H]$^+$ |
| 267 | 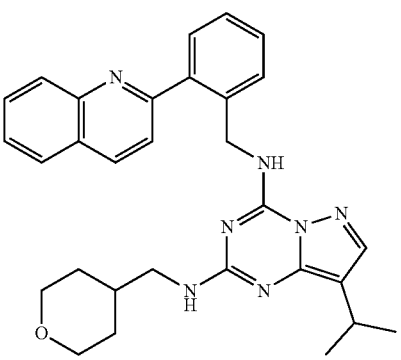 [SMILES: CC(C)c1cnn2c(NCc3ccccc3-c3ccc4ccccc4n3)nc(NCC3CCOCC3)nc12] | white solid; $^1$H NMR (400 MHz, CDCl$_3$): δ ppm 9.20 (1H, br s), 8.63 (1H, d, J = 8.4 Hz), 8.30 (1H, d, J = 8.4 Hz), 7.88 (1H, d, J = 8.0 Hz), 7.80 (1H, m), 7.70-7.74 (2H, m), 7.57-7.69 (3H, m), 7.38-7.48 (2H, m), 4.96-5.03 (1H, m), 4.74 (2H, d, J = 6.4 Hz), 3.95-4.05 (2H, m), 3.40-3.45 (4H, m), 3.01-3.10 (1H, m), 1.87-1.98 (1H, m), 1.70-1.79 (2H, m), 1.36-1.45 (2H, m), 1.29 (6H, d, J = 7.2 Hz); LCMS: 100%, MS (ESI): m/z 508.2 [M + H]$^+$ |
| 268 | 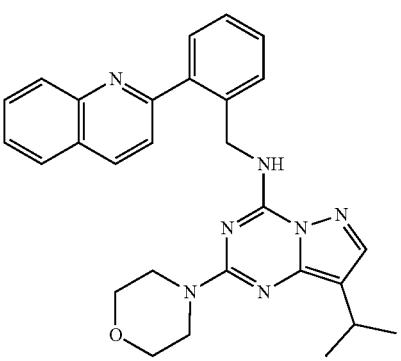 [SMILES: CC(C)c1cnn2c(NCc3ccccc3-c3ccc4ccccc4n3)nc(N3CCOCC3)nc12] | white powder; 1H NMR (400 MHz, CDCl$_3$): δ ppm 9.17 (1H, br t, J = 6.4 Hz), 8.62 (1H, d, J = 8.4 Hz), 8.29 (1H, d, J = 8.4 Hz), 7.88 (1H, d, J = 8.0 Hz), 7.78-7.83 (1H, m), 7.69-7.74 (2H, m), 7.56-7.66 (3H, m), 7.43 (2H, m), 4.75 (2H, d, J = 6.4 Hz), 3.87-3.92 (4H, m), 3.78-3.83 (4H, m), 3.05 (1H, m), 1.30 (6H, d, J = 7.2 Hz); LCMS: 100%, MS (ESI): m/z 480.2 [M + H]$^+$ |

TABLE 11-continued

Summarized compounds 1-279 in terms of their structures and corresponding characteristics.

| # cpds | Structure | Characterization Data |
|---|---|---|
| 269 | 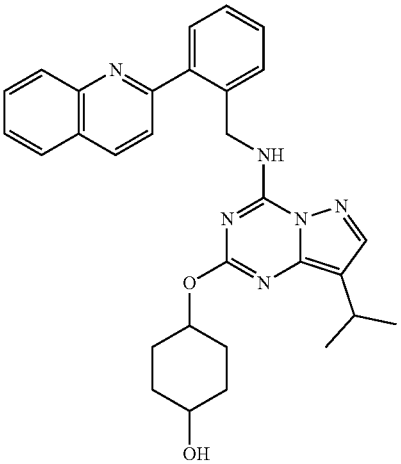 [SMILES: CC(C)c1cnn2c(NCc3ccccc3-c3ccc4ccccc4n3)nc(OC3CCC(O)CC3)nc12] | white powder; $^1$H NMR (400 MHz, DMSO-d$_6$): δ ppm 9.50 (1H, br t, J = 6.4 Hz), 8.56 (1H, d, J = 8.4 Hz), 8.32 (1H, d, J = 8.0 Hz), 8.08 (1H, d, J = 7.6 Hz), 7.97 (1H, s), 7.88-7.92 (1H, m), 7.81-7.87 (1H, m), 7.64-7.74 (2H, m), 7.53-7.59 (1H, m), 7.45-7.53 (2H, m), 4.89-4.95 (1H, m), 4.74-4.83 (2H, m), 4.57-4.60 (0.2H, m), 4.47-4.51 (0.8H, m), 3.55-3.65 (1H, m), 2.90-3.03 (1H, m), 1.78-1.93 (2H, m), 1.51-1.71 (5H, m), 1.18-1.32 (7H, m); LCMS: 99.7%, MS (ESI): m/z 509.2 [M + H]$^+$ |
| 270 | 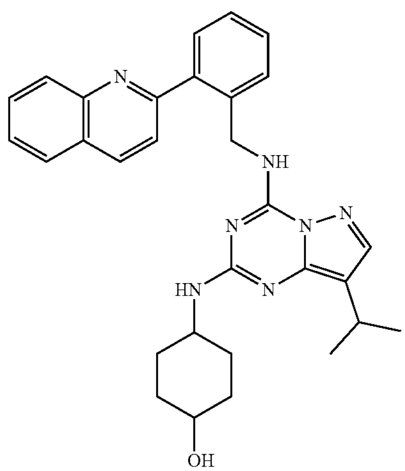 [SMILES: CC(C)c1cnn2c(NCc3ccccc3-c3ccc4ccccc4n3)nc(NC3CCC(O)CC3)nc12] | white powder; $^1$H NMR (400 MHz, DMSO-d$_6$): δ ppm 8.86-9.49 (1H, m), 8.57 (1H, d, J = 8.8 Hz), 8.35 (1H, br d, J = 8.4 Hz), 8.09 (1H, d, J = 8.0 Hz), 7.83-7.96 (2H, m), 7.65-7.83 (3H, m), 7.57-7.64 (1H, m), 7.46-7.54 (2H, m), 6.57-7.10 (1H, m), 4.72-4.81 (2H, m), 4.20-4.63 (1H, m), 3.65-3.80 (1H, m), 3.24-3.30 (1H, m), 2.83-2.98 (1H, m), 1.79-2.02 (2H, m), 1.41-1.75 (5H, m), 1.18-1.31 (9H, br s); LCMS: 96.8%, MS (ESI): m/z 508.2 [M + H]$^+$ |
| 271 | 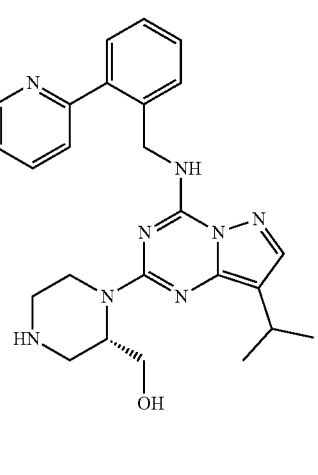 | (2S); white powder; $^1$H NMR (400 MHz, CDCl$_3$): δ 9.20-9.27 (1H, m), 8.62 (1H, d, J = 8.8 Hz), 8.29 (1H, d, J = 8.4 Hz), 7.88 (1H, d, J = 7.6 Hz), 7.78-7.83 (1H, m), 7.68-7.75 (2H, m), 7.57-7.66 (3H, m), 7.39-7.48 (2H, m), 4.74 (2H, d, J = 6.4 Hz), 4.51-4.60 (2H, m), 3.86-3.94 (1H, m), 3.73-3.82 (1H, m), 3.50-3.57 (1H, m), 3.28-3.43 (2H, m), 3.14-3.21 (1H, m), 2.96-3.08 (2H, m), 1.29 (6H, d, J = 6.8 Hz); LCMS: 100%, MS (ESI): m/z 590.2 [M + H]$^+$ |

TABLE 11-continued

Summarized compounds 1-279 in terms of their structures and corresponding characteristics.

| # cpds | Structure | Characterization Data |
|---|---|---|
| 272 | 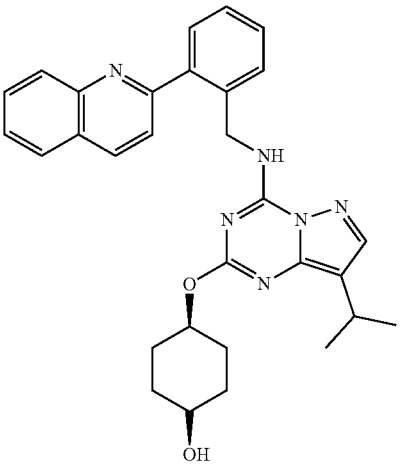 | (1S, 4S); white powder; $^1$H-NMR (CDCl$_3$, 400 MHz): δ 9.67 (1H, br t, J = 6.4 Hz), 8.66 (1H, d, J = 8.4 Hz), 8.32 (1H, d, J = 8.4 Hz), 7.89 (1H, d, J = 8.4 Hz), 7.83 (1H, s), 7.77-7.82 (1H, m), 7.70-7.75 (2H, m), 7.57-7.66 (2H, m), 7.41-7.49 (2H, m), 5.18 (1H, br t, J = 6.8 Hz), 4.79 (2H, d, J = 6.4 Hz), 3.88 (1H, br s), 3.03-3.19 (1H, m), 2.09-2.21 (2H, m), 1.74-1.97 (6H, m) 1.34-1.40 (1H, d, J = 4.4 Hz), 1.32 (6 H, d, J = 6.8 Hz); LCMS: 100%, MS (ESI): m/z 509.2 [M + H]$^+$ |
| 273 | 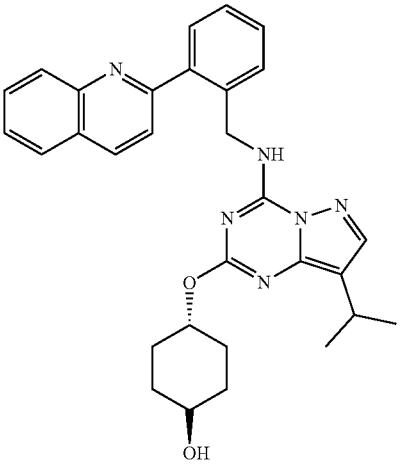 | (1R, 4R); white powder; 1H NMR (400 MHz, CDCl$_3$): δ 9.71 (1H, br t, J = 6.4 Hz), 8.66 (1H, d, J = 8.4 Hz), 8.31 (1H, d, J = 8.8 Hz), 7.89 (1H, d, J = 8.4 Hz), 7.84 (1H, s), 7.80 (1H, td, J = 7.2, 1.6 Hz), 7.69-7.75 (2H, m), 7.58-7.66 (2H, m), 7.44 (2H, m), 5.05-5.15 (1H, m), 4.79 (2H, d, J = 6.4 Hz), 3.74-3.85 (1H, m), 3.06-3.19 (1H, m), 2.23-2.31 (2H, m), 2.08-2.13 (2H, m), 1.63-1.76 (2H, m), 1.50-1.56 (2H, m), 1.42-1.49 (1H, m), 1.32 (6H, d, J = 7.2 Hz); LCMS: 100%, MS (ESI): m/z 509.2 [M + H]$^+$ |
| 274 | 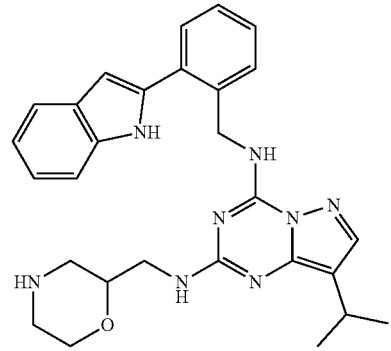 [SMILES: CC(C)c1cnn2c(NCc3ccccc3-c3cc4ccccc4[nH]3)nc(NCC3CNCCO3)nc12] | Racemic mixture; white solid; $^1$H-NMR (CDCl$_3$, 400 MHz): δ 7.63-7.70 (2H, m), 7.43-7.59 (3H, m), 7.33-7.40 (2H, m), 7.21 (1H, t, J = 8.0 Hz), 7.14 (1H, t, J = 8.0 Hz), 6.96 (1H, brs), 6.62 (1H, s), 5.18-5.21 (1H, m), 4.84 (2H, s), 3.84 (1H, d, J = 11.6 Hz), 3.45-3.70 (3H, m), 3.23-3.37 (1H, m), 2.97-3.07 (1H, m), 2.75-2.95 (3H, m), 2.61 (1H, s), 1.28 (6H, d, J = 6.8 Hz); LCMS: 100%, MS (ESI): m/z 497.3 [M + H]$^+$ |

TABLE 11-continued

Summarized compounds 1-279 in terms of their structures and corresponding characteristics.

| # cpds | Structure | Characterization Data |
|---|---|---|
| 275 | 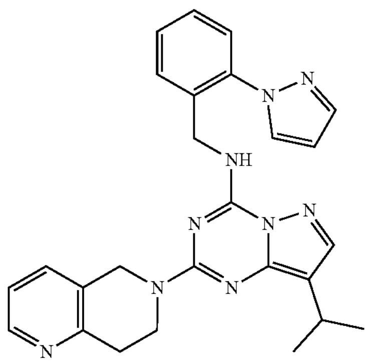 [SMILES: CC(C)c1cnn2c(NCc3ccccc3-n3cccn3)nc(N3CCc4ncccc4C3)nc12] | White solid; $^1$H NMR (CDCl$_3$, 400 MHz): δ 8.44 (1H, d, J = 4.4 Hz), 7.87 (1H, s), 7.75 (1H, d, J = 2.0 Hz), 7.65-7.70 (2H, m), 7.64 (1H, s), 7.50-7.55 (1H, m), 7.29-7.43 (3H, m), 7.15-7.25 (1H, m), 6.51 (1H, s), 5.01 (2H, s), 4.74 (2H, d, J = 6.0 Hz), 4.25 (2H, t, J = 6.0 Hz), 3.13 (2H, t, J = 5.6 Hz), 3.00-3.10 (1H, m), 1.29 (6H, d, J = 6.4 Hz); LCMS: 100%, MS (ESI): m/z 466.1 [M + H]$^+$ |
| 276 | 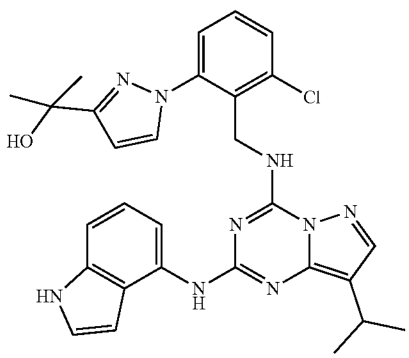 [SMILES: CC(C)c1cnn2c(NCc3c(Cl)cccc3-n3ccc(C(C)(C)O)n3)nc(Nc3cccc4[nH]ccc34)nc12] | white powder; $^1$H NMR (400 MHz, CDCl$_3$): δ 8.85 (1H, br s), 8.19 (2H, br s), 7.68 (1H, s), 7.60 (1 H, d, J = 2.40 z), 7.43 (1H, d, J = 8.00 Hz), 7.27 (1H, t, J = 8.00 Hz), 7.1-7.18 (4H, m), 7.04 (1H, d, J = 8.00 Hz), 6.60 (1H, br s), 6.34 (1H, d, J = 2.38 Hz), 4.82 (2H, d, J = 6.40 Hz), 4.61 (1H, s), 3.02-3.13 (1H, m), 6.80 Hz), 1.59 (6H, s), 1.27 (6 H, d, J = 6.80 Hz); HPLC: 96.1% MS (ESI): m/z 556.2 [M + H]$^+$ |
| 277 | 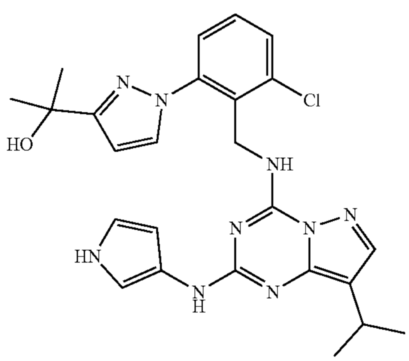 [SMILES: CC(C)c1cnn2c(NCc3c(Cl)cccc3-n3ccc(C(C)(C)O)n3)nc(Nc3cc[nH]c3)nc12] | yellow powder; $^1$H NMR (400 MHz, CDCl$_3$): δ 8.58-8.97 (2H, m), 7.69 (1H, s), 7.59 (1H, d, J = 2.4 Hz), 7.41-7.45 (1H, m), 7.28 (1H, t, J = 8.0 Hz), 7.16-7.19 (1H, m), 6.68 (1H, t, J = 2.8 Hz), 6.34 (1H, d, J = 2.4 Hz), 5.77 (1H, t, J = 2.8 Hz), 4.70-4.92 (3H, m), 3.03-3.12 (1H, m), 1.60 (6H, s), 1.25 (6H, d, J = 7.2 Hz); HPLC: 99.4% MS (ESI): m/z 506.1 [M + H]$^+$ |
| 278 | 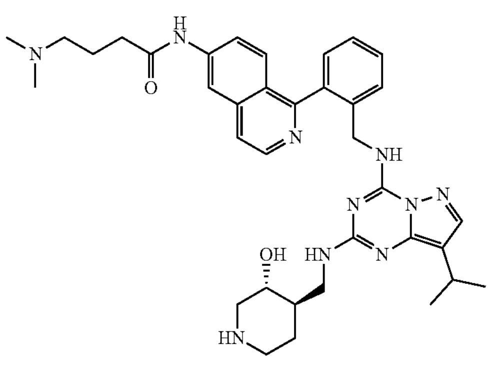 [SMILES: CC(C)c1cnn2c(NCc3ccccc3-c3nccc4cc(NC(=O)CCCN(C)C)ccc34)nc(NC[C@H]3CCNC[C@@H]3O)nc12] | Yellow solid; $^1$H-NMR (CD$_3$OD, 400 MHz): δ 8.47-8.53 (1H, m), 8.36 (1H, d, J = 6.4 Hz), 7.95-8.04 (1H, m), 7.47-7.81 (7H, m), 5.02-5.11 (1H, m), 4.63-4.72 (1H, m), 3.62-3.74 (1H, m), 3.27-3.61 (4H, m), 3.21-3.25 (1H, m), 2.64-3.03 (12H, m), 2.08-2.17 (2H, m), 1.97-2.04 (1H, m), 1.75-1.88 (1H, m), 1.49-1.62 (1H, m), 1.23 (6H, d, J = 6.4 Hz); LCMS: 97.9%, MS (ESI): 651.3 m/z [M + H]$^+$ |

TABLE 11-continued

Summarized compounds 1-279 in terms of their structures and corresponding characteristics.

| # cpds | Structure | Characterization Data |
|---|---|---|
| 279 | 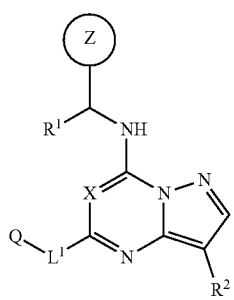 | White powder; $^1$H NMR (CD$_3$OD, 400 MHz): δ 8.63 (1H, d, J = 6.0 Hz), 8.46-8.49 (1H, m), 8.21 (1H, d, J = 8.4 Hz), 8.01-8.05 (1H, m), 7.82-7.98 (2H, m), 7.69-7.81 (3H, m), 7.59-7.67 (2H, m), 5.02-5.11 (1H, m), 4.70-4.79 (1H, m), 3.73-3.79 (1H, m), 3.56-3.62 (1H, m), 3.33-3.51 (3H, m), 2.79-3.02 (3H, m), 1.83-2.07 (2H, m), 1.51-1.68 (1H, m), 1.29 (6H, d, J = 7.2 Hz); LCMS: 100%, MS (ESI): 523.2 m/z [M + H]$^+$ |

The invention claimed is:

1. A compound having general formula I

Formula I

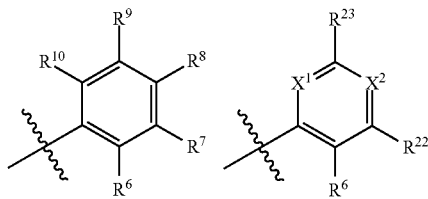

wherein

X is, independently at each occurrence, selected from CH and N;

L$^1$ is either absent or independently, at each occurrence, selected from the group consisting of —NH—, —NH(CH$_2$)—, —NH(C═O)—, —NHSO$_2$—, —O—, —O(CH$_2$)—, —(C═O)—, —(C═O)NH— and —(C═O)(CH$_2$)—;

Q is, independently at each occurrence, selected from the group consisting of C3-C8 cycloalkyl, aryl, heteroaryl, heterocyclyl, and C1-C6 alkyl, wherein C1-C6 alkyl is substituted with one or two of —OR$^5$, —N(R$^5$)R$^5$, aryl, heteroaryl and heterocyclyl, C3-C8 cycloalkyl can be substituted with one or two of R$^3$ and R$^4$ and —(C═O)R$^5$, heterocyclyl can be substituted with one or two of R$^3$ and R$^4$ and —(C═O)R$^5$, aryl or heteroaryl can be substituted with one or two of C1-C6 alkyl, —OR$^5$, —N(R$^5$)R$^5$, —(C═O)R$^5$, halogen, heteroaryl and heterocyclyl;

R$^1$ is hydrogen;

R$^2$ is, at each occurrence, independently selected from the group consisting of C1-C6 alkyl, C3-C10 cycloalkyl, —CN, —(C═O)CH$_3$, —NR$^9$R$^{12}$ and C1-C3 haloalkyl, any of which is optionally substituted;

R$^3$ is independently, at each occurrence, selected from the group consisting of hydrogen, —OR$^5$, halogen, —N(R$^5$)R$^5$, —NR$^9$R$^{12}$, —NH(C═O)R$^5$, —(C═O)NH$_2$, aryl, heteroaryl, heterocyclyl, C1-C6 alkyl and C1-C6 alkyl substituted with —OH or —NH$_2$;

R$^4$ is, independently, at each occurrence, selected from the group consisting of hydrogen, halogen, —OR$^5$, —N(R$^5$)R$^5$, (═O), aryl, heteroaryl, heterocyclyl, C1-C6 alkyl and C1-C6 alkyl substituted with —OH or —NH$_2$;

R$^5$ is, at each occurrence, independently selected from the group consisting of hydrogen, C1-C6 alkyl, C3-C8 cycloalkyl, C1-C3 haloalkyl, heteroaryl optionally substituted with one or two of halogen, —OR$^{11}$, —N(R$^{11}$)R$^{11}$, and C1-C6 alkyl optionally substituted with —OH or —NH$_2$, heterocyclyl optionally substituted with one or two of halogen, —OR$^{11}$, —N(R$^{11}$)R$^{11}$, C1-C6 alkyl and C1-C6 alkyl substituted with —OH or —NH$_2$;

Z is

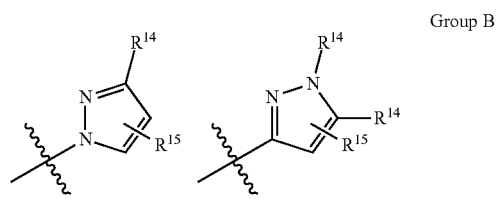

wherein

X$^1$ is CR$^{24}$;

X$^2$ is CR$^{25}$;

R$^6$ is, at each occurrence, independently selected from hydrogen, and any structure of the following group B;

Group B

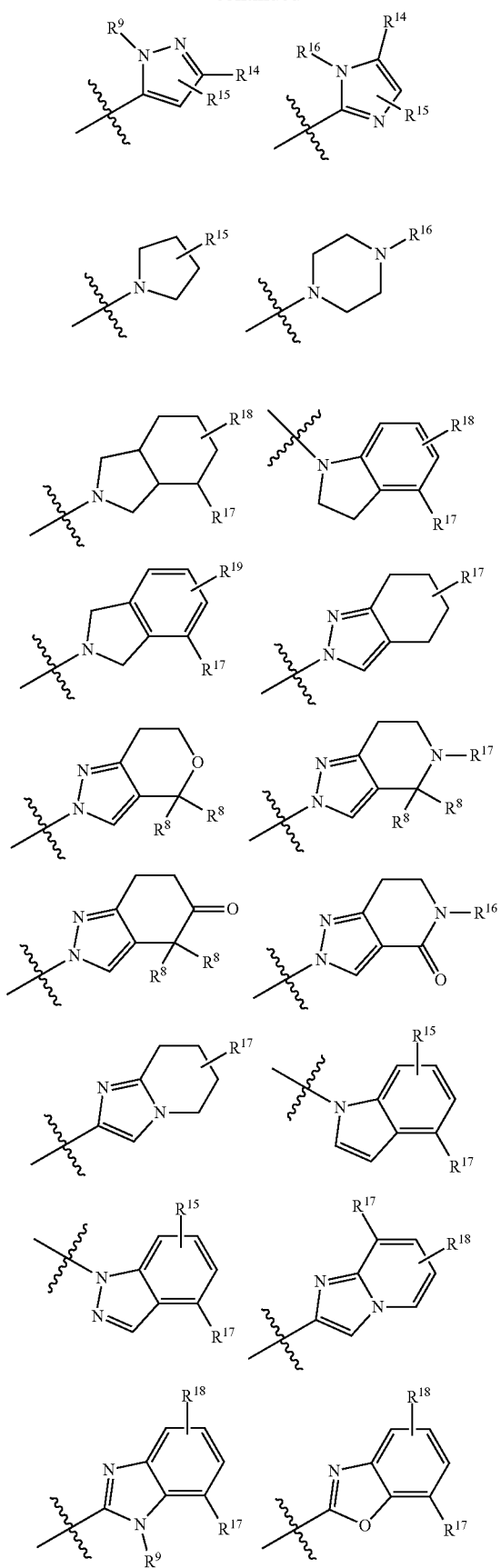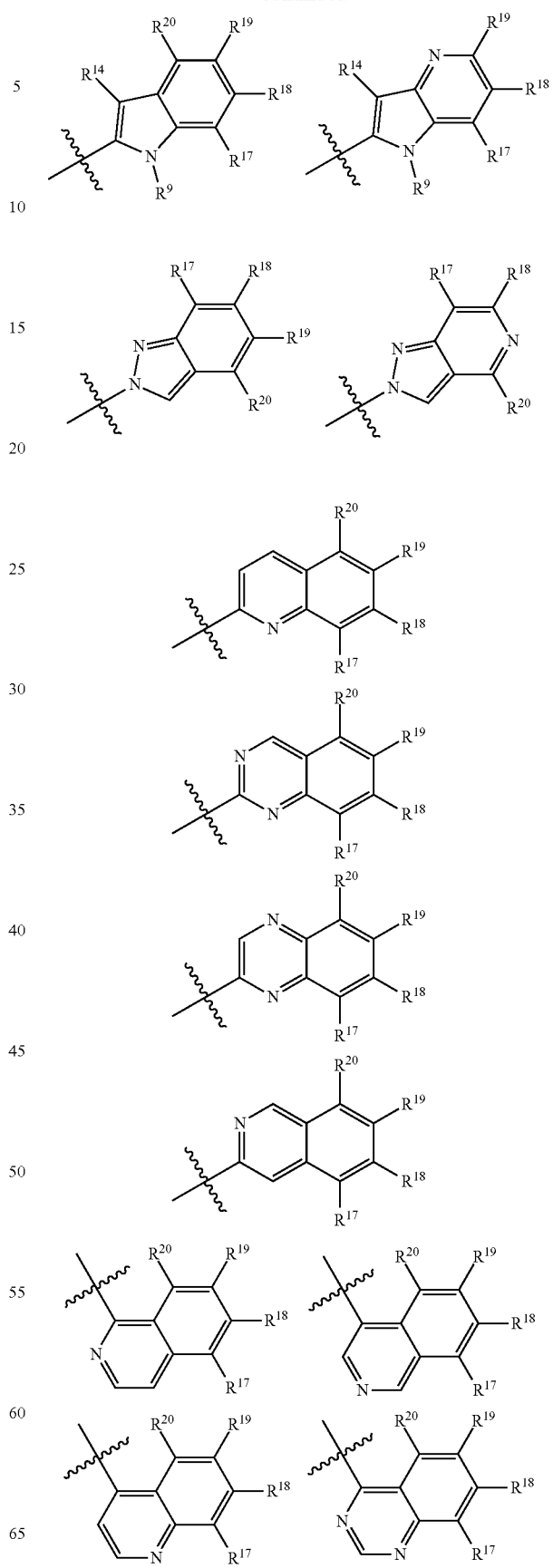

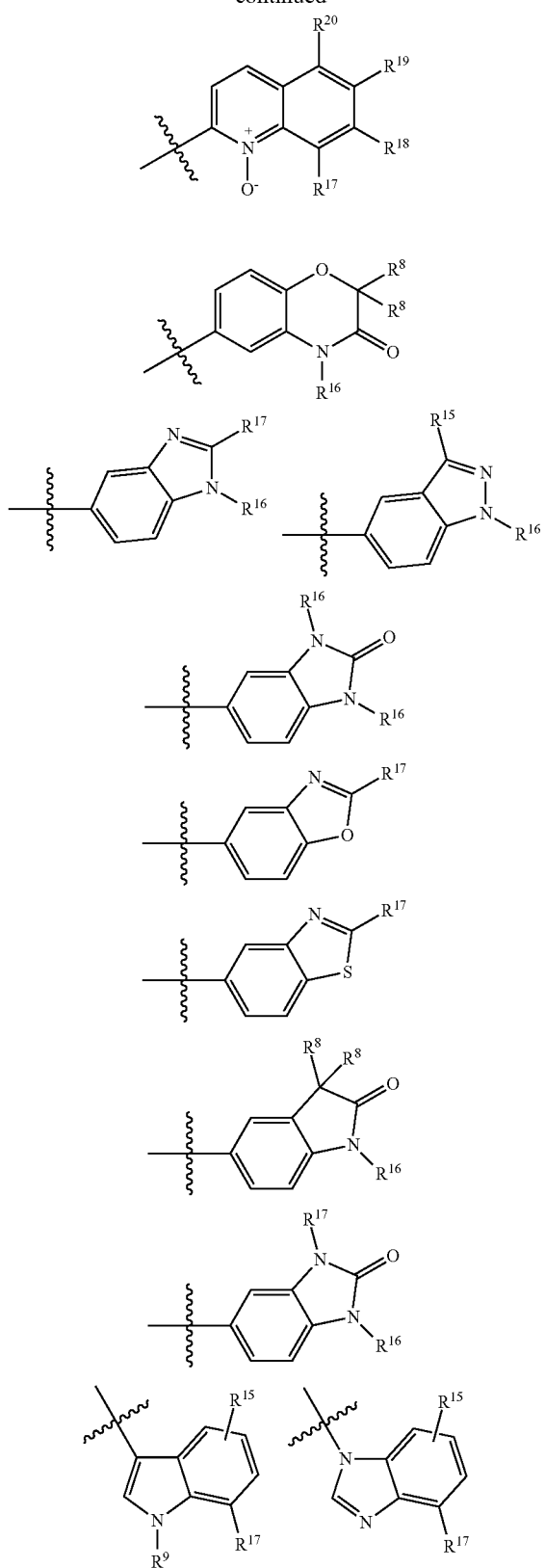
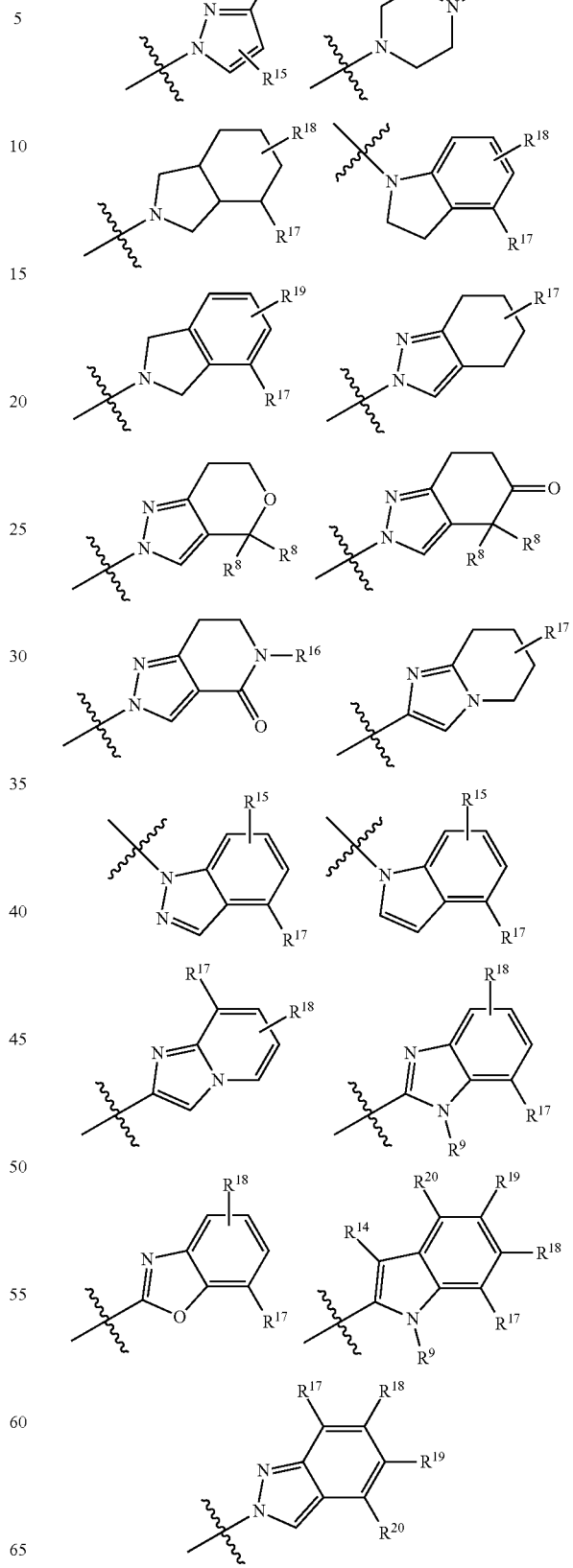
R[7] is, at each occurrence, independently selected from the group consisting of hydrogen, C1-C6 alkyl, and any structure of the following group C;

-continued

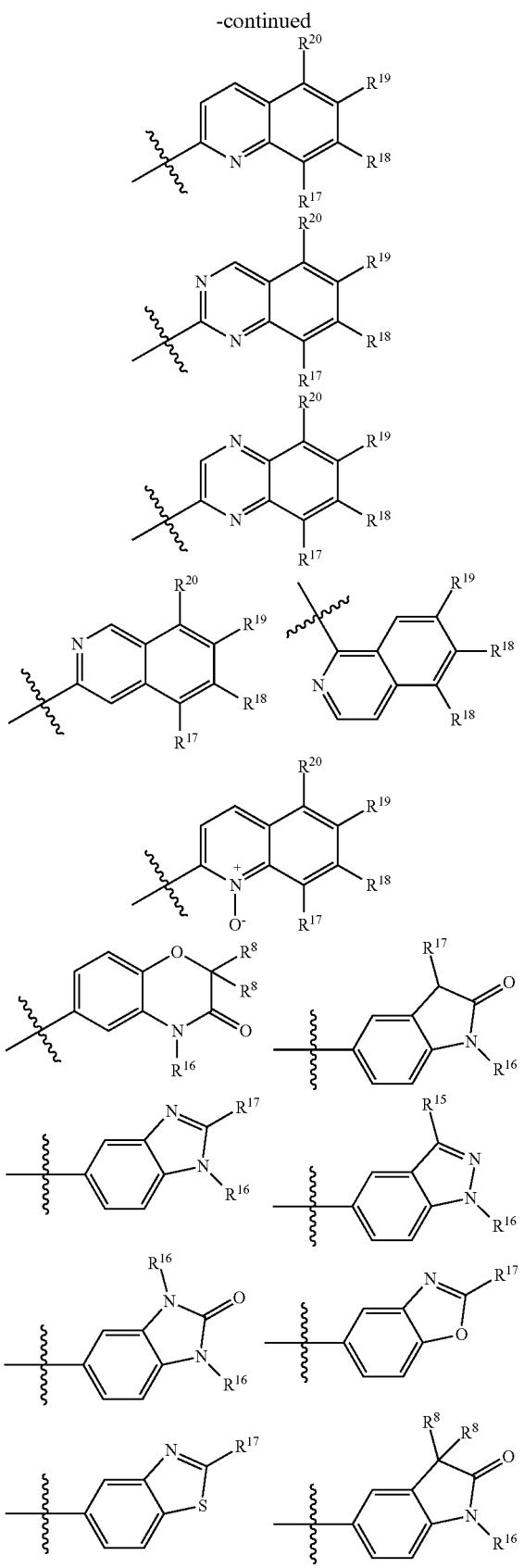

R[8] and R[10] are, at each occurrence, independently selected from the group consisting of hydrogen, halogen, C1-C6 alkyl, C1-C3 haloalkyl, $-NH_2$, $-OH$, $-OR^5$, $-CN$, $-(C=O)R^5$, $-(C=O)OR^5$, $-(C=O)NH_2$, $-(C=O)NHR^{21}$, $-CH_2(C=O)NHR^{21}$, $-NH(C=O)R^{13}$, $-NHS(=O)_2R^5$, $-S(=O)_2NH_2$, $-S(=O)_2NHR^{21}$, and C1-C6 alkyl substituted with $-OH$, $-OR^5$ or $-NHR^9$;

$R^9$ is, at each occurrence, independently selected from the group consisting of hydrogen, halogen, C1-C6 alkyl, C1-C3 haloalkyl, $-OR^5$, $-CN$, C3-C10 cycloalkyl, C3-C10 heterocyclyl and C1-C6 alkyl substituted with $-OH$ or $-OR^5$;

$R^{11}$ is, at each occurrence, independently selected from the group consisting of hydrogen, C1-C6 alkyl and C3-C10 cycloalkyl;

$R^{12}$ is, at each occurrence, absent or independently selected from the group consisting of C1-C6 alkyl optionally substituted with $-OR^5$ or $-N(R^5)R^5$, benzyl optionally substituted with one to four halogens or C1-C3 alkyls, C3-C9 heteroaryl optionally substituted with one to four halogens or C1-C3 alkyls, C3-C6 heterocyclyl optionally substituted with C1-C3 alkyl, and C6-C10 aryl optionally substituted with one to four halogens and/or one to four $-NH(C=O)R^{13}$;

$R^{13}$ is, at each occurrence, independently selected from the group consisting of hydrogen, C1-C6 alkyl, C1-C6 alkyl substituted with $-CN$, $-OH$, $-OR^5$, $-NH_2$, $-NHR^5$ or $-N(R^5)R^5$ and C3-C10 cycloalkyl;

$R^{14}$ and $R^{15}$ are, at each occurrence, independently selected from the group consisting of hydrogen, halogen, C1-C6 alkyl, C1-C6 alkyl substituted with $-OH$ or $-NH_2$, C3-C10 cycloalkyl, $-(C=O)R^5$, $-(C=O)NHR^{21}$, $-C(R^9)(R^{11})OR^{21}$, $-NH(C=O)R^{21}$, $-NR^9R^{21}$, $-OR^{21}$, $-OC(R^9)(R^{11})(R^{21})$, C3-C10 heterocyclyl, C3-C10 heterocyclyl substituted with $R^4$, C3-C10 heteroaryl substituted with one to four halogens or C1-C3 alkyl, C6-C10 aryl, and aryl substituted with $-(C=O)R^5$, $-(C=O)OR^5$, $-(C=O)NH_2$, $-(C=O)NHR^{21}$, $-CH_2(C=O)NHR^{21}$, $-NH(C=O)R^{13}$, $-NHS(=O)_2R^5$, $-S(=O)_2NH_2$ or $-S(=O)_2NHR^{21}$;

$R^{16}$ is, at each occurrence, independently selected from the group consisting of hydrogen, C1-C6 alkyl, $-(C=O)R^{13}$ and C1-C6 alkyl substituted with $-OR^5$;

$R^{17}$, $R^{18}$, $R^{19}$ and $R^{20}$ are, at each occurrence, independently selected from the group consisting of hydrogen, halogen, C1-C6 alkyl, C1-C3 haloalkyl, C6-C10 aryl, $-CN$, $-CHCF_3NR^9R^{11}$, $-OH$, $-OR^{21}$, $-NO_2$, $-(C=O)R^5$, $-(C=O)OR^5$, $-(C=O)NH_2$, $-(C=O)NHR^{21}$, $-NH(C=O)R^{13}$, $-NHR^5$, $-NHS(=O)_2R^5$, $-S(=O)_2NH_2$, $-S(=O)_2NHR^{21}$ and C1-C6 alkyl substituted with $-CN$, $-OH$, $-OR^5$, $-(C=O)NHR^5$, $-NH_2$, $-NH(C=O)R^5$, $-NHR^5$ or $-N(R^5)R^5$;

$R^{21}$ is, at each occurrence, independently selected from the group consisting of C3-C10 cycloalkyl, C1-C3 haloalkyl, benzyl, C1-C6 alkyl optionally substituted with $-CN$, $-OH$, $-OR^5$, $-NH_2$, $-NHR^5$ or $-N(R^5)R^5$, aryl optionally substituted with halogen or C1-C3 haloalkyl, C3-C10 heteroaryl substituted with one to four halogens or C1-C3 alkyl and C3-C10 heterocyclyl optionally substituted with $R^4$;

$R^{22}$ and $R^{23}$ are, at each occurrence, independently selected from the group consisting of hydrogen, halogen, C1-C6 alkyl, C1-C3 haloalkyl, $-OH$, $-OR^5$, $-CN$ and C1-C6 alkyl substituted with $-OH$, $-OR^5$ or $-NHR^9$;

$R^{24}$ and $R^{25}$ are, at each occurrence, independently selected from the group consisting of hydrogen, halogen, C1-C6 alkyl, C1-C3 haloalkyl, —$NH_2$, —OH, —$OR^5$, —CN, —(C=O)$R^5$, —(C=O)$OR^5$, —(C=O)$NH_2$, —(C=O)$NHR^{21}$, —$CH_2$(C=O)$NHR^{21}$, —NH(C=O)$R^{13}$, —NHS(=O)$_2R^5$, —S(=O)$_2NH_2$ or —S(=O)$_2NHR^{21}$ and C1-C6 alkyl substituted with —OH, —$OR^5$ or —$NHR^9$;

with the proviso that when Z is

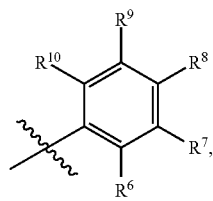

then one of $R^6$ and $R^7$ is not H;

with the proviso that when Z is

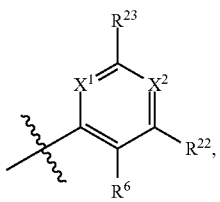

then one of $R^6$ and $R^{22}$ is not H;

with the proviso that when $R^6$ is

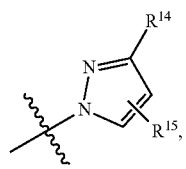

then one of $R^{14}$ and $R^{15}$ is not H, and if $R^{14}$ is H, then $R^{15}$ is not Cl;

wherein, if $R^1$ is H, $R^2$ is $CH(CH_3)_2$, $L^1$ is absent, Q is heterocycyl substituted with $R^3$ and $R^4$, $R^3$ is $N(R^5)R^5$, $R^4$ is H, $R^5$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is O, Q is heterocycyl substituted with $R^3$ and $R^4$, $R^3$ is $CH_3$, $R^4$ is H, X is N, Z is phenyl, $R^7$ is H, $R^8$ is H, $R^9$ is H and $R^{10}$ is H, then $R^6$ is 1H-pyrazole;

wherein, if $R^1$ is H, $R^2$ is $CH(CH_3)_2$, $L^1$ is —(C=O)—, Q is heterocycyl substituted with $R^3$ and $R^4$, $R^4$ is H, X is N, Z is phenyl, $R^6$ is 1H-pyrazole, $R^7$ is H, $R^8$ is H, $R^9$ is H and $R^{10}$ is H, then $R^3$ is not H;

wherein, if $R^1$ is H, $R^2$ is $CH(CH_3)_2$, $L^1$ is —(C=O)—, Q is heterocycyl substituted with $R^3$ and $R^4$, $R^3$ is $N(R^5)R^5$, $R^4$ is H, $R^5$ is H, X is N, Z is phenyl, $R^7$ is H, $R^8$ is H, $R^9$ is H and $R^{10}$ is H, then $R^6$ is not 1H-pyrazole, wherein, if $R^1$ is H, $R^2$ is $CH(CH_3)_2$, $L^1$ is O, Q is heterocycyl substituted with $R^3$ and $R^4$, $R^3$ is H, $R^4$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is O, Q is C3-C8 cycloalkyl substituted with $R^3$ and $R^4$, $R^3$ is $N(R^5)R^5$, $R^4$ is H, $R^5$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is NH, Q is heterocycyl substituted with $R^3$ and $R^4$, $R^3$ is H, $R^4$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is NH, Q is C3-C8 cycloalkyl substituted with $R^3$ and $R^4$, $R^3$ is $N(R^5)R^5$, $R^4$ is H, $R^5$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is O, Q is heterocycyl substituted with $R^3$ and $R^4$, $R^3$ is H, $R^4$ is H, X is N, Z is phenyl, $R^7$ is H, $R^8$ is H, $R^9$ is H and $R^{10}$ is F, then $R^6$ is not 1H-pyrazole;

wherein, if $R^1$ is $CH_3$, $R^2$ is $CH(CH_3)_2$, $L^1$ is O, Q is heterocycyl substituted with $R^3$ and $R^4$, $R^3$ is H, $R^4$ is H, X is N, Z is phenyl, $R^7$ is H, $R^8$ is H, $R^9$ is H and $R^{10}$ is H, then $R^6$ is not 1H-pyrazole;

wherein, if $R^1$ is $CH_3$, $R^2$ is $CH(CH_3)_2$, $L^1$ is O, Q is heterocycyl substituted with $R^3$ and $R^4$, $R^3$ is $CH_3$, $R^4$ is H, X is N, Z is phenyl, $R^7$ is H, $R^8$ is H, $R^9$ is H and $R^{10}$ is H, then $R^6$ is not 1H-pyrazole;

wherein, if $R^1$ is $CH_3$, $R^2$ is $CH(CH_3)_2$, $L^1$ is O, Q is heterocycyl substituted with $R^3$ and $R^4$, $R^3$ is H, $R^4$ is H, X is N, Z is phenyl, $R^6$ is H, $R^7$ is $OR^{12}$, $R^8$ is H, $R^9$ is H and $R^{10}$ is H, then $R^{12}$ is not $CH_3$;

or an enantiomer, stereoisomeric form, mixture of enantiomers, diastereomer, mixture of diastereomers, racemate of the above compounds, or a pharmaceutically acceptable salt thereof.

2. The compound according to claim 1, wherein $R^{14}$, $R^{15}$, $R^{17}$, $R^{18}$, $R^{19}$ or $R^{20}$ is phenyl.

3. The compound according to claim 1, wherein $R^1$ is hydrogen and the compound has the general formula II

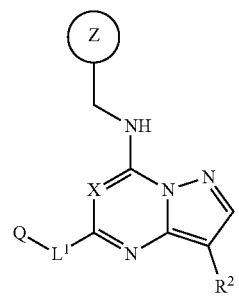

Formula II wherein X, Q, $L^1$, $R^2$ and Z are as defined in claim 1.

4. The compound according to claim 1, having the general formula III

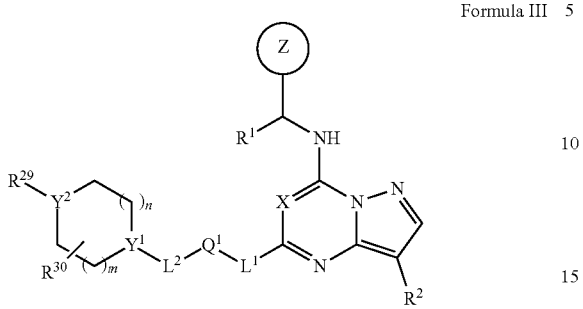

Formula III wherein X, $L^1$, $R^1$, $R^2$ and Z are as defined in claim 1, and $Q^1$ is either absent or independently, at each occurrence, selected from the group consisting of aryl optionally substituted with one or two of C1-C6 alkyl, —$OR^5$, —$N(R^5)R^5$, and halogen;

heteroaryl optionally substituted with one or two of C1-C6 alkyl, —$OR^5$, —$N(R^5)R^5$ and halogen;

and heterocyclyl optionally substituted with one or two of $R^{29}$ and $R^{30}$;

$R^{29}$ is either absent or independently, at each occurrence, selected from the group consisting of hydrogen, —$OR^5$, halogen, —$N(R^5)R^5$, —$NR^9R^{12}$, —NH(C=O) $R^5$, —(C=O)$NH_2$, aryl, heteroaryl, heterocyclyl, and C1-C6 alkyl optionally substituted with —OH or —$NH_2$;

$R^{30}$ is, independently, at each occurrence, selected from the group consisting of hydrogen, halogen, —$OR^5$, —$N(R^5)R^5$, (=O), aryl, heteroaryl, heterocyclyl, and C1-C6 alkyl optionally substituted with —OH or —$NH_2$;

wherein $R^5$, $R^9$ and $R^{12}$ are as defined in claim 1;

$L^2$ is either absent or independently, at each occurrence, selected from the group consisting of —O—, —NH—, —(C=O)— and —(C=O)NH—;

$Y^1$ is, independently at each occurrence, selected from CH, C(OH) and N;

$Y^2$ is, independently at each occurrence, selected from CH, $CR^{30}$, O and N;

m is, independently at each occurrence, selected from 0, 1 and 2;

n is, independently at each occurrence, selected from 0 and 1;

wherein, if $R^1$ is H, $R^2$ is $CH(CH_3)_2$, $L^1$ is absent, $Q^1$ is absent, $L^2$ is absent, $Y^1$ is N, $Y^2$ is CH, m is 1, n is 1, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is —(C=O)—, $Q^1$ is absent, $L^2$ is absent, $Y^1$ is N, $Y^2$ is N, m is 1, n is 1, $R^{30}$ is H, X is N, Z is phenyl, $R^6$ is 1H-pyrazole, $R^7$ is H, $R^8$ is H, $R^9$ is H and $R^{10}$ is H, then $R^{29}$ is not H;

wherein, if $R^1$ is H, $R^2$ is $CH(CH_3)_2$, $L^1$ is —(C=O)—, $Q^1$ is absent, $L^2$ is absent, $Y^1$ is N, $Y^2$ is CH, m is 1, n is 1, $R^{29}$ is $N(R^5)R^5$, $R^{30}$ is H, $R^5$ is H, $R^{30}$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is H, $R^{30}$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 0, $R^{29}$ is H, $R^{30}$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is O, $Q^1$ is absent, $L^2$ is absent, $Y^1$ is CH, $Y^2$ is CH, m is 1, n is 1, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is NH, $Q^1$ is absent, $L^2$ is absent, $Y^1$ is CH, $Y^2$ is N, m is 1, n is 0, $R^{29}$ is H, $R^{30}$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is absent, $Q^1$ is absent, $L^2$ is absent, $Y^1$ is N, $Y^2$ is CH, m is 1, n is 0, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is NH, $Q^1$ is absent, $L^2$ is absent, $Y^1$ is CH, $Y^2$ is CH, m is 1, n is 1, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is absent, $Q^1$ is absent, $L^2$ is absent, $Y^1$ is N, $Y^2$ is CH, m is 2, n is 0, $R^{29}$ is $N(R^5)R^5$, $R^{30}$ is H, $R^5$ is H, X is N, Z is phenyl, $R^7$ is H, $R^8$ is H, $R^9$ is H and $R^{10}$ is H, then $R^6$ is not 1H-pyrazole;

wherein, if $R^1$ is H, $R^2$ is $CH(CH_3)_2$, $L^1$ is O, $Q^1$ is absent, $L^2$ is absent, V is CH, $Y^2$ is N, m is 2, n is 0, $R^{29}$ is H, $R^{30}$ is H, X is N, Z is phenyl, $R^7$ is H, $R^8$ is H, $R^9$ is H and $R^{10}$ is F, then $R^6$ is not 1H-pyrazole;

wherein, if $R^1$ is H, $R^2$ is $CH(CH_3)_2$, $L^1$ is O, $Q^1$ is absent, $L^2$ is absent, $Y^1$ is CH, $Y^2$ is N, m is 1, n is 1, $R^{29}$ is $CH_3$, $R^{30}$ is H, X is N, Z is phenyl, $R^7$ is H, $R^8$ is H, $R^9$ is H and $R^{10}$ is H, then $R^6$ is not 1H-pyrazole;

wherein, if $R^1$ is $CH_3$, $R^2$ is $CH(CH_3)_2$, $L^1$ is O, $Q^1$ is absent, $L^2$ is absent, $Y^1$ is CH, $Y^2$ is N, m is 2, n is 0, $R^{29}$ is H, $R^{30}$ is H, X is N, Z is phenyl, $R^7$ is H, $R^8$ is H, $R^9$ is H and $R^{10}$ is H, then $R^6$ is not 1H-pyrazole;

or an enantiomer, stereoisomeric form, mixture of enantiomers, diastereomer, mixture of diastereomers, racemate of the above compounds, or a pharmaceutically acceptable salt thereof.

5. The compound according to claim 1, having the general formula IV

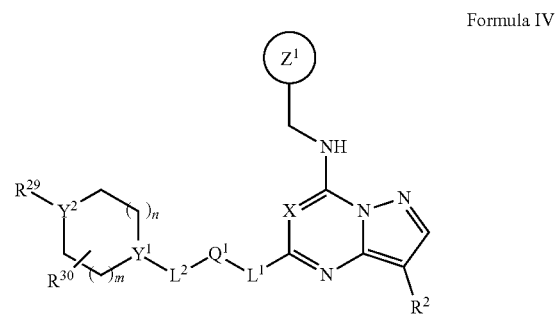

Formula IV wherein X, and $R^2$ are as defined in claim 1;

wherein $Q^1$ is either absent or independently, at each occurrence, selected from the group consisting of aryl optionally substituted with one or two of C1-C6 alkyl, —$OR^5$, —$N(R^5)R^5$, and halogen; heteroaryl optionally substituted with one or two of C1-C6 alkyl, —$OR^5$, —$N(R^5)R^5$ and halogen; and heterocyclyl optionally substituted with one or two of $R^{29}$ and $R^{30}$;

$R^{29}$ is either absent or independently, at each occurrence, selected from the group consisting of hydrogen, —Ole, halogen, —$N(R^5)R^5$, —$NR^9R^{12}$, —$NH(C=O)R^5$, —$(C=O)NH_2$, aryl, heteroaryl, heterocyclyl, C1-C6 alkyl and C1-C6 alkyl substituted with —OH or —$NH_2$;

$R^{30}$ is, independently, at each occurrence, selected from the group consisting of hydrogen, halogen, —$OR^5$, —$N(R^5)R^5$, (=O), aryl, heteroaryl, heterocyclyl, C1-C6 alkyl and C1-C6 alkyl substituted with —OH or —$NH_2$;

$L^2$ is either absent or independently, at each occurrence, selected from the group consisting of —O—, —NH—, —(C=O)— and —(C=O)NH—;

$Y^1$ is, independently at each occurrence, selected from CH, C(OH) and N;

$Y^2$ is, independently at each occurrence, selected from CH, $CR^{30}$, O and N;

m is, independently at each occurrence, selected from 0, 1 and 2;

n is, independently at each occurrence, selected from 0 and 1;

wherein $Z^1$ is

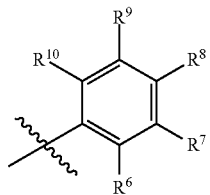

and wherein $R^6$, $R^7$, $R^8$, $R^9$ and $R^{10}$ are as defined in claim 1.

6. The compound according to claim 1, having the general formula V

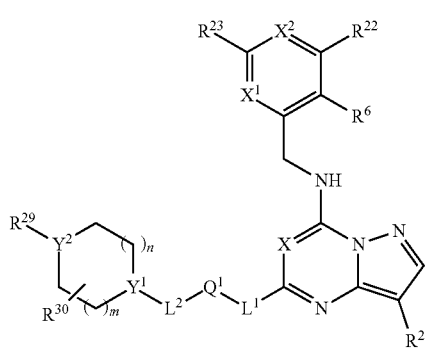

Formula V wherein X, $X^1$, $X^2$, $L^1$, $R^2$, $R^6$, $R^{22}$ and $R^{23}$ are as defined in claim 1;

wherein $Q^1$ is either absent or independently, at each occurrence, selected from the group consisting of aryl optionally substituted with one or two of C1-C6 alkyl, —$OR^5$, —$N(R^5)R^5$, and halogen; heteroaryl optionally substituted with one or two of C1-C6 alkyl, —$OR^5$, —$N(R^5)R^5$ and halogen; and heterocyclyl optionally substituted with one or two of $R^{29}$ and $R^{30}$;

$R^{29}$ is either absent or independently, at each occurrence, selected from the group consisting of hydrogen, —$OR^5$, halogen, —$N(R^5)R^5$, —$NR^9R^{12}$, —$NH(C=O)R^5$, —$(C=O)NH_2$, aryl, heteroaryl, heterocyclyl, C1-C6 alkyl and C1-C6 alkyl substituted with —OH or —$NH_2$;

$R^{30}$ is, independently, at each occurrence, selected from the group consisting of hydrogen, halogen, —$OR^5$, —$N(R^5)R^5$, (=O), aryl, heteroaryl, heterocyclyl, C1-C6 alkyl and C1-C6 alkyl substituted with —OH or —$NH_2$;

$L^2$ is either absent or independently, at each occurrence, selected from the group consisting of —O—, —NH—, —(C=O)— and —(C=O)NH—;

$Y^1$ is, independently at each occurrence, selected from CH, C(OH) and N;

$Y^2$ is, independently at each occurrence, selected from CH, $CR^{30}$, O and N;

m is, independently at each occurrence, selected from 0, 1 and 2; and n is, independently at each occurrence, selected from 0 and 1.

7. The compound according to claim 1, having the general formula VI

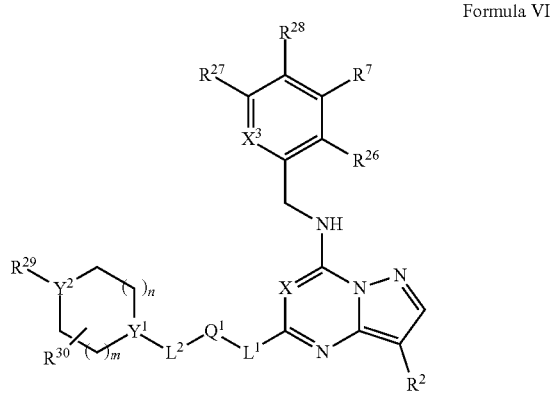

Formula VI wherein X, $L^1$ and $R^2$ are as defined in claim 1;

wherein $Q^1$ is either absent or independently, at each occurrence, selected from the group consisting of aryl optionally substituted with one or two of C1-C6 alkyl, —$OR^5$, —$N(R^5)R^5$, and halogen; heteroaryl optionally substituted with one or two of C1-C6 alkyl, —$OR^5$, —$N(R^5)R^5$ and halogen; and heterocyclyl optionally substituted with one or two of $R^{29}$ and $R^{30}$;

$R^{29}$ is either absent or independently, at each occurrence, selected from the group consisting of hydrogen, —$OR^5$, halogen, —$N(R^5)R^5$, —$NR^9R'2$, —$NH(C=O)R^5$, —$(C=O)NH_2$, aryl, heteroaryl, heterocyclyl, C1-C6 alkyl and C1-C6 alkyl substituted with —OH or —$NH_2$;

$R^{30}$ is, independently, at each occurrence, selected from the group consisting of hydrogen, halogen, —$OR^5$, —$N(R^5)R^5$, (=O), aryl, heteroaryl, heterocyclyl, C1-C6 alkyl and C1-C6 alkyl substituted with —OH or —$NH_2$;

L² is either absent or independently, at each occurrence, selected from the group consisting of —O—, —NH—, —(C=O)— and —(C=O)NH—;

Y¹ is, independently at each occurrence, selected from CH, C(OH) and N;

Y² is, independently at each occurrence, selected from CH, CR³⁰, O and N;

m is, independently at each occurrence, selected from 0, 1 and 2;

n is, independently at each occurrence, selected from 0 and 1;

X³ is, independently at each occurrence, selected from CR¹⁰ and N;

R²⁶, R²⁷ and R²⁸ are, at each occurrence, independently selected from the group consisting of hydrogen, halogen, C1-C6 alkyl, C1-C3 haloalkyl, —OR⁵, —CN and C1-C6 alkyl substituted with —OH, —OR⁵ or —NHR⁹;

R⁵, R⁹ and R¹⁰ are as defined in claim 1;

R⁷ is any structure of the following group E;

Group E

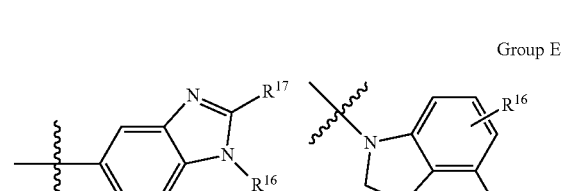
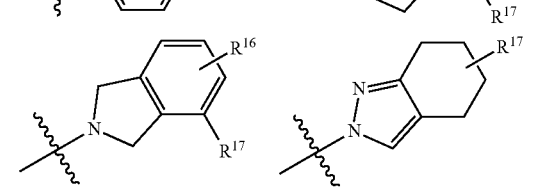
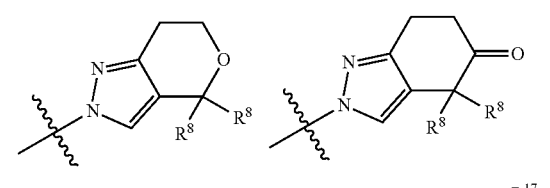
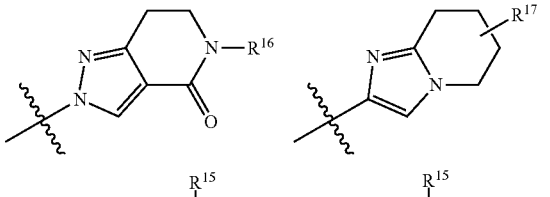
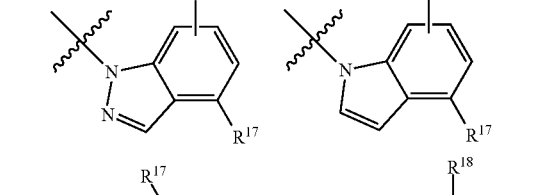
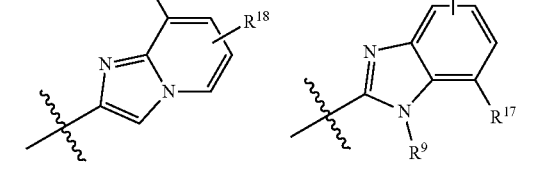
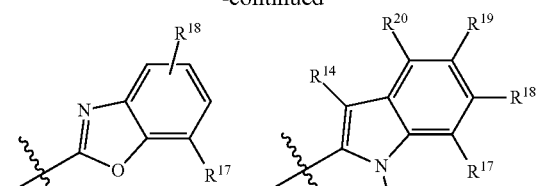
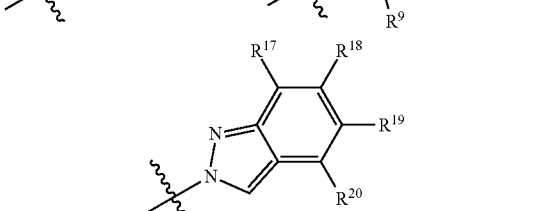
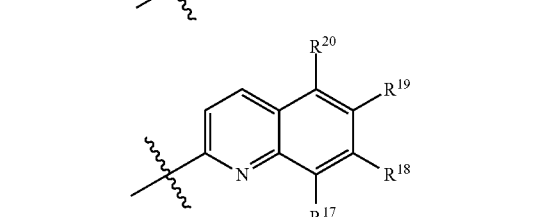
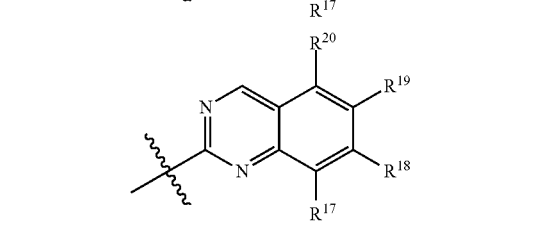
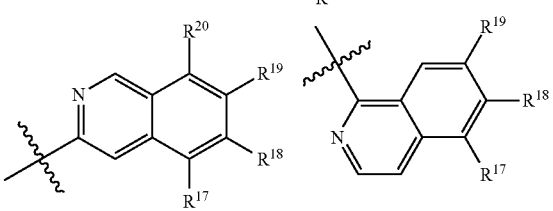
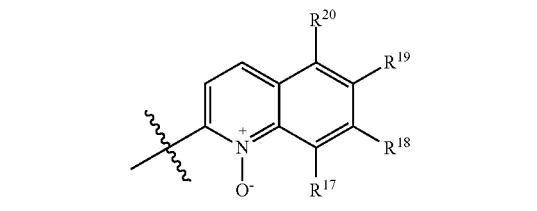
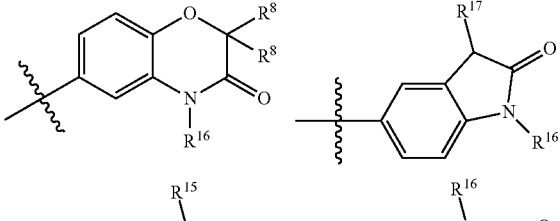
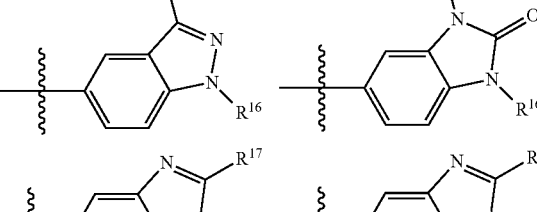
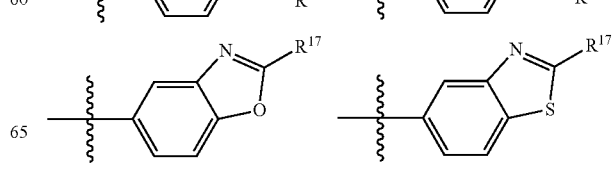

-continued

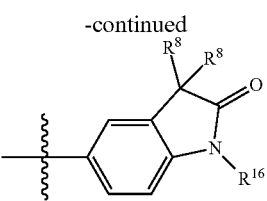

and wherein $R^8$ and $R^{14}$-$R^{20}$ are as defined in claim 1.

8. The compound according to claim 1, having the general formula VII

Formula VII

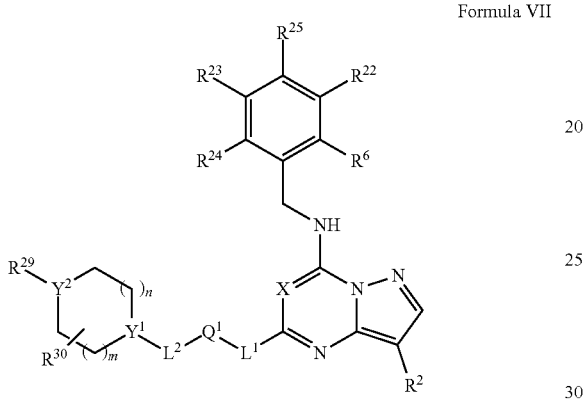

wherein X, $L^1$, $R^2$, $R^6$, $R^{22}$, $R^{23}$, $R^{24}$ and $R^{25}$ are as defined in claim 1;

$Q^1$ is either absent or independently, at each occurrence, selected from the group consisting of aryl optionally substituted with one or two of C1-C6 alkyl, —$OR^5$, —$N(R^5)R^5$, and halogen;

heteroaryl optionally substituted with one or two of C1-C6 alkyl, —$OR^5$, —$N(R^5)R^5$ and halogen;

and heterocyclyl optionally substituted with one or two of $R^{29}$ and $R^{30}$;

$R^{29}$ is either absent or independently, at each occurrence, selected from the group consisting of hydrogen, —$OR^5$, halogen, —$N(R^5)R^5$, —$NR^9R^{12}$, —NH(C=O) $R^5$, —(C=O)$NH_2$, aryl, heteroaryl, heterocyclyl, C1-C6 alkyl and C1-C6 alkyl substituted with —OH or —$NH_2$;

$R^{30}$ is, independently, at each occurrence, selected from the group consisting of hydrogen, halogen, —$OR^5$, —$N(R^5)R^5$, (=O), aryl, heteroaryl, heterocyclyl, C1-C6 alkyl and C1-C6 alkyl substituted with —OH or —$NH_2$;

$L^2$ is either absent or independently, at each occurrence, selected from the group consisting of —O—, —NH—, —(C=O)— and —(C=O)NH—;

$Y^1$ is, independently, at each occurrence, selected from CH, C(OH) and N;

$Y^2$ is, independently, at each occurrence, selected from CH, $CR^{30}$, O and N;

m is, independently, at each occurrence, selected from 0, 1 and 2; and n is, independently, at each occurrence, selected from 0 and 1.

9. The compound according to claim 1, having the general formula VIII

Formula VIII

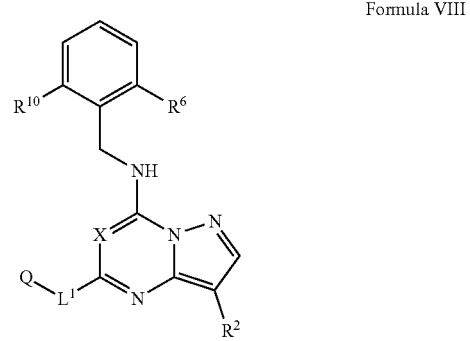

wherein X, $L^1$, $R^2$, $R^6$ and $R^{10}$ are as defined in claim 1, with the proviso that not both of $R^6$ and $R^{10}$ are hydrogen.

10. The compound according to claim 1, having the general formula IX

Formula IX

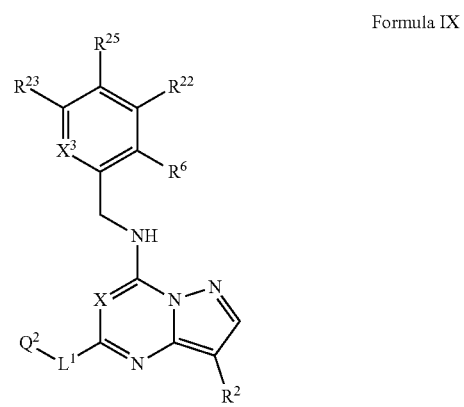

wherein X is N; $L^1$, $R^2$, $R^6$, $R^{22}$, $R^{24}$ and $R^{25}$ are as defined in claim 1, and $X^3$ is, independently at each occurrence, selected from $CR^{10}$ and N;

$R^{23}$ is selected from the group consisting of hydrogen, halogen, C1-C3 haloalkyl, —$OR^5$, —CN and C1-C6 alkyl optionally substituted with —OH, or —$OR^5$;

wherein $Q^2$ is any structure of the following group F;

Group F

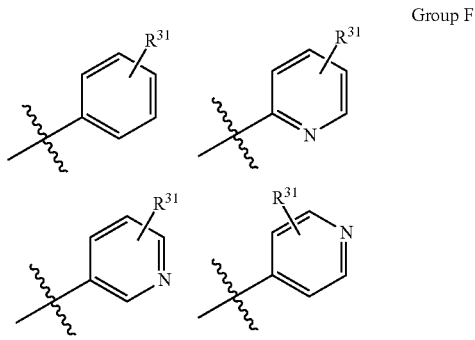

295

-continued

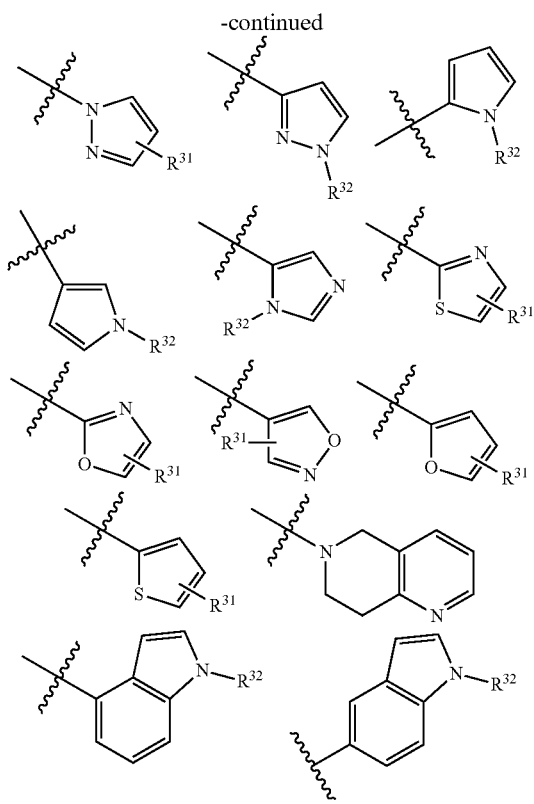

296

-continued

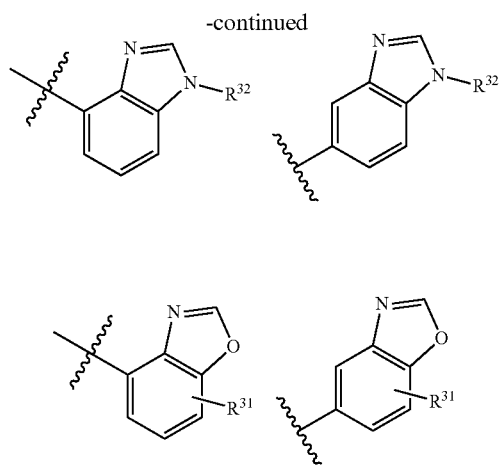

$R^{31}$ and $R^{32}$ are either absent or independently, at each occurrence, selected from the group consisting of hydrogen, —$OR^5$, halogen, —$N(R^5)R^5$, —$NR^9R^{12}$, —$NH(C=O)R^5$, —$(C=O)NH_2$, aryl, heteroaryl, heterocyclyl, C1-C6 alkyl and C1-C6 alkyl substituted with —OH or —$NH_2$; and wherein $R^5$, $R^9$ and $R^{12}$ are as defined in claim 1.

11. The compound according to claim 1, having a structure selected from

| #cpds | Structure |
|---|---|
| 14 | 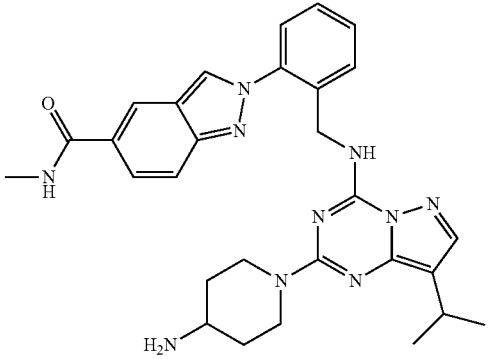 |
| 17 | 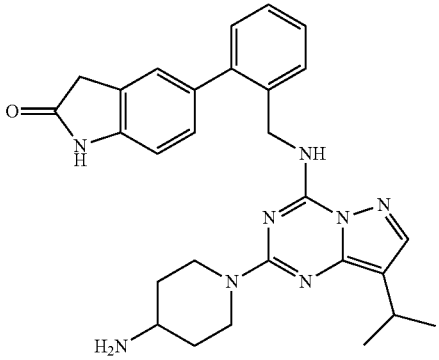 [SMILES: CC(C)c1cnn2c(NCc3ccccc3-c3ccc4c(c3)CC(=O)N4)nc(N3CCC(N)CC3)nc12] |

| #cpds | Structure |
|---|---|
| 47 | 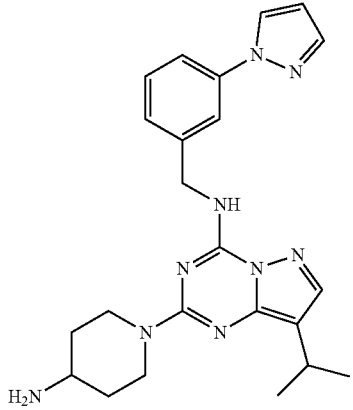 |
| 48 | 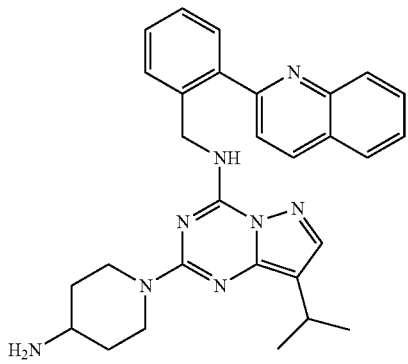 |
| 58 | 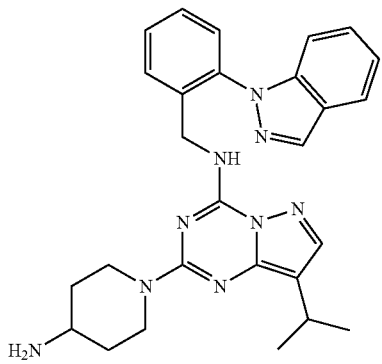 [SMILES: CC(C)c1cnn2c(NCc3ccccc3-n3ncc4ccccc43)nc(N3CCC(N)CC3)nc12] |
| 65 | 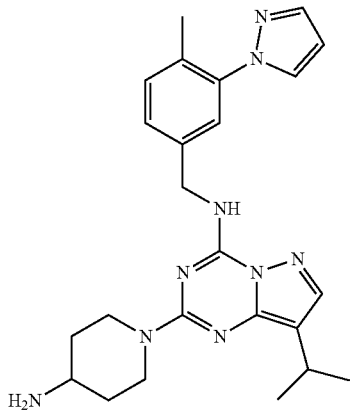 |

| #cpds | Structure |
|---|---|
| 67 | 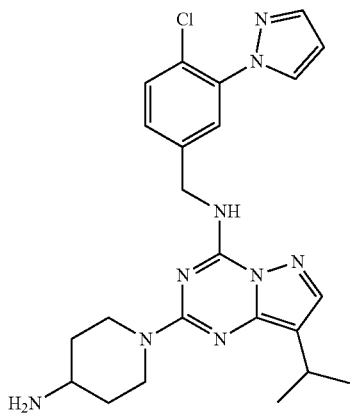 |
| 68 | 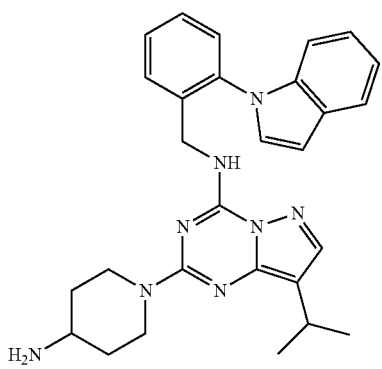 [SMILES: CC(C)c1cnn2c(NCc3ccccc3-n3ccc4ccccc43)nc(N3CCC(N)CC3)nc12] |
| 72 | 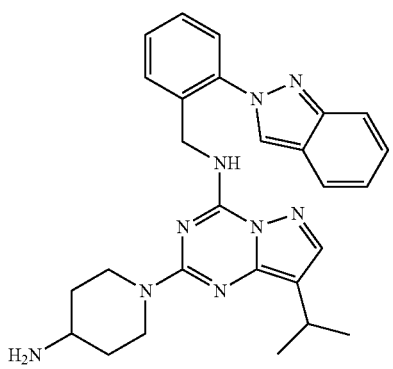 [SMILES: CC(C)c1cnn2c(NCc3ccccc3-n3cc4ccccc4n3)nc(N3CCC(N)CC3)nc12] |
| 73 | 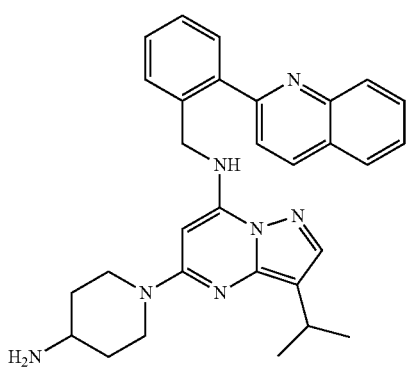 [SMILES: CC(C)c1cnn2c(NCc3ccccc3-c3ccc4ccccc4n3)cc(N3CCC(N)CC3)nc12] |

| #cpds | Structure |
|---|---|
| 75 | 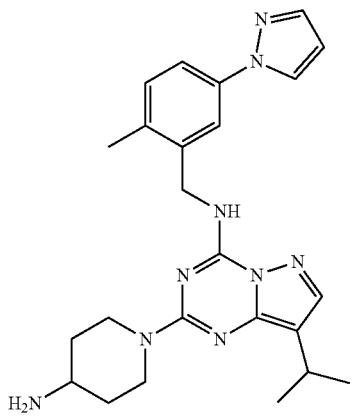 |
| 76 | 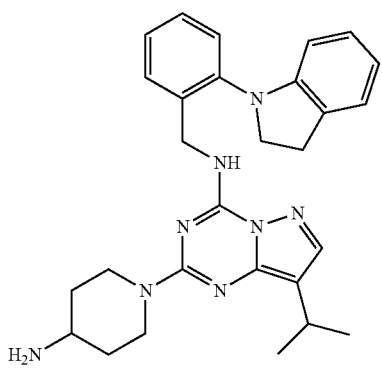 [SMILES: CC(C)c1cnn2c(NCc3ccccc3N3CCc4ccccc43)nc(N3CCC(N)CC3)nc12] |
| 77 | 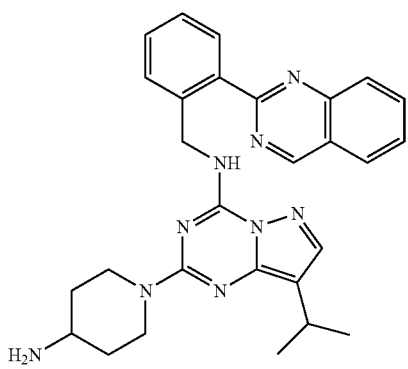 |
| 78 | 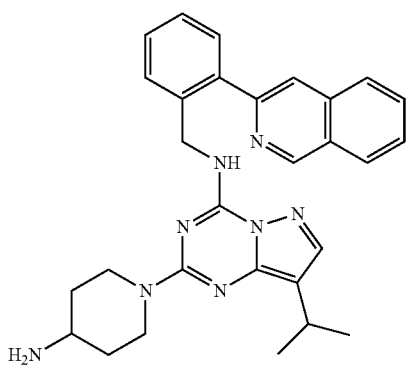 |

| #cpds | Structure |
|---|---|
| 79 | 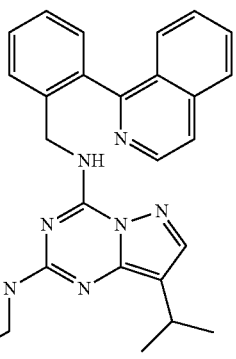 |
| 80 | 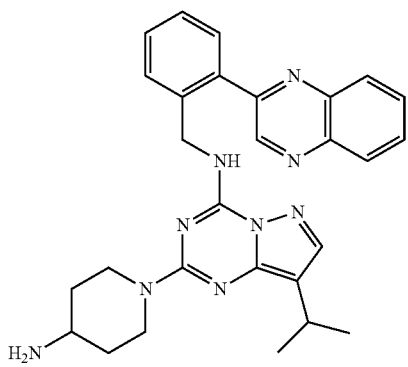 |
| 81 | 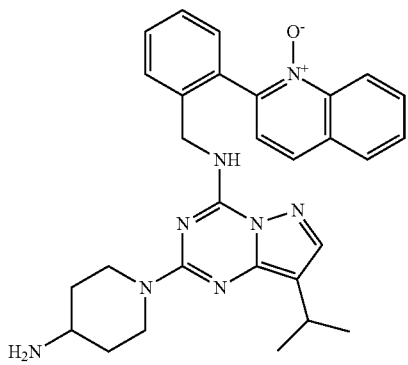 |
| 90 | 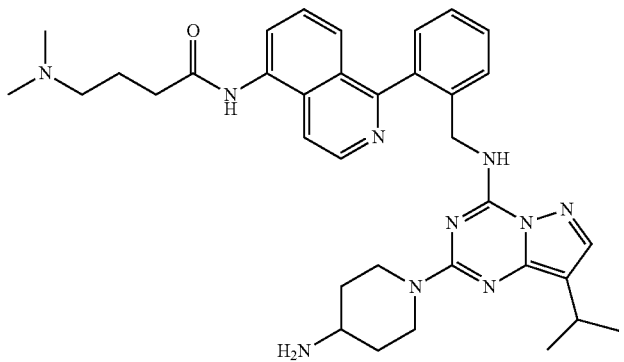 [SMILES: CC(C)c1cnn2c(NCc3ccccc3-c3nccc4c(NC(=O)CCCN(C)C)cccc34)nc(N3CCC(N)CC3)nc12] |

-continued
| #cpds | Structure |
|---|---|
| 92 | 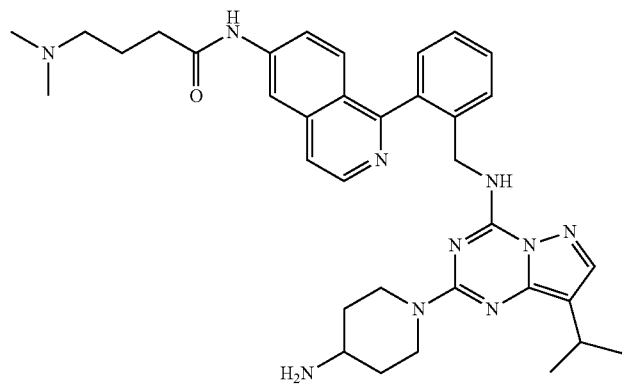 [SMILES: CC(C)c1cnn2c(NCc3ccccc3-c3nccc4cc(NC(=O)CCCN(C)C)ccc34)nc(N3CCC(N)CC3)nc12] |
| 96 | 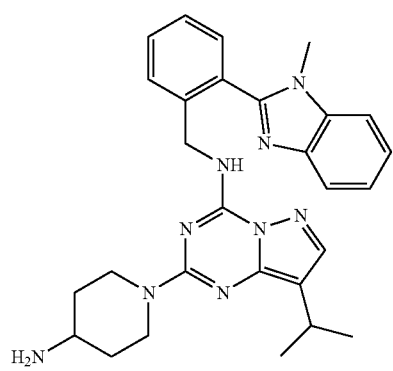 [SMILES: CC(C)c1cnn2c(NCc3ccccc3-c3nc4ccccc4n3C)nc(N3CCC(N)CC3)nc12] |
| 97 | 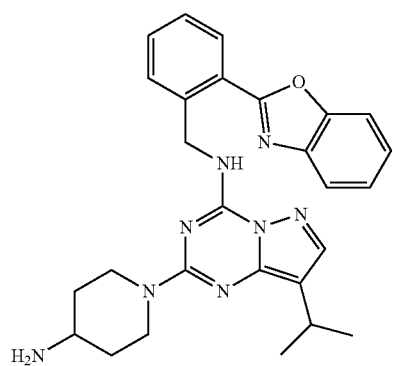 [SMILES: CC(C)c1cnn2c(NCc3ccccc3-c3nc4ccccc4o3)nc(N3CCC(N)CC3)nc12] |
| 98 | 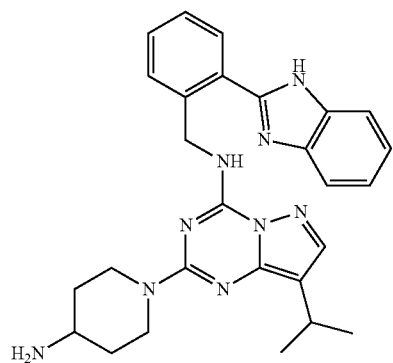 [SMILES: CC(C)c1cnn2c(NCc3ccccc3-c3nc4ccccc4[nH]3)nc(N3CCC(N)CC3)nc12] |

| #cpds | Structure |
|---|---|
| 99 | 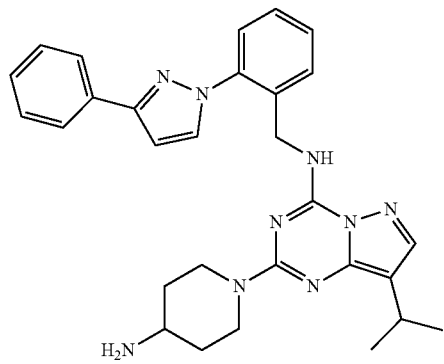 [SMILES: CC(C)c1cnn2c(NCc3ccccc3-n3ccc(-c4ccccc4)n3)nc(N3CCC(N)CC3)nc12] |
| 100 | 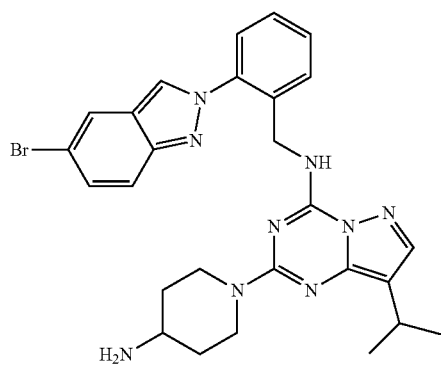 |
| 101 | 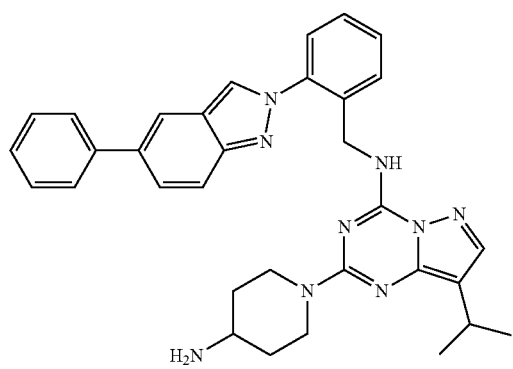 [SMILES: CC(C)c1cnn2c(NCc3ccccc3-n3cc4cc(-c5ccccc5)ccc4n3)nc(N3CCC(N)CC3)nc12] |
| 102 | 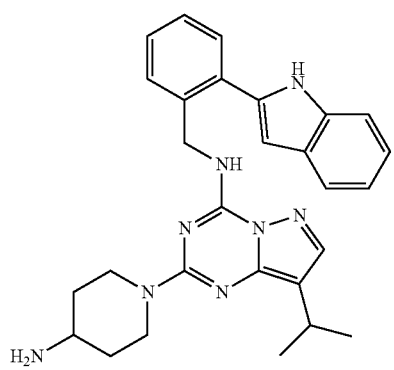 |

| #cpds | Structure |
|---|---|
| 103 | 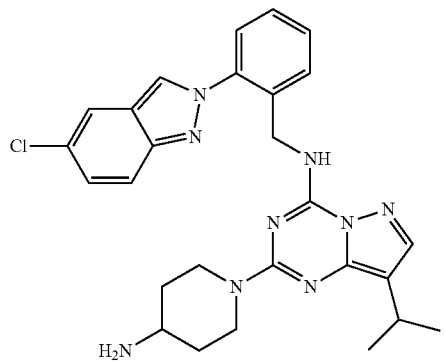 [SMILES: CC(C)c1cnn2c(NCc3ccccc3-n3cc4cc(Cl)ccc4n3)nc(N3CCC(N)CC3)nc12] |
| 104 | 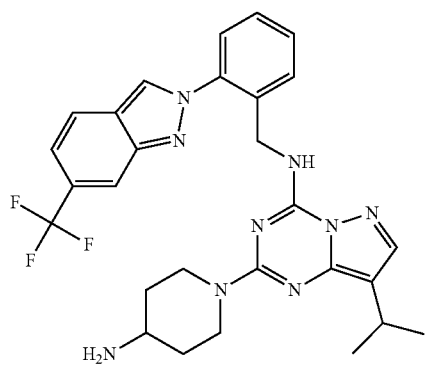 [SMILES: CC(C)c1cnn2c(NCc3ccccc3-n3cc4ccc(C(F)(F)F)cc4n3)nc(N3CCC(N)CC3)nc12] |
| 105 | 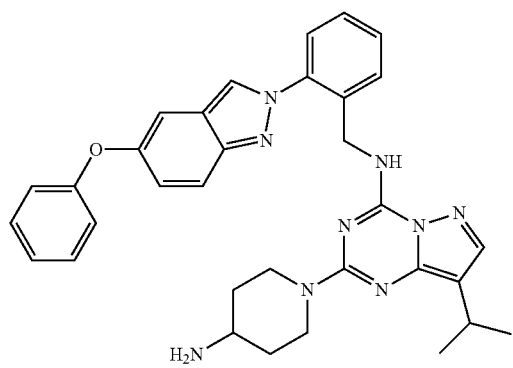 [SMILES: CC(C)c1cnn2c(NCc3ccccc3-n3cc4cc(Oc5ccccc5)ccc4n3)nc(N3CCC(N)CC3)nc12] |
| 106 | 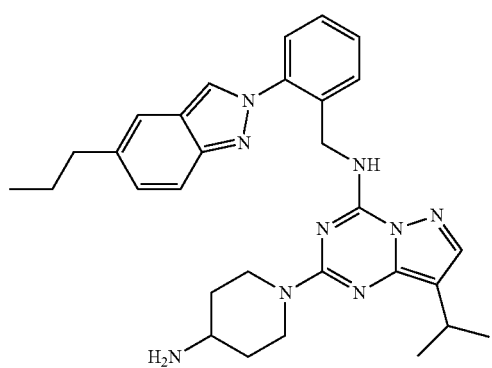 [SMILES: CCCc1ccc2nn(-c3ccccc3CNc3nc(N4CCC(N)CC4)nc4c(C(C)C)cnn34)cc2c1] |

-continued
| #cpds | Structure |
|---|---|
| 107 | 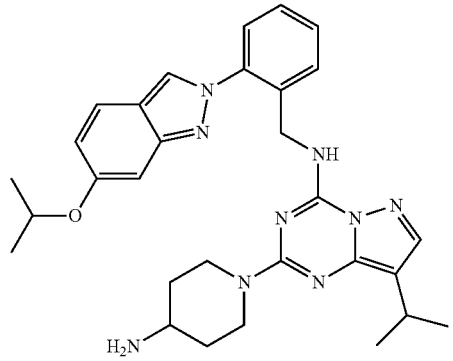 [SMILES: CC(C)Oc1ccc2cn(-c3ccccc3CNc3nc(N4CCC(N)CC4)nc4c(C(C)C)cnn34)nc2c1] |
| 108 | 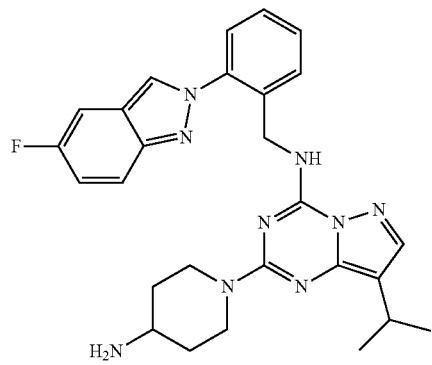 [SMILES: CC(C)c1cnn2c(NCc3ccccc3-n3cc4cc(F)ccc4n3)nc(N3CCC(N)CC3)nc12] |
| 109 | 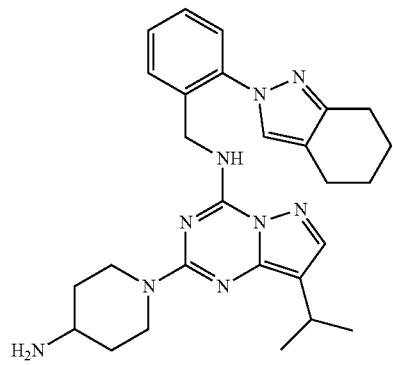 [SMILES: CC(C)c1cnn2c(NCc3ccccc3-n3cc4c(n3)CCCC4)nc(N3CCC(N)CC3)nc12] |
| 110 | 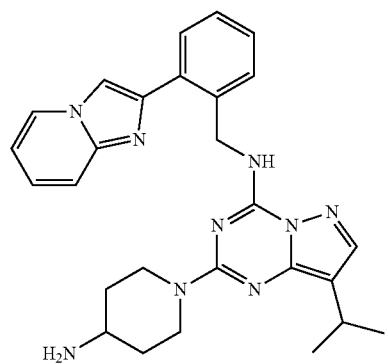 [SMILES: CC(C)c1cnn2c(NCc3ccccc3-c3cn4ccccc4n3)nc(N3CCC(N)CC3)nc12] |

-continued
| #cpds | Structure |
|---|---|
| 111 | 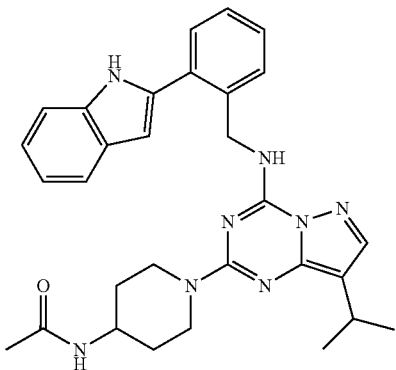 [SMILES: CC(=O)NC1CCN(c2nc(NCc3ccccc3-c3cc4ccccc4[nH]3)n3ncc(C(C)C)c3n2)CC1] |
| 112 | 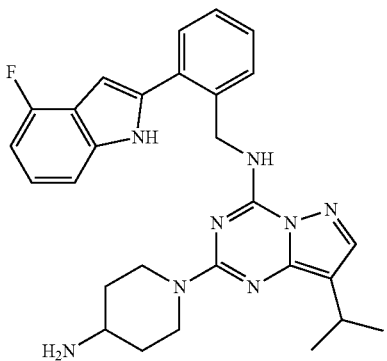 |
| 113 | 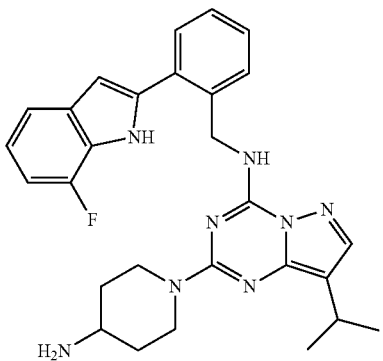 [SMILES: CC(C)c1cnn2c(NCc3ccccc3-c3cc4cccc(F)c4[nH]3)nc(N3CCC(N)CC3)nc12] |
| 114 | 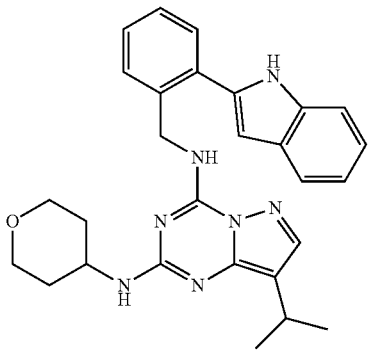 [SMILES: CC(C)c1cnn2c(NCc3ccccc3-c3cc4ccccc4[nH]3)nc(NC3CCOCC3)nc12] |

-continued
| #cpds | Structure |
|---|---|
| 115 | 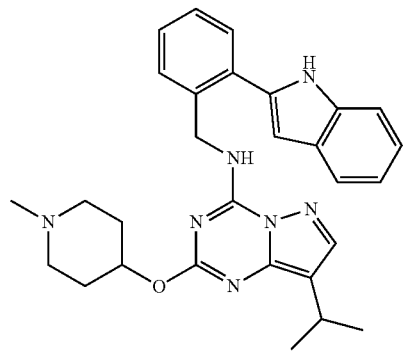 [SMILES: CC(C)c1cnn2c(NCc3ccccc3-c3cc4ccccc4[nH]3)nc(OC3CCN(C)CC3)nc12] |
| 116 | 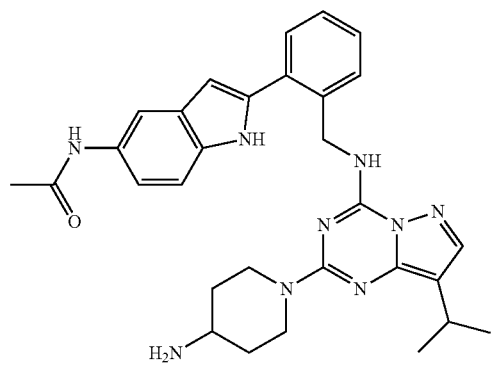 [SMILES: CC(=O)Nc1ccc2[nH]c(-c3ccccc3CNc3nc(N4CCC(N)CC4)nc4c(C(C)C)cnn34)cc2c1] |
| 117 | 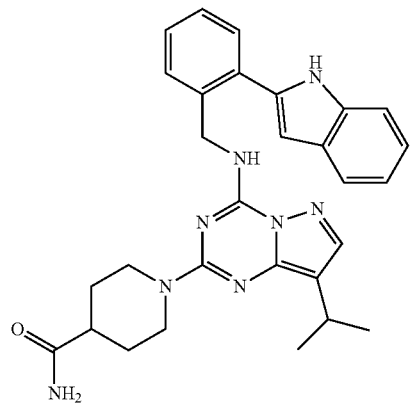 [SMILES: CC(C)c1cnn2c(NCc3ccccc3-c3cc4ccccc4[nH]3)nc(N3CCC(C(N)=O)CC3)nc12] |
| 118 | 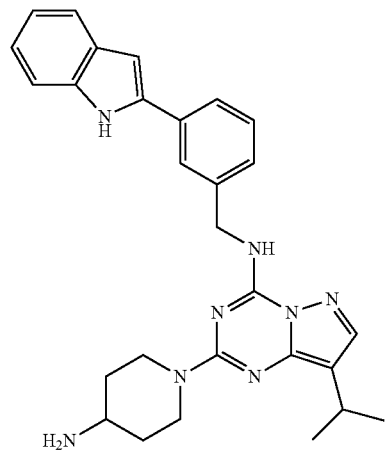 [SMILES: CC(C)c1cnn2c(NCc3cccc(-c4cc5ccccc5[nH]4)c3)nc(N3CCC(N)CC3)nc12] |

| #cpds | Structure |
|---|---|
| 119 | 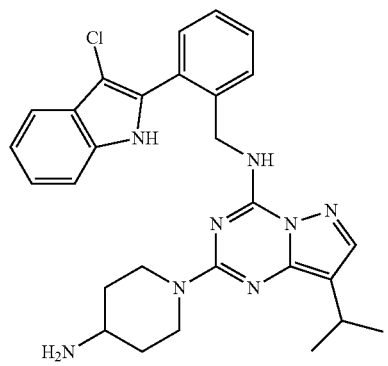 [SMILES: CC(C)c1cnn2c(NCc3ccccc3-c3[nH]c4ccccc4c3Cl)nc(N3CCC(N)CC3)nc12] |
| 120 | 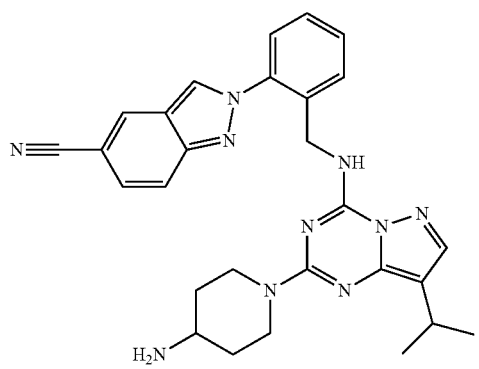 [SMILES: CC(C)c1cnn2c(NCc3ccccc3-n3cc4cc(C#N)ccc4n3)nc(N3CCC(N)CC3)nc12] |
| 121 | 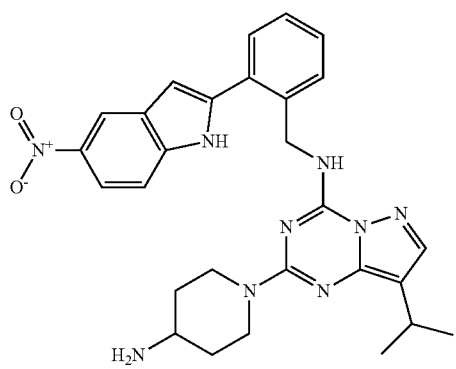 [SMILES: CC(C)c1cnn2c(NCc3ccccc3-c3cc4cc([N+](=O)[O-])ccc4[nH]3)nc(N3CCC(N)CC3)nc12] |
| 122 | 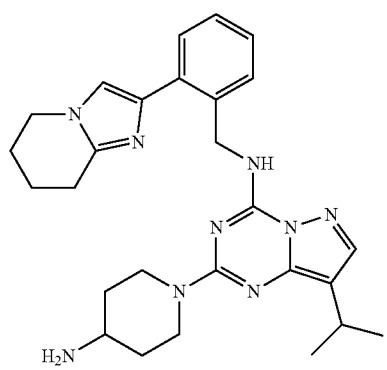 [SMILES: CC(C)c1cnn2c(NCc3ccccc3-c3cn4c(n3)CCCC4)nc(N3CCC(N)CC3)nc12] |

| #cpds | Structure |
|---|---|
| 123 | 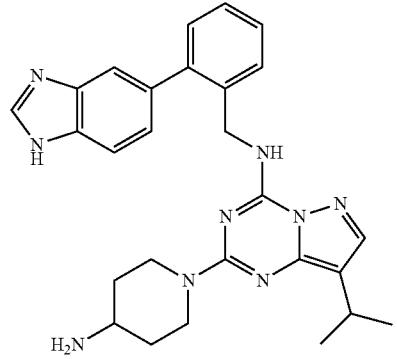 [SMILES: CC(C)c1cnn2c(NCc3ccccc3-c3ccc4[nH]cnc4c3)nc(N3CCC(N)CC3)nc12] |
| 124 | 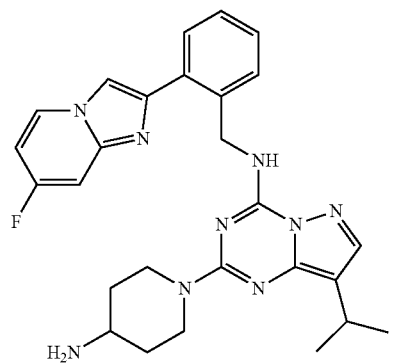 [SMILES: CC(C)c1cnn2c(NCc3ccccc3-c3cn4ccc(F)cc4n3)nc(N3CCC(N)CC3)nc12] |
| 125 | 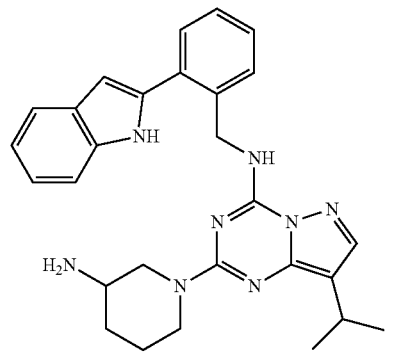 [SMILES: CC(C)c1cnn2c(NCc3ccccc3-c3cc4ccccc4[nH]3)nc(N3CCCC(N)C3)nc12] |
| 126 | 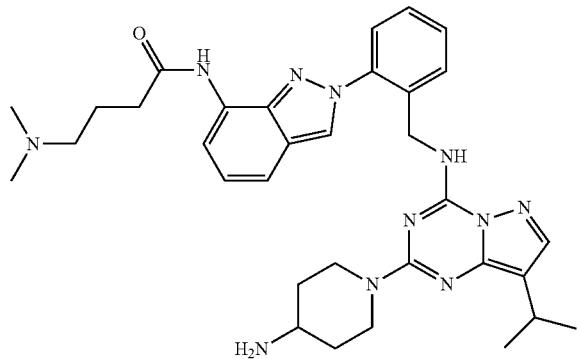 [SMILES: CC(C)c1cnn2c(NCc3ccccc3-n3cc4cccc(NC(=O)CCCN(C)C)c4n3)nc(N3CCC(N)CC3)nc12] |

| #cpds | Structure |
|---|---|
| 127 | 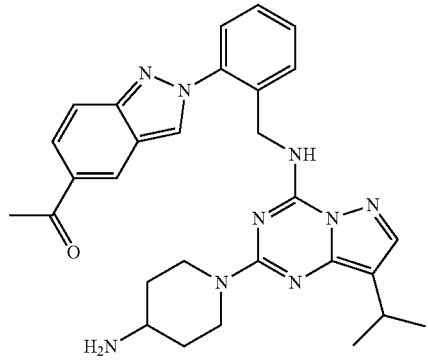 [SMILES: CC(=O)c1ccc2nn(-c3ccccc3CNc3nc(N4CCC(N)CC4)nc4c(C(C)C)cnn34)cc2c1] |
| 128 | 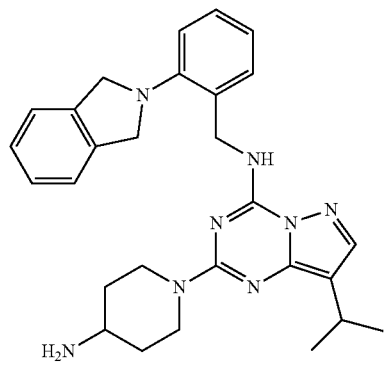 [SMILES: CC(C)c1cnn2c(NCc3ccccc3N3Cc4ccccc4C3)nc(N3CCC(N)CC3)nc12] |
| 129 | 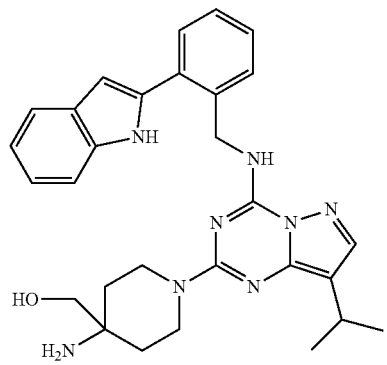 [SMILES: CC(C)c1cnn2c(NCc3ccccc3-c3cc4ccccc4[nH]3)nc(N3CCC(N)(CO)CC3)nc12] |
| 130 | 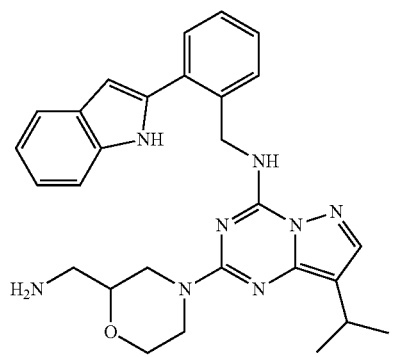 [SMILES: CC(C)c1cnn2c(NCc3ccccc3-c3cc4ccccc4[nH]3)nc(N3CCOC(CN)C3)nc12] |

-continued
| #cpds | Structure |
|---|---|
| 131 | 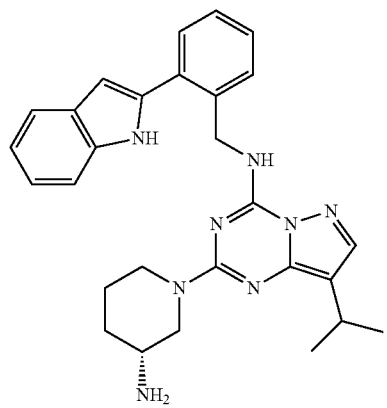 [SMILES: CC(C)c1cnn2c(NCc3ccccc3-c3cc4ccccc4[nH]3)nc(N3CCC[C@@H](N)C3)nc12] |
| 132 | 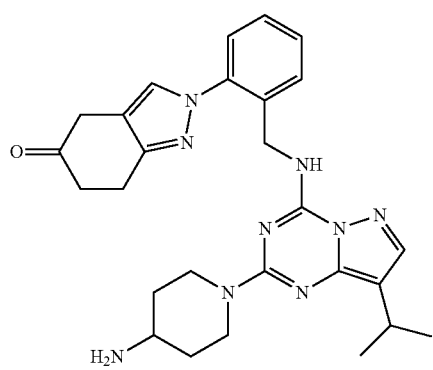 [SMILES: CC(C)c1cnn2c(NCc3ccccc3-n3cc4c(n3)CCC(=O)C4)nc(N3CCC(N)CC3)nc12] |
| 133 | 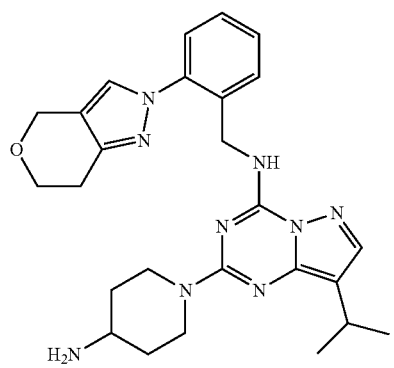 [SMILES: CC(C)c1cnn2c(NCc3ccccc3-n3cc4c(n3)CCOC4)nc(N3CCC(N)CC3)nc12] |
| 134 | 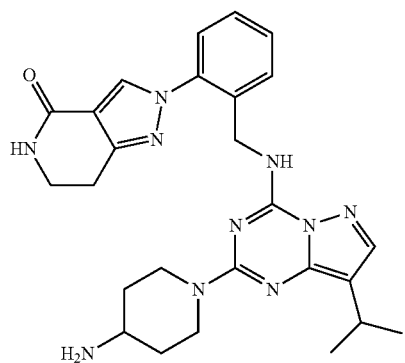 |

| #cpds | Structure |
|---|---|
| 135 | 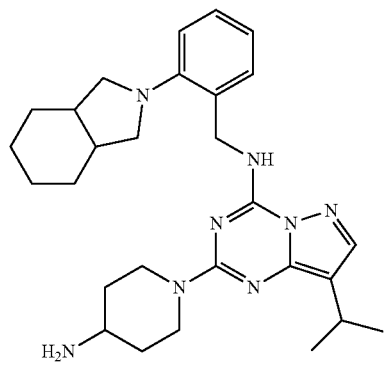 [SMILES: CC(C)c1cnn2c(NCc3ccccc3N3CC4CCCCC4C3)nc(N3CCC(N)CC3)nc12] |
| 136 | 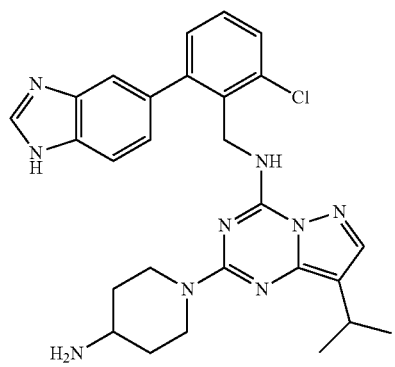 [SMILES: CC(C)c1cnn2c(NCc3c(Cl)cccc3-c3ccc4[nH]cnc4c3)nc(N3CCC(N)CC3)nc12] |
| 137 | 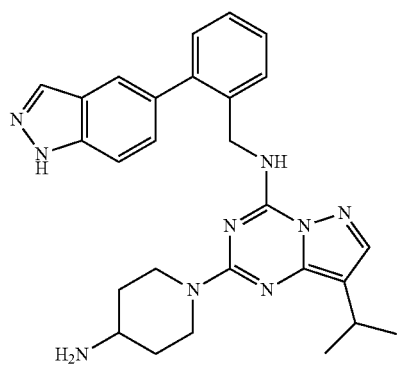 [SMILES: CC(C)c1cnn2c(NCc3ccccc3-c3ccc4[nH]ncc4c3)nc(N3CCC(N)CC3)nc12] |
| 138 | 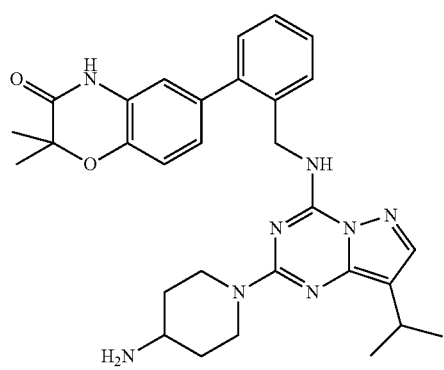 [SMILES: CC(C)c1cnn2c(NCc3ccccc3-c3ccc4c(c3)NC(=O)C(C)(C)O4)nc(N3CCC(N)CC3)nc12] |

| #cpds | Structure |
|---|---|
| 139 | 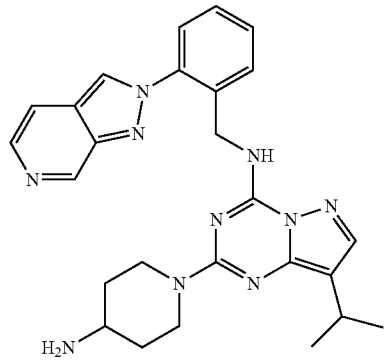 [SMILES: CC(C)c1cnn2c(NCc3ccccc3-n3cc4ccncc4n3)nc(N3CCC(N)CC3)nc12] |
| 140 | 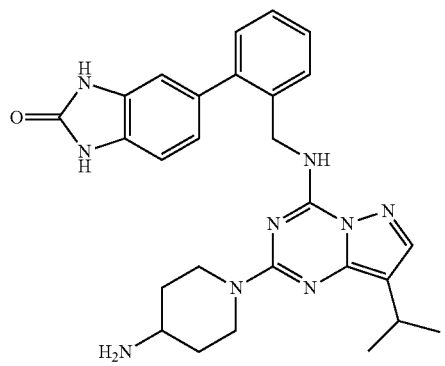 [SMILES: CC(C)c1cnn2c(NCc3ccccc3-c3ccc4[nH]c(=O)[nH]c4c3)nc(N3CCC(N)CC3)nc12] |
| 141 | 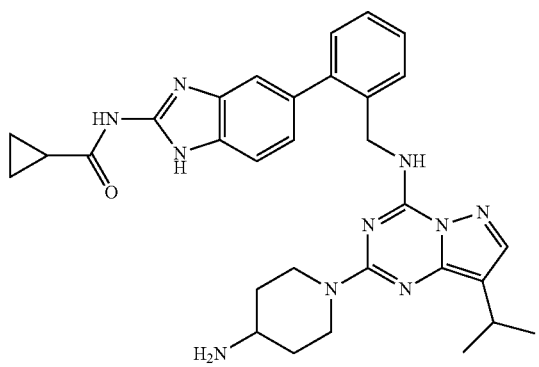 [SMILES: CC(C)c1cnn2c(NCc3ccccc3-c3ccc4[nH]c(NC(=O)C5CC5)nc4c3)nc(N3CCC(N)CC3)nc12] |
| 142 | 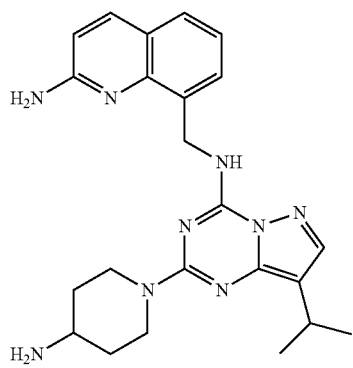 |

-continued
| #cpds | Structure |
|---|---|
| 143 | 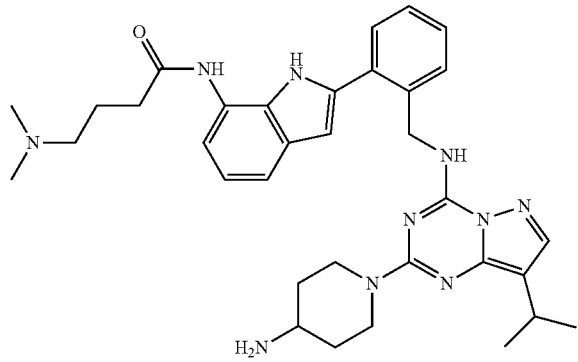 [SMILES: CC(C)c1cnn2c(NCc3ccccc3-c3cc4cccc(NC(=O)CCCN(C)C)c4[nH]3)nc(N3CCC(N)CC3)nc12] |
| 144 | 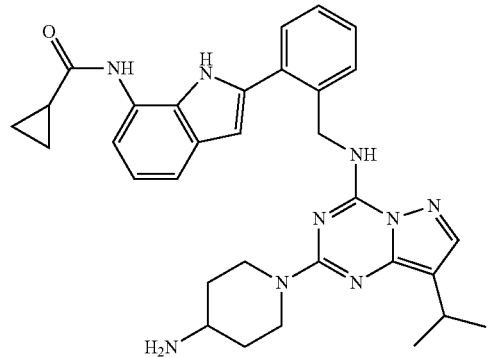 [SMILES: CC(C)c1cnn2c(NCc3ccccc3-c3cc4cccc(NC(=O)C5CC5)c4[nH]3)nc(N3CCC(N)CC3)nc12] |
| 145 | 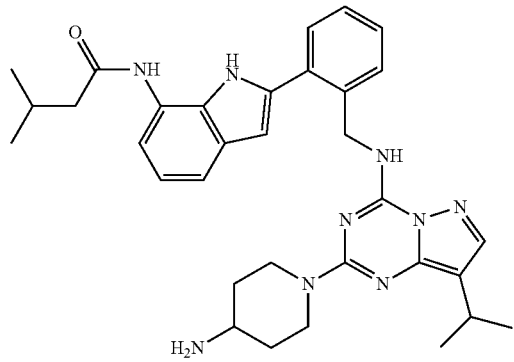 [SMILES: CC(C)CC(=O)Nc1cccc2cc(-c3ccccc3CNc3nc(N4CCC(N)CC4)nc4c(C(C)C)cnn34)[nH]c12] |
| 146 | 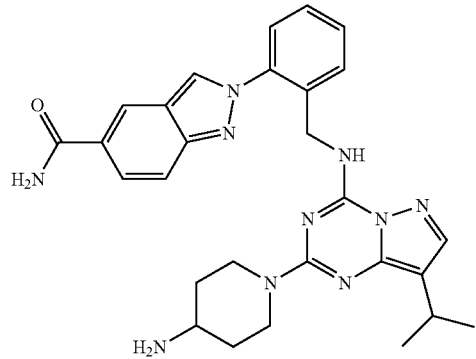 [SMILES: CC(C)c1cnn2c(NCc3ccccc3-n3cc4cc(C(N)=O)ccc4n3)nc(N3CCC(N)CC3)nc12] |

| #cpds | Structure |
|---|---|
| 147 | 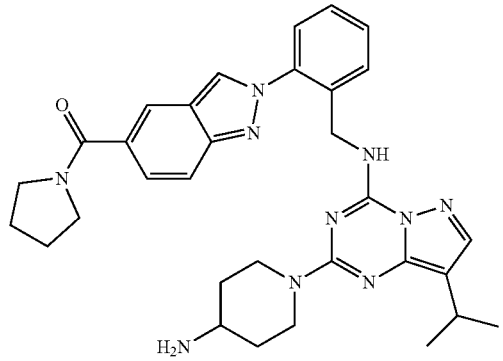 [SMILES: CC(C)c1cnn2c(NCc3ccccc3-n3cc4cc(C(=O)N5CCCC5)ccc4n3)nc(N3CCC(N)CC3)nc12] |
| 148 | 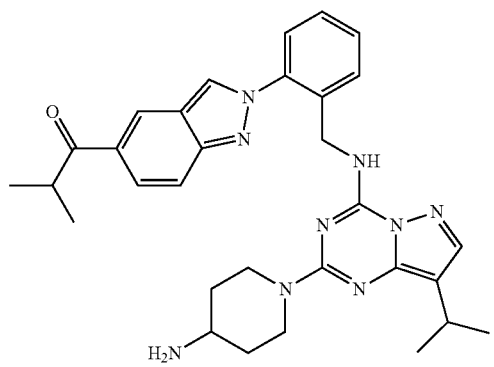 [SMILES: CC(C)C(=O)c1ccc2nn(-c3ccccc3CNc3nc(N4CCC(N)CC4)nc4c(C(C)C)cnn34)cc2c1] |
| 149 | 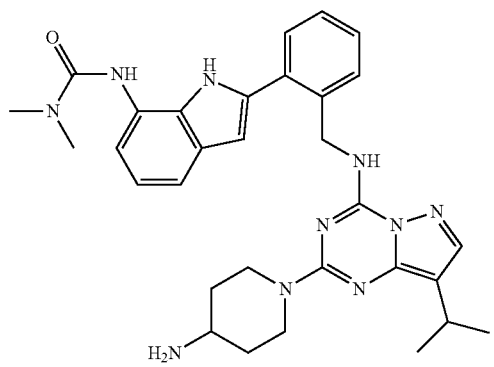 [SMILES: CC(C)c1cnn2c(NCc3ccccc3-c3cc4cccc(NC(=O)N(C)C)c4[nH]3)nc(N3CCC(N)CC3)nc12] |
| 150 | 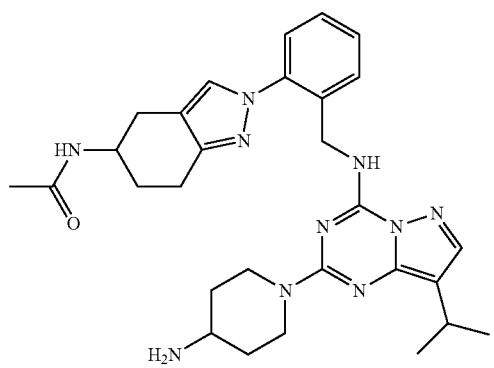 [SMILES: CC(=O)NC1CCc2nn(-c3ccccc3CNc3nc(N4CCC(N)CC4)nc4c(C(C)C)cnn34)cc2C1] |

-continued
| #cpds | Structure |
|---|---|
| 151 | 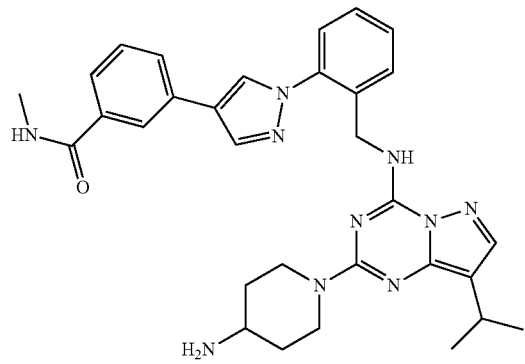 [SMILES: CNC(=O)c1cccc(-c2cnn(-c3ccccc3CNc3nc(N4CCC(N)CC4)nc4c(C(C)C)cnn34)c2)c1] |
| 152 | 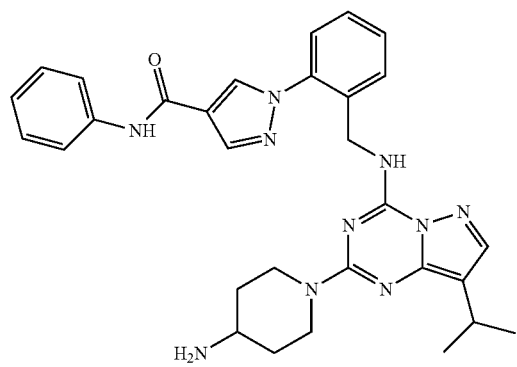 [SMILES: CC(C)c1cnn2c(NCc3ccccc3-n3cc(C(=O)Nc4ccccc4)cn3)nc(N3CCC(N)CC3)nc12] |
| 153 | 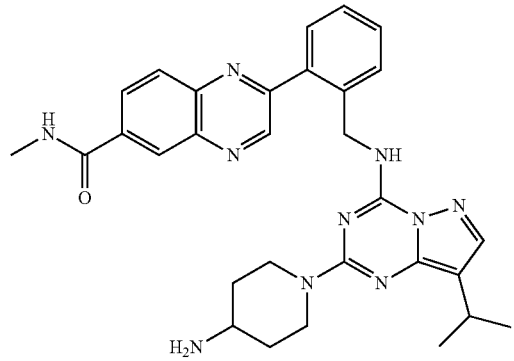 [SMILES: CNC(=O)c1ccc2nc(-c3ccccc3CNc3nc(N4CCC(N)CC4)nc4c(C(C)C)cnn34)cnc2c1] |
| 154 | 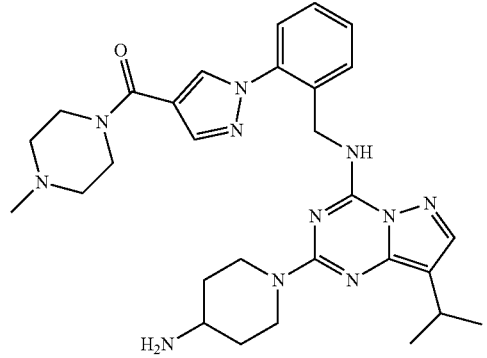 [SMILES: CC(C)c1cnn2c(NCc3ccccc3-n3cc(C(=O)N4CCN(C)CC4)cn3)nc(N3CCC(N)CC3)nc12] |

-continued
| #cpds | Structure |
|---|---|
| 155 | 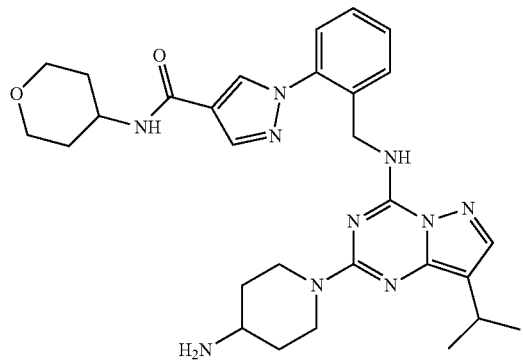 [SMILES: CC(C)c1cnn2c(NCc3ccccc3-n3cc(C(=O)NC4CCOCC4)cn3)nc(N3CCC(N)CC3)nc12] |
| 156 | 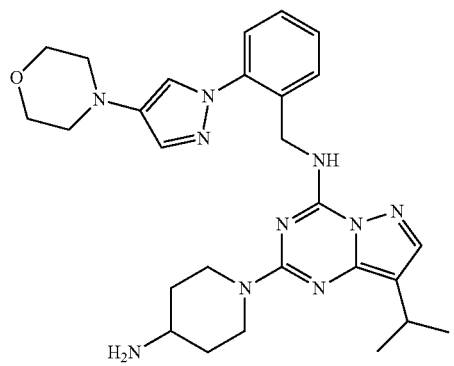 [SMILES: CC(C)c1cnn2c(NCc3ccccc3-n3cc(N4CCOCC4)cn3)nc(N3CCC(N)CC3)nc12] |
| 157 | 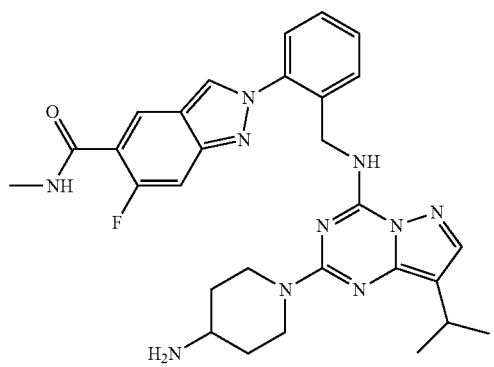 [SMILES: CNC(=O)c1cc2cn(-c3ccccc3CNc3nc(N4CCC(N)CC4)nc4c(C(C)C)cnn34)nc2cc1F] |
| 158 | 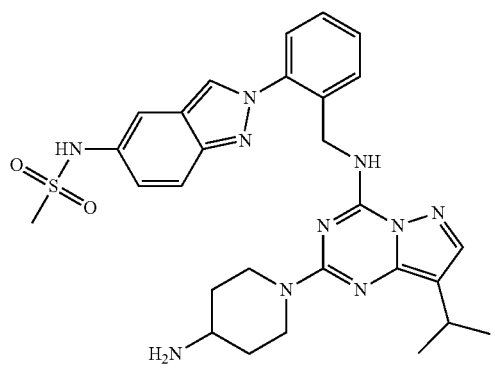 [SMILES: CC(C)c1cnn2c(NCc3ccccc3-n3cc4cc(NS(C)(=O)=O)ccc4n3)nc(N3CCC(N)CC3)nc12] |

| #cpds | Structure |
|---|---|
| 159 | 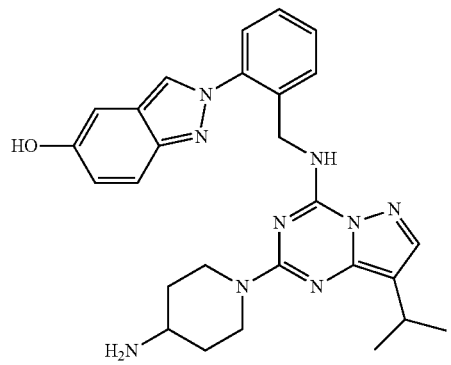 |
| 160 | 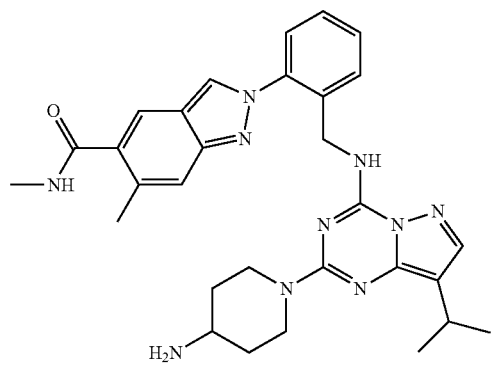 |
| 161 | 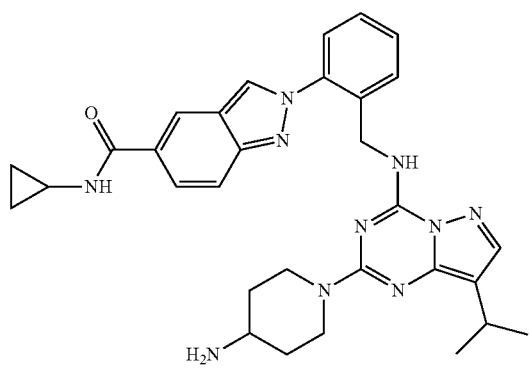 [SMILES: CC(C)c1cnn2c(NCc3ccccc3-n3cc4cc(C(=O)NC5CC5)ccc4n3)nc(N3CCC(N)CC3)nc12] |
| 175 | 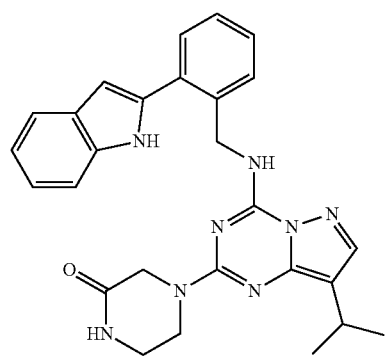 [SMILES: CC(C)c1cnn2c(NCc3ccccc3-c3cc4ccccc4[nH]3)nc(N3CCNC(=O)C3)nc12] |

| #cpds | Structure |
|---|---|
| 176 | 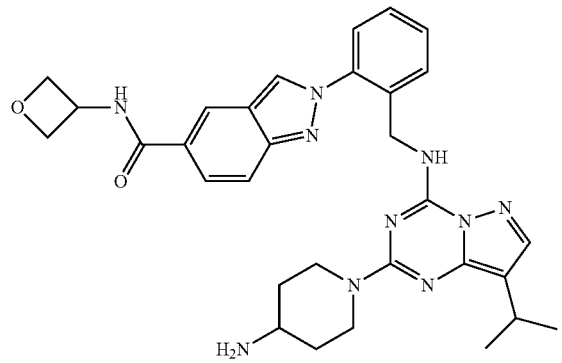 [SMILES: CC(C)c1cnn2c(NCc3ccccc3-n3cc4cc(C(=O)NC5COC5)ccc4n3)nc(N3CCC(N)CC3)nc12] |
| 177 | 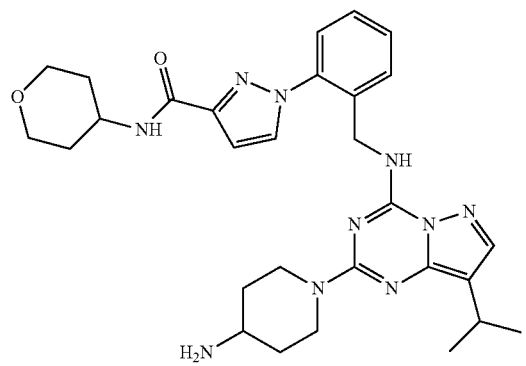 [SMILES: CC(C)c1cnn2c(NCc3ccccc3-n3ccc(C(=O)NC4CCOCC4)n3)nc(N3CCC(N)CC3)nc12] |
| 178 | 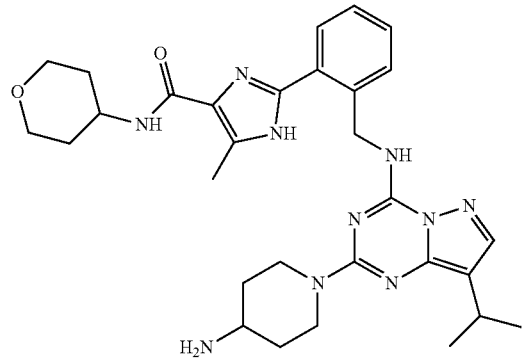 [SMILES: Cc1[nH]c(-c2ccccc2CNc2nc(N3CCC(N)CC3)nc3c(C(C)C)cnn23)nc1C(=O)NC1CCOCC1] |
| 179 | 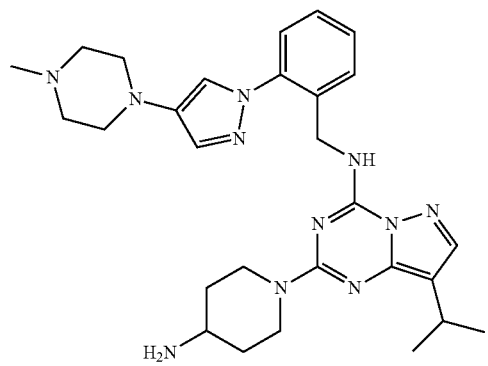 [SMILES: CC(C)c1cnn2c(NCc3ccccc3-n3cc(N4CCN(C)CC4)cn3)nc(N3CCC(N)CC3)nc12] |

| #cpds | Structure |
|---|---|
| 180 | 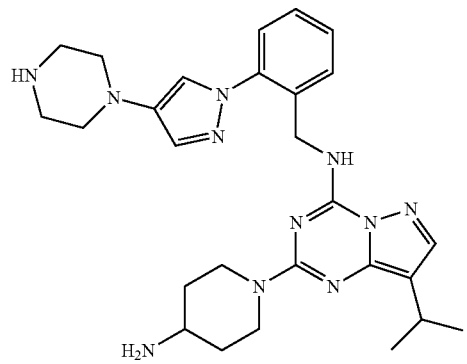 [SMILES: CC(C)c1cnn2c(NCc3ccccc3-n3cc(N4CCNCC4)cn3)nc(N3CCC(N)CC3)nc12] |
| 181 | 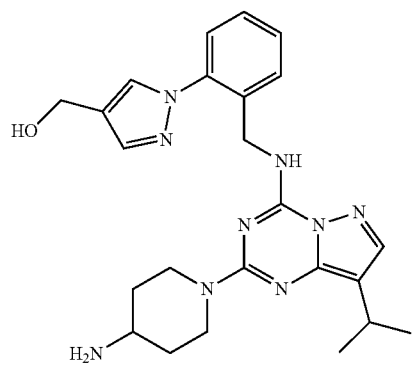 [SMILES: CC(C)c1cnn2c(NCc3ccccc3-n3cc(CO)cn3)nc(N3CCC(N)CC3)nc12] |
| 182 | 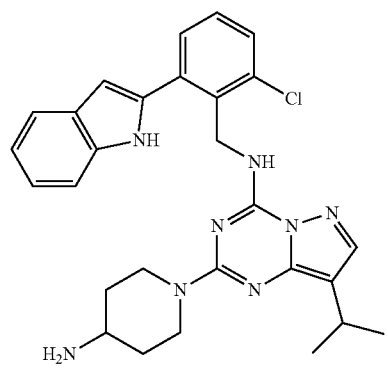 [SMILES: CC(C)c1cnn2c(NCc3c(Cl)cccc3-c3cc4ccccc4[nH]3)nc(N3CCC(N)CC3)nc12] |
| 184 | 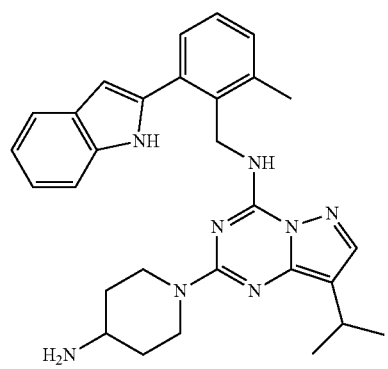 [SMILES: Cc1cccc(-c2cc3ccccc3[nH]2)c1CNc1nc(N2CCC(N)CC2)nc2c(C(C)C)cnn12] |

| #cpds | Structure |
|---|---|
| 185 | 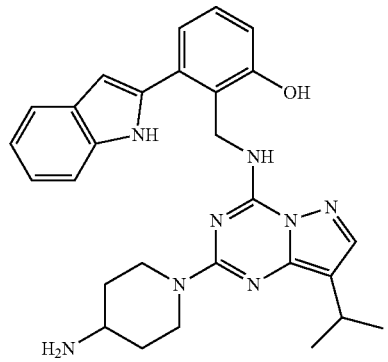 [SMILES: CC(C)c1cnn2c(NCc3c(O)cccc3-c3cc4ccccc4[nH]3)nc(N3CCC(N)CC3)nc12] |
| 186 | 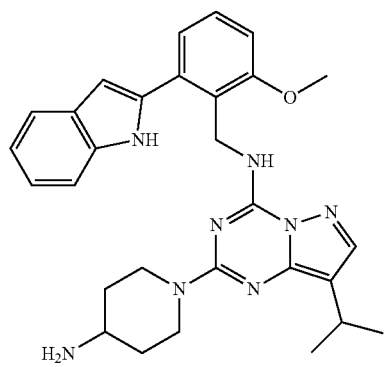 [SMILES: COc1cccc(-c2cc3ccccc3[nH]2)c1CNc1nc(N2CCC(N)CC2)nc2c(C(C)C)cnn12] |
| 189 | 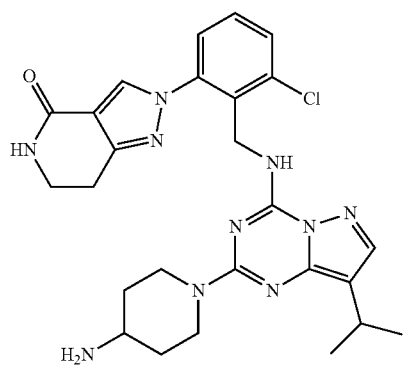 [SMILES: CC(C)c1cnn2c(NCc3c(Cl)cccc3-n3cc4c(n3)CCNC4=O)nc(N3CCC(N)CC3)nc12] |
| 190 | 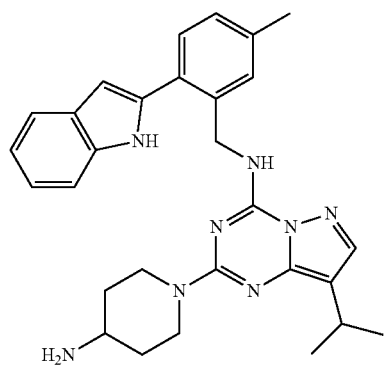 [SMILES: Cc1ccc(-c2cc3ccccc3[nH]2)c(CNc2nc(N3CCC(N)CC3)nc3c(C(C)C)cnn23)c1] |

-continued
| #cpds | Structure |
|---|---|
| 191 | 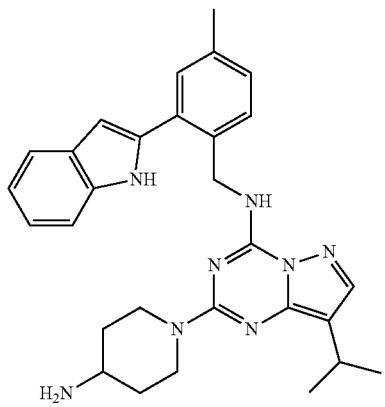 [SMILES: Cc1ccc(CNc2nc(N3CCC(N)CC3)nc3c(C(C)C)cnn23)c(-c2cc3ccccc3[nH]2)c1] |
| 193 | 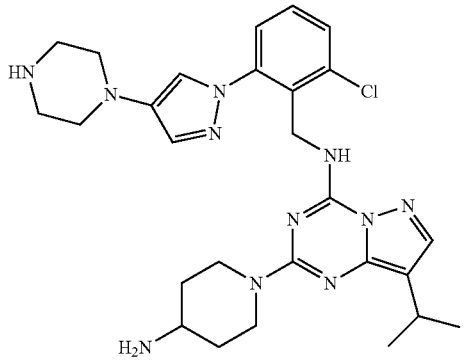 [SMILES: CC(C)c1cnn2c(NCc3c(Cl)cccc3-n3cc(N4CCNCC4)cn3)nc(N3CCC(N)CC3)nc12] |
| 194 | 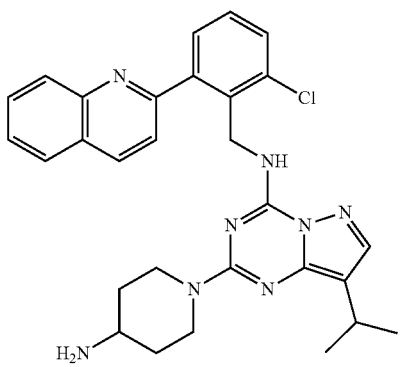 [SMILES: CC(C)c1cnn2c(NCc3c(Cl)cccc3-c3ccc4ccccc4n3)nc(N3CCC(N)CC3)nc12] |
| 195 | 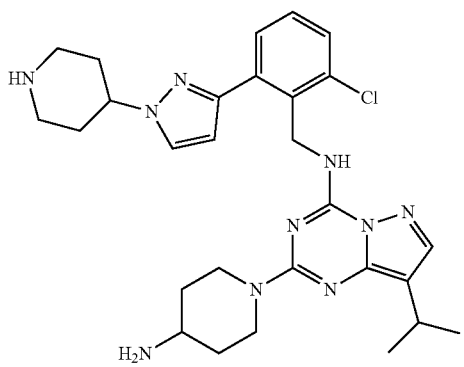 [SMILES: CC(C)c1cnn2c(NCc3c(Cl)cccc3-c3ccn(C4CCNCC4)n3)nc(N3CCC(N)CC3)nc12] |

| #cpds | Structure |
|---|---|
| 196 | 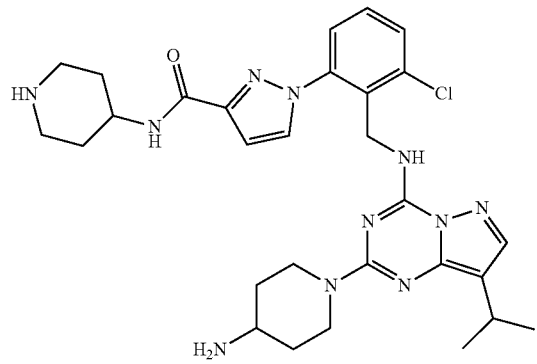 [SMILES: CC(C)c1cnn2c(NCc3c(Cl)cccc3-n3ccc(C(=O)NC4CCNCC4)n3)nc(N3CCC(N)CC3)nc12] |
| 197 | 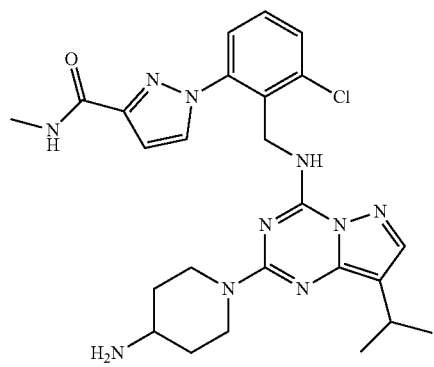 [SMILES: CNC(=O)c1ccn(-c2cccc(Cl)c2CNc2nc(N3CCC(N)CC3)nc3c(C(C)C)cnn23)n1] |
| 198 | 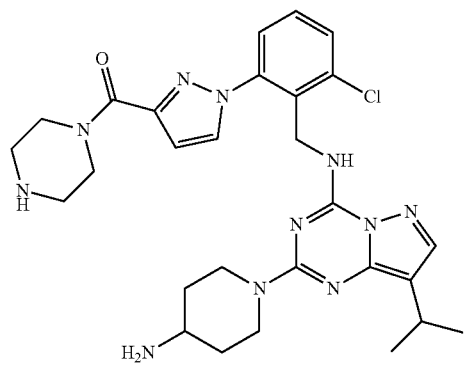 [SMILES: CC(C)c1cnn2c(NCc3c(Cl)cccc3-n3ccc(C(=O)N4CCNCC4)n3)nc(N3CCC(N)CC3)nc12] |
| 199 | 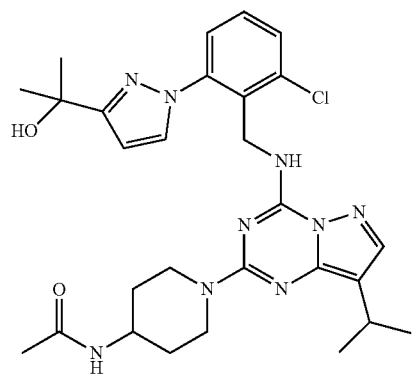 [SMILES: CC(=O)NC1CCN(c2nc(NCc3c(Cl)cccc3-n3ccc(C(C)(C)O)n3)n3ncc(C(C)C)c3n2)CC1] |

| #cpds | Structure |
|---|---|
| 200 | 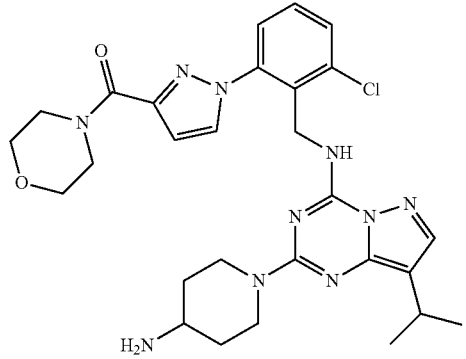 [SMILES: CC(C)c1cnn2c(NCc3c(Cl)cccc3-n3ccc(C(=O)N4CCOCC4)n3)nc(N3CCC(N)CC3)nc12] |
| 201 | 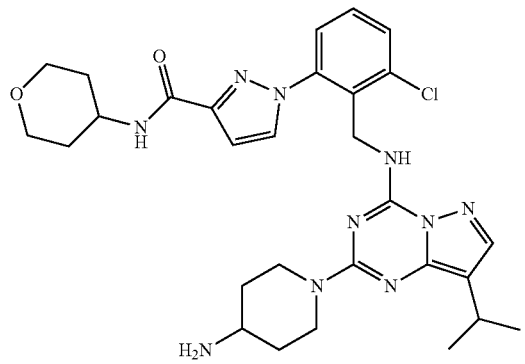 [SMILES: CC(C)c1cnn2c(NCc3c(Cl)cccc3-n3ccc(C(=O)NC4CCOCC4)n3)nc(N3CCC(N)CC3)nc12] |
| 202 | 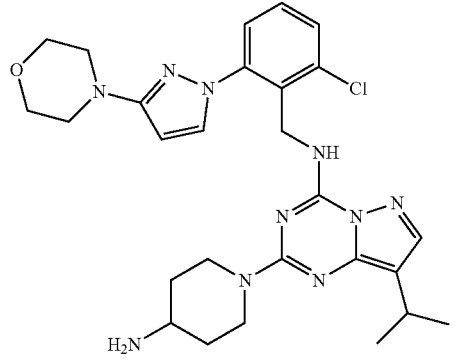 [SMILES: CC(C)c1cnn2c(NCc3c(Cl)cccc3-n3ccc(N4CCOCC4)n3)nc(N3CCC(N)CC3)nc12] |
| 203 | 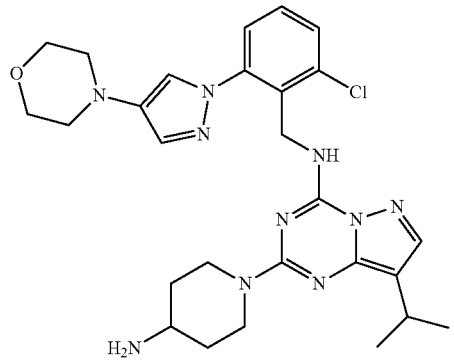 |

| #cpds | Structure |
|---|---|
| 204 | 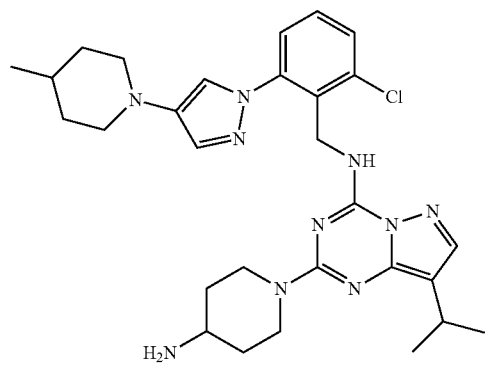 [SMILES: CC1CCN(c2cnn(-c3cccc(Cl)c3CNc3nc(N4CCC(N)CC4)nc4c(C(C)C)cnn34)c2)CC1] |
| 205 | 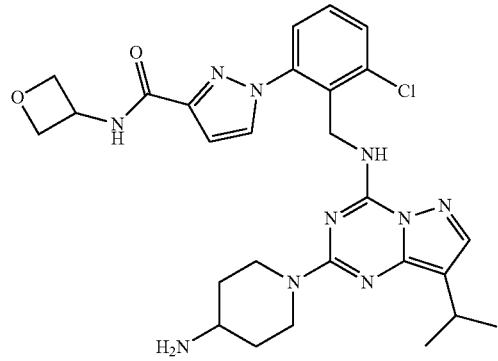 [SMILES: CC(C)c1cnn2c(NCc3c(Cl)cccc3-n3ccc(C(=O)NC4COC4)n3)nc(N3CCC(N)CC3)nc12] |
| 207 | 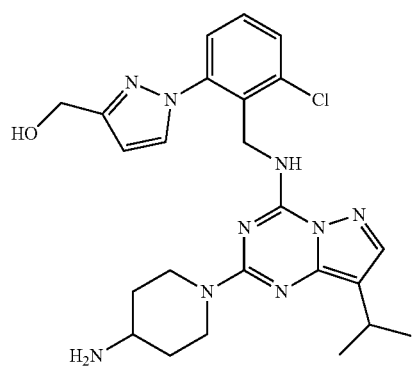 [SMILES: CC(C)c1cnn2c(NCc3c(Cl)cccc3-n3ccc(CO)n3)nc(N3CCC(N)CC3)nc12] |
| 208 | 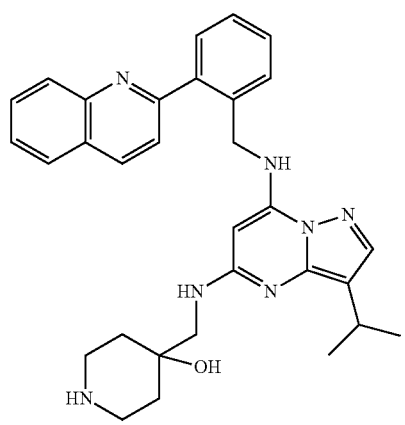 [SMILES: CC(C)c1cnn2c(NCc3ccccc3-c3ccc4ccccc4n3)cc(NCC3(O)CCNCC3)nc12] |

| #cpds | Structure |
|---|---|
| 209 | 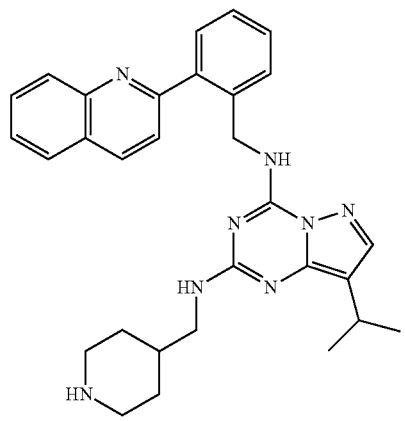 [SMILES: CC(C)c1cnn2c(NCc3ccccc3-c3ccc4ccccc4n3)nc(NCC3CCNCC3)nc12] |
| 210 | 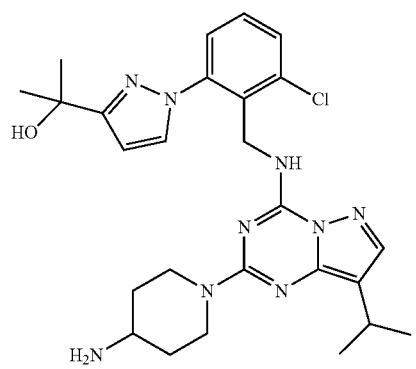 [SMILES: CC(C)c1cnn2c(NCc3c(Cl)cccc3-n3ccc(C(C)(C)O)n3)nc(N3CCC(N)CC3)nc12] |
| 211 | 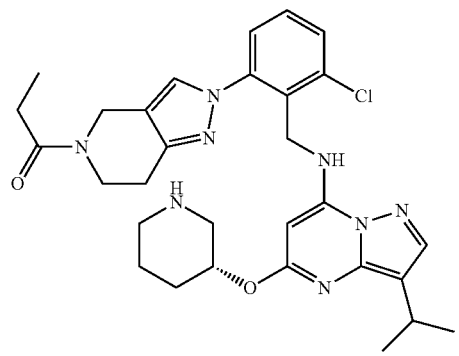 [SMILES: CCC(=O)N1CCc2nn(-c3cccc(Cl)c3CNc3cc(O[C@@H]4CCCNC4)nc4c(C(C)C)cnn34)cc2C1] |
| 212 | 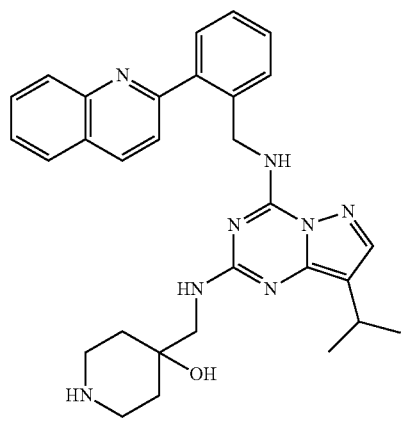 [SMILES: CC(C)c1cnn2c(NCc3ccccc3-c3ccc4ccccc4n3)nc(NCC3(O)CCNCC3)nc12] |

| #cpds | Structure |
|---|---|
| 213 | 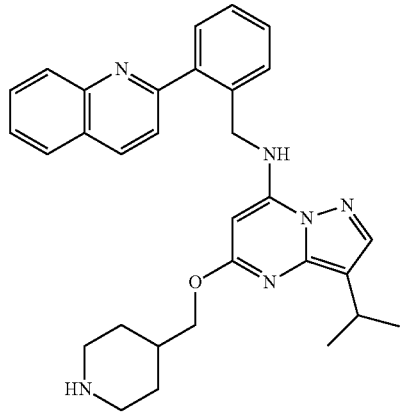 [SMILES: CC(C)c1cnn2c(NCc3ccccc3-c3ccc4ccccc4n3)cc(OCC3CCNCC3)nc12] |
| 214 | 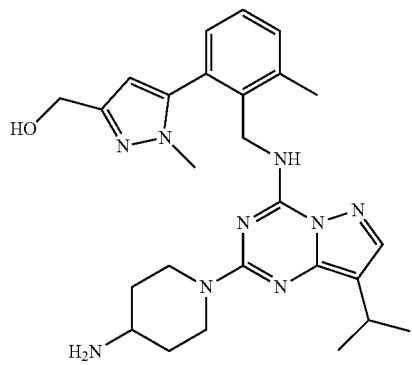 [SMILES: Cc1cccc(-c2cc(CO)nn2C)c1CNc1nc(N2CCC(N)CC2)nc2c(C(C)C)cnn12] |
| 215 | 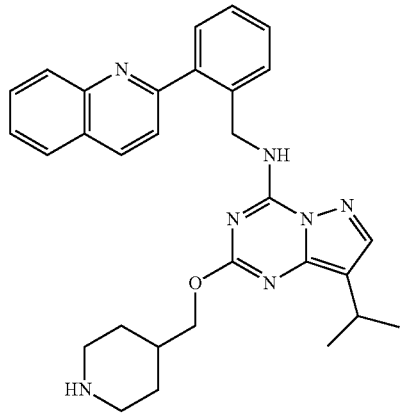 [SMILES: CC(C)c1cnn2c(NCc3ccccc3-c3ccc4ccccc4n3)nc(OCC3CCNCC3)nc12] |

| #cpds | Structure |
|---|---|
| 216 | 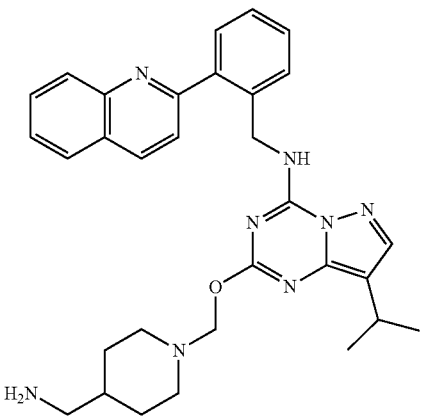 [SMILES: CC(C)c1cnn2c(NCc3ccccc3-c3ccc4ccccc4n3)nc(OCN3CCC(CN)CC3)nc12] |
| 217 | 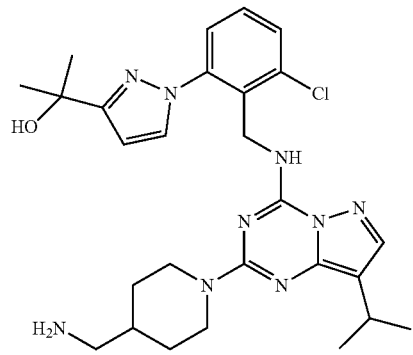 [SMILES: CC(C)c1cnn2c(NCc3c(Cl)cccc3-n3ccc(C(C)(C)O)n3)nc(N3CCC(CN)CC3)nc12] |
| 218 | 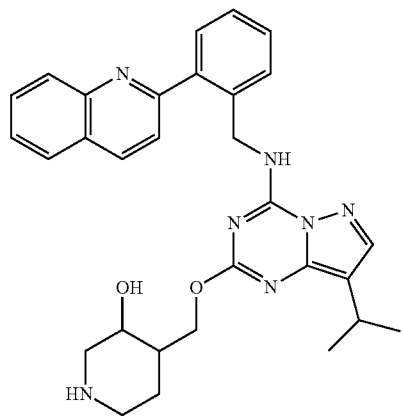 [SMILES: CC(C)c1cnn2c(NCc3ccccc3-c3ccc4ccccc4n3)nc(OCC3CCNCC3O)nc12] |
| 219 | 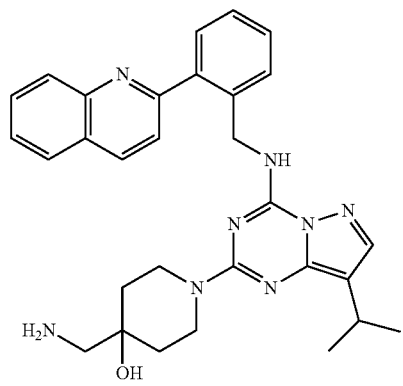 [SMILES: CC(C)c1cnn2c(NCc3ccccc3-c3ccc4ccccc4n3)nc(N3CCC(O)(CN)CC3)nc12] |

| #cpds | Structure |
|---|---|
| 220 | 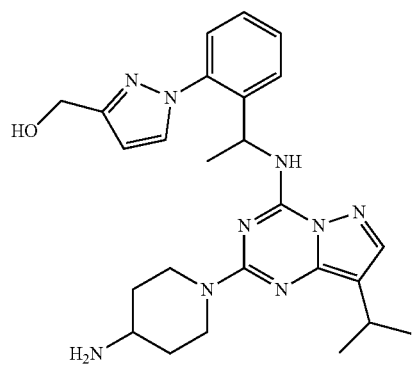 [SMILES: CC(C)c1cnn2c(NC(C)c3ccccc3-n3ccc(CO)n3)nc(N3CCC(N)CC3)nc12] |
| 221 | 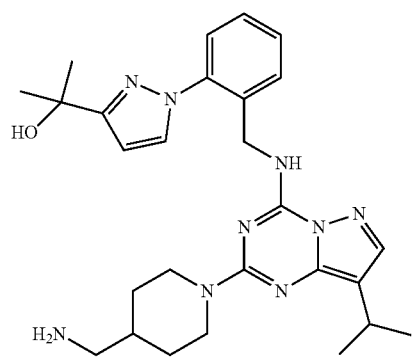 [SMILES: CC(C)c1cnn2c(NCc3ccccc3-n3ccc(C(C)(C)O)n3)nc(N3CCC(CN)CC3)nc12] |
| 222 | 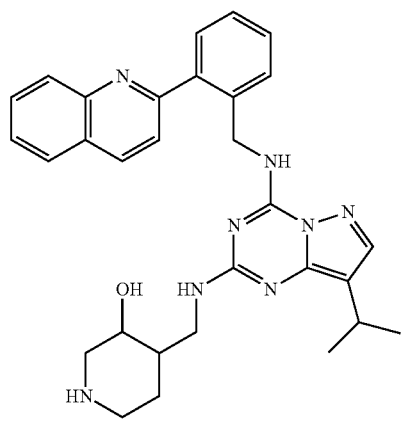 [SMILES: CC(C)c1cnn2c(NCc3ccccc3-c3ccc4ccccc4n3)nc(NCC3CCNCC3O)nc12] |
| 223 | 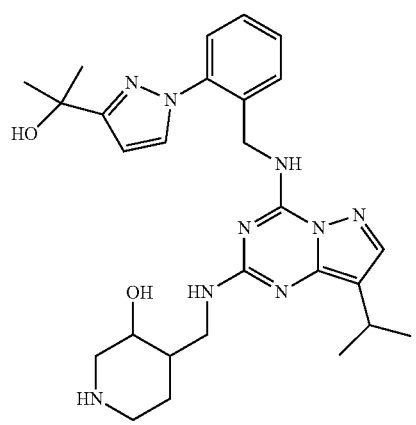 [SMILES: CC(C)c1cnn2c(NCc3ccccc3-n3ccc(C(C)(C)O)n3)nc(NCC3CCNCC3O)nc12] |

| #cpds | Structure |
|---|---|
| 224 | 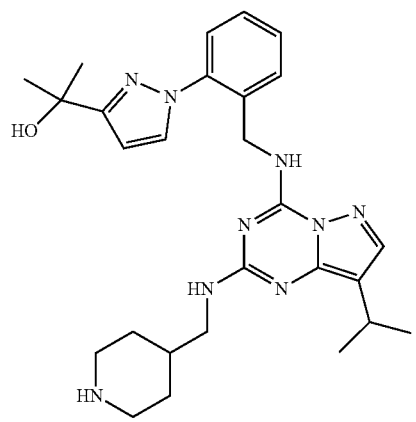 [SMILES: CC(C)c1cnn2c(NCc3ccccc3-n3ccc(C(C)(C)O)n3)nc(NCC3CCNCC3)nc12] |
| 225 | 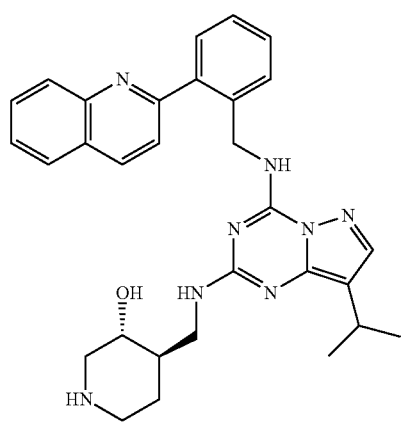 [SMILES: CC(C)c1cnn2c(NCc3ccccc3-c3ccc4ccccc4n3)nc(NC[C@H]3CCNC[C@@H]3O)nc12] |
| 226 | 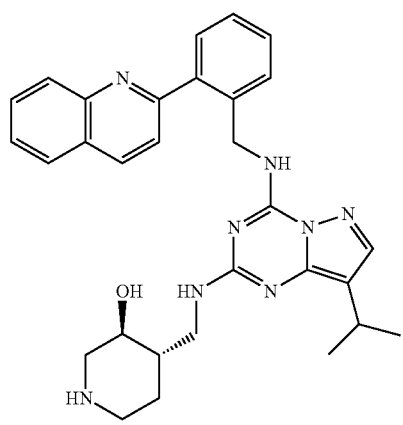 [SMILES: CC(C)c1cnn2c(NCc3ccccc3-c3ccc4ccccc4n3)nc(NC[C@@H]3CCNC[C@H]3O)nc12] |

| #cpds | Structure |
|---|---|
| 227 | 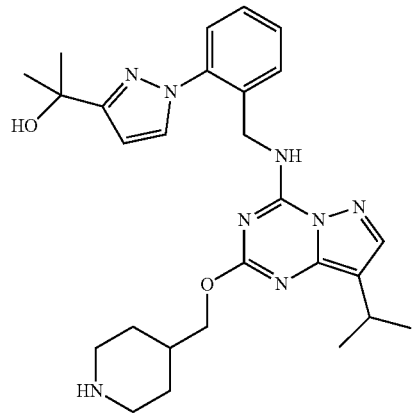 [SMILES: CC(C)c1cnn2c(NCc3ccccc3-n3ccc(C(C)(C)O)n3)nc(OCC3CCNCC3)nc12] |
| 228 | 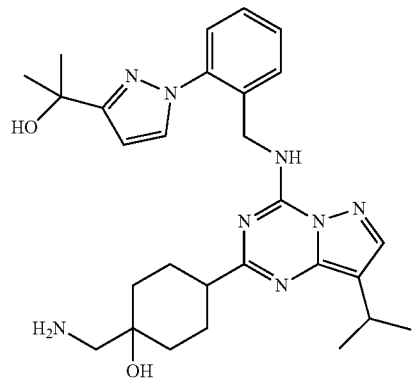 [SMILES: CC(C)c1cnn2c(NCc3ccccc3-n3ccc(C(C)(C)O)n3)nc(C3CCC(O)(CN)CC3)nc12] |
| 229 | 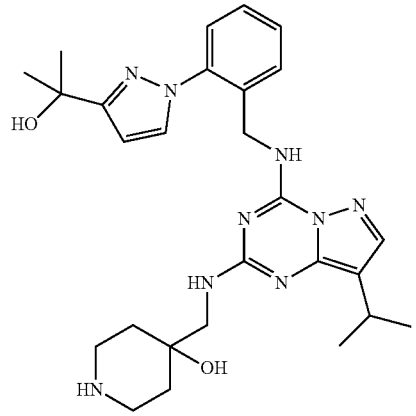 [SMILES: CC(C)c1cnn2c(NCc3ccccc3-n3ccc(C(C)(C)O)n3)nc(NCC3(O)CCNCC3)nc12] |
| 230 | 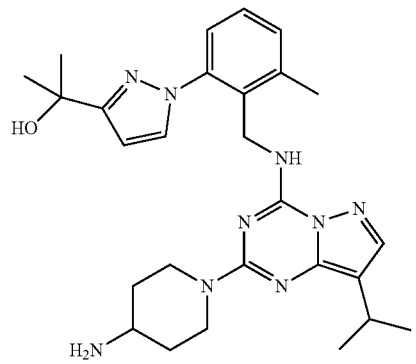 [SMILES: Cc1cccc(-n2ccc(C(C)(C)O)n2)c1CNc1nc(N2CCC(N)CC2)nc2c(C(C)C)cnn12] |

| #cpds | Structure |
|---|---|
| 231 | 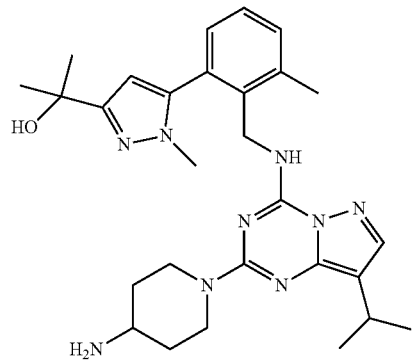 [SMILES: Cc1cccc(-c2cc(C(C)(C)O)nn2C)c1CNc1nc(N2CCC(N)CC2)nc2c(C(C)C)cnn12] |
| 232 | 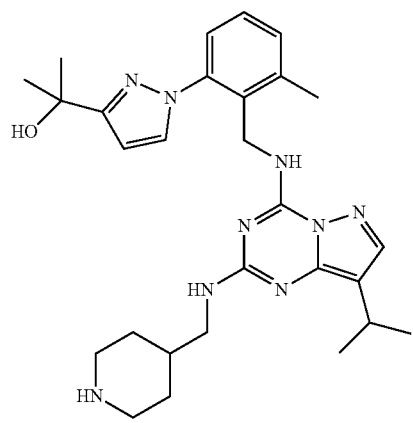 [SMILES: Cc1cccc(-n2ccc(C(C)(C)O)n2)c1CNc1nc(NCC2CCNCC2)nc2c(C(C)C)cnn12] |
| 233 | 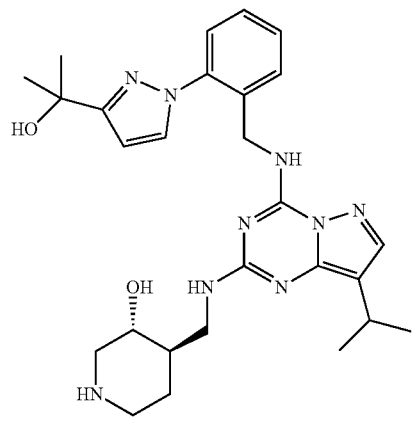 [SMILES: CC(C)c1cnn2c(NCc3ccccc3-n3ccc(C(C)(C)O)n3)nc(NC[C@H]3CCNC[C@@H]3O)nc12] |
| 234 | 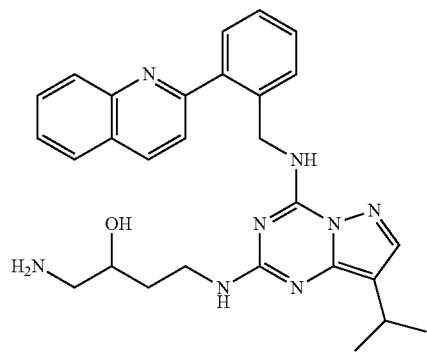 [SMILES: CC(C)c1cnn2c(NCc3ccccc3-c3ccc4ccccc4n3)nc(NCCC(O)CN)nc12] |

| #cpds | Structure |
|---|---|
| 236 | 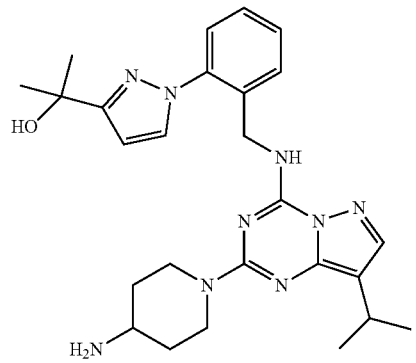 [SMILES: CC(C)c1cnn2c(NCc3ccccc3-n3ccc(C(C)(C)O)n3)nc(N3CCC(N)CC3)nc12] |
| 237 | 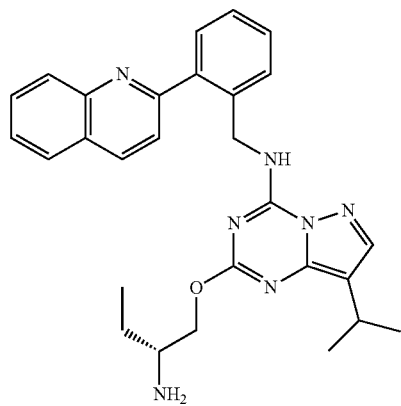 [SMILES: CC[C@@H](N)COc1nc(NCc2ccccc2-c2ccc3ccccc3n2)n2ncc(C(C)C)c2n1] |
| 238 | 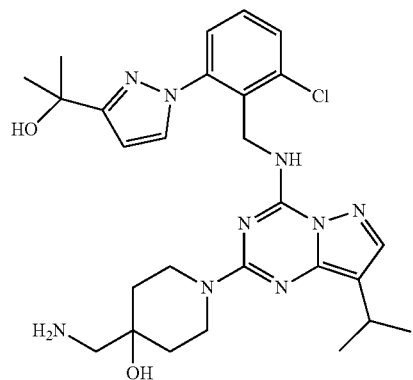 [SMILES: CC(C)c1cnn2c(NCc3c(Cl)cccc3-n3ccc(C(C)(C)O)n3)nc(N3CCC(O)(CN)CC3)nc12] |
| 240 | 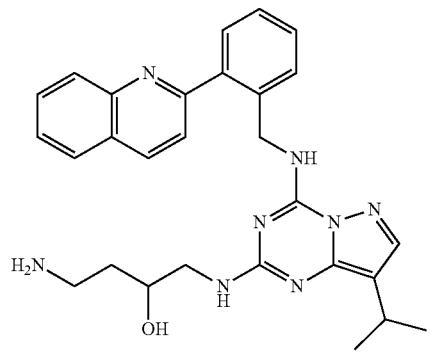 [SMILES: CC(C)c1cnn2c(NCc3ccccc3-c3ccc4ccccc4n3)nc(NCC(O)CCN)nc12] |

| #cpds | Structure |
|---|---|
| 241 | 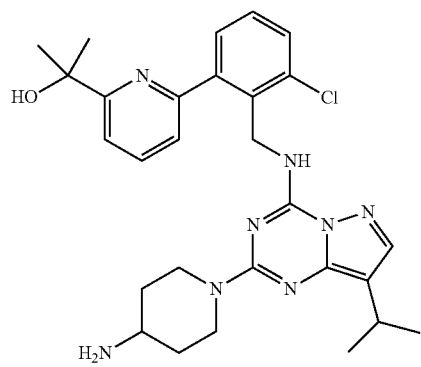 [SMILES: CC(C)c1cnn2c(NCc3c(Cl)cccc3-c3cccc(C(C)(C)O)n3)nc(N3CCC(N)CC3)nc12] |
| 243 | 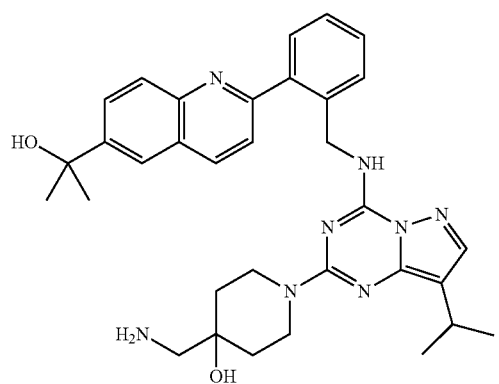 [SMILES: CC(C)c1cnn2c(NCc3ccccc3-c3ccc4cc(C(C)(C)O)ccc4n3)nc(N3CCC(O)(CN)CC3)nc12] |
| 244 | 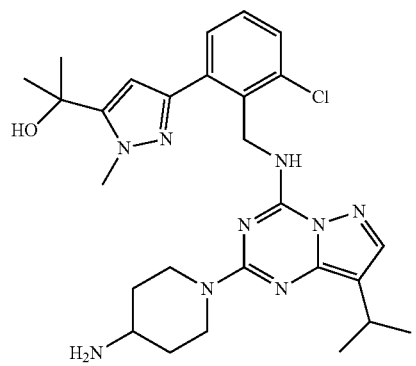 [SMILES: CC(C)c1cnn2c(NCc3c(Cl)cccc3-c3cc(C(C)(C)O)n(C)n3)nc(N3CCC(N)CC3)nc12] |
| 245 | 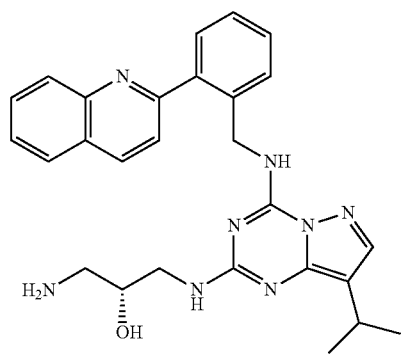 [SMILES: CC(C)c1cnn2c(NCc3ccccc3-c3ccc4ccccc4n3)nc(NC[C@H](O)CN)nc12] |

| #cpds | Structure |
|---|---|
| 246 | 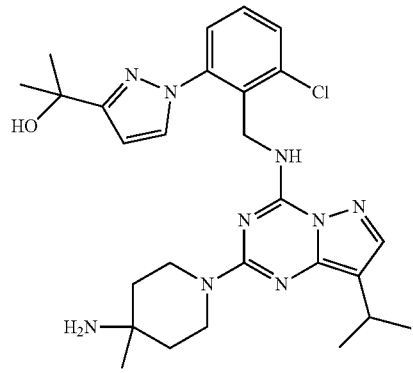 [SMILES: CC(C)c1cnn2c(NCc3c(Cl)cccc3-n3ccc(C(C)(C)O)n3)nc(N3CCC(C)(N)CC3)nc12] |
| 247 | 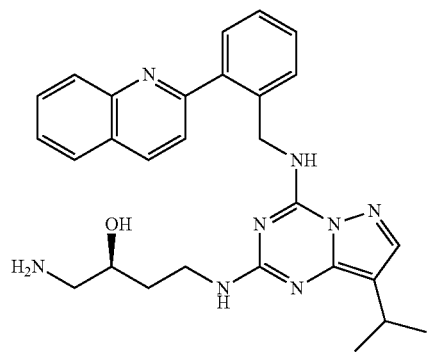 |
| 248 | 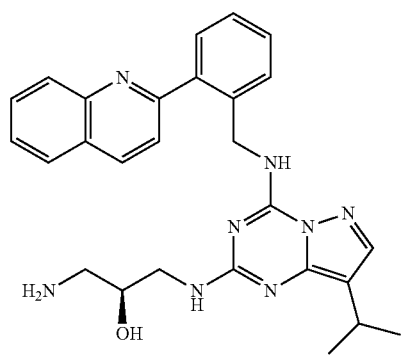 [SMILES: CC(C)c1cnn2c(NCc3ccccc3-c3ccc4ccccc4n3)nc(NC[C@@H](O)CN)nc12] |
| 249 | 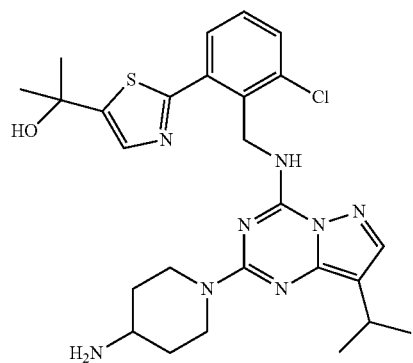 [SMILES: CC(C)c1cnn2c(NCc3c(Cl)cccc3-c3ncc(C(C)(C)O)s3)nc(N3CCC(N)CC3)nc12] |

| #cpds | Structure |
|---|---|
| 250 | 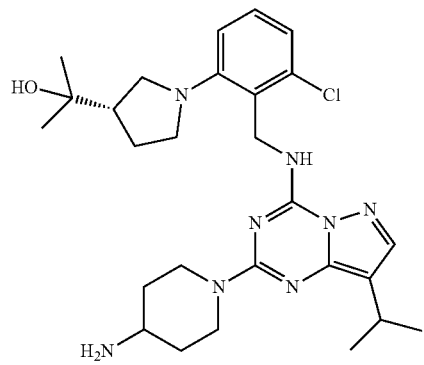 [SMILES: CC(C)c1cnn2c(NCc3c(Cl)cccc3N3CC[C@H](C(C)(C)O)C3)nc(N3CCC(N)CC3)nc12] |
| 251 | 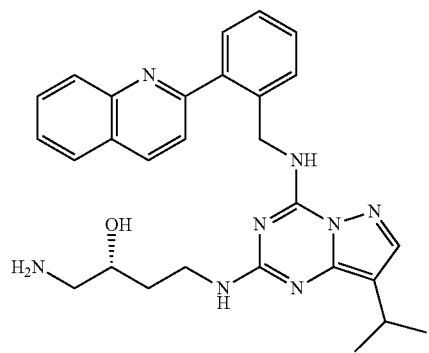 |
| 252 | 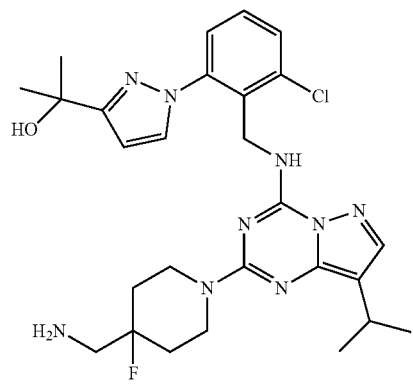 [SMILES: CC(C)c1cnn2c(NCc3c(Cl)cccc3-n3ccc(C(C)(C)O)n3)nc(N3CCC(F)(CN)CC3)nc12] |
| 253 | 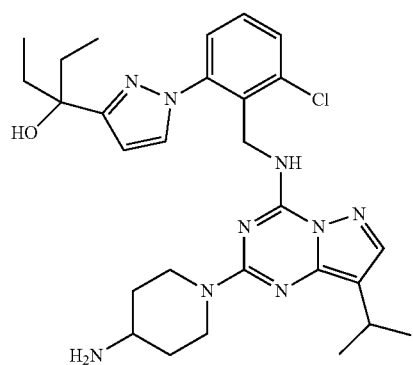 [SMILES: CCC(O)(CC)c1ccn(-c2cccc(Cl)c2CNc2nc(N3CCC(N)CC3)nc3c(C(C)C)cnn23)n1] |

-continued
| #cpds | Structure |
|---|---|
| 254 | 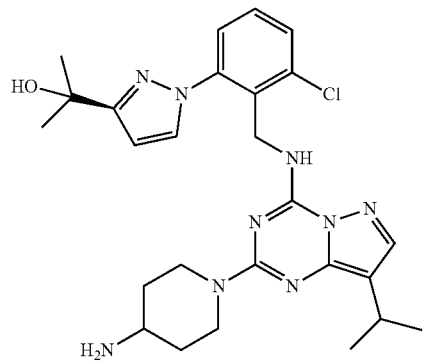 |
| 255 | 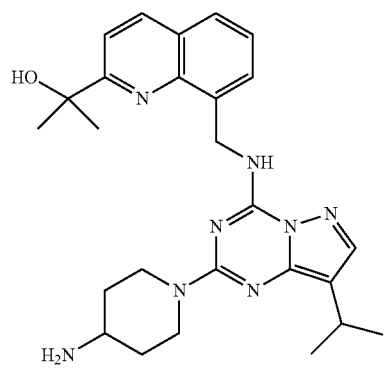 [SMILES: CC(C)c1cnn2c(NCc3cccc4ccc(C(C)(C)O)nc34)nc(N3CCC(N)CC3)nc12] |
| 256 | 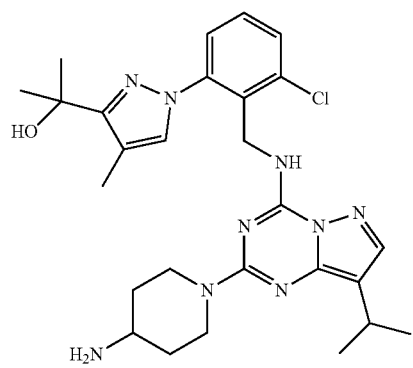 [SMILES: Cc1cn(-c2cccc(Cl)c2CNc2nc(N3CCC(N)CC3)nc3c(C(C)C)cnn23)nc1C(C)(C)O] |
| 258 | 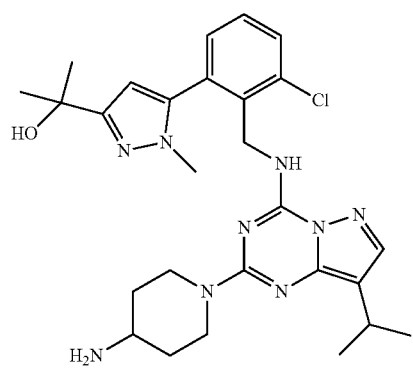 |

| #cpds | Structure |
|---|---|
| 259 | 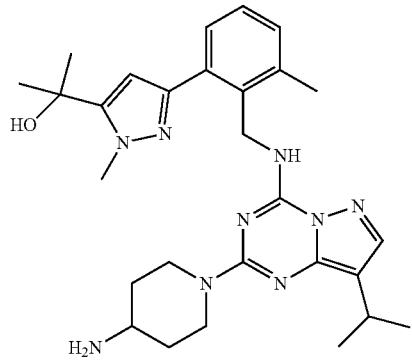 [SMILES: Cc1cccc(-c2cc(C(C)(C)O)n(C)n2)c1CNc1nc(N2CCC(N)CC2)nc2c(C(C)C)cnn12] |
| 260 | 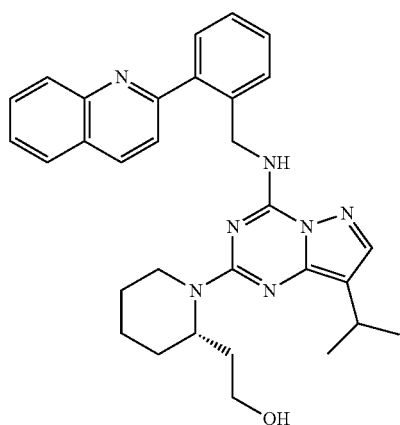 [SMILES: CC(C)c1cnn2c(NCc3ccccc3-c3ccc4ccccc4n3)nc(N3CCCC[C@H]3CCO)nc12] |
| 261 | 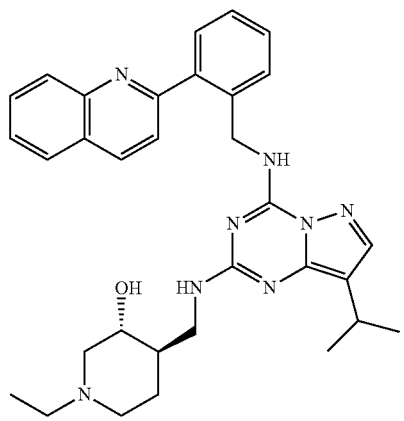 [SMILES: CCN1CC[C@H](CNc2nc(NCc3ccccc3-c3ccc4ccccc4n3)n3ncc(C(C)C)c3n2)[C@@H](O)C1] |

-continued
| #cpds | Structure |
|---|---|
| 262 | 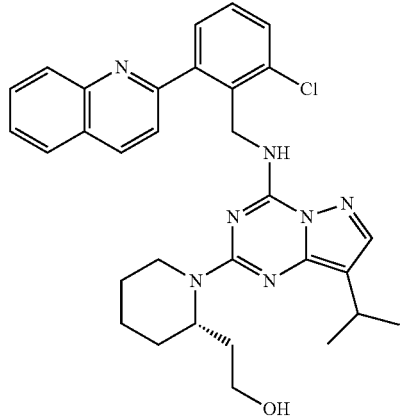 [SMILES: CC(C)c1cnn2c(NCc3c(Cl)cccc3-c3ccc4ccccc4n3)nc(N3CCCC[C@H]3CCO)nc12] |
| 263 | 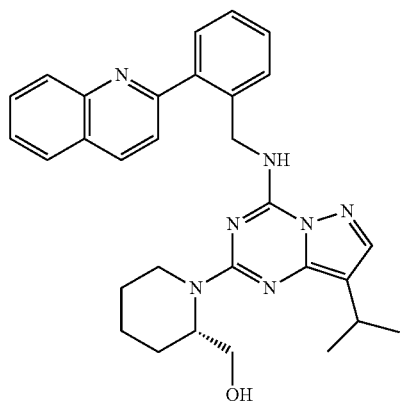 [SMILES: CC(C)c1cnn2c(NCc3ccccc3-c3ccc4ccccc4n3)nc(N3CCCC[C@H]3CO)nc12] |
| 264 | 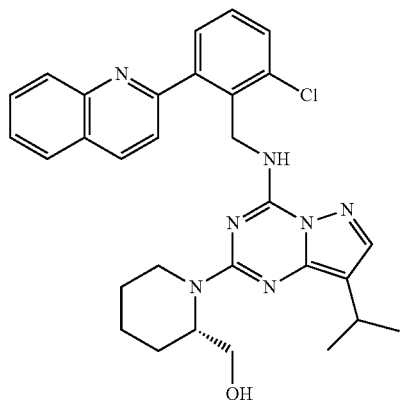 [SMILES: CC(C)c1cnn2c(NCc3c(Cl)cccc3-c3ccc4ccccc4n3)nc(N3CCCC[C@H]3CO)nc12] |

| #cpds | Structure |
|---|---|
| 265 | 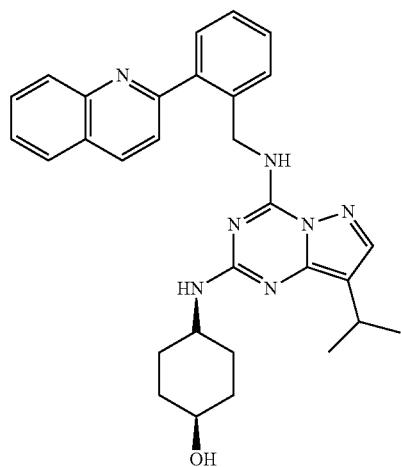 |
| 266 | 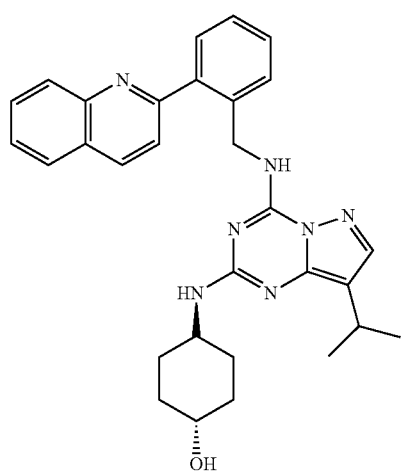 |
| 267 | 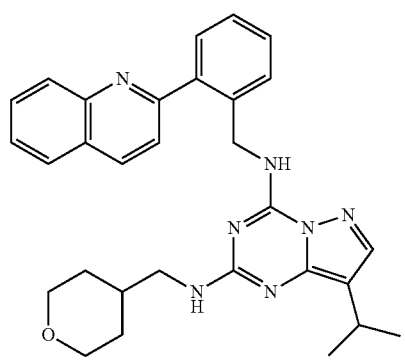 [SMILES: CC(C)c1cnn2c(NCc3ccccc3-c3ccc4ccccc4n3)nc(NCC3CCOCC3)nc12] |

-continued
| #cpds | Structure |
|---|---|
| 268 | 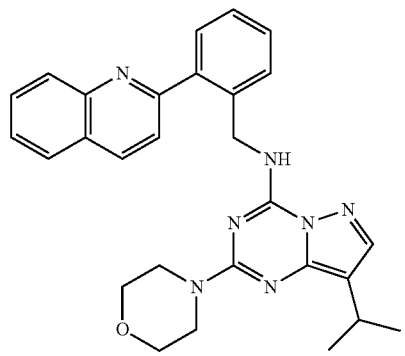 [SMILES: CC(C)c1cnn2c(NCc3ccccc3-c3ccc4ccccc4n3)nc(N3CCOCC3)nc12] |
| 269 | 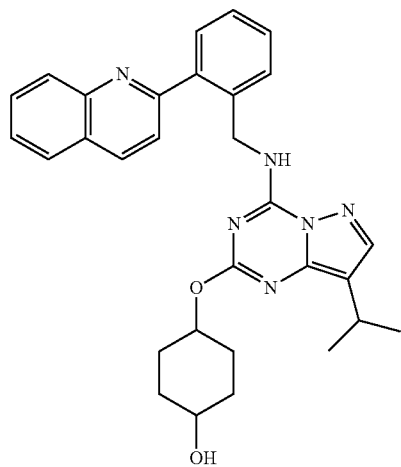 [SMILES: CC(C)c1cnn2c(NCc3ccccc3-c3ccc4ccccc4n3)nc(OC3CCC(O)CC3)nc12] |
| 270 | 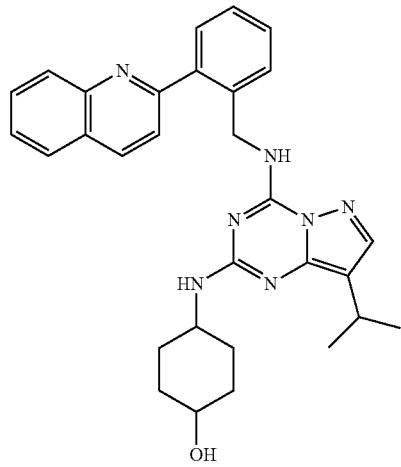 [SMILES: CC(C)c1cnn2c(NCc3ccccc3-c3ccc4ccccc4n3)nc(NC3CCC(O)CC3)nc12] |

-continued
| #cpds | Structure |
|---|---|
| 271 | 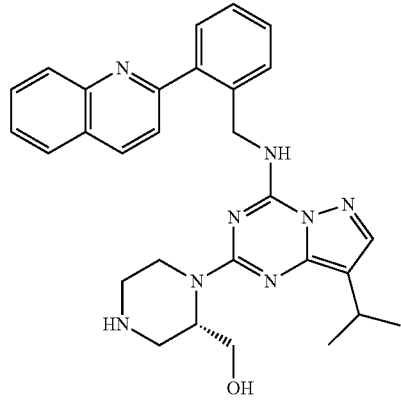 [SMILES: CC(C)c1cnn2c(NCc3ccccc3-c3ccc4ccccc4n3)nc(N3CCNC[C@H]3CO)nc12] |
| 272 | 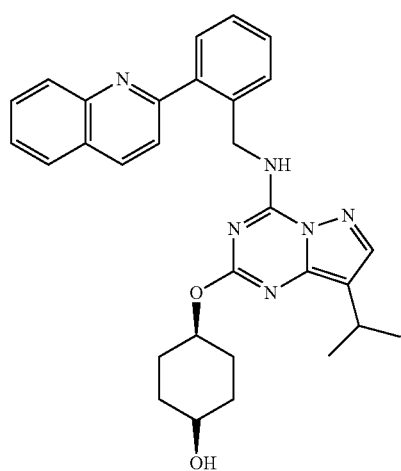 |
| 273 | 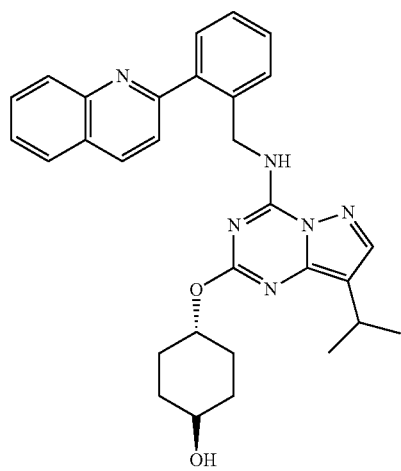 |

| #cpds | Structure |
|---|---|
| 274 | 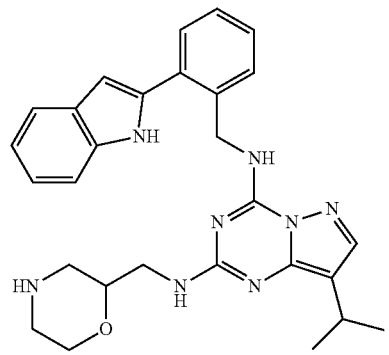 [SMILES: CC(C)c1cnn2c(NCc3ccccc3-c3cc4ccccc4[nH]3)nc(NCC3CNCCO3)nc12] |
| 276 | 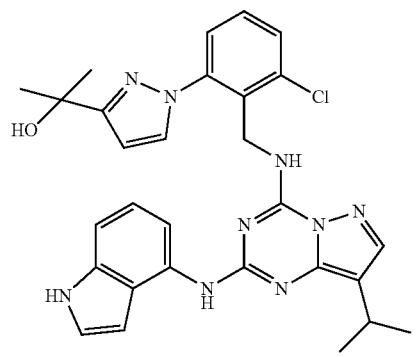 [SMILES: CC(C)c1cnn2c(NCc3c(Cl)cccc3-n3ccc(C(C)(C)O)n3)nc(Nc3cccc4[nH]ccc34)nc12] |
| 277 | 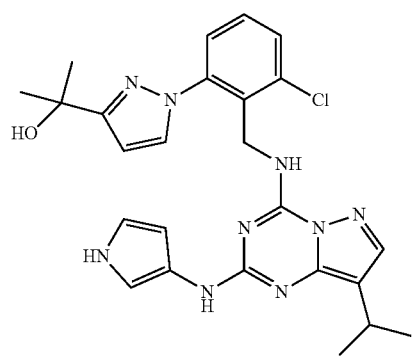 [SMILES: CC(C)c1cnn2c(NCc3c(Cl)cccc3-n3ccc(C(C)(C)O)n3)nc(Nc3cc[nH]c3)nc12] |
| 278 | 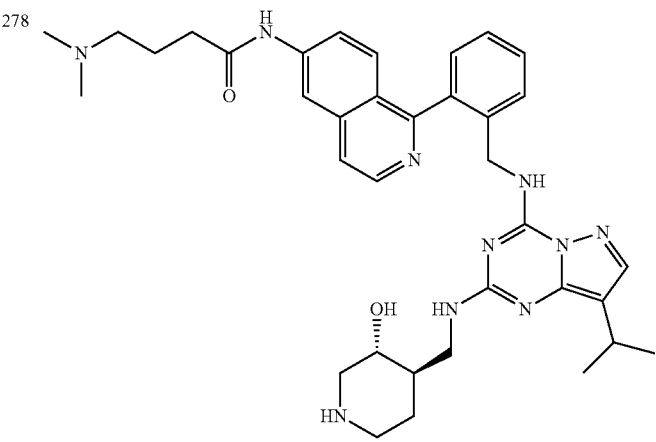 |

| #cpds | Structure |
|---|---|
| 279 | 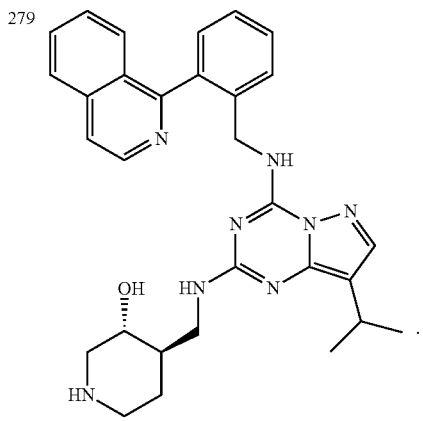 |

12. A pharmaceutical composition comprising a compound according to claim 1, as an active ingredient, together with at least one pharmaceutically acceptable carrier, excipient and/or diluent.

13. A compound according to claim 1 for use as pharmaceutically active agent, wherein said pharmaceutically active agent has an inhibitory activity on cyclin-dependent kinase 7 (CDK7).

14. A method of treatment of a disease which is associated with inhibition of apoptosis, abnormal transcriptional activity and/or cell cycle arrest by aberrant activity and/or overexpression of one or several cyclin-dependent kinases (CDKs), wherein the disease is selected from proliferative diseases, infectious diseases, including opportunistic diseases, immunological diseases, autoimmune diseases, and inflammatory diseases and wherein the method comprises administering, to a subject in need of such treatment, a compound of claim 1.

15. The method according to claim 14, wherein the proliferative disease is a cancer selected from the group consisting of: adenocarcinoma, choroidal melanoma, acute leukemia, acoustic neurinoma, ampullary carcinoma, anal carcinoma, astrocytoma, basal cell carcinoma, pancreatic cancer, Desmoid tumor, bladder cancer, bronchial carcinoma, estrogen dependent and independent breast cancer, Burkitt's lymphoma, corpus cancer, Carcinoma unknown primary tumor (CUP-syndrome), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic tumor, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymphomas, stomach cancer, malignant melanoma, malignant neoplasia, malignant tumors gastrointestinal tract, breast carcinoma, rectal cancer, medulloblastomas, melanoma, meningiomas, Hodgkin's/Non-Hodgkin's lymphoma, mycosis fungoides, nasal cancer, neurinoma, neuroblastoma, kidney cancer, renal cell carcinomas, oligodendroglioma, esophageal carcinoma, osteolytic carcinomas and osteoplastic carcinomas, osteosarcomas, ovarian carcinoma, pancreatic carcinoma, penile cancer, plasmacytoma, prostate cancer, pharyngeal cancer, rectal carcinoma, retinoblastoma, vaginal cancer, thyroid carcinoma, esophageal cancer, T-cell lymphoma, thymoma, tube carcinoma, eye tumors, urethral cancer, urologic tumors, urothelial carcinoma, vulva cancer, wart appearance, soft tissue tumors, soft tissue sarcoma, Nephroblastoma, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypothalamic glioma, cerebellar astrocytoma, cerebral astrocytoma, neuroectodermal tumor, pineal tumors, sarcoma of the uterus, salivary gland cancers, anal gland adenocarcinomas, mast cell tumors, pelvis tumor, ureter tumor, hereditary papillary renal cancers, sporadic papillary renal cancers, intraocular melanoma, hepatocellular carcinoma, cholangiocarcinoma, mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-cell lymphoma, lymphoma of the central nervous system, malignant fibrous histiocytoma, lymph sarcoma, rhabdomyosarcoma, malignant histiocytosis, fibroblastic sarcoma, hemangiosarcoma, hemangiopericytoma, leiomyosarcoma (LMS), canine mammary carcinoma, and feline mammary carcinoma.

16. The method according to claim 14, wherein the infectious disease is selected from the group consisting of AIDS, Adenovirus Infection, Alveolar Hydatid Disease (AHD), Amoebiasis, Angiostrongyliasis, Anisakiasis, Anthrax, Babesiosis, Balantidiasis, *Baylisascaris* Infection, *Bilharzia* (Schistosomiasis), *Blastocystis hominis* Infection, Lyme Borreliosis, Botulism, Brainerd Diarrhea, Brucellosis, Bovine Spongiform Encephalopathy (BSE), Candidiasis, Capillariasis, Chronic Fatigue Syndrome (CFS), Chagas Disease, Chickenpox, *Chlamydia pneumoniae* Infection, Cholera, Chronic Fatigue Syndrome, Creutzfeldt-Jakob Disease (CJD), Clonorchiasis, Cutaneous Larva migrans (CLM), Coccidioidomycosis, Conjunctivitis, Coxsackievirus A16 (Cox A16), Cryptococcal disease, Cryptosporidiosis, West Nile fever, Cyclosporiasis, Neurocysticercosis, Cytomegalovirus Infection, Dengue Fever, *Dipylidium caninum* Infection, Ebola Hemorrhagic Fever (EHF), Alveolar Echinococcosis (AE), Encephalitis, *Entamoeba coli* Infection, *Entamoeba dispar* Infection, *Entamoeba hartmanni* Infection, *Entamoeba polecki* Infection, Pinworm Infection, Enterovirus Infection (Polio/Non-Polio), Epstein Barr Virus Infection, *Escherichia coli* Infection, Foodborne Infection, Aphthae epizooticae, Fungal Dermatitis, Fungal Infections, Gastroenteritis, Group A streptococcal Disease, Group B streptococcal Disease, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis, Lassa Fever, Leishmaniasis, Visceral leishmaniasis (VL), Malaria, Marburg Hemorrhagic Fever, Measles, Meningitis, *Mycobacterium avium* Complex (MAC) Infection, *Naegleria* Infection, Nosocomial Infections, Nonpathogenic Intestinal Amebae Infection, Onchocerciasis, Opisthorchiasis, Papilloma virus Infection, Parvovirus Infection, Plague, *Pneumocystis* Pneumonia (PCP), Polyomavirus Infection, Q Fever, Rabies, Respiratory Syncytial Virus (RSV) Infection, Rheumatic Fever, Rift Valley Fever, Rotavirus Infection, Roundworms Infection, *Salmonellosis*, Scabies, Shigellosis, Shingles, Sleeping Sickness, Smallpox, Streptococcal Infection, Tapeworm Infection, Tetanus, Toxic Shock Syndrome, Tuberculosis, duodenum, *Vibrio parahaemolyticus* Infection, *Vibrio* septicemia, Viral Hemorrhagic Fever, Warts, Waterborne infectious Diseases, Varicella-Zoster Virus infection, Pertussis and Yellow Fever.

17. The method according to claim 14, wherein the immunological disease and/or autoimmune disease is selected from the group consisting of: asthma, diabetes, rheumatic diseases, AIDS, rejection of transplanted organs and tissues, rhinitis, chronic obstructive pulmonary diseases, osteoporosis, ulcerative colitis, sinusitis, lupus erythematosus, recurrent infections, atopic dermatitis/eczema and occupational allergies, food allergies, drug allergies, severe anaphylactic reactions, anaphylaxis, manifestations of allergic diseases, primary immunodeficiencies, antibody deficiency states, cell mediated immunodeficiencies, severe combined immunodeficiency, DiGeorge syndrome, Hyper IgE syndrome (HIES), Wiskott-Aldrich syndrome (WAS), ataxia-telangiectasia, immune mediated cancers, white cell defects, autoimmune diseases, systemic lupus erythematosus (SLE), rheumatoid arthritis (RA), multiple sclerosis (MS), immune-mediated or Type 1 Diabetes Mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, Hashimoto's disease, dermatomyositis, Goodpasture syndrome (GPS), myasthenia gravis (MG), Sympathetic ophthalmia, Phakogene Uveitis, chronical aggressive hepatitis, primary biliary cirrhosis, autoimmune hemolytic anemia, and Werlhof's disease.

18. The method according to claim 14, wherein the inflammatory disease is caused, induced, initiated and/or enhanced by bacteria, viruses, prions, parasites, fungi, and/or caused by irritative, traumatic, metabolic, allergic, autoimmune, or idiopathic agents.

19. The method according to claim 14, wherein the inflammatory disease is selected from the group consisting of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, and inflammatory diseases of the larynx.

20. The method according to claim 14, wherein the inflammatory disease is selected from inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx, wherein preferably said inflammatory diseases are selected from the group comprising abscessation, acanthamoeba infection, acne vulgaris, actinomycosis, acute inflammatory dermatoses, acute laryngeal infections of adults, acute multifocal placoid pigment epitheliopathy, acute (thermal) injury, acute retinal necrosis, acute suppurative otitis media, algal disorders, allergic contact dermatitis, amyloidosis angioedema, ankylosing spondylitis, aspergillosis, atopic dermatitis, pseudorabies, autoantibodies in vasculitis, bacterial disorders, bacterial laryngitis, bacterial meningitis, Behcet's disease (BD), birdshot choroidopathy, Gilchrist's disease, Borna disease, brucellosis, bullous myringitis, bursitis, candidiasis, canine distemper encephalomyelitis, canine distemper encephalomyelitis in immature animals, canine hemorrhagic fever, canine herpes virus encephalomyelitis, cholesteatoma, chronic granulomatous diseases (CGD), chronic inflammatory dermatoses, chronic relapsing encephalomyelitis, chronic suppurative otitis media, Ocular Cicatricial pemphigoid (OCP), common upper respiratory infection, granuloma, Crohn's disease, cryptococcal disease, dermatomyositis, diphtheria, discoid lupus erythematosus (DLE), drug-induced vasculitis, drug or hypersensitivity reaction, encephalitozoonosis, eosinophilic meningoencephalitis, Erythema multiforme (EM), feline leukemia virus, feline immunodeficiency virus, feline infectious peritonitis, feline Polioencephalitis, feline spongiform encephalopathy, fibromyalgia, Fuchs Heterochromic Uveitis, gastroesophageal (laryngopharyngeal) reflux disease, giant cell arteritis, glanders, glaucomatocyclitic crisis, gonorrhea granular myringitis, Granulomatous meningoencephalitis (GME), herpes simplex, histoplasmosis, idiopathic diseases, idiopathic inflammatory disorders, immune and idiopathic disorders, infections of the immunocompromised host, infectious canine hepatitis, inhalation laryngitis, interstitial nephritis, irritant contact dermatitis, juvenile rheumatoid arthritis, Kawasaki's disease, La Crosse virus encephalitis, laryngeal abscess, laryngotracheobronchitis, leishmaniasis, lens-induced uveitis, leprosy, leptospirosis, leukemia, lichen planus, lupus, lymphoma, meningitis, meningoencephalitis in greyhounds, miscellaneous meningitis/meningoencephalitis, microscopic polyangiitis, multifocal choroiditis, multifocal distemper encephalomyelitis in mature animals, multiple sclerosis, Muscle Tension Dysphonia (MTD), mycotic (fungal) diseases, mycotic diseases of the CNS, necrotizing encephalitis, neosporosis, old dog encephalitis, onchocerciasis, parasitic encephalomyelitis, parasitic infections, Pars planitis, parvovirus encephalitis, pediatric laryngitis, pollution and inhalant allergy, polymyositis, post-vaccinal canine distemper encephalitis, prion protein induced diseases, protothecosis, protozoal encephalitis-encephalomyelitis, psoriasis, psoriatic arthritis, pug dog encephalitis, radiation injury, radiation laryngitis, radionecrosis, relapsing polychondritis, Reiter's syndrome, retinitis pigmentosa, retinoblastoma, rheumatoid arthritis, Rickettsial disorders, rocky mountain spotted fever, salmon poisoning disease (SPD), Sarcocystosis, sarcoidosis, schistosomiasis, scleroderma, Rhinoscleroma, serpiginous choroiditis, shaker dog disease, Sjogren's syndrome, spasmodic croup, spirochetal (syphilis) diseases, spongiotic dermatitis, sporotrichosis, steroid responsive meningitis-arteritis, Stevens-Johnson syndrome (SJS, EM major), epiglottitis, sympathetic ophthalmia, Syngamosis, syphilis, systemic vasculitis in sarcoidosis, Takayasu's arteritis, tendinitis (tendonitis), Thromboangiitis obliterans (Buerger Disease), tick-borne encephalitis in dogs, toxic epidermal necrolysis (TEN), toxocariasis, toxoplasmosis, trauma, traumatic laryngitis, trichinosis, trypanosomiasis, tuberculosis, tularemia, ulcerative colitis, urticaria (hives), vasculitis, vasculitis and malignancy, vasculitis and rheumatoid arthritis, vasculitis in the idiopathic inflammatory myopathies, vasculitis of the central nervous system, vasculitis secondary to bacterial, fungal, and parasitic infection, viral disorders, viral laryngitis, vitiligo, vocal abuse, vocal-cord hemorrhage, Vogt-Koyanagi-Harada syndrome (VKH), Wegener's granulomatosis, and Whipple's disease.

\* \* \* \* \*

UNITED STATES PATENT AND TRADEMARK OFFICE
CERTIFICATE OF CORRECTION

PATENT NO. : 11,945,822 B2
APPLICATION NO. : 17/045030
DATED : April 2, 2024
INVENTOR(S) : Kiyean Nam et al.

It is certified that error appears in the above-identified patent and that said Letters Patent is hereby corrected as shown below:

On the Title Page

Item (54) and in the Specification Column 1,
Line 2, "PYRAZOLO-PXRIMIDINE" should read --PYRAZOLO-PYRIMIDINE--

In the Specification

Column 2,
Line 28, "More" should read --The more--

Column 3,
Line 42, "and –(CO)" should read --and –(C=O)--
Line 47, "two of $OR^5$," should read --two of $–OR^5$,--
Line 50, "and $–(CO)R^5$," should read --and $–(C=O)R^5$,--
Line 52, "and $–(CO)R^5$," should read --and $–(C=O)R^5$,--
Line 54, "and $–(CO)R^5$," should read --and $–(C=O)R^5$,--

Signed and Sealed this
Fifteenth Day of October, 2024

Katherine Kelly Vidal
*Director of the United States Patent and Trademark Office*

CERTIFICATE OF CORRECTION (continued)
U.S. Pat. No. 11,945,822 B2

Column 17,
Lines 43-44, "

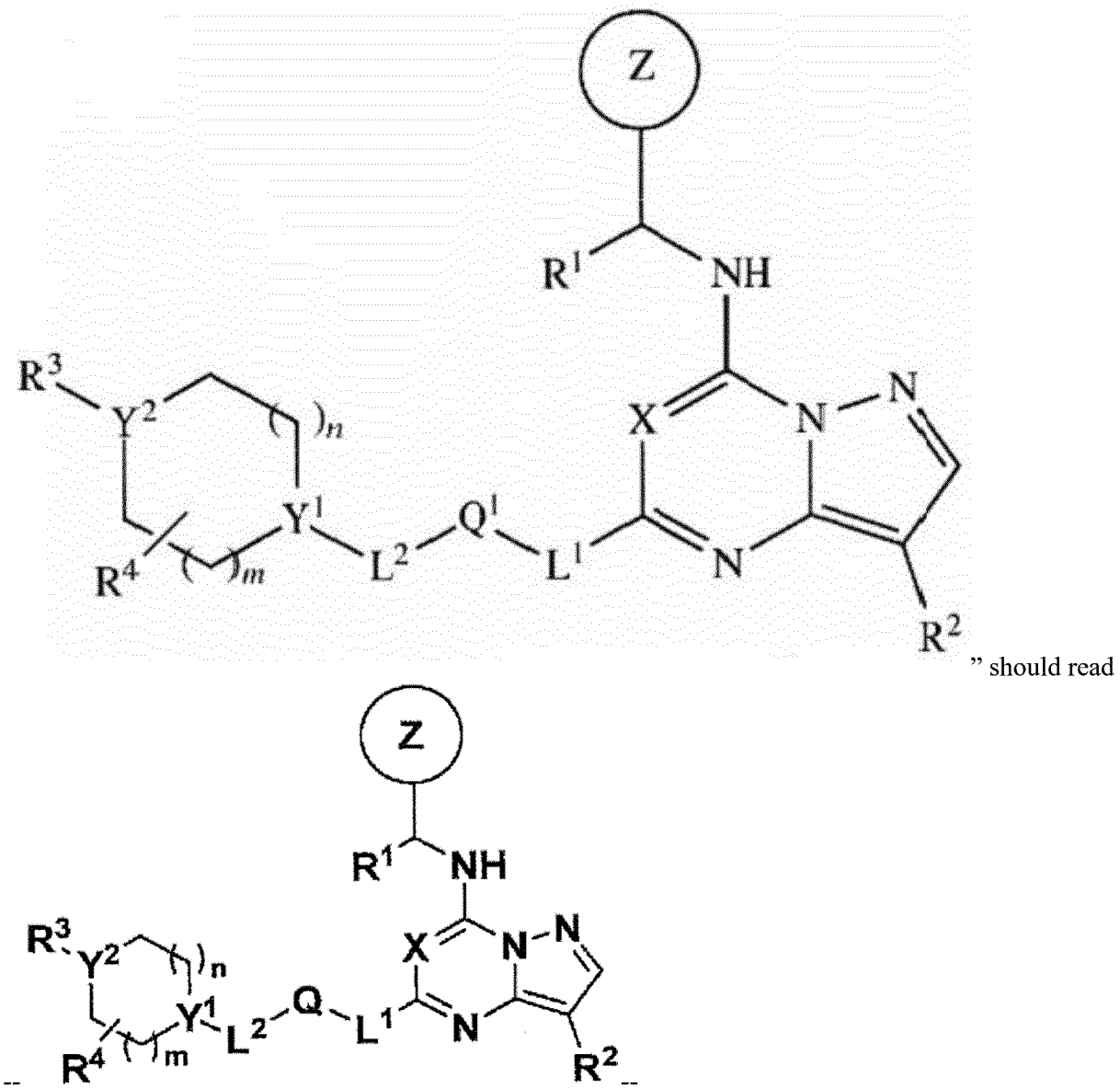

" should read

Column 45,
Line 43, "Compound $C_{1-3}$" should read --Compound C13--

Column 48,
Line 31, "A1 (11 0mg)" should read --A1 (110mg)--

Column 49,
Line 67, "powder" should read --powder.--

Column 55,

Line 17, "1b the" should read --To the--
Column 59,
Line 34, "yellow gum" should read --yellow gum.--
Column 66,
Lines 6-7, " 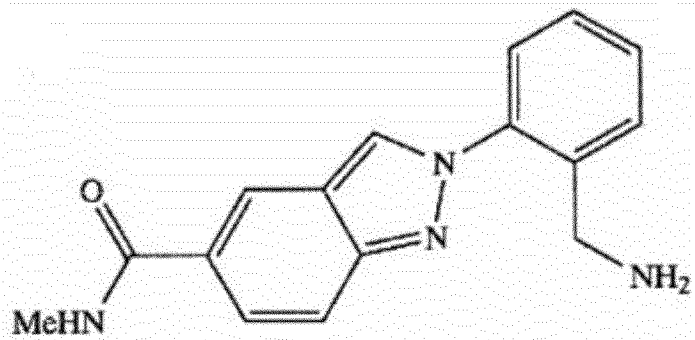 " should read -- 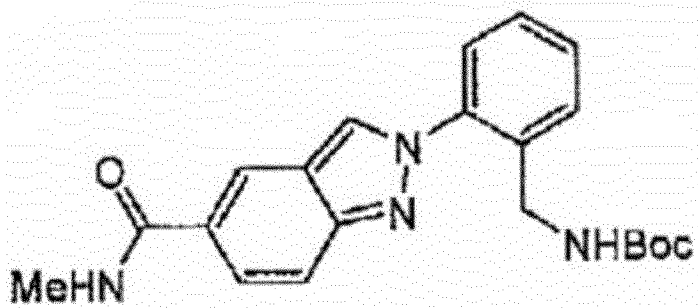 --
Column 70,
Lines 1-6, " 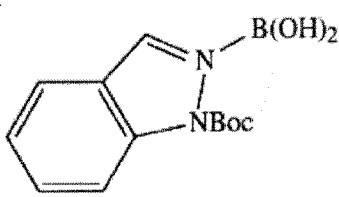 " should read -- 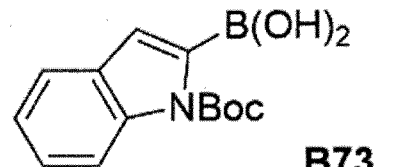 --

CERTIFICATE OF CORRECTION (continued)
U.S. Pat. No. 11,945,822 B2

Lines 16-19, " 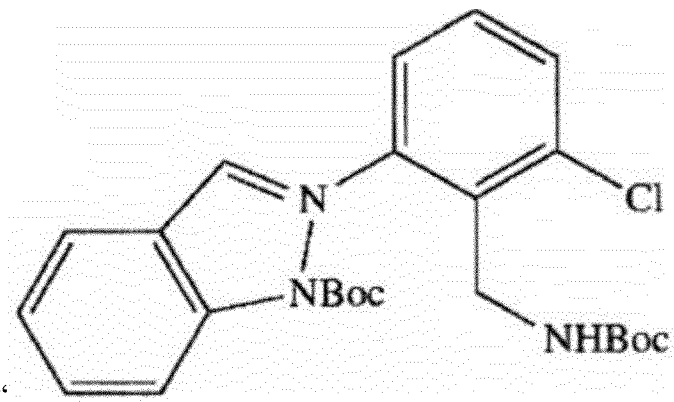 " should read

-- 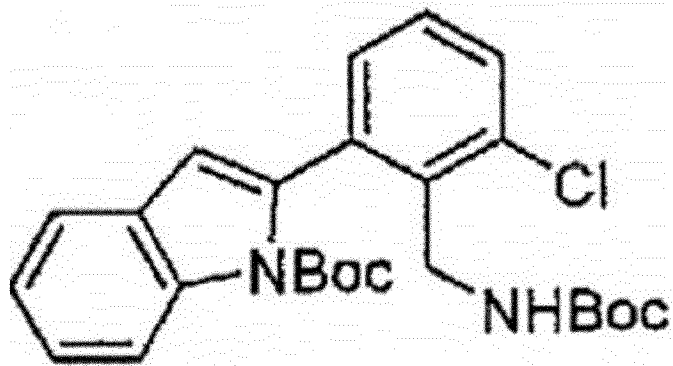 --

Column 82,
Line 43, "solid" should read --solid.--

Column 86,
Line 32, "yellow oil" should read --yellow oil.--

Column 98,
Line 9, " 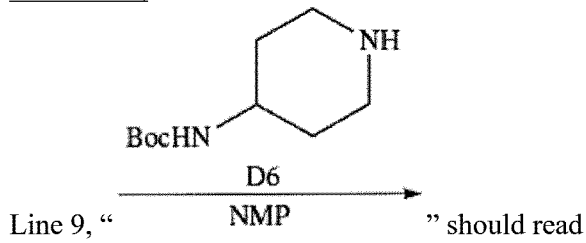 " should read

-- 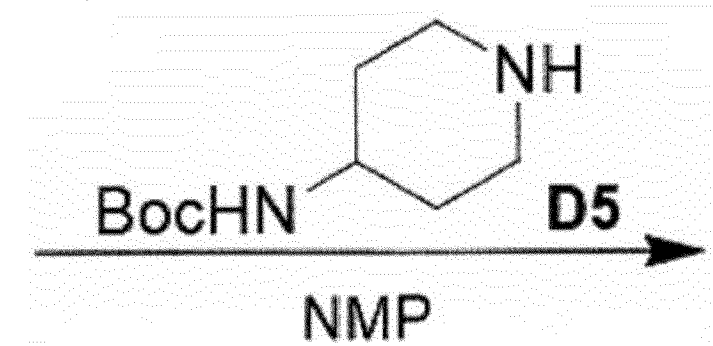 --

Column 100,
Line 50, "pH = 7-8," should read --pH = 7~8,--

Column 103,
Line 10, "for 2 horns." should read --for 2 hours.--

Column 114,
Lines 47-48, "T. I. Lee" should begin a new paragraph
Line 55, "J. Kam." should read --J. Karn.--

Column 127,
Lines 42-43, "161 A" (that represent #cpds being 161 and IC50 being A) are missing Column 131,
Lines 35-36, "102 A" (that represent #cpds being 102 and IC50 being A) are missing In the Claims Column 289,
Line 10, "-Ole" should read -- -$OR^5$--